(12) United States Patent
Barker et al.

(10) Patent No.: US 8,895,733 B2
(45) Date of Patent: Nov. 25, 2014

(54) TRIAZINE-OXADIAZOLES

(71) Applicants: Oliver Barker, Oxon (GB); Jonathan Mark Bentley, Oxon (GB); Mark G. Bock, Boston, MA (US); Thomas Cain, Oxon (GB); Praful Chovatia, Berkshire (GB); Jennifer Ruth Dod, Oxon (GB); Florence Eustache, Oxon (GB); Laura Gleave, Oxon (GB); Jonathan Hargrave, Somerset (GB); Alexander Heifetz, Oxon (GB); Richard Law, Oxon (GB); Ali Raoof, Lancashire (GB); David Willows, Oxon (GB)

(72) Inventors: Oliver Barker, Oxon (GB); Jonathan Mark Bentley, Oxon (GB); Mark G. Bock, Boston, MA (US); Thomas Cain, Oxon (GB); Praful Chovatia, Berkshire (GB); Jennifer Ruth Dod, Oxon (GB); Florence Eustache, Oxon (GB); Laura Gleave, Oxon (GB); Jonathan Hargrave, Somerset (GB); Alexander Heifetz, Oxon (GB); Richard Law, Oxon (GB); Ali Raoof, Lancashire (GB); David Willows, Oxon (GB)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/054,221

(22) Filed: Oct. 15, 2013

(65) Prior Publication Data
US 2014/0051676 A1    Feb. 20, 2014

Related U.S. Application Data

(63) Continuation of application No. 13/820,644, filed as application No. PCT/EP2011/065868 on Sep. 13, 2011.

(60) Provisional application No. 61/382,158, filed on Sep. 13, 2010.

(51) Int. Cl.
| | | |
|---|---|---|
| *C07D 413/04* | (2006.01) | |
| *C07D 413/14* | (2006.01) | |
| *A61K 31/53* | (2006.01) | |
| *A61P 29/00* | (2006.01) | |
| *A61K 45/06* | (2006.01) | |
| *C07D 498/08* | (2006.01) | |
| *C07D 491/10* | (2006.01) | |
| *C07D 451/02* | (2006.01) | |
| *C07D 491/107* | (2006.01) | |
| *C07D 417/14* | (2006.01) | |
| *C07D 487/04* | (2006.01) | |

(52) U.S. Cl.
CPC ............ *C07D 413/04* (2013.01); *A61K 45/06* (2013.01); *C07D 498/08* (2013.01); *C07D 491/10* (2013.01); *C07D 451/02* (2013.01); *C07D 413/14* (2013.01); *C07D 491/107* (2013.01); *C07D 417/14* (2013.01); *C07D 487/04* (2013.01); *A61K 31/53* (2013.01)

USPC .......................................... 544/212; 514/245

(58) Field of Classification Search
CPC ...... C07D 413/04; C07D 413/14; A61K 31/53
USPC ........................................ 544/212; 514/245
See application file for complete search history.

(56) References Cited

U.S. PATENT DOCUMENTS

2008/0227799 A1    9/2008    Liotta et al.
2009/0270201 A1   10/2009    Kim et al.

FOREIGN PATENT DOCUMENTS

| WO | 2009/002964 | 12/2008 |
|---|---|---|
| WO | 2009/010784 | 1/2009 |
| WO | 2009/091388 | 7/2009 |
| WO | 2009/118567 | 10/2009 |
| WO | 2010/017368 | 2/2010 |
| WO | 2010/022055 A2 | 2/2010 |
| WO | 2011/103196 A1 | 8/2011 |

OTHER PUBLICATIONS

Krafte et al., Current Opinion in Pharmacology 2008, 8:50-56.*
Rush et al., Molecular Interventions 2007, vol. 4, issue 7, 192-195.*
Dermer et al., Bio/Technology, 1994, 12:320.*
Clare et al, Drug Discovery Today 2000, vol. 5, No. 11,506-520.*
Freshney et al.,Culture of Animal Cells, A Manual of Basic Technique, Alan R. Liss, Inc., 1983, New York, p. 4.*
Bregman et al., Bioorg Med Chem Letters, 22(8):2033-2042 (2012).
Bregman et al., Journal Med Chem, 54(13):4427-4445 (2011).
Chesnyuk et al., Russian Chem Bulletin, 54(8):1900-1906 (2005).
Seyour et al., Journal Org Chem, 25(3):384-387 (1960).
CAS Registry No. 899373-19-4, STN entry date Aug. 7, 2006.

* cited by examiner

*Primary Examiner* — Venkataraman Balasubramanian
(74) *Attorney, Agent, or Firm* — Joshua Roth

(57) ABSTRACT

The invention relates to new derivatives of formula (I),

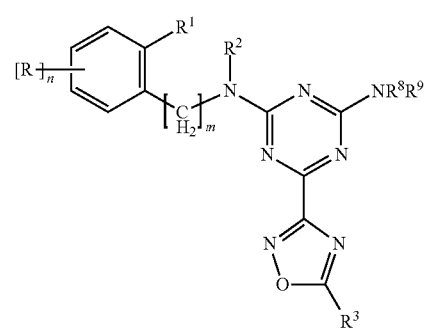

wherein the substituents are as defined in the specification; to processes for the preparation of such derivatives; pharmaceutical compositions comprising such derivatives; such derivatives as a medicament; such derivatives for the treatment of chronic pain.

14 Claims, No Drawings

TRIAZINE-OXADIAZOLES

FIELD OF THE INVENTION

The present invention relates to new triazine-oxadiazoles; processes for the preparation of such triazine-oxadiazoles; pharmaceutical compositions comprising such triazine-oxadiazoles optionally in combination with one or more other pharmaceutically active compounds; such triazine-oxadiazoles optionally in combination with one or more other pharmaceutically active compounds as a medicament; such triazine-oxadiazoles optionally in combination with one or more other pharmaceutically active compounds for the treatment of chronic pain, such as positive symptoms of chronic pain e.g. parethesias, dyesthesias, hyperalgesia, allodynia and spontaneous pain (also including a method for the treatment of such diseases in mammals, especially in humans); and the use of such triazine-oxadiazoles for the preparation of a pharmaceutical composition (medicament) for the treatment of chronic pain, such as positive symptoms of chronic pain e.g. parethesias, dyesthesias, hyperalgesia, allodynia and spontaneous pain as well as negative symptoms e.g. loss of sensation.

BACKGROUND OF THE INVENTION

The compounds of the present invention are sodium channel blockers, in particular selective inhibitors of the voltage-gated sodium channel 1.7 (Nav1.7) which is involved in pain. Since other sodium channel subtypes are involved in different essential physiological processes such as heart activity (Nav1.5), muscle contraction (Nav1.4) and CNS neurotransmission (Nav1.1, 1.2 and 1.6), selectivity for Nav1.7 is believed to be associated with the potential elimination of side effects.

Several Nav1.7 blockers are described: The tarantula venom peptide Pro-TX-II is a potent inhibitor of Nav1.7 (Schmalhofer et al, Molecular Pharmacology 2008, 74, 1476-1484). A series of Benzazepinone Nav1.7 blockers are described to show activity in pre-clinical pharmacological models of pain (Williams et al, Biochemistry, 2007, 46(50), 14693-14703; McGowan et al., Anesth Analg, 2009, 109, 951-958). Amino-thiazoles and amino-pyridines are described as Nav1.7 inhibitors (WO2007109324) and isoxazoles are described as Nav1.7 inhibitors (WO2009010784).

Nonsense mutations in SCN9A, the gene coding Nav1.7, appear to be linked to Congenital Indifference to Pain (CIP) (Cox et al, Nature, 2006, 444(7121), 894-898). Patients with CIP are essentially completely indifferent to sensations that would cause pain in most individuals e.g. bone fractures, burns, dental abscesses, appendicitis and childbirth. Concurrently, they are able to distinguish between other sensations, such as thermal (hot/cold) and tactile (sharp/dull) stimuli (Goldberg et al, Clinical Genetics, 2007, 71(4), 311-319).

Recent clinical reports indicate that gain of function mutations in human Nav1.7 are typically associated with severe pathological conditions. Primary Erythermalgia has been associated with mutations T2573A and T2543C in Nav1.7 (Yang et al, Journal of Medical Genetics, 2004, 41(3), 171-4). Paroxysmal Extreme Pain Disorder is described in association with mutations M1627K, T1464I and I1461T located in the inactivation gate area of Nav1.7 (Fertleman et al, Neuron, 2006, 52(5), 767-774).

Thus selective inhibition of Nav1.7 channels may provide comprehensive analgesia.

Hence, there is a continuing need for compounds which may be useful for treating and preventing disorders or diseases which respond to inhibition of Nav1.7, particularly for compounds with improved efficacy, tolerability and/or selectivity.

Related, but structurally distinct triazines have been reported, e.g. as kinase inhibitors by Janssen (WO2004009562); as integrin inhibitors by Biochem Pharma (WO2000075129).

DETAILED DESCRIPTION OF THE INVENTION

In a first aspect, the invention relates to triazine-oxadiazoles of the formula (I) and/or pharmaceutically acceptable salts and/or solvates thereof,

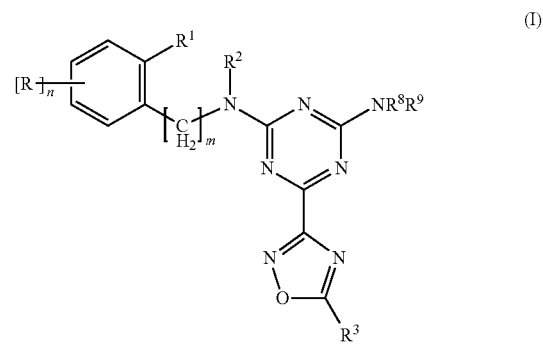

(I)

wherein
$R^1$ is selected from
   hydrogen-
   halogen-
   $C_1$-$C_7$-alkyl-
   halo-$C_1$-$C_7$-alkyl-;
$R^2$ is selected from
   hydrogen-
   $C_1$-$C_7$-alkyl-
   halo-$C_2$-$C_7$-alkyl-
   amino-$C_2$-$C_7$-alkyl-
   N—$C_1$-$C_7$-alkyl-amino-$C_2$-$C_7$-alkyl-
   N,N-di-$C_1$-$C_7$-alkyl-amino-$C_2$-$C_7$-alkyl-
   hydroxy-$C_2$-$C_7$-alkyl-
   $C_1$-$C_7$-alkoxy-$C_2$-$C_7$-alkyl-
   $C_3$-$C_{10}$-cycloalkyl-$C_1$-$C_7$-alkyl-
   cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
   $C_1$-$C_7$-alkyl-
   halo-$C_1$-$C_7$-alkyl-
   amino-$C_1$-$C_7$-alkyl-
   N—$C_1$-$C_7$-alkyl-amino-$C_1$-$C_7$-alkyl-
   N,N-di-$C_1$-$C_7$-alkyl-amino-$C_1$-$C_7$-alkyl-
   hydroxy-$C_1$-$C_7$-alkyl-
   $C_1$-$C_7$-alkoxy-$C_1$-$C_7$-alkyl-
   $C_3$-$C_{10}$-cycloalkyl-$C_1$-$C_7$-alkyl-
   cyano-$C_1$-$C_7$-alkyl-;
R is selected from
   halogen-
   $C_1$-$C_7$-alkyl-
   halo-$C_1$-$C_7$-alkyl-
   $C_1$-$C_7$-alkoxy-
   cyanohalo-$C_1$-$C_7$-alkoxy-
nitro;
—C(O)—O—R', wherein R' is selected from hydrogen, $C_1$-$C_7$-alkyl; $C_3$-$C_{10}$-cycloalkyl; $C_1$-$C_7$-alkoxy; halo-$C_1$-$C_7$-alkyl aryl-$C_1$-$C_7$-alkyl-; heteroaryl; heteroaryl $C_1$-$C_7$-alkyl-; heterocyclyl;
—S(=O)$_2$—$C_1$-$C_7$-alkyl; —S(=O)$_2$—$C_3$-$C_{10}$-cycloalkyl; —S(=O)$_2$—$C_1$-$C_7$-alkoxy;

$R^3$ is selected from
(a) -L-Y, wherein
 -L- is selected from a direct bond; —(CH$_2$)$_p$—, —C(O)—, —NR$^7$—, —NR$^7$—C(O)— or —C(O)—NR$^7$—, wherein p is selected from 1, 2 or 3
 $R^7$ is selected from hydrogen and $C_1$-$C_7$-alkyl
 Y is selected from cycloalkyl, aryl, heteroaryl, heterocyclyl, spirocyclyl, which are unsubstituted or substituted by 1-3 substituents selected from
 halogen-;
 $C_1$-$C_7$-alkyl-;
 halo-$C_1$-$C_7$-alkyl-;
 halo-$C_1$-$C_7$-alkyl-oxy-$C_1$-$C_7$-alkyl; halo-$C_1$-$C_7$-alkyl-oxy-$C_1$-$C_7$-alkyl-oxy;
 $C_1$-$C_7$-alkoxy-; $C_1$-$C_7$-alkoxy-$C_1$-$C_7$-alkoxy-; NC—$C_1$-$C_7$-alkoxy-;
 $C_1$-$C_7$-alkoxy-$C_1$-$C_7$-alkyl-;
 $C_3$-$C_{10}$-cycloalkyl-oxy-$C_1$-$C_7$-alkyl-;
 $C_3$-$C_{10}$-cycloalkyl-$C_1$-$C_7$-alkyl-oxy-;
 $C_3$-$C_{10}$-cycloalkyl-oxy-;
 $C_3$-$C_{10}$-cycloalkyl-NR$^{7'}$—$C_1$-$C_7$-alkyl-, wherein R$^{7'}$ is selected from $R^7$ is selected from hydrogen and $C_1$-$C_7$-alkyl;
 $C_3$-$C_{10}$-cycloalkyl-$C_1$-$C_7$-alkoxy-$C_1$-$C_7$-alkyl-;
 $C_2$-$C_7$-alkenyl; halo-$C_2$-$C_7$-alkenyl;
 hydroxy-;
 hydroxy-$C_1$-$C_7$-alkyl-;
 halo-$C_1$-$C_7$-alkyl-oxy-;
 amino-;
 N—$C_1$-$C_7$-alkyl-amino-;
 N-halo-$C_1$-$C_7$-alkyl-amino-;
 N-heterocyclyl-amino-, N—$C_3$-$C_{10}$-cycloalkyl-amino-, wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;
 N—$C_3$-$C_{10}$-cycloalkyl-$C_1$-$C_7$-alkyl-amino-;
 N,N-di-$C_1$-$C_7$-alkyl-amino-; N,N-di-halo-$C_1$-$C_7$-alkyl-amino-;
 N,N-di-heterocyclyl-amino-, N,N-di-$C_3$-$C_{10}$-cycloalkyl-amino- wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;
 cyano-; oxo;
 $C_1$-$C_7$-alkoxy-carbonyl-;
 $C_1$-$C_7$-alkoxy-$C_1$-$C_7$-alkoxy-$C_1$-$C_7$-alkyl-; aryl; aryl-$C_1$-$C_7$-alkyl-; aryl-oxy;
 heterocyclyl;
 heterocyclyl-$C_1$-$C_7$-alkyl-; heterocyclyl-oxy-;
 heterocyclyl-oxy-$C_1$-$C_7$-alkyl-; aryl-oxy-$C_1$-$C_7$-alkyl-; heteroaryl-oxy-$C_1$-$C_7$-alkyl-;
 hydroxy-carbonyl-;
 —S— halo-$C_1$-$C_7$-alkyl; —S—$C_1$-$C_7$-alkyl; —S—aryl;
 halo-$C_1$-$C_7$-alkyl-S—$C_1$-$C_7$-alkyl; $C_1$-$C_7$-alkyl-S—$C_1$-$C_7$-alkyl;
 —S(=O)$_2$—$C_1$-$C_7$-alkyl; —S(=O)$_2$— halo-$C_1$-$C_7$-alkyl; —S(=O)$_2$-aryl; —S(=O)$_2$-heteroaryl; —S(=O)$_2$—NR$^{4'}$R$^4$; —S(=O)$_2$-heterocyclyl;
 halo-$C_1$-$C_7$-alkyl-S(=O)$_2$—$C_1$-$C_7$-alkyl; $C_1$-$C_7$-alkyl-S(=O)$_2$—$C_1$-$C_7$-alkyl;
 —S(=O)—$C_1$-$C_7$-alkyl; —S(=O)-halo-$C_1$-$C_7$-alkyl; —S(=O)—$C_1$-$C_7$-alkoxy; —S(=O)—$C_3$-$C_{10}$-cycloalkyl;
 —C(O)—$C_1$-$C_7$-alkyl; —C(O)— halo-$C_1$-$C_7$-alkyl; —C(O)—$C_1$-$C_7$-alkoxy; —C(O)—$C_3$-$C_{10}$-cycloalkyl;
 —C(O)O—$C_1$-$C_7$-alkyl; —C(O)O—$C_3$-$C_{10}$-cycloalkyl; —C(O)O-halo-$C_1$-$C_7$-alkyl; —C(O)O—$C_1$-$C_7$-alkoxy;
 —C(O)—NR$^{4'}$R$^4$ or —NHC(O)—R$^4$, wherein
 $R^4$ is selected from hydrogen, $C_1$-$C_7$-alkyl, halo-$C_1$-$C_7$-alky, $C_3$-$C_{10}$-cycloalkyl, $C_3$-$C_{10}$-cycloalkyl-$C_1$-$C_7$-alkyl and $C_1$-$C_7$-alkoxy;
 $R^{4'}$ is selected from hydrogen;
 or $R^4$ and $R^{4'}$ together with the nitrogen atom to which they are attached, form a 4-7 membered, saturated or partially saturated monocyclic heterocyclic ring, optionally containing a further heteroatom selected from N, O or S, and wherein said heterocyclic ring is optionally substituted with aryl, aryl-oxy-, $C_1$-$C_7$-alkyl, halo-$C_1$-$C_7$-alkyl or $C_1$-$C_7$-alkoxy, and said aryl is optionally substituted with halogen, $C_1$-$C_7$-alkyl, halo-$C_1$-$C_7$-alkyl or $C_1$-$C_7$-alkoxy.
or
(b) —C(O)—NR$^{5'}$R$^5$ or —C(O)—O—R$^5$, wherein
 $R^5$ and $R^{5'}$ are selected from hydrogen, $C_1$-$C_7$-alkyl; $C_3$-$C_{10}$-cycloalkyl; $C_1$-$C_7$-alkoxy; halo-$C_1$-$C_7$-alkyl aryl; aryl-$C_1$-$C_7$-alkyl-; aryl; heteroaryl; heteroaryl $C_1$-$C_7$-alkyl-; heterocyclyl; indane; or $R^5$ and $R^{5'}$ together with the nitrogen atom to which they are attached, form a 4-9 membered, saturated or partially saturated monocyclic or bicyclic heterocyclic ring, optionally containing a further heteroatom selected from N, O or S;
 wherein said $C_3$-$C_{10}$-cycloalkyl; aryl, heteroaryl, heterocyclyl and indane are optionally substituted with 1 to 3 substituents selected from $C_1$-$C_7$-alkyl, halo-$C_1$-$C_7$-alkyl, $C_1$-$C_7$-alkoxy, halo-$C_1$-$C_7$-alkyl-oxy-, halo-$C_1$-$C_7$-alkyl-oxy-$C_1$-$C_7$-alkyl, $C_1$-$C_7$-alkyl-oxy-$C_1$-$C_7$-alkyl and hydroxy-$C_1$-$C_7$-alkyl;
or
(c) —NR$^{6'}$R$^6$, wherein
 $R^6$ is selected from hydrogen, $C_1$-$C_7$-alkyl,
 $R^{6'}$ is selected from hydrogen, $C_1$-$C_7$-alkyl, $C_1$-$C_7$-alkyl carbonyl-; $C_3$-$C_{10}$-cycloalkyl;
 or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which monocyclic and bicyclic heterocyclic ring is unsubstituted or substituted by 1-3 substituents selected from
 $C_1$-$C_7$-alkyl-, halo-$C_1$-$C_7$-alkyl-, $C_1$-$C_7$-alkoxy-, halo-$C_1$-$C_7$-alkoxy-, halo-$C_1$-$C_7$-alkoxy-$C_1$-$C_7$-alkyl-, hydroxy- and $C_1$-$C_7$-alkoxy-carbonyl-;
(d) —NR$^{5'}$-C(O)—R$^5$, wherein
 $R^5$ is selected from hydrogen, $C_1$-$C_7$-alkyl; $C_3$-$C_{10}$-cycloalkyl; $C_1$-$C_7$-alkoxy; halo-$C_1$-$C_7$-alkyl; aryl; aryl-$C_1$-$C_7$-alkyl-; heteroaryl; heteroaryl-$C_1$-$C_7$-alkyl-; heterocyclyl; $R^{5'}$ is selected from hydrogen, $C_1$-$C_7$-alkyl;
m is 0-1; and
n is 0-2;

$R^8$ is hydrogen and $R^9$ is selected from hydrogen, $C_1$-$C_7$-alkoxy-$C_1$-$C_7$-alkyl-, $C_1$-$C_7$-alkyl, $C_1$-$C_7$-alkoxy and halo-$C_1$-$C_7$-alkyl;

wherein $C_1$-$C_7$-alkyl, $C_1$-$C_7$-alkoxy, heterocyclyl, aryl, heteroaryl are optionally substituted by aryl, heteroaryl, heterocyclyl, $C_1$-$C_7$-alkyl, $C_1$-$C_7$-alkoxy, halo-$C_1$-$C_7$-alkyl; OH; with the proviso that 6-[5-(2-furanyl)-1,2,4-oxadiazol-3-yl]-N2-methyl-N2-phenyl-1,3,5-triazine-2,4-diamine and 6-[5-(2-furanyl)-1,2,4-oxadiazol-3-yl]-N,N,N'-methyl-N'-phenyl-1,3,5-triazine-2,4-diamine are excluded.

6-[5-(2-Furanyl)-1,2,4-oxadiazol-3-yl]-N2-methyl-N2-phenyl-1,3,5-triazine-2,4-diamine, (CAS-899373-19-4) and 6-[5-(2-furanyl)-1,2,4-oxadiazol-3-yl]-N,N,N'-methyl-N'-phenyl-1,3,5-triazine-2,4-diamine (CAS-899373-21-8) are compounds from a chemical library.

In a further aspect, the invention relates to triazine-oxadiazoles of the formula (I) and/or pharmaceutically acceptable salts and/or solvates thereof,

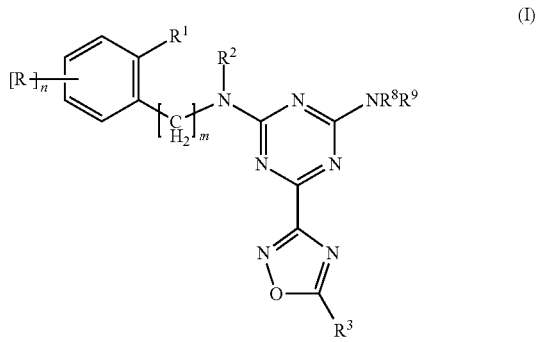

(I)

wherein
$R^1$ is selected from
hydrogen-
halogen-
$C_1$-$C_7$-alkyl-
halo-$C_1$-$C_7$-alkyl-;
$R^2$ is selected from
hydrogen-
$C_1$-$C_7$-alkyl-
halo-$C_2$-$C_7$-alkyl-
amino-$C_2$-$C_7$-alkyl-
N—$C_1$-$C_7$-alkyl-amino-$C_2$-$C_7$-alkyl-
N,N-di-$C_1$-$C_7$-alkyl-amino-$C_2$-$C_7$-alkyl-
hydroxy-$C_2$-$C_7$-alkyl-
$C_1$-$C_7$-alkoxy-$C_2$-$C_7$-alkyl-
$C_3$-$C_{10}$-cycloalkyl-$C_2$-$C_7$-alkyl-
cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
$C_1$-$C_7$-alkyl-
halo-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
hydroxy-$C_1$-$C_7$-alkyl-
$C_1$-$C_7$-alkoxy-$C_1$-$C_7$-alkyl-
$C_3$-$C_{10}$-cycloalkyl-$C_1$-$C_7$-alkyl-
cyano-$C_1$-$C_7$-alkyl-;

R is selected from
halogen-
$C_1$-$C_7$-alkyl-
halo-$C_1$-$C_7$-alkyl-
$C_1$-$C_7$-alkoxy-
cyano-
halo-$C_1$-$C_7$-alkoxy-
nitro;
$R^3$ is selected from
(a) -L-Y, wherein
-L- is selected from a direct bond; —(CH$_2$)$_p$—, —C(O)—, —NR$^7$—, —NR$^7$—C(O)— or —C(O)—NR$^7$—, wherein p is selected from 1, 2 or 3
$R^7$ is selected from hydrogen, $C_1$-$C_7$-alkyl
Y is selected from cycloalkyl, aryl, heteroaryl, heterocyclyl, which are unsubstituted or substituted by 1-3 substituents selected from
halogen-
$C_1$-$C_7$-alkyl-
halo-$C_1$-$C_7$-alkyl-
$C_1$-$C_7$-alkoxy-
$C_3$-$C_{10}$-cycloalkyl-oxy-
hydroxy-
halo-$C_1$-$C_7$-alkyl-oxy-
amino-
N—$C_1$-$C_7$-alkyl-amino-
N,N-di-$C_1$-$C_7$-alkyl-amino-
cyano-
$C_1$-$C_7$-alkoxy-carbonyl-
hydroxy-carbonyl-
—C(O)—NR$^{4'}$R$^4$, wherein
$R^4$ is selected from hydrogen, $C_1$-$C_7$-alkyl;
$R^{4'}$ is selected from hydrogen,
or $R^4$ and $R^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—NR$^{5'}$R$^5$ or —C(O)—O—R$^5$, wherein
$R^5$ and $R^{5'}$ are selected from hydrogen, $C_1$-$C_7$-alkyl;
or
(c) —NR$^{6'}$R$^6$, wherein
$R^6$ is selected from hydrogen, $C_1$-$C_7$-alkyl,
$R^{6'}$ is selected from hydrogen, $C_1$-$C_7$-alkyl, $C_1$-$C_7$-alkyl carbonyl-,
m is 0-1; and
n is 0-2;
with the proviso that 6-[5-(2-furanyl)-1,2,4-oxadiazol-3-yl]-N2-methyl-N2-phenyl-1,3,5-triazine-2,4-diamine is excluded.

6-[5-(2-Furanyl)-1,2,4-oxadiazol-3-yl]-N2-methyl-N2-phenyl-1,3,5-triazine-2,4-diamine, (CAS-899373-19-4) is a compound from a chemical library.

In a second aspect, the invention relates to the use of triazine-oxadiazoles of the formula (I) and/or pharmaceutically acceptable salts and/or solvates thereof, (I)

[Structure: a 1,3,5-triazine with substituents — phenyl group bearing $R^1$ and $[R]_n$ connected through $(CH_2)_m$ and $NR^2$ to triazine; triazine also bears $NR^8R^9$ and a 1,2,4-oxadiazole bearing $R^3$]

wherein
$R^1$ is selected from
   hydrogen-
   halogen-
   $C_1$-$C_7$-alkyl-
   halo-$C_1$-$C_7$-alkyl-;
$R^2$ is selected from
   hydrogen-
   $C_1$-$C_7$-alkyl-
   halo-$C_2$-$C_7$-alkyl-
   amino-$C_2$-$C_7$-alkyl-
   N—$C_1$-$C_7$-alkyl-amino-$C_2$-$C_7$-alkyl-
   N,N-di-$C_1$-$C_7$-alkyl-amino-$C_2$-$C_7$-alkyl-
   hydroxy-$C_2$-$C_7$-alkyl-
   $C_1$-$C_7$-alkoxy-$C_2$-$C_7$-alkyl-
   $C_3$-$C_{10}$-cycloalkyl-$C_1$-$C_7$-alkyl-
   cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
   $C_1$-$C_7$-alkyl-
   halo-$C_1$-$C_7$-alkyl-
   amino-$C_1$-$C_7$-alkyl-
   N—$C_1$-$C_7$-alkyl-amino-$C_1$-$C_7$-alkyl-
   N,N-di-$C_1$-$C_7$-alkyl-amino-$C_1$-$C_7$-alkyl-
   hydroxy-$C_1$-$C_7$-alkyl-
   $C_1$-$C_7$-alkoxy-$C_1$-$C_7$-alkyl-
   $C_3$-$C_{10}$-cycloalkyl-$C_1$-$C_7$-alkyl-
   cyano-$C_1$-$C_7$-alkyl-;
R is selected from
   halogen-
   $C_1$-$C_7$-alkyl-
   halo-$C_1$-$C_7$-alkyl-
   $C_1$-$C_7$-alkoxy-
   cyano-
   halo-$C_1$-$C_7$-alkoxy-
   nitro;
$R^3$ is selected from
(a) —$(CH_2)_p$—Y, wherein
   p is selected from 0, 1, 2 or 3, and
   Y is selected from aryl, heteroaryl, heterocyclyl, which are unsubstituted or substituted by 1-3 substituents selected from
     halogen-
     $C_1$-$C_7$-alkyl-
     halo-$C_1$-$C_7$-alkyl-
     $C_1$-$C_7$-alkoxy-
     $C_3$-$C_{10}$-cycloalkyl-oxy-
     hydroxy-
     halo-$C_1$-$C_7$-alkyl-oxy-
     amino-
     N—$C_1$-$C_7$-alkyl-amino-
     N,N-di-$C_1$-$C_7$-alkyl-amino-
     cyano-
     $C_1$-$C_7$-alkoxy-carbonyl-
     hydroxy-carbonyl-
     —C(O)—$NR^{4'}R^4$, wherein
        $R^4$ is selected from hydrogen, $C_1$-$C_7$-alkyl;
        $R^{4'}$ is selected from hydrogen,
        or $R^4$ and $R^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—$NR^{5'}R^5$ or —C(O)—O—$R^5$, wherein
   $R^5$ is selected from hydrogen, benzyl, indanyl, tetrahydrofuranyl, tetrahydropyranyl, oxiranyl, $C_3$-$C_{10}$-cycloalkyl, $C_1$-$C_7$-alkyl;
   $R^{5'}$ is selected from hydrogen, $C_1$-$C_7$-alkyl,
   or $R^5$ and $R^{5'}$ together with the nitrogen atom to which they are attached, form a 4-7 membered, saturated or partially saturated monocyclic or bicyclic heterocyclic ring, optionally containing a further heteroatom selected from N, O or S;
or
(c) —$NR^{6'}R^6$, wherein
   $R^6$ is selected from hydrogen, benzyl, $C_3$-$C_{10}$-cycloalkyl, $C_1$-$C_7$-alkyl,
   $R^{6'}$ is selected from hydrogen, $C_1$-$C_7$-alkyl, $C_1$-$C_7$-alkyl carbonyl-,
   or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from $C_1$-$C_7$-alkyl-
   hydroxy-
   $C_1$-$C_7$-alkoxy-carbonyl-
or
(d) —$NR^{5'}$-C(O)—$R^5$, wherein
   $R^5$ is selected from $C_3$-$C_{10}$-cycloalkyl;
   $R^{5'}$ is selected from hydrogen, $C_1$-$C_7$-alkyl;
m is 0-1; and
n is 0-1;
with the proviso that 6-[5-(2-furanyl)-1,2,4-oxadiazol-3-yl]-N2-methyl-N2-phenyl-1,3,5-triazine-2,4-diamine is excluded.

Wherever a compound or compounds of the formula (I) are mentioned, this is further also intended to include N-oxides of such compounds, tautomers thereof, and/or a (preferably pharmaceutically acceptable) salt thereof.

For purposes of interpreting this specification, the following definitions will apply and whenever appropriate, terms used in the singular will also include the plural and vice versa.

The term "halogen" is used herein to describe, unless otherwise stated, a group selected from fluoro (fluorine), chloro (chlorine), bromo (bromine) or iodo (iodine).

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms.

Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Typically, alkyl groups have 1-7, more preferably 1-4 carbons.

As used herein, the term "halo-alkyl" refers to an alkyl as defined herein, that is substituted by one or more halo groups as defined herein. The halo-alkyl can be mono-halo-alkyl, di-halo-alkyl or poly-halo-alkyl including per-halo-alkyl. A mono-halo-alkyl can have one iodo, bromo, chloro or fluoro within the alkyl group. Di-halo-alky and poly-halo-alkyl groups can have two or more of the same halo atoms or a combination of different halo groups within the alkyl. Typically the poly-halo-alkyl contains up to 12, or 10, or 8, or 6, or 4, or 3, or 2 halo groups. Non-limiting examples of halo-alkyl include fluoro-methyl, di-fluoro-methyl, tri-fluoro-methyl, chloro-methyl, di-chloro-methyl, tri-chloro-methyl, penta-fluoro-ethyl, hepta-fluoro-propyl, di-fluoro-chloro-methyl, di-chloro-fluoro-methyl, di-fluoro-ethyl, di-fluoro-propyl, di-chloro-ethyl and dichloro-propyl. A per-halo-alkyl refers to an alkyl having all hydrogen atoms replaced with halo atoms.

As used herein, the term "cycloalkyl" refers to saturated or partially unsaturated monocyclic, bicyclic or tricyclic hydrocarbon groups of 3-12 carbon atoms. Unless otherwise provided, cycloalkyl refers to cyclic hydrocarbon groups having between 3 and ring carbon atoms or between 3 and 7 ring carbon atoms. Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include octahydroindyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic hydrocarbon groups include adamantyl. As used herein, the term "cycloalkyl" preferably refers to cyclopropyl, cyclopentyl or, cyclohexyl.

As used herein, the term "$C_2$-$C_7$-alkenyl" refers to a linear or branched hydrocarbon group containing from 2 to 5 carbon atoms that contains at least one carbon to carbon double bond. Examples of such groups include ethenyl, propenyl, butenyl and pentenyl. Unless a particular structure is specified, the terms butenyl and pentenyl etc. include all possible E and Z isomers.

As used herein, the term "aryl" refers to 6-carbon monocyclic, 10-carbon bicyclic, 14-carbon tricyclic aromatic ring system. Examples of "aryl" are phenyl and naphthyl. As used herein, the term "aryl" preferably refers to phenyl.

As used herein, the term "heteroaryl" refers to a 4-, 5-, 6-, or 7-membered monocyclic, 7-, 8-, 9-, 10-, 11-, or 12-membered bicyclic or 10-, 11-, 12-, 13-, 14- or 15-membered tricyclic unsaturated ring or ring system—carrying the highest possible number of conjugated double bonds in the ring(s), which contain at least one heteroatom selected from N, O and S, wherein the N and S can also optionally be oxidized to various oxidation states. 'Heteroaryl' can be attached at a heteroatom or a carbon atom. 'Heteroaryl' can include fused or bridged rings as well as spirocyclic rings. Examples of heteroaryl include pyridyl, quinolinyl, isoquinolinyl, pyridazinyl, pyrimidinyl, pyrazinyl, quinoxalinyl, furanyl, benzofuranyl, dibenzofuranyl, thiophenyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl—such as 1,2,5-oxadiazolyl, 1,2,4-oxadiazolyl, 1,2,3-oxadiazolyl, 1,3,4-oxadiazolyl, thiadiazolyl—such as 1,2,5-thiadiazolyl, 1,2,4-thiadiazolyl, 1,2,3-thiadiazolyl, 1,3,4-thiadiazolyl, triazolyl—such as 1,2,3-triazolyl, 1,2,4-triazolyl, 1,2,5-triazolyl, triazinyl—such as 1,2,3-triazinyl, 1,2,4-triazinyl and 1,3,5-triazinyl, tetrazolyl. As used herein, the term "heteroaryl" preferably refers to furanyl, thiophenyl, pyridyl, thiazolyl, pyrazolyl, isoxazolyl, imidazolyl, pyrrolyl, benzofuranyl, pyrimidinyl, oxazolyl.

As used herein, the term "heterocyclyl" refers to a 4-, 5-, 6-, 7 or 8-membered monocyclic, 7-, 8-, 9-, 10-, 11-, or 12-membered bicyclic or 10-, 11-, 12-, 13-, 14- or 15-membered tricyclic saturated or partially unsaturated ring or ring system, which contain at least one heteroatom selected from N, O and S, wherein the N and S can also optionally be oxidized to various oxidation states. 'Heterocyclyl' can be attached at a heteroatom or a carbon atom. 'Heterocyclyl' can include fused or bridged rings as well as spirocyclic rings. Examples of heterocyclyl include dioxolanyl, imidazolinyl, imidazolidinyl, isothiazolidinyl, isoxazolidinyl, morpholinyl, oxazolidinyl, piperidinyl, piperazinyl, pyrrolidinyl, pyrazolidinyl, thiazolidinyl, tetrahydrofuranyl, trithianyl, tetrahydropyranyl, thiamorpholinyl as well as di-, tetra-, hexa-, octa- or deca-hydro derivatives of "heteroaryl". As used herein, the term "heterocyclyl" preferably refers to morpholinyl, piperidinyl, tetrahydrofuranyl, tetrahydropyranyl, pyrrolidinyl, dihydrobenzofuranyl. As used herein, the term "heterocyclyl" in the context of Y preferably refers to tetrahydrofuranyl, tetrahydropyranyl, dihydrobenzofuranyl.

As used herein, the term "heterocyclyl" in the context of a heterocyclic ring formed by $R^4$ and $R^{4'}$ together with the nitrogen atom to which they are attached or by $R^5$ and $R^{5'}$ together with the nitrogen atom to which they are attached or by $R^6$ and $R^{6'}$ together with the nitrogen atom to which they are attached, preferably refers to morpholinyl, piperidinyl, pyrrolidinyl.

As used herein, the term "spirocyclyl" refers to a "4 to 7 membered monocyclic heterocyclyl" as defined hereinbefore which is fused to a second 3 to 6 membered saturated ring via one single atom, and wherein the second ring contains 0, 1 or 2 heteroatoms independently selected from oxygen, nitrogen and sulphur.

As used herein, the term "oxy" refers to an —O— linking group.

The term "oxo" as used herein refers to a bivalent oxygen substituent, i.e. =O.

As used herein, all substituents are written in a way to show the order of functional groups (groups) they are composed of. The functional groups are defined herein above. The point of their attachment is indicated with a hyphen (-) or an equal sign (=), as appropriate.

In one embodiment, the invention provides a compound of the formula (I) and/or a pharmaceutically acceptable salt and/or a solvate thereof, wherein

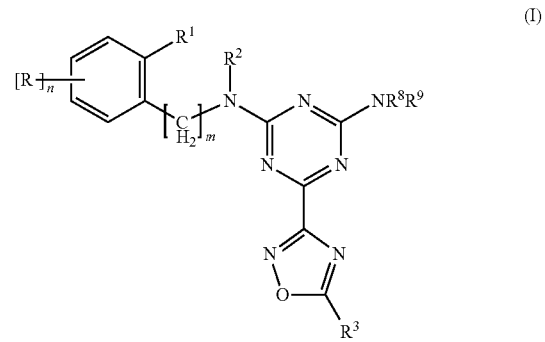

wherein
$R^1$ is selected from
  hydrogen-
  halogen-
  $C_1$-$C_7$-alkyl-
  halo-$C_1$-$C_7$-alkyl-;

R² is selected from
  hydrogen-
  $C_1$-$C_7$-alkyl-
  halo-$C_2$-$C_7$-alkyl-
  amino-$C_2$-$C_7$-alkyl-
  N—$C_1$-$C_7$-alkyl-amino-$C_2$-$C_7$-alkyl-
  N,N-di-$C_1$-$C_7$-alkyl-amino-$C_2$-$C_7$-alkyl-
  hydroxy-$C_2$-$C_7$-alkyl-
  $C_1$-$C_7$-alkoxy-$C_2$-$C_7$-alkyl-
  $C_3$-$C_{10}$-cycloalkyl-$C_1$-$C_7$-alkyl-
  cyano-$C_2$-$C_7$-alkyl-;
or
R¹ and R², together with the atoms to which they are attached, form a 4-7 membered, saturated or partially saturated heterocyclic ring, which is unsubstituted or substituted by 1-3 substituents selected from
  $C_1$-$C_7$-alkyl-
  halo-$C_1$-$C_7$-alkyl-
  amino-$C_1$-$C_7$-alkyl-
  N—$C_1$-$C_7$-alkyl-amino-$C_1$-$C_7$-alkyl-
  N,N-di-$C_1$-$C_7$-alkyl-amino-$C_1$-$C_7$-alkyl-
  hydroxy-$C_1$-$C_7$-alkyl-
  $C_1$-$C_7$-alkoxy-$C_1$-$C_7$-alkyl-
  $C_3$-$C_{10}$-cycloalkyl-$C_1$-$C_7$-alkyl-
  cyano-$C_1$-$C_7$-alkyl-;
R is selected from
  halogen-
  $C_1$-$C_7$-alkyl-
  halo-$C_1$-$C_7$-alkyl-
  $C_1$-$C_7$-alkoxy-
  cyano-
  halo-$C_1$-$C_7$-alkoxy-
  nitro;
R³ is selected from
(a) —$(CH_2)_p$—Y, wherein
  p is selected from 0, 1, 2 or 3, and
  Y is selected from aryl, heteroaryl, heterocyclyl, which are unsubstituted or substituted by 1-3 substituents selected from
    halogen-
    $C_1$-$C_7$-alkyl-
    halo-$C_1$-$C_7$-alkyl-
    $C_1$-$C_7$-alkoxy-
    $C_3$-$C_{10}$-cycloalkyl-oxy-
    hydroxy-
    halo-$C_1$-$C_7$-alkyl-oxy-
    amino-
    N—$C_1$-$C_7$-alkyl-amino-
    N,N-di-$C_1$-$C_7$-alkyl-amino-
    cyano-
    $C_1$-$C_7$-alkoxy-carbonyl-
    hydroxy-carbonyl-
    —C(O)—$NR^4R^{4'}$, wherein
      R⁴ is selected from hydrogen, $C_1$-$C_7$-alkyl;
      R⁴' is selected from hydrogen,
      or R⁴ and R⁴' together with the nitrogen atom to which they are attached, form a 4-7 membered, saturated or partially saturated monocyclic heterocyclic ring, optionally containing a further heteroatom selected from N, O or S;
or
(b) —C(O)—$NR^{5'}R^5$ or —C(O)—O—R⁵, wherein
  R⁵ is selected from hydrogen, benzyl, indanyl, tetrahydrofuranyl, tetrahydropyranyl, oxiranyl, $C_3$-$C_{10}$-cycloalkyl, $C_1$-$C_7$-alkyl;
  R⁵' is selected from hydrogen, $C_1$-$C_7$-alkyl,
  or R⁵ and R⁵' together with the nitrogen atom to which they are attached, form a 4-7 membered, saturated or partially saturated monocyclic or bicyclic heterocyclic ring, optionally containing a further heteroatom selected from N, O or S;
or
(c) —$NR^{6'}R^6$, wherein
  R⁶ is selected from hydrogen, benzyl, $C_3$-$C_{10}$-cycloalkyl, $C_1$-$C_7$-alkyl,
  R⁶' is selected from hydrogen, $C_1$-$C_7$-alkyl, $C_1$-$C_7$-alkyl carbonyl-,
  or R⁶ and R⁶' together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from
    $C_1$-$C_7$-alkyl-
    hydroxy-
    $C_1$-$C_7$-alkoxy-carbonyl-
or
(d) —$NR^{5'}$-C(O)—R⁵, wherein
  R⁵ is selected from $C_3$-$C_{10}$-cycloalkyl;
  R⁵' is selected from hydrogen, $C_1$-$C_7$-alkyl;
m is 0-1; and
n is 0-1;
with the proviso that 6-[5-(2-furanyl)-1,2,4-oxadiazol-3-yl]-N2-methyl-N2-phenyl-1,3,5-triazine-2,4-diamine is excluded.

6-[5-(2-Furanyl)-1,2,4-oxadiazol-3-yl]-N2-methyl-N2-phenyl-1,3,5-triazine-2,4-diamine, (CAS-899373-19-4) is a compound from a chemical library.

In another embodiment, the invention provides a compound of the formula (I) and/or a pharmaceutically acceptable salt and/or a solvate thereof, wherein
R¹ is selected from
  hydrogen-
  halogen-
  $C_1$-$C_4$-alkyl-
  halo-$C_1$-$C_4$-alkyl-.

In another embodiment, the invention provides a compound of the formula (I) and/or a pharmaceutically acceptable salt and/or a solvate thereof, wherein
R¹ is selected from
  hydrogen-
  chloro-
  fluoro-
  methyl-.

In another embodiment, the invention provides a compound of the formula (I) and/or a pharmaceutically acceptable salt and/or a solvate thereof, wherein
R¹ is selected from
  hydrogen-
  fluoro-.

In another embodiment, the invention provides a compound of the formula (I) and/or a pharmaceutically acceptable salt and/or a solvate thereof, wherein
R² is selected from
  hydrogen-
  $C_1$-$C_4$-alkyl-
  halo-$C_2$-$C_4$-alkyl-
  N,N-di-$C_1$-$C_2$-alkyl-amino-$C_2$-$C_4$-alkyl-
  hydroxy-$C_2$-$C_4$-alkyl-
  $C_1$-$C_2$-alkoxy-$C_2$-$C_4$-alkyl-
  $C_3$-$C_6$-cycloalkyl-$C_1$-$C_7$-alkyl-.

In another embodiment, the invention provides a compound of the formula (I) and/or a pharmaceutically acceptable salt and/or a solvate thereof, wherein
$R^2$ is selected from
 hydrogen-
 methyl-
 ethyl-
 isopropyl-
 2,2,2-trifluoro-ethyl-
 N,N-di-methyl-amino-ethyl-
 hydroxy-ethyl-
 methoxy-ethyl-
 cyclopropyl-methyl-.

In another embodiment, the invention provides a compound of the formula (I) and/or a pharmaceutically acceptable salt and/or a solvate thereof, wherein
$R^2$ is selected from
 hydrogen-
 methyl-
 ethyl-
 2,2,2-trifluoro-ethyl-.

In another embodiment, the invention provides a compound of the formula (I) and/or a pharmaceutically acceptable salt and/or a solvate thereof, wherein
$R^1$ and $R^2$, together are selected from
 —CH$_2$—CH$_2$—, —CH$_2$—CH$_2$—CH$_2$—, —CH═CH—, —CH═CH—CH$_2$— or —CH$_2$—CH═CH—.

In another embodiment, the invention provides a compound of the formula (I) and/or a pharmaceutically acceptable salt and/or a solvate thereof, wherein
$R^1$ and $R^2$, together are selected from
 —CH$_2$—CH$_2$— or —CH$_2$—CH$_2$—CH$_2$—.

In another embodiment, the invention provides a compound of the formula (I) and/or a pharmaceutically acceptable salt and/or a solvate thereof, wherein
$R^1$ is selected from
 hydrogen-
 chloro-
 fluoro-
 methyl-;
$R^2$ is selected from
 hydrogen-
 $C_1$-$C_4$-alkyl-
 halo-$C_2$-$C_4$-alkyl-
 N,N-di-$C_1$-$C_2$-alkyl-amino-$C_2$-$C_4$-alkyl-
 hydroxy-$C_2$-$C_4$-alkyl-
 $C_1$-$C_2$-alkoxy-$C_2$-$C_4$-alkyl-
 $C_3$-$C_6$-cycloalkyl-$C_1$-$C_7$-alkyl-.

In another embodiment, the invention provides a compound of the formula (I) and/or a pharmaceutically acceptable salt and/or a solvate thereof, wherein
R is selected from
 halogen-
 $C_1$-$C_4$-alkyl-
 halo-$C_1$-$C_4$-alkyl-
 $C_1$-$C_4$-alkoxy-
 cyano-.

In another embodiment, the invention provides a compound of the formula (I) and/or a pharmaceutically acceptable salt and/or a solvate thereof, wherein
R is selected from
 chloro-
 fluoro-
 methyl-
 trifluoromethyl-
 methoxy-
 cyano-.

In another embodiment, the invention provides a compound of the formula (I) and/or a pharmaceutically acceptable salt and/or a solvate thereof, wherein
$R^3$ is selected from
 —(CH$_2$)$_p$—Y, wherein
  p is selected from 0, 1, 2 or 3, and
  Y is selected from aryl, heteroaryl, heterocyclyl, which are unsubstituted or substituted by 1-3 substituents selected from
   halogen-
   $C_1$-$C_7$-alkyl-
   halo-$C_1$-$C_7$-alkyl-
   $C_1$-$C_7$-alkoxy-
   $C_3$-$C_{10}$-cycloalkyl-oxy-
   hydroxy-
   halo-$C_1$-$C_7$-alkyl-oxy-
   amino-
   N—$C_1$-$C_7$-alkyl-amino-
   N,N-di-$C_1$-$C_7$-alkyl-amino-
   cyano-
   $C_1$-$C_7$-alkoxy-carbonyl-
   hydroxy-carbonyl-
   —C(O)—NR$^4$R$^{4'}$, wherein
    $R^4$ is selected from hydrogen, $C_1$-$C_7$-alkyl;
    $R^{4'}$ is selected from hydrogen,
    or $R^4$ and $R^{4'}$ together with the nitrogen atom to which they are attached, form a 4-7 membered, saturated or partially saturated monocyclic heterocyclic ring, optionally containing a further heteroatom selected from N, O or S.

In another embodiment, the invention provides a compound of the formula (I) and/or a pharmaceutically acceptable salt and/or a solvate thereof, wherein
$R^3$ is selected from
 —Y, wherein
  Y is selected from aryl, heteroaryl, heterocyclyl, which are unsubstituted or substituted by 1-2 substituents selected from
   halogen-
   $C_1$-$C_4$-alkyl-
   halo-$C_1$-$C_4$-alkyl-
   $C_1$-$C_4$-alkoxy-
   $C_3$-$C_7$-cycloalkyl-oxy-
   hydroxy-
   halo-$C_1$-$C_4$-alkyl-oxy-
   amino-
   cyano-
   $C_1$-$C_4$-alkoxy-carbonyl-
   hydroxy-carbonyl-
   —C(O)—NR$^4$R$^{4'}$, wherein
    $R^4$ is selected from hydrogen, $C_1$-$C_4$-alkyl;
    $R^{4'}$ is selected from hydrogen,
    or $R^4$ and $R^{4'}$ together with the nitrogen atom to which they are attached, form a 4-7 membered, saturated or partially saturated monocyclic heterocyclic ring, optionally containing a further heteroatom selected from N, O or S.

In another embodiment, the invention provides a compound of the formula (I) and/or a pharmaceutically acceptable salt and/or a solvate thereof, wherein
$R^3$ is selected from
 phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from halogen-
C$_1$-C$_4$-alkyl-
halo-C$_1$-C$_4$-alkyl-
C$_1$-C$_4$-alkoxy-
C$_3$-C$_7$-cycloalkyl-oxy-
hydroxy-
halo-C$_1$-C$_4$-alkyl-oxy-
amino-
cyano-
C$_1$-C$_4$-alkoxy-carbonyl-
—C(O)—NR$^{4'}$R$^4$, wherein
R$^4$ is selected from hydrogen, C$_1$-C$_4$-alkyl;
R$^{4'}$ is selected from hydrogen,
or R$^4$ and R$^{4'}$ together with the nitrogen atom to which they are attached, form morpholinyl, piperidinyl, pyrrolidinyl.

In another embodiment, the invention provides a compound of the formula (I) and/or a pharmaceutically acceptable salt and/or a solvate thereof, wherein
R$^3$ is selected from
phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
chloro-
bromo-
fluoro-
methyl-
trifluoromethyl-
2,2,2-trifluoro-ethyl-
methoxy-
cyclopentyl-oxy-
trifluoromethyl-oxy-
2,2,2-trifluoro-ethyl-oxy-
amino-
cyano-
methoxy-carbonyl-
—C(O)—NR$^{4'}$R$^4$, wherein
R$^4$ is selected from hydrogen, methyl;
R$^{4'}$ is selected from hydrogen,
or R$^4$ and R$^{4'}$ together with the nitrogen atom to which they are attached, form morpholinyl, piperidinyl, pyrrolidinyl.

In another embodiment, the invention provides a compound of the formula (I) and/or a pharmaceutically acceptable salt and/or a solvate thereof, wherein
R$^3$ is selected from
—C(O)—NR$^1$R$^5$ or —C(O)—O—R$^5$, wherein
R$^5$ is selected from hydrogen, benzyl, indanyl, tetrahydrofuranyl, tetrahydropyranyl, oxiranyl, C$_3$-C$_{10}$-cycloalkyl, C$_1$-C$_7$-alkyl;
R$^{5'}$ is selected from hydrogen, C$_1$-C$_7$-alkyl,
or R$^5$ and R$^{5'}$ together with the nitrogen atom to which they are attached, form a 4-7 membered, saturated or partially saturated monocyclic or bicyclic heterocyclic ring, optionally containing a further heteroatom selected from N, O or S.

In another embodiment, the invention provides a compound of the formula (I) and/or a pharmaceutically acceptable salt and/or a solvate thereof, wherein
R$^3$ is selected from
—NR$^{6'}$R$^6$, wherein
R$^6$ is selected from hydrogen, benzyl, C$_3$-C$_{10}$-cycloalkyl, C$_1$-C$_7$-alkyl,
R$^{6'}$ is selected from hydrogen, C$_1$-C$_7$-alkyl, C$_1$-C$_7$-alkyl carbonyl-,
or R$^6$ and R$^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from
C$_1$-C$_7$-alkyl-
hydroxy-
C$_1$-C$_7$-alkoxy-carbonyl- In another embodiment, the invention provides a compound of the formula (I) and/or a pharmaceutically acceptable salt and/or a solvate thereof, wherein
R$^3$ is selected from
—NR$^{5'}$-C(O)—R$^5$, wherein
R$^5$ is selected from C$_3$-C$_{10}$-cycloalkyl;
R$^{5'}$ is selected from hydrogen, C$_1$-C$_7$-alkyl.

In another embodiment, the invention provides a compound of the formula (I) and/or a pharmaceutically acceptable salt and/or a solvate thereof, wherein
wherein
m is 0.

In another embodiment, the invention provides a compound of the formula (I) and/or a pharmaceutically acceptable salt and/or a solvate thereof, wherein
R$^1$ is selected from
hydrogen-
fluoro-;
R$^2$ is selected from
hydrogen-
C$_1$-C$_4$-alkyl-
halo-C$_2$-C$_4$-alkyl-
N,N-di-C$_1$-C$_2$-alkyl-amino-C$_2$-C$_4$-alkyl-
hydroxy-C$_2$-C$_4$-alkyl-
C$_1$-C$_2$-alkoxy-C$_2$-C$_4$-alkyl-
C$_3$-C$_6$-cycloalkyl-C$_1$-C$_7$-alkyl-;
or
R$^1$ and R$^2$, together are selected from
—CH$_2$—CH$_2$— or —CH$_2$—CH$_2$—CH$_2$—;
R is selected from
halogen-
C$_1$-C$_4$-alkyl-
halo-C$_1$-C$_4$-alkyl-
C$_1$-C$_4$-alkoxy-
cyano-; and
R$^3$ is selected from
—(CH$_2$)$_p$—Y, wherein
p is selected from 0, 1, 2 or 3, and
Y is selected from aryl, heteroaryl, heterocyclyl, which are unsubstituted or substituted
by 1-3 substituents selected from
halogen-
C$_1$-C$_7$-alkyl-
halo-C$_1$-C$_7$-alkyl-
C$_1$-C$_7$-alkoxy-
C$_3$-C$_{10}$-cycloalkyl-oxy-
hydroxy-
halo-C$_1$-C$_7$-alkyl-oxy-
amino-
N—C$_1$-C$_7$-alkyl-amino-
N,N-di-C$_1$-C$_7$-alkyl-amino-
cyano-
C$_1$-C$_7$-alkoxy-carbonyl-
—C(O)—NR$^{4'}$R$^4$, wherein
R$^4$ is selected from hydrogen, C$_1$-C$_7$-alkyl;
R$^{4'}$ is selected from hydrogen, or R⁴ and R⁴' together with the nitrogen atom to which they are attached, form a 4-7 membered, saturated or partially saturated monocyclic heterocyclic ring, optionally containing a further heteroatom selected from N, O or S, m is 0; and
n is 0-1.

In another embodiment, the invention provides a compound of the formula (I) and/or a pharmaceutically acceptable salt and/or a solvate thereof, wherein $R^1$ is selected from
  hydrogen-
  fluoro-;
$R^2$ is selected from
  hydrogen-
  $C_1$-$C_4$-alkyl-
  halo-$C_2$-$C_4$-alkyl-
  N,N-di-$C_1$-$C_2$-alkyl-amino-$C_2$-$C_4$-alkyl-
  hydroxy-$C_2$-$C_4$-alkyl-
  $C_1$-$C_2$-alkoxy-$C_2$-$C_4$-alkyl-
  $C_3$-$C_6$-cycloalkyl-$C_1$-$C_7$-alkyl-;
  or
$R^1$ and $R^2$, together are selected from
  —CH₂—CH₂— or —CH₂—CH₂—CH₂—;
R is selected from
  halogen-
  $C_1$-$C_4$-alkyl-
  halo-$C_1$-$C_4$-alkyl-
  $C_1$-$C_4$-alkoxy-
  cyano-; and
$R^3$ is selected from
  phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
    halogen-
    $C_1$-$C_4$-alkyl-
    halo-$C_1$-$C_4$-alkyl-
    $C_1$-$C_4$-alkoxy-
    $C_3$-$C_7$-cycloalkyl-oxy-
    hydroxy-
    halo-$C_1$-$C_4$-alkyl-oxy-
    amino-
    cyano-
    $C_1$-$C_4$-alkoxy-carbonyl-
    —C(O)—NR⁴'R⁴, wherein
      R⁴ is selected from hydrogen, $C_1$-$C_4$-alkyl;
      R⁴' is selected from hydrogen,
      or R⁴ and R⁴' together with the nitrogen atom to which they are attached, form morpholinyl, piperidinyl, pyrrolidinyl, m is 0; and
n is 0-1.

In another embodiment the invention provides a compound of the formula (I) is selected from 6-(5-Furan-2-yl-[1,2,4]oxadiazol-3-yl)-N-methyl-N-phenyl-[1,3,5]triazine-2,4-diamine,
6-(5-Furan-2-yl-[1,2,4]oxadiazol-3-yl)-N-phenyl-[1,3,5]triazine-2,4-diamine,
6-(5-Furan-2-yl-[1,2,4]oxadiazol-3-yl)-N-methyl-N-(3-methylphenyl)-[1,3,5]triazine-2,4-diamine,
6-(5-Furan-2-yl-[1,2,4]oxadiazol-3-yl)-N-methyl-N-(4-methylphenyl)-[1,3,5]triazine-2,4-diamine,
6-(5-Furan-2-yl-[1,2,4]oxadiazol-3-yl)-N-methyl-N-(3-methoxyphenyl)-[1,3,5]triazine-2,4-diamine,
6-(5-Furan-2-yl-[1,2,4]oxadiazol-3-yl)-N-methyl-N-(4-methoxyphenyl)-[1,3,5]triazine-2,4-diamine,
6-(5-Furan-2-yl-[1,2,4]oxadiazol-3-yl)-N-methyl-N-(3-chlorophenyl)-[1,3,5]triazine-2,4-diamine,
6-(5-Furan-2-yl-[1,2,4]oxadiazol-3-yl)-N-methyl-N-(4-chlorophenyl)-[1,3,5]triazine-2,4-diamine,
N-Methyl-N-phenyl-6-(5-pyridin-2-yl-[1,2,4]oxadiazol-3-yl)-[1,3,5]triazine-2,4-diamine,
N-Methyl-N-phenyl-6-(5-phenyl-[1,2,4]oxadiazol-3-yl)-[1,3,5]triazine-2,4-diamine,
N-Methyl-N-phenyl-6-(5-thiophen-2-yl-[1,2,4]oxadiazol-3-yl)-[1,3,5]triazine-2,4-diamine,
N-Methyl-6-[5-(5-chloro-thiophen-2-yl)-[1,2,4]oxadiazol-3-yl]-N-phenyl-[1,3,5]triazine-2,4-diamine,
6-[5-(6-Cyclopentoxy-pyridin-3-yl)-[1,2,4]oxadiazol-3-yl]-N-methyl-N-phenyl-[1,3,5]triazine-2,4-diamine,
N-(2-Fluoro-phenyl)-6-(5-furan-2-yl-[1,2,4]oxadiazol-3-yl)-N-methyl-[1,3,5]triazine-2,4-diamine,
N-(3-Fluoro-phenyl)-6-(5-furan-2-yl-[1,2,4]oxadiazol-3-yl)-N-methyl-[1,3,5]triazine-2,4-diamine,
N-(4-Fluoro-phenyl)-6-(5-furan-2-yl-[1,2,4]oxadiazol-3-yl)-N-methyl-[1,3,5]triazine-2,4-diamine,
N-(2-Chloro-phenyl)-6-(5-furan-2-yl-[1,2,4]oxadiazol-3-yl)-N-methyl-[1,3,5]triazine-2,4-diamine,
6-(5-Furan-2-yl-[1,2,4]oxadiazol-3-yl)-N-methyl-N-o-tolyl-[1,3,5]triazine-2,4-diamine,
N-Methyl-6-[5-(5-methyl-furan-2-yl)-[1,2,4]oxadiazol-3-yl]-N-phenyl-[1,3,5]triazine-2,4-diamine,
N-Benzyl-6-(5-furan-2-yl-[1,2,4]oxadiazol-3-yl)-N-methyl-[1,3,5]triazine-2,4-diamine,
N-Ethyl-6-(5-furan-2-yl-[1,2,4]oxadiazol-3-yl)-N-phenyl-[1,3,5]triazine-2,4-diamine,
4-(2,3-Dihydro-indol-1-yl)-6-(5-furan-2-yl-[1,2,4]oxadiazol-3-yl)-[1,3,5]triazin-2-ylamine,
6-[5-(2-Chloro-phenyl)-[1,2,4]oxadiazol-3-yl]-N-methyl-N-phenyl-[1,3,5]triazine-2,4-diamine,
6-[5-(3-Methoxy-phenyl)-[1,2,4]oxadiazol-3-yl]-N-methyl-N-phenyl-[1,3,5]triazine-2,4-diamine,
6-[5-(2-Methoxy-phenyl)-[1,2,4]oxadiazol-3-yl]-N-methyl-N-phenyl-[1,3,5]triazine-2,4-diamine,
6-[5-(4-Methoxy-phenyl)-[1,2,4]oxadiazol-3-yl]-N-methyl-N-phenyl-[1,3,5]triazine-2,4-diamine,
N-Methyl-N-phenyl-6-(5-o-tolyl-[1,2,4]oxadiazol-3-yl)-[1,3,5]triazine-2,4-diamine,
N-Methyl-N-phenyl-6-(5-m-tolyl-[1,2,4]oxadiazol-3-yl)-[1,3,5]triazine-2,4-diamine,
N-Methyl-N-phenyl-6-(5-p-tolyl-[1,2,4]oxadiazol-3-yl)-[1,3,5]triazine-2,4-diamine,
6-(5-Furan-2-yl-[1,2,4]oxadiazol-3-yl)-N-isopropyl-N-phenyl-[1,3,5]triazine-2,4-diamine,
6-(5-Benzyl-[1,2,4]oxadiazol-3-yl)-N-methyl-N-phenyl-[1,3,5]triazine-2,4-diamine,
N-(3-Chloro-phenyl)-6-(5-furan-2-yl-[1,2,4]oxadiazol-3-yl)-[1,3,5]triazine-2,4-diamine,
N-(3-Chloro-phenyl)-6-(5-furan-2-yl-[1,2,4]oxadiazol-3-yl)-[1,3,5]triazine-2,4-diamine,
6-(5-Furan-2-yl-[1,2,4]oxadiazol-3-yl)-N-methyl-N-(2,3-difluorophenyl)-[1,3,5]triazine-2,4-diamine,
6-[5-(3-Chloro-phenyl)-[1,2,4]oxadiazol-3-yl]-N-methyl-N-phenyl-[1,3,5]triazine-2,4-diamine,
6-[5-(4-Chloro-phenyl)-[1,2,4]oxadiazol-3-yl]-N-methyl-N-phenyl-[1,3,5]triazine-2,4-diamine,
6-(5-Furan-3-yl-[1,2,4]oxadiazol-3-yl)-N-methyl-N-phenyl-[1,3,5]triazine-2,4-diamine,
N-Ethyl-N-phenyl-6-(5-thiazol-2-yl-[1,2,4]oxadiazol-3-yl)-[1,3,5]triazine-2,4-diamine, N-Phenyl-6-(pyridin-2-yl-[1,2,4]oxadiazol-3-yl)-[1,3,5]triazine-2,4-diamine,
N-Phenyl-6-[5-(1H-pyrazol-3-yl)-[1,2,4]oxadiazol-3-yl]-[1,3,5]triazine-2,4-diamine,
N-Phenyl-6-{5-[6-(2,2,2-trifluoro-ethoxy)-pyridin-3-yl]-[1,2,4]oxadiazol-3-yl}-[1,3,5]triazine-2,4-diamine,
N-Methyl-N-phenyl-6-{5-[3-(2,2,2-trifluoro-ethoxy)-pyridin-2-yl]-[1,2,4]oxadiazol-3-yl}-[1,3,5]triazine-2,4-diamine,
6-[5-(3-Bromopyridin-2-yl)-[1,2,4]oxadiazol-3-yl]-N-methyl-N-phenyl-[1,3,5]triazine-2,4-diamine,
N-Methyl-6-[5-(5-methyl-isoxazol-3-yl)-[1,2,4]oxadiazol-3-yl]-N-phenyl-[1,3,5]triazine-2,4-diamine,
N-Methyl-6-(5-morpholin-4-yl-[1,2,4]oxadiazol-3-yl)-N-phenyl-[1,3,5]triazine-2,4-diamine,
N-Methyl-N-phenyl-6-(5-piperidin-1-yl-[1,2,4]oxadiazol-3-yl)-[1,3,5]triazine-2,4-diamine,
6-[5-(6-Methoxy-pyridin-3-yl)-[1,2,4]oxadiazol-3-yl]-N-methyl-N-phenyl-[1,3,5]triazine-2,4-diamine,
6-[5-(6-Methoxy-pyridin-3-yl)-[1,2,4]oxadiazol-3-yl]-N-methyl-N-phenyl-[1,3,5]triazine-2,4-diamine,
6-[5-(4,5-Dimethyl-furan-2-yl)-[1,2,4]oxadiazol-3-yl]-N-methyl-N-phenyl-[1,3,5]triazine-2,4-diamine,
6-[5-(3-Amino-pyridin-2-yl)-[1,2,4]oxadiazol-3-yl]-N-methyl-N-phenyl-[1,3,5]triazine-2,4-diamine,
6-[5-(3-Amino-pyridin-2-yl)-[1,2,4]oxadiazol-3-yl]-N-methyl-N-phenyl-[1,3,5]triazine-2,4-diamine,
N-Methyl-N-phenyl-6-(5-thiazol-5-yl-[1,2,4]oxadiazol-3-yl)-[1,3,5]triazine-2,4-diamine,
6-[5-(2-Amino-pyridin-3-yl)-[1,2,4]oxadiazol-3-yl]-N-methyl-N-phenyl-[1,3,5]triazine-2,4-diamine,
6-[5-(5-Amino-pyridin-3-yl)-[1,2,4]oxadiazol-3-yl]-N-methyl-N-phenyl-[1,3,5]triazine-2,4-diamine,
6-[5-(6-Amino-pyridin-3-yl)-[1,2,4]oxadiazol-3-yl]-N-methyl-N-phenyl-[1,3,5]triazine-2,4-diamine,
N-Methyl-N-phenyl-6-[5-(tetrahydro-pyran-2-yl)-[1,2,4]oxadiazol-3-yl]-[1,3,5]triazine-2,4-diamine,
N-Methyl-N-phenyl-6-[5-(tetrahydro-pyran-4-yl)-[1,2,4]oxadiazol-3-yl]-[1,3,5]triazine-2,4-diamine,
N-Methyl-6-[5-(5-methyl-1H-pyrazol-3-yl)-[1,2,4]oxadiazol-3-yl]-N-phenyl-[1,3,5]triazine-2,4-diamine,
6-[5-(1H-Imidazol-4-yl)-[1,2,4]oxadiazol-3-yl]-N-methyl-N-phenyl-[1,3,5]triazine-2,4-diamine,
N-Methyl-N-phenyl-6-[5-(1H-pyrrol-2-yl)-[1,2,4]oxadiazol-3-yl]-[1,3,5]triazine-2,4-diamine,
N-Methyl-N-phenyl-6-[5-(2H-pyrazol-3-yl)-[1,2,4]oxadiazol-3-yl]-[1,3,5]triazine-2,4-diamine,
N-Methyl-6-[5-(5-methyl-thiophen-2-yl)-[1,2,4]oxadiazol-3-yl]-N-phenyl-[1,3,5]triazine-2,4-diamine,
6-[5-(2,3-Dihydro-benzofuran-7-yl)-[1,2,4]oxadiazol-3-yl]-N-methyl-N-phenyl-[1,3,5]triazine-2,4-diamine,
6-(5-Benzofuran-2-yl-[1,2,4]oxadiazol-3-yl)-N-methyl-N-phenyl-[1,3,5]triazine-2,4-diamine,
6-(5-Imidazol-2-yl-[1,2,4]oxadiazol-3-yl)-N-methyl-N-phenyl-[1,3,5]triazine-2,4-diamine,
N-Methyl-N-phenyl-6-[5-(tetrahydro-furan-2-yl)-[1,2,4]oxadiazol-3-yl]-[1,3,5]triazine-2,4-diamine,
N-Methyl-N-phenyl-6-{5-[6-(2,2,2-trifluoroethoxy)-pyridin-3-yl]-[1,2,4]oxadiazol-3-yl}-[1,3,5]triazine-2,4-diamine,
6-(5-Furan-2-yl-[1,2,4]oxadiazol-3-yl)-N-phenyl-N-(2,2,2-trifluoro-ethyl)-[1,3,5]triazine-2,4-diamine,
N-(2-Dimethylamino-ethyl)-6-(5-furan-2-yl-[1,2,4]oxadiazol-3-yl)-N-phenyl-[1,3,5]triazine-2,4-diamine,
2-{[4-Amino-6-(5-furan-2-yl-[1,2,4]oxadiazol-3-yl)-[1,3,5]triazin-2-yl]-phenyl-amino}-ethanol,
3-[4-Amino-6-(methyl-phenyl-amino)-[1,3,5]triazin-2-yl]-[1,2,4]oxadiazole-5-carboxylic acid benzylamide,
3-[4-Amino-6-(methyl-phenyl-amino)-[1,3,5]triazin-2-yl]-[1,2,4]oxadiazole-5-carboxylic acid cyclopentylamide,
3-[4-Amino-6-(methyl-phenyl-amino)-[1,3,5]triazin-2-yl]-[1,2,4]oxadiazole-5-carboxylic acid ethyl ester,
6-[5-(3-Methoxy-thiophen-2-yl)-[1,2,4]oxadiazol-3-yl]-N-methyl-N-phenyl-[1,3,5]triazine-2,4-diamine,
5-{3-[4-Amino-6-(methyl-phenyl-amino)-[1,3,5]triazin-2-yl]-[1,2,4]oxadiazol-5-yl}-thiophene-2-carboxylic acid methylamide,
6-[5-(2-Methoxy-pyridin-3-yl)-[1,2,4]oxadiazol-3-yl]-N-methyl-N-phenyl-[1,3,5]triazine-2,4-diamine,
6-[5-(2,4-Dimethoxy-phenyl)-[1,2,4]oxadiazol-3-yl]-N-methyl-N-phenyl-[1,3,5]triazine-2,4-diamine,
5-{3-[4-Amino-6-(methyl-phenyl-amino)-[1,3,5]triazin-2-yl]-[1,2,4]oxadiazol-5-yl}-pyridine-2-carbonitrile,
(5-{3-[4-Amino-6-(methyl-phenyl-amino)-[1,3,5]triazin-2-yl]-[1,2,4]oxadiazol-5-yl}-thiophen-2-yl)-morpholin-4-yl-methanone,
2-{3-[4-Amino-6-(methyl-phenyl-amino)-[1,3,5]triazin-2-yl]-[1,2,4]oxadiazol-5-yl}-benzonitrile,
6-[5-(2-Fluoro-6-methoxy-phenyl)-[1,2,4]oxadiazol-3-yl]-N-methyl-N-phenyl-[1,3,5]triazine-2,4-diamine,
5-{3-[4-Amino-6-(methyl-phenyl-amino)-[1,3,5]triazin-2-yl]-[1,2,4]oxadiazol-5-yl}-thiophene-2-carboxylic acid methyl ester,
N-(3-Chloro-phenyl)-6-[5-(3-methoxy-phenyl)-[1,2,4]oxadiazol-3-yl]-N-methyl-[1,3,5]triazine-2,4-diamine,
N-(3-Chloro-phenyl)-6-[5-(2-chloro-phenyl)-[1,2,4]oxadiazol-3-yl]-N-methyl-[1,3,5]triazine-2,4-diamine,
N-(3-Fluoro-phenyl)-6-[5-(3-methoxy-phenyl)-[1,2,4]oxadiazol-3-yl]-N-methyl-[1,3,5]triazine-2,4-diamine,
6-[5-(2-Chloro-phenyl)-[1,2,4]oxadiazol-3-yl]-N-(3-fluoro-phenyl)-N-methyl-[1,3,5]triazine-2,4-diamine,
N-(3-Fluoro-phenyl)-N-methyl-6-[5-(5-methyl-furan-2-yl)-[1,2,4]oxadiazol-3-yl]-[1,3,5]triazine-2,4-diamine,
N-(2-Fluoro-phenyl)-6-[5-(3-methoxy-phenyl)-[1,2,4]oxadiazol-3-yl]-N-methyl-[1,3,5]triazine-2,4-diamine,
N-(2-Fluoro-phenyl)-6-[5-(2-methoxy-phenyl)-[1,2,4]oxadiazol-3-yl]-N-methyl-[1,3,5]triazine-2,4-diamine,
N-(2-Fluoro-phenyl)-N-methyl-6-(5-thiophen-2-yl-[1,2,4]oxadiazol-3-yl)-[1,3,5]triazine-2,4-diamine,
N-(2-Fluoro-phenyl)-N-methyl-6-[5-(5-methyl-furan-2-yl)-[1,2,4]oxadiazol-3-yl]-[1,3,5]triazine-2,4-diamine,
6-[5-(2-Methoxy-phenyl)-[1,2,4]oxadiazol-3-yl]-N-methyl-N-m-tolyl-[1,3,5]triazine-2,4-diamine,
N-Methyl-6-(5-thiophen-2-yl-[1,2,4]oxadiazol-3-yl)-N-m-tolyl-[1,3,5]triazine-2,4-diamine,
N-Ethyl-6-[5-(3-methoxy-phenyl)-[1,2,4]oxadiazol-3-yl]-N-phenyl-[1,3,5]triazine-2,4-diamine,
N-Ethyl-6-[5-(2-methoxy-phenyl)-[1,2,4]oxadiazol-3-yl]-N-phenyl-[1,3,5]triazine-2,4-diamine,
N-Ethyl-N-phenyl-6-(5-thiophen-2-yl-[1,2,4]oxadiazol-3-yl)-[1,3,5]triazine-2,4-diamine,
N-Ethyl-6-[5-(5-methyl-furan-2-yl)-[1,2,4]oxadiazol-3-yl]-N-phenyl-[1,3,5]triazine-2,4-diamine,
N-(3-Fluoro-phenyl)-6-[5-(2-methoxy-phenyl)-[1,2,4]oxadiazol-3-yl]-N-methyl-[1,3,5]triazine-2,4-diamine,
N-(3-Fluoro-phenyl)-N-methyl-6-(5-thiophen-2-yl-[1,2,4]oxadiazol-3-yl)-[1,3,5]triazine-2,4-diamine,
N-(3-Chloro-phenyl)-6-[5-(2-methoxy-phenyl)-[1,2,4]oxadiazol-3-yl]-N-methyl-[1,3,5]triazine-2,4-diamine,
N-(3-Chlorophenyl)-N-methyl-6-(5-thiophen-2-yl-[1,2,4]oxadiazol-3-yl)-[1,3,5]triazine-2,4-diamine,
N-(3-Chloro-phenyl)-N-methyl-6-[5-(5-methyl-furan-2-yl)-[1,2,4]oxadiazol-3-yl]-[1,3,5]triazine-2,4-diamine, N-(5-Chloro-2-fluoro-phenyl)-6-(5-furan-2-yl-[1,2,4]oxadiazol-3-yl)-N-methyl-[1,3,5]triazine-2,4-diamine,
N-(2,5-Difluoro-phenyl)-6-(5-furan-2-yl-[1,2,4]oxadiazol-3-yl)-N-methyl-[1,3,5]triazine-2,4-diamine,
N-(2-Fluoro-5-methyl-phenyl)-6-(5-furan-2-yl-[1,2,4]oxadiazol-3-yl)-N-methyl-[1,3,5]triazine-2,4-diamine,
N-(3-Chloro-2-fluoro-phenyl)-6-(5-furan-2-yl-[1,2,4]oxadiazol-3-yl)-N-methyl-[1,3,5]triazine-2,4-diamine,
N-(2-Fluoro-3-methyl-phenyl)-6-(5-furan-2-yl-[1,2,4]oxadiazol-3-yl)-N-methyl-[1,3,5]triazine-2,4-diamine,
N-(5-Chloro-2-fluoro-phenyl)-6-(5-furan-2-yl-[1,2,4]oxadiazol-3-yl)-[1,3,5]triazine-2,4-diamine,
N-(2,5-Difluoro-phenyl)-6-(5-furan-2-yl-[1,2,4]oxadiazol-3-yl)-[1,3,5]triazine-2,4-diamine,
N-(2-Fluoro-3-methyl-phenyl)-6-(5-furan-2-yl-[1,2,4]oxadiazol-3-yl)-[1,3,5]triazine-2,4-diamine,
N-(3-Chloro-2-fluoro-phenyl)-6-(5-furan-2-yl-[1,2,4]oxadiazol-3-yl)-[1,3,5]triazine-2,4-diamine,
N-(2-Fluoro-3-methyl-phenyl)-6-(5-furan-2-yl-[1,2,4]oxadiazol-3-yl)-[1,3,5]triazine-2,4-diamine,
N-(2,3-Difluoro-phenyl)-6-(5-furan-2-yl-[1,2,4]oxadiazol-3-yl)-[1,3,5]triazine-2,4-diamine,
N-Methyl-N-phenyl-6-(5-pyridin-4-yl-[1,2,4]oxadiazol-3-yl)-[1,3,5]triazine-2,4-diamine,
N-Methyl-N-phenyl-6-(5-pyridin-3-yl-[1,2,4]oxadiazol-3-yl)-[1,3,5]triazine-2,4-diamine,
4-(3,4-Dihydroquinolin-1-yl)-6-(5-furan-2-yl-[1,2,4]oxadiazol-3-yl)-[1,3,5]triazine-2-amine,
N-(3-Fluorophenyl)-6-(5-furan-2-yl-[1,2,4]oxadiazol-3-yl)-[1,3,5]triazine-2,4-diamine,
6-[5-(5-Methoxy-pyridin-2-yl)-[1,2,4]oxadiazol-3-yl]-N-methyl-N-phenyl-[1,3,5]triazine-2,4-diamine,
6-(5-Furan-2-yl-[1,2,4]oxadiazol-3-yl)-N-(2-methoxyethyl)-N-phenyl-[1,3,5]triazine-2,4-diamine,
N-Methyl-N-phenyl-6-(5-pyrimidin-4-yl-[1,2,4]oxadiazol-3-yl)-[1,3,5]triazine-2,4-diamine,
N-Cyclopropylmethyl-6-(5-furan-2-yl-[1,2,4]oxadiazol-3-yl)-N-phenyl-[1,3,5]triazine-2,4-diamine,
6-[5-(4-Fluoro-phenyl)-[1,2,4]oxadiazol-3-yl]-N-methyl-N-phenyl-[1,3,5]triazine-2,4-diamine,
6-[5-(3-Fluoro-phenyl)-[1,2,4]oxadiazol-3-yl]-N-methyl-N-phenyl-[1,3,5]triazine-2,4-diamine,
6-[5-(2-Fluoro-phenyl)-[1,2,4]oxadiazol-3-yl]-N-methyl-N-phenyl-[1,3,5]triazine-2,4-diamine,
N-Methyl-N-phenyl-6-(5-thiazol-2-yl-[1,2,4]oxadiazol-3-yl)-[1,3,5]triazine-2,4-diamine,
N-Methyl-6-[5-(3-methyl-thiophen-2-yl)-[1,2,4]oxadiazol-3-yl]-N-phenyl-[1,3,5]triazine-2,4-diamine,
N-Methyl-6-(5-oxazol-5-yl-[1,2,4]oxadiazol-3-yl)-N-phenyl-[1,3,5]triazine-2,4-diamine,
N-Methyl-6-(5-oxazol-2-yl-[1,2,4]oxadiazol-3-yl)-N-phenyl-[1,3,5]triazine-2,4-diamine,
N-Methyl-6-[5-(5-methyl-thiophen-2-yl)-[1,2,4]oxadiazol-3-yl]-N-phenyl-[1,3,5]triazine-2,4-diamine,
N-Phenyl-6-(5-thiazol-2-yl-[1,2,4]oxadiazol-3-yl)-[1,3,5]triazine-2,4-diamine,
N-Methyl-N-phenyl-6-(5-pyrrolidin-1-yl-[1,2,4]oxadiazol-3-yl)-[1,3,5]triazine-2,4-diamine,
6-[5-(3-Methoxy-2-pyridyl)-[1,2,4]oxadiazol-3-yl]-N-methyl-N-phenyl-[1,3,5]triazine-2,4-diamine;
2-N-methyl-2-N-phenyl-6-{5-[6-(trifluoromethoxy)pyridin-3-yl]-1,2,4-oxadiazol-3-yl}-1,3,5-triazine-2,4-diamine;
6-{5-[6-(cyclopropylmethoxy)pyridin-3-yl]-1,2,4-oxadiazol-3-yl}-2-N-(2-fluorophenyl)-2-N-methyl-1,3,5-triazine-2,4-diamine;
6-{5-[6-(cyclopropylmethoxy)pyridin-3-yl]-1,2,4-oxadiazol-3-yl}-2-N-(3-fluorophenyl)-2-N-methyl-1,3,5-triazine-2,4-diamine;
6-{5-[6-(cyclopropylmethoxy)pyridin-3-yl]-1,2,4-oxadiazol-3-yl}-2-N-(3-fluorophenyl)-1,3,5-triazine-2,4-diamine;
6-(5-{[3-(4-fluorophenoxy)azetidin-1-yl]carbonyl}-1,2,4-oxadiazol-3-yl)-2-N-methyl-2-N-phenyl-1,3,5-triazine-2,4-diamine;
6-{5-[6-(cyclopropylmethoxy)pyridin-3-yl]-1,2,4-oxadiazol-3-yl}-2-N-(2-fluorophenyl)-1,3,5-triazine-2,4-diamine;
6-{5-[6-(cyclopropylmethoxy)pyridin-3-yl]-1,2,4-oxadiazol-3-yl}-2-N-(2,3-difluorophenyl)-1,3,5-triazine-2,4-diamine;
6-{5-[6-(cyclopropylmethoxy)pyridin-3-yl]-1,2,4-oxadiazol-3-yl}-2-N-(2,3-difluorophenyl)-2-N-methyl-1,3,5-triazine-2,4-diamine;
2-N-methyl-6-{5-[6-(oxolan-3-yloxy)pyridin-3-yl]-1,2,4-oxadiazol-3-yl}-2-N-phenyl-1,3,5-triazine-2,4-diamine;
6-{5-[2-chloro-6-(trifluoromethyl)pyridin-3-yl]-1,2,4-oxadiazol-3-yl}-2-N-methyl-2-N-phenyl-1,3,5-triazine-2,4-diamine;
6-(5-{6-[(2-methoxyethoxy)methyl]pyridin-3-yl}-1,2,4-oxadiazol-3-yl)-2-N-methyl-2-N-phenyl-1,3,5-triazine-2,4-diamine;
2-N-methyl-6-(5-{6-[(oxolan-3-yloxy)methyl]pyridin-3-yl}-1,2,4-oxadiazol-3-yl)-2-N-phenyl-1,3,5-triazine-2,4-diamine;
2-N-methyl-2-N-phenyl-6-{5-[(1R,5S)-8-(3,3,3-trifluoropropyl)-8-azabicyclo[3.2.1]octan-3-yl]-1,2,4-oxadiazol-3-yl}-1,3,5-triazine-2,4-diamine;
6-{5-[6-(cyclopropylmethoxy)pyridin-3-yl]-1,2,4-oxadiazol-3-yl}-2-N-methyl-2-N-phenyl-1,3,5-triazine-2,4-diamine;
2-N-ethyl-2-N-phenyl-6-{5-[6-(2,2,2-trifluoroethoxy)pyridin-3-yl]-1,2,4-oxadiazol-3-yl}-1,3,5-triazine-2,4-diamine;
6-[5-(6-ethoxypyridin-3-yl)-1,2,4-oxadiazol-3-yl]-2-N-methyl-2-N-phenyl-1,3,5-triazine-2,4-diamine;
2-N-methyl-2-N-phenyl-6-{5-[6-(propan-2-yloxy)pyridin-3-yl]-1,2,4-oxadiazol-3-yl}-1,3,5-triazine-2,4-diamine;
2-N-phenyl-6-{5-[6-(2,2,2-trifluoroethoxy)pyridin-3-yl]-1,2,4-oxadiazol-3-yl}-2-N-(2,2,2-trifluoroethyl)-1,3,5-triazine-2,4-diamine;
2-N-phenyl-6-{5-[6-(2,2,2-trifluoroethoxy)pyridin-3-yl]-1,2,4-oxadiazol-3-yl}-4-N-(2,2,2-trifluoroethyl)-1,3,5-triazine-2,4-diamine;
2-N-methyl-6-[5-(3-methylpyridin-2-yl)-1,2,4-oxadiazol-3-yl]-2-N-phenyl-1,3,5-triazine-2,4-diamine;
6-[5-(5-fluoropyridin-2-yl)-1,2,4-oxadiazol-3-yl]-2-N-methyl-2-N-phenyl-1,3,5-triazine-2,4-diamine;
6-[5-(4,6-dimethylpyridin-3-yl)-1,2,4-oxadiazol-3-yl]-2-N-methyl-2-N-phenyl-1,3,5-triazine-2,4-diamine;
2-N-methyl-2-N-phenyl-6-{5-[6-(2,2,2-trifluoroethoxy)pyridin-2-yl]-1,2,4-oxadiazol-3-yl}-1,3,5-triazine-2,4-diamine;
2-N-(2-methoxyethyl)-2-N-phenyl-6-{5-[6-(2,2,2-trifluoroethoxy)pyridin-3-yl]-1,2,4-oxadiazol-3-yl}-1,3,5-triazine-2,4-diamine;
2-N-(2-methoxyethyl)-4-N-phenyl-6-{5-[6-(2,2,2-trifluoroethoxy)pyridin-3-yl]-1,2,4-oxadiazol-3-yl}-1,3,5-triazine-2,4-diamine;
6-[5-(6-fluoropyridin-3-yl)-1,2,4-oxadiazol-3-yl]-2-N-methyl-2-N-phenyl-1,3,5-triazine-2,4-diamine;

1-[4-(3-{4-amino-6-[methyl(phenyl)amino]-1,3,5-triazin-2-yl}-1,2,4-oxadiazol-5-yl)piperidin-1-yl]-2,2,2-trifluoroethan-1-one;
6-[5-(1-methanesulfonylpiperidin-4-yl)-1,2,4-oxadiazol-3-yl]-2-N-methyl-2-N-phenyl-1,3,5-triazine-2,4-diamine;
1-[4-(3-{4-amino-6-[methyl(phenyl)amino]-1,3,5-triazin-2-yl}-1,2,4-oxadiazol-5-yl)piperidin-1-yl]-2-methylpropan-1-one;
1-[4-(3-{4-amino-6-[methyl(phenyl)amino]-1,3,5-triazin-2-yl}-1,2,4-oxadiazol-5-yl)piperidin-1-yl]ethan-1-one;
2-N-methyl-2-N-phenyl-6-{5-[1-(3,3,3-trifluoropropyl)piperidin-4-yl]-1,2,4-oxadiazol-3-yl}-1,3,5-triazine-2,4-diamine;
1-[4-(3-{4-amino-6-[methyl(phenyl)amino]-1,3,5-triazin-2-yl}-1,2,4-oxadiazol-5-yl)piperidin-1-yl]-3,3,3-trifluoropropan-1-one;
6-{5-[4-(methoxymethyl)piperidin-1-yl]-1,2,4-oxadiazol-3-yl}-2-N-methyl-2-N-phenyl-1,3,5-triazine-2,4-diamine;
2-N-methyl-6-{5-[4-(phenoxymethyl)piperidin-1-yl]-1,2,4-oxadiazol-3-yl}-2-N-phenyl-1,3,5-triazine-2,4-diamine;
2-N-methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine;
2-N-methyl-2-N-phenyl-6-{5-[1-(propane-1-sulfonyl)piperidin-4-yl]-1,2,4-oxadiazol-3-yl}-1,3,5-triazine-2,4-diamine;
2-N-methyl-2-N-phenyl-6-(5-{1-[(2,2,2-trifluoroethane)sulfonyl]piperidin-4-yl}-1,2,4-oxadiazol-3-yl)-1,3,5-triazine-2,4-diamine;
6-{5-[1-(ethanesulfonyl)piperidin-4-yl]-1,2,4-oxadiazol-3-yl}-2-N-methyl-2-N-phenyl-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine;
6-{5-[1-(benzenesulfonyl)piperidin-4-yl]-1,2,4-oxadiazol-3-yl}-2-N-methyl-2-N-phenyl-1,3,5-triazine-2,4-diamine;
6-[5-(1-benzylpiperidin-4-yl)-1,2,4-oxadiazol-3-yl]-2-N-methyl-2-N-phenyl-1,3,5-triazine-2,4-diamine;
2-N-phenyl-6-(5-{4-[(2,2,2-trifluoroethoxy)methyl]piperidin-1-yl}-1,2,4-oxadiazol-3-yl)-1,3,5-triazine-2,4-diamine;
2-N-methyl-2-N-phenyl-6-[5-(4-{[(2,2,2-trifluoroethyl)sulfanyl]methyl}piperidin-1-yl)-1,2,4-oxadiazol-3-yl]-1,3,5-triazine-2,4-diamine;
2-N-methyl-2-N-phenyl-6-(5-{4-[(phenylsulfanyl)methyl]piperidin-1-yl}-1,2,4-oxadiazol-3-yl)-1,3,5-triazine-2,4-diamine;
2-N-methyl-2-N-phenyl-6-(5-{4-[(propan-2-ylsulfanyl)methyl]piperidin-1-yl}-1,2,4-oxadiazol-3-yl)-1,3,5-triazine-2,4-diamine;
2-N-methyl-2-N-phenyl-6-[5-(4-{[(2,2,2-trifluoroethane)sulfonyl]methyl}piperidin-1-yl)-1,2,4-oxadiazol-3-yl]-1,3,5-triazine-2,4-diamine;
6-(5-{4-[(benzenesulfonyl)methyl]piperidin-1-yl}-1,2,4-oxadiazol-3-yl)-2-N-methyl-2-N-phenyl-1,3,5-triazine-2,4-diamine;
2-N-methyl-2-N-phenyl-6-(5-{4-[(propane-2-sulfinyl)methyl]piperidin-1-yl}-1,2,4-oxadiazol-3-yl)-1,3,5-triazine-2,4-diamine;
2-N-methyl-2-N-phenyl-6-(5-{4-[(propane-2-sulfonyl)methyl]piperidin-1-yl}-1,2,4-oxadiazol-3-yl)-1,3,5-triazine-2,4-diamine;
methyl 3-[(4-amino-6-{5-[6-(2,2,2-trifluoroethoxy)pyridin-3-yl]-1,2,4-oxadiazol-3-yl}-1,3,5-triazin-2-yl)amino]benzoate;
6-[5-(2-ethoxyphenyl)-1,2,4-oxadiazol-3-yl]-2-N-methyl-2-N-(3-methyl phenyl)-1,3,5-triazine-2,4-diamine;
6-[5-(4-methoxyphenyl)-1,2,4-oxadiazol-3-yl]-2-N-methyl-2-N-(3-methylphenyl)-1,3,5-triazine-2,4-diamine;
6-[5-(2-fluoro-6-methoxyphenyl)-1,2,4-oxadiazol-3-yl]-2-N-methyl-2-N-(3-methyl phenyl)-1,3,5-triazine-2,4-diamine;
6-[5-(5-fluoro-2-methoxyphenyl)-1,2,4-oxadiazol-3-yl]-2-N-methyl-2-N-(3-methyl phenyl)-1,3,5-triazine-2,4-diamine;
6-[5-(4-fluoro-2-methoxyphenyl)-1,2,4-oxadiazol-3-yl]-2-N-methyl-2-N-(3-methyl phenyl)-1,3,5-triazine-2,4-diamine;
6-[5-(2,4-dimethoxyphenyl)-1,2,4-oxadiazol-3-yl]-2-N-methyl-2-N-(3-methyl phenyl)-1,3,5-triazine-2,4-diamine;
2-N-(3-methanesulfonylphenyl)-6-{5-[6-(2,2,2-trifluoroethoxy)pyridin-3-yl]-1,2,4-oxadiazol-3-yl}-1,3,5-triazine-2,4-diamine;
2-N-ethyl-6-[5-(4-methoxyphenyl)-1,2,4-oxadiazol-3-yl]-2-N-phenyl-1,3,5-triazine-2,4-diamine;
2-N-ethyl-6-[5-(2-fluoro-6-methoxyphenyl)-1,2,4-oxadiazol-3-yl]-2-N-phenyl-1,3,5-triazine-2,4-diamine;
6-[5-(2-chlorophenyl)-1,2,4-oxadiazol-3-yl]-2-N-ethyl-2-N-phenyl-1,3,5-triazine-2,4-diamine;
6-[5-(2-chloro-4-fluorophenyl)-1,2,4-oxadiazol-3-yl]-2-N-ethyl-2-N-phenyl-1,3,5-triazine-2,4-diamine;
2-N-methyl-2-N-(3-methyl phenyl)-6-{5-[2-(trifluoromethoxy)phenyl]-1,2,4-oxadiazol-3-yl}-1,3,5-triazine-2,4-diamine;
6-[5-(2-chlorophenyl)-1,2,4-oxadiazol-3-yl]-2-N-methyl-2-N-(3-methyl phenyl)-1,3,5-triazine-2,4-diamine;
6-[5-(2-ethoxyphenyl)-1,2,4-oxadiazol-3-yl]-2-N-ethyl-2-N-phenyl-1,3,5-triazine-2,4-diamine;
2-N-ethyl-6-[5-(5-fluoro-2-methoxyphenyl)-1,2,4-oxadiazol-3-yl]-2-N-phenyl-1,3,5-triazine-2,4-diamine;
2-N-ethyl-2-N-phenyl-6-{5-[2-(trifluoromethoxy)phenyl]-1,2,4-oxadiazol-3-yl}-1,3,5-triazine-2,4-diamine;
6-{5-[(2-methoxyphenyl)methyl]-1,2,4-oxadiazol-3-yl}-2-N-methyl-2-N-phenyl-1,3,5-triazine-2,4-diamine;
2-N-methyl-2-N-phenyl-6-{5-[1-(propane-1-sulfonyl)pyrrolidin-3-yl]-1,2,4-oxadiazol-3-yl}-1,3,5-triazine-2,4-diamine;
2-N-methyl-2-N-phenyl-6-{5-[1-(propane-2-sulfonyl)pyrrolidin-3-yl]-1,2,4-oxadiazol-3-yl}-1,3,5-triazine-2,4-diamine;
2-N-methyl-2-N-phenyl-6-(5-{1-[(2,2,2-trifluoroethane)sulfonyl]pyrrolidin-3-yl}-1,2,4-oxadiazol-3-yl)-1,3,5-triazine-2,4-diamine;
6-{5-[1-(benzenesulfonyl)pyrrolidin-3-yl]-1,2,4-oxadiazol-3-yl}-2-N-methyl-2-N-phenyl-1,3,5-triazine-2,4-diamine;
2-N-methyl-2-N-phenyl-6-{5-[1-(3,3,3-trifluoropropyl)pyrrolidin-3-yl]-1,2,4-oxadiazol-3-yl}-1,3,5-triazine-2,4-diamine;
2-N-methyl-2-N-phenyl-6-{5-[1-(4,4,4-trifluorobutan-2-yl)pyrrolidin-3-yl]-1,2,4-oxadiazol-3-yl}-1,3,5-triazine-2,4-diamine;
2-N-methyl-2-N-phenyl-6-[5-(6-{[(1,1,1-trifluoropropan-2-yl)oxy]methyl}pyridin-3-yl)-1,2,4-oxadiazol-3-yl]-1,3,5-triazine-2,4-diamine;
6-[5-(1-benzylpyrrolidin-3-yl)-1,2,4-oxadiazol-3-yl]-2-N-methyl-2-N-phenyl-1,3,5-triazine-2,4-diamine;
6-(5-{6-[(cyclopropylmethoxy)methyl]pyridin-3-yl}-1,2,4-oxadiazol-3-yl)-2-N-methyl-2-N-phenyl-1,3,5-triazine-2,4-diamine;

2-N-methyl-2-N-phenyl-6-(5-{6-[1-(2,2,2-trifluoroethoxy)ethyl]pyridin-3-yl}-1,2,4-oxadiazol-3-yl)-1,3,5-triazine-2,4-diamine;
2-N-phenyl-6-[5-(6-{[(1,1,1-trifluoropropan-2-yl)oxy]methyl}pyridin-3-yl)-1,2,4-oxadiazol-3-yl]-1,3,5-triazine-2,4-diamine;
6-(5-{6-[(cyclopropylmethoxy)methyl]pyridin-3-yl}-1,2,4-oxadiazol-3-yl)-2-N-phenyl-1,3,5-triazine-2,4-diamine;
2-N-phenyl-6-(5-{6-[1-(2,2,2-trifluoroethoxy)ethyl]pyridin-3-yl}-1,2,4-oxadiazol-3-yl)-1,3,5-triazine-2,4-diamine;
6-{5-[6-(cyclobutoxymethyl)pyridin-3-yl]-1,2,4-oxadiazol-3-yl}-2-N-phenyl-1,3,5-triazine-2,4-diamine;
6-(5-{4-[(cyclopropylmethoxy)methyl]piperidin-1-yl}-1,2,4-oxadiazol-3-yl)-2-N-phenyl-1,3,5-triazine-2,4-diamine;
6-(5-{4-(cyclobutoxymethyl)piperidin-1-yl]-1,2,4-oxadiazol-3-yl}-2-N-phenyl-1,3,5-triazine-2,4-diamine;
6-(5-{4-[(cyclopropylmethoxy)methyl]piperidin-1-yl}-1,2,4-oxadiazol-3-yl)-2-N-methyl-2-N-phenyl-1,3,5-triazine-2,4-diamine;
6-{5-[4-(cyclobutoxymethyl)piperidin-1-yl]-1,2,4-oxadiazol-3-yl}-2-N-methyl-2-N-phenyl-1,3,5-triazine-2,4-diamine;
3-[4-amino-6-(phenylamino)-1,3,5-triazin-2-yl]-N-cyclopentyl-1,2,4-oxadiazole-5-carboxamide;
3-{4-amino-6-[(3-fluorophenyl)amino]-1,3,5-triazin-2-yl}-N-cyclopentyl-1,2,4-oxadiazole-5-carboxamide;
2-N-phenyl-6-{5-[(pyrrolidin-1-yl)carbonyl]-1,2,4-oxadiazol-3-yl}-1,3,5-triazine-2,4-diamine;
2-N-phenyl-6-[5-(piperidin-1-yl)-1,2,4-oxadiazol-3-yl]-1,3,5-triazine-2,4-diamine;
3-[4-amino-6-(phenylamino)-1,3,5-triazin-2-yl]-1,2,4-oxadiazole-5-carboxamide;
3-{4-amino-6-[(3-fluorophenyl)amino]-1,3,5-triazin-2-yl}-1,2,4-oxadiazole-5-carboxamide;
3-{4-amino-6-[(3-fluorophenyl)amino]-1,3,5-triazin-2-yl}-N-cyclobutyl-1,2,4-oxadiazole-5-carboxamide;
3-{4-amino-6-[(3-fluorophenyl)amino]-1,3,5-triazin-2-yl}-N-(2,3-dihydro-1H-inden-2-yl)-1,2,4-oxadiazole-5-carboxamide;
3-{4-amino-6-[(3-fluorophenyl)amino]-1,3,5-triazin-2-yl}-N-(2,3-dihydro-1H-inden-1-yl)-1,2,4-oxadiazole-5-carboxamide;
2-N-(3-fluorophenyl)-6-{5-[(pyrrolidin-1-yl)carbonyl]-1,2,4-oxadiazol-3-yl}-1,3,5-triazine-2,4-diamine;
3-[4-amino-6-(phenylamino)-1,3,5-triazin-2-yl]-N-cyclobutyl-1,2,4-oxadiazole-5-carboxamide;
3-[4-amino-6-(phenylamino)-1,3,5-triazin-2-yl]-N-(2,3-dihydro-1H-inden-2-yl)-1,2,4-oxadiazole-5-carboxamide;
6-{5-[(2,3-dihydro-1H-isoindol-2-yl)carbonyl]-1,2,4-oxadiazol-3-yl}-2-N-phenyl-1,3,5-triazine-2,4-diamine;
6-[5-(cyclopentylamino)-1,2,4-oxadiazol-3-yl]-2-N-phenyl-1,3,5-triazine-2,4-diamine
2-N-(3-fluorophenyl)-6-{5-[(morpholin-4-yl)carbonyl]-1,2,4-oxadiazol-3-yl}-1,3,5-triazine-2,4-diamine;
3-{4-amino-6-[(3-fluorophenyl)amino]-1,3,5-triazin-2-yl}-N-[(3R)-oxolan-3-yl]-1,2,4-oxadiazole-5-carboxamide;
3-{4-amino-6-[(3-fluorophenyl)amino]-1,3,5-triazin-2-yl}-N-(propan-2-yl)-1,2,4-oxadiazole-5-carboxamide;
6-[5-(cyclopentylamino)-1,2,4-oxadiazol-3-yl]-2-N-(3-fluorophenyl)-1,3,5-triazine-2,4-diamine;
2-N-(3-fluorophenyl)-6-[5-(piperidin-1-yl)-1,2,4-oxadiazol-3-yl]-1,3,5-triazine-2,4-diamine
2-N-(3-fluorophenyl)-6-[5-(4-methoxypiperidin-1-yl)-1,2,4-oxadiazol-3-yl]-1,3,5-triazine-2,4-diamine;
6-[5-(4-methoxypiperidin-1-yl)-1,2,4-oxadiazol-3-yl]-2-N-phenyl-1,3,5-triazine-2,4-diamine;
6-[5-(2-methoxypyridin-4-yl)-1,2,4-oxadiazol-3-yl]-2-N-phenyl-1,3,5-triazine-2,4-diamine
2-N-(3-fluorophenyl)-6-[5-(3-fluoropyridin-2-yl)-1,2,4-oxadiazol-3-yl]-1,3,5-triazine-2,4-diamine;
2-N-(4-fluorophenyl)-6-[5-(1,3-thiazol-2-yl)-1,2,4-oxadiazol-3-yl]-1,3,5-triazine-2,4-diamine;
6-[5-(cyclohexylamino)-1,2,4-oxadiazol-3-yl]-2-N-phenyl-1,3,5-triazine-2,4-diamine;
6-[5-(4-methylpiperidin-1-yl)-1,2,4-oxadiazol-3-yl]-2-N-phenyl-1,3,5-triazine-2,4-diamine;
3-[4-amino-6-(phenylamino)-1,3,5-triazin-2-yl]-N-(2,3-dihydro-1H-inden-1-yl)-1,2,4-oxadiazole-5-carboxamide;
2-N-(3-fluorophenyl)-6-[5-(4-methylpiperidin-1-yl)-1,2,4-oxadiazol-3-yl]-1,3,5-triazine-2,4-diamine;
6-(5-{2-oxa-7-azaspiro[3.5]nonan-7-yl}-1,2,4-oxadiazol-3-yl)-2-N-phenyl-1,3,5-triazine-2,4-diamine;
6-[5-(2-methoxyphenyl)-1,2,4-oxadiazol-3-yl]-2-N-phenyl-1,3,5-triazine-2,4-diamine
2-N-(3-fluorophenyl)-6-[5-(2-methoxyphenyl)-1,2,4-oxadiazol-3-yl]-1,3,5-triazine-2,4-diamine;
6-[5-(5-aminopyridin-2-yl)-1,2,4-oxadiazol-3-yl]-2-N-(3-fluorophenyl)-1,3,5-triazine-2,4-diamine;
3-{4-amino-6-[(3-fluorophenyl)amino]-1,3,5-triazin-2-yl}-N-(oxetan-3-yl)-1,2,4-oxadiazole-5-carboxamide;
6-[5-(4-bromo-1H-pyrazol-3-yl)-1,2,4-oxadiazol-3-yl]-2-N-methyl-2-N-phenyl-1,3,5-triazine-2,4-diamine;
2-N-methyl-6-[5-(1-methyl-1H-pyrazol-3-yl)-1,2,4-oxadiazol-3-yl]-2-N-phenyl-1,3,5-triazine-2,4-diamine;
2-N-methyl-6-[5-(1-methyl-1H-pyrazol-5-yl)-1,2,4-oxadiazol-3-yl]-2-N-phenyl-1,3,5-triazine-2,4-diamine;
6-[5-(4-chloro-1H-pyrazol-3-yl)-1,2,4-oxadiazol-3-yl]-2-N-methyl-2-N-phenyl-1,3,5-triazine-2,4-diamine;
2-N-methyl-2-N-phenyl-6-{5-[5-(trifluoromethyl)-1H-pyrazol-3-yl]-1,2,4-oxadiazol-3-yl}-1,3,5-triazine-2,4-diamine;
2-N-methyl-2-N-phenyl-6-{5-[1-(2,2,2-trifluoroethyl)-1H-pyrazol-3-yl]-1,2,4-oxadiazol-3-yl}-1,3,5-triazine-2,4-diamine;
2-N-methyl-2-N-phenyl-6-{5-[1-(2,2,2-trifluoroethyl)-1H-pyrazol-5-yl]-1,2,4-oxadiazol-3-yl}-1,3,5-triazine-2,4-diamine;
3-{4-amino-6-[methyl(phenyl)amino]-1,3,5-triazin-2-yl}-N-(6-methoxypyridin-3-yl)-1,2,4-oxadiazole-5-carboxamide;
3-{4-amino-6-[methyl(phenyl)amino]-1,3,5-triazin-2-yl}-N-{[6-(2,2,2-trifluoroethoxy)pyridin-3-yl]methyl}-1,2,4-oxadiazole-5-carboxamide;
3-{4-amino-6-[methyl(phenyl)amino]-1,3,5-triazin-2-yl}-N-[(6-methoxypyridin-3-yl)methyl]-1,2,4-oxadiazole-5-carboxamide;
2-N-methyl-6-[5-(3-phenoxycyclobutyl)-1,2,4-oxadiazol-3-yl]-2-N-phenyl-1,3,5-triazine-2,4-diamine;
2-N-methyl-2-N-phenyl-6-(5-{[4-(2,2,2-trifluoroethoxy)piperidin-1-yl]carbonyl}-1,2,4-oxadiazol-3-yl)-1,3,5-triazine-2,4-diamine;
3-{4-amino-6-[methyl(phenyl)amino]-1,3,5-triazin-2-yl}-N-[6-(trifluoromethyl)pyridin-3-yl]-1,2,4-oxadiazole-5-carboxamide;
2-N-(3-chloro-2-fluorophenyl)-6-[5-(pyridin-2-yl)-1,2,4-oxadiazol-3-yl]-1,3,5-triazine-2,4-diamine;
2-N-(3-chlorophenyl)-6-[5-(pyridin-2-yl)-1,2,4-oxadiazol-3-yl]-1,3,5-triazine-2,4-diamine;
6-(5-cyclohexyl-1,2,4-oxadiazol-3-yl)-2-N-methyl-2-N-phenyl-1,3,5-triazine-2,4-diamine
2-N-methyl-2-N-phenyl-6-{5-[6-(trifluoromethyl)pyridin-3-yl]-1,2,4-oxadiazol-3-yl}-1,3,5-triazine-2,4-diamine;

2-N-methyl-6-[5-(2-methylpyridin-3-yl)-1,2,4-oxadiazol-3-yl]-2-N-phenyl-1,3,5-triazine-2,4-diamine;
2-N-phenyl-6-[5-(1,3-thiazol-2-yl)-1,2,4-oxadiazol-3-yl]-1,3,5-triazine-2,4-diamine
2-N-methyl-6-{5-[6-(morpholin-4-yl)pyridin-2-yl]-1,2,4-oxadiazol-3-yl}-2-N-phenyl-1,3,5-triazine-2,4-diamine;
2-N-methyl-6-[5-(6-methylpyridin-2-yl)-1,2,4-oxadiazol-3-yl]-2-N-phenyl-1,3,5-triazine-2,4-diamine;
2-N-(3-chlorophenyl)-6-[5-(3-fluoropyridin-2-yl)-1,2,4-oxadiazol-3-yl]-2-N-methyl-1,3,5-triazine-2,4-diamine;
6-[5-(3-chloropyridin-2-yl)-1,2,4-oxadiazol-3-yl]-2-N-methyl-2-N-phenyl-1,3,5-triazine-2,4-diamine;
N-[1-(3-{4-amino-6-[methyl(phenyl)amino]-1,3,5-triazin-2-yl}-1,2,4-oxadiazol-5-yl)piperidin-4-yl]-2,2,2-trifluoroacetamide;
6-[5-(2-chloropyridin-3-yl)-1,2,4-oxadiazol-3-yl]-2-N-methyl-2-N-phenyl-1,3,5-triazine-2,4-diamine;
2-N-methyl-2-N-phenyl-6-{5-[(pyrrolidin-1-yl)carbonyl]-1,2,4-oxadiazol-3-yl}-1,3,5-triazine-2,4-diamine;
2-N-methyl-2-N-phenyl-6-{5-[(piperidin-1-yl)carbonyl]-1,2,4-oxadiazol-3-yl}-1,3,5-triazine-2,4-diamine;
2-N-methyl-2-N-phenyl-6-[5-(pyrimidin-2-yl)-1,2,4-oxadiazol-3-yl]-1,3,5-triazine-2,4-diamine;
methyl 5-(3-{4-amino-6-[methyl(phenyl)amino]-1,3,5-triazin-2-yl}-1,2,4-oxadiazol-5-yl)pyridine-2-carboxylate;
5-(3-{4-amino-6-[methyl(phenyl)amino]-1,3,5-triazin-2-yl}-1,2,4-oxadiazol-5-yl)-N-(2,2,2-trifluoroethyl)pyridine-2-carboxamide;
6-[5-(3,5-difluoropyridin-2-yl)-1,2,4-oxadiazol-3-yl]-2-N-methyl-2-N-phenyl-1,3,5-triazine-2,4-diamine;
6-[5-(3,5-dimethoxypyridin-2-yl)-1,2,4-oxadiazol-3-yl]-2-N-methyl-2-N-phenyl-1,3,5-triazine-2,4-diamine;
2-N-methyl-6-[5-(6-methylpyridin-3-yl)-1,2,4-oxadiazol-3-yl]-2-N-phenyl-1,3,5-triazine-2,4-diamine;
5-(3-{4-amino-6-[methyl(phenyl)amino]-1,3,5-triazin-2-yl}-1,2,4-oxadiazol-5-yl)pyridine-2-carboxamide;
methyl 6-(3-{4-amino-6-[methyl(phenyl)amino]-1,3,5-triazin-2-yl}-1,2,4-oxadiazol-5-yl)pyridine-3-carboxylate;
5-(3-{4-amino-6-[methyl(phenyl)amino]-1,3,5-triazin-2-yl}-1,2,4-oxadiazol-5-yl)-N-cyclobutylpyridine-2-carboxamide;
5-(3-{4-amino-6-[methyl(phenyl)amino]-1,3,5-triazin-2-yl}-1,2,4-oxadiazol-5-yl)-N-cyclopropylpyridine-2-carboxamide;
5-(3-{4-amino-6-[methyl(phenyl)amino]-1,3,5-triazin-2-yl}-1,2,4-oxadiazol-5-yl)-N-(cyclopropylmethyl)pyridine-2-carboxamide;
propan-2-yl 5-(3-{4-amino-6-[methyl(phenyl)amino]-1,3,5-triazin-2-yl}-1,2,4-oxadiazol-5-yl)pyridine-2-carboxylate;
cyclopentyl 5-(3-{4-amino-6-[methyl(phenyl)amino]-1,3,5-triazin-2-yl}-1,2,4-oxadiazol-5-yl)pyridine-2-carboxylate;
2-N-methyl-2-N-phenyl-6-(5-{6-[(2,2,2-trifluoroethoxy)methyl]pyridin-3-yl}-1,2,4-oxadiazol-3-yl)-1,3,5-triazine-2,4-diamine;
6-(3-{4-amino-6-[methyl(phenyl)amino]-1,3,5-triazin-2-yl}-1,2,4-oxadiazol-5-yl)-N-(2,2,2-trifluoroethyl)pyridine-3-carboxamide;
2-N-methyl-2-N-phenyl-6-{5-[6-(pyrrolidin-1-ylmethyl)pyridin-3-yl]-1,2,4-oxadiazol-3-yl}-1,3,5-triazine-2,4-diamine;
2-N-methyl-2-N-phenyl-6-(5-{5-[1-(pyrrolidin-1-yl)ethyl]pyridin-2-yl}-1,2,4-oxadiazol-3-yl)-1,3,5-triazine-2,4-diamine;
[5-(3-{4-amino-6-[methyl(phenyl)amino]-1,3,5-triazin-2-yl}-1,2,4-oxadiazol-5-yl)pyridin-2-yl]methanol;
1-[6-(3-{4-amino-6-[methyl(phenyl)amino]-1,3,5-triazin-2-yl}-1,2,4-oxadiazol-5-yl)pyridin-3-yl]ethan-1-one;
methyl 5-{3-[4-amino-6-(phenylamino)-1,3,5-triazin-2-yl]-1,2,4-oxadiazol-5-yl}pyridine-2-carboxylate;
2-N-methyl-2-N-phenyl-6-(5-{6-[(2,2,2-trifluoroethoxy)methyl]pyridin-3-yl}-1,2,4-oxadiazol-3-yl)-1,3,5-triazine-2,4-diamine;
2-N-methyl-6-{5-[6-(morpholin-4-ylmethyl)pyridin-3-yl]-1,2,4-oxadiazol-3-yl}-2-N-phenyl-1,3,5-triazine-2,4-diamine;
6-(5-{6-[(cyclobutylamino)methyl]pyridin-3-yl}-1,2,4-oxadiazol-3-yl)-2-N-methyl-2-N-phenyl-1,3,5-triazine-2,4-diamine;
2-N-methyl-2-N-phenyl-6-(5-{2-[(2,2,2-trifluoroethoxy)methyl]pyridin-3-yl}-1,2,4-oxadiazol-3-yl)-1,3,5-triazine-2,4-diamine;
2-N-methyl-2-N-phenyl-6-(5-{3-[(2,2,2-trifluoroethoxy)methyl]pyridin-2-yl}-1,2,4-oxadiazol-3-yl)-1,3,5-triazine-2,4-diamine;
2-N-phenyl-6-(5-{6-[(2,2,2-trifluoroethoxy)methyl]pyridin-3-yl}-1,2,4-oxadiazol-3-yl)-1,3,5-triazine-2,4-diamine;
1-[5-(3-{4-amino-6-[methyl(phenyl)amino]-1,3,5-triazin-2-yl}-1,2,4-oxadiazol-5-yl)pyridin-2-yl]ethan-1-one;
6-[5-(4-ethenylphenyl)-1,2,4-oxadiazol-3-yl]-2-N-methyl-2-N-phenyl-1,3,5-triazine-2,4-diamine;
6-[5-(1,3-dihydro-2-benzofuran-5-yl)-1,2,4-oxadiazol-3-yl]-2-N-methyl-2-N-phenyl-1,3,5-triazine-2,4-diamine;
2-N-methyl-2-N-phenyl-6-{5-[1-(propane-1-sulfonyl)azetidin-3-yl]-1,2,4-oxadiazol-3-yl}-1,3,5-triazine-2,4-diamine;
2-N-methyl-2-N-phenyl-6-{5-[1-(propane-2-sulfonyl)azetidin-3-yl]-1,2,4-oxadiazol-3-yl}-1,3,5-triazine-2,4-diamine;
6-{5-[1-(ethanesulfonyl)azetidin-3-yl]-1,2,4-oxadiazol-3-yl}-2-N-methyl-2-N-phenyl-1,3,5-triazine-2,4-diamine;
2-N-methyl-2-N-phenyl-6-(5-{1-[(2,2,2-trifluoroethane)sulfonyl]azetidin-3-yl}-1,2,4-oxadiazol-3-yl)-1,3,5-triazine-2,4-diamine;
methyl 5-(3-{4-amino-6-[(2-methoxyethyl)(phenyl)amino]-1,3,5-triazin-2-yl}-1,2,4-oxadiazol-5-yl)pyridine-2-carboxylate;
2-N-(2-methoxyethyl)-2-N-phenyl-6-(5-{6-[(2,2,2-trifluoroethoxy)methyl]pyridin-3-yl}-1,2,4-oxadiazol-3-yl)-1,3,5-triazine-2,4-diamine;
6-{5-[1-(benzenesulfonyl)azetidin-3-yl]-1,2,4-oxadiazol-3-yl}-2-N-methyl-2-N-phenyl-1,3,5-triazine-2,4-diamine;
2-N-methyl-2-N-phenyl-6-{5-[1-(2,2,2-trifluoroethyl)azetidin-3-yl]-1,2,4-oxadiazol-3-yl}-1,3,5-triazine-2,4-diamine;
2-N-methyl-2-N-phenyl-6-{5-[6-(3,3,3-trifluoropropyl)pyridin-3-yl]-1,2,4-oxadiazol-3-yl}-1,3,5-triazine-2,4-diamine;
2-N-methyl-2-N-phenyl-6-[5-(6-{[(2,2,2-trifluoroethyl)sulfanyl]methyl}pyridin-3-yl)-1,2,4-oxadiazol-3-yl]-1,3,5-triazine-2,4-diamine;
2-N-methyl-2-N-phenyl-6-[5-(6-{[(2,2,2-trifluoroethane)sulfinyl]methyl}pyridin-3-yl)-1,2,4-oxadiazol-3-yl]-1,3,5-triazine-2,4-diamine;
2-N-methyl-2-N-phenyl-6-(5-{6-[(2,2,2-trifluoroethyl)sulfanyl]pyridin-3-yl}-1,2,4-oxadiazol-3-yl)-1,3,5-triazine-2,4-diamine;
2-N-phenyl-6-{5-[6-(3,3,3-trifluoropropyl)pyridin-3-yl]-1,2,4-oxadiazol-3-yl}-1,3,5-triazine-2,4-diamine;
2-N-methyl-2-N-phenyl-6-(5-{6-[(2,2,2-trifluoroethane)sulfinyl]pyridin-3-yl}-1,2,4-oxadiazol-3-yl)-1,3,5-triazine-2,4-diamine;

2-N-methyl-2-N-phenyl-6-[5-(6-{[(2,2,2-trifluoroethane) sulfonyl]methyl}pyridin-3-yl)-1,2,4-oxadiazol-3-yl]-1,3,5-triazine-2,4-diamine;
2-N-methyl-2-N-phenyl-6-(5-{[4-(3,3,3-trifluoropropylidene)piperidin-1-yl]carbonyl}-1,2,4-oxadiazol-3-yl)-1,3,5-triazine-2,4-diamine;
2-N-methyl-2-N-phenyl-6-(5-{5H,6H,7H-pyrrolo[3,4-d]pyrimidin-6-yl}-1,2,4-oxadiazol-3-yl)-1,3,5-triazine-2,4-diamine;
2-N-methyl-2-N-phenyl-6-{5-[4-(3,3,3-trifluoropropylidene)piperidin-1-yl]-1,2,4-oxadiazol-3-yl}-1,3,5-triazine-2,4-diamine;
2-N-(5-chloro-2-fluorophenyl)-6-[5-(pyridin-2-yl)-1,2,4-oxadiazol-3-yl]-1,3,5-triazine-2,4-diamine;
6-{5-[5-(cyclopropylmethoxy)pyridin-2-yl]-1,2,4-oxadiazol-3-yl}-2-N-methyl-2-N-phenyl-1,3,5-triazine-2,4-diamine;
2-N-methyl-2-N-phenyl-6-(5-{6-[(2,2,2-trifluoroethyl)amino]pyridin-3-yl}-1,2,4-oxadiazol-3-yl)-1,3,5-triazine-2,4-diamine;
2-N-methyl-6-(5-{6-[(oxolan-3-yl)amino]pyridin-3-yl}-1,2,4-oxadiazol-3-yl)-2-N-phenyl-1,3,5-triazine-2,4-diamine;
6-{5-[6-(2-methoxyethoxy)pyridin-3-yl]-1,2,4-oxadiazol-3-yl}-2-N-methyl-2-N-phenyl-1,3,5-triazine-2,4-diamine;
2-{[5-(3-{4-amino-6-[methyl(phenyl)amino]-1,3,5-triazin-2-yl}-1,2,4-oxadiazol-5-yl)pyridin-2-yl]oxy}acetonitrile;
6-[5-(6-cyclobutoxypyridin-3-yl)-1,2,4-oxadiazol-3-yl]-2-N-methyl-2-N-phenyl-1,3,5-triazine-2,4-diamine;
2-N-methyl-2-N-phenyl-6-(5-{6-[(propan-2-yl)amino]pyridin-3-yl}-1,2,4-oxadiazol-3-yl)-1,3,5-triazine-2,4-diamine;
6-(5-{6-[(cyclopropylmethyl)amino]pyridin-3-yl}-1,2,4-oxadiazol-3-yl)-2-N-methyl-2-N-phenyl-1,3,5-triazine-2,4-diamine;
5-(3-{4-amino-6-[methyl(phenyl)amino]-1,3,5-triazin-2-yl}-1,2,4-oxadiazol-5-yl)-1,2-dihydropyridin-2-one;
2-N-methyl-2-N-phenyl-6-{5-[4-(2,2,2-trifluoroethoxy)piperidin-1-yl]-1,2,4-oxadiazol-3-yl}-1,3,5-triazine-2,4-diamine;
2-N-methyl-6-[5-(4-phenoxypiperidin-1-yl)-1,2,4-oxadiazol-3-yl]-2-N-phenyl-1,3,5-triazine-2,4-diamine;
2-N-methyl-2-N-phenyl-6-(5-{[(1r,4r)-4-(2,2,2-trifluoroethoxy)cyclohexyl]amino}-1,2,4-oxadiazol-3-yl)-1,3,5-triazine-2,4-diamine;
6-{5-[4-(benzyloxy)piperidin-1-yl]-1,2,4-oxadiazol-3-yl}-2-N-methyl-2-N-phenyl-1,3,5-triazine-2,4-diamine;
6-[5-(2,3-dihydro-1-benzofuran-5-yl)-1,2,4-oxadiazol-3-yl]-2-N-methyl-2-N-phenyl-1,3,5-triazine-2,4-diamine;
2-N-methyl-2-N-phenyl-6-{5-[5-(2,2,2-trifluoroethoxy)pyridin-2-yl]-1,2,4-oxadiazol-3-yl}-1,3,5-triazine-2,4-diamine;
2-N-methyl-6-[5-(4-methyl-1,3-thiazol-2-yl)-1,2,4-oxadiazol-3-yl]-2-N-phenyl-1,3,5-triazine-2,4-diamine;
2-N-methyl-6-[5-(5-methyl-1,3-thiazol-2-yl)-1,2,4-oxadiazol-3-yl]-2-N-phenyl-1,3,5-triazine-2,4-diamine;
2-N-(2,5-difluorophenyl)-6-{5-[6-(2,2,2-trifluoroethoxy)pyridin-3-yl]-1,2,4-oxadiazol-3-yl}-1,3,5-triazine-2,4-diamine;
2-N-methyl-6-{5-[(4-methylpiperazin-1-yl)carbonyl]-1,2,4-oxadiazol-3-yl}-2-N-phenyl-1,3,5-triazine-2,4-diamine;
2-N-methyl-2-N-phenyl-6-{5-[4-(trifluoromethyl)-1,3-thiazol-2-yl]-1,2,4-oxadiazol-3-yl}-1,3,5-triazine-2,4-diamine;
6-[5-(3-fluoropyridin-2-yl)-1,2,4-oxadiazol-3-yl]-2-N-phenyl-1,3,5-triazine-2,4-diamine
1-[4-(3-{4-amino-6-[methyl(phenyl)amino]-1,3,5-triazin-2-yl}-1,2,4-oxadiazol-5-yl)piperazin-1-yl]-2,2,2-trifluoroethan-1-one;
2-N-methyl-2-N-phenyl-6-{5-[3-(trifluoromethyl)pyridin-2-yl]-1,2,4-oxadiazol-3-yl}-1,3,5-triazine-2,4-diamine;
2-N-methyl-2-N-phenyl-6-(5-{5-[(2,2,2-trifluoroethoxy)methyl]pyridin-2-yl}-1,2,4-oxadiazol-3-yl)-1,3,5-triazine-2,4-diamine;
2-N-phenyl-6-(5-{5-[(2,2,2-trifluoroethoxy)methyl]pyridin-2-yl}-1,2,4-oxadiazol-3-yl)-1,3,5-triazine-2,4-diamine;
2-N-methyl-2-N-phenyl-6-(5-{4-[(2,2,2-trifluoroethoxy)methyl]phenyl}-1,2,4-oxadiazol-3-yl)-1,3,5-triazine-2,4-diamine;
2-N-methyl-2-N-phenyl-6-[5-(4-phenylpiperidin-1-yl)-1,2,4-oxadiazol-3-yl]-1,3,5-triazine-2,4-diamine;
tert-butyl (2R)-2-(3-{4-amino-6-[methyl(phenyl)amino]-1,3,5-triazin-2-yl}-1,2,4-oxadiazol-5-yl)pyrrolidine-1-carboxylate;
2-N-methyl-2-N-phenyl-6-{5-[4-(pyridin-2-yloxy)piperidin-1-yl]-1,2,4-oxadiazol-3-yl}-1,3,5-triazine-2,4-diamine;
1-(3-{4-amino-6-[methyl(phenyl)amino]-1,3,5-triazin-2-yl}-1,2,4-oxadiazol-5-yl)-4-phenylpiperidin-4-ol;
6-{5-[6-(cyclohexyloxy)pyridin-3-yl]-1,2,4-oxadiazol-3-yl}-2-N-methyl-2-N-phenyl-1,3,5-triazine-2,4-diamine;
2-N-methyl-2-N-phenyl-6-(5-{6-[(1,1,1-trifluoropropan-2-yl)oxy]pyridin-3-yl}-1,2,4-oxadiazol-3-yl)-1,3,5-triazine-2,4-diamine;
2-N-methyl-2-N-phenyl-6-(5-{5-[1-(2,2,2-trifluoroethoxy)ethyl]pyridin-2-yl}-1,2,4-oxadiazol-3-yl)-1,3,5-triazine-2,4-diamine;
2-N-methyl-2-N-phenyl-6-{5-[6-(3,3,3-trifluoropropoxy)pyridin-3-yl]-1,2,4-oxadiazol-3-yl}-1,3,5-triazine-2,4-diamine;
6-[5-(4-methoxy-4-phenylpiperidin-1-yl)-1,2,4-oxadiazol-3-yl]-2-N-methyl-2-N-phenyl-1,3,5-triazine-2,4-diamine;
2-N-methyl-6-{5-[6-(oxan-4-yloxy)pyridin-3-yl]-1,2,4-oxadiazol-3-yl}-2-N-phenyl-1,3,5-triazine-2,4-diamine;
2-N-methyl-2-N-phenyl-6-(5-{4-[(2,2,2-trifluoroethyl)sulfanyl]piperidin-1-yl}-1,2,4-oxadiazol-3-yl)-1,3,5-triazine-2,4-diamine;
2-N-phenyl-6-{5-[6-(3,3,3-trifluoropropoxy)pyridin-3-yl]-1,2,4-oxadiazol-3-yl}-1,3,5-triazine-2,4-diamine;
2-N-methyl-6-(5-{6-[(1-methylpyrrolidin-3-yl)oxy]pyridin-3-yl}-1,2,4-oxadiazol-3-yl)-2-N-phenyl-1,3,5-triazine-2,4-diamine;
2-N-methyl-2-N-phenyl-6-(5-{4-[(2,2,2-trifluoroethane)sulfonyl]piperidin-1-yl}-1,2,4-oxadiazol-3-yl)-1,3,5-triazine-2,4-diamine;
2-N-methyl-2-N-phenyl-6-(5-{6-[2-(2,2,2-trifluoroethoxy)ethoxy]pyridin-3-yl}-1,2,4-oxadiazol-3-yl)-1,3,5-triazine-2,4-diamine;
2-N-methyl-2-N-phenyl-6-{5-[4-(propan-2-ylsulfanyl)piperidin-1-yl]-1,2,4-oxadiazol-3-yl}-1,3,5-triazine-2,4-diamine;
2-N-methyl-2-N-phenyl-6-{5-[4-(propane-2-sulfinyl)piperidin-1-yl]-1,2,4-oxadiazol-3-yl}-1,3,5-triazine-2,4-diamine;
2-(3-{4-amino-6-[methyl(phenyl)amino]-1,3,5-triazin-2-yl}-1,2,4-oxadiazol-5-yl)-N-(cyclopropylmethyl)pyridine-3-carboxamide;
3-(3-{4-amino-6-[methyl(phenyl)amino]-1,3,5-triazin-2-yl}-1,2,4-oxadiazol-5-yl)-N-(cyclopropylmethyl)pyridine-2-carboxamide;
2-(3-{4-amino-6-[methyl(phenyl)amino]-1,3,5-triazin-2-yl}-1,2,4-oxadiazol-5-yl)-N-cyclobutylpyridine-3-carboxamide;

6-{5-[6-(2,2-difluoroethoxy)pyridin-3-yl]-1,2,4-oxadiazol-3-yl}-2-N-methyl-2-N-phenyl-1,3,5-triazine-2,4-diamine;
3-(3-{4-amino-6-[methyl(phenyl)amino]-1,3,5-triazin-2-yl}-1,2,4-oxadiazol-5-yl)-N-cyclopropylpyridine-2-carboxamide;
3-(3-{4-amino-6-[methyl(phenyl)amino]-1,3,5-triazin-2-yl}-1,2,4-oxadiazol-5-yl)-N-cyclobutylpyridine-2-carboxamide;
3-(3-{4-amino-6-[methyl(phenyl)amino]-1,3,5-triazin-2-yl}-1,2,4-oxadiazol-5-yl)-N-(2,2,2-trifluoroethyl)pyridine-2-carboxamide;
2-(3-{4-amino-6-[methyl(phenyl)amino]-1,3,5-triazin-2-yl}-1,2,4-oxadiazol-5-yl)-N-cyclopropylpyridine-3-carboxamide;
cyclopropylmethyl 2-(3-{4-amino-6-[methyl(phenyl)amino]-1,3,5-triazin-2-yl}-1,2,4-oxadiazol-5-yl)pyridine-3-carboxylate;
cyclopropylmethyl 3-(3-{4-amino-6-[methyl(phenyl)amino]-1,3,5-triazin-2-yl}-1,2,4-oxadiazol-5-yl)pyridine-2-carboxylate;
cyclopentyl 2-(3-{4-amino-6-[methyl(phenyl)amino]-1,3,5-triazin-2-yl}-1,2,4-oxadiazol-5-yl)pyridine-3-carboxylate;
cyclopentyl 3-(3-{4-amino-6-[methyl(phenyl)amino]-1,3,5-triazin-2-yl}-1,2,4-oxadiazol-5-yl)pyridine-2-carboxylate;
2-(3-{4-amino-6-[methyl(phenyl)amino]-1,3,5-triazin-2-yl}-1,2,4-oxadiazol-5-yl)-N-(2,2,2-trifluoroethyl)pyridine-3-carboxamide;
tert-butyl 3-(3-{4-amino-6-[methyl(phenyl)amino]-1,3,5-triazin-2-yl}-1,2,4-oxadiazol-5-yl)azetidine-1-carboxylate;
6-[5-(1-benzylazetidin-3-yl)-1,2,4-oxadiazol-3-yl]-2-N-methyl-2-N-phenyl-1,3,5-triazine-2,4-diamine;
1-[3-(3-{4-amino-6-[methyl(phenyl)amino]-1,3,5-triazin-2-yl}-1,2,4-oxadiazol-5-yl)azetidin-1-yl]ethan-1-one;
2-N-methyl-2-N-phenyl-6-{5-[1-(3,3,3-trifluoropropyl)azetidin-3-yl]-1,2,4-oxadiazol-3-yl}-1,3,5-triazine-2,4-diamine;
6-(3-{4-amino-6-[methyl(phenyl)amino]-1,3,5-triazin-2-yl}-1,2,4-oxadiazol-5-yl)-3-benzyl-3-azabicyclo[3.1.0]hexane-2,4-dione;
2-N-methyl-2-N-phenyl-6-{5-[6-[(2,2,2-trifluoroethoxy)methyl]-3-azabicyclo[3.1.0]hexan-3-yl]-1,2,4-oxadiazol-3-yl}-1,3,5-triazine-2,4-diamine;
4-(3-{4-amino-6-[methyl(phenyl)amino]-1,3,5-triazin-2-yl}-1,2,4-oxadiazol-5-yl)-N,N-dimethylpiperazine-1-sulfonamide;
2-N-methyl-2-N-phenyl-6-(5-{4-[(2,2,2-trifluoroethane)sulfonyl]piperazin-1-yl}-1,2,4-oxadiazol-3-yl)-1,3,5-triazine-2,4-diamine;
2-N-phenyl-6-{5-[6-[(2,2,2-trifluoroethoxy)methyl]-3-azabicyclo[3.1.0]hexan-3-yl]-1,2,4-oxadiazol-3-yl}-1,3,5-triazine-2,4-diamine;
2-N-methyl-6-{5-[6-(phenoxymethyl)-3-azabicyclo[3.1.0]hexan-3-yl]-1,2,4-oxadiazol-3-yl}-2-N-phenyl-1,3,5-triazine-2,4-diamine;
6-{5-[6-(phenoxymethyl)-3-azabicyclo[3.1.0]hexan-3-yl]-1,2,4-oxadiazol-3-yl}-2-N-phenyl-1,3,5-triazine-2,4-diamine;
6-{5-[6-[(cyclopropylmethoxy)methyl]-3-azabicyclo[3.1.0]hexan-3-yl]-1,2,4-oxadiazol-3-yl}-2-N-phenyl-1,3,5-triazine-2,4-diamine;
2-N-phenyl-6-{5-[6-[(3,3,3-trifluoropropoxy)methyl]-3-azabicyclo[3.1.0]hexan-3-yl]-1,2,4-oxadiazol-3-yl}-1,3,5-triazine-2,4-diamine;
6-{5-[6-[(cyclopropylmethoxy)methyl]-3-azabicyclo[3.1.0]hexan-3-yl]-1,2,4-oxadiazol-3-yl}-2-N-methyl-2-N-phenyl-1,3,5-triazine-2,4-diamine;
2-N-methyl-2-N-phenyl-6-{5-[6-[(3,3,3-trifluoropropoxy)methyl]-3-azabicyclo[3.1.0]hexan-3-yl]-1,2,4-oxadiazol-3-yl}-1,3,5-triazine-2,4-diamine;
2-N-methyl-2-N-phenyl-6-{5-[6-[(propan-2-yloxy)methyl]-3-azabicyclo[3.1.0]hexan-3-yl]-1,2,4-oxadiazol-3-yl}-1,3,5-triazine-2,4-diamine;
2-N-phenyl-6-{5-[(1R,5S,6S)-6-[(propan-2-yloxy)methyl]-3-azabicyclo[3.1.0]hexan-3-yl]-1,2,4-oxadiazol-3-yl}-1,3,5-triazine-2,4-diamine;
6-{5-[6-[(cyclopentyloxy)methyl]-3-azabicyclo[3.1.0]hexan-3-yl]-1,2,4-oxadiazol-3-yl}-2-N-methyl-2-N-phenyl-1,3,5-triazine-2,4-diamine;
6-{5-[6-[(cyclopentyloxy)methyl]-3-azabicyclo[3.1.0]hexan-3-yl]-1,2,4-oxadiazol-3-yl}-2-N-phenyl-1,3,5-triazine-2,4-diamine;
2-N-methyl-2-N-phenyl-6-{5-[(4-{[(2,2,2-trifluoroethyl)sulfanyl]methyl}piperidin-1-yl)carbonyl]-1,2,4-oxadiazol-3-yl}-1,3,5-triazine-2,4-diamine;
2-N-methyl-2-N-phenyl-6-(5-{[-6-[(2,2,2-trifluoroethoxy)methyl]-3-azabicyclo[3.1.0]hexan-3-yl]carbonyl}-1,2,4-oxadiazol-3-yl)-1,3,5-triazine-2,4-diamine;
2-N-methyl-2-N-phenyl-6-(5-{[-6-[(3,3,3-trifluoropropoxy)methyl]-3-azabicyclo[3.1.0]hexan-3-yl]carbonyl}-1,2,4-oxadiazol-3-yl)-1,3,5-triazine-2,4-diamine;
6-(5-{[-6-[(cyclopropylmethoxy)methyl]-3-azabicyclo[3.1.0]hexan-3-yl]carbonyl}-1,2,4-oxadiazol-3-yl)-2-N-methyl-2-N-phenyl-1,3,5-triazine-2,4-diamine;
6-(5-{[-6-[(cyclopentyloxy)methyl]-3-azabicyclo[3.1.0]hexan-3-yl]carbonyl}-1,2,4-oxadiazol-3-yl)-2-N-methyl-2-N-phenyl-1,3,5-triazine-2,4-diamine;
2-N-methyl-6-(5-{[-6-(phenoxymethyl)-3-azabicyclo[3.1.0]hexan-3-yl]carbonyl}-1,2,4-oxadiazol-3-yl)-2-N-phenyl-1,3,5-triazine-2,4-diamine;
2-N-(3-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine;
2-N-(2-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine;
2-N-(3-chlorophenyl)-2-N-methyl-6-{5-[6-(2,2,2-trifluoroethoxy)pyridin-3-yl]-1,2,4-oxadiazol-3-yl}-1,3,5-triazine-2,4-diamine;
2-N-(4-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine;
2-N-(2,3-difluorophenyl)-2-N-methyl-6-{5-[6-(2,2,2-trifluoroethoxy)pyridin-3-yl]-1,2,4-oxadiazol-3-yl}-1,3,5-triazine-2,4-diamine;
2-N-methyl-2-N-(3-methylphenyl)-6-{5-[6-(2,2,2-trifluoroethoxy)pyridin-3-yl]-1,2,4-oxadiazol-3-yl}-1,3,5-triazine-2,4-diamine;
2-N-(3-chloro-4-fluorophenyl)-6-{5-[6-(2,2,2-trifluoroethoxy)pyridin-3-yl]-1,2,4-oxadiazol-3-yl}-1,3,5-triazine-2,4-diamine;
2-N-(3-chloro-4-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine;
6-[5-(6-methoxypyridin-2-yl)-1,2,4-oxadiazol-3-yl]-2-N-methyl-2-N-phenyl-1,3,5-triazine-2,4-diamine;
2-N-(3,4-difluorophenyl)-6-{5-[6-(2,2,2-trifluoroethoxy)pyridin-3-yl]-1,2,4-oxadiazol-3-yl}-1,3,5-triazine-2,4-diamine;

2-N-(2,4-difluorophenyl)-2-N-methyl-6-{5-[6-(2,2,2-trifluoroethoxy)pyridin-3-yl]-1,2,4-oxadiazol-3-yl}-1,3,5-triazine-2,4-diamine;

6-[5-(6-chloropyridin-3-yl)-1,2,4-oxadiazol-3-yl]-2-N-methyl-2-N-phenyl-1,3,5-triazine-2,4-diamine;

6-[5-(2-ethoxypyridin-3-yl)-1,2,4-oxadiazol-3-yl]-2-N-methyl-2-N-phenyl-1,3,5-triazine-2,4-diamine;

2-N-methyl-2-N-phenyl-6-{5-[5-(trifluoromethyl)pyridin-2-yl]-1,2,4-oxadiazol-3-yl}-1,3,5-triazine-2,4-diamine;

6-[5-(4-methanesulfonylphenyl)-1,2,4-oxadiazol-3-yl]-2-N-methyl-2-N-phenyl-1,3,5-triazine-2,4-diamine;

6-[5-(4-aminocyclohexyl)-1,2,4-oxadiazol-3-yl]-2-N-methyl-2-N-phenyl-1,3,5-triazine-2,4-diamine;

tert-butyl N-[4-(3-{4-amino-6-[methyl(phenyl)amino]-1,3,5-triazin-2-yl}-1,2,4-oxadiazol-5-yl)cyclohexyl]carbamate;

4-(3-{4-amino-6-[methyl(phenyl)amino]-1,3,5-triazin-2-yl}-1,2,4-oxadiazol-5-yl)cyclohexan-1-ol;

N-[4-(3-{4-amino-6-[methyl(phenyl)amino]-1,3,5-triazin-2-yl}-1,2,4-oxadiazol-5-yl)cyclohexyl]-2-methylpropanamide;

N-[4-(3-{4-amino-6-[methyl(phenyl)amino]-1,3,5-triazin-2-yl}-1,2,4-oxadiazol-5-yl)cyclohexyl]-2-cyclopropylacetamide;

N-[4-(3-{4-amino-6-[methyl(phenyl)amino]-1,3,5-triazin-2-yl}-1,2,4-oxadiazol-5-yl)cyclohexyl]-3,3,3-trifluoropropanamide;

N-[4-(3-{4-amino-6-[methyl(phenyl)amino]-1,3,5-triazin-2-yl}-1,2,4-oxadiazol-5-yl)cyclohexyl]-2,2,2-trifluoroacetamide;

2-N-methyl-6-[5-(4-phenoxycyclohexyl)-1,2,4-oxadiazol-3-yl]-2-N-phenyl-1,3,5-triazine-2,4-diamine;

2-N-phenyl-6-{5-[3-(trifluoromethyl)pyridin-2-yl]-1,2,4-oxadiazol-3-yl}-1,3,5-triazine-2,4-diamine;

6-[5-(3-chloropyridin-2-yl)-1,2,4-oxadiazol-3-yl]-2-N-phenyl-1,3,5-triazine-2,4-diamine 2-N-(6-fluoropyridin-3-yl)-2-N-methyl-6-{5-[6-(2,2,2-trifluoroethoxy)pyridin-3-yl]-1,2,4-oxadiazol-3-yl}-1,3,5-triazine-2,4-diamine;

2-N-methyl-6-{5-[(3S)-3-phenoxypyrrolidin-1-yl]-1,2,4-oxadiazol-3-yl}-2-N-phenyl-1,3,5-triazine-2,4-diamine;

2-N-methyl-6-{5-[(3R)-3-phenoxypyrrolidin-1-yl]-1,2,4-oxadiazol-3-yl}-2-N-phenyl-1,3,5-triazine-2,4-diamine;

2-N-(2-methoxyethyl)-2-N-phenyl-6-{5-[6-(2,2,2-trifluoroethoxy)pyridin-3-yl]-1,2,4-oxadiazol-3-yl}-1,3,5-triazine-2,4-diamine;

2-N-(2-methoxyethyl)-6-[5-(3-phenoxyazetidin-1-yl)-1,2,4-oxadiazol-3-yl]-2-N-phenyl-1,3,5-triazine-2,4-diamine;

6-[5-(2-fluoro-6-methoxyphenyl)-1,2,4-oxadiazol-3-yl]-2-N-(2-methoxyethyl)-2-N-phenyl-1,3,5-triazine-2,4-diamine;

2-N-methyl-2-N-phenyl-6-{5-[(2S)-pyrrolidin-2-yl]-1,2,4-oxadiazol-3-yl}-1,3,5-triazine-2,4-diamine hydrochloride;

2-N-methyl-2-N-phenyl-6-{5-[(2R)-pyrrolidin-2-yl]-1,2,4-oxadiazol-3-yl}-1,3,5-triazine-2,4-diamine hydrochloride;

tert-butyl (2S)-2-(3-{4-amino-6-[methyl(phenyl)amino]-1,3,5-triazin-2-yl}-1,2,4-oxadiazol-5-yl)pyrrolidine-1-carboxylate;

2-N-methyl-2-N-phenyl-6-{5-[(2S)-1-(3,3,3-trifluoropropyl)pyrrolidin-2-yl]-1,2,4-oxadiazol-3-yl}-1,3,5-triazine-2,4-diamine;

2-N-methyl-2-N-phenyl-6-{5-[(2R)-1-(3,3,3-trifluoropropyl)pyrrolidin-2-yl]-1,2,4-oxadiazol-3-yl}-1,3,5-triazine-2,4-diamine;

2-N-methyl-2-N-phenyl-6-{5-[(3R)-3-(2,2,2-trifluoroethoxy)pyrrolidin-1-yl]-1,2,4-oxadiazol-3-yl}-1,3,5-triazine-2,4-diamine;

6-{5-[(2R)-2-(methoxymethyl)pyrrolidin-1-yl]-1,2,4-oxadiazol-3-yl}-2-N-methyl-2-N-phenyl-1,3,5-triazine-2,4-diamine;

2-N-methyl-2-N-phenyl-6-{5-[(3S)-3-(2,2,2-trifluoroethoxy)pyrrolidin-1-yl]-1,2,4-oxadiazol-3-yl}-1,3,5-triazine-2,4-diamine;

6-{5-[(2S)-2-(methoxymethyl)pyrrolidin-1-yl]-1,2,4-oxadiazol-3-yl}-2-N-methyl-2-N-phenyl-1,3,5-triazine-2,4-diamine;

2-N-methyl-6-{5-[(2R)-1-[(2-methylpropane)sulfonyl]pyrrolidin-2-yl]-1,2,4-oxadiazol-3-yl}-2-N-phenyl-1,3,5-triazine-2,4-diamine;

2-N-methyl-2-N-phenyl-6-{5-[(2R)-1-[(2,2,2-trifluoroethane)sulfonyl]pyrrolidin-2-yl]-1,2,4-oxadiazol-3-yl}-1,3,5-triazine-2,4-diamine;

1-[(2R)-2-(3-{4-amino-6-[methyl(phenyl)amino]-1,3,5-triazin-2-yl}-1,2,4-oxadiazol-5-yl)pyrrolidin-1-yl]-2-cyclopropylethan-1-one;

1-[(2S)-2-(3-{4-amino-6-[methyl(phenyl)amino]-1,3,5-triazin-2-yl}-1,2,4-oxadiazol-5-yl)pyrrolidin-1-yl]-2-cyclopropylethan-1-one;

1-[(2S)-2-(3-{4-amino-6-[methyl(phenyl)amino]-1,3,5-triazin-2-yl}-1,2,4-oxadiazol-5-yl)pyrrolidin-1-yl]-3,3,3-trifluoropropan-1-one;

6-(5-{6-[(cyclopropylmethyl)sulfanyl]pyridin-3-yl}-1,2,4-oxadiazol-3-yl)-2-N-methyl-2-N-phenyl-1,3,5-triazine-2,4-diamine;

2-N-methyl-2-N-phenyl-6-(5-{6-[(3,3,3-trifluoropropyl)sulfanyl]pyridin-3-yl}-1,2,4-oxadiazol-3-yl)-1,3,5-triazine-2,4-diamine;

2-N-methyl-2-N-phenyl-6-(5-{6-[(3,3,3-trifluoropropane)sulfonyl]pyridin-3-yl}-1,2,4-oxadiazol-3-yl)-1,3,5-triazine-2,4-diamine;

2-N-methyl-2-N-phenyl-6-(5-{6-[(3,3,3-trifluoropropane)sulfinyl]pyridin-3-yl}-1,2,4-oxadiazol-3-yl)-1,3,5-triazine-2,4-diamine;

6-{5-[6-(cyclopropylmethane)sulfinylpyridin-3-yl]-1,2,4-oxadiazol-3-yl}-2-N-methyl-2-N-phenyl-1,3,5-triazine-2,4-diamine;

2-N-phenyl-6-(5-{[4-(2,2,2-trifluoroethoxy)piperidin-1-yl]carbonyl}-1,2,4-oxadiazol-3-yl)-1,3,5-triazine-2,4-diamine;

6-{5-[(4-ethoxypiperidin-1-yl)carbonyl]-1,2,4-oxadiazol-3-yl}-2-N-methyl-2-N-phenyl-1,3,5-triazine-2,4-diamine;

6-[5-({4-[(cyclopropylmethoxy)methyl]piperidin-1-yl}carbonyl)-1,2,4-oxadiazol-3-yl]-2-N-methyl-2-N-phenyl-1,3,5-triazine-2,4-diamine;

2-N-methyl-2-N-phenyl-6-[5-({4-[(2,2,2-trifluoroethoxy)methyl]piperidin-1-yl}carbonyl)-1,2,4-oxadiazol-3-yl]-1,3,5-triazine-2,4-diamine;

2-N-phenyl-6-[5-({4-[(2,2,2-trifluoroethoxy)methyl]piperidin-1-yl}carbonyl)-1,2,4-oxadiazol-3-yl]-1,3,5-triazine-2,4-diamine;

6-(5-{[4-(cyclopropylmethoxy)piperidin-1-yl]carbonyl}-1,2,4-oxadiazol-3-yl)-2-N-phenyl-1,3,5-triazine-2,4-diamine;

6-[5-({4-[(cyclopropylmethoxy)methyl]piperidin-1-yl}carbonyl)-1,2,4-oxadiazol-3-yl]-2-N-phenyl-1,3,5-triazine-2,4-diamine;

2-N-methyl-2-N-phenyl-6-[5-({4-[(3,3,3-trifluoropropoxy)methyl]piperidin-1-yl}carbonyl)-1,2,4-oxadiazol-3-yl]-1,3,5-triazine-2,4-diamine;

2-N-methyl-2-N-phenyl-6-[5-({4-[(2,2,2-trifluoroethyl)sulfanyl]piperidin-1-yl}carbonyl)-1,2,4-oxadiazol-3-yl]-1,3,5-triazine-2,4-diamine;
2-N-phenyl-6-[5-({4-[(2,2,2-trifluoroethyl)sulfanyl]piperidin-1-yl}carbonyl)-1,2,4-oxadiazol-3-yl]-1,3,5-triazine-2,4-diamine;
2-N-methyl-6-[5-(2-methylpyrimidin-5-yl)-1,2,4-oxadiazol-3-yl]-2-N-phenyl-1,3,5-triazine-2,4-diamine;
2-N-methyl-2-N-phenyl-6-[5-(pyrazin-2-yl)-1,2,4-oxadiazol-3-yl]-1,3,5-triazine-2,4-diamine;
2-N-methyl-2-N-phenyl-6-[5-(pyridazin-4-yl)-1,2,4-oxadiazol-3-yl]-1,3,5-triazine-2,4-diamine;
6-[5-(2-methoxypyridin-4-yl)-1,2,4-oxadiazol-3-yl]-2-N-methyl-2-N-phenyl-1,3,5-triazine-2,4-diamine;
2-N-methyl-2-N-phenyl-6-(5-{5-[(2,2,2-trifluoroethyl)amino]pyridin-2-yl}-1,2,4-oxadiazol-3-yl)-1,3,5-triazine-2,4-diamine;
2-N-methyl-2-N-phenyl-6-{5-[2-(2,2,2-trifluoroethoxy)pyridin-4-yl]-1,2,4-oxadiazol-3-yl}-1,3,5-triazine-2,4-diamine;
2-N-methyl-2-N-phenyl-6-{5-[6-(piperidin-1-yl)pyridin-3-yl]-1,2,4-oxadiazol-3-yl}-1,3,5-triazine-2,4-diamine;
2-N-(4-fluorophenyl)-6-[5-(3-fluoropyridin-2-yl)-1,2,4-oxadiazol-3-yl]-2-N-methyl-1,3,5-triazine-2,4-diamine;
2-N-(2-fluorophenyl)-6-[5-(3-fluoropyridin-2-yl)-1,2,4-oxadiazol-3-yl]-2-N-methyl-1,3,5-triazine-2,4-diamine;
2-N-(3-fluorophenyl)-6-[5-(3-fluoropyridin-2-yl)-1,2,4-oxadiazol-3-yl]-2-N-methyl-1,3,5-triazine-2,4-diamine;
2-N-methyl-2-N-phenyl-6-{5-[2-(2,2,2-trifluoroethoxy)pyridin-3-yl]-1,2,4-oxadiazol-3-yl}-1,3,5-triazine-2,4-diamine;
5-(3-{4-amino-6-[methyl(phenyl)amino]-1,3,5-triazin-2-yl}-1,2,4-oxadiazol-5-yl)-N,N-dimethylpyridine-2-carboxamide;
2-N-methyl-2-N-phenyl-6-[5-(pyridazin-3-yl)-1,2,4-oxadiazol-3-yl]-1,3,5-triazine-2,4-diamine;
6-[5-(3-ethoxypyridin-2-yl)-1,2,4-oxadiazol-3-yl]-2-N-methyl-2-N-phenyl-1,3,5-triazine-2,4-diamine;
6-{5-[3-(cyclopropylamino)pyridin-2-yl]-1,2,4-oxadiazol-3-yl}-2-N-methyl-2-N-phenyl-1,3,5-triazine-2,4-diamine;
6-[5-(3-fluoropyridin-2-yl)-1,2,4-oxadiazol-3-yl]-2-N-methyl-2-N-phenyl-1,3,5-triazine-2,4-diamine;
6-{5-[3-(2-methoxyethoxy)pyridin-2-yl]-1,2,4-oxadiazol-3-yl}-2-N-methyl-2-N-phenyl-1,3,5-triazine-2,4-diamine;
2-N-methyl-2-N-phenyl-6-{5-[3-(propan-2-yloxy)pyridin-2-yl]-1,2,4-oxadiazol-3-yl}-1,3,5-triazine-2,4-diamine;
6-[5-(3-methoxypyridin-2-yl)-1,2,4-oxadiazol-3-yl]-2-N-methyl-2-N-phenyl-1,3,5-triazine-2,4-diamine;
2-N-methyl-2-N-phenyl-6-{5-[3-(2,2,2-trifluoroethoxy)pyridin-2-yl]-1,2,4-oxadiazol-3-yl}-1,3,5-triazine-2,4-diamine;
6-(5-{3-[(cyclopropylmethyl)amino]pyridin-2-yl}-1,2,4-oxadiazol-3-yl)-2-N-methyl-2-N-phenyl-1,3,5-triazine-2,4-diamine;
6-{5-[3-(cyclobutylamino)pyridin-2-yl]-1,2,4-oxadiazol-3-yl}-2-N-methyl-2-N-phenyl-1,3,5-triazine-2,4-diamine;
2-N-methyl-6-[5-(3-phenoxyazetidin-1-yl)-1,2,4-oxadiazol-3-yl]-2-N-phenyl-1,3,5-triazine-2,4-diamine;
2-N-methyl-6-{5-[3-(morpholin-4-yl)pyridin-2-yl]-1,2,4-oxadiazol-3-yl}-2-N-phenyl-1,3,5-triazine-2,4-diamine;
6-[5-(3-cyclobutoxypyridin-2-yl)-1,2,4-oxadiazol-3-yl]-2-N-methyl-2-N-phenyl-1,3,5-triazine-2,4-diamine;
2-N-methyl-2-N-phenyl-6-{5-[3-(propan-2-yloxy)azetidin-1-yl]-1,2,4-oxadiazol-3-yl}-1,3,5-triazine-2,4-diamine;
6-[5-(3-methoxyazetidin-1-yl)-1,2,4-oxadiazol-3-yl]-2-N-methyl-2-N-phenyl-1,3,5-triazine-2,4-diamine;
2-N-methyl-2-N-phenyl-6-{5-[3-(2,2,2-trifluoroethoxy)azetidin-1-yl]-1,2,4-oxadiazol-3-yl}-1,3,5-triazine-2,4-diamine;
2-N-methyl-6-{5-[3-(phenoxymethyl)azetidin-1-yl]-1,2,4-oxadiazol-3-yl}-2-N-phenyl-1,3,5-triazine-2,4-diamine;
2-N-methyl-2-N-phenyl-6-(5-{3-[(3,3,3-trifluoropropoxy)methyl]azetidin-1-yl}-1,2,4-oxadiazol-3-yl)-1,3,5-triazine-2,4-diamine;
2-N-methyl-2-N-phenyl-6-(5-{5-[(2,2,2-trifluoroethoxy)methyl]furan-2-yl}-1,2,4-oxadiazol-3-yl)-1,3,5-triazine-2,4-diamine;
6-{5-[3-(cyclopropylmethoxy)azetidin-1-yl]-1,2,4-oxadiazol-3-yl}-2-N-methyl-2-N-phenyl-1,3,5-triazine-2,4-diamine;
2-N-methyl-2-N-phenyl-6-{5-[3-(pyridin-2-yloxy)azetidin-1-yl]-1,2,4-oxadiazol-3-yl}-1,3,5-triazine-2,4-diamine;
2-N-methyl-6-(5-{8-oxa-3-azabicyclo[3.2.1]octan-3-yl}-1,2,4-oxadiazol-3-yl)-2-N-phenyl-1,3,5-triazine-2,4-diamine;
2-N-methyl-2-N-phenyl-6-(5-{4-[(3,3,3-trifluoropropoxy)methyl]piperidin-1-yl}-1,2,4-oxadiazol-3-yl)-1,3,5-triazine-2,4-diamine;
2-N-phenyl-6-{5-[2-(2,2,2-trifluoroethoxy)pyridin-3-yl]-1,2,4-oxadiazol-3-yl}-1,3,5-triazine-2,4-diamine;
6-[5-(3-phenoxyazetidin-1-yl)-1,2,4-oxadiazol-3-yl]-2-N-phenyl-1,3,5-triazine-2,4-diamine
2-N-methyl-2-N-phenyl-6-{5-[4-(propane-2-sulfonyl)piperazin-1-yl]-1,2,4-oxadiazol-3-yl}-1,3,5-triazine-2,4-diamine;
tert-butyl 4-(3-{4-amino-6-[methyl(phenyl)amino]-1,3,5-triazin-2-yl}-1,2,4-oxadiazol-5-yl)piperidine-1-carboxylate;
6-{5-[1-(cyclopropanesulfonyl)piperidin-4-yl]-1,2,4-oxadiazol-3-yl}-2-N-methyl-2-N-phenyl-1,3,5-triazine-2,4-diamine;
2-N-methyl-6-(5-{1-[(2-methylpropane)sulfonyl]piperidin-4-yl}-1,2,4-oxadiazol-3-yl)-2-N-phenyl-1,3,5-triazine-2,4-diamine;
6-{5-[1-(butane-2-sulfonyl)piperidin-4-yl]-1,2,4-oxadiazol-3-yl}-2-N-methyl-2-N-phenyl-1,3,5-triazine-2,4-diamine;
6-{5-[1-(cyclopentanesulfonyl)piperidin-4-yl]-1,2,4-oxadiazol-3-yl}-2-N-methyl-2-N-phenyl-1,3,5-triazine-2,4-diamine;
2-N-methyl-6-{5-[1-(2-methylpropyl)piperidin-4-yl]-1,2,4-oxadiazol-3-yl}-2-N-phenyl-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine;
tert-butyl 4-{3-[4-amino-6-(phenylamino)-1,3,5-triazin-2-yl]-1,2,4-oxadiazol-5-yl}piperidine-1-carboxylate;
6-{5-[1-(cyclopropanesulfonyl)piperidin-4-yl]-1,2,4-oxadiazol-3-yl}-2-N-phenyl-1,3,5-triazine-2,4-diamine;
6-{5-[1-(butane-2-sulfonyl)piperidin-4-yl]-1,2,4-oxadiazol-3-yl}-2-N-phenyl-1,3,5-triazine-2,4-diamine;
2-N-phenyl-6-{5-[1-(propane-2-sulfonyl)piperidin-4-yl]-1,2,4-oxadiazol-3-yl}-1,3,5-triazine-2,4-diamine;
6-{5-[1-(cyclopentanesulfonyl)piperidin-4-yl]-1,2,4-oxadiazol-3-yl}-2-N-phenyl-1,3,5-triazine-2,4-diamine; and
4-{3-[4-amino-6-(phenylamino)-1,3,5-triazin-2-yl]-1,2,4-oxadiazol-5-yl}-N,N-dimethylpiperidine-1-sulfonamide;
or a pharmaceutically acceptable salt thereof.

Compounds of the formula (I) may have different isomeric forms. As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers, rotamers, atropisomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. If the compound contains an axis of chirality, it might be present in form of atropisomers, which are conformational isomers, where rotation around a single bond is restricted. Atopisomers may be specified either as the $(R_a)$- or $(S_a)$-enantiomer. All rotameric forms are also intended to be included. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns 1 to 12 of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). For isolation or purification purposes it is also possible to use pharmaceutically unacceptable salts, for example picrates or perchlorates. For therapeutic use, only pharmaceutically acceptable salts or free compounds are employed.

In view of the close relationship between the novel compounds of the formula (I) in free form and those in the form of their salts, including those salts that can be used as intermediates, for example in the purification or identification of the novel compounds, any reference to the compounds or a compound of the formula (I) hereinbefore and hereinafter is to be understood as referring to the compound in free form and/or also to one or more salts thereof, as appropriate and expedient, as well as to one or more solvates, e.g. hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$ or those into which non-radioactive isotopes, such as $^{13}C$, are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the formula (I) can generally be prepared by conventional techniques known to those skilled in the art or by processes analogous to those described in the accompanying Examples and Preparations using an appropriate isotopically-labeled reagents in place of the non-labeled reagent previously employed. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the formula (I) that contain groups capable of acting as donors and/or acceptors for hydrogen bonds may be capable of forming co-crystals with suitable co-crystal formers. These co-crystals may be prepared from compounds of the formula (I) by known co-crystal forming procedures. Such procedures include grinding, heating, co-subliming, co-melting, or contacting in solution compounds of the or (I) I) with the co-crystal former under crystallization conditions and isolating co-crystals thereby formed. Suitable co-crystal formers include those described in WO 2004/078163. Hence the invention further provides co-crystals comprising a compound of the formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) selected from chronic pain, such as positive symptoms of chronic pain e.g. parethesias, dyesthesias, hyperalgesia, allodynia and spontaneous pain as well as negative symptoms e.g. loss of sensation, or (ii) mediated by the dysregulation of Nav1.7, or (iii) associated with the dysregulation of Nav1.7, or (iv) characterized by the dysregulation of Nav1.7; or (2) reducing or inhibiting the activity of Nav1.7.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting Nav1.7.

As used herein, the term "subject" refers to an animal. Typically the animal is a mammal.

A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the omega-(amino, mono- or di-lower alkylamino, carboxy, lower alkoxycarbonyl)-lower alkyl esters, the alpha-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, J. Med. Chem. 2503 (1989)). Moreover, drugs containing an acidic NH group, such as imidazole, imide, indole and the like, have been masked with N-acyloxymethyl groups (Bundgaard, Design of Prodrugs, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

The invention relates in a third aspect to the manufacture of a compound of formula (I) as described above The compounds of formula (I) or salts thereof are prepared in accordance with processes known per se, e.g. the synthesis and structures of 4,6-disubstituted 2-(5-alkyl-1,2,4-oxadiazol-3-yl)-1,3,5-triazines have been reported (Russian Chemical Bulletin, 2005, 54(8), 1900-1906), though not previously described for the manufacture of the compounds of the formula (I).

A compound of formula (I) may be prepared according to Schemes 1 to 4.

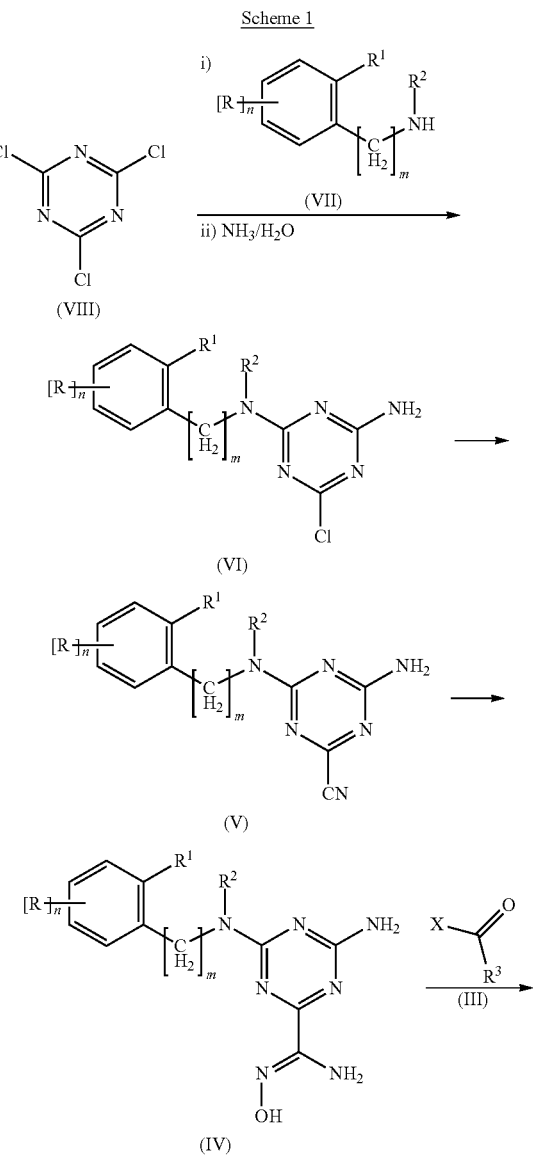

-continued
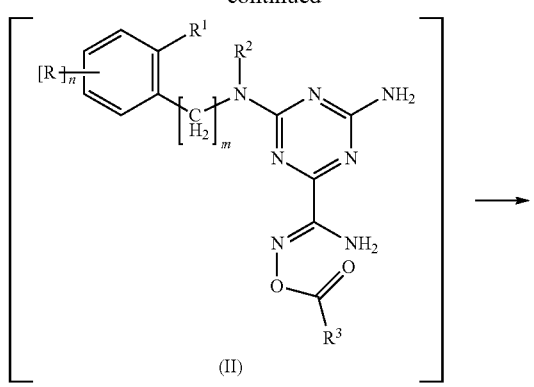
(II)
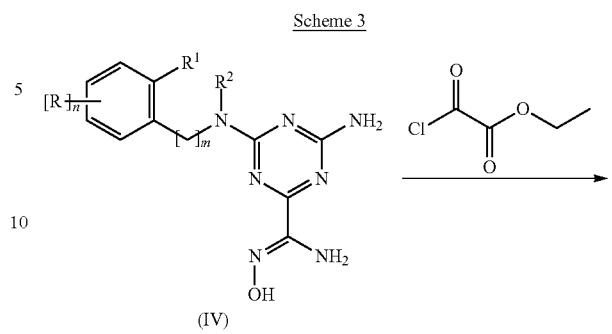
Scheme 3
(IV)
(I) or (Ia)
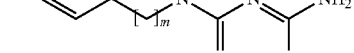
(IX)
Scheme 2
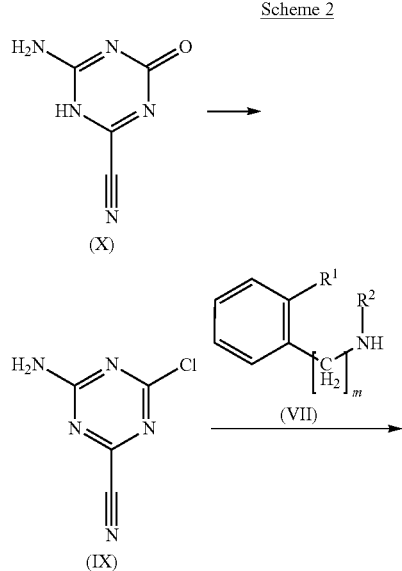
(X)
(VII)
(IX)
(V)
(I) or (Ia)
Scheme 4
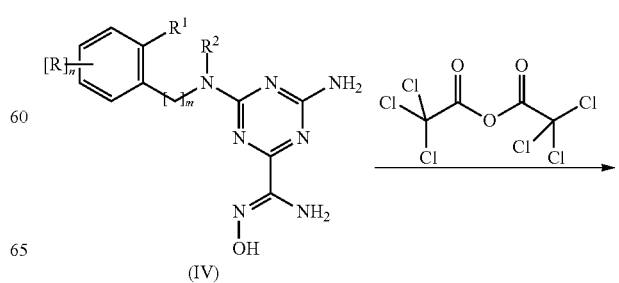
(IV)

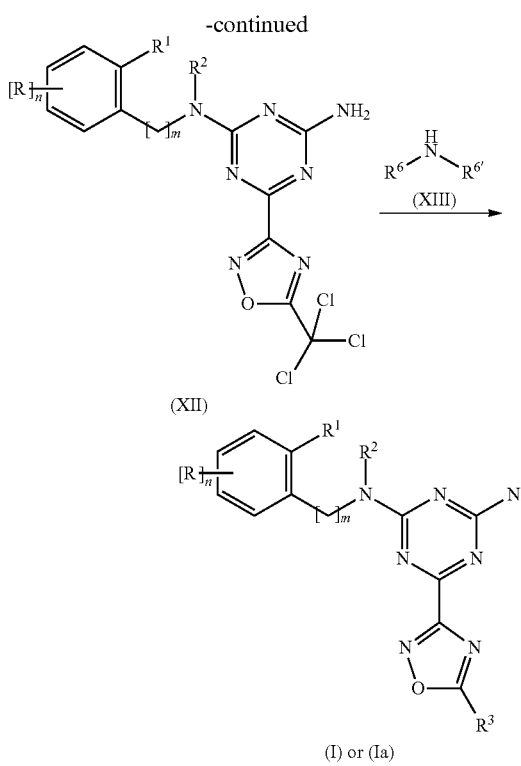

(XII)

(I) or (Ia)

General Reaction Processes:

In one embodiment (Method I), the invention relates to a process for manufacturing a compound of formula (I) comprising the step a) of reacting a compound of formula (IV)

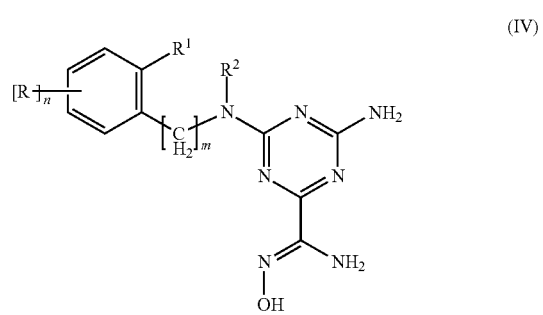

(IV)

wherein the substituents are as defined above, with an acylating agent of formula (III),

(III)

wherein the substituents are as defined above, in the presence of a base e.g. pyridine, suitably in the presence of one or more diluents, particular solvents, e.g. toluene; followed by dehydration leading to cyclization, typically induced by heating. Typical reaction conditions for acylations and dehydrations are known in the field and may applied to the present process. Many compounds of formula (III, X=Cl) are commercially available, alternatively they can be prepared from the corresponding carboxylic acids of formula (III, X=OH) using, for example, oxalyl, phosphoryl or thionyl chloride in the presence of a suitable solvent such as dichloromethane or dichloroethane, optionally in the presence of catalytic DMF at a temperature ranging from room temperature to reflux.

The compound of formula (IV) is obtained comprising the step b) of reacting a compound of formula (V)

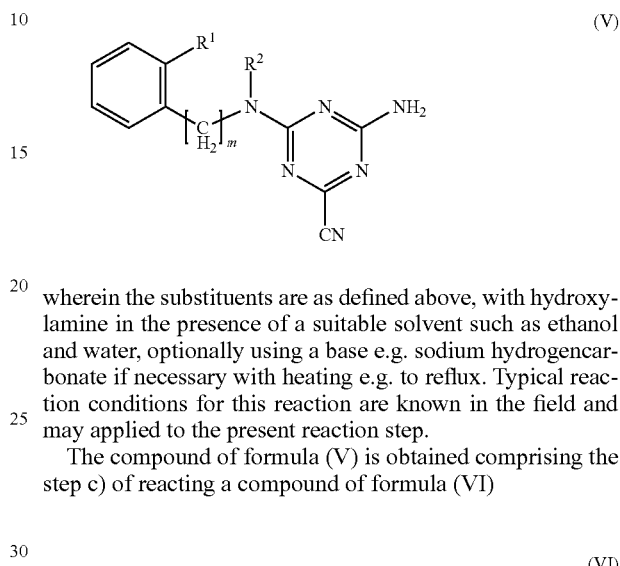

(V)

wherein the substituents are as defined above, with hydroxylamine in the presence of a suitable solvent such as ethanol and water, optionally using a base e.g. sodium hydrogencarbonate if necessary with heating e.g. to reflux. Typical reaction conditions for this reaction are known in the field and may applied to the present reaction step.

The compound of formula (V) is obtained comprising the step c) of reacting a compound of formula (VI)

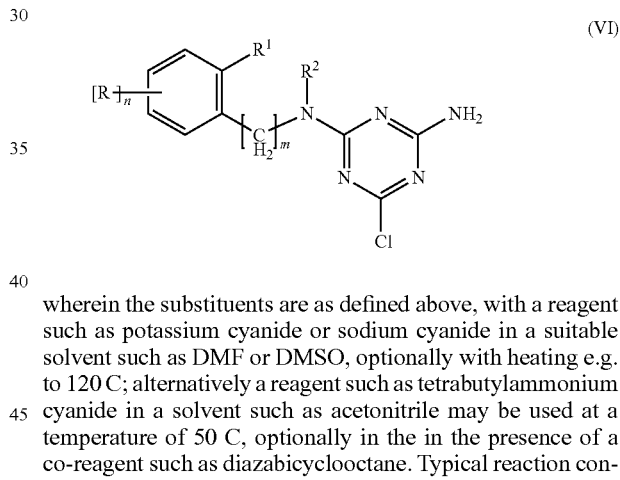

(VI)

wherein the substituents are as defined above, with a reagent such as potassium cyanide or sodium cyanide in a suitable solvent such as DMF or DMSO, optionally with heating e.g. to 120 C; alternatively a reagent such as tetrabutylammonium cyanide in a solvent such as acetonitrile may be used at a temperature of 50 C, optionally in the in the presence of a co-reagent such as diazabicyclooctane. Typical reaction conditions for this reaction are known in the field and may applied to the present reaction step.

The compound of formula (V) where $R^2$=alkyl can be prepared from the compound of formula (V) where $R^2$=H by reaction with an alkylating agent e.g. iodomethane in the presence of a base such as potassium carbonate in a suitable solvent e.g. DMF.

The compound of formula (VI) is obtained comprising the step d) of reacting a compound of formula (VII)

(VII)

wherein the substituents are as defined above, first with, cyanuric chloride (VIII) at 0 C to room temperature followed by treatment with aqueous ammonia in a suitable solvent such as THF. Typical reaction conditions are known in the field and may applied to the present reaction step. Amines of formula (VII) are commercially available, or may be prepared according to standard methods known to those skilled in the art.

In another embodiment (Method II), the invention relates to a process for manufacturing a compound of formula (I) comprising the steps a) and b), wherein the compound of formula (V) is obtained comprising the step c') of reacting a compound of formula (VII)

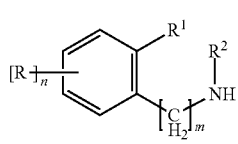
(VII)

wherein the substituents are as defined above, with chlorotriazine (IX) in a suitable solvent such as DMF or DMSO in the presence of a suitable base e.g. DIPEA, optionally with heating to e.g. 90 C. Typical reaction conditions are known in the field and may applied to the present reaction step.

Chlorotriazine (IX) is obtained comprising the step d') of treating 6-amino-4,5-dihydro-4-oxo-1,3,5-triazine-2-carbonitrile (X) (J. Am. Chem. Soc., 1961, 83, 1261-2) with a chlorinating reagent e.g. phosphoryl chloride at reflux. Typical chlorination conditions are known in the field and may applied to the present reaction step.

In another embodiment (Method 2), the invention relates to a process for manufacturing a compound of formula (I) comprising the step a) of reacting an ester of formula (IX)

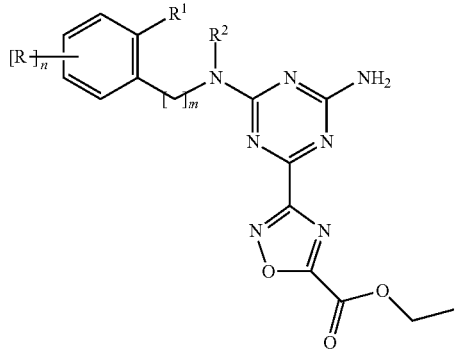
(IX)

with an amine of formula (X) or alcohol of formula (XI), optionally in the presence of a reagent such as trimethylaluminium diazabicyclo-octane complex (for amine (X)) or an acid or base.

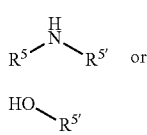
(X)

or (XI)

Typical amide or transesterification conditions are known in the field and may applied to the present reaction step. Amines and alcohols of formulae (X) and (XI) are commercially available, or may be prepared according to standard methods known to those skilled in the art.

An ester of formula (IX) is prepared in step b) by reaction of a compound of formula (IV) with ethyl oxalyl chloride.

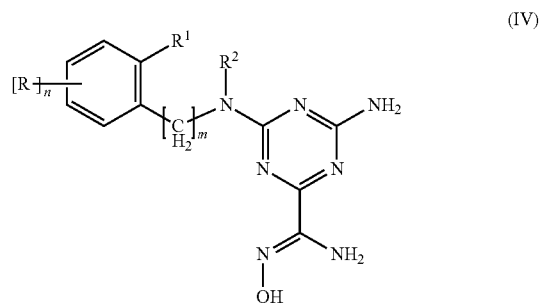
(IV)

In another embodiment (Method 3), the invention relates to a process for manufacturing a compound of formula (I) comprising the step a) of reacting a compound of formula (XII)

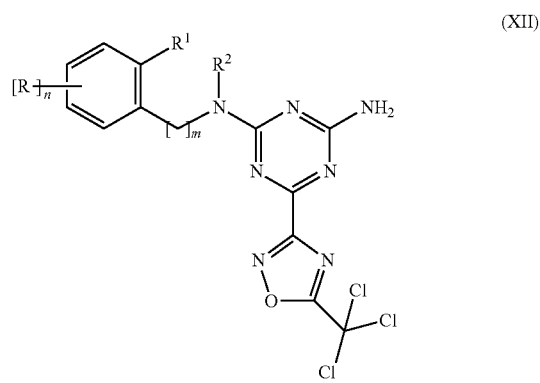
(XII)

with an amine of formula (XIII) in the presence of a suitable base e.g. potassium carbonate in a suitable solvent such as DMF, optionally with heating. Amines of formula (XIII) are commercially available, or may be prepared according to standard methods known to those skilled in the art.

(XIII)

A compound of formula (XIII) is prepared in step b) by reaction of a compound of formula (IV) with trichloroacetic anhydride.

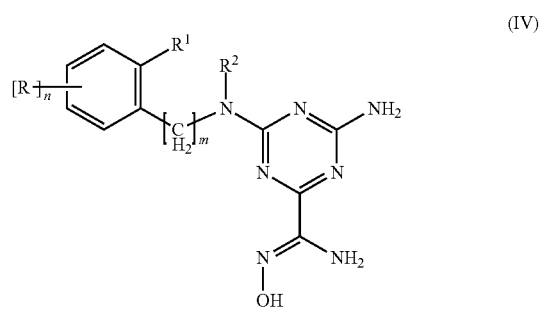
(IV)

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

In the methods describe above, functional groups which are present in the starting materials and are not intended to take part in the reaction, are present in protected form if necessary, and protective groups that are present are cleaved, whereby said starting compounds may also exist in the form of salts provided that a salt-forming group is present and a reaction in salt form is possible. In additional process steps, carried out as desired, functional groups of the starting compounds which should not take part in the reaction may be present in unprotected form or may be protected for example by one or more protective groups. The protective groups are then wholly or partly removed according to one of the known methods. protective groups, and the manner in which they are introduced and removed are described, for example, in "Protective Groups in Organic Chemistry", Plenum Press, London, N.Y. 1973, and in "Methoden der Organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protective groups is that they can be removed readily, i.e. without the occurrence of undesired secondary reactions, for example by solvolysis, reduction, photolysis or alternatively under physiological conditions.

The invention relates in a fourth aspect to the use of compounds of the present invention as pharmaceuticals. Particularly, the compounds of formula (I) have valuable pharmacological properties, as described hereinbefore and hereinafter. The invention thus provides:

a compound of the formula (I) as defined herein, as pharmaceutical/for use as pharmaceutical;

a compound of the formula (I) as defined herein, as medicament/for use as medicament;

a compound of the formula (I) as defined herein, for the treatment of/for use in the treatment of chronic pain;

a compound of the formula (I) as defined herein, for the treatment of/for use in the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation;

a compound of the formula (I) as defined herein, for the treatment of/for use in the treatment of one or more Nav 1.7 mediated disorders or diseases;

the use of a compound of formula (I) as defined herein, for the manufacture of a medicament for the treatment of chronic pain;

the use of a compound of formula (I) as defined herein, for the manufacture of a medicament for the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation;

the use of a compound of formula (I) as defined herein, for the manufacture of a medicament for the treatment of one or more Nav 1.7 mediated disorders or disease;

the use of a compound of formula (I) as defined herein, for the treatment of one or more Nav 1.7 mediated disorders or diseases;

the use of a compound of formula (I) as defined herein, for the treatment of chronic pain;

the use of a compound of formula (I) as defined herein, for the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation;

the use of a compound of formula (I) as defined herein for the inhibition of the Nav 1.7;

the use of a compound of formula (I) as defined herein, for the treatment of one or more Nav 1.7 mediated disorders or diseases;

the use of a compound of formula (I) as defined herein, for the treatment of chronic pain;

the use of a compound of formula (I) as defined herein, for the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation;

a method for the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation, comprising the step of administering to a subject a therapeutically effective amount of a compound of formula (I) as defined herein;

a method of modulating Nav 1.7 activity in a subject, comprising the step of administering to a subject a therapeutically effective amount of a compound of formula (I) as defined herein;

a method for the treatment of a Nav 1.7 mediated disorder or disease comprising the step of administering to a subject a therapeutically effective amount of a compound of formula (I) as defined herein;

a method for inhibition Nav 1.7 in a cell, comprising contacting said cell with an effective amount of a compound of formula (I) as defined herein.

The invention relates in a fifth aspect to pharmaceutical compositions comprising a compound of the present invention. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The invention thus provides
a pharmaceutical composition comprising (i.e. containing or consisting of) a compound of formula (I) as defined herein and one or more carriers/excipients;
a pharmaceutical composition comprising a therapeutically effective amount of a compound of formula (I) as defined herein, and one or more pharmaceutically acceptable carriers/excipients.

The invention relates in a sixth aspect to combinations comprising a compound of formula (I) and one or more additional active ingredients. The invention thus provides
a combination in particular a pharmaceutical combination, comprising a therapeutically effective amount of a compound of formula (I) and one or more therapeutically active agents, particularly pain-relieving agents;
a combined pharmaceutical composition, adapted for simultaneous or sequential administration, comprising a therapeutically effective amount of a compound of formula (I) as defined herein; therapeutically effective amount(s) of one or more combination partners, particularly pain-relieving agents; one or more pharmaceutically acceptable excipients;
a combined pharmaceutical composition as defined herein (i) as pharmaceutical, (ii) for use in the treatment of a Nav1.7 mediated disease, (iii) in a method of treatment of a Nav1.7 mediated disease.

Pain treatment as defined herein may be applied as a sole therapy or may involve, in addition to a compound according to the invention, administration of other analgesics or adjuvant therapy. Such therapy may for example include in combination with a compound of the present invention, one or more of the following categories of pain-relieving ingredients:
a) opioid analgesics, for example morphine, ketobemidone or fentanyl; b) analgesics of the NSAID or COX-1/2 class, for example ibuprofen, naproxen, celecoxib or acetylsalicylic acid, and their analogues containing nitric oxide-donating groups; c) analgesic adjuvants such as amitriptyline, imipramine, duloxetine or mexiletine; d) NMDA antagonists for example ketamine or dextrometorfan; e) sodium channel blocking agents, for example lidocaine; f) anticonvulsants, for example carbamazepine, topiramate or lamotrigine; g) anticonvulsant/analgesic amino acids such as gabapentin or pregabalin; h) cannabinoids.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula (I), can be prepared and administered as described in the art such as in the documents cited above.

In one further embodiment, the additional active ingredient is a hormonal medicine.

EXPERIMENTAL

Examples

The following Examples serve to illustrate the invention without limiting its scope. Abbreviations used are those conventional in the art.

In the procedures that follow, after each starting material, reference to a description is typically provided. This is provided merely for assistance to the skilled chemist. The starting material may not necessarily have been prepared from the batch referred to.

NMR Methods

NMR Spectroscopy was determined using either a Bruker DPX 250 MHz NMR or a Bruker DRX 500 MHz NMR. Values are reported as shifts (in ppm), with zero corresponding to tetramethylsilane as an internal standard. Chemical shifts are reported in ppm ([delta]). Splitting patterns are designed as s, singlet; d, doublet; t, triplet; q, quartet; m, multiplet; b, broad. The NMR spectra were recorded at a temperature ranging from 25 to 90 C. When more than one conformer was detected the chemical shifts for the most abundant one are reported.

Analytical HPLC-MS
Method A
Column: Waters Atlantis dC18 (2.1×100 mm, 3 um column)
Flow rate: 0.6 ml/min
Solvent A: 0.1% Formic acid/water
Solvent B: 0.1% Formic acid/acetonitrile
Injection Volume: 3 µl
Column temperature: 40° C.
UV Detection wavelength: 215 nm
Eluent: 0 mins to 5 mins, constant gradient from 95% solvent A+5% solvent B to 100% solvent B; 5 mins to 5.4 mins, 100% solvent B; 5.4 mins to 5.42 mins, constant gradient from 100% solvent B to 95% solvent A+5% solvent B; 5.42 mins to 7.00 mins, 95% solvent A+5% solvent B
Method B
Column: Waters Atlantis dC18 (2.1×50 mm, 3 um)
Solvent A=Formic acid (aq) 0.1%
Solvent B=Formic acid (acetonitrile) 0.1%
Flow rate 1 ml/min
Injection volume 3 ul
UV Detection wavelength: 215 nm
Eluent: 0 to 2.5 minutes, constant gradient from 95% solvent A+5% solvent B to 100% solvent B; 2.5 minutes to 2.7 minutes, 100% solvent B; 2.71 to 3.0 minutes, 95% solvent A+5% solvent B.

Method C
  Column: Waters Atlantis dC18 (2.1×30 mm, 3 um column)
  Flow rate: 1 ml/min
  Solvent A: 0.1% Formic acid/water
  Solvent B: 0.1% Formic acid/acetonitrile
  Injection volume: 3 ul
  UV Detection wavelength: 215 nm
  Eluent: 0 mins to 1.5 mins, constant gradient from 95% solvent A+5% solvent B to 100% solvent B; 1.5 mins to 1.6 mins, 100% solvent B; 1.60 min to 1.61 mins, constant gradient from 100% solvent B to 95% solvent A+5% solvent B; 1.61 mins to 2.00 min, 95% solvent A+5% solvent B.
Method D
  Column: Waters Atlantis dC18 (3.0×50 mm, 3 um)
  Flow rate 1.2 ml/min
  Solvent A=Formic acid (aq) 0.1%
  Solvent B=Formic acid (acetonitrile) 0.1%
  Injection volume 5 ul
  UV Detection wavelength: 215 nm
  Eluent: 0 to 3.5 minutes, constant gradient from 95% solvent A+5% solvent B to 100% solvent B; 3.5 minutes to 3.8 minutes, 100% solvent B; 3.9 to 4.5 minutes, 95% solvent A+5% solvent B.
Method E
  Column: Waters Atlantis dC18 (2.1×50 mm, 5 um)
  Flow rate 1.0 ml/min
  Solvent A=Formic acid (aq) 0.1%
  Solvent B=Formic acid (acetonitrile) 0.1%
  Injection volume 15 ul
  UV Detection wavelength: 215 nm
  Eluent: 0 to 2.5 minutes, constant gradient from 95% solvent A+5% solvent B to 100% solvent B; 2.5 minutes to 2.7 minutes, 100% solvent B; 2.71 to 3.5 minutes, 95% solvent A+5% solvent B.
  MS detection using Waters LCT or LCT Premier, or ZQ or ZMD
  UV detection using Waters 2996 photodiode array or Waters 2787 UV or Waters 2788 UV
Preparative HPLC-MS
Method A
  Column: Waters SunFire Prep C18 OBD (5 um 19×100 mm)
  Flow rate: 26 ml/min
  Solvent A: 0.1% TFA/water
  Solvent B: 0.1% TFA/acetonitrile
  Injection Volume: 1000 μl
  Column Temperature: room temperature
  Detection: Mass directed
  Eluent: 0 mins to 1 minute, 90% solvent A+10% solvent B; 1 minute to 7.5 mins, constant gradient from 90% solvent A+10% solvent B to 100% solvent B; 7.5 mins to 9 mins, 100% solvent B; 9 mins to 9.1 mins, constant gradient from 100% solvent B to 90% solvent A+10% solvent B; 9.1 mins to 10 mins, 90% solvent A+10% solvent B.
  Waters Micromass Platform LCZ single quadrupole mass spectrometer
  Waters 600 solvent delivery module
  Waters 515 ancillary pumps
  Waters 2487 UV detector
  Gilson 215 autosampler and fraction collector
Method B
  Column: Waters XBridge Prep C18 OBD (5 μm 19×100 mm)
  Solvent A: 0.2% Ammonium Hydroxide/water
  Solvent B: 0.2% Ammonium Hydroxide/Acetonitrile
  Injection Vol: 1000 μl
  Column temp: room temp.
  Detection: UV directed
  Eluent: 0 mins to 2.5 mins, 90% solvent A+10% solvent B; 2.5 mins to 14.5 mins, from constant gradient of 90% solvent A+10% solvent B to 100% solvent B; 14.5 mins to 16.5 mins, 100% solvent B; 16.5 mins to 16.1 mins, 100% solvent B to 90% solvent A+10% solvent B; 16.1 mins to 17 mins, 90% solvent A+10% solvent B.
  Gilson 119 UV/VIS detector
  Gilson 306 pumps
  Gilson 215 autosampler and fraction collector
Method C
  Column: Waters Sunfire Prep C18 OBD (5 μm 19×100 mm)
  Solvent A: Water 100% (milli-Q grade, 18.2 mega ohms)
  Solvent B: Acetonitrile 100% HPLC grade
  Injection Vol: up to 1500 μl
  Column temp: room temp.
  Detection: UV directed
  Eluent: 0 mins to 2.0 mins, 95% solvent A+5% solvent B; 2.0-2.5 mins 90% solvent A+10% solvent B; 2.5 mins to 14.5 mins, gradient of 90% solvent A+10% solvent B to 100% solvent B; 14.5 mins to 16.5 mins, 100% solvent B gradient hold; 16.5 mins to 16.7 mins, 100% solvent B to 95% solvent A+5% solvent B; 16.1 mins to 17.2 mins, 95% solvent A+5% solvent B.
  Gilson 119 UV/VIS detector
  Gilson 306 pumps
  Gilson 215 autosampler and fraction collector
Method D
  Column: Waters SunFire Prep C18 OBD (5 um 19×100 mm)
  Flow rate: 26 ml/min
  Solvent A: 0.1% Formic acid/water
  Solvent B: 0.1% Formic acid/acetonitrile
  Injection Volume: 1000 μl
  Column Temperature: room temperature
  Detection: Mass directed
  Eluent: 0 mins to 1 minute, 90% solvent A+10% solvent B; 1 minute to 7.5 mins, constant gradient from 90% solvent A+10% solvent B to 100% solvent B; 7.5 mins to 9 mins, 100% solvent B; 9 mins to 9.1 mins, constant gradient from 100% solvent B to 90% solvent A+10% solvent B; 9.1 mins to 10 mins, 90% solvent A+10% solvent B.
  Waters Micromass Platform LCZ single quadrupole mass spectrometer
  Waters 600 solvent delivery module
  Waters 515 ancillary pumps
  Waters 2487 UV detector
  Gilson 215 autosampler and fraction collector
Compound Naming
  All compounds are named either using ACD Labs 10.0 naming software and ChemAxon Marvin sketch 5.5.1.0 naming tool (which conforms to IUPAC naming protocols) or by analogy to conventional nomenclature familiar to a skilled practitioner. Some compounds are isolated as TFA salts, which is not reflected by the chemical name. Within the meaning of the present invention the chemical name represents the compound in neutral form as well as its TFA salt or any other salt, especially pharmaceutically acceptable salt, if applicable.
  Flash silica gel chromatography was carried out on silica gel 230-400 mesh or on pre-packed silica cartridges.

Abbreviations aq. aqueous
br broad
C degrees Celcius
CDI 1,1'-carbonyl di-imidazole
conc. concentrated DABCO 1,4-diazabicyclo[2.2.2]octane
DCE 1,2-dichloroethane
DCM dichloromethane
DIPEA N,N-diisopropylethylamine
DMF N,N-dimethyl formamide
DMSO dimethylsulfoxide
EtOAc ethyl acetate
EtOH ethanol
FCC flash column chromatography
h hours
HCl hydrochloric acid
HOAt 1-hydroxy-7-azabenzotriazole
HPLC-MS high performance liquid chromatography and mass spectrometry
m multiplet
MeOH methanol
mg milligrams
min minutes
mmol millimoles
mL milliliters
MHz megahertz
NMR nuclear magnetic resonance
rt room temperature
RBF round bottomed flask
s singlet
t triplet
µmol micromoles
THF tetrahydrofuran All used acid chlorides were either commercially available or prepared according to the following general method:

4-Chlorobenzoic acid (67 mg, 425 µmol), DCM (2 ml) and DMF (1 drop) were charged to a RBF under nitrogen. The mixture was cooled to 0 C then treated with oxalyl chloride (70 µL, 811 µmol) while stirring. The mixture was allowed to warm to room temperature and stirred for 1 h. The mixture was concentrated under vacuum and used without further purification.

Example 1

6-(5-Furan-2-yl-[1,2,4]oxadiazol-3-yl)-N-methyl-N-phenyl-[1,3,5]triazine-2,4-diamine 6-(5-Furan-2-yl-[1,2,4]oxadiazol-3-yl)-N-methyl-N-phenyl-[1,3,5]triazine-2,4-diamine is commercially available ((CAS-899373-19-4) e.g. Ambinter, Aurora Fine Chemicals, Tim Tec Inc., Interchim). Alternatively it may be prepared according to the following procedure (Method 1):

To a suspension of 4-amino-N-hydroxy-6-(methyl-phenyl-amino)-[1,3,5]triazine-2-carboxamidine (Intermediate 1, 95 mg, 0.37 mmol) in anhydrous toluene (3 mL) and anhydrous pyridine (1 mL) was added 2-furoyl chloride (53 mg, 0.41 mmol) in a solution of anhydrous toluene (3 mL) at 0 C in a sealed tube under an atmosphere of nitrogen.

The mixture was stirred at room temperature for 2 h. After this time the mixture was heated at 115 C for 18 h, allowed to cool to room temperature and concentrated under reduced pressure. The crude product was diluted with DCM (10 mL), extracted with water (5 mL) and dried over anhydrous sodium sulfate. After concentration under reduced pressure the crude product was purified by Preparative HPLC, Method A to give Example 1 (62 mg, 50%).

Example 39

N-Phenyl-6-(pyridin-2-yl-[1,2,4]oxadiazol-3-yl)-[1,3,5]triazine-2,4-diamine (Method 2)

A mixture of picolinic acid (90 mg, 0.73 mmol) and carbonyl di-imidazole (0.12 g, 0.73 mmol) in pyridine (1 ml) was stirred for 2 h. N-Phenyl-6-(5-thiazol-2-yl-[1,2,4]oxadiazol-3-yl)-[1,3,5]triazine-2,4-diamine (prepared in an analogous manner to Intermediate 4, 100 mg, 0.41 mmol) was added and the resulting mixture was heated to 100 C and stirred for 24 h. In a separate vessel, a second mixture of picolinic acid (90 mg, 0.73 mmol) and carbonyl di-imidazole (0.12 g, 0.73 mmol) in pyridine (1 ml) was stirred for 90 minutes and added to the first mixture, which was stirred for a further 24 h at 100 C. The mixture was cooled to room temperature, concentrated under vacuum and suspended in aqueous sodium hydrogencarbonate solution. The solid was filtered off, washed with water, ethyl acetate and methanol and dried under vacuum to give the title compound (73 mg, 54%).

Example 42

N-Methyl-N-phenyl-6-{5-[3-(2,2,2-trifluoro-ethoxy)-pyridin-2-yl]-[1,2,4]oxadiazol-3-yl}-[1,3,5]triazine-2,4-diamine (Method 3)

To a solution of 2-{3-[4-amino-6-(methyl-phenyl-amino)-[1,3,5]triazin-2-yl]-[1,2,4]oxadiazol-5-yl}-pyridin-3-ol (prepared in an analogous manner to Intermediate 58, 85 mg, 0.23 mmol) in DMSO (5 mL) was added potassium hydroxide (77 mg, 138 µmol) and 1,1,1-trifluoro-2-iodo-ethane (159 mg, 760 µmol). The resultant solution was heated at 120 C for 12 h, allowed to cool to room temperature, diluted with ethyl acetate (10 mL) and washed with brine (3×10 mL). The organic layer was dried over anhydrous sodium sulfate, filtered and concentrated under reduced pressure. The crude product was purified by prep HPLC (Method A) to give the title compound as a cream solid (58 mg, 57%).

Example 46

N-Methyl-N-phenyl-6-(5-piperidin-1-yl-[1,2,4]oxadiazol-3-yl)-[1,3,5]triazine-2,4-diamine (Method 4)

Piperidine (51 µL, 518 µmol), was added to N-methyl-N-phenyl-6-(5-trichloromethyl-[1,2,4]oxadiazol-3-yl)-[1,3,5]triazine-2,4-diamine (Intermediate 60, 100 mg, 259 µmol) in anhydrous DMF (1 mL) which had previously been charged to a RBF under nitrogen. The mixture was stirred at room temperature for 18 h. The mixture was then diluted with 35 mL EtOAc. The solution was then extracted with sat. aq. ammonium chloride solution (3×6 ml), brine (6 mL), dried over sodium sulfate, and concentrated in vacuo. After purification by preparative HPLC, Method A and subsequent free basing with sat.aq. sodium hydrogencarbonate solution, the title compound was obtained (17 mg, 19%).

Example 67

N-Methyl-N-phenyl-6-{5-[6-(2,2,2-trifluoroethoxy)-pyridin-3-yl]-[1,2,4]oxadiazol-3-yl}-[1,3,5]triazine-2,4-diamine In a sealed tube under nitrogen was placed 4-amino-N-hydroxy-6-(methyl-3-methylphenyl-amino)-[1,3,5]triazine-2-carboxamidine (Intermediate 1, 100 mg, 380 µmol). Then 5 mL anhydrous pyridine was added followed by 6-(2,2,2-trifluoroethoxy)-nicotinoyl chloride (prepared in an analogous manner to Intermediate 57, 91 mg, 380 µmol). The mixture was stirred at room temperature for 48 hrs. After this time the mixture was heated at 115 C for 18 h, allowed to cool and concentrated in vacuo. The crude residue was loaded onto a 2 g isolute silica column in a minimal amount of DCM and eluted with ethyl acetate-heptane 20-50% to give the title compound (54 mg, 32%).

Example 70

2-{[4-Amino-6-(5-furan-2-yl-[1,2,4]oxadiazol-3-yl)-[1,3,5]triazin-2-yl]-phenyl-amino}-ethanol (Method 5)

6-(5-Furan-2-yl-[1,2,4]oxadiazol-3-yl)-N-phenyl-[1,3,5]triazine-2,4-diamine (prepared in an analogous manner to Example 2, 100 mg, 310 µmol) and potassium carbonate (86 mg, 620 µmol) were stirred together in a sealed tube in DMF (5 ml). 2-Bromoethanol (26 µL, 310 µmol) was added and the reaction was heated at 110 C for 18 h. Potassium carbonate (43 mg, 310 µmol) and 2-bromoethanol (26 µL, 310 µmol) were added and the reaction stirred at 110 C for a further 18 h. After cooling and evaporation of the solvent the crude residue was dissolved in water (30 mL) and extracted twice with DCM (30 mL). The combined organic extracts were washed with brine (30 mL), dried over anhydrous sodium sulfate and concentrated under vacuum. The crude residue was purified using prep HPLC method B to give the desired title compound (14 mg, 12%).

Example 71

3-[4-Amino-6-(methyl-phenyl-amino)-[1,3,5]triazin-2-yl]-[1,2,4]oxadiazole-5-carboxylic acid benzylamide (Method 6)

3-[4-Amino-6-(methyl-phenyl-amino)-[1,3,5]triazin-2-yl]-[1,2,4]oxadiazole-5-carboxylic acid ethyl ester (prepared in an analogous manner to Example 73, Example 73, 80 mg, 230 µmol), benzylamine (50 µL, 230 µmol) and ethanol (4 mL) were heated under reflux for 4 h. After evaporation of the solvent, the crude residue was loaded onto a 5 g isolute pre-pack silica column in a minimal amount of DCM and eluted with 10-30% ethyl acetate-heptane to give the title compound (79 mg, 85%).

Example 75

5-{3-[4-Amino-6-(methyl-phenyl-amino)-[1,3,5]triazin-2-yl]-[1,2,4]oxadiazol-5-yl}-thiophene-2-carboxylic acid methylamide To 5-{3-[4-Amino-6-(methyl-phenyl-amino)-[1,3,5]triazin-2-yl]-[1,2,4]oxadiazol-5-yl}-thiophene-2-carboxylic acid (Intermediate 62, 316 mg, 0.80 mmol) in anhydrous DMF (4 mL) was added CDI (190 mg, 1.17 mmol). The mixture was stirred for 2 h and then heated at 50 C for 3 h. After this time more CDI (190 mg, 1.17 mmol) was added and the mixture heated at 65 C for 18 h. After cooling to room temperature, methylamine (2 M in THF, 3.5 mL, 7 mmol) was added and the mixture stirred at room temperature for 1 hr The reaction mixture was then diluted with DCM (20 mL), extracted with aqueous sodium hydroxide solution (1M, 20 mL), saturated brine (20 mL) and dried over sodium sulfate. Evaporation of the solvent gave an orange gum which was purified by preparative HPLC (Method A) and then by chromatography on silica eluting with 4% MeOH-DCM to give the title compound (27 mg, 8%).

Example 76

6-[5-(2-Methoxy-pyridin-3-yl)-[1,2,4]oxadiazol-3-yl]-N-methyl-N-phenyl-[1,3,5]triazine-2,4-diamine To 3-{3-[4-Amino-6-(methyl-phenyl-amino)-[1,3,5]triazin-2-yl]-[1,2,4]oxadiazol-5-yl}-pyridin-2-ol (Intermediate 63, 0.31 mmol) was added DMF (2 mL), potassium carbonate (85 mg, 0.52 mmol) and methyl iodide (19 µL, 0.31 mmol). The resulting mixture was stirred for 2 h, after which time further methyl iodide (40 µL, 0.62 mmol) was added. The reaction was stirred for a further 1.5 h after which time further methyl iodide (60 µL, 0.93 mmol) was added. This sequence was repeated two more times after which the starting material had been consumed. The crude mixture was diluted with ethyl acetate (10 mL), extracted with water (5 mL) and dried over anhydrous sodium sulfate. After concentration under reduced pressure, the crude product was purified by chromatography on silica eluting with a gradient of 2% to 6% MeOH-DCM and then by trituration with hot methanol (2 mL) to give the title compound (44 mg, 38%)

Example 79

(5-{3-[4-Amino-6-(methyl-phenyl-amino)-[1,3,5]triazin-2-yl]-[1,2,4]oxadiazol-5-yl}-thiophen-2-yl)-morpholin-4-yl-methanone To 5-{3-[4-amino-6-(methyl-phenyl-amino)-[1,3,5]triazin-2-yl]-[1,2,4]oxadiazol-5-yl}-thiophene-2-carboxylic acid (prepared in an analogous manner to Intermediate 62, 24 mg, 61 µmol) in anhydrous DMF (0.5 mL) was added (3-dimethylamino-propyl)-ethyl-carbodiimide hydrochloride (17 mg, 73 µmol), HOAt (4.1 mg, 31 µmol) and morpholine (10 µL, 92 µmol). The reaction mixture was stirred for 2 h, further morpholine (10 µL, 92 µmol) and (3-dimethylamino-propyl)-ethyl-carbodiimide hydrochloride (9 mg, 39 µmol) were added. The mixture was stirred for a further 2 h then diluted with ethyl acetate (5 mL) and extracted with aqueous citric acid (1M, 5 mL), 1 M NaOH (5 mL), saturated brine (5 mL) and dried over sodium sulphate. Removal of the solvent gave a gum with was purified on silica eluting with ethyl acetate-10% heptanes to give the title compound (20 mg, 71%).

Example 137

{3-[4-Amino-6-(methyl-phenyl-amino)-[1,3,5]triazin-2-yl]-[1,2,4]oxadiazol-5-yl}-[3-(4-fluoro-phenyl)-azetidin-1-yl]-methanone To N-methyl-N-phenyl-6-(5-trichloromethyl-[1,2,4]oxadiazol-3-yl)-[1,3,5]triazine-2,4-diamine (prepared in an analogous manner to Intermediate 60, 63 mg, 0.16 mmol) was added 3-(4-fluoro-phenyl)-azetidine hydrochloride (Intermediate 122, 39 mg, 0.19 mmol). Disisopropylethylamine (42 µL) and dioxane (1 mL) were added and the mixture heated at 70 C for 4 h. The mixture was diluted with 1 M citric acid to give a precipitate which was filtered. The pad was washed with a 1 M aq. solution of sodium bicarbonate (2 mL), water (2 mL) and then the solid was slurried in MeOH (2 mL) to give the title compound (48 mg, 65%).

Example 143

6-{5-[6-(2-Methoxy-ethoxymethyl)-pyridin-3-yl]-[1,2,4]oxadiazol-3-yl}-N-methyl-N-phenyl-[1,3,5]triazine-2,4-diamine (Method 7)

To dry THF (2 mL) under an atmosphere of nitrogen was added 2-methoxyethanol (20 mg, 0.26 mmol) followed by sodium hydride (60% dispersion in mineral oil, 10 mg, 0.26 mmol). The mixture was stirred at room temperature for 10 min when 5-(3-{4-amino-6-[methyl(phenyl)amino]-1,3,5-triazin-2-yl}-1,2,4-oxadiazol-5-yl)pyridin-2-yl]methyl methanesulfonate (Intermediate 128, 78 mg, 0.17 mmol) was added. The mixture turned black and was stirred at room temperature for 18 h. The mixture was diluted with DCM (5 mL) and washed with a 1 M aq. solution of sodium bicarbonate solution (5 mL), saturated brine (5 mL) and dried over sodium sulfate. Evaporation of the solvent gave a gum which was purified by HPLC, Method A, to give the title compound (6.8 mg, 8%).

Example 144

N-Methyl-N-phenyl-6-{5-[6-(tetrahydro-furan-3-yloxymethyl)-pyridin-3-yl]-[1,2,4]oxadiazol-3-yl}-[1,3,5]triazine-2,4-diamine To a solution of rhodium acetate (3 mg, 0.007 mmol), triethylamine (15 µL, 0.11 mmol) in 3-hydroxytetrahydrofuran (0.15 mL) was added 6-[5-(6-N-toluene sulfonyl-hydrazonomethyl-pyridin-3-yl)-[1,2,4]oxadiazol-3-yl]-N-methyl-N-phenyl-[1,3,5]triazine-2,4-diamine (Intermediate 100, 30 mg, 0.55 mmol). The mixture was heated at 90 C for 2.5 h. After cooling to room temperature, the mixture was diluted with DCM (2 mL), extracted with a 1M aq. solution of sodium bicarbonate (2 mL) and dried over anhydrous sodium sulfate. Evaporation of the solvent gave a red gum which was purified by HPLC (Method C) to give the title compound (2.3 mg, 9.4%).

Example 145

Racemic N-Methyl-N-phenyl-6-{5-[(1R,3R,5S)-8-(3,3,3-trifluoro-propyl)-8-aza-bicyclo[3.2.1]oct-3-yl]-[1,2,4]oxadiazol-3-yl}-[1,3,5]triazine-2,4-diamine (Method 8)

To racemic 6-[(1R,3R,5S)-5-(8-aza-bicyclo[3.2.1]oct-3-yl)-[1,2,4]oxadiazol-3-yl]-N-methyl-N-phenyl-[1,3,5]triazine-2,4-diamine (Intermediate 101, 30 mg, 0.08 mmol) was added DCE (1 mL), glacial acetic acid (14 mg), sodium cyanoborohydride (8 mg, 0.12 mmol) and 3,3,3-trifluoropropanal (13 mg, 0.1 mmol). The mixture was stirred at for 2 h when further sodium cyanoborohydride (8 mg, 0.12 mmol) and 3,3,3-trifluoropropanal (13 mg, 0.1 mmol) were added and the mixture stirred at room temperature for 18 h. Further sodium cyanoborohydride (16 mg, 0.24 mmol) and 3,3,3-trifluoropropanal (26 mg, 0.2 mmol) was then added ad the mixture stirred at room temperature for 2 h. The reaction was then diluted with DCM (3 mL), extracted with a 1M aq. solution of sodium bicarbonate solution (5 mL) and dried over sodium sulfate. Evaporation gave a pale yellow solid which was purified by HPLC, Method A, to give the title compound (20 mg, 53%).

Example 156

2-N-(2-Methoxyethyl)-2-N-phenyl-6-{5-[6-(2,2,2-trifluoroethoxy)pyridin-3-yl]-1,2,4-oxadiazol-3-yl}-1,3,5-triazine-2,4-diamine 2-N-Phenyl-6-{5-[6-(2,2,2-trifluoroethoxy)pyridin-3-yl]-1,2,4-oxadiazol-3-yl}-1,3,5-triazine-2,4-diamine (prepared in an analogous manner to Example 41, 0.100 g, 0.232 mmol) was added to cesium carbonate (0.151 g, 0.465 mmol) in DMF (3 mL) at room temperature followed by the addition of 1-bromo-2-methoxyethane (22 µL, 0.232 mmol). The reaction mixture was stirred at room temperature for 1 h and then heated to 50 C for 18 h. The reaction mixture was cooled to room temperature and concentrated under reduced pressure. The residue was dissolved in EtOAc and washed with water. The organic layer was dried over anhydrous sodium sulfate, filtered and concentrated under reduced pressure to obtain a brown solid. The solid was purified by preparative HPLC, Method A to afford the title compound (2.8 mg, 2.5%).

Example 157

2-N-(2-methoxyethyl)-4-N-phenyl-6-{5-[6-(2,2,2-trifluoroethoxy)pyridin-3-yl]-1,2,4-oxadiazol-3-yl}-1,3,5-triazine-2,4-diamine 2-N-(2-methoxyethyl)-4-N-phenyl-6-{5-[6-(2,2,2-trifluoroethoxy)pyridin-3-yl]-1,2,4-oxadiazol-3-yl}-1,3,5-triazine-2,4-diamine was prepared from 2-N-phenyl-6-{5-[6-(2,2,2-trifluoroethoxy)pyridin-3-yl]-1,2,4-oxadiazol-3-yl}-1,3,5-triazine-2,4-diamine (prepared in an analogous manner to Example 41, 0.100 g, 0.232 mmol) according to the method described for Example 156. The crude compound was purified by preparative HPLC, Method A, to afford the title compound (1.6 mg, 1.4%).

Example 159

1-[4-(3-{4-Amino-6-[methyl(phenyl)amino]-1,3,5-triazin-2-yl}-1,2,4-oxadiazol-5-yl)piperidin-1-yl]-2,2,2-trifluoroethan-1-one (Method 9)

To 2-N-Methyl-2-N-phenyl-6-[5-(piperidin-4-yl)-1,2,4-oxadiazol-3-yl]-1,3,5-triazine-2,4-diamine hydrochloride (Intermediate 105, 0.050 g, 0.129 mmol) in DCM (5 mL) was added triethylamine (44.8 µL, 0.321 mmol) and the reaction mixture was stirred at room temperature for 10 min. Trifluoroacetic anhydride (24 µL, 0.257 mmol) was added and the mixture was stirred at room temperature for 36 h. The mixture was diluted with DCM and washed with a saturated aqueous solution of sodium bicarbonate. The organic layer was dried over anhydrous sodium sulfate, filtered and concentrated under reduced pressure. The crude compound was purified by trituration with heptane and the precipitate collected by filtration under vacuum to afford the title compound (2.4 mg, 4.2%).

Example 161

1-[4-(3-{4-Amino-6-[methyl(phenyl)amino]-1,3,5-triazin-2-yl}-1,2,4-oxadiazol-5-yl)piperidin-1-yl]-2-methylpropan-1-one To 2-methylpropanoic acid (27.0 µL, 0.299 mmol) in DMF (5 mL) was added DIPEA (109 µL, 0.624 mmol) at room temperature and the mixture was stirred for 5 min. (1H-Benzotriazol-1-yloxy)[tris(dimethylamino)]phosphonium hexafluorophosphate (0.121 g, 0.274 mmol) was added to the reaction mixture and stirred for 5 min. 2-N-Methyl-2-N-phenyl-6-[5-(piperidin-4-yl)-1,2,4-oxadiazol-3-yl]-1,3,5-triazine-2,4-diamine hydrochloride (Intermediate 105, 0.100 g, 0.249 mmol) was added and the mixture was stirred at room temperature for 18 h. The reaction mixture was diluted with water, extracted with EtOAc and the organic layer washed with brine. The combined organic extracts were dried over anhydrous sodium sulfate, filtered and concentrated under reduced pressure. The crude compound was purified by FCC (DCM:MeOH 90:10) to afford the title compound (96 mg, 88%).

Example 167

2-N-Methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine 2-N-methyl-2-N-phenyl-6-[5-(trichloromethyl)-1,2,4-oxadiazol-3-yl]-1,3,5-triazine-2,4-diamine (prepared in an analogous manner to Intermediate 60, 0.110 g, 0.285 mmol) was added to a mixture of potassium carbonate (0.071 g, 0.518 mmol) in DMF (2 mL) at room temperature and the mixture was stirred for 5 min. 4-[(2,2,2-trifluoroethoxy)methyl]piperidine hydrochloride (Intermediate 179, 0.060 g, 0.259 mmol) was added to the reaction mixture and stirred at room temperature for 2 h. The reaction mixture was concentrated under reduced pressure, dissolved in water and extracted with EtOAc. The combined organic extracts was dried over anhydrous sodium sulfate, filtered and concentrated under reduced pressure. The crude compound was purified by FCC (EtOAc:heptane 1:1) and preparative HPLC, Method A, to afford the title compound (22.1 mg, 18%).

Example 173

6-[5-(1-Benzylpiperidin-4-yl)-1,2,4-oxadiazol-3-yl]-2-N-methyl-2-N-phenyl-1,3,5-triazine-2,4-diamine To 2-N-methyl-2-N-phenyl-6-[5-(piperidin-4-yl)-1,2,4-oxadiazol-3-yl]-1,3,5-triazine-2,4-diamine hydrochloride (Intermediate 105, 0.100 g, 0.257 mmol) in DMF (2 mL) was added sodium hydride (60% dispersion in mineral oil, 0.012 g, 0.309 mmol) at 0 C and stirred for 5 min. Benzyl bromide (30.6 µL, 0.257 mmol) was added, the reaction mixture was warmed to room temperature and stirred for 18 h. The mixture was then heated at 45 C for 18 h and re-treated with benzyl bromide (30.6 L, 0.257 mmol). The mixture was then heated at 50 C for 18 h and stirred room temperature for 72 h. The reaction mixture was diluted with DCM and then washed with a saturated aqueous solution of sodium bicarbonate and brine. The organic layer was dried over anhydrous sodium sulfate, filtered and concentrated under reduced pressure. The crude compound was purified by preparative HPLC, Method A, to afford the title compound (2.2 mg, 1.9%).

Example 174

2-N-Phenyl-6-(5-{4-[(2,2,2-trifluoroethoxy)methyl]piperidin-1-yl}-1,2,4-oxadiazol-3-yl)-1,3,5-triazine-2,4-diamine To 2-N-phenyl-6-[5-(trichloromethyl)-1,2,4-oxadiazol-3-yl]-1,3,5-triazine-2,4-diamine (Intermediate 134, 0.100 g, 0.268 mmol) in DMF (2 mL) was added DIPEA (93.6 µL, 0.537 mmol) at the mixture was stirred at room temperature for 5 min. 4-[(2,2,2-trifluoroethoxy)methyl]piperidine hydrochloride (Intermediate 179, 0.063 g, 0.268 mmol) was added and the mixture was stirred at room temperature for 18 h. The reaction mixture was then heated to 50 C for 18 h and to 70 C for 36 h. The reaction mixture was concentrated under reduced pressure, dissolved in EtOAc and washed with water. The organic layer was dried over anhydrous sodium sulfate, filtered and concentrated under reduced pressure. The crude compound was purified by preparative HPLC, Method C, to afford the title compound (10.8 mg, 8.9%).

Example 178

2-N-Methyl-2-N-phenyl-6-[5-(4-{[(2,2,2-trifluoroethane)sulfonyl]methyl}piperidin-1-yl)-1,2,4-oxadiazol-3-yl]-1,3,5-triazine-2,4-diamine (Method 10)

To 2-N-methyl-2-N-phenyl-6-[5-(4-{[(2,2,2-trifluoroethyl)sulfanyl]methyl}piperidin-1-yl)-1,2,4-oxadiazol-3-yl]-1,3,5-triazine-2,4-diamine (batch 1 from Example 175, 36.8 mg, 0.077 mmol) in DCM (2 mL) was added 3-chloroperoxybenzoic acid (13.22 mg, 0.077 mmol) at 0 C. The reaction mixture was stirred at 0 C for 1 h and then at room temperature for 1 h. The reaction mixture was re-treated with 3-chloroperoxybenzoic acid (13.22 mg, 0.077 mmol) and stirred at room temperature for 1 h. The reaction mixture was washed with a 5% aqueous solution of sodium thiosulfate and saturated aqueous solution of sodium bicarbonate. The organic layer was dried over anhydrous sodium sulfate, filtered and concentrated under reduced pressure. The crude compound was purified by preparative HPLC, Method A, to afford the title compound (6.2 mg, 16%).

Example 216

6-(5-{4-[(Cyclopropylmethoxy)methyl]piperidin-1-yl}-1,2,4-oxadiazol-3-yl)-2-N-methyl-2-N-phenyl-1,3,5-triazine-2,4-diamine Potassium carbonate (0.107 g, 0.776 mmol) and 2-N-methyl-2-N-phenyl-6-[5-(trichloromethyl)-1,2,4-oxadiazol-3-yl]-1,3,5-triazine-2,4-diamine (prepared in an analogous manner to Intermediate 60, 0.150 g, 0.388 mmol) were added to a solution of 4-[(cyclopropylmethoxy)methyl]piperidine hydrochloride salt (Intermediate 198, 0.160 g, 0.776 mmol) in DMF (5 mL) at room temperature. The reaction mixture was stirred at room temperature for 18 h and then evaporated under vacuum to remove the DMF. The crude residue was dissolved in EtOAc (5 mL) and washed with water (3×3 mL). The aqueous washes were combined, re-extracted with EtOAc (2×3 mL). The organic extracts were combined, dried over sodium sulfate, filtered and evaporated to provide a crude brown residue which was purified by preparative HPLC, Method B, to afford the title compound as an off-white solid (28 mg, 16%).

Example 221

2-N-Phenyl-6-[5-(piperidin-1-yl)-1,2,4-oxadiazol-3-yl]-1,3,5-triazine-2,4-diamine (Method 11)

Piperidine (0.483 mL, 4.902 mmol) was added to a solution of 2-N-phenyl-6-[5-(trichloromethyl)-1,2,4-oxadiazol-3-yl]-1,3,5-triazine-2,4-diamine (prepared in an analogous manner to Intermediate 134, 0.913 g, 2.451 mmol) in dioxane (4 mL) at room temperature. The reaction mixture was stirred at room temperature for two days before being concentrated. The resulting residue was dissolved in EtOAc and water, and washed successively with 1M aq. HCl and brine. The organic phase was dried over sodium sulfate, filtered and concentrated. The crude compound was purified by flash chromatography (heptane:EtOAc 3:2) to afford the title compound (100 mg, 26%).

Example 256

2-N-Methyl-2-N-phenyl-6-{5-[1-(2,2,2-trifluoroethyl)-1H-pyrazol-3-yl]-1,2,4-oxadiazol-3-yl}-1,3,5-triazine-2,4-diamine (Method 12)

Methyl 1-(2,2,2-trifluoroethyl)-1H-pyrazole-3-carboxylate (Intermediate 204, 0.312 g, 1.5 mmol) was dissolved in a mixture of THF (2 mL), MeOH (2 mL) and water (1 mL); lithium hydroxide (0.188 g, 4.5 mmol) was added and the mixture was stirred at room temperature for 16 h. The mixture was concentrated, the residue dissolved in water (1 mL) and the mixture was neutralised. This was extracted with EtOAc (2×10 mL), the organic extracts were dried over sodium sulfate and concentrated under vacuum. The crude material was washed with pentane (2×10 mL) to afford 1-(2,2,2-trifluoroethyl)-1H-pyrazole-3-carboxylic acid (0.200 g, 69%). 2-N-methyl-2-N-phenyl-6-{5-[1-(2,2,2-trifluoroethyl)-1H-pyrazol-3-yl]-1,2,4-oxadiazol-3-yl}-1,3,5-triazine-2,4-diamine was then prepared from 1-(2,2,2-trifluoroethyl)-1H-pyrazole-3-carboxylic acid (0.159 g, 0.820 mmol) and 4-amino-N-hydroxy-6-[methyl(phenyl)amino]-1,3,5-triazine-2-carboximidamide (prepared in an analogous manner to Intermediate 1, 0.125 g, 0.483 mmol) according to the method described for Example 251 to afford the title compound (0.110 g, 55%).

Example 258

3-{4-Amino-6-[methyl(phenyl)amino]-1,3,5-triazin-2-yl}-N-(6-methoxypyridin-3-yl)-1,2,4-oxadiazole-5-carboxamide (Method 13)

To a solution of ethyl 3-{4-amino-6-[methyl(phenyl) amino]-1,3,5-triazin-2-yl}-1,2,4-oxadiazole-5-carboxylate (prepared in an analogous manner to Example 73, 0.2 g, 0.58 mmol) in toluene (10 mL) at 0 C was added trimethylaluminium (2M in toluene, 0.88 mL, 1.7 mmol) over a period of 5 min and the mixture was then stirred at room temperature for 2 h. 6-Methoxypyridin-3-amine (0.21 g, 1.7 mmol) was added and the mixture was heated to 60 C for 15 h. The mixture was cooled to room temperature and quenched with ice water. The mixture was extracted with EtOAc (3×20 mL) and the organic layers were concentrated under vacuum. The residue was slurried in acetonitrile for 30 min and the resultant precipitate was filtered off to afford the title compound (0.100 g, 43%).

Example 261

2-N-Methyl-6-[5-(3-phenoxycyclobutyl)-1,2,4-oxadiazol-3-yl]-2-N-phenyl-1,3,5-triazine-2,4-diamine Triethylamine (2 mL, 14.04 mmol) and benzyl bromide (1.2 mL, 10.0 mmol) were added to a solution of 3-oxocyclobutane-1-carboxylic acid (1.0 g, 8.77 mmol) in THF (10 mL) and the mixture was stirred at room temperature for 2 h. EtOAc (10 mL) was added and the mixture was washed with water followed by 1M hydrochloric acid and then brine. The organic layer was dried over sodium sulfate and concentrated under vacuum. The residue was purified by FCC, eluting with a gradient of 0-15% EtOAc in hexane to afford benzyl 3-oxocyclobutane-1-carboxylate (0.938 g, 53%). A portion of benzyl 3-oxocyclobutane-1-carboxylate (0.800 g, 3.92 mmol) was dissolved in a mixture of THF (2.5 mL) and water (2.5 mL) and cooled to 0 C. Sodium borohydride (0.051 g, 1.96 mmol) was added and the mixture was stirred at room temperature for 1 h. The mixture was concentrated under vacuum and EtOAc (10 mL) was added. This was washed with water and then brine and the organic layer was then dried over sodium sulfate and concentrated. The residue was purified by FCC, eluting with a gradient of 0-10% EtOAc in hexane to afford benzyl 3-hydroxycyclobutane-1-carboxylate (0.715 g, 88%). A portion of benzyl 3-hydroxycyclobutane-1-carboxylate (0.400 g, 1.94 mmol) was dissolved in THF (10 mL) and phenol (0.547 g, 5.83 mmol) and triphenylphosphine (0.662 g, 2.52 mmol) were added. Diethyl azodicarboxylate (0.4 mL, 2.52 mmol) was added gradually and the mixture was stirred at room temperature for 24 h. The mixture was evaporated and then extracted with EtOAc (3×10 mL). The organic layer was washed with brine and concentrated under vacuum. The residue was purified by FCC, eluting with a gradient of 0-15% EtOAc in hexane to afford benzyl 3-phenoxycyclobutane-1-carboxylate (0.450 g, 82%). A portion of benzyl 3-phenoxycyclobutane-1-carboxylate (0.400 g, 1.42 mmol) was dissolved in EtOH (10 mL) and 10% palladium on carbon (0.010 g) was added. The mixture was stirred under an atmosphere of hydrogen at room temperature for 2 h. The mixture was filtered and the filtrate was evaporated. The residue was purified by FCC, eluting with a gradient of 0-10% EtOAc in hexane to afford 3-phenoxycyclobutane-1-carboxylic acid (0.245 g, 95%). 2-N-Methyl-6-[5-(3-phenoxycyclobutyl)-1,2,4-oxadiazol-3-yl]-2-N-phenyl-1,3,5-triazine-2,4-diamine was then prepared from 3-phenoxycyclobutane-1-carboxylic acid (0.190 g, 0.985 mmol) and 4-amino-N-hydroxy-6-[methyl(phenyl)amino]-1,3,5-triazine-2-carboximidamide (prepared in an analogous manner to Intermediate 1, 0.150 g, 0.579 mmol) according to the method described for Example 209. The residue was purified by FCC, eluting with 10% MeOH in hexane to afford the title compound as a mixture of isomers (0.095 g, 42%).

Example 264

2-N-(3-Chloro-2-fluorophenyl)-6-[5-(pyridin-2-yl)-1,2,4-oxadiazol-3-yl]-1,3,5-triazine-2,4-diamine (Method 14)

Triethylamine (1.10 mL, 7.58 mmol) and 1H-benzotriazol-1-ol (0.77 g, 5.05 mmol) were added to a solution of N-[3-(dimethylamino)propyl]-N'-ethylcarbodiimide hydrochloride (0.97 g, 5.05 mmol) in DMF (10 mL) and the mixture was stirred for 20 min at room temperature. Picolinic acid (0.62 g, 5.05 mmol) was added and the mixture was stirred for 30 min at room temperature. 4-Amino-6-[(3-chloro-2-fluorophenyl) amino]-N'-hydroxy-1,3,5-triazine-2-carboximidamide (prepared in an analogous manner to Intermediate 73, 1.50 g, 5.05 mmol) was added and the mixture was stirred at room temperature overnight before being heated to 85 C for approximately 24 h. The crude compound was purified over Ambersep resin but the impurities remained. The residue was then successively washed with EtOAc, acetone and MeOH and finally hot MeOH to afford the title compound (330 mg, 17%).

Example 279

(Methyl 5-(3-{4-amino-6-[methyl(phenyl)amino]-1,3,5-triazin-2-yl}-1,2,4-oxadiazol-5-yl)pyridine-2-carboxylate)

Oxalyl chloride (91 μL, 1078 μmol) was added to a solution of pyridine-2,5-dicarboxylic acid 2-methyl ester (91 mg, 501 μmol) under an inert atmosphere in DCM (3 mL) and DMF (0.3 mL). The solution was stirred at room temperature for 1 h and then evaporated to dryness. The resulting solid was suspended in anhydrous pyridine (10 mL) and 4-amino-N-hydroxy-6-(methyl-phenyl-amino)-[1,3,5]triazine-2-carboxamidine (prepared in an analogous manner to Intermediate 1, 100 mg, 385 µmol) was added. The resulting solution was stirred at room temperature for 16 h under nitrogen. On formation of the ester intermediate, detected by LCMS, the reaction mixture was heated to 100 C for a further 4 h and then cooled to room temperature. The reaction mixture was then poured into water and extracted with DCM (3×25 mL). Combined organics were dried over magnesium sulfate and evaporated to dryness. The resulting residue was purified further by re-crystallisation in hot MeOH to afford the title compound as a light brown solid (59 mg, 38%). Method A HPLC-MS: MH+ requires m/z=405. Found: m/z=405.1, Rt=3.72 min (96%). 1H NMR (500 MHz, DMSO-d6) δ ppm 9.39 (1H, s), 8.69 (1H, d), 8.29 (1H, d), 7.52 (1H, s), 7.42 (4H, m), 7.28 (2H, d), 3.94 (3H, s) and 3.48 (3H, s).

Example 280

(5-(3-{4-Amino-6-[methyl(phenyl)amino]-1,3,5-triazin-2-yl}-1,2,4-oxadiazol-5-yl)-N-(2,2,2-trifluoroethyl)pyridine-2-carboxamide)

To a suspension of 2,2,2-trifluoro-ethylamine (39 mg, 395 µmol) in anhydrous toluene (3 mL) was added bis(trimethylaluminum)-1,4-diazabicyclo[2.2.2]-octane (DABAL-Me$_3$) (101 mg, 395 µmol). The resulting solution was stirred at 40 C for 1 h. Methyl 5-(3-{4-amino-6-[methyl(phenyl)amino]-1,3,5-triazin-2-yl}-1,2,4-oxadiazol-5-yl)pyridine-2-carboxylate (prepared in an analogous manner to Example 279, 80 mg, 197 µmol) was then added to the solution and the reaction mixture was stirred for a further 16 h at 80 C. The reaction mixture was quenched with 1M HCl (1 mL), evaporated to dryness and re-dissolved in DCM. The organic solution was washed with water (3×25 mL), dried over magnesium sulfate, evaporated and purified by silica chromatography (50:50 EtOAc:heptane) to afford the title compound as a white solid (40 mg, 43%).

Example 282

6-[5-(3,5-Dimethoxypyridin-2-yl)-1,2,4-oxadiazol-3-yl]-2-N-methyl-2-N-phenyl-1,3,5-triazine-2,4-diamine 6-[5-(3,5-Difluoropyridin-2-yl)-1,2,4-oxadiazol-3-yl]-2-N-methyl-2-N-phenyl-1,3,5-triazine-2,4-diamine was prepared by dissolving 2-N-methyl-2-N-phenyl-6-[5-(pyrimidin-2-yl)-1,2,4-oxadiazol-3-yl]-1,3,5-triazine-2,4-diamine (Example 281, 20 mg, 52.3 µmol) and cesium carbonate (20 mg, 61.3 µmol) in MeOH (1 mL). The resulting mixture was evaporated to dryness, suspended in hot water and filtered. The white solid collected was washed further with distilled water and dried under vacuum to afford the title compound as a white solid (13 mg, 62%).

Example 284

5-(3-{4-Amino-6-[methyl(phenyl)amino]-1,3,5-triazin-2-yl}-1,2,4-oxadiazol-5-yl)pyridine-2-carboxamide (Method 15)

To a solution of 5-(3-{4-amino-6-[methyl(phenyl)amino]-1,3,5-triazin-2-yl}-1,2,4-oxadiazol-5-yl)pyridine-2-carboxylic acid (Intermediate 124, 50 mg, 128 µmol) in DCE (10 mL) and DMF (100 µL) was added oxalyl chloride (22 µL, 256 µmol). The resulting solution was stirred at room temperature for 2 h, evaporated to dryness and re-suspended in a solution of ammonia in dioxane (7N, 10 mL). The reaction mixture was stirred overnight at room temperature and then poured into water (50 mL). The mixture was extracted with DCM (3×50 mL) and the combined organics were dried and concentrated under vacuum to afford a crude yellow solid. The crude material was suspended in MeOH, filtered and washed with further MeOH. The resulting solid was recrystallised in dioxane and water to afford the title compound as a white solid (15 mg, 30%).

Example 291

2-N-Methyl-2-N-phenyl-6-(5-{6-[(2,2,2-trifluoroethoxy)methyl]pyridin-3-yl}-1,2,4-oxadiazol-3-yl)-1,3,5-triazine-2,4-diamine To a solution of [5-(3-{4-amino-6-[methyl(phenyl)amino]-1,3,5-triazin-2-yl}-1,2,4-oxadiazol-5-yl)pyridin-2-yl]methanol (Example 295, 30 mg, 79 µmol) in anhydrous THF (10 mL) was added trifluoromethanesulfonic acid 2,2,2-trifluoro-ethyl ester (56 mg, 239 µmol). The solution was cooled to 0 C and sodium hydride (60% dispersion in mineral oil, 7 mg, 159 µmol) was added under an inert atmosphere and the mixture was stirred at room temperature for 24 h. The reaction mixture was then re-treated with trifluoromethanesulfonic acid 2,2,2-trifluoro-ethyl ester (56 mg, 239 µmol) and sodium hydride (60% dispersion in mineral oil, 7 mg, 159 µmol) and stirred for an additional 48 h at room temperature. The reaction mixture was quenched with water (20 mL) and extracted into EtOAc (3×25 mL). Combined organics were dried over magnesium sulfate and evaporated to dryness. The crude product was purified by silica chromatography (3% MeOH in DCM) and then re-purified by preparative HPLC-MS (Method B) to afford the title compound as an off white solid (5.6 mg, 15%).

Example 293

2-N-Methyl-2-N-phenyl-6-{5-[6-(pyrrolidin-1-ylmethyl)pyridin-3-yl]-1,2,4-oxadiazol-3-yl}-1,3,5-triazine-2,4-diamine (Method 16)

To a solution of [5-(3-{4-amino-6-[methyl(phenyl)amino]-1,3,5-triazin-2-yl}-1,2,4-oxadiazol-5-yl)pyridin-2-yl]methanol (Intermediate 125, 50 mg, 132 µmol) in DCM (10 mL) was added methanesulfonyl chloride (11 µL, 139 µmol) and triethylamine (20 µL, 145 µmol). The reaction mixture was stirred for 90 min at room temperature under an inert atmosphere and then evaporated to dryness. The resulting solid was dissolved in DCM (10 mL), pyrrolidine (24 µL, 333 µmol) and triethylamine (46 µL, 333 µmol) and stirred for a further 3 h at room temperature. Incomplete reaction was observed so the reaction was heated at 35 C for a further 16 h. The reaction mixture was then washed with water (3×25 mL) and combined organics were dried over magnesium sulfate and evaporated to dryness. The resulting crude product was purified by silica chromatography (5% MeOH in DCM) to afford the title compound as a beige solid (25 mg, 45%).

Example 294

2-N-Methyl-2-N-phenyl-6-(5-{5-[1-(pyrrolidin-1-yl)ethyl]pyridin-2-yl}-1,2,4-oxadiazol-3-yl)-1,3,5-triazine-2,4-diamine To a solution of 1-[6-(3-{4-amino-6-[methyl(phenyl)amino]-1,3,5-triazin-2-yl}-1,2,4-oxadiazol-5-yl)pyridin-3- yl]ethan-1-one (prepared in an analogous manner to Example 296, 100 mg, 257 μmol) and pyrrolidine (53 μL, 643 μmol) in anhydrous THF (5 mL) at 0 C under nitrogen was added titanium isopropoxide (183 mg, 643 μmol) drop-wise. The reaction mixture was allowed to warm to room temperature and stirred overnight. The reaction mixture was then cooled to 0 C and sodium borohydride (29 mg, 771 μmol) was added. The reaction mixture was stirred at room temperature for 3 h and then was quenched with water (10 mL) and extracted into EtOAc (3×25 mL). Combined organics were dried over magnesium sulfate, evaporated and the crude product was purified by silica chromatography (2% MeOH in DCM) to afford the title compound as a beige solid (13 mg, 12%).

Example 295

[5-(3-{4-Amino-6-[methyl(phenyl)amino]-1,3,5-triazin-2-yl}-1,2,4-oxadiazol-5-yl)pyridin-2-yl] methanol To a solution of methyl 5-(3-{4-amino-6-[methyl(phenyl)amino]-1,3,5-triazin-2-yl}-1,2,4-oxadiazol-5-yl)pyridine-2-carboxylate (prepared in an analogous manner to Example 279, 500 mg, 1.23 mmol) in anhydrous THF (50 mL) at 0 C, was added sodium borohydride (95 mg, 2.46 mmol) portion-wise under nitrogen. The resulting solution was sonicated briefly and stirred at 40 C for 1 h. The reaction mixture was then allowed to stir at room temperature for a further 16 h. The reaction was quenched with water (25 mL) and extracted with EtOAc (3×25 mL). Combined organics were dried over magnesium sulfate and evaporated to dryness to afford the crude product as a yellow solid. The solid was triturated with MeOH, filtered and washed further with diethyl ether (100 mL) to afford the title compound as a salmon coloured solid (305 mg, 67%).

Example 304

1-[5-(3-{4-Amino-6-[methyl(phenyl)amino]-1,3,5-triazin-2-yl}-1,2,4-oxadiazol-5-yl)pyridin-2-yl] ethan-1-one To a solution of methyl 5-(3-{4-amino-6-[methyl(phenyl)amino]-1,3,5-triazin-2-yl}-1,2,4-oxadiazol-5-yl)pyridine-2-carboxylate (prepared in an analogous manner to Example 279, 1.00 g, 2.47 mmol) in anhydrous THF (30 mL) at −78 C was added methyl magnesium bromide (3M sol. in ether, 907 μL, 2.72 mmol) drop wise under an inert atmosphere. The resulting solution was stirred at −78 C for 1 h and then allowed to warm to room temperature where upon stirring was continued for a further 1 h. The reaction mixture was cooled again and quenched with acetone (1 mL) and a 10% citric acid aq. solution (5 mL). The reaction mixture was extracted with EtOAc (3×50 mL) and the resultant organics washed with brine (25 mL), dried over magnesium sulfate and evaporated to dryness. 50 milligrams of the resulting crude material was purified by preparative HPLC-MS (Method C) to afford the title compound as an off white solid (21 mg).

Example 312

2-N-(2-Methoxyethyl)-2-N-phenyl-6-(5-{6-[(2,2,2-trifluoroethoxy)methyl]pyridin-3-yl}-1,2,4-oxadiazol-3-yl)-1,3,5-triazine-2,4-diamine (Method 17)

To a solution of [5-(3-{4-amino-6-[(2-methoxy-ethyl)-phenyl-amino]-[1,3,5]triazin-2-yl}-[1,2,4]oxadiazol-5-yl)-pyridin-2-yl]-methanol (Intermediate 130, 185 mg, 0.44 mmol) in DCM (40 mL) was added methanesulfonyl chloride (48 μL, 0.61 mmol) drop-wise, followed by triethylamine (92 μL, 0.66 mmol). The resulting solution was stirred for 3 h under an inert atmosphere. Incomplete reaction was observed so additional methanesulfonyl chloride (9 μL, 0.10 mmol) and triethylamine (16 μL, 0.11 mmol) were added and stirring was continued for 1 h. The reaction mixture was washed with water (2×50 mL) and the organic phase dried over magnesium sulfate and evaporated to dryness to afford the methanesulfonic acid 5-(3-{4-amino-6-[(2-methoxy-ethyl)-phenyl-amino]-[1,3,5]triazin-2-yl}-[1,2,4]oxadiazol-5-yl)-pyridin-2-ylmethyl ester intermediate. In a separate flask 2,2,2-trifluoro-ethanol (190 μL, 2.64 mmol) was added dropwise to a suspension of sodium hydride (60% dispersion in mineral oil, 97 mg, 2.42 mmol) in anhydrous THF (30 mL) at 0 C under nitrogen. The resulting solution was stirred at 0 C for 30 min and then transferred via cannula to a solution of the methanesulfonic acid 5-(3-{4-amino-6-[(2-methoxy-ethyl)-phenyl-amino]-[1,3,5]triazin-2-yl}-[1,2,4]oxadiazol-5-yl)-pyridin-2-ylmethyl ester intermediate (220 mg, 0.44 mmol) in anhydrous THF (30 mL) at 0 C drop wise. The reaction mixture was stirred at room temperature for 18 h. The reaction was quenched with a saturated ammonium chloride aq. solution (5 mL) and extracted with EtOAc (3×50 mL). Combined organics were washed with brine (25 mL), dried over magnesium sulfate and evaporated to dryness. The crude product was purified by silica chromatography (2% MeOH in DCM) and then further by preparative HPLC-MS (Method C) to afford the title compound as an off-white solid (21 mg, 10%).

Example 314

2-N-Methyl-2-N-phenyl-6-{5-[1-(2,2,2-trifluoroethyl)azetidin-3-yl]-1,2,4-oxadiazol-3-yl}-1,3,5-triazine-2,4-diamine To a solution of sodium hydride (60% dispersion in mineral oil, 16 mg, 0.41 mmol) in anhydrous DMF (20 mL) at 0 C was added 6-[5-(azetidin-3-yl)-1,2,4-oxadiazol-3-yl]-2-N-methyl-2-N-phenyl-1,3,5-triazine-2,4-diamine hydrochloride (Intermediate 129, 50 mg, 0.138 mmol) and trifluoromethanesulfonic acid 2,2,2-trifluoro-ethyl ester (160 mg, 0.69 mmol) under nitrogen. The reaction mixture was stirred at room temperature for 16 h and then was quenched with saturated ammonium chloride aqueous solution (10 mL) and evaporated to dryness. The solid obtained was dissolved in EtOAc (20 mL), washed with water (2×25 mL), dried over magnesium sulfate and evaporated to dryness. The resulting crude product was purified by silica chromatography (2% MeOH in DCM) and then further by preparative HPLC-MS (Method B) to afford the title compound as white solid (5 mg, 9%).

Example 317

2-N-Methyl-2-N-phenyl-6-[5-(6-{[(2,2,2-trifluoroethane)sulfinyl]methyl}pyridin-3-yl)-1,2,4-oxadiazol-3-yl]-1,3,5-triazine-2,4-diamine (Method 18)

To a solution of 2-N-methyl-2-N-phenyl-6-[5-(6-{[(2,2,2-trifluoroethyl)sulfanyl]methyl}pyridin-3-yl)-1,2,4-oxadiazol-3-yl]-1,3,5-triazine-2,4-diamine (Example 316, 75 mg, 0.158 mmol) in THF (2.5 mL) and acetone (2.5 mL) was added oxone (202 mg, 0.328 mmol) and a saturated sodium bicarbonate aq. solution (2 mL). The resulting suspension was stirred at room temperature for 4 h and 30 C for 16 h.

Additional oxone (97 mg, 0.158 mmol) was added to the reaction mixture and stirring was continued for a further 12 h at 35 C. The solution was cooled to room temperature, diluted with EtOAc (50 mL) and washed with water (2×25 mL) and brine (25 mL). Combined organics were dried over magnesium sulfate, evaporated to dryness and purified by preparative HPLC-MS (Method C) to afford the title compound as a white solid (16 mg, 21%).

Example 323

2-N-Methyl-2-N-phenyl-6-(5-{5H,6H,7H-pyrrolo[3,4-d]pyrimidin-6-yl}-1,2,4-oxadiazol-3-yl)-1,3,5-triazine-2,4-diamine To a solution of 6,7-dihydro-5H-pyrrolo[3,4-d]pyrimidine hydrochloride salt (38 mg, 0.231 mmol) in anhydrous THF (3 mL) was added DABAL-Me$_3$ (bis(trimethylaluminum)-1,4-diazabicyclo[2.2.2]-octane) (57 mg, 0.231 mmol) at room temperature. The solution was heated under nitrogen at 40 C for 3 h and N-methyl-N-phenyl-6-(5-trichloromethyl-[1,2,4]oxadiazol-3-yl)-[1,3,5]triazine-2,4-diamine (Intermediate 60, 60 mg, 0.155 mmol) was added. The resulting reaction mixture was heated at 80 C for 5 h and then quenched with water (2 mL) drop-wise. The solution was extracted into EtOAc (3×25 mL) and the combined organics washed with a 1M aq. solution of HCl (20 mL), brine (20 mL), dried over magnesium sulfate, evaporated to dryness and purified by preparative HPLC-MS (Method B) to afford the title compound as a white solid (5 mg, 8%).

Example 324

2-N-Methyl-2-N-phenyl-6-{5-[4-(3,3,3-trifluoropropylidene)piperidin-1-yl]-1,2,4-oxadiazol-3-yl}-1,3,5-triazine-2,4-diamine To a solution of triphenyl-(3,3,3-trifluoro-propyl)-phosphonium iodide (146 mg, 0.30 mmol) in anhydrous dioxane (10 mL) at 0 C under nitrogen was added potassium tert-butoxide (34 mg, 0.3 mmol) portion-wise. The suspension was stirred for 10 min at 0 C and then added drop-wise to a solution of 1-{3-[4-amino-6-(methyl-phenyl-amino)-[1,3,5]triazin-2-yl]-[1,2,4]oxadiazol-5-yl}-piperidin-4-one (Intermediate 131, 55 mg, 0.150 mmol) in anhydrous dioxane (10 mL). The resulting reaction mixture was stirred at room temperature for 16 h and evaporated to dryness. The solid obtained was dissolved in DCM (25 mL) and washed with water (25 mL), a saturated ammonium chloride aq. solution (25 mL) and brine (25 mL). The organic phase was dried over magnesium sulfate, evaporated to dryness and purified by preparative HPLC-MS (Method B) to afford the title compound as an off-white solid (8 mg, 12%).

Example 327

2-N-Methyl-2-N-phenyl-6-(5-{6-[(2,2,2-trifluoroethyl)amino]pyridin-3-yl}-1,2,4-oxadiazol-3-yl)-1,3,5-triazine-2,4-diamine (Method 19)

DavePhos (2-dicyclohexylphosphino-2'-(N,N-dimethylamino)biphenyl, 0.023 g, 0.058 mmol) and tris(dibenzylideneacetone)dipalladium(0) (0.024 g, 0.026 mmol) were added to a mixture of 6-[5-(6-chloropyridin-3-yl)-1,2,4-oxadiazol-3-yl]-2-N-methyl-2-N-phenyl-1,3,5-triazine-2,4-diamine (Intermediate 135, 0.100 g, 0.263 mmol) and 2,2,2-trifluoroethan-1-amine (0.084 mL, 1.050 mmol) in THF (1 mL) under nitrogen at room temperature. The reaction mixture was degassed by nitrogen bubbling and a 1M solution of LiHMDS in THF (2.10 mL, 2.10 mmol) was added drop wise at room temperature. The reaction mixture was heated under microwave conditions (200 W, T=120 C) for 40 min (20 min ramp, 20 min at 120 C) while being stirred. At room temperature the reaction mixture was diluted with EtOAc and filtered. The collected solid was taken in MeOH, filtered and wash with a large amount of MeOH and further purified by preparative HPLC, to afford the title compound (7 mg, 6%).

Example 330

2-{[5-(3-{4-Amino-6-[methyl(phenyl)amino]-1,3,5-triazin-2-yl}-1,2,4-oxadiazol-5-yl)pyridin-2-yl]oxy}acetonitrile A mixture of 5-(3-{4-amino-6-[methyl(phenyl)amino]-1,3,5-triazin-2-yl}-1,2,4-oxadiazol-5-yl)pyridin-2-ol (Intermediate 136, 0.150 g, 0.414 mmol), 2-iodoacetonitrile (0.036 mL, 0.497 mmol), cesium carbonate (0.270 g, 0.827 mmol) in DMF (2 mL) was stirred at 90 C in a pressure tube for 18 h. A further 0.6 equivalent of 2-iodoacetonitrile was added and the mixture was stirred overnight at 90 C. The reaction mixture was cooled to room temperature, diluted with water, the precipitate was collected by filtration, washed with water and dried under vacuum. The resulting solid was purified by preparative HPLC to afford the title compound (3 mg, 2%).

Example 332

2-N-Methyl-2-N-phenyl-6-(5-{6-[(propan-2-yl)amino]pyridin-3-yl}-1,2,4-oxadiazol-3-yl)-1,3,5-triazine-2,4-diamine (Method 20)

A mixture of 6-[5-(6-chloropyridin-3-yl)-1,2,4-oxadiazol-3-yl]-2-N-methyl-2-N-phenyl-1,3,5-triazine-2,4-diamine (Intermediate 135, 0.100 g, 0.263 mmol), isopropylamine (0.087 mL, 1.052 mmol), DIPEA (0.091 mL, 0.525 mmol) in EtOH (1 mL) was heated 3 times under microwave conditions (first treatment: 100 W, 130 C, 40 min; second treatment: 100 W, 130 C, 45 min; third treatment: 100W, 130 C, 45 min). The reaction mixture was cooled down and concentrated under vacuum. The resulting dark oil was purified by preparative HPLC, to afford the title compound (29 mg, 27%).

Example 346

6-[5-(3-Fluoropyridin-2-yl)-1,2,4-oxadiazol-3-yl]-2-N-phenyl-1,3,5-triazine-2,4-diamine 3-Fluoropyridine-2-carboxylic acid (1.75 g, 12.38 mmol) was dissolved in pyridine (15 mL) and N-(3-dimethylaminopropyl)-N'-ethylcarbodiimide hydrochloride (2.74 g, 14.28 mmol) was added. The mixture was stirred at room temperature for 2 h. 4-Amino-N'-hydroxy-6-(phenylamino)-1,3,5-triazine-2-carboximidamide (prepared in an analogous manner to Intermediate 4, 2.33 g, 9.52 mmol) was added and the mixture stirred at room temperature for 16 h. LCMS showed incomplete conversion, so further N-(3-dimethylaminopropyl)-N'-ethylcarbodiimide hydrochloride (1.30 g, 6.8 mmol) was added and the mixture stirred at room temperature for 3 h, before being heated to 60 C under nitrogen for 16 h. Pyridine was removed under vacuum and water (100 mL) was added to the residue. The mixture was extracted with EtOAc (100 mL), with the addition of brine (100 mL) to aid separation of an emulsion. The aqueous phase was then extracted with DCM (100 mL), which also formed an emulsion. After separation the aqueous phase was filtered to remove an insoluble gum. The aqueous phase was then further extracted with DCM (2×100 mL). The combined DCM and EtOAc layers were dried over sodium sulfate and concentrated under vacuum to yield a pale orange solid. This was purified by FCC using a gradient of 0-8% MeOH in DCM. The crude product was further purified by trituration with DCM to afford the title compound as a white solid (0.425 g, 13%).

Example 358

2-N-Methyl-2-N-phenyl-6-(5-{5-[1-(2,2,2-trifluoro-ethoxy)ethyl]pyridin-2-yl}-1,2,4-oxadiazol-3-yl)-1,3,5-triazine-2,4-diamine 1-[6-(3-{4-Amino-6-[methyl(phenyl)amino]-1,3,5-triazin-2-yl}-1,2,4-oxadiazol-5-yl)pyridin-3-yl]ethyl 2,2,2-trichloroethanecarboximidate (Intermediate 139, 0.497 g, 0.93 mmol) was suspended in DCE (8 mL). 2,2,2-Trifluoroethanol (0.669 mL, 9.29 mmol) and tetrafluoroboric acid diethyl ether complex (0.025 mL, 0.19 mmol) were added and the mixture was stirred at room temperature for 7 h. LCMS showed incomplete conversion, so further tetrafluoroboric acid diethyl ether complex (0.125 mL, 0.93 mmol) was added and the mixture stirred at room temperature for 21 h. DCM (100 mL) and saturated aq. sodium bicarbonate (50 mL) were added. The organic layer was separated, washed with brine (30 mL), dried over sodium sulfate and concentrated under vacuum to yield a brown solid, which was purified by FCC using a gradient of 0-5% MeOH in DCM. The crude product was then purified by preparative HPLC, Method D, to afford an off-white solid. This was further purified by FCC using a gradient of 0-3% MeOH in DCM to afford the title compound as an off-white solid (0.022 g, 5%).

Example 366

2-N-Methyl-2-N-phenyl-6-(5-{6-[2-(2,2,2-trifluoro-ethoxy)ethoxy]pyridin-3-yl}-1,2,4-oxadiazol-3-yl)-1,3,5-triazine-2,4-diamine 6-[2-(2,2,2-Trifluoroethoxy)ethoxy]pyridine-3-carboxylic acid (Intermediate 242, 0.133 g, 0.50 mmol) and 1,1'-carbonyldiimidazole (0.081 g, 0.50 mmol) were combined in pyridine (3 mL) and stirred at room temperature for 3 h. 4-Amino-N-hydroxy-6-[methyl(phenyl)amino]-1,3,5-triazine-2-carboximidamide (prepared in an analogous manner to Intermediate 1, 0.100 g, 0.39 mmol) was added and the mixture stirred at room temperature for 4 h before being heated to 80 C for 16 h. Pyridine was removed under vacuum and the residue was partitioned between EtOAc (20 mL) and water (20 mL). The organic layer was dried over sodium sulfate and concentrated to yield an orange solid. This was purified by FCC, using a gradient of 30-70% EtOAc in heptane to afford the title compound as a white solid (0.116 g, 61%). Method A HPLC-MS: MH+ requires m/z=489 Found: m/z=489, Rt=4.58 min (100%). 1H NMR (500 MHZ, CDCl$_3$) δ ppm 9.06 (1H, s), 8.41 (1H, d), 7.47 (2H, m), 7.34 (3H, m), 6.96 (1H, d), 5.34 (2H, br s), 4.64 (2H, t), 4.04 (2H, t), 3.97 (2H, q) and 3.65 (3H, s).

Example 384

1-[3-(3-{4-Amino-6-[methyl(phenyl)amino]-1,3,5-triazin-2-yl}-1,2,4-oxadiazol-5-yl)azetidin-1-yl]ethan-1-one 6-[5-(Azetidin-3-yl)-1,2,4-oxadiazol-3-yl]-2-N-methyl-2-N-phenyl-1,3,5-triazine-2,4-diamine (Intermediate 149, 85 mg, 0.26 mmol), 3,3,3-trifluoropropanal (32 µL, 0.28 mmol) and acetic acid (45 µL, 0.78 mmol) were combined in DCE (5 mL) and stirred for 3 h at room temperature. Sodium triacetoxyborohydride (83 mg, 0.39 mmol) was added and the mixture was heated to 70 C for 5 h. The reaction mixture was cooled at room temperature, concentrated under vacuum and purified by preparative HPLC, Method C, to afford the title compound as a white solid (25 mg, 26%).

Example 386

(1R,5S,6S)-6-(3-{4-Amino-6-[methyl(phenyl)amino]-1,3,5-triazin-2-yl}-1,2,4-oxadiazol-5-yl)-3-benzyl-3-azabicyclo[3.1.0]hexane-2,4-dione)

Ethyl (1R,5S,6S)-3-benzyl-2,4-dioxo-3-azabicyclo[3.1.0]hexane-6-carboxylate (Intermediate 254, 0.300 g, 1.098 mmol) was dissolved in THF (9 mL) and water (3 mL) and lithium hydroxide (32 mg, 1.31 mmol) was added and the mixture was stirred at room temperature for 3 h. A further 1 equivalent of lithium hydroxide was then added and the mixture was stirred at room temperature for 2 h to afford (1S,5R,6S)-3-benzyl-2,4-dioxo-3-azabicyclo[3.1.0]hexane-6-carboxylic acid. A portion of this acid (0.090 g, 0.367 mmol) was dissolved in pyridine (2 mL) and 1,1'-carbonyldiimidazole (0.089 g, 0.551 mmol) was added and the mixture was stirred at room temperature for 3 h. 4-Amino-N-hydroxy-6-[methyl(phenyl)amino]-1,3,5-triazine-2-carboximidamide (prepared in an analogous manner to Intermediate 1, 0.095 g, 0.367 mmol) was added and the mixture was heated to 90 C overnight. An extra 0.5 equivalents of acid which had been activated using 1,1'-carbonyldiimidazole were then added and the mixture stirred at 90 C for approximately 1 h. An extra 0.5 equivalents of acid which had been activated using 1,1'-carbonyldiimidazole were then added and the mixture stirred at 100 C for approximately 3 h. The reaction mixture was concentrated under vacuum and the residue was triturated with MeOH. The crude material was then purified by preparative HPLC, Method C, to afford the title compound as an off white solid (0.085 g, 49%).

Example 401

2-N-Methyl-2-N-phenyl-6-{5-[(4-{[(2,2,2-trifluoro-ethyl)sulfanyl]methyl}piperidin-1-yl)carbonyl]-1,2,4-oxadiazol-3-yl}-1,3,5-triazine-2,4-diamine
(Method 21)

Bis(trimethylaluminum)-1,4-diazabicyclo[2.2.2]octane adduct (225 mg, 0.88 mmol) was added to 4-{[(2,2,2-trifluoroethyl)sulfanyl]methyl}piperidine hydrochloride (Intermediate 267, 219 mg, 0.88 mmol) in dry THF (6 mL) in a sealed tube at room temperature. The reaction mixture was stirred at 40 C for 2 h. Ethyl 3-{4-amino-6-[methyl(phenyl)amino]-1,3,5-triazin-2-yl}-1,2,4-oxadiazole-5-carboxylate (prepared in an analogous manner to Example 73, 200 mg, 0.58 mmol) was added at 40 C. The reaction was heated at 80 C for 2 h before being concentrated under vacuum. The residue was taken up in DMSO (6 mL) and the inorganic residue was filtered off. The filtrate was purified by preparative HPLC, Method C, to provide two batches of the title compound (batch 1: 33 mg, 11%). Some impure product was recovered from the preparative HPLC purification, this material was concentrated, diluted with water (50 mL), acidified with a 1N aq. solution of HCl (to pH 4) and extracted with EtOAc (3×50 mL). The combined organic layers were washed with brine (50 mL) and dried over magnesium sulfate. This crude material was then purified by preparative HPLC, Method C, to provide the title compound (Batch 2: 83 mg, 28%).

Example 414

2-N-(3-Chloro-4-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine To a solution of 2-N-(3-Chloro-4-fluorophenyl)-6-{5-[6-(2,2,2-trifluoroethoxy)pyridin-3-yl]-1,2,4-oxadiazol-3-yl}-1,3,5-triazine-2,4-diamine (Example 413, 0.049 g, 0.101 mmol) in DMF (1 mL) was added potassium carbonate (0.028 g, 0.028 mmol) and iodomethane (0.021 g, 0.152 mmol). The reaction mixture was stirred at room temperature for 14 h after which time further iodomethane (0.042 g, 0.304 mmol) was added and the mixture was stirred at room temperature for 56 h. LCMS indicated incomplete conversion so further iodomethane (0.014 g, 0.105 mmol) was added and the mixture was heated to 50 C for 12 h. After this time cesium carbonate (0.032 g, 0.105 mmol) was added and the mixture was heated to 50 C for 1 h. Further iodomethane (0.021 g, 0.152 mmol) and cesium carbonate (0.064 g, 0.201 mmol) were added and the mixture was heated to 50 C for 14 h. Sodium hydride (60% dispersion in mineral oil, 0.004 g, 0.105 mmol) and further iodomethane (0.042 g, 0.304 mmol) were added and the mixture stirred for 1 h at 50 C. The mixture was quenched with water/ammonia/MeOH (1 mL) and extracted with EtOAc. The organic layer was washed with water, dried over sodium sulfate and concentrated under vacuum. The solid was dissolved in DMF (0.5 mL) and Sodium hydride (60% dispersion in mineral oil, 0.006 g, 0.152 mmol) and iodomethane (0.042 g, 0.304 mmol) were added. The reaction mixture was stirred at room temperature for 2 h. The reaction mixture was quenched with water/ammonia/MeOH (1 mL) and extracted with EtOAc. The organic layer was washed with water, dried over sodium sulfate and concentrated under vacuum. The residue was purified by HPLC Method B to afford the title compound (0.004 g, 8%).

Example 422

6-[5-(4-Aminocyclohexyl)-1,2,4-oxadiazol-3-yl]-2-N-methyl-2-N-phenyl-1,3,5-triazine-2,4-diamine (Method 23)

To tert-butyl N-[4-(3-{4-amino-6-[methyl(phenyl)amino]-1,3,5-triazin-2-yl}-1,2,4-oxadiazol-5-yl)cyclohexyl]carbamate (Example 423, 2.349 g, 5.035 mmol) was added hydrogen chloride solution (4M in 1,4-dioxane, 10 mL, 40 mmol) and the mixture was stirred at room temperature for 4 h. The mixture was concentrated under vacuum, water was added and the aqueous was neutralized to pH7 using saturated aq. sodium bicarbonate. The resultant precipitate was collected by filtration to afford the title compound as a white solid (0.877 g, 48%).

Example 425

N-[4-(3-{4-Amino-6-[methyl(phenyl)amino]-1,3,5-triazin-2-yl}-1,2,4-oxadiazol-5-yl)cyclohexyl]-2-methylpropanamide (Method 22)

To a solution of 2-methylpropanoic acid (0.03 g, 0.327 mmol) in DMF (5 mL) was added DIPEA (0.122 mL, 0.682 mmol) followed by (1H-benzotriazol-1-yloxy)[tris(dimethylamino)]phosphonium hexafluorophosphate (0.13 g, 0.3 mmol). The reaction mixture was stirred at room temperature for 5 min and 6-[5-(4-aminocyclohexyl)-1,2,4-oxadiazol-3-yl]-2-N-methyl-2-N-phenyl-1,3,5-triazine-2,4-diamine (batch 1 from Example 422, 0.1 g, 0.273 mmol) was added. The reaction mixture was stirred at room temperature for 16 h and then concentrated, extracted with EtOAc, washed with water, dried over sodium sulfate and concentrated. The residue was purified by FCC, eluting with 0-10% MeOH in DCM. The crude product was dissolved in EtOAc, washed with saturated aq. sodium bicarbonate, dried over sodium sulfate and concentrated under vacuum to afford the title compound (0.0255 g, 21%).

Example 429

2-N-methyl-6-[5-(4-phenoxycyclohexyl)-1,2,4-oxadiazol-3-yl]-2-N-phenyl-1,3,5-triazine-2,4-diamine To a solution of 4-(3-{4-amino-6-[methyl(phenyl)amino]-1,3,5-triazin-2-yl}-1,2,4-oxadiazol-5-yl)cyclohexan-1-ol (Example 424, 0.1 g, 0.272 mmol) in THF (4 mL) was added phenol (0.03 g, 0.272 mmol), triphenylphosphine (0.09 g, 0.327 mmol) and N-{[(tert-butoxy)carbonyl]imino}(tert-butoxy)formamide (0.08 g, 0.327 mmol). The reaction mixture was stirred at room temperature 16 h. The mixture was then concentrated and purified by preparative HPLC, Method D, to afford the title compound (0.010 g, 8%).

Example 432

2-N-(6-Fluoropyridin-3-yl)-2-N-methyl-6-{5-[6-(2,2,2-trifluoroethoxy)pyridin-3-yl]-1,2,4-oxadiazol-3-yl}-1,3,5-triazine-2,4-diamine 6-(2,2,2-Trifluoroethoxy)pyridine-3-carboxylic acid (prepared in an analogous manner to Intermediate 206, 0.216 g, 0.051 mmol) was added to a solution of N-(3-dimethylaminopropyl)-N'-ethylcarbodiimide hydrochloride (0.049 g, 0.252 mmol) in pyridine (1 mL) and the mixture was stirred at room temperature for 16 h. Further N-(3-dimethylaminopropyl)-N'-ethylcarbodiimide hydrochloride (0.0255 g, 0.1 mmol) was added and the mixture was stirred at 50 C for 4 h. 4-Amino-6-[(6-fluoropyridin-3-yl)(methyl)amino]-N'-hydroxy-1,3,5-triazine-2-carboximidamide (Intermediate 156, 0.05 g, 0.18 mmol) and N-(3-dimethylaminopropyl)-N'-ethylcarbodiimide hydrochloride (0.0163 g, 0.09 mmol) were added and the mixture was stirred at 50 C for 16 h and then at 60 C for 5 h. The mixture was dissolved in EtOAc and washed with water, and then saturated aq. ammonium chloride, saturated aq. sodium bicarbonate and then brine. The organic layer was dried over sodium sulfate and concentrated under vacuum. The residue was purified by preparative HPLC, Method B, to afford the title compound (0.002 g, 3%).

Example 436

2-N-(2-Methoxyethyl)-6-[5-(3-phenoxyazetidin-1-yl)-1,2,4-oxadiazol-3-yl]-2-N-phenyl-1,3,5-triazine-2,4-diamine Trichloroacetic anhydride (0.181 mL, 0.989 mmol) was added to 4-amino-N'-hydroxy-6-[(2 methoxyethyl)(phenyl)amino]-1,3,5-triazine-2-carboximidamide (Intermediate 160, 0.250 g, 0.824 mmol) in toluene (10 mL) and stirred at room temperature for 5 min. Pyridine (3 mL) was added and the mixture was heated to 85 C for 1 h. The mixture was concentrated under vacuum and the residue dissolved in EtOAc. This was washed with water, saturated aq. sodium bicarbonate and then brine. The organic layer was dried over sodium sulfate and concentrated. The residue was dissolved in DMF (2 mL) and 3-phenoxyazetidine hydrochloride (0.13 g, 0.685 mmol) and DIPEA (0.499 mL, 1.370 mmol) were added. The mixture was stirred at room temperature for 13 h and was then concentrated under vacuum. The mixture was extracted with EtOAc (30 mL), washed with water, saturated aq. sodium bicarbonate and then brine. The organic layer was dried over sodium sulfate and concentrated under vacuum. The residue was purified by FCC, eluting with 0-2% MeOH in DCM. The crude material was further purified by FCC, eluting with 50% EtOAc in heptane then 0-2% MeOH in DCM to afford the title compound (0.091 g, 29%).

Example 441

2-N-Methyl-2-N-phenyl-6-{5-[(2S)-1-(3,3,3-trifluoropropyl)pyrrolidin-2-yl]-1,2,4-oxadiazol-3-yl}-1,3,5-triazine-2,4-diamine (Method 24)

To a solution of 2-N-methyl-2-N-phenyl-6-{5-[(2S)-pyrrolidin-2-yl]-1,2,4-oxadiazol-3-yl}-1,3,5-triazine-2,4-diamine hydrochloride (Example 438, 0.2 g, 0.535 mmol) in DCE (5 mL) was added sodium acetate (0.07 g, 0.8 mmol) and 3,3,3-trifluoropropanal (0.12 g, 1.070 mmol) and the mixture was stirred for 1 h at room temperature. Sodium triacetoxyborohydride (0.17 g, 0.8 mmol) was added and the reaction mixture was stirred for 2 h at room temperature. DCM was added and the mixture was washed with saturated aq. sodium bicarbonate, and then brine. The organic layer was dried over sodium sulfate and concentrated under vacuum. The residue was purified by FCC, eluting with 20-100% EtOAc in heptane to afford the title compound (0.045 g, 19%).

Example 445

2-N-methyl-2-N-phenyl-6-{5-[(3S)-3-(2,2,2-trifluoroethoxy)pyrrolidin-1-yl]-1,2,4-oxadiazol-3-yl}-1,3,5-triazine-2,4-diamine Di-tert-butyl azodicarboxylate (2.96 g, 12.83 mmol) was added to an ice cooled mixture of tert-butyl (3R)-3-hydroxypyrrolidine-1-carboxylate (2.00 g, 10.70 mmol), 2,2,2-trifluoroethanol (10.70 g, 106.95 mmol) and triphenylphosphine (3.37 g, 12.83 mmol) in THF (24 mL). The mixture was stirred at 70 C for 18 h. The mixture was concentrated under vacuum and the residue was purified by FCC, eluting with a gradient of EtOAc in heptane to afford tert-butyl (3S)-3-(2,2,2-trifluoroethoxy)pyrrolidine-1-carboxylate (0.393 g, 14%). This was dissolved in hydrogen chloride solution (4M in 1,4-dioxane, 3 mL, 12 mmol) and the mixture was stirred for 2 h. The mixture was concentrated to afford (3S)-3-(2,2,2-trifluoroethoxy)pyrrolidine hydrochloride (0.203 g, 68% yield). This was combined with 2-N-methyl-2-N-phenyl-6-[5-(trichloromethyl)-1,2,4-oxadiazol-3-yl]-1,3,5-triazine-2,4-diamine (prepared in an analogous manner to Intermediate 60, 0.1 g, 0.259 mmol) and potassium carbonate (0.13 g, 0.952 mmol) in DMF (2 mL) and the reaction mixture was stirred at room temperature for 16 h. The mixture was then concentrated and the residue dissolved in EtOAc. This was washed with saturated aq. sodium bicarbonate followed by brine, then dried over sodium sulfate and concentrated under vacuum. The residue was purified by preparative HPLC, Method D, to afford the title compound (0.006 g, 6%).

Example 464

2-N-Methyl-2-N-phenyl-6-[5-({4-[(3,3,3-trifluoropropoxy)methyl]piperidin-1-yl}carbonyl)-1,2,4-oxadiazol-3-yl]-1,3,5-triazine-2,4-diamine tert-Butyl 4-[(3,3,3-trifluoropropoxy)methyl]piperidine-1-carboxylate (Intermediate 291, 0.256 g, 0.82 mmol) was dissolved in a 4M solution of HCl in dioxane, the mixture was stirred at room temperature for 2 h before being concentrated and azeotroped twice with toluene. A portion of the resulting residue ([(3,3,3-trifluoropropoxy)methyl]piperidine hydrochloride) (97 mg, 0.39 mmol) and ethyl 3-{4-amino-6-[methyl(phenyl)amino]-1,3,5-triazin-2-yl}-1,2,4-oxadiazole-5-carboxylate (prepared in an analogous manner to Example 73, 90 mg, 0.26 mmol) were used according to the method described for Example 463 to prepare the title compound. The crude residue was purified by preparative HPLC, Method C, to afford the title compound (36 mg, 27%).

Example 478

5-{3-[4-Amino-6-(methyl-phenyl-amino)-[1,3,5]triazin-2-yl]-[1,2,4]oxadiazol-5-yl}-pyridine-2-carboxylic acid dimethylamide Dimethylamine (248 µL, 0.495 mmol) and bis(trimethylaluminum)-1,4-diazabicyclo[2.2.2]-octane (128 mg, 0.495 mmol) were stirred together in anhydrous toluene (2 mL) at 40 C under nitrogen for 1 h. 5-{3-[4-Amino-6-(methyl-phenyl-amino)-[1,3,5]triazin-2-yl]-[1,2,4]oxadiazol-5-yl}-pyridine-2-carboxylic acid methyl ester (prepared in an analogous manner to Example 279, 80 mg, 0.198 mmol) was added and the reaction stirred at 80 C for approximately 18 h. The mixture was then allowed to cool to room temperature and diluted with EtOAc (20 mL). The solution was then washed with 2M HCl (2×6 mL), saturated aq. sodium bicarbonate (2×6 mL), dried over sodium sulfate and evaporated under vacuum. The crude residue was purified by flash chromatography (0-3% MeOH in DCM) and the material obtained was then further purified by flash chromatography (0-80% EtOAc in heptane) to afford the title compound (10 mg, 12%).

Example 481

6-{5-[3-(Cyclopropylamino)pyridin-2-yl]-1,2,4-oxadiazol-3-yl}-2-N-methyl-2-N-phenyl-1,3,5-triazine-2,4-diamine 1,1'-Carbonyldiimidazole (62 mg, 0.380 mmol) was added to a solution of 3-fluoropyridine-2-carboxylic acid (50 mg, 0.354 mmol) in anhydrous pyridine (1 mL) in a sealed tube at room temperature and the mixture was stirred for 1 h. 4-Amino-N-hydroxy-6-(methyl-3-methylphenyl-amino)-[1,3,5]triazine-2-carboxamidine (prepared in an analogous manner to Intermediate 1, 66 mg, 0.253 mmol) was added and the mixture was stirred at room temperature for 60 min and then at 90 C for approximately 18 h. The mixture was then treated with cyclopropanamine (300 µL, 4.32 mmol) and stirred at 80 C for 7 h. The mixture was then diluted with EtOAc (35 mL) and washed with water (10 mL), saturated aq.

ammonium chloride (2×6 mL) and 2M hydrochloric acid (3×5 mL). The combined hydrochloric acid extractions were washed with DCM (2×6 mL) and then made alkaline by the addition of 2M aq. sodium hydroxide. The resulting solution was extracted with DCM (4×7 mL), the combined organic extractions were washed with brine (10 mL), dried over sodium sulfate and evaporated under vacuum. The crude residue was purified by flash chromatography (0-3% MeOH in DCM) to afford the title compound (17 mg, 17%).

Example 482

6-[5-(3-Fluoropyridin-2-yl)-[1,2,4]oxadiazol-3-yl]-N-methyl-N-phenyl-[1,3,5]triazine-2,4-diamine (Method 26)

N-[3-(Dimethylamino)propyl]-N'-ethylcarbodiimide hydrochloride (633 mg, 3.3 mmol) was added to a solution of 3-fluoropyridine-2-carboxylic acid (400 mg, 2.83 mmol) in anhydrous pyridine (6 mL) in a sealed tube at room temperature under nitrogen. The reaction mixture was stirred at room temperature for 1 h. 4-Amino-N-hydroxy-6-(methyl-3-methylphenyl-amino)-[1,3,5]triazine-2-carboxamidine (prepared in an analogous manner to Intermediate 1, 611 mg, 2.36 mmol) was added and the mixture was stirred at room temperature for approximately 18 h. A solution of N-[3-(dimethylamino)propyl]-N'-ethylcarbodiimide hydrochloride (315 mg, 1.15 mmol) in anhydrous pyridine (1 mL) was added and the mixture was stirred for 2 h. Further N-[3-(dimethylamino)propyl]-N'-ethylcarbodiimide hydrochloride (100 mg, 0.52 mmol) and 3-fluoropyridine-2-carboxylic acid (70 mg, 0.5 mmol) were then added and the mixture was stirred at room temperature for 1 h and then at 60 C for approximately 18 h. The mixture was then diluted with EtOAc (75 mL) and washed with saturated aq. ammonium chloride (4×15 mL), then saturated aq. sodium bicarbonate (3×15 mL) and brine (15 mL). The organic layer was dried over sodium sulfate and evaporated under vacuum. The crude residue was purified by flash chromatography (0-2% MeOH in DCM) to afford the title compound (220 mg). 20 mg of this material was dissolved in hot DMSO (0.3 mL) and MeOH (0.5 mL) and then 1:1 MeCN:water (1 mL) was added. The resultant precipitate was filtered, the solids were washed with water (2×1 mL) and then dried under vacuum to afford the title compound as a white solid (14 mg, 2%).

Example 487

6-{5-[3-(Cyclopropylmethylamino)-pyridin-2-yl]-[1,2,4]oxadiazol-3-yl}-N-methyl-N-phenyl-[1,3,5]triazine-2,4-diamine (Method 25)

6-[5-(3-Fluoropyridin-2-yl)-[1,2,4]oxadiazol-3-yl]-N-methyl-N-phenyl-[1,3,5]triazine-2,4-diamine (prepared in an analogous manner to Example 482, 50 mg, 0.137 mmol), 1-cyclopropylmethanamine (24 µL, 0.274 mmol) and potassium carbonate (57 mg, 0.411 mmol) were suspended in anhydrous DMF (2 mL) in a sealed tube at room temperature under nitrogen. The reaction mixture was stirred at 90 C for 3 h and then at 100 C for 18 h. The mixture was diluted with DCM (10 mL) and then washed with saturated aq. ammonium chloride (3×5 mL) and then brine (5 mL). The organic layer was dried over sodium sulfate and evaporated under vacuum. The crude residue was purified by flash chromatography (0-1% (7M ammonia in MeOH) in DCM) to afford the title compound (25 mg, 44%).

Example 492

6-[5-(3-Isopropoxyazetidin-1-yl)-[1,2,4]oxadiazol-3-yl]-N-methyl-N-phenyl-[1,3,5]triazine-2,4-diamine (Method 27)

Sodium hydride (60% dispersion in mineral oil, 9 mg, 0.22 mmol) was added to a solution of 1-{3-[4-amino-6-(methyl-phenyl-amino)-[1,3,5]triazin-2-yl]-[1,2,4]oxadiazol-5-yl}-azetidin-3-ol (Intermediate 166, 50 mg, 0.147 mol) in anhydrous DMF (0.5 mL) at 0 C under nitrogen and the mixture was stirred for 10 min. A solution of propan-2-yl methanesulfonate (26.7 µL, 0.221 mmol) in anhydrous DMF (0.5 mL) was then added and the mixture was stirred at room temperature for 18 h. Further sodium hydride (60% dispersion in mineral oil, 9 mg, 0.22 mmol) and propan-2-yl methanesulfonate (26.7 µL, 0.221 mmol) were then added and the mixture was stirred at room temperature for 4 h. The mixture was diluted with EtOAc (10 mL) then washed with saturated aq. sodium carbonate (4×5 mL), brine (5 mL) and evaporated under vacuum. The crude residue was purified by flash chromatography (0-2% (7M ammonia in MeOH) in DCM) to afford the title compound as a light yellow glass (22 mg, 39%).

Example 495

N-Methyl-6-[5-(3-phenoxymethylazetidin-1-yl)-[1,2,4]oxadiazol-3-yl]-N-phenyl-[1,3,5]triazine-2,4-diamine (Method 28)

3-Phenoxymethyl-azetidine-1-carboxylic acid tert-butyl ester (Intermediate 166, 50 mg, 0.189 mmol) was stirred in a mixture of DCM (1 mL) and trifluoroacetic acid (0.25 mL) at room temperature for 30 min. The mixture was evaporated under vacuum and the residue was dissolved in anhydrous DMF (0.5 mL). DIPEA (165 µL, 0.945 mmol) was added, followed by a solution of N-methyl-N-phenyl-6-(5-trichloromethyl-[1,2,4]oxadiazol-3-yl)-[1,3,5]triazine-2,4-diamine (prepared in an analogous manner to Intermediate 60, 37 mg, 0.095 mmol) in DMF (1.5 mL). The reaction was stirred at room temperature for approximately 42 h. The mixture was diluted with EtOAc (15 mL) then washed with saturated aq. ammonium chloride (3×5 mL), saturated aq. sodium carbonate (3×5 mL), brine (5 mL), dried over sodium sulfate and evaporated under vacuum. The crude residue was purified by flash chromatography (0-2% MeOH in DCM) and then further purified by preparative HPLC, Method D, to afford the title compound (6 mg, 7%).

Table of Examples

The following Examples in the table have been prepared according to the method (M) indicated in the third column.

When method 4 was used, depending of the examples, the presence of a base (for example diisopropylethylamine or potassium carbonate) was optional.

a.IonWork Quattro data, b=Manual patch clamp data, c=Automated patch clamp data M=Method

| Example | Name Structure | M | Spectral data | Nav 1.7 activity (nM) |
|---|---|---|---|---|
| 1 | 6-(5-Furan-2-yl-[1,2,4]oxadiazol-3-yl)-N-methyl-N-phenyl-[1,3,5]triazine-2,4-diamine | 1 | Method A HPLC-MS: MH+ requires m/z = 336; Found: m/z = 336, Rt = 3.93 min (100%). 1H NMR (500 MHz, CDCl3) δ ppm 7.75 (1H, s), 7.52-7.42 (3H, m), 7.38-7.28 (3H, m), 6.68 (1H, s), 6.00-5.00 (2H, br s) and 3.65 (3H, s). | 212[b] |
| 2 | 6-(5-Furan-2-yl-[1,2,4]oxadiazol-3-yl)-N-phenyl-[1,3,5]triazine-2,4-diamine | 1 | Method A HPLC-MS: MH+ requires m/z = 322; Found: m/z = 322, Rt = 3.62 min (99%). 1H NMR (500 MHz, CDCl3) δ ppm 7.68 (1H, s), 7.62-7.53 (3H, m), 7.48-7.43 (1H, m), 7.35-7.28 (2H, m) 7.10-7.05 (1H, m) 6.60 (1H, s) and 6.10-5.40 (2H, br d). | 91[b] |
| 3 | 6-(5-Furan-2-yl-[1,2,4]oxadiazol-3-yl)-N-methyl-N-(3-methylphenyl)-[1,3,5]triazine-2,4-diamine | 1 | Method A HPLC-MS: MH+ requires m/z = 350; Found: m/z = 350, Rt = 4.28 min (95%). 1H NMR (400 MHz, CDCl3) δ ppm 7.72 (1H, d), 7.56 (1H, d), 7.32 (1H, m), 7.13 (3H, m), 6.66 (1H, d), 6.0-5.0 (2H, br d), 3.61 (3H, s) and 2.38 (3H, s). | 272[b] |

| Example | Name Structure | M | Spectral data | Nav 1.7 activity (nM) |
|---|---|---|---|---|
| 4 | 6-(5-Furan-2-yl-[1,2,4]oxadiazol-3-yl)-N-methyl-N-(4-methylphenyl)-[1,3,5]triazine-2,4-diamine 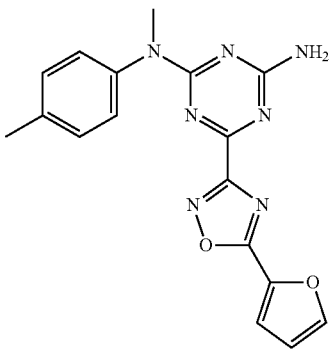 [SMILES: Cc1ccc(N(C)c2nc(N)nc(-c3noc(-c4ccco4)n3)n2)cc1] | 1 | Method A HPLC-MS: MH+ requires m/z = 350; Found: m/z = 350, Rt = 4.01 min (100%). 1H NMR (400 MHz, CDCl3) δ ppm 7.71 (1H, d), 7.46 (1H, d), 7.21 (4H, m), 6.66 (1H, d), 6.1-5.1 (2H, br s), 3.59 (3H, s) and 2.38 (3H, s). | 661[b] |
| 5 | 6-(5-Furan-2-yl-[1,2,4]oxadiazol-3-yl)-N-methyl-N-(3-methoxyphenyl)-[1,3,5]triazine-2,4-diamine 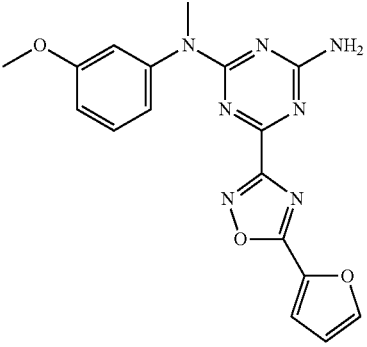 [SMILES: COc1cccc(N(C)c2nc(N)nc(-c3noc(-c4ccco4)n3)n2)c1] | 1 | Method A HPLC-MS: MH+ requires m/z = 366; Found: m/z = 366, Rt = 4.12 min (98%). 1H NMR (400 MHz, CDCl3) δ ppm 7.72 (1H, d), 7.46 (1H, d), 7.33 (1H, t), 6.92 (2H, m), 6.85 (1H, d), 6.66 (1H, d), 5.98-5.08 (2H, br s), 3.84 (3H, s) and 3.62 (3H, s). | 791[b] |
| 6 | 6-(5-Furan-2-yl-[1,2,4]oxadiazol-3-yl)-N-methyl-N-(4-methoxyphenyl)-[1,3,5]triazine-2,4-diamine 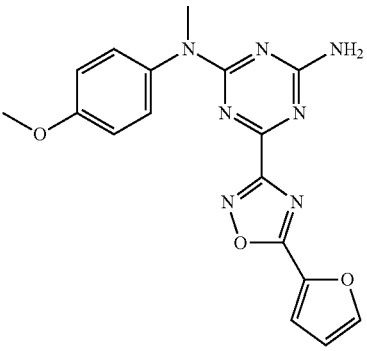 [SMILES: COc1ccc(N(C)c2nc(N)nc(-c3noc(-c4ccco4)n3)n2)cc1] | 1 | Method A HPLC-MS: MH+ requires m/z = 366; Found: m/z = 366, Rt = 4.09 min (98%). 1H NMR (400 MHz, CDCl3) δ ppm 7.72 (1H, d), 7.46 (1H, br s), 7.22 (2H, d), 6.95 (2H, d), 6.65 (1H, d), 5.97-5.00 (2H, br s), 3.85 (3H, s) and 3.58 (3H, brs). | 1944[b] |

| Example | Name Structure | M | Spectral data | Nav 1.7 activity (nM) |
|---|---|---|---|---|
| 7 | 6-(5-Furan-2-yl-[1,2,4]oxadiazol-3-yl)-N-methyl-N-(3-chlorophenyl)-[1,3,5]triazine-2,4-diamine | 1 | Method A HPLC-MS: MH+ requires m/z = 370/372; Found: m/z = 370/372, Rt = 4.39 min (97%). 1H NMR (400 MHz, CDCl3) δ ppm 7.72 (1H, d), 7.46 (1H, d), 7.36 (2H, m), 7.26 (2H, m), 6.66 (1H, d), 6.05-5.00 (2H, br s) and 3.60 (3H, s). | 187[b] |
| 8 | 6-(5-Furan-2-yl-[1,2,4]oxadiazol-3-yl)-N-methyl-N-(4-chlorophenyl)-[1,3,5]triazine-2,4-diamine | 1 | Method A HPLC-MS: MH+ requires m/z = 370/372; Found: m/z = 370/372, Rt = 4.39 min (100%). 1H NMR (400 MHz, CDCl3) δ ppm 7.71 (1H, d), 7.46 (1H, brs), 7.38 (2H, d), 7.32 (2H, d), 6.66 (1H, d), 5.97-5.00 (2H, br s) and 3.60 (3H, br s). | 339[b] |
| 9 | N-Methyl-N-phenyl-6-(5-pyridin-2-yl-[1,2,4]oxadiazol-3-yl)-[1,3,5]triazine-2,4-diamine | 1 | Method A HPLC-MS: MH+ requires m/z = 347; Found: m/z = 347, Rt = 3.56 min (98%). 1H NMR (500 MHz, CDCl3) δ ppm 8.79 (1H, m), 8.32 (1H, m), 8.85 (1H, m), 7.48 (1H, m), 7.36 (2H, m), 7.25 (3H, m), 5.0-5.58 (2H, br, d), 3.59 (3H, s). | 769[b] |

| Example | Name Structure | M | Spectral data | Nav 1.7 activity (nM) |
|---|---|---|---|---|
| 10 | N-Methyl-N-phenyl-6-(5-phenyl-[1,2,4]oxadiazol-3-yl)-[1,3,5]triazine-2,4-diamine | 1 | Method A HPLC-MS: MH+ requires m/z = 346; Found: m/z = 346, Rt = 4.23 min (98%). 1H NMR (500 MHz, CDCl3) δ ppm 8.21 (2H, m), 7.53 (1h, m), 7.49 (2H, m), 7.38 (2H, m), 7.25 (3H, m), 5.03-5.65, (2H, br, d), 3.53 (3H, s). | 348[b] |
| 11 | N-Methyl-N-phenyl-6-(5-thiophen-2-yl-[1,2,4]oxadiazol-3-yl)-[1,3,5]triazine-2,4-diamine | 1 | Method A HPLC-MS: MH+ requires m/z = 352; Found: m/z = 352, Rt = 4.12 min (100%). 1H NMR (500 MHz, CDCl3) δ ppm 7.98 (1H, m), 7.61 (1H, m), 7.38 (2H, m), 7.22 (3H, m), 7.15 (1H, m), 5.02-5.65 (2H, br, d) 3.54 (3H, s). | 216[b] |
| 12 | N-Methyl-6-[5-(5-chloro-thiophen-2-yl)-[1,2,4]oxadiazol-3-yl]-N-phenyl-[1,3,5]triazine-2,4-diamine | 1 | Method A HPLC-MS: MH+ requires m/z = 386; Found: m/z = 386, Rt = 4.51 min (100%). 1H NMR (500 MHz, CDCl3) δ ppm 7.26 (1H, m), 7.38 (2H, m), 7.22 (3H, m), 6.99 (1H, m), 5.01-5.69 (2H, br, d), 3.54 (3H, s). | 2319[b] |

| Example | Name Structure | M | Spectral data | Nav 1.7 activity (nM) |
|---|---|---|---|---|
| 13 | 6-[5-(6-Cyclopentoxy-pyridin-3-yl)-[1,2,4]oxadiazol-3-yl]-N-methyl-N-phenyl-[1,3,5]triazine-2,4-diamine | 1 | Method A HPLC-MS: MH+ requires m/z = 431; Found: m/z = 431, Rt = 4.75 min (96%). 1H NMR (400 MHz, CDCl3) δ ppm 9.03 (1H, s), 8.34 (1H, d), 7.45 (2H, m), 7.31 (3H, m), 6.81 (1H, d), 5.87-5.00 (2H, br s), 5.51 (1H, m), 3.61 (3H, s), 2.00 (2H, m), 1.82 (4H, m) and 1.67 (2H, m). | 4[b] |
| 14 | N-(2-Fluoro-phenyl)-6-(5-furan-2-yl-[1,2,4]oxadiazol-3-yl)-N-methyl-[1,3,5]triazine-2,4-diamine | 1 | Method A HPLC-MS: MH+ requires m/z = 354; Found: m/z = 354, Rt = 3.80 min (100%). 1H NMR (500 MHz, CDCl3) δ ppm 7.65 (1H, br, m), 7.1-7.5 (7H, m), 6.58 (1H, br, m), 5.2-5.48 (2H, br, d), 3.4-3.6 (3H, m). | 198[b] |
| 15 | N-(3-Fluoro-phenyl)-6-(5-furan-2-yl-[1,2,4]oxadiazol-3-yl)-N-methyl-[1,3,5]triazine-2,4-diamine | 1 | Method A HPLC-MS: MH+ requires m/z = 354; Found: m/z = 354, Rt = 3.88 min (97%). 1H NMR (500 MHz, CDCl3) δ ppm 7.65 (1H, s), 7.4 (1H, m), 7.31 (1H, m), 7.03 (2H, m), 6.94 (1H, m), 6.6 (1H, m), 5.12-5.57 (2H, br, d), 3.52 (3H, s). | 152[b] |

| Example | Name Structure | M | Spectral data | Nav 1.7 activity (nM) |
|---|---|---|---|---|
| 16 | N-(4-Fluoro-phenyl)-6-(5-furan-2-yl-[1,2,4]oxadiazol-3-yl)-N-methyl-[1,3,5]triazine-2,4-diamine | 1 | Method A HPLC-MS: MH+ requires m/z = 354; Found: m/z = 354, Rt = 3.84 min (100%). 1H NMR (500 MHz, CDCl3) δ ppm 7.65 (1H, s), 7.4 (1H, s), 7.22 (2H, m), 7.03 (2H, m), 6.59 (1H, s), 5.0-5.63 (2H, d), 3.51 (3H, s) | 264[b] |
| 17 | N-(2-Chloro-phenyl)-6-(5-furan-2-yl-[1,2,4]oxadiazol-3-yl)-N-methyl-[1,3,5]triazine-2,4-diamine | 1 | Method A HPLC-MS: MH+ requires m/z = 370; Found: m/z = 370, Rt = 3.92 min (98%). 1H NMR (500 MHz, CDCl3) δ ppm 7.61 (1H, m), 7.42 (2H, m), 7.28 (3H, br, m), 6.57 (1H, m), 5.04-5.65 (2H, br, d). 3.34-3.52 (3H, br, m). | <5000[a] |
| 18 | 6-(5-Furan-2-yl-[1,2,4]oxadiazol-3-yl)-N-methyl-N-o-tolyl-[1,3,5]triazine-2,4-diamine | 1 | Method A HPLC-MS: MH+ requires m/z = 350; Found: m/z = 350, Rt = 4.03 min (100%). 1H NMR (500 MHz, CDCl3) δ ppm 7.66 (1H, d), 7.41 (1H, d), 7.05-7.14 (1H, m), 6.59 (1H, dd), 5.50-5.76 (2H, m), 3.47 (3H, s), 2.07-2.12 (3H, m). | <5000[a] |

| Example | Name Structure | M | Spectral data | Nav 1.7 activity (nM) |
|---|---|---|---|---|
| 19 | N-Methyl-6-[5-(5-methyl-furan-2-yl)-[1,2,4]oxadiazol-3-yl]-N-phenyl-[1,3,5]triazine-2,4-diamine | 1 | Method A HPLC-MS: MH+ requires m/z = 350; Found: m/z = 350, Rt = 4.00 min (100%). 1H NMR (250 MHz, CDCl3) δ ppm 7.50-7.28 (6H, m), 6.30-6.22 (1H, m), 5.95-5.10 (2H, br s), 3.65 (3H, s) and 2.45 (3H, s). | 61[a] |
| 20 | N-Benzyl-6-(5-furan-2-yl-[1,2,4]oxadiazol-3-yl)-N-methyl-[1,3,5]triazine-2,4-diamine | 1 | Method A HPLC-MS: MH+ requires m/z = 350; Found: m/z = 350, Rt = 4.02 min (97%). 1H NMR (250 MHz, CDCl3) δ ppm 7.75 (1H, s), 7.55-7.45 (1H, m), 7.40-7.20 (5H, m), 6.65-6.70 (1H, m) 5.75-5.20 (2H, br s) 5.00 (2H, d) and 3.21 (3H, d). | <3000[a] |
| 21 | N-Ethyl-6-(5-furan-2-yl-[1,2,4]oxadiazol-3-yl)-N-phenyl-[1,3,5]triazine-2,4-diamine | 1 | Method A HPLC-MS: MH+ requires m/z = 350; Found: m/z = 350, Rt = 4.01 min (100%). 1H NMR (250 MHz, CDCl3) δ ppm 7.65 (1H, s), 7.48-7.30 (3H, m), 7.29-7.15 (3H, m), 6.69-6.50 (1H, m), 6.25-5.35 (2H, br s), 4.05 (2H, q) and 0.85 (3H, t). | 249[b] |

-continued

| Example | Name Structure | M | Spectral data | Nav 1.7 activity (nM) |
|---|---|---|---|---|
| 22 | 4-(2,3-Dihydro-indol-1-yl)-6-(5-furan-2-yl-[1,2,4]oxadiazol-3-yl)-[1,3,5]triazin-2-ylamine | 1 | Method A HPLC-MS: MH+ requires m/z = 348; Found: m/z = 348, Rt = 4.19 min (97%). 1H NMR (500 MHz, CDCl3) δ ppm 8.63-8.74 (0.5H, m), 8.39-8.48 (0.5H, m), 7.76 (1H, s), 7.52 (1H, d), 7.30-7.41 (0.5H, m), 7.22-7.28 (1.5H, m), 7.02-7.10 (1H, m), 6.69 (1H, dd), 5.27-5.93 (2H, m), 4.47 (1H, m), 4.16-4.31 (1H, m), 3.23 (2H, t). | <1000a |
| 23 | 6-[5-(2-Chloro-phenyl)-[1,2,4]oxadiazol-3-yl]-N-methyl-N-phenyl-[1,3,5]triazine-2,4-diamine | 1 | Method A HPLC-MS: MH+ requires m/z = 380; Found: m/z = 380, Rt = 4.26 min (100%). 1H NMR (500 MHz, CDCl3) δ ppm 8.18 (3H, d), 7.56-7.62 (3 H, m), 7.54 (4 H, td), 7.41-7.49 (11H, m), 7.28-7.39 (3H, m), 5.17-5.85 (2H, br. s.), 3.63 (3H, s). | 106b |
| 24 | 6-[5-(3-Methoxy-phenyl)-[1,2,4]oxadiazol-3-yl]-N-methyl-N-phenyl-[1,3,5]triazine-2,4-diamine | 1 | Method A HPLC-MS: MH+ requires m/z = 376; Found: m/z = 376, Rt = 4.20 min (99%). 1H NMR (250 MHz, CDCl3) δ ppm 7.86 (2H, d), 7.40-7.52 (6H, m), 7.28-7.39 (3H, m), 7.12-7.21 (1H, m), 5.23-5.76 (2H, m), 3.91 (3H, s), 3.64 (3H, s). | <500a |

| Example | Name Structure | M | Spectral data | Nav 1.7 activity (nM) |
|---|---|---|---|---|
| 25 | 6-[5-(2-Methoxy-phenyl)-[1,2,4]oxadiazol-3-yl]-N-methyl-N-phenyl-[1,3,5]triazine-2,4-diamine | 1 | Method A HPLC-MS: MH+ requires m/z = 376; Found: m/z = 376, Rt = 4.13 min (95%). 1H NMR (250 MHz, CDCl3) δ ppm 8.11 (2H, s), 7.39-7.50 (4H, m), 7.27-7.38 (3H, m), 5.20-5.58 (2H, m), 3.64 (3H, s), 2.45 (3H, s), 1.62 (3H, s). | 47b |
| 26 | 6-[5-(4-Methoxy-phenyl)-[1,2,4]oxadiazol-3-yl]-N-methyl-N-phenyl-[1,3,5]triazine-2,4-diamine | 1 | Method A HPLC-MS: MH+ requires m/z = 376; Found: m/z = 376, Rt = 4.27 min (98%). 1H NMR (500 MHz, CDCl3) δ ppm 8.13 (2 H, d), 7.32-7.43 (2H, m), 7.16-7.31 (3H, m), 6.96 (2H), 5.02-5.93 (2H, br. s.), 3.83 (3H, s), 3.55 (3H, s). | 148[b] |
| 27 | N-Methyl-N-phenyl-6-(5-o-tolyl-[1,2,4]oxadiazol-3-yl)-[1,3,5]triazine-2,4-diamine | 1 | Method A HPLC-MS: MH+ requires m/z = 360; Found: m/z = 360, Rt = 4.32 min (99%). 1H NMR (250 MHz, CDCl3) δ ppm 8.00-8.17 (2H, m), 7.39-7.52 (4H, m), 7.29-7.39 (3H, m), 5.26-5.83 (2H, m), 3.64 (3H, s), 2.45 (3H, s) | 923[c] |

| Example | Name Structure | M | Spectral data | Nav 1.7 activity (nM) |
|---|---|---|---|---|
| 28 | N-Methyl-N-phenyl-6-(5-m-tolyl-[1,2,4]oxadiazol-3-yl)-[1,3,5]triazine-2,4-diamine | 1 | Method A HPLC-MS: MH+ requires m/z = 360; Found: m/z = 360, Rt = 4.35 min (100%). 1H NMR (500 MHz, CDCl3) δ ppm 8.21 (1H, d), 7.43-7.54 (3H, m), 7.35-7.42 (4H, m), 7.30-7.35 (1H, m), 5.09-5.80 (2H, m), 3.65 (3H, s), 2.76 (3H, s), 1.65 (3H, s). | 955[c] |
| 29 | N-Methyl-N-phenyl-6-(5-p-tolyl-[1,2,4]oxadiazol-3-yl)-[1,3,5]triazine-2,4-diamine | 1 | Method A HPLC-MS: MH+ requires m/z = 360; Found: m/z = 360, Rt = 4.34 min (99%). 1H NMR (250 MHz, CDCl3) δ ppm 8.07 (2H, d), 7.16-7.43 (7H, m), 5.17-6.00 (2H, m), 3.55 (3H, s), 2.37 (3H, s). | 1380[c] |
| 30 | 6-(5-Furan-2-yl-[1,2,4]oxadiazol-3-yl)-N-isopropyl-N-phenyl-[1,3,5]triazine-2,4-diamine | 1 | Method A HPLC-MS: MH+ requires m/z = 364; Found: m/z = 364, Rt = 4.20 min (100%). 1H NMR (500 MHz, CDCl3) δ ppm 7.75 (1H, s), 7.60-7.35 (4H, m), 7.18 (2H, d), 6.65 (1H, s), 5.80-5.00 (2H, br s) and 1.20 (3H, d). | 933[c] |

-continued

| Example | Name Structure | M | Spectral data | Nav 1.7 activity (nM) |
|---|---|---|---|---|
| 31 | 6-(5-Benzyl-[1,2,4]oxadiazol-3-yl)-N-methyl-N-phenyl-[1,3,5]triazine-2,4-diamine | 1 | Method A HPLC-MS: MH+ requires m/z = 360; Found: m/z = 360, Rt = 4.09 min (100%). 1H NMR (250 MHz, CDCl3) δ ppm 7.58-7.42 (2H, m), 7.38-7.25 (8H, m), 6.10-5.00 (2H, br d), 4.35 (2H, s) and 3.60 (3H, s). | 363[c] |
| 32 | N-(3-Chloro-phenyl)-6-(5-furan-2-yl-[1,2,4]oxadiazol-3-yl)-[1,3,5]triazine-2,4-diamine | 1 | Method A HPLC-MS: MH+ requires m/z = 356/358; Found: m/z = 356/358, Rt = 3.96 min (100%). 1H NMR (500 MHz, CDCl3) δ ppm 7.78 (1H, s), 7.68 (1H, s), 7.48-7.42 (1H, m), 7.43-7.25 (2H, m), 7.23-7.19 (1H, m), 7.05 (1H, d), 6.62-6.59 (1H, m) and 5.88-5.33 (2H, br d). | <500[a] |
| 33 | N-(3-Chloro-phenyl)-6-(5-furan-2-yl-[1,2,4]oxadiazol-3-yl)-[1,3,5]triazine-2,4-diamine | 1 | Method A HPLC-MS: MH+ requires m/z = 404; Found: m/z = 404, Rt = 4.20 min (99%). 1H NMR (500 MHz, CDCl3) δ ppm 7.65 (1H, s), 7.58 (1H, s), 7.52-7.42 (3H, m), 7.40-7.38 (1H, m), 6.58 (1H, s), 6.10-4.95 (2H, br d) and 3.58 (3H, s). | <1000[a] |

| Example | Name Structure | M | Spectral data | Nav 1.7 activity (nM) |
|---|---|---|---|---|
| 34 | 6-(5-Furan-2-yl-[1,2,4]oxadiazol-3-yl)-N-methyl-N-(2,3-difluorophenyl)-[1,3,5]triazine-2,4-diamine | 1 | Method A HPLC-MS: MH+ requires m/z = 372; Found: m/z = 372, Rt = 4.47 min (99%). 1H NMR (400 MHz, CDCl3) δ ppm 7.73 (1H, br s), 7.48 (1H, br s), 7.13 (3H, m), 6.64 (1H, br s), 5.90-4.87 (2H, 2 × br s) and 3.61 (3H, br s). | <500[a] |
| 35 | 6-[5-(3-Chloro-phenyl)-[1,2,4]oxadiazol-3-yl]-N-methyl-N-phenyl-[1,3,5]triazine-2,4-diamine | 1 | Method A HPLC-MS: MH+ requires m/z = 380; Found: m/z = 380, Rt = 4.39 min (100%). 1H NMR (500 MHz, CDCl3) δ ppm 8.22 (1H, br. s.), 8.08 (1H, d), 7.53 (1H, d), 7.34-7.47 (3H, m), 7.21-7.31 (3H, m), 5.02-5.62 (2H, br. s.), 3.56 (3H, s). | 44% (10 μM)[b] |
| 36 | 6-[5-(4-Chloro-phenyl)-[1,2,4]oxadiazol-3-yl]-N-methyl-N-phenyl-[1,3,5]triazine-2,4-diamine | 1 | Method A HPLC-MS: MH+ requires m/z = 380; Found: m/z = 380, Rt = 4.52 min (100%). 1H NMR (500 MHz, CDCl3) δ ppm 8.17-8.26 (2H, m), 7.54 (2H, d), 7.45 (2H, d), 7.36 (3H, s), 4.96-5.60 (2H, m), 3.64 (3H, s). | 165[b] |

| Example | Name Structure | M | Spectral data | Nav 1.7 activity (nM) |
|---|---|---|---|---|
| 37 | 6-(5-Furan-3-yl-[1,2,4]oxadiazol-3-yl)-N-methyl-N-phenyl-[1,3,5]triazine-2,4-diamine | 1 | Method A HPLC-MS: MH+ requires m/z = 336; Found: m/z = 336, Rt = 3.78 min (100%). 1H NMR (250 MHz, CDCl3) δ ppm 8.35 (1H, s), 7.62-7.58 (1H, m), 7.50-7.40 (2H, m), 7.39-7.25 (3H, m), 7.10-7.00 (1H, m), 5.65-5.10 (2H, br s) and 3.65 (3H, s). | 50% (10 μM)[b] |
| 38 | N-Ethyl-N-phenyl-6-(5-thiazol-2-yl-[1,2,4]oxadiazol-3-yl)-[1,3,5]triazine-2,4-diamine | 1 | Method A HPLC-MS: MH+ requires m/z = 367; Found: m/z = 367, Rt = 4.06 min (95%). | 1119[b] |
| 39 | N-Phenyl-6-(pyridin-2-yl-[1,2,4]oxadiazol-3-yl)-[1,3,5]triazine-2,4-diamine | 2 | Method A HPLC-MS: MH+ requires m/z = 333; Found: m/z = 333, Rt = 3.74 min (100%). 1H NMR (500 MHz, CDCl3) δ ppm 8.85 (2H, d), 8.44 (1H, d), 7.94 (1H, m), 7.69 (1H, br s, NH), 7.62 (2H, d), 7.56 (1H, m), 7.35 (2H, t), 7.12 (1H, t), 5.97 (1H, br s, NH) and 5.75 (1H, br s, NH). | 319[b] |

| Example | Name Structure | M | Spectral data | Nav 1.7 activity (nM) |
|---|---|---|---|---|
| 40 | N-Phenyl-6-[5-(1H-pyrazol-3-yl)-[1,2,4]oxadiazol-3-yl]-[1,3,5]triazine-2,4-diamine | 1 | Method A HPLC-MS: MH+ requires m/z = 321; Found: m/z = 321, Rt = 3.22 min (100%). | 2721[c] |
| 41 | N-Phenyl-6-{5-[6-(2,2,2-trifluoro-ethoxy)-pyridin-3-yl]-[1,2,4]oxadiazol-3-yl}-[1,3,5]triazine-2,4-diamine | 1 | Method A HPLC-MS: MH+ requires m/z = 431; Found: m/z = 431, Rt = 4.33 min (100%). | 673[c] |
| 42 | N-Methyl-N-phenyl-6-{5-[3-(2,2,2-trifluoro-ethoxy)-pyridin-2-yl]-[1,2,4]oxadiazol-3-yl}-[1,3,5]triazine-2,4-diamine | 3 | Method A HPLC-MS: MH+ requires m/z = 445; Found: m/z = 445, Rt = 4.03 min (100%). | 1409[c] |

| Ex-ample | Name Structure | M | Spectral data | Nav 1.7 activity (nM) |
|---|---|---|---|---|
| 43 | 6-[5-(3-Bromopyridin-2-yl)-[1,2,4]oxadiazol-3-yl]-N-methyl-N-phenyl-[1,3,5]triazine-2,4-diamine | 1 | Method A HPLC-MS: MH+ requires m/z = 426; Found: m/z = 427, Rt = 3.96 min (98%). | 102[c] |
| 44 | N-Methyl-6-[5-(5-methyl-isoxazol-3-yl)-[1,2,4]oxadiazol-3-yl]-N-phenyl-[1,3,5]triazine-2,4-diamine | 1 | Method A HPLC-MS: MH+ requires m/z = 351; Found: m/z = 351, Rt = 3.94 min (95%). | 2719[c] |
| 45 | N-Methyl-6-(5-morpholin-4-yl-[1,2,4]oxadiazol-3-yl)-N-phenyl-[1,3,5]triazine-2,4-diamine | 4 | Method A HPLC-MS: MH+ requires m/z = 355; Found: m/z = 355, Rt = 3.42 min (99%). | 3522[c] |

| Example | Name Structure | M | Spectral data | Nav 1.7 activity (nM) |
|---|---|---|---|---|
| 46 | N-Methyl-N-phenyl-6-(5-piperidin-1-yl-[1,2,4]oxadiazol-3-yl)-[1,3,5]triazine-2,4-diamine | 4 | Method A HPLC-MS: MH+ requires m/z = 353; Found: m/z = 353, Rt = 3.89 min (100%). 1H NMR (500 MHz, CDCl3) δ ppm 7.40-7.48 (2H, m), 7.26-7.35 (4H, m), 5.00-5.93 (2 H, br. s), 3.69 (4H, s), 3.61 (3H, s) and 1.69 (6H, br. s). | 511[b] |
| 47 | 6-[5-(6-Methoxy-pyridin-3-yl)-[1,2,4]oxadiazol-3-yl]-N-methyl-N-phenyl-[1,3,5]triazine-2,4-diamine | 1 | Method A HPLC-MS: MH+ requires m/z = 377; Found: m/z = 377, Rt = 4.11 min (99%). | 1921[c] |
| 48 | 6-[5-(6-Methoxy-pyridin-3-yl)-[1,2,4]oxadiazol-3-yl]-N-methyl-N-phenyl-[1,3,5]triazine-2,4-diamine | 1 | Method A HPLC-MS: MH+ requires m/z = 340; Found: m/z = 340, Rt = 3.54 min (100%). | 4630[b] |

| Example | Name Structure | M | Spectral data | Nav 1.7 activity (nM) |
|---|---|---|---|---|
| 49 | 6-[5-(4,5-Dimethyl-furan-2-yl)-[1,2,4]oxadiazol-3-yl]-N-methyl-N-phenyl-[1,3,5]triazine-2,4-diamine | 1 | Method A HPLC-MS: MH+ requires m/z = 363; Found: m/z = 363, Rt = 3.62 min (98%). | 1231[c] |
| 50 | 6-[5-(3-Amino-pyridin-2-yl)-[1,2,4]oxadiazol-3-yl]-N-methyl-N-phenyl-[1,3,5]triazine-2,4-diamine | 2 | Method A HPLC-MS: MH+ requires m/z = 362; Found: m/z = 362, Rt = 4.30 min (98%). | 291[c] |
| 51 | 6-[5-(3-Amino-pyridin-2-yl)-[1,2,4]oxadiazol-3-yl]-N-methyl-N-phenyl-[1,3,5]triazine-2,4-diamine | 2 | Method A HPLC-MS: MH+ requires m/z = 362; Found: m/z = 362, Rt = 3.55 min (100%). | 3472[c] |

| Example | Name Structure | M | Spectral data | Nav 1.7 activity (nM) |
|---|---|---|---|---|
| 52 | N-Methyl-N-phenyl-6-(5-thiazol-5-yl-[1,2,4]oxadiazol-3-yl)-[1,3,5]triazine-2,4-diamine | 2 | Method A HPLC-MS: MH+ requires m/z = 353; Found: m/z = 353, Rt = 3.64 min (100%). | 909[b] |
| 53 | 6-[5-(2-Amino-pyridin-3-yl)-[1,2,4]oxadiazol-3-yl]-N-methyl-N-phenyl-[1,3,5]triazine-2,4-diamine | 2 | Method A HPLC-MS: MH+ requires m/z = 362; Found: m/z = 362, Rt = 3.47 min (100%). | 703[c] |
| 54 | 6-[5-(5-Amino-pyridin-3-yl)-[1,2,4]oxadiazol-3-yl]-N-methyl-N-phenyl-[1,3,5]triazine-2,4-diamine | 2 | Method A HPLC-MS: MH+ requires m/z = 362; Found: m/z = 362, Rt = 3.35 min (100%). | 2218[b] |

| Example | Name Structure | M | Spectral data | Nav 1.7 activity (nM) |
|---|---|---|---|---|
| 55 | 6-[5-(6-Amino-pyridin-3-yl)-[1,2,4]oxadiazol-3-yl]-N-methyl-N-phenyl-[1,3,5]triazine-2,4-diamine | 2 | Method A HPLC-MS: MH+ requires m/z = 362; Found: m/z = 362, Rt = 3.15 min (100%). | 4909$^c$ |
| 56 | N-Methyl-N-phenyl-6-[5-(tetrahydro-pyran-2-yl)-[1,2,4]oxadiazol-3-yl]-[1,3,5]triazine-2,4-diamine | 1 | Method A HPLC-MS: MH+ requires m/z = 354; Found: m/z = 354, Rt = 3.91 min (100%). | 4580$^c$ |
| 57 | N-Methyl-N-phenyl-6-[5-(tetrahydro-pyran-4-yl)-[1,2,4]oxadiazol-3-yl]-[1,3,5]triazine-2,4-diamine | 1 | Method A HPLC-MS: MH+ requires m/z = 354; Found: m/z = 354, Rt = 3.62 min (99%). | 1140$^c$ |

-continued

| Example | Name Structure | M | Spectral data | Nav 1.7 activity (nM) |
|---|---|---|---|---|
| 58 | N-Methyl-6-[5-(5-methyl-1H-pyrazol-3-yl)-[1,2,4]oxadiazol-3-yl]-N-phenyl-[1,3,5]triazine-2,4-diamine | 1 | Method A HPLC-MS: MH+ requires m/z = 350; Found: m/z = 350, Rt = 3.57 min (99%). | 855[c] |
| 59 | 6-[5-(1H-Imidazol-4-yl)-[1,2,4]oxadiazol-3-yl]-N-methyl-N-phenyl-[1,3,5]triazine-2,4-diamine | 2 | Method A HPLC-MS: MH+ requires m/z = 336; Found: m/z = 336, Rt = 3.18 min (100%). | 8124[c] |
| 60 | N-Methyl-N-phenyl-6-[5-(1H-pyrrol-2-yl)-[1,2,4]oxadiazol-3-yl]-[1,3,5]triazine-2,4-diamine | 2 | Method A HPLC-MS: MH+ requires m/z = 335; Found: m/z = 335, Rt = 3.80 min (100%). | 4910[c] |

| Example | Name Structure | M | Spectral data | Nav 1.7 activity (nM) |
|---|---|---|---|---|
| 61 | N-Methyl-N-phenyl-6-[5-(2H-pyrazol-3-yl)-[1,2,4]oxadiazol-3-yl]-[1,3,5]triazine-2,4-diamine | 2 | Method A HPLC-MS: MH+ requires m/z = 336; Found: m/z = 336, Rt = 3.43 min (100%). 1H NMR (500 MHz, CDCl3) δ ppm 7.89-7.94 (1H, m), 7.41-7.48 (2H, m), 7.33-7.38 (2H, m), 7.27-7.33 (1H, m), 7.09-7.14 (1H, m) and 3.58 (3 H, s). | 561[b] |
| 62 | N-Methyl-6-[5-(5-methyl-thiophen-2-yl)-[1,2,4]oxadiazol-3-yl]-N-phenyl-[1,3,5]triazine-2,4-diamine | 1 | Method A HPLC-MS: MH+ requires m/z = 366; Found: m/z = 366, Rt = 4.30 min (100%). | 1100[c] |
| 63 | 6-[5-(2,3-Dihydro-benzofuran-7-yl)-[1,2,4]oxadiazol-3-yl]-N-methyl-N-phenyl-[1,3,5]triazine-2,4-diamine | 2 | Method A HPLC-MS: MH+ requires m/z = 388; Found: m/z = 388, Rt = 4.20 min (94%). | 3381[c] |

| Example | Name Structure | M | Spectral data | Nav 1.7 activity (nM) |
|---|---|---|---|---|
| 64 | 6-(5-Benzofuran-2-yl-[1,2,4]oxadiazol-3-yl)-N-methyl-N-phenyl-[1,3,5]triazine-2,4-diamine | 1 | Method A HPLC-MS: MH+ requires m/z = 340; Found: m/z = 340, Rt = 3.66 min (100%). | 1934[c] |
| 65 | 6-(5-Imidazol-2-yl-[1,2,4]oxadiazol-3-yl)-N-methyl-N-phenyl-[1,3,5]triazine-2,4-diamine | 2 | Method A HPLC-MS: MH+ requires m/z = 336; Found: m/z = 336, Rt = 3.29 min (100%). | 5222[c] |
| 66 | N-Methyl-N-phenyl-6-[5-(tetrahydro-furan-2-yl)-[1,2,4]oxadiazol-3-yl]-[1,3,5]triazine-2,4-diamine | 1 | Method A HPLC-MS: MH+ requires m/z = 340; Found: m/z = 340, Rt = 3.66 min (100%). 1H NMR (500 MHz, CDCl3) δ ppm 7.41-7.48 (2H, m), 7.29-7.38 (3H, m), 5.75-5.00 (2H, br. s), 5.33 (1H, dd, J = 7.6, 5.5 Hz), 4.15 (1H, q, J = 7.2 Hz), 4.04 (1H, q, J = 7.5 Hz), 3.62 (3H, s), 2.41-2.51 (1H, m), 2.34 (1H, m, J = 7.3 Hz), 2.05-2.22 (2H, m) | 1681[c] |

| Example | Name Structure | M | Spectral data | Nav 1.7 activity (nM) |
|---|---|---|---|---|
| 67 | N-Methyl-N-phenyl-6-{5-[6-(2,2,2-trifluoroethoxy)-pyridin-3-yl]-[1,2,4]oxadiazol-3-yl}-[1,3,5]triazine2,4-diamine | 1 | Method A HPLC-MS: MH+ requires m/z = 445; Found: m/z = 445, Rt = 4.52 min (97%). 1H NMR (500 MHz, CDCl3) δ ppm 9.02-9.16 (4H, m), 8.39-8.59 (1H, m), 7.47 (2H, m, J = 7.6 Hz), 7.35 (3H, m, J = 8.1 Hz), 7.02-7.08 (1H, m), 4.87 (2H, q, J = 8.4 Hz) and 3.66 (2H, s). | 110[b] |
| 68 | 6-(5-Furan-2-yl-[1,2,4]oxadiazol-3-yl)-N-phenyl-N-(2,2,2-trifluoro-ethyl)-[1,3,5]triazine-2,4-diamine | 1 | Method A, HPLC-MS: MH+ requires m/z = 404; Found: m/z = 404, Rt = 4.62 min (99%). 1H NMR (500 MHz, CDCl3) δ ppm 7.75 (1H, s), 7.54-7.63 (2H, m), 7.52 (1H, d, J = 3.4 Hz), 7.40 (2H, t, J = 7.9 Hz), 7.17 (1H, t, J = 7.3 Hz), 6.67-6.70 (1H, m), 4.21 (2H, dd, J = 8.5, 7.2 Hz) and 2.31-2.65 (2H, m). | 225[c] |
| 69 | N-(2-Dimethylamino-ethyl)-6-(5-furan-2-yl-[1,2,4]oxadiazol-3-yl)-N-phenyl-[1,3,5]triazine-2,4-diamine | 1 | Method A HPLC-MS: MH+ requires m/z = 393; Found: m/z = 393, Rt = 2.82 min (99%). | 1368[c] |

| Example | Name Structure | M | Spectral data | Nav 1.7 activity (nM) |
|---|---|---|---|---|
| 70 | 2-{[4-Amino-6-(5-furan-2-yl-[1,2,4]oxadiazol-3-yl)-[1,3,5]triazin-2-yl]-phenyl-amino}-ethanol | 5 | Method A HPLC-MS: MH+ requires m/z = 366; Found: m/z = 366, Rt = 3.56 min (100%). | 1019[c] |
| 71 | 3-[4-Amino-6-(methyl-phenyl-amino)-[1,3,5]triazin-2-yl]-[1,2,4]oxadiazole-5-carboxylic acid benzylamide | 6 | Method A HPLC-MS: MH+ requires m/z = 403; Found: m/z = 403. Rt = 4.06 min (100%). | 814[b] |
| 72 | 3-[4-Amino-6-(methyl-phenyl-amino)-[1,3,5]triazin-2-yl]-[1,2,4]oxadiazole-5-carboxylic acid cyclopentylamide | 6 | Method A HPLC-MS: MH+ requires m/z = 381; Found: m/z = 381, Rt = 3.96 min (100%). 1H NMR (500 MHz, CDCl3) δ ppm 7.42-7.47 (2H, m), 7.30-7.35 (2H, m), 7.24 (1H, d), 5.31 (1H, s), 4.41 (1H, d), 3.61 (3H, s), 2.10 (2H, dd), 1.71-1.80 (2H, m), 1.63-1.71 (2H, m) and 1.55 (2H, dd). | 288[c] |

| Example | Name Structure | M | Spectral data | Nav 1.7 activity (nM) |
|---|---|---|---|---|
| 73 | 3-[4-Amino-6-(methyl-phenyl-amino)-[1,3,5]triazin-2-yl]-[1,2,4]oxadiazole-5-carboxylic acid ethyl ester | 1 | Method A HPLC-MS: MH+ requires m/z = 342; Found: m/z = 342, Rt = 3.92 min (97%). | 1492[c] |
| 74 | 6-[5-(3-Methoxy-thiophen-2-yl)-[1,2,4]oxadiazol-3-yl]-N-methyl-N-phenyl-[1,3,5]triazine-2,4-diamine | 2 | Method A HPLC-MS: MH+ requires m/z = 382; Found: m/z = 382, Rt = 4.13 min (98%). | 1407[c] |
| 75 | 5-{3-[4-Amino-6-(methyl-phenyl-amino)-[1,3,5]triazin-2-yl]-[1,2,4]oxadiazol-5-yl}-thiophene-2-carboxylic acid methylamide | | Method A HPLC-MS: MH+ requires m/z = 409; Found: m/z = 409, Rt = 3.63 min (99%). | 1191[c] |

| Example | Name Structure | M | Spectral data | Nav 1.7 activity (nM) |
|---|---|---|---|---|
| 76 | 6-[5-(2-Methoxy-pyridin-3-yl)-[1,2,4]oxadiazol-3-yl]-N-methyl-N-phenyl-[1,3,5]triazine-2,4-diamine | | Method A HPLC-MS: MH+ requires m/z = 377; Found: m/z = 377, Rt = 3.30 min (99%). | 925$^c$ |
| 77 | 6-[5-(2,4-Dimethoxy-phenyl)-[1,2,4]oxadiazol-3-yl]-N-methyl-N-phenyl-[1,3,5]triazine-2,4-diamine | 1 | Method B HPLC-MS: MH+ requires m/z = 406; Found: m/z = 406, Rt = 1.96 min (100%). | 246$^c$ |
| 78 | 5-{3-[4-Amino-6-(methyl-phenyl-amino)-[1,3,5]triazin-2-yl]-[1,2,4]oxadiazol-5-yl}-pyridine-2-carbonitrile | 2 | Method A HPLC-MS: MH+ requires m/z = 372; Found: m/z = 372, Rt = 3.85 min (100%). | 1656$^c$ |

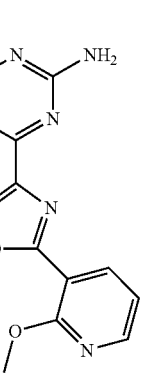

| Example | Name Structure | M | Spectral data | Nav 1.7 activity (nM) |
|---|---|---|---|---|
| 79 | (5-{3-[4-Amino-6-(methyl-phenyl-amino)-[1,3,5]triazin-2-yl]-[1,2,4]oxadiazol-5-yl}-thiophen-2-yl)-morpholin-4-yl-methanone | | Method A HPLC-MS: MH+ requires m/z = 465; Found: m/z = 465, Rt = 3.72 min (100%). | 977[c] |
| 80 | 2-{3-[4-Amino-6-(methyl-phenyl-amino)-[1,3,5]triazin-2-yl]-[1,2,4]oxadiazol-5-yl}-benzonitrile | 2 | Method A HPLC-MS: MH+ requires m/z = 371; Found: m/z = 371, Rt = 3.99 min (94%). | 260[c] |
| 81 | 6-[5-(2-Fluoro-6-methoxy-phenyl)-[1,2,4]oxadiazol-3-yl]-N-methyl-N-phenyl-[1,3,5]triazine-2,4-diamine | 2 | Method A HPLC-MS: MH+ requires m/z = 394; Found: m/z = 394, Rt = 4.14 min (99%). | 21[b] |

| Example | Name Structure | M | Spectral data | Nav 1.7 activity (nM) |
|---|---|---|---|---|
| 82 | 5-{3-[4-Amino-6-(methyl-phenyl-amino)-[1,3,5]triazin-2-yl]-[1,2,4]oxadiazol-5-yl}-thiophene-2-carboxylic acid methyl ester | 2 | Method A HPLC-MS: MH+ requires m/z = 410; Found: m/z = 410, Rt = 4.01 min (97%). 1H NMR (500 MHz, CDCl3) δ ppm 7.99 (1H, dd s), 7.75 (1H, dd), 7.45 (2H, m), 7.32 (3H. m), 5.85-4.95 (2H, br s), 3.96 (3H, s) and 3.42 (3H, s). | 195[b] |
| 83 | N-(3-Chloro-phenyl)-6-[5-(3-methoxy-phenyl)-[1,2,4]oxadiazol-3-yl]-N-methyl-[1,3,5]triazine-2,4-diamine | 1 | Method A HPLC-MS: MH+ requires m/z = 410; Found: m/z = 410, Rt = 4.66 min (99%) | 691[c] |
| 84 | N-(3-Chloro-phenyl)-6-[5-(2-chloro-phenyl)-[1,2,4]oxadiazol-3-yl]-N-methyl-[1,3,5]triazine-2,4-diamine | 1 | Method A HPLC-MS: MH+ requires m/z = 414; Found: m/z = 414, Rt = 4.66 min (99%). | 170[c] |

-continued

| Example | Name Structure | M | Spectral data | Nav 1.7 activity (nM) |
|---|---|---|---|---|
| 85 | N-(3-Fluoro-phenyl)-6-[5-(3-methoxy-phenyl)-[1,2,4]oxadiazol-3-yl]-N-methyl-[1,3,5]triazine-2,4-diamine | 1 | Method A HPLC-MS: MH+ requires m/z = 394; Found: m/z = 394, Rt = 4.3 min (99%). | 1266[c] |
| 86 | 6-[5-(2-Chloro-phenyl)-[1,2,4]oxadiazol-3-yl]-N-(3-fluoro-phenyl)-N-methyl-[1,3,5]triazine-2,4-diamine | 1 | Method A HPLC-MS: MH+ requires m/z = 398; Found: m/z = 398, Rt = 4.4 min (100%). 1H NMR (500 MHz, CDCl3) δ ppm 8.16-8.22 (1H, m), 7.58-7.62 (1H, m), 7.54 (1H, td, J = 7.7, 1.5 Hz), 7.36-7.47 (2H, m), 7.10-7.20 (2H, m), 6.97-7.03 (1H, m), 5.20-5.74 (2H, m) and 3.63 (3H, s). | 126[b] |
| 87 | N-(3-Fluoro-phenyl)-N-methyl-6-[5-(5-methyl-furan-2-yl)-[1,2,4]oxadiazol-3-yl]-[1,3,5]triazine-2,4-diamine | 1 | Method A HPLC-MS: MH+ requires m/z = 368; Found: m/z = 368, Rt = 4.08 min (97%). | 3492[c] |

| Example | Name Structure | M | Spectral data | Nav 1.7 activity (nM) |
|---|---|---|---|---|
| 88 | N-(2-Fluoro-phenyl)-6-[5-(3-methoxy-phenyl)-[1,2,4]oxadiazol-3-yl]-N-methyl-[1,3,5]triazine-2,4-diamine | 1 | Method A HPLC-MS: MH+ requires m/z = 394; Found: m/z = 394, Rt = 4.31 min (100%). | 361[c] |
| 89 | N-(2-Fluoro-phenyl)-6-[5-(2-methoxy-phenyl)-[1,2,4]oxadiazol-3-yl]-N-methyl-[1,3,5]triazine-2,4-diamine | 1 | Method A HPLC-MS: MH+ requires m/z = 394; Found: m/z = 394, Rt = 4.13 min (92%). 1H NMR (500 MHz, CDCl3) ppm 8.18-8.29 (2H, m), 7.54-7.63 (2H, m), 7.32-7.38 (2H, m), 7.16-7.26 (2H, m), 7.05-7.15 (2H, m), 3.97 (3H, br. s.), 3.62 (2H, br. s.) and 2.02 (3H, s). | 200[c] |
| 90 | N-(2-Fluoro-phenyl)-N-methyl-6-(5-thiophen-2-yl-[1,2,4]oxadiazol-3-yl)-[1,3,5]triazine-2,4-diamine | 1 | Method A HPLC-MS: MH+ requires m/z = 370; Found: m/z = 370, Rt = 4.09 min (100%). | 415[c] |

-continued

| Example | Name Structure | M | Spectral data | Nav 1.7 activity (nM) |
|---|---|---|---|---|
| 91 | N-(2-Fluoro-phenyl)-N-methyl-6-[5-(5-methyl-furan-2-yl)-[1,2,4]oxadiazol-3-yl]-[1,3,5]triazine-2,4-diamine | 1 | %). Method A HPLC-MS: MH+ requires m/z = 368; Found: m/z = 368, Rt = 4.10 min (99%). | 547[c] |
| 92 | 6-[5-(2-Methoxy-phenyl)-[1,2,4]oxadiazol-3-yl]-N-methyl-N-m-tolyl-[1,3,5]triazine-2,4-diamine | 1 | Method A HPLC-MS: MH+ requires m/z = 390; Found: m/z = 390, Rt = 4.34 min (98%). | 511[c] |
| 93 | N-Methyl-6-(5-thiophen-2-yl-[1,2,4]oxadiazol-3-yl)-N-m-tolyl-[1,3,5]triazine-2,4-diamine | 1 | Method A HPLC-MS: MH+ requires m/z = 366; Found: m/z = 366, Rt = 4.30 min (97%). | 931[c] |

-continued

| Example | Name Structure | M | Spectral data | Nav 1.7 activity (nM) |
|---|---|---|---|---|
| 94 | N-Ethyl-6-[5-(3-methoxy-phenyl)-[1,2,4]oxadiazol-3-yl]-N-phenyl-[1,3,5]triazine-2,4-diamine | 1 | Method A HPLC-MS: MH+ requires m/z = 390; Found: m/z = 390, Rt = 4.51 min (94%). | 813[c] |
| 95 | N-Ethyl-6-[5-(2-methoxy-phenyl)-[1,2,4]oxadiazol-3-yl]-N-phenyl-[1,3,5]triazine-2,4-diamine | 1 | Method A HPLC-MS: MH+ requires m/z = 390; Found: m/z = 390, Rt = 4.33 min (94%). 1H NMR (500 MHz, CDCl3) δ ppm 8.13 (1H, br. s.), 7.55 (1H, t), 7.40-7.46 (2H, m), 7.29-7.35 (1H, m), 7.27 (2H, br. s.), 7.08 (1H, t), 7.03 (1H, d), 5.50-5.89 (2H, m), 4.11 (2H, br. s.), 3.85 (3H, s) and 1.23 (3H, t). | 46[b] |
| 96 | N-Ethyl-N-phenyl-6-(5-thiophen-2-yl-[1,2,4]oxadiazol-3-yl)-[1,3,5]triazine-2,4-diamine | 1 | Method A HPLC-MS: MH+ requires m/z = 366; Found: m/z = 366, Rt = 4.31 min (94%). | 518[c] |

| Example | Name Structure | M | Spectral data | Nav 1.7 activity (nM) |
|---|---|---|---|---|
| 97 | N-Ethyl-6-[5-(5-methyl-furan-2-yl)-[1,2,4]oxadiazol-3-yl]-N-phenyl-[1,3,5]triazine-2,4-diamine | 1 | Method A HPLC-MS: MH+ requires m/z = 364; Found: m/z = 364, Rt = 4.32 min (93%). | 1303[c] |
| 98 | N-(3-Fluoro-phenyl)-6-[5-(2-methoxy-phenyl)-[1,2,4]oxadiazol-3-yl]-N-methyl-[1,3,5]triazine-2,4-diamine | 1 | Method A HPLC-MS: MH+ requires m/z = 394; Found: m/z = 394, R = 4.23 min (97%). | 318[c] |
| 99 | N-(3-Fluoro-phenyl)-N-methyl-6-(5-thiophen-2-yl-[1,2,4]oxadiazol-3-yl)-[1,3,5]triazine-2,4-diamine | 1 | Method A HPLC-MS: MH+ requires m/z = 370; Found: m/z = 370, Rt = 4.20 min (98%). | 1131[c] |

-continued

| Example | Name Structure | M | Spectral data | Nav 1.7 activity (nM) |
|---|---|---|---|---|
| 100 | N-(3-Chloro-phenyl)-6-[5-(2-methoxy-phenyl)-[1,2,4]oxadiazol-3-yl]-N-methyl-[1,3,5]triazine-2,4-diamine | 1 | Method A HPLC-MS: MH+ requires m/z = 410; Found: m/z = 410, Rt = 4.43 min (95%). | 118[c] |
| 101 | N-(3-Chlorophenyl)-N-methyl-6-(5-thiophen-2-yl-[1,2,4]oxadiazol-3-yl)-[1,3,5]triazine-2,4-diamine | 1 | Method A HPLC-MS: MH+ requires m/z = 386; Found: m/z = 386, Rt = 4.40 min (88%-broad peak). | 206[c] |
| 102 | N-(3-Chloro-phenyl)-N-methyl-6-[5-(5-methyl-furan-2-yl)-[1,2,4]oxadiazol-3-yl]-[1,3,5]triazine-2,4-diamine | 1 | Method A HPLC-MS: MH+ requires m/z = 390; Found: m/z = 390, Rt = 4.51 min (95%). | 489[c] |

| Example | Name Structure | M | Spectral data | Nav 1.7 activity (nM) |
|---|---|---|---|---|
| 103 | N-(5-Chloro-2-fluoro-phenyl)-6-(5-furan-2-yl-[1,2,4]oxadiazol-3-yl)-N-methyl-[1,3,5]triazine-2,4-diamine | 5 | 1H NMR (500 MHz, CDCl3) δ ppm 7.72 (1H, s), 7.49 (1H, m), 7.47-7.26 (2H, m), 7.22 (1H, t), 6.66 (1H, s), 5.97-4.92 (2H, br s) and 3.57 (3H, br s). | 42[b] |
| 104 | N-(2,5-Difluoro-phenyl)-6-(5-furan-2-yl-[1,2,4]oxadiazol-3-yl)-N-methyl-[1,3,5]triazine-2,4-diamine | 5 | Method A HPLC-MS: MH+ requires m/z = 372; Found: m/z = 372, Rt = 4.01 min (100%). 1H NMR (500 MHz, CDCl3) δ ppm 7.72 (1H, s), 7.47 (1H, m), 7.17-6.95 (3H, m), 7.22 (1H, t), 6.65 (1H, s), 5.95-4.92 (2H, br s) and 3.57 (3H, br s). | 93[b] |
| 105 | N-(2-Fluoro-5-methyl-phenyl)-6-(5-furan-2-yl-[1,2,4]oxadiazol-3-yl)-N-methyl-[1,3,5]triazine-2,4-diamine | 5 | Method A HPLC-MS: MH+ requires m/z = 368; Found: m/z = 368, Rt = 4.14 min (100%). 1H NMR (500 MHz, CDCl3) δ ppm 7.72 (1H, m), 7.45 (1H, m), 7.17-7.02 (3H, m), 7.22 (1H, t), 6.62 (1H, m), 5.78-4.95 (2H, br s), 3.58 (3H, br s) and 2.35 (3H, s). | 59[b] |

-continued

| Example | Name Structure | M | Spectral data | Nav 1.7 activity (nM) |
|---|---|---|---|---|
| 106 | N-(3-Chloro-2-fluoro-phenyl)-6-(5-furan-2-yl-[1,2,4]oxadiazol-3-yl)-N-methyl-[1,3,5]triazine-2,4-diamine | 5 | Method A HPLC-MS: MH+ requires m/z = 443; Found: m/z = 443, Rt = 4.05 min (100%). 1H NMR (500 MHz, CDCl3) δ ppm 7.72 (1H, m), 7.47 (1H, m), 7.41 (1H, t), 7.25 (1H, m), 7.16 (1H, m), 6.65 (1H, m), 6.25-4.95 (2H, br s), and 3.58 (3H, br s). | 82[b] |
| 107 | N-(2-Fluoro-3-methyl-phenyl)-6-(5-furan-2-yl-[1,2,4]oxadiazol-3-yl)-N-methyl-[1,3,5]triazine-2,4-diamine | 5 | Method A HPLC-MS: MH+ requires m/z = 368; Found: m/z = 368, Rt = 4.01 min (97%). | 749[c] |
| 108 | N-(5-Chloro-2-fluoro-phenyl)-6-(5-furan-2-yl-[1,2,4]oxadiazol-3-yl)-[1,3,5]triazine-2,4-diamine | 1 | Method A HPLC-MS: MH+ requires m/z = 374; Found: m/z = 374, Rt = 3.95 min (94%). | 235[b] |

-continued

| Example | Name Structure | M | Spectral data | Nav 1.7 activity (nM) |
|---|---|---|---|---|
| 109 | N-(2,5-Difluoro-phenyl)-6-(5-furan-2-yl-[1,2,4]oxadiazol-3-yl)-[1,3,5]triazine-2,4-diamine | 1 | Method A HPLC-MS: MH+ requires m/z = 358; Found: m/z = 358, Rt = 3.66 min (100%). | 369[c] |
| 110 | N-(2-Fluoro-3-methyl-phenyl)-6-(5-furan-2-yl-[1,2,4]oxadiazol-3-yl)-[1,3,5]triazine-2,4-diamine | 1 | Method A HPLC-MS: MH+ requires m/z = 354; Found: m/z = 354, Rt = 3.82 min (97%). 1H NMR (500 MHz, DMSO) δ ppm 9.50 (1H, br s), 8.21 (1H, d), 7.67 (1H, dd), 7.57 (1H, br s), 7.48 (1H, m), 7.36 (1H, m), 7.08 (2H, m), 6.89 (1H, dd), and 2.26 (3H, s). | 71[b] |
| 111 | N-(3-Chloro-2-fluoro-phenyl)-6-(5-furan-2-yl-[1,2,4]oxadiazol-3-yl)-[1,3,5]triazine-2,4-diamine | 1 | Method A HPLC-MS: MH+ requires m/z = 374; Found: m/z = 374, Rt = 3.89 min (92%). 1H NMR (500 MHz, DMSO) δ ppm 9.81 (1H, br s), 8.20 (1H, d), 7.68 (3H, m), 7.44 (1H, br s), 7.40 (1H, m), 7.22 (1H, dd), and 6.89 (1H, dd). | 54[b] |

-continued

| Example | Name Structure | M | Spectral data | Nav 1.7 activity (nM) |
|---|---|---|---|---|
| 112 | N-(2-Fluoro-3-methyl-phenyl)-6-(5-furan-2-yl-[1,2,4]oxadiazol-3-yl)-[1,3,5]triazine-2,4-diamine | 1 | Method A HPLC-MS: MH+ requires m/z = 354; Found: m/z = 354, Rt = 3.82 min (97%). 1H NMR (500 MHz, DMSO) δ ppm 9.50 (1H, br s), 8.21 (1H, d), 7.67 (1H, dd), 7.57 (1H, br s), 7.48 (1H, m), 7.36 (1H, m), 7.08 (2H, m), 6.89 (1H, dd), and 2.26 (3H, s). | 87[b] |
| 113 | N-(2,3-Difluoro-phenyl)-6-(5-furan-2-yl-[1,2,4]oxadiazol-3-yl)-[1,3,5]triazine-2,4-diamine | 1 | Method A HPLC-MS: MH+ requires m/z = 358; Found: m/z = 358, Rt = 3.57 min (100%). 1H NMR (500 MHz, DMSO-d6) δ ppm 9.83 (1H, br s), 8.21 (1H, d), 7.65 (2H, m), 7.44 (2H, m), 7.22 (2H, m), and 6.89 (1H, dd). | 118[b] |
| 114 | N-Methyl-N-phenyl-6-(5-pyridin-4-yl-[1,2,4]oxadiazol-3-yl)-[1,3,5]triazine-2,4-diamine | 1 | Method A HPLC-MS: MH+ requires m/z = 347; Found: m/z = 347, Rt = 3.59 min (100%). | 606[c] |

-continued

| Example | Name Structure | M | Spectral data | Nav 1.7 activity (nM) |
|---|---|---|---|---|
| 115 | N-Methyl-N-phenyl-6-(5-pyridin-3-yl-[1,2,4]oxadiazol-3-yl)-[1,3,5]triazine-2,4-diamine | 1 | Method A HPLC-MS: MH+ requires m/z = 347; Found: m/z = 347, Rt = 3.57 min (100%). | 1322[c] |
| 116 | 4-(3,4-Dihydroquinolin-1-yl)-6-(5-furan-2-yl-[1,2,4]oxadiazol-3-yl)-[1,3,5]triazine-2-amine | 1 | Method A HPLC-MS: MH+ requires m/z = 362; Found: m/z = 362, Rt = 4.26 min (100%). | 1617 |
| 117 | N-(3-Fluorophenyl)-6-(5-furan-2-yl-[1,2,4]oxadiazol-3-yl)-[1,3,5]triazine-2,4-diamine | 1 | Method A HPLC-MS: MH+ requires m/z = 340; Found: m/z = 340, Rt = 4.69 min (97%). 1H NMR (500 MHz, DMSO) δ ppm 10.40-10.08 (1H, s), 7.68 (1H, br s), 8.20 (1H, s), 7.45 (1H, d), 7.85-7.50 (3H, m), 7.40-7.28 (1H, m) and 6.95-6.80 (2H, m). | 42[b] |

-continued

| Example | Name Structure | M | Spectral data | Nav 1.7 activity (nM) |
|---|---|---|---|---|
| 118 | 6-[5-(5-Methoxy-pyridin-2-yl)-[1,2,4]oxadiazol-3-yl]-N-methyl-N-phenyl-[1,3,5]triazine-2,4-diamine | 1 | Method A HPLC-MS: MH+ requires m/z = 377; Found: m/z = 377, Rt = 3.76 min (100%). 1H NMR (500 MHz, CDCl3) δ ppm 8.45 (1H, s), 8.30 (1H, d), 7.40-7.32 (2H, m), 7.30-7.20 (4H, m), 6.15-5.25 (2H, br s), 3.90 (3H, s) and 3.55 (3H, s). | 294[c] |
| 119 | 6-(5-Furan-2-yl-[1,2,4]oxadiazol-3-yl)-N-(2-methoxy-ethyl)-N-phenyl-[1,3,5]triazine-2,4-diamine | 1 | Method A HPLC-MS: MH+ requires m/z = 380; Found: m/z = 380, Rt = 3.92 min (94%). 1H NMR (500 MHz, CDCl3) δ ppm 7.75 (1H, s), 7.55-7.30 (6H, m), 6.68 (1H, s), 5.60-5.05 (2H, br s), 4.35-4.20 (2H, m), 3.70-3.63 (2H, m) and 3.38 (3H, s). | 400[b] |
| 120 | N-Methyl-N-phenyl-6-(5-pyrimidin-4-yl-[1,2,4]oxadiazol-3-yl)-[1,3,5]triazine-2,4-diamine | 2 | Method A HPLC-MS: MH+ requires m/z = 348; Found: m/z = 348, Rt = 3.44 min (100%). | 2242[c] |

-continued

| Example | Name Structure | M | Spectral data | Nav 1.7 activity (nM) |
|---|---|---|---|---|
| 121 | N-Cyclopropylmethyl-6-(5-furan-2-yl-[1,2,4]oxadiazol-3-yl)-N-phenyl-[1,3,5]triazine-2,4-diamine | 1 | Method A HPLC-MS: MH+ requires m/z = 376; Found: m/z = 376, Rt = 4.36 min (99%). | 395$^c$ |
| 122 | 6-[5-(4-Fluoro-phenyl)-[1,2,4]oxadiazol-3-yl]-N-methyl-N-phenyl-[1,3,5]triazine-2,4-diamine | 1 | Method A HPLC-MS: MH+ requires m/z = 364; Found: m/z = 364, Rt = 4.28 min (98%). | 644$^c$ |
| 123 | 6-[5-(3-Fluoro-phenyl)-[1,2,4]oxadiazol-3-yl]-N-methyl-N-phenyl-[1,3,5]triazine-2,4-diamine | 1 | Method A HPLC-MS: MH+ requires m/z = 364; Found: m/z = 364, Rt = 4.30 min (98%). | 929$^c$ |

| Example | Name Structure | M | Spectral data | Nav 1.7 activity (nM) |
|---|---|---|---|---|
| 124 | 6-[5-(2-Fluoro-phenyl)-[1,2,4]oxadiazol-3-yl]-N-methyl-N-phenyl-[1,3,5]triazine-2,4-diamine 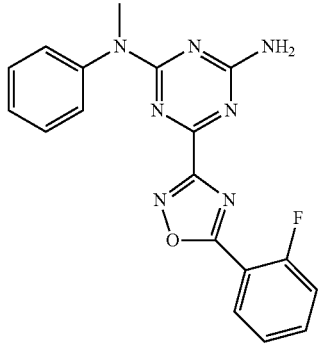 [SMILES: CN(c1ccccc1)c1nc(N)nc(-c2noc(-c3ccccc3F)n2)n1] | 1 | Method A HPLC-MS: MH+ requires m/z = 364; Found: m/z = 364, Rt = 4.18 min (97%). | 428[c] |
| 125 | N-Methyl-N-phenyl-6-(5-thiazol-2-yl-[1,2,4]oxadiazol-3-yl)-[1,3,5]triazine-2,4-diamine 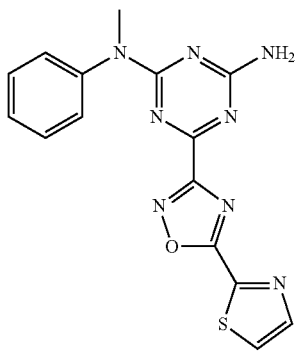 [SMILES: CN(c1ccccc1)c1nc(N)nc(-c2noc(-c3nccs3)n2)n1] | 1 | Method A HPLC-MS: MH+ requires m/z = 353; Found: m/z = 353, Rt = 3.79 min (98%). 1H NMR (500 MHz, CDCl3) δ ppm 8.18 (1H, d, J = 2.9 Hz), 7.78 (1H, d, J = 2.9 Hz), 7.43-7.50 (2H, m), 7.30-7.40 (3H, m), 5.19-5.98 (2H, m) and 3.65 (3H, s). | 560[b] |
| 126 | N-Methyl-6-[5-(3-methyl-thiophen-2-yl)-[1,2,4]oxadiazol-3-yl]-N-phenyl-[1,3,5]triazine-2,4-diamine 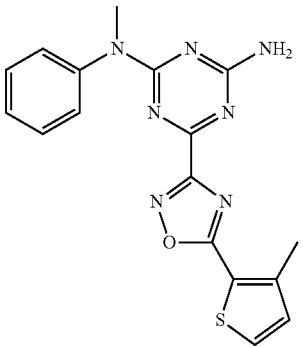 [SMILES: Cc1ccsc1-c1nc(-c2nc(N)nc(N(C)c3ccccc3)n2)no1] | 1 | Method A HPLC-MS: MH+ requires m/z = 366; Found: m/z = 366, Rt = 4.32 min (100%). | 782[c] |

| Example | Name Structure | M | Spectral data | Nav 1.7 activity (nM) |
|---|---|---|---|---|
| 127 | N-Methyl-6-(5-oxazol-5-yl-[1,2,4]oxadiazol-3-yl)-N-phenyl-[1,3,5]triazine-2,4-diamine | 1 | Method A HPLC-MS: MH+ requires m/z = 337; Found: m/z = 337, Rt = 3.58 min (99%). | 2084[c] |
| 128 | N-Methyl-6-(5-oxazol-2-yl-[1,2,4]oxadiazol-3-yl)-N-phenyl-[1,3,5]triazine-2,4-diamine | 1 | Method A HPLC-MS: MH+ requires m/z = 337; Found: m/z = 337, Rt = 3.66 min (96%). | 1505[c] |
| 129 | N-Methyl-6-[5-(5-methyl-thiophen-2-yl)-[1,2,4]oxadiazol-3-yl]-N-phenyl-[1,3,5]triazine-2,4-diamine | 1 | Method A HPLC-MS: MH+ requires m/z = 366; Found: m/z = 366, Rt = 4.30 min (100%). | 2541[c] |

| Example | Name Structure | M | Spectral data | Nav 1.7 activity (nM) |
|---|---|---|---|---|
| 130 | N-Phenyl-6-(5-thiazol-2-yl-[1,2,4]oxadiazol-3-yl)-[1,3,5]triazine2,4-diamine | 1 | Method B HPLC-MS: MH+ requires m/z = 339; Found: m/z = 339, Rt = 1.67 min (98%). 1H NMR (250 MHz, DMSO-d6) δ ppm 10.05 (1H, m, NH), 8.40 (2H, dd), 7.88 (2H, d), 7.75 (1H, m, NH), 7.50 (1H, m, NH), 7.30 (2H, t) and 7.0 (1H, t). | 44[b] |
| 131 | N-Methyl-N-phenyl-6-(5-pyrrolidin-1-yl-[1,2,4]oxadiazol-3-yl)-[1,3,5]triazine-2,4-diamine | 4 | Method B HPLC-MS: MH+ requires m/z = 339; Found: m/z = 339, Rt = 1.69 min (97%). | 5110[c] |
| 132 | 6-[5-(3-Methoxy-2-pyridyl)-[1,2,4]oxadiazol-3-yl]-N-methyl-N-phenyl-[1,3,5]triazine-2,4-diamine | 1 | Method B HPLC-MS: MH+ requires m/z = 377; Found: m/z = 377, Rt = 1.71 min (95%). 1H NMR (500 MHz, CDCl3) δ ppm 8.47 (1H, d), 7.52 (1H, m), 7.43 (3H, m), 7.39-7.30 (3H, m), 3.79 (3H, s) and 3.68 (3H, s). | 397[c] |

| Example | Name Structure | M | Spectral data | Nav 1.7 activity (nM) |
|---|---|---|---|---|
| 133 | 2-N-methyl-2-N-phenyl-6-{5-[6-(trifluoromethoxy)pyridin-3-yl]-1,2,4-oxadiazol-3-yl}-1,3,5-triazine-2,4-diamine | 1 | Method A HPLC-MS: MH+ requires m/z = 431 Found: m/z = 431, Rt = 4.34 min (99%). 1H NMR (500 MHZ, DMSO-d6) δ ppm 8.95 (1H, d), 8.40 (1H, d), 8.20 (1H, dd), 7.42 (5H, m), 7.27 (2H, m) and 3.48 (3H, s). | 635[b] |
| 134 | 6-{5-[6-(cyclopropylmethoxy)pyridin-3-yl]-1,2,4-oxadiazol-3-yl}-2-N-(2-fluorophenyl)-2-N-methyl-1,3,5-triazine-2,4-diamine | 2 | Method A HPLC-MS: MH+ requires m/z = 435; Found: m/z = 435, Rt = 4.66 min (84%). 1H NMR (400 MHz, DMSO) δ ppm 8.92 (1H, b s), 8.37 (1H, br s), 7.50 (2H, m), 7.22-7.42 (4H, m), 7.07 (1H, dd), 4.22 (2H, d), 3.43 (3H, s), 1.28 (1H, m), 0.59 (2H, d) and 0.37 (2H, d). | 67[c] |

| Example | Name Structure | M | Spectral data | Nav 1.7 activity (nM) |
|---|---|---|---|---|
| 135 | 6-{5-[6-(cyclopropylmethoxy)pyridin-3-yl]-1,2,4-oxadiazol-3-yl}-2-N-(3-fluorophenyl)-2-N-methyl-1,3,5-triazine-2,4-diamine | 2 | Method A HPLC-MS: MH+ requires m/z = 435; Found: m/z = 435, Rt = 4.64 min (94%). 1H NMR (400 MHz, DMSO) δ ppm 8.92 (1H, s), 8.36 (1H, dd), 7.56 (1H, br s), 7.40-7.49 (2H, m), 7.30-7.39 (2H, m), 7.28 (1H, dd), 7.07-7.13 (2H, m), 4.22 (2H, d), 3.50 (3H, s), 1.28 (1H, m), 0.51 (2H, d) and 0.37 (2H, d). | 44[b] |
| 136 | 6-{5-[6-(cyclopropylmethoxy)pyridin-3-yl]-1,2,4-oxadiazol-3-yl}-2-N-(3-fluorophenyl)-1,3,5-triazine-2,4-diamine | 2 | Method A HPLC-MS: MH+ requires m/z = 421; Found: m/z = 421, Rt = 4.55 min (89%). 1H NMR (400 MHz, DMSO) δ ppm 10.22 (1H, br s), 8.92 (1H, s), 8.38 (1H, dd), 7.97 (1H, m), 7.78 (1H, s), 7.54-7.65 (2H, m), 7.32 (1H, m), 7.09 (1H, dd), 6.82 (1H, m), 4.23 (2H, d), 1.28 (1H, m), 0.59 (2H, d) and 0.36 (2H, d). | 65[c] |
| 137 | 6-(5-{[3-(4-fluorophenoxy)azetidin-1-yl]carbonyl}-1,2,4-oxadiazol-3-yl)-2-N-methyl-2-N-phenyl-1,3,5-triazine-2,4-diamine | | Method A HPLC-MS: MH+ requires m/z = 463; Found: m/z = 463, Rt = 4.26 min (100%). 1H NMR (400 MHz, DMSO) δ ppm 7.47 (1H, br s), 7.42 (4H, m), 7.33 (1H, br s), 7.22 (3H, m), 6.99 (2H, m), 5.19 (1H, m), 5.20 (1H, m), 4.63 (1H, m), 4.51 (1H, m), 4.13 (1H, m) and 3.52 (3H, s). | 564[c] |

| Example | Name Structure | M | Spectral data | Nav 1.7 activity (nM) |
|---|---|---|---|---|
| 138 | 6-{5-[6-(cyclopropylmethoxy)pyridin-3-yl]-1,2,4-oxadiazol-3-yl}-2-N-(2-fluorophenyl)-1,3,5-thazine-2,4-diamine 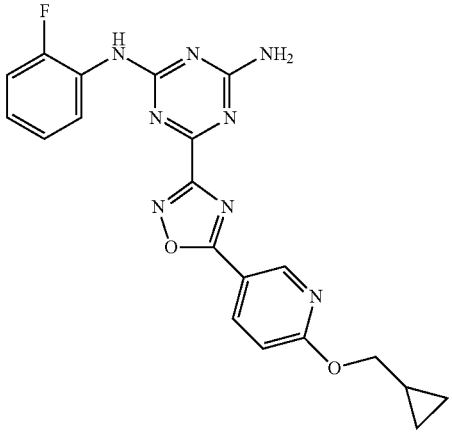 [SMILES: Nc1nc(Nc2ccccc2F)nc(-c2noc(-c3ccc(OCC4CC4)nc3)n2)n1] | 1 | Method A HPLC-MS: MH+ requires m/z = 421; Found: m/z = 421, Rt = 4.56 min (92%). 1H NMR (400 MHz, MeOD) δ ppm 9.03 (1H, s), 8.44 (1H, m), 8.21 (1H, m), 7.17-7.24 (3H, m), 7.02 (1H, m), 4.30 (2H, d), 1.31 (1H, m), 0.56 (2H, m) and 0.41 (2H, m). | 106[c] |
| 139 | 6-{5-[6-(cyclopropylmethoxy)pyridin-3-yl]-1,2,4-oxadiazol-3-yl}-2-N-(2,3-difluorophenyl)-1,3,5-triazine-2,4-diamine 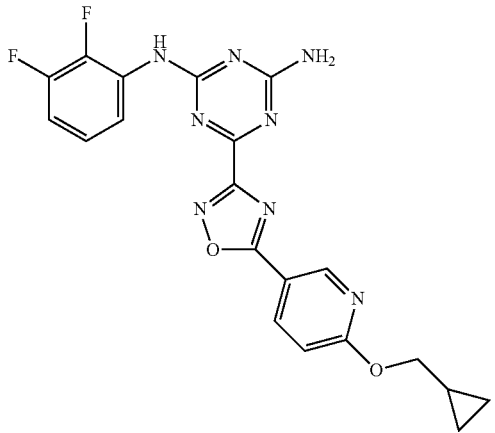 [SMILES: Nc1nc(Nc2cccc(F)c2F)nc(-c2noc(-c3ccc(OCC4CC4)nc3)n2)n1] | 1 | Method A HPLC-MS: MH+ requires m/z = 439; Found: m/z = 439, Rt = 4.59 min (83%). 1H NMR (400 MHz, DMSO) δ ppm 9.83 (1H, s), 8.92 (1H, s), 8.38 (1H, m), 7.69 (1H, br s), 7.47 (1H, m), 7.41 (1H, br s), 7.16-7.30 (2H, m), 7.09 (1H, dd), 4.23 (2H, d), 1.28 (1H, m), 0.49 (2H, m) and 0.37 (2H, m). | 144[c] |

-continued

| Example | Name Structure | M | Spectral data | Nav 1.7 activity (nM) |
|---|---|---|---|---|
| 140 | 6-{5-[6-(cyclopropylmethoxy)pyridin-3-yl]-1,2,4-oxadiazol-3-yl}-2-N-(2,3-difluorophenyl)-2-N-methyl-1,3,5-triazine-2,4-diamine | 1 | Method A HPLC-MS: MH+ requires m/z = 453; Found: m/z = 453, Rt = 4.72 min (83%). 1H NMR (400 MHz, DMSO) δ ppm 8.91 (1H, br s), 8.33 (1H, br s), 7.45-7.75 (2H, br s), 7.25-7.45 (3H, m), 7.09 (1H, dd), 4.23 (2H, d), 3.48 (3H, s), 1.28 (1H, m), 0.61 (2H, m) and 0.37 (2H, m). | 85[c] |
| 141 | 2-N-methyl-6-{5-[6-(oxolan-3-yloxy)pyridin-3-yl]-1,2,4-oxadiazol-3-yl}-2-N-phenyl-1,3,5-triazine-2,4-diamine | 1 | Method A HPLC-MS: MH+ requires m/z = 433; Found: m/z = 433, Rt = 4.12 min (100%). 1H NMR (400 MHz, DMSO) δ ppm 8.91 (1H, s), 8.37 (1H, dd), 7.37-7.50 (4H, m), 7.25 (1H, m), 7.08 (1H, dd), 5.12 (1H, m), 3.76-3.98 (4H, m), 3.49 (3H, s), 2.30 (1H, m) and 2.07 (1H, m). | 261[c] |
| 142 | 6-{5-[2-chloro-6-(trifluoromethyl)pyridin-3-yl]-1,2,4-oxadiazol-3-yl}-2-N-methyl-2-N-phenyl-1,3,5-triazine-2,4-diamine | 1 | Method A HPLC-MS: MH+ requires m/z = 449; Found: m/z = 449, Rt = 4.50 min (91%). 1H NMR (400 MHz, CDCl$_3$) δ ppm 8.65 (1H, dd), 7.72 (1H, dd), 7.36 (2H, m), 7.21-7.35 (3H, m), 5.00-6.00 (2H, 2 × br s) and 3.52 (3H, s). | 5817[c] |

-continued

| Example | Name Structure | M | Spectral data | Nav 1.7 activity (nM) |
|---|---|---|---|---|
| 143 | 6-(5-{6-[(2-methoxyethoxy)methyl]pyridin-3-yl}-1,2,4-oxadiazol-3-yl)-2-N-methyl-2-N-phenyl-1,3,5-triazine-2,4-diamine | 7 | Method B HPLC-MS: MH+ requires m/z = 435; Found: m/z = 435, Rt = 1.83 min (100%). 1H NMR (400 MHz, CDCl$_3$) δ ppm 9.42 (1H, d), 8.53 (1H, dd), 7.74 (1H, d), 7.45 (2H, m), 7.33 (3H, m), 5.32 (2H, br s), 4.81 (2H, s), 3.81 (2H, m), 3.17 (5H, m) and 3.43 (3H, s). | 3575$^c$ |
| 144 | 2-N-methyl-6-(5-{6-[(oxolan-3-yloxy)methyl]pyridin-3-yl}-1,2,4-oxadiazol-3-yl)-2-N-phenyl-1,3,5-triazine-2,4-diamine | | Method A HPLC-MS: MH+ requires m/z = 447; Found: m/z = 447, Rt = 3.93 min (98%). 1H NMR (400 MHz, CDCl$_3$) δ ppm 9.32 (1H, d), 8.45 (1H, dd), 7.62 (1H, d), 7.38 (2H, m), 7.27 (3H, m), 5.21 (2H, br s), 4.65 (2H, m), 4.24 (1H, m), 3.89 (2H, m), 3.71 (2H, m), 3.55 (3H, s) and 2.02 (2H, m). | 1724$^c$ |

| Example | Name Structure | M | Spectral data | Nav 1.7 activity (nM) |
|---|---|---|---|---|
| 145 | 2-N-methyl-2-N-phenyl-6-{5-[(1R,5S)-8-(3,3,3-trifluoropropyl)-8-azabicyclo[3.2.1]octan-3-yl]-1,2,4-oxadiazol-3-yl}-1,3,5-triazine-2,4-diamine | 8 | Method A HPLC-MS: MH+ requires m/z = 475; Found: m/z = 475, Rt = 2.94 min (99%). 1H NMR (400 MHz, MeOD) δ ppm 8.23 (1H, s), 7.44 (2H, m), 7.38 (3H, m), 4.01 (2H, m), 3.72 (1H, m), 3.56 (3H, s), 3.21 (2H, m), 2.72 (2H, m), 2.30 (6H, m) and 2.13 (2H, m). | 1144[c] |
| 146 | 6-{5-[6-(cyclopropylmethoxy)pyridin-3-yl]-1,2,4-oxadiazol-3-yl}-2-N-methyl-2-N-phenyl-1,3,5-triazine-2,4-diamine | 2 | Method A HPLC-MS: MH+ requires m/z = 417 Found: m/z = 417, Rt = 4.61 min (100%). 1H NMR (500 MHz, DMSO-d6) δ ppm 8.92 (1H, br s), 8.35 (1H, d), 7.42 (5H, m), 7.27 (2H, m), 7.08 (1H, d), 4.23 (2H, d). 3.48 (3H, s), 1.29 (1H, br s), 0.58 (2H, d) and 0.37 (2H, d). | 188[c] |

| Example | Name Structure | M | Spectral data | Nav 1.7 activity (nM) |
|---|---|---|---|---|
| 147 | 2-N-ethyl-2-N-phenyl-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 459 Found: m/z = 459, Rt = 477 min (96%). 1H NMR (500 MHz, DMSO-d6) δ ppm 8.95 (1H, s), 8.45 (1H, d), 7.43 (2H, m), 7.27 (6H, m), 5.12 (2H, q), 3.99 (2H, q) and 1.12 (3H, d). | 42[c] |
| 148 | 6-[5-(6-ethoxypyridin-3-yl)-1,2,4-oxadiazol-3-yl]-2-N-methyl-2-N-phenyl-1,3,5-triazine-2,4-diamine | 2 | Method A HPLC-MS: MH+ requires m/z = 391 Found: m/z = 391, Rt = 4.36 min (94%). 1H NMR (500 MHz, CDCl3) δ ppm 9.06 (1H, s), 8.37 (1H, d), 7.45 (2H, m), 7.35 (2H, d), 7.31 (1H, t), 5.34 (2H, br s), 4.48 (2H, q), 3.63 (3H, s) and 1.44 (3H, t). | 323[c] |

-continued

| Example | Name Structure | M | Spectral data | Nav 1.7 activity (nM) |
|---|---|---|---|---|
| 149 | 2-N-methyl-2-N-phenyl-6-{5-[6-(propan-2-yloxy)pyridin-3-yl]-1,2,4-oxadiazol-3-yl}-1,3,5-triazine-2,4-diamine | 2 | Method A HPLC-MS: MH+ requires m/z = 405 Found: m/z = 405, Rt = 4.66 min (91%). 1H NMR (500 MHz, CDCl$_3$) δ ppm 9.05 (1H, s), 8.35(1H, d), 7.45 (2H, m), 7.35 (2H, d), 7.32 (1H, d), 6.81 (1H, d), 5.45 (1H, m), 5.31 (2H, br s), 3.64 (3H, s) and 1.39 (6H, d). | 142[c] |
| 150 | 2-N-phenyl-6-{5-[6-(2,2,2-trifluoroethoxy)pyridin-3-yl]-1,2,4-oxadiazol-3-yl}-2-N-(2,2,2-trifluoroethyl)-1,3,5-triazine-2,4-diamine | 5 | Method B HPLC-MS: MH+ requires m/z = 513 Found: m/z = 513, Rt = 2.33 min (98%). 1H NMR (500 MHz, CDCl$_3$) δ ppm 9.06 (1H, br. s.), 8.47 (1H, br. s.), 7.49 (2H, m), 7.39 (1H, m), 7.33 (2H, d), 7.05 (1H,d), 5.40 (2H, m), 4.87 (2H, q) and 4.80 (2H, br s). | 222[c] |

| Example | Name Structure | M | Spectral data | Nav 1.7 activity (nM) |
|---|---|---|---|---|
| 151 | 2-N-phenyl-6-{5-[6-(2,2,2-trifluoroethoxy)pyridin-3-yl]-1,2,4-oxadiazol-3-yl}-4-N-(2,2,2-trifluoroethyl)-1,3,5-triazine-2,4-diamine | 5 | Method B HPLC-MS: MH+ requires m/z = 513 Found: m/z = 513, Rt = 2.40 min (98%). 1H NMR (500 MHz, CDCl$_3$) δ ppm 9.10 (1H, s), 8.50 (1H, d), 7.58 (3H, br s), 7.41 (2H, t), 7.18 (1H, t), 7.06 (1H,d), 5.96 (1H, br. s.), 4.88 (2H, q) and 4.21 (2H, m). | 1480[c] |
| 152 | 2-N-methyl-6-[5-(3-methylpyridin-2-yl)-1,2,4-oxadiazol-3-yl]-2-N-phenyl-1,3,5-triazine-2,4-diamine | 2 | Method A HPLC-MS: MH+ requires m/z = 361 Found: m/z = 361, Rt = 3.86 min (100%). 1H NMR (500 MHz, CDCl$_3$) δ ppm 8.69 (1H, d), 7.74 (1H, d), 7.43 (3H, m), 7.37 (2H, d), 7.30 (1H, m), 5.41 (2H, br. s.), 3.64 (3H, s) and 2.79 (3H, s). | 1622[c] |
| 153 | 6-[5-(5-fluoropyridin-2-yl)-1,2,4-oxadiazol-3-yl]-2-N-methyl-2-N-phenyl-1,3,5-triazine-2,4-diamine | 2 | Method A HPLC-MS: MH+ requires m/z = 365 Found: m/z = 365, Rt = 3.89 min (100%). 1H NMR (500 MHz, CDCl$_3$) δ ppm 8.70 (1H, d), 8.45 (1H, dd), 7.64 (1H, td), 7.45 (2H, m), 7.34 (2H, m), 7.30 (1H, m), 5.45 (2H, m) and 3.64 (3H, s). | 1387[c] |

-continued

| Example | Name Structure | M | Spectral data | Nav 1.7 activity (nM) |
|---|---|---|---|---|
| 154 | 6-[5-(4,6-dimethylpyridin-3-yl)-1,2,4-oxadiazol-3-yl]-2-N-methyl-2-N-phenyl-1,3,5-triazine-2,4-diamine | 2 | Method B HPLC-MS: MH+ requires m/z = 375 Found: m/z = 375, Rt = 1.80 min (100%). 1H NMR (500 MHz, DMSO-d6) δ ppm 7.41 (5H, m), 7.27 (2H, m), 3.49 (3H, s), 2.65 (3H, s) and 2.54 (3H, s). | 5060[c] |
| 155 | 2-N-methyl-2-N-phenyl-6-{5-[6-(2,2,2-trifluoroethoxy)pyridin-2-yl]-1,2,4-oxadiazol-3-yl}-1,3,5-triazine-2,4-diamine | 2 | Method A HPLC-MS: MH+ requires m/z = 445 Found: m/z = 445, Rt = 4.56 min (100%). 1H NMR (500 MHz, CDCl$_3$) δ ppm 8.09 (1H, d), 7.87 (1H, t), 7.46 (2H, m), 7.35 (2H, d), 7.31 (1H, m), 7.13 (1H, d), 5.33 (2H, br s), 4.94 (2H, q) and 3.64 (3H, s). | 4570[c] |

| Ex-ample | Name Structure | M Spectral data | Nav 1.7 activity (nM) |
|---|---|---|---|
| 156 | 2-N-(2-methoxyethyl)-2-N-phenyl-6-{5-[6-(2,2,2-trifluoroethoxy)pyridin-3-yl]-1,2,4-oxadiazol-3-yl}-1,3,5-triazine-2,4-diamine | Method A HPLC-MS: MH+ requires m/z = 489 Found: m/z = 489, Rt = 4.91 min (97%). 1H NMR (500 MHz, CDCl$_3$) δ ppm 9.06 (1H, br s), 8.47 (1 H, br s), 7.45 (2H, m), 7.34 (3H, m), 7.04 (1H, d), 5.31 (2H, m), 4.87 (2H, q), 4.27 (2H, br s), 3.66 (2H, t) and 3.36 (3H, s). | 65[b] |
| 157 | 2-N-(2-methoxyethyl)-4-N-phenyl-6-{5-[6-(2,2,2-trifluoroethoxy)pyridin-3-yl]-1,2,4-oxadiazol-3-yl}-1,3,5-triazine-2,4-diamine | Method A HPLC-MS: MH+ requires m/z = 489 Found: m/z = 489, Rt = 5.08 min (100%). 1H NMR (500 MHz, CDCl$_3$) δ ppm 9.10 (1H, m), 8.51 (1H, m), 7.65 (2H, m), 7.38 (3H, m), 7.13 (1H, m), 7.06 (1H, m), 6.13 (1H, m), 4.88 (2H, q), 3.74 (2H, m), 3.62 (2H, m) and 3.40 (3H, s). | 477[c] |

| Example | Name Structure | M | Spectral data | Nav 1.7 activity (nM) |
|---|---|---|---|---|
| 158 | 6-[5-(6-fluoropyridin-3-yl)-1,2,4-oxadiazol-3-yl]-2-N-methyl-2-N-phenyl-1,3,5-triazine-2,4-diamine | 1 | Method A HPLC-MS: MH+ requires m/z = 365 Found: m/z = 365, Rt = 4.26 min (95%). 1H NMR (500 MHz, CDCl$_3$) δ ppm 9.15 (1H, br s), 8.64 (1H, t), 7.45 (2H, m), 7.32 (3H, m), 7.15 (1H, dd), 5.52 (2H, br s) and 3.62 (3H, s). | 3306[c] |
| 159 | 1-[4-(3-{4-amino-6-[methyl(phenyl)amino]-1,3,5-triazin-2-yl}-1,2,4-oxadiazol-5-yl)piperidin-1-yl]-2,2,2-trifluoroethan-1-one | 9 | Method A HPLC-MS: MH+ requires m/z = 449 Found: m/z = 449, Rt = 4.37 min (97%). 1H NMR (500 MHz, CDCl$_3$) δ ppm 7.46 (2H, m), 7.34 (3H, m), 5.28 (2H, br s), 4.44 (1H, d), 4.08 (1H, d), 3.63 (3H, s), 3.41 (2H, m), 3.19 (1H, t), 2.29 (2H, d) and 2.08 (2H, m). | 8674[c] |
| 160 | 6-[5-(1-methanesulfonylpiperidin-4-yl)-1,2,4-oxadiazol-3-yl]-2-N-methyl-2-N-phenyl-1,3,5-triazine-2,4-diamine | 9 | Method A HPLC-MS: MH+ requires m/z = 431 Found: m/z = 431, Rt = 3.89 min (100%). 1H NMR (500 MHz, CDCl$_3$) δ ppm 7.45 (2H, m), 7.33 (3H, m), 5.31 (2H, br s), 3.78 (2H, d), 3.62 (3H, s), 3.26 (1H, m), 3.03 (2H, m), 2.83 (3H, s), 2.29 (2H, m) and 2.16 (2H, m). | 2727[c] |

| Example | Name Structure | M | Spectral data | Nav 1.7 activity (nM) |
|---|---|---|---|---|
| 161 | 1-[4-(3-{4-amino-6-[methyl(phenyl)amino]-1,3,5-triazin-2-yl}-1,2,4-oxadiazol-5-yl)piperidin-1-yl]-2-methylpropan-1-one | | Method A HPLC-MS: MH+ requires m/z = 423 Found: m/z = 423, Rt = 3.71 min (100%). 1H NMR (500 MHz, CDCl$_3$) δ ppm 7.44 (2H, m), 7.31 (3H, m), 5.28 (2H, br s), 4.62 (1H, d), 4.02 (1H, d), 3.60 (3H, s), 3.32 (1H, m), 3.25 (1H, t), 2.84 (2H, m), 2.20 (2H, br s), 1.95 (2H, m) and 1.15 (6H, d). | 8497[c] |
| 162 | 1-[4-(3-{4-amino-6-[methyl(phenyl)amino]-1,3,5-triazin-2-yl}-1,2,4-oxadiazol-5-yl)piperidin-1-yl]ethan-1-one | 9 | Method A HPLC-MS: MH+ requires m/z = 395 Found: m/z = 395, Rt = 3.37 min (98%). 1H NMR (500 MHz, CDCl$_3$) δ ppm 7.43 (2H, m), 7.30 (3H, m), 5.43 (2H, br s), 4.56 (1H, d), 3.90 (1H, d), 3.59 (3H, s), 3.28 (2H, m), 2.89 (1H, m), 2.18 (2H, m), 2.13 (3H, s) and 1.94 (2H, m). | 8982[c] |
| 163 | 2-N-methyl-2-N-phenyl-6-{5-[1-(3,3,3-trifluoropropyl)piperidin-4-yl]-1,2,4-oxadiazol-3-yl}-1,3,5-triazine-2,4-diamine | 8 | Method A HPLC-MS: MH+ requires m/z = 449 Found: m/z = 449, Rt = 2.82 min (98%). 1H NMR (500 MHz, CDCl$_3$) δ ppm 7.43 (2H, m), 7.31 (3H, m), 5.36 (2H, br s), 3.60 (3H, s), 3.06 (1H, m), 2.95 (2H, d), 2.63 (2H, m), 2.32 (2H, m), 2.19 (4H, m) and 2.04 (2H, m). | 558.5[c] |

| Example | Name Structure | M | Spectral data | Nav 1.7 activity (nM) |
|---|---|---|---|---|
| 164 | 1-[4-(3-{4-amino-6-[methyl(phenyl)amino]-1,3,5-triazin-2-yl}-1,2,4-oxadiazol-5-yl)piperidin-1-yl]-3,3,3-trifluoropropan-1-one 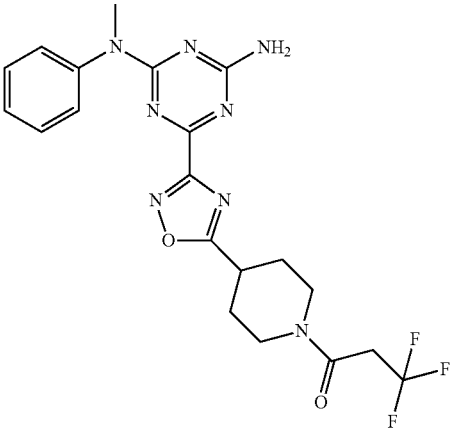 [SMILES: CN(c1ccccc1)c1nc(N)nc(-c2noc(C3CCN(C(=O)CC(F)(F)F)CC3)n2)n1] | 9 | Method A HPLC-MS: MH+ requires m/z = 463 Found: m/z = 463, Rt = 3.96 min (97%). 1H NMR (500 MHz, CDCl$_3$) δ ppm 7.44 (2H, m), 7.30 (3H, m), 5.28 (2H, br s), 4.56 (1H, d), 3.88 (1H, d), 3.60 (3H, s), 3.35 (2H, m), 3.28 (2H, q), 3.01 (1H, m), 2.24 (2H, m) and 2.00 (2H, m). | 9043$^c$ |
| 165 | 6-{5-[4-(methoxymethyl)piperidin-1-yl]-1,2,4-oxadiazol-3-yl}-2-N-methyl-2-N-phenyl-1,3,5-triazine-2,4-diamine 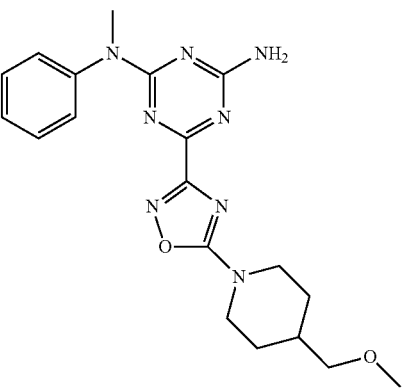 [SMILES: COCC1CCN(c2nc(-c3nc(N)nc(N(C)c4ccccc4)n3)no2)CC1] | 4 | Method B HPLC-MS: MH+ requires m/z = 397 Found: m/z = 397, Rt = 1.85 min (84%). 1H NMR (500 MHz, CDCl$_3$) δ ppm 7.42 (2H, m), 7.29 (3H, m), 5.38 (2H, br s), 4.30 (2H, d), 3.59 (3H, s), 3.35 (3H, s), 3.26 (2H, d), 3.12 (2H, m), 1.85 (3H, m) and 1.33 (2H, m). | 7690$^c$ |

-continued

| Example | Name Structure | M | Spectral data | Nav 1.7 activity (nM) |
|---|---|---|---|---|
| 166 | 2-N-methyl-6-{5-[4-(phenoxymethyl)piperidin-1-yl]-1,2,4-oxadiazol-3-yl}-2-N-phenyl-1,3,5-triazine-2,4-diamine 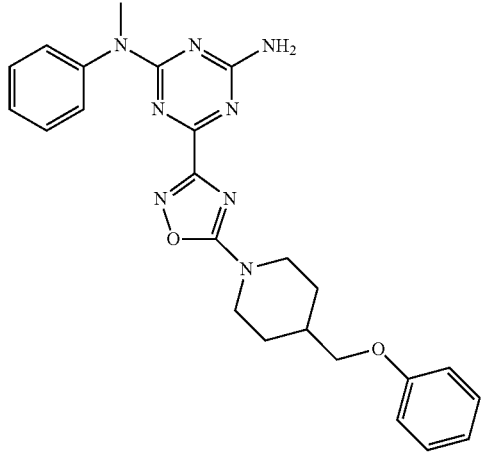 [SMILES: CN(c1ccccc1)c1nc(N)nc(-c2noc(N3CCC(COc4ccccc4)CC3)n2)n1] | 4 | Method B HPLC-MS: MH+ requires m/z = 459 Found: m/z = 459, Rt = 2.18 min (94%). 1H NMR (500 MHz, CDCl$_3$) δ ppm 7.43 (2H, m), 7.31 (4H, m), 7.28 (1H, m), 6.96 (1H, t), 6.90 (2H, d), 5.29 (2H, br s), 4.37 (2H, d), 3.85 (2H, d), 3.61 (3H, s), 3.19 (2H, m), 2.09 (1H, dd), 1.99 (2H, d) and 1.48 (2H, m). | 60$^c$ |
| 167 | 2-N-methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine 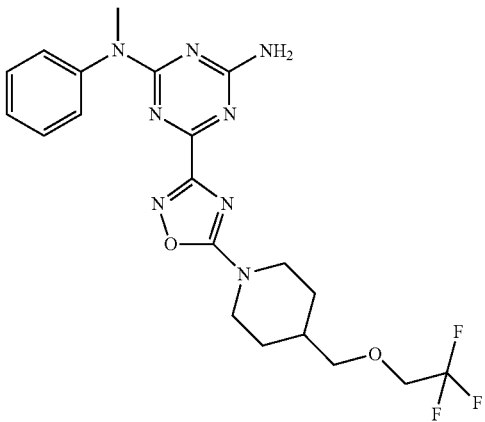 [SMILES: CN(c1ccccc1)c1nc(N)nc(-c2noc(N3CCC(COCC(F)(F)F)CC3)n2)n1] | 4 | Method B HPLC-MS: MH+ requires m/z = 465 Found: m/z = 465, Rt = 2.02 min (92%). 1H NMR (500 MHz, CDCl$_3$) δ ppm 7.41 (2H, m), 7.28 (3H, m), 5.44 (2H, br s), 4.31 (1H, d), 3.81 (2H, m), 3.58 (3H, s), 3.49 (2H, d), 3.13 (1H, m), 2.01 (3H, m), 1.87 (2H, d) and 1.34 (2H, m). | 235$^b$ |

| Example | Name Structure | M | Spectral data | Nav 1.7 activity (nM) |
|---|---|---|---|---|
| 168 | 2-N-methyl-2-N-phenyl-6-{5-[1-(propane-1-sulfonyl)piperidin-4-yl]-1,2,4-oxadiazol-3-yl}-1,3,5-triazine-2,4-diamine | 9 | Method B HPLC-MS: MH+ requires m/z = 459 Found: m/z = 459, Rt = 1.91 min (96%). 1H NMR (500 MHz, CDCl$_3$) δ ppm 7.44 (2H, m), 7.31 (3H, m), 5.31 (2H, br s), 3.80 (2H, d), 3.60 (3H, s), 3.23 (1H, m), 3.06 (2H, m), 2.91 (2H, m), 2.26 (2H, d), 2.10 (2H, m), 1.87 (2H, m) and 1.04 (3H, br s). | 1466$^c$ |
| 169 | 2-N-methyl-2-N-phenyl-6-(5-{1-[(2,2,2-trifluoroethane)sulfonyl]piperidin-4-yl}-1,2,4-oxadiazol-3-yl)-1,3,5-triazine-2,4-diamine | 9 | Method B HPLC-MS: MH+ requires m/z = 499 Found: m/z = 499, Rt = 1.93 min (100%). 1H NMR (500 MHz, CDCl$_3$) δ ppm 7.44 (2H, m), 7.31 (3H, m), 5.32 (2H, br s), 3.89 (2H, d), 3.74 (2H, q), 3.60 (3H, s), 3.27 (1H, t), 3.15 (2H, t), 2.28 (2H, d) and 2.13 (2H, m). | 1026$^c$ |

| Example | Name Structure | M | Spectral data | Nav 1.7 activity (nM) |
|---|---|---|---|---|
| 170 | 6-{5-[1-(ethanesulfonyl)piperidin-4-yl]-1,2,4-oxadiazol-3-yl}-2-N-methyl-2-N-phenyl-1,3,5-triazine-2,4-diamine | 9 | Method B HPLC-MS: MH+ requires m/z = 445 Found: m/z = 445, Rt = 1.80 min (100%). 1H NMR (500 MHz, CDCl$_3$) δ ppm 7.44 (2H, m), 7.31 (3H, m), 5.31 (2H, br s), 3.82 (2H, d), 3.60 (3H, s), 3.23 (1H, m), 3.07 (2H, m), 2.98 (2H, q), 2.26 (2H, d), 2.11 (2H, q) and 1.38 (3H, d). | 1881[c] |
| 171 | 2-N-methyl-2-N-phenyl-6-{5-[1-(propane-2-sulfonyl)piperidin-4-yl]-1,2,4-oxadiazol-3-yl}-1,3,5-triazine-2,4-diamine | 9 | Method B HPLC-MS: MH+ requires m/z = 459 Found: m/z = 459, Rt = 1.87 min (100%). 1H NMR (500 MHz, CDCl$_3$) δ ppm 7.43 (2H, m), 7.31 (3H, m), 5.39 (2H, br s), 3.85 (2H, d), 3.60 (3H, s), 3.21 (2H, m), 3.13 (2H, m), 2.22 (2H, d), 2.08 (2H, q) and 1.36 (6H, d). | 254[c] |
| 172 | 6-{5-[1-(benzenesulfonyl)piperidin-4-yl]-1,2,4-oxadiazol-3-yl}-2-N-methyl-2-N-phenyl-1,3,5-triazine-2,4-diamine | 9 | Method B HPLC-MS: MH+ requires m/z = 493 Found: m/z = 493, Rt = 1.99 min (100%). 1H NMR (500 MHz, DMSO-d6) δ ppm 7.76 (2H, m), 7.73 (1H, m), 7.67 (2H, m), 7.40 (2H, m), 7.35 (2H, m), 7.25 (1H, t), 3.66 (5H, br s), 3.43 (3H, s), 3.17 (1H, m), 2.46 (1H, m), 2.15 (2H, d) and 1.78 (2H, m). | 1079[c] |

| Example | Name Structure | M | Spectral data | Nav 1.7 activity (nM) |
|---|---|---|---|---|
| 173 | 6-[5-(1-benzylpiperidin-4-yl)-1,2,4-oxadiazol-3-yl]-2-N-methyl-2-N-phenyl-1,3,5-triazine-2,4-diamine | | Method B HPLC-MS: MH+ requires m/z = 443 Found: m/z = 443, Rt = 1.60 min (82%). 1H NMR (500 MHz, CDCl$_3$) δ ppm 7.43 (2H, m), 7.36 (4H, m), 7.30 (4H, m), 5.33 (2H, br s), 3.70 (2H, s), 3.60 (3H, s), 3.14 (1H, br s), 3.04 (2H, d), 2.38 (2H, br s) and 2.16 (4H, m). | 1002[c] |
| 174 | 2-N-phenyl-6-(5-{4-[(2,2,2-trifluoroethoxy)methyl]piperidin-1-yl}-1,2,4-oxadiazol-3-yl)-1,3,5-triazine-2,4-diamine | 4 | Method B HPLC-MS: MH+ requires m/z = 451 Found: m/z = 451, Rt = 2.13 min (99%). 1H NMR (500 MHz, CDCl$_3$) δ ppm 7.60 (2H, m), 7.46 (1H, d), 7.35 (2H, m), 7.14 (1H, m), 5.97 (1H, br s), 5.51 (1H, br s), 4.75 (1H, m), 3.97 (1H, m), 3.82 (2H, m), 3.51 (2H, m), 3.24 (1H, m), 2.88 (1H, m), 1.98 (1H, m), 1.90 (2H, m) and 1.37 (2H, m). | 340[c] |
| 175 | 2-N-methyl-2-N-phenyl-6-[5-(4-{[(2,2,2-trifluoroethyl)sulfanyl]methyl}piperidin-1-yl)-1,2,4-oxadiazol-3-yl]-1,3,5-triazine-2,4-diamine | 4 | Method B HPLC-MS: MH+ requires m/z = 481 Found: m/z = 481, Rt = 2.09 min (100%). 1H NMR (250 MHz, CDCl$_3$) δ ppm 7.43 (2H, m), 7.29 (3H, m), 5.30 (2H, br s), 4.33 (2H, d), 3.59 (3H, s), 3.15 (3H, m), 2.65 (2H, d), 1.97 (2H, d), 1.75 (2H, m) and 1.33 (2H, m). | 20[c] |

| Example | Name Structure | M | Spectral data | Nav 1.7 activity (nM) |
|---|---|---|---|---|
| 176 | 2-N-methyl-2-N-phenyl-6-(5-{4-[(phenylsulfanyl)methyl]piperidin-1-yl}-1,2,4-oxadiazol-3-yl)-1,3,5-triazine-2,4-diamine | 4 | Method B HPLC-MS: MH+ requires m/z = 475 Found: m/z = 475, Rt = 2.22 min (100%). 1H NMR (500 MHz, CDCl$_3$) δ ppm 7.43 (2H, m), 7.31 (7H, m), 7.21 (1H, m), 5.26 (2H, br s), 4.30 (2H, d), 3.59 (3H, s), 3.10 (2H, t), 2.89 (2H, d), 2.01 (3H, m) and 1.36 (2H, m). | 223[c] |
| 177 | 2-N-methyl-2-N-phenyl-6-(5-{4-[(propan-2-ylsulfanyl)methyl]piperidin-1-yl}-1,2,4-oxadiazol-3-yl)-1,3,5-triazine-2,4-diamine | 4 | Method B HPLC-MS: MH+ requires m/z = 441 Found: m/z = 441, Rt = 2.16 min (100%). 1H NMR (500 MHz, CDCl$_3$) δ ppm 7.42 (2H, m), 7.30 (3H, m), 5.31 (2H, br s), 4.30 (2H, d), 3.59 (3H, s), 3.11 (2H, m), 2.90 (1H, dt), 2.49 (2H, d), 1.97 (2H, d), 1.71 (1H, m), 1.34 (2H, m) and 1.27 (6H, m). | 306[c] |

| Example | Name Structure | M | Spectral data | Nav 1.7 activity (nM) |
|---|---|---|---|---|
| 178 | 2-N-methyl-2-N-phenyl-6-[5-(4-{[(2,2,2-trifluoroethane)sulfonyl]methyl}piperidin-1-yl)-1,2,4-oxadiazol-3-yl]-1,3,5-triazine-2,4-diamine | 10 | Method B HPLC-MS: MH+ requires m/z = 513 Found: m/z = 513, Rt = 1.90 min (100%). 1H NMR (500 MHz, CDCl$_3$) δ ppm 7.42 (2H, m), 7.30 (3H, m), 5.27 (2H, br s), 4.33 (2H, d), 3.81 (2H, q), 3.59 (3H, s), 3.21 (2H, t), 3.14 (2H, d), 2.46 (1H, m), 2.10 (2H, d) and 1.53 (2H, m). | 2646$^c$ |
| 179 | 6-(5-{4-[(benzenesulfonyl)methyl]piperidin-1-yl}-1,2,4-oxadiazol-3-yl)-2-N-methyl-2-N-phenyl-1,3,5-triazine-2,4-diamine | 10 | Method B HPLC-MS: MH+ requires m/z = 507 Found: m/z = 507, Rt = 1.94 min (96%). 1H NMR (500 MHz, CDCl$_3$) δ ppm 7.94 (2H, m), 7.69 (1H, m), 7.61 (2H, m), 7.42 (2H, m), 7.30 (3H, m), 5.26 (2H, br s), 4.28 (2H, d), 3.59 (3H, s), 3.17 (2H, t), 3.05 (2H, d), 2.34 (1H, m), 2.05 (2H, d) and 1.45 (2H, m). | 810$^c$ |

| Example | Name Structure | M | Spectral data | Nav 1.7 activity (nM) |
|---|---|---|---|---|
| 180 | 2-N-methyl-2-N-phenyl-6-(5-{4-[(propane-2-sulfinyl)methyl]piperidin-1-yl}-1,2,4-oxadiazol-3-yl)-1,3,5-triazine-2,4-diamine 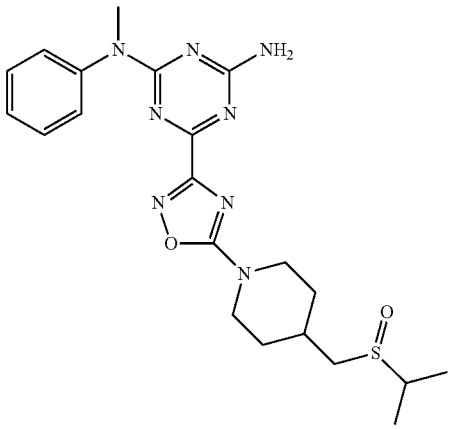 [SMILES: CC(C)S(=O)CC1CCN(c2nc(-c3nc(N)nc(N(C)c4ccccc4)n3)no2)CC1] | 10 | Method B HPLC-MS: MH+ requires m/z = 457 Found: m/z = 457, Rt = 1.65 min (99%). 1H NMR (500 MH,. CDCl₃) δ ppm 7.42 (2H, m), 7.30 (3H, m), 5.34 (2H, br s), 4.33 (2H, d), 3.58 (3H, s), 3.19 (2H, t), 2.78 (1H, dt), 2.65 (1H, m), 2.36 (1H, m), 2.26 (1H, m), 2.18 (1H, d), 1.89 (1H, d), 1.48 (1H, qd), 1.39 (1H, m), 1.33 (3H, d) and 1.27 (3H, m). | >7709ᶜ |
| 181 | 2-N-methyl-2-N-phenyl-6-(5-{4-[(propane-2-sulfonyl)methyl]piperidin-1-yl}-1,2,4-oxadiazol-3-yl)-1,3,5-triazine-2,4-diamine 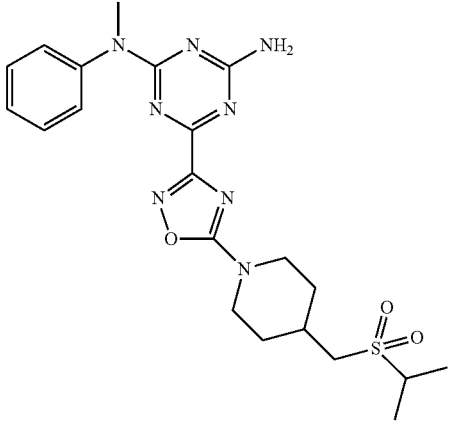 [SMILES: CC(C)S(=O)(=O)CC1CCN(c2nc(-c3nc(N)nc(N(C)c4ccccc4)n3)no2)CC1] | 10 | Method B HPLC-MS: MH+ requires m/z = 474 Found: m/z = 474, Rt = 1.77 min (99%). 1H NMR (500 MHz, CDCl₃) δ ppm 7.42 (2H, m), 7.30 (3H, m), 5.27 (2H, br s), 4.32 (2H, d), 3.59 (3H, s), 3.21 (2H, t), 3.10 (1H, dt), 2.86 (2H, d), 2.44 (1H, d), 2.12 (2H, d), 1.50 (2H, m) and 1.42 (6H, d). | 9081ᶜ |

| Example | Name Structure | M | Spectral data | Nav 1.7 activity (nM) |
|---|---|---|---|---|
| 182 | methyl 3-[(4-amino-6-{5-[6-(2,2,2-trifluoroethoxy)pyridin-3-yl]-1,2,4-oxadiazol-3-yl}-1,3,5-triazin-2-yl)amino]benzoate 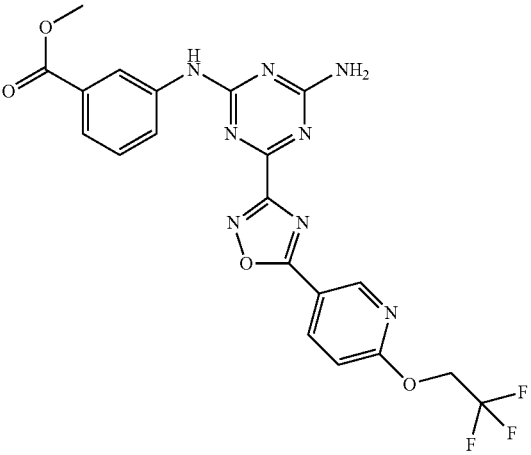 [SMILES: COC(=O)c1cccc(Nc2nc(N)nc(-c3noc(-c4ccc(OCC(F)(F)F)nc4)n3)n2)c1] | 2 | Method A HPLC-MS: MH+ requires m/z = 489 Found: m/z = 489, Rt = 4.56 min (93%). 1H NMR (500 MHZ, DMSO-d6) δ ppm 10.23 (1H, br. s.), 9.01 (1H, d), 8.50 (1H, dd), 8.20-8.41 (2H, m), 7.76 (1H, br. s.), 7.61 (1H, d), 7.42-7.53 (2H, m), 7.29 (1H, d), 5.15 (3H, q) and 3.83-3.91 (3H, m). | 8694[c] |
| 183 | 6-[5-(2-ethoxyphenyl)-1,2,4-oxadiazol-3-yl]-2-N-methyl-2-N-(3-methylphenyl)-1,3,5-triazine-2,4-diamine 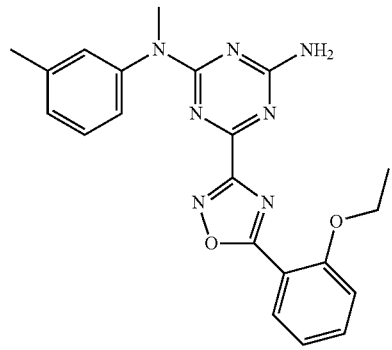 [SMILES: CCOc1ccccc1-c1nc(-c2nc(N)nc(N(C)c3cccc(C)c3)n2)no1] | 2 | Method A HPLC-MS: MH+ requires m/z = 404 Found: m/z = 404. Rt = 477 min (96%). 1H NMR (500 MHz, DMSO-d6) δ ppm 8.00 (1H, d), 7.65 (1H, t), 7.22 (9H, m), 4.23 (2H, q), 3.45 (3H, s), 2.33 (3H, s) and 1.39 (3H, t). | 67[c] |
| 184 | 6-[5-(4-methoxyphenyl)-1,2,4-oxadiazol-3-yl]-2-N-methyl-2-N-(3-methylphenyl)-1,3,5-triazine-2,4-diamine 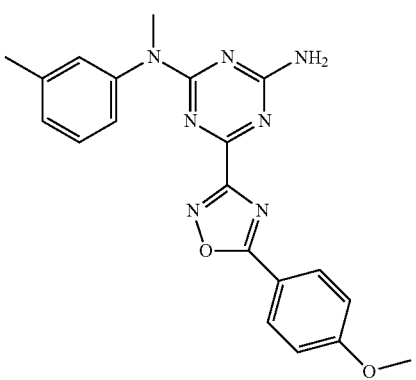 | 2 | Method A HPLC-MS: MH+ requires m/z = 390 Found: m/z = 390, Rt = 4.38 min (99%). 1H NMR (500 MHz, DMSO-d6) δ ppm 8.09 (2H, d), 7.22 (7H, m), 3.88 (3H, s), 3.45 (3H, s), 3.32 (3H, s) and 2.33 (3H, s). | 62[c] |

| Example | Name Structure | M | Spectral data | Nav 1.7 activity (nM) |
|---|---|---|---|---|
| 185 | 6-[5-(2-fluoro-6-methoxyphenyl)-1,2,4-oxadiazol-3-yl]-2-N-methyl-2-N-(3-methylphenyl)-1,3,5-triazine-2,4-diamine | 2 | Method A HPLC-MS: MH+ requires m/z = 408 Found: m/z = 408, Rt = 4.32 min (98%). 1H NMR (500 MHz, DMSO-d6) δ ppm 7.72 (1H, m), 7.42 (1H, br. s.), 7.19 (7H, m), 3.88 (3H, s), 3.44 (3H, s) and 2.33 (3H, s). | 144[c] |
| 186 | 6-[5-(5-fluoro-2-methoxyphenyl)-1,2,4-oxadiazol-3-yl]-2-N-methyl-2-N-(3-methylphenyl)-1,3(5-triazine-2,4-diamine | 2 | Method A HPLC-MS: MH+ requires m/z = 408 Found: m/z = 408, Rt = 4.38 min (100%). 1H NMR (500 MHz, DMSO-d6) δ ppm 7.77 (1H, dd), 7.57 (1H, m), 7.41 (1H, m), 7.35 (1H, dd), 7.19 (3H, m), 7.08 (1H, d), 3.93 (3H, s), 3.45 (3H, s) and 2.33 (3H, s). | 87[c] |
| 187 | 6-[5-(4-fluoro-2-methoxyphenyl)-1,2,4-oxadiazol-3-yl]-2-N-methyl-2-N-(3-methylphenyl)-1,3,5-triazine-2,4-diamine | 2 | Method B HPLC-MS: MH+ requires m/z = 408 Found: m/z = 408, Rt = 2.13 min (99%). 1H NMR (500 MHz, DMSO-$d_6$) δ ppm 8.07 (1H, dd), 7.39 (1H, m), 7.24 (5H, m), 7.04 (2H, m), 3.96 (3H, s), 3.45 (3H, s) and 2.33 (3H, s). | 458[c] |

| Example | Name Structure | M | Spectral data | Nav 1.7 activity (nM) |
|---|---|---|---|---|
| 188 | 6-[5-(2,4-dimethoxyphenyl)-1,2,4-oxadiazol-3-yl]-2-N-methyl-2-N-(3-methylphenyl)-1,3,5-triazine-2,4-diamine | 2 | Method A HPLC-MS: MH+ requires m/z = 420 Found: m/z = 420, Rt = 4.56 min (100%). 1H NMR (500 MHz, DMSO-d6) δ ppm 7.98 (1H, d), 7.40 (1H, br. s.), 7.30 (1H, m), 7.20 (1H, s), 7.16 (1H, d), 7.08 (1H, d), 6.77 (2H, m), 3.95 (3H, s), 3.89 (3H, s), 3.45 (3H, s) and 2.33 (3H, s). | 7629[c] |
| 189 | 2-N-(3-methanesulfonylphenyl)-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 508 Found: m/z = 508, Rt = 4.21 min (98%). 1H NMR (500 MHz, DMSO-d6) δ ppm 9.02 (1H, d), 8.51 (2H, dd), 8.17 (1H, br. s.), 7.83 (1H, br. s.), 7.58 (3H, m), 7.29 (1H, d), 5.16 (2H, q) and 3.24 (3H, s). | 287[c] |
| 190 | 2-N-ethyl-6-[5-(4-methoxyphenyl)-1,2,4-oxadiazol-3-yl]-2-N-phenyl-1,3,5-triazine-2,4-diamine | 2 | Method A HPLC-MS: MH+ requires m/z = 390 Found: m/z = 390, Rt = 4.39 min (95%). 1H NMR (500 MHz, DMSO-d6) δ ppm 8.08 (2H, d), 7.32 (9H, m), 4.00 (2H, q), 3.88 (3H, s) and 1.13 (3H, t). | 106[c] |

-continued

| Example | Name Structure | M | Spectral data | Nav 1.7 activity (nM) |
|---|---|---|---|---|
| 191 | 2-N-ethyl-6-[5-(2-fluoro-6-methoxyphenyl)-1,2,4-oxadiazol-3-yl]-2-N-phenyl-1,3,5-triazine-2,4-diamine | 2 | Method A HPLC-MS: MH+ requires m/z = 408 Found: m/z = 408, Rt = 4.39 min (95%). 1H NMR (500 MHz, DMSO-$d_6$) δ ppm 7.72 (1H, m), 7.25 (9H, m), 3.99 (2H, q), 3.88 (3H, s) and 1.12 (3H, t). | 67[c] |
| 192 | 6-[5-(2-chlorophenyl)-1,2,4-oxadiazol-3-yl]-2-N-ethyl-2-N-phenyl-1,3,5-triazine-2,4-diamine | 2 | Method A HPLC-MS: MH+ requires m/z = 395 Found: m/z = 395, Rt = 4.75 min (96%). 1H NMR (500 MHz, DMSO-$d_6$), δ ppm 8.11 (1H, d), 7.74 (2H, m), 7.62 (1H, t), 7.43 (3H, m), 7.28 (4H, m), 4.00 (2H, q) and 1.13 (3H, t). | 123[c] |
| 193 | 6-[5-(2-chloro-4-fluorophenyl)-1,2,4-oxadiazol-3-yl]-2-N-ethyl-2-N-phenyl-1,3,5-triazine-2,4-diamine | 2 | Method A HPLC-MS: MH+ requires m/z = 412 Found: m/z = 412, Rt = 4.91 min (99%). 1H NMR (500 MHz, DMSO-$d_6$) δ ppm 8.19 (1H, dd), 7.81 (1H, dd), 7.52 (1H, td), 7.33 (7H, m), 3.99 (2H, q) and 1.13 (3H, t). | 83[c] |

| Example | Name Structure | M | Spectral data | Nav 1.7 activity (nM) |
|---|---|---|---|---|
| 194 | 2-N-methyl-2-N-(3-methylphenyl)-6-{5-[2-(trifluoromethoxy)phenyl]-1,2,4-oxadiazol-3-yl}-1,3,5-triazine-2,4-diamine | 2 | Method A HPLC-MS: MH+ requires m/z = 444 Found: m/z = 444, Rt = 4.94 min (96%). 1H NMR (500 MHz, CDCl$_3$) δ ppm 8.46 (1H, d), 7.79 (1H, td), 7.61 (2H, m), 7.44 (1H, m), 7.25 (3H, m), 6.34 (1H, m), 5.85 (1H, m), 3.73 (3H, s) and 2.52 (3H, s). | 843[c] |
| 195 | 6-[5-(2-chlorophenyl)-1,2,4-oxadiazol-3-yl]-2-N-methyl-2-N-(3-methylphenyl)-1,3,5-triazine-2,4-diamine | 2 | Method A HPLC-MS: MH+ requires m/z = 395 Found: m/z = 395, Rt = 4.76 min (96%). 1H NMR (500 MHz, DMSO-d$_6$) δ ppm 8.12 (1H, dd), 7.74 (2H, m), 7.62 (1H, m), 7.44 (1H, br. s.), 7.30 (2H, m), 7.18 (2H, m), 7.08 (1H, d), 3.45 (3H, s) and 2.33 (3H, s). | 431[c] |
| 196 | 6-[5-(2-ethoxyphenyl)-1,2,4-oxadiazol-3-yl]-2-N-ethyl-2-N-phenyl-1,3,5-triazine-2,4-diamine | 2 | Method A HPLC-MS: MH+ requires m/z = 404 Found: m/z = 404, Rt = 4.74 min (100%). 1H NMR (500 MHz, DMSO-d$_6$) δ ppm 7.99 (1H, d), 7.65 (1H, m), 7.42 (3H, m), 7.25 (6H, m), 4.22 (2H, q), 4.00 (2H, q), 1.39 (3H, t) and 1.13 (3H, t). | 764[c] |

| Example | Name Structure | M | Spectral data | Nav 1.7 activity (nM) |
|---|---|---|---|---|
| 197 | 2-N-ethyl-6-[5-(5-fluoro-2-methoxyphenyl)-1,2,4-oxadiazol-3-yl]-2-N-phenyl-1,3,5-triazine-2,4-diamine | 2 | Method A HPLC-MS: MH+ requires m/z = 408 Found: m/z = 408. Rt = 4.59 min (100%). 1H NMR (500 MHz, DMSO-d$_6$) δ ppm 7.76 (1H, dd), 7.57 (1H, td), 7.36 (7H, m), 7.20 (1H, br. s.), 3.99 (2H, q), 3.93 (3H, s) and 1.13 (3H, t). | 571$^c$ |
| 198 | 2-N-ethyl-2-N-phenyl-6-{5-[2-(trifluoromethoxy)phenyl]-1,2,4-oxadiazol-3-yl}-1,3,5-triazine-2,4-diamine | 2 | Method A HPLC-MS: MH+ requires m/z = 444 Found: m/z = 444, Rt = 4.93 min (99%). 1H NMR (500 MHz, DMSO-d$_6$) δ ppm 8.25 (1H, d), 7.88 (1H, m), 7.70 (2H, m), 7.44 (3H, m), 7.29 (4H, m), 4.00 (2H, q) and 1.14 (3H, t). | 777$^c$ |
| 199 | 6-{5-[(2-methoxyphenyl)methyl]-1,2,4-oxadiazol-3-yl}-2-N-methyl-2-N-phenyl-1,3,5-triazine-2,4-diamine | 2 | Method A HPLC-MS: MH+ requires m/z = 390 Found: m/z = 390, Rt = 4.39 min (100%). 1H NMR (500 MHz, CDCl$_3$) δ ppm 7.45 (2H, m), 7.31 (3H, m), 7.22 (1H, dd), 7.16 (1H, td), 6.85 (1H, td), 6.78 (1H, d), 4.27 (2H, s), 3.71 (3H, s) and 3.58 (3H, s). | 8729$^c$ |

| Example | Name Structure | M | Spectral data | Nav 1.7 activity (nM) |
|---|---|---|---|---|
| 200 | 2-N-methyl-2-N-phenyl-6-{5-[1-(propane-1-sulfonyl)pyrrolidin-3-yl]-1,2,4-oxadiazol-3-yl}-1,3,5-triazine-2,4-diamine | 9 | Method A HPLC-MS: MH+ requires m/z = 445 Found: m/z = 445, Rt = 3.88 min (98%). 1H NMR (500 MHz, CDCl$_3$) δ ppm 7.44 (2H, m), 7.31 (3H, m), 5.28 (2H, m), 3.96 (1H, d), 3.88 (1H, m), 3.75 (1H, m), 3.61 (5H, m), 3.00 (2H, m), 2.50 (2H, m), 1.87 (2H, dq) and 1.06 (3H, t). | 8595$^c$ |
| 201 | 2-N-methyl-2-N-phenyl-6-{5-[1-(propane-2-sulfonyl)pyrrolidin-3-yl]-1,2,4-oxadiazol-3-yl}-1,3,5-triazine-2,4-diamine | 9 | Method A HPLC-MS: MH+ requires m/z = 445 Found: m/z = 445t Rt = 3.92 min (99%). 1H NMR (500 MHz, CDCl$_3$) δ ppm 7.44 (2H, m),7.31 (3H, m), 5.31 (2H, br s), 4.04 (1H, dd), 3.87 (1H, t), 3.73 (2H, m), 3.60 (4H, s), 3.25 (1H, m), 2.49 (2H, m) and 1.38 (6H, dd). | 3292$^c$ |

| Example | Name Structure | M | Spectral data | Nav 1.7 activity (nM) |
|---|---|---|---|---|
| 202 | 2-N-methyl-2-N-phenyl-6-(5-{1-[(2,2,2-trifluoroethane)sulfonyl]pyrrolidin-3-yl}-1,2,4-oxadiazol-3-yl)-1,3,5-triazine-2,4-diamine | 9 | Method A HPLC-MS: MH+ requires m/z = 485 Found: m/z = 485, Rt = 4.11 min (100%). 1H NMR (500MHz. CDCl$_3$) δ ppm 7.45 (2H, m), 7.31 (3H, m), 5.28 (2H, m), 3.94 (5H, m), 3.65 (5H, m) and 2.53 (2H, m). | 1788$^c$ |
| 203 | 6-{5-[1-(benzenesulfonyl)pyrrolidin-3-yl]-1,2,4-oxadiazol-3-yl}-2-N-methyl-2-N-phenyl-1,3,5-triazine-2,4-diamine | 9 | Method A HPLC-MS: MH+ requires m/z = 479 Found: m/z = 479, Rt = 4.18 min (98%). 1H NMR (500 MHz, CDCl$_3$) δ ppm 7.81 (2H, m), 7.68 (1H, m), 7.61 (2H, m), 7.39 (5H, m), 7.27 (2H, m), 3.78 (1H, m), 3.67 (1H, dd), 3.49 (1H, dd), 3.45 (3H, s), 3.33 (2H, m), 2.25 (1H, m) and 2.07 (1H, m). | 4559$^c$ |

| Example | Name Structure | M | Spectral data | Nav 1.7 activity (nM) |
|---|---|---|---|---|
| 204 | 2-N-methyl-2-N-phenyl-6-{5-[1-(3,3,3-trifluoropropyl)pyrrolidin-3-yl]-1,2,4-oxadiazol-3-yl}-1,3,5-triazine-2,4-diamine | 8 | Method A HPLC-MS: MH+ requires m/z = 435 Found: m/z = 435, Rt = 2.92 min (100%). 1H NMR (500 MHz, CDCl$_3$) δ ppm 7.44 (2H, m), 7.31 (3H, m), 5.45 (2H, m), 3.76 (1H, m), 3.60 (3H, s), 3.10 (1H, t), 2.93 (1H, m), 2.74 (4H, m) and 2.36 (4H, m). | >7830[e] |
| 205 | 2-N-methyl-2-N-phenyl-6-{5-[1-(4,4,4-trifluorobutan-2-yl)pyrrolidin-3-yl]-1,2,4-oxadiazol-3-yl}-1,3,5-triazine-2,4-diamine | 8 | Method A HPLC-MS: MH+ requires m/z = 449 Found: m/z = 449, Rt = 3.32 min (99%). 1H NMR (500 MHz, CDCl$_3$) δ ppm 7.44 (2H, m), 7.31 (3H, m), 5.36 (2H, m), 3.73 (1H, m), 3.60 (3H, s), 3.18 (1H, q), 2.88 (4H, m), 2.38 (3H, m), 2.10 (1H, m) and 1.22 (3H, t). | 1526[e] |

| Example | Name Structure | M | Spectral data | Nav 1.7 activity (nM) |
|---|---|---|---|---|
| 206 | 2-N-methyl-2-N-phenyl-6-[5-(6-{[(1,1,1-trifluoropropan-2-yl)oxy]methyl}pyridin-3-yl)-1,2,4-oxadiazol-3-yl]-1,3,5-triazine-2,4-diamine | 2 | Method A HPLC-MS: MH+ requires m/z = 473 Found: m/z = 473 Rt = 4.77 min (100%). 1H NMR (500 MHz, CDCl3) δ ppm 9.41 (1H, s), 8.56 (1H, d), 7.71 (1H, d), 7.46 (2H, m), 7.33 (3H, m), 5.31 (2H, br. s.), 4.93 (2H, m), 4.01 (1H, dt), 3.64 (3H, s) and 1.45 (3H, m). | 17[c] |
| 207 | 6-[5-(1-benzylpyrrolidin-3-yl)-1,2,4-oxadiazol-3-yl]-2-N-methyl-2-N-phenyl-1,3,5-triazine-2,4-diamine | 8 | Method A HPLC-MS: MH+ requires m/z = 429 Found: m/z = 429, Rt = 3.43 min (100%). 1H NMR (500 MHz, CDCl3) δ ppm 7.42 (2H, m), 7.29 (8H, m), 5.31 (2H, s), 3.69 (6H, m), 3.11 (1H, t), 2.82 (2H, m), 2.70 (1H, m) and 2.37 (2H, m). | 97[b] |

| Example | Name Structure | M | Spectral data | Nav 1.7 activity (nM) |
|---|---|---|---|---|
| 208 | 6-(5-{6-[(cyclopropylmethoxy)methyl]pyridin-3-yl}-1,2,4-oxadiazol-3-yl)-2-N-methyl-2-N-phenyl-1,3,5-triazine-2,4-diamine | 2 | Method A HPLC-MS: MH+ requires m/z = 431 Found: m/z = 431, Rt = 4.33 min (100%). 1H NMR (500 MHz, CDCl$_3$) δ ppm 9.41 (1H, s), 8.54 (1H, d), 7.72 (1H, d), 7.46 (2H, m), 7.33 (3H, m), 5.31 (2H, br. s.), 4.77 (2H, s), 3.64 (3H, s), 3.48 (2H, d), 1.17 (1H, m), 0.60 (2H, m) and 0.28 (2H, m). | 113[c] |
| 209 | 2-N-methyl-2-N-phenyl-6-(5-{6-[1-(2,2,2-trifluoroethoxy)ethyl]pyridin-3-yl}-1,2,4-oxadiazol-3-yl)-1,3,5-triazine-2,4-diamine | 2 | Method A HPLC-MS: MH+ requires m/z = 473 Found: m/z = 473, Rt = 4.49 min (100%). 1H NMR (500 MHz, CDCl$_3$) δ ppm 9.42 (1H, s), 8.58 (1H, d), 7.69 (1H, d), 7.45 (2H, m), 7.33 (3H, m), 5.35 (2H, br. s.), 4.80 (1H, q), 3.87 (2H, m), 3.64 (3H, s) and 1.60 (3H, d). | 74[c] |
| 210 | 2-N-phenyl-6-[5-(6-{[(1,1,1-trifluoropropan-2-yl)oxy]methyl}pyridin-3-yl)-1,2,4-oxadiazol-3-yl]-1,3,5-triazine-2,4-diamine | 2 | Method A HPLC-MS: MH+ requires m/z = 459 Found: m/z = 459 Rt = 4.34 min (100%). 1H NMR (500 MHz, CDCl3) δ ppm 9.45 (1H, d), 8.60 (1H, dd), 7.73 (1H, d), 7.63 (2H,d), 7.41 (3H, m), 7.16 (1H, m), 5.56 (2H, m), 4.94 (2H, m), 4.02 (1H, dt) and 1.46 (3H, d). | 33[c] |

-continued

| Example | Name Structure | M | Spectral data | Nav 1.7 activity (nM) |
|---|---|---|---|---|
| 211 | 6-(5-{6-[(cyclopropylmethoxy)methyl]pyridin-3-yl}-1,2,4-oxadiazol-3-yl)-2-N-phenyl-1,3,5-triazine-2,4-diamine | 2 | Method A HPLC-MS: MH+ requires m/z = 417 Found: m/z = 417 Rt = 4.16 min (100%). 1H NMR (500 MHz, CDCl3) δ ppm 9.44 (1H, d), 8.57 (1H, dd), 7.74 (1H, d), 7.63 (2H, d), 7.42 (3H, m), 7.16 (1H, t), 5.60 (2H, m), 4.78 (2H, s), 3.49 (2H, d), 1.17 (1H, m), 0.61 (2H, m) and 0.29 (2H, m). | 44[c] |
| 212 | 2-N-phenyl-6-(5-{6-[1-(2,2,2-trifluoroethoxy)ethyl]pyridin-3-yl}-1,2,4-oxadiazol-3-yl)-1,3,5-triazine-2,4-diamine | 2 | Method A HPLC-MS MH+ requires m/z = 459 Found: m/z = 459, Rt = 4.34 min (100%). 1H NMR (500 MHz, CDCl$_3$) δ ppm 9.46 (1H, m), 8.61 (1H, dd), 7.71 (1H, d), 7.63 (2H, d), 7.41 (3H, m), 7.16 (1H, t), 5.63 (2H, m), 4.82 (1H, q), 3.88 (2H, m) and 1.60 (3H, d). | 211[c] |
| 213 | 6-{5-[6-(cyclobutoxymethyl)pyridin-3-yl]-1,2,4-oxadiazol-3-yl}-2-N-phenyl-1,3,5-triazine-2,4-diamine | 2 | Method A HPLC-MS: MH+ requires m/z = 417 Found: m/z = 417, Rt = 4.25 min (100%). 1H NMR (500 MHz, CDCl$_3$) δ ppm 9.44 (1H, d), 8.57 (1H, dd), 7.71 (1H, d), 7.63 (2H, d), 7.39 (3H, t), 7.16 (1H, t), 5.59 (2H, m), 4.65 (2H, s), 4.13 (1H, m), 2.29 (2H, m), 2.06 (2H, m), 1.77 (1H, q) and 1.56 (1H, m). | 67[c] |

-continued

| Example | Name Structure | M | Spectral data | Nav 1.7 activity (nM) |
|---|---|---|---|---|
| 214 | 6-(5-{4-[(cyclopropylmethoxy)methyl]piperidin-1-yl}-1,2,4-oxadiazol-3-yl)-2-N-phenyl-1,3,5-triazine-2,4-diamine | 4 | Method A HPLC-MS: MH− requires m/z = 421 Found: m/z = 421, Rt = 4.23 min (93%). 1H NMR (500 MHz, CDCl$_3$) δ ppm 7.60 (2H, d), 7.36 (3H, t), 7.13 (1H, m), 5.50 (2H, m), 4.35 (2H, d), 3.33 (2H, d), 3.27 (2H, d), 3.15 (2H, m), 1.89 (3H, m), 1.33 (2H, m), 1.06 (1H, m), 0.55 (2H, m) and 0.21 (2H, m). | 233[c] |
| 215 | 6-{5-[4-(cyclobutoxymethyl)piperidin-1-yl]-1,2,4-oxadiazol-3-yl}-2-N-phenyl-1,3,5-triazine-2,4-diamine | 4 | Method A HPLC-MS: MH− requires m/z = 421 Found: m/z = 421, Rt = 4.32 min (100%). 1H NMR (500 MHz, CDCl$_3$) δ ppm 7.60 (2H, d), 7.36 (3H, t), 7.13 (1H, m), 5.51 (2H, m), 4.34 (2H, d), 3.90 (1H, quin), 3.16 (4H, m), 2.20 (2H, m), 1.86 (5H, m), 1.70 (1H, q), 1.51 (1H, m) and 1.32 (2H, m). | 280[c] |
| 216 | 6-(5-{4-[(cyclopropylmethoxy)methyl]piperidin-1-yl}-1,2,4-oxadiazol-3-yl)-2-N-methyl-2-N-phenyl-1,3,5-triazine-2,4-diamine | 4 | Method A HPLC-MS: MH+ requires m/z = 437 Found: m/z = 437, Rt = 4.35 min (100%). | 283[b] |

| Example | Name Structure | M | Spectral data | Nav 1.7 activity (nM) |
|---|---|---|---|---|
| 217 | 6-{5-[4-(cyclobutoxymethyl)piperidin-1-yl]-1,2,4-oxadiazol-3-yl}-2-N-methyl-2-N-phenyl-1,3,5-triazine-2,4-diamine | 4 | Method A HPLC-MS: MH− requires m/z = 437 Found: m/z = 437, Rt = 4.48 min (100%). | 415[c] |
| 218 | 3-[4-amino-6-(phenylamino)-1,3,5-triazin-2-yl]-N-cyclopentyl-1,2,4-oxadiazole-5-carboxamide | 6 | Method D HPLC-MS: MH+ requires m/z = 367 Found: m/z = 367, Rt = 2.68 min (100%). | 2512[c] |
| 219 | 3-{4-amino-6-[(3-fluorophenyl)amino]-1,3,5-triazin-2-yl}-N-cyclopentyl-1,2,4-oxadiazole-5-carboxamide | 6 | Method D HPLC-MS: MH+ requires m/z = 385 Found: m/z = 385, Rt = 2.74 min (100%). | 1961[c] |

| Example | Name Structure | M | Spectral data | Nav 1.7 activity (nM) |
|---|---|---|---|---|
| 220 | 2-N-phenyl-6-{5-[(pyrrolidin-1-yl)carbonyl]-1,2,4-oxadiazol-3-yl}-1,3,5-triazine-2,4-diamine | 6 | Method D HPLC-MS: MH+ requires m/z = 353 Found: m/z = 353, Rt = 2.42 min (100%). | 833[c] |
| 221 | 2-N-phenyl-6-[5-(piperidin-1-yl)-1,2,4-oxadiazol-3-yl]-1,3,5-triazine-2,4-diamine | 11 | Method D HPLC-MS: MH+ requires m/z = 339 Found: m/z = 339, Rt = 2.60 min (100%). | 729[c] |
| 222 | 3-[4-amino-6-(phenylamino)-1,3,5-triazin-2-yl]-1,2,4-oxadiazole-5-carboxamide | 6 | Method E HPLC-MS: MH+ requires m/z = 299 Found: m/z = 299, Rt = 1.53 min (100%). | 7706[c] |

| Example | Name Structure | M | Spectral data | Nav 1.7 activity (nM) |
|---|---|---|---|---|
| 223 | 3-{4-amino-6-[(3-fluorophenyl)amino]-1,3,5-triazin-2-yl}-1,2,4-oxadiazole-5-carboxamide | 6 | Method D HPLC-MS: MH+ requires m/z = 317 Found: m/z = 317, Rt = 2.14 min (88%). | 6502+ |
| 224 | 3-{4-amino-6-[(3-fluorophenyl)amino]-1,3,5-triazin-2-yl}-N-cyclobutyl-1,2,4-oxadiazole-5-carboxamide | 6 | Method D HPLC-MS: MH+ requires m/z = 371 Found: m/z = 371, Rt = 2.63 min (97%). | 1524[c] |
| 225 | 3-{4-amino-6-[(3-fluorophenyl)amino]-1,3,5-triazin-2-yl}-N-(2,3-dihydro-1H-inden-2-yl)-1,2,4-oxadiazole-5-carboxamide | 6 | Method D HPLC-MS: MH+ requires m/z = 433 Found: m/z = 433, [f]Rt = 2.99 min (98%). | 776[c] |

-continued

| Example | Name Structure | M | Spectral data | Nav 1.7 activity (nM) |
|---|---|---|---|---|
| 226 | 3-{4-amino-6-[(3-fluorophenyl)amino]-1,3,5-triazin-2-yl}-N-(2,3-dihydro-1H-inden-1-yl)-1,2,4-oxadiazole-5-carboxamide | 6 | Method D HPLC-MS: MH+ requires m/z = 433 Found: m/z = 433, Rt = 2.96 min (100%). | 3425[c] |
| 227 | 2-N-(3-fluorophenyl)-6-{5-[(pyrrolidin-1-yl)carbonyl]-1,2,4-oxadiazol-3-yl}-1,3,5-triazine-2,4-diamine | 6 | Method D HPLC-MS: MH+ requires m/z = 371 Found: m/z = 371, Rt = 2.53 min (92%). | 241[c] |
| 228 | 3-[4-amino-6-(phenylamino)-1,3,5-triazin-2-yl]-N-cyclobutyl-1,2,4-oxadiazole-5-carboxamide | 6 | Method E HPLC-MS: MH+ requires m/z = 353 Found: m/z = 353, Rt = 2.49 min (100%). | 401[c] |

| Example | Name Structure | M | Spectral data | Nav 1.7 activity (nM) |
|---|---|---|---|---|
| 229 | 3-[4-amino-6-(phenylamino)-1,3,5-triazin-2-yl]-N-(2,3-dihydro-1H-inden-2-yl)-1,2,4-oxadiazole-5-carboxamide | 6 | Method D HPLC-MS: MH+ requires m/z = 415 Found: m/z = 415, Rt = 2.90 min (97%). | 9191[c] |
| 230 | 6-{5-[(2,3-dihydro-1H-isoindol-2-yl)carbonyl]-1,2,4-oxadiazol-3-yl}-2-N-phenyl-1,3,5-triazine-2,4-diamine | 6 | Method D HPLC-MS: MH+ requires m/z = 401 Found: m/z = 401, Rt = 2.78 min (96%). | 9252[c] |
| 231 | 6-[5-(cyclopentylamino)-1,2,4-oxadiazol-3-yl]-2-N-phenyl-1,3,5-triazine-2,4-diamine | 11 | Method D HPLC-MS: MH+ requires m/z = 339 Found: m/z = 339, Rt = 2.56 min (96%), | 3212[c] |

-continued

| Example | Name Structure | M | Spectral data | Nav 1.7 activity (nM) |
|---|---|---|---|---|
| 232 | 2-N-(3-fluorophenyl)-6-{5-[(morpholin-4-yl)carbonyl]-1,2,4-oxadiazol-3-yl}-1,3,5-triazine-2,4-diamine | 6 | Method D HPLC-MS: MH+ requires m/z = 387 Found: m/z = 387, Rt = 2.37 min (90%). | 9333[c] |
| 233 | 3-{4-amino-6-[(3-fluorophenyl)amino]-1,3,5-triazin-2-yl}-N-[(3R)-oxolan-3-yl]-1,2,4-oxadiazole-5-carboxamide | 6 | Method D HPLC-MS: MH+ requires m/z = 387 Found: m/z = 387, Rt = 2.32 min (100%). | 5663[c] |
| 234 | 3-{4-amino-6-[(3-fluorophenyl)amino]-1,3,5-triazin-2-yl}-N-(propan-2-yl)-1,2,4-oxadiazole-5-carboxamide | 6 | Method D HPLC-MS: MH+ requires m/z = 359 Found: m/z = 359, Rt = 2.54 min (97%). | 1270[c] |

| Example | Name Structure | M | Spectral data | Nav 1.7 activity (nM) |
|---|---|---|---|---|
| 235 | 6-[5-(cyclopentylamino)-1,2,4-oxadiazol-3-yl]-2-N-(3-fluorophenyl)-1,3,5-triazine-2,4-diamine | 11 | Method D HPLC-MS: MH+ requires m/z = 357 Found: m/z = 357, Rt = 2.67 min (97%). | 1695[c] |
| 236 | 2-N-(3-fluorophenyl)-6-[5-(piperidin-1-yl)-1,2,4-oxadiazol-3-yl]-1,3,5-triazine-2,4-diamine | 11 | Method D HPLC-MS: MH+ requires m/z = 357 Found: m/z = 357, Rt = 2.67 min (96%). | 406[c] |
| 237 | 2-N-(3-fluorophenyl)-6-[5-(4-methoxypiperidin-1-yl)-1,2,4-oxadiazol-3-yl]-1,3,5-triazine-2,4-diamine | 11 | Method D HPLC-MS: MH+ requires m/z = 387 Found: m/z = 387, Rt = 2.57 min (100%). | 3991[c] |

-continued

| Example | Name Structure | M | Spectral data | Nav 1.7 activity (nM) |
|---|---|---|---|---|
| 238 | 6-[5-(4-methoxypiperidin-1-yl)-1,2,4-oxadiazol-3-yl]-2-N-phenyl-1,3,5-triazine-2,4-diamine | 11 | Method D HPLC-MS: MH+ requires m/z = 369 Found: m/z = 369, Rt = 2.36 min (100%). | 761[b] |
| 239 | 6-[5-(2-methoxypyridin-4-yl)-1,2,4-oxadiazol-3-yl]-2-N-phenyl-1,3,5-triazine-2,4-diamine | 2 | Method D HPLC-MS: MH+ requires m/z = 369 Found: m/z = 369, Rt = 2.72 min (98%). | 5866[c] |
| 240 | 2-N-(3-fluorophenyl)-6-[5-(3-fluoropyridin-2-yl)-1,2,4-oxadiazol-3-yl]-1,3,5-triazine-2,4-diamine | 2 | Method D HPLC-MS: MH+ requires m/z = 369 Found: m/z = 369, Rt = 2.56 min (94%). | 172[c] |

| Example | Name Structure | M | Spectral data | Nav 1.7 activity (nM) |
|---|---|---|---|---|
| 241 | 2-N-(4-fluorophenyl)-6-[5-(1,3-thiazol-2-yl)-1,2,4-oxadiazol-3-yl]-1,3,5-triazine-2(4-diamine | 2 | Method D HPLC-MS: MH+ requires m/z = 357 Found: m/z = 357, Rt = 2.47 min (100%). | 89[c] |
| 242 | 6-[5-(cyclohexylamino)-1,2,4-oxadiazol-3-yl]-2-N-phenyl-1,3,5-triazine-2,4-diamine | 11 | Method D HPLC-MS: MH+ requires m/z = 353 Found: m/z = 353, Rt = 2.70 min (97%). | 5372[c] |
| 243 | 6-[5-(4-methylpiperidin-1-yl)-1,2,4-oxadiazol-3-yl]-2-N-phenyl-1,3,5-triazine-2,4-diamine | 11 | Method D HPLC-MS: MH+ requires m/z = 353 Found: m/z = 353, Rt = 2.75 min (100%). | 7949[c] |

-continued

| Example | Name Structure | M | Spectral data | Nav 1.7 activity (nM) |
|---|---|---|---|---|
| 244 | 3-[4-amino-6-(phenylamino)-1,3,5-triazin-2-yl]-N-(2,3-dihydro-1H-inden-1-yl)-1,2,4-oxadiazole-5-carboxamide | 6 | Method D HPLC-MS: MH+ requires m/z = 415 Found: m/z = 4153, Rt = 2.85 min (94%). | 2966[c] |
| 245 | 2-N-(3-fluorophenyl)-6-[5-(4-methylpiperidin-1-yl)-1,2,4-oxadiazol-3-yl]-1,3,5-triazine-2,4-diamine | 11 | Method D HPLC-MS: MH+ requires m/z = 371 Found: m/z = 371, Rt = 2.86 min (100%). | 3087[c] |
| 246 | 6-(5-{2-oxa-7-azaspiro[3.5]nonan-7-yl}-1,2,4-oxadiazol-3-yl)-2-N-phenyl-1,3,5-triazine-2,4-diamine | 11 | Method D HPLC-MS: MH+ requires m/z = 381 Found: m/z = 381, Rt = 2.28 min (98%). | 9363[c] |

| Example | Name Structure | M | Spectral data | Nav 1.7 activity (nM) |
|---|---|---|---|---|
| 247 | 6-[5-(2-methoxyphenyl)-1,2,4-oxadiazol-3-yl]-2-N-phenyl-1,3,5-triazine-2,4-diamine 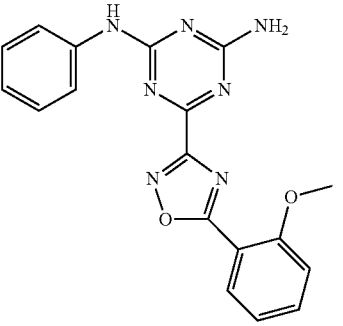 [SMILES: COc1ccccc1-c1nc(-c2nc(N)nc(Nc3ccccc3)n2)no1] | 1 | Method D HPLC-MS: MH+ requires m/z = 362 Found: m/z = 362, Rt = 2.74 min (95%). | 40[c] |
| 248 | 2-N-(3-fluorophenyl)-6-[5-(2-methoxyphenyl)-1,2,4-oxadiazol-3-yl]-1,3,5-triazine-2,4-diamine 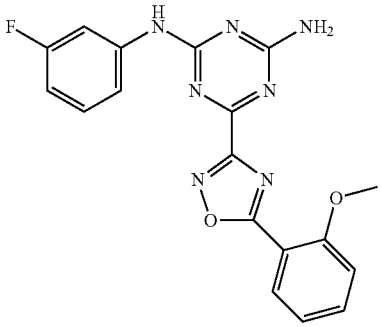 [SMILES: COc1ccccc1-c1nc(-c2nc(N)nc(Nc3cccc(F)c3)n2)no1] | 1 | Method D HPLC-MS: MH+ requires m/z = 380 Found: m/z = 380, Rt = 2.86 min (97%). | 376[c] |
| 249 | 6-[5-(5-aminopyridin-2-yl)-1,2,4-oxadiazol-3-yl]-2-N-(3-fluorophenyl)-1,3,5-triazine-2,4-diamine 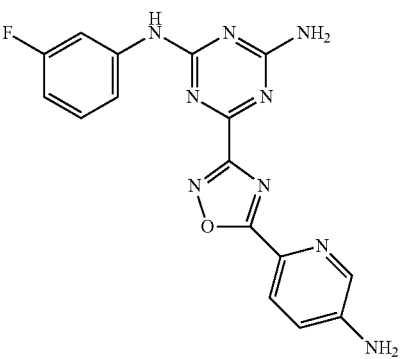 [SMILES: Nc1ccc(-c2nc(-c3nc(N)nc(Nc4cccc(F)c4)n3)no2)nc1] | 2 | Method D HPLC-MS: MH+ requires m/z = 366 Found: m/z = 366, Rt = 2.34 min (96%). | 9027[c] |

| Example | Name Structure | M | Spectral data | Nav 1.7 activity (nM) |
|---|---|---|---|---|
| 250 | 3-{4-amino-6-[(3-fluorophenyl)amino]-1,3,5-triazin-2-yl}-N-(oxetan-3-yl)-1,2,4-oxadiazole-5-carboxamide | 6 | Method D HPLC-MS: MH+ requires m/z = 373 Found: m/z = 373, Rt = 2.23 min (92%). | 9854[c] |
| 251 | 6-[5-(4-bromo-1H-pyrazol-3-yl)-1,2,4-oxadiazol-3-yl]-2-N-methyl-2-N-phenyl-1,3,5-triazine-2,4-diamine | 2 | Method A HPLC-MS: MH+ requires m/z = 414/416 Found: m/z = 414/416, Rt = 3.74 min (92%). | 2533[c] |
| 252 | 2-N-methyl-6-[5-(1-methyl-1H-pyrazol-3-yl)-1,2,4-oxadiazol-3-yl]-2-N-phenyl-1,3,5-triazine-2,4-diamine | 2 | Method A HPLC-MS: MH+ requires m/z = 350 Found: m/z = 350, Rt = 3.63 min (98%). | 2384[c] |

| Example | Name Structure | M | Spectral data | Nav 1.7 activity (nM) |
|---|---|---|---|---|
| 253 | 2-N-methyl-6-[5-(1-methyl-1H-pyrazol-5-yl)-1,2,4-oxadiazol-3-yl]-2-N-phenyl-1,3,5-triazine-2,4-diamine | 2 | Method A HPLC-MS: MH+ requires m/z = 350 Found: m/z = 350, Rt = 3.81 min (91%). | 4562[c] |
| 254 | 6-[5-(4-chloro-1H-pyrazol-3-yl)-1,2,4-oxadiazol-3-yl]-2-N-methyl-2-N-phenyl-1,3,5-triazine-2,4-diamine | 2 | Method A HPLC-MS: MH+ requires m/z = 370 Found: m/z = 370, Rt = 3.71 min (99%). | 548[c] |
| 255 | 2-N-methyl-2-N-phenyl-6-{5-[5-(trifluoromethyl)-1H-pyrazol-3-yl]-1,2,4-oxadiazol-3-yl}-1,3,5-triazine-2,4-diamine | 2 | Method A HPLC-MS: MH+ requires m/z = 404 Found: m/z = 404, Rt = 4.10 min (96%). | 6447[c] |

| Example | Name Structure | M | Spectral data | Nav 1.7 activity (nM) |
|---|---|---|---|---|
| 256 | 2-N-methyl-2-N-phenyl-6-{5-[1-(2,2,2-trifluoroethyl)-1H-pyrazol-3-yl]-1,2,4-oxadiazol-3-yl}-1,3,5-triazine-2,4-diamine | 12 | Method A HPLC-MS: MH+ requires m/z = 418 Found: m/z = 418, Rt = 4.12 min (100%). | 815[b] |
| 257 | 2-N-methyl-2-N-phenyl-6-{5-[1-(2,2,2-trifluoroethyl)-1H-pyrazol-5-yl]-1,2,4-oxadiazol-3-yl}-1,3,5-triazine-2,4-diamine | 12 | Method A HPLC-MS: MH+ requires m/z = 418 Found: m/z = 418, Rt = 4.22 min (100%). | 3252[c] |
| 258 | 3-{4-amino-6-[methyl(phenyl)amino]-1,3,5-triazin-2-yl}-N-(6-methoxypyridin-3-yl)-1,2,4-oxadiazole-5-carboxamide | | Method A HPLC-MS: MH+ requires m/z = 420 Found: m/z = 420, Rt = 4.15 min (100%). | 1847[c] |

| Example | Name Structure | M | Spectral data | Nav 1.7 activity (nM) |
|---|---|---|---|---|
| 259 | 3-{4-amino-6-[methyl(phenyl)amino]-1,3,5-triazin-2-yl}-N-{[6-(2,2,2-trifluoroethoxy)pyridin-3-yl]methyl}-1,2,4-oxadiazole-5-carboxamide | 6 | Method A HPLC-MS: MH+ requires m/z = 502 Found: m/z = 502, Rt = 4.52 min (100%). | 422[c] |
| 260 | 3-{4-amino-6-[methyl(phenyl)amino]-1,3,5-triazin-2-yl}-N-[(6-methoxypyridin-3-yl)methyl]-1,2,4-oxadiazole-5-carboxamide | 6 | Method A HPLC-MS: MH+ requires m/z = 434 Found: m/z = 434, Rt = 4.00 min (98%). | 1203[c] |
| 261 | 2-N-methyl-6-[5-(3-phenoxycyclobutyl)-1,2,4-oxadiazol-3-yl]-2-N-phenyl-1,3,5-triazine-2,4-diamine | | Method A HPLC-MS: MH+ requires m/z = 416 Found: m/z = 416, Rt = 4.77 min (100%). | 1393[c] |

| Example | Name Structure | M | Spectral data | Nav 1.7 activity (nM) |
|---|---|---|---|---|
| 262 | 2-N-methyl-2-N-phenyl-6-(5-{[4-(2,2,2-trifluoroethoxy)piperidin-1-yl]carbonyl}-1,2,4-oxadiazol-3-yl)-1,3,5-triazine-2,4-diamine | 6 | Method A HPLC-MS: MH+ requires m/z = 479 Found: m/z = 479, Rt = 4.17 min (97%). | 400[b] |
| 263 | 3-{4-amino-6-[methyl(phenyl)amino]-1,3,5-triazin-2-yl}-N-[6-(trifluoromethyl)pyridin-3-yl]-1,2,4-oxadiazole-5-carboxamide | 13 | Method A HPLC-MS: MH+ requires m/z = 458 Found: m/z = 458, Rt = 4.19 min (96%). | 6010[c] |

-continued

| Example | Name Structure | M | Spectral data | Nav 1.7 activity (nM) |
|---|---|---|---|---|
| 264 | 2-N-(3-chloro-2-fluorophenyl)-6-[5-(pyridin-2-yl)-1,2,4-oxadiazol-3-yl]-1,3,5-triazine-2,4-diamine | 14 | Method B HPLC-MS: MH+ requires m/z = 385 Found: m/z = 385, Rt = 1.82 min (100%). | 774[c] |
| 265 | 2-N-(3-chlorophenyl)-6-[5-(pyridin-2-yl)-1,2,4-oxadiazol-3-yl]-1,3,5-triazine-2,4-diamine | 14 | Method D HPLC-MS: MH+ requires m/z = 367 Found: m/z = 367, Rt = 1.51 min (95%). | 386[c] |
| 266 | 6-(5-cyclohexyl-1,2,4-oxadiazol-3-yl)-2-N-methyl-2-N-phenyl-1,3,5-triazine-2,4-diamine | 1 | Method A HPLC-MS: MH+ requires m/z = 352 Found: m/z = 352, Rt = 4.36 min (99%). 1H NMR (500 MHz, CDCl$_3$) δ ppm 7.43 (2H, m), 7.31 (3H, m), 5.27 (2H, br. s.), 3.61 (3H, s), 3.07 (1H, m), 2.14 (2H, d), 1.87 (2H, m), 1.73 (3H, m) and 1.35 (3H, m). | 4372[c] |

| Example | Name Structure | M | Spectral data | Nav 1.7 activity (nM) |
|---|---|---|---|---|
| 267 | 2-N-methyl-2-N-phenyl-6-{5-[6-(trifluoromethyl)pyridin-3-yl]-1,2,4-oxadiazol-3-yl}-1,3,5-triazine-2,4-diamine | 1 | Method A HPLC-MS: MH+ requires m/z = 415 Found: m/z = 415, Rt = 4.32 min (94%). 1H NMR (500 MHz, CDCl$_3$) δ ppm 9.59 (1H, br s), 8.74 (1H, d), 7.91 (1H, d), 7.46 (2H, m), 7.32 (3H, m), 5.40 (2H, br s) and 3.64 (3H, s). | >8256[c] |
| 268 | 2-N-methyl-6-[5-(2-methylpyridin-3-yl)-1,2,4-oxadiazol-3-yl]-2-N-phenyl-1,3,5-triazine-2,4-diamine | 1 | Method A HPLC-MS: MH+ requires m/z = 361 Found: m/z = 361, Rt = 3.75 min (100%). 1H NMR (500 MHz, CDCl$_3$) δ ppm 8.72 (1H, d), 8.48 (1H, d), 7.45 (2H, m), 7.33 (4H, m), 5.40 (2H, m), 3.63 (3H, s) and 3.00 (3H, s). | 1361[c] |
| 270 | 2-N-methyl-6-{5-[6-(morpholin-4-yl)pyridin-2-yl]-1,2,4-oxadiazol-3-yl}-2-N-phenyl-1,3,5-triazine-2,4-diamine | 1 | Method A HPLC-MS: MH+ requires m/z = 432 Found: m/z = 432, Rt = 4.17 min (99%). 1H NMR (500 MHz, CDCl$_3$) δ ppm 7.73 (1H, m), 7.67 (1H, m), 7.44 (2H, m), 7.35 (2H, d), 7.30 (1H, m), 6.84 (1H, d), 5.52 (2H, m), 3.85 (4H, m) and 3.66 (7H, m). | 3647[c] |

| Example | Name Structure | M | Spectral data | Nav 1.7 activity (nM) |
|---|---|---|---|---|
| 271 | 2-N-methyl-6-[5-(6-methylpyridin-2-yl)-1,2,4-oxadiazol-3-yl]-2-N-phenyl-1,3,5-triazine-2,4-diamine | 2 | Method A HPLC-MS: MH+ requires m/z = 361 Found: m/z = 361, Rt = 3.86 min (100%). 1H NMR (500 MHz. CDCl$_3$) δ ppm 8.17 (1H, d), 7.80 (1H, t), 7.44 (2H, m), 7.37 (3H, m), 7.30 (1H, m), 5.91 (2H, m), 3.64 (3H, s) and 2.66 (3H, s). | 945[b] |
| 272 | 2-N-(3-chlorophenyl)-6-[5-(3-fluoropyridin-2-yl)-1,2,4-oxadiazol-3-yl]-2-N-methyl-1,3,5-triazine-2,4-diamine | 2 | Method A HPLC-MS: MH+ requires m/z = 399 Found: m/z = 39, Rt = 4.11 min (95%). 1H NMR (500 MHz, CDCl$_3$) δ ppm 8.69 (1H, d), 7.72 (1H, m), 7.62 (1H, dt), 7.38 (2H, m), 7.28 (3H, m), 6.34 (1H, br s), 5.52 (1H, br s) and 3.63 (3H, s). | 478[c] |
| 273 | 6-[5-(3-chloropyridin-2-yl)-1,2,4-oxadiazol-3-yl]-2-N-methyl-2-N-phenyl-1,3,5-triazine-2,4-diamine | 2 | Method A HPLC-MS: MH+ requires m/z = 381 Found: m/z = 381, Rt = 3.95 min (96%). 1H NMR (500 MHz, CDCl$_3$) δ ppm 8.75 (1H, dd), 7.96 (1H, dd), 7.50 (1H, dd), 7.46 (2H, s), 7.34 (3H, m), 5.44 (2H, br. s.) and 3.64 (3H, s). | 253[c] |

| Example | Name Structure | M | Spectral data | Nav 1.7 activity (nM) |
|---|---|---|---|---|
| 274 | N-[1-(3-{4-amino-6-[methyl(phenyl)amino]-1,3,5-triazin-2-yl}-1,2,4-oxadiazol-5-yl)piperidin-4-yl]-2,2,2-trifluoroacetamide | 9 | Method A HPLC-MS: MH+ requires m/z = 464 Found: m/z = 464 Rt = 3.99 min (97%). | 8584[c] |
| 275 | 6-[5-(2-chloropyridin-3-yl)-1,2,4-oxadiazol-3-yl]-2-N-methyl-2-N-phenyl-1,3,5-triazine-2,4-diamine | 2 | Method A HPLC-MS: MH+ requires m/z = 381 Found: m/z = 381 Rt = 3.95 min (100%). 1H NMR (500 MHz, CDCl$_3$) δ ppm 8.64 (1H, dd), 8.57 (1H, d), 7.47 (3H, m), 7.34 (3H, m) and 3.65 (3H, s). | 3485[c] |
| 276 | 2-N-methyl-2-N-phenyl-6-{5-[(pyrrolidin-1-yl)carbonyl]-1,2,4-oxadiazol-3-yl}-1,3,5-triazine-2,4-diamine | 6 | Method A HPLC-MS: MH+ requires m/z = 367 Found: m/z = 367, Rt = 3.87 min (99%). 1H NMR (250 MHZ, CDCl$_3$) δ ppm 7.35 (2H, t), 7.30-7.18 (3H, m), 3.85 (2H, t), 3.65 (2H, t), 3.51 (3H, s) and 2.01-1.81 (4H, m). | 1679[c] |

| Example | Name Structure | M | Spectral data | Nav 1.7 activity (nM) |
|---|---|---|---|---|
| 277 | 2-N-methyl-2-N-phenyl-6-{5-[(piperidin-1-yl)carbonyl]-1,2,4-oxadiazol-3-yl}-1,3,5-triazine-2,4-diamine | 6 | Method A HPLC-MS: MH+ requires m/z = 381 Found: m/z = 381, Rt = 4.19 min (99%). 1H NMR (250 MHZ, CDCl$_3$) δ ppm 7.42 (2H, t), 7.36-7.22 (3H, m), 3.76 (2H, m), 3.61 (3H, s), 3.57 (2H, t), and 1.80-1.52 (6H, m). | 3258[c] |
| 278 | 2-N-methyl-2-N-phenyl-6-[5-(pyrimidin-2-yl)-1,2,4-oxadiazol-3-yl]-1,3,5-triazine-2,4-diamine | 1 | Method C HPLC-MS: MH+ requires m/z = 348; Found: m/z = 348, Rt = 1.16 min (97%). 1H NMR (500 MHz, DMSO-d6) δ ppm 9.11 (2H, d), 7.81 (1H, t), 7.41 (5H, dt), 7.26 (2H, dd) and 3.48 (3H, s). | 1063[b] |
| 279 | methyl 5-(3-{4-amino-6-[methyl(phenyl)amino]-1,3,5-triazin-2-yl}-1,2,4-oxadiazol-5-yl)pyridine-2-carboxylate | 1 | Method A HPLC-MS: MH+ requires m/z = 405; Found: m/z = 405.1, Rt = 3.72 min (96%). 1H NMR (500 MHz, DMSO-d6) δ ppm 9.39 (1H, s), 8.69 (1H, d), 8.29 (1H, d), 7.52 (1H, s), 7.42 (4H, m), 7.28 (2H, d), 3.94 (3H, s) and 3.48 (3H, s). | 444[c] |

-continued

| Example | Name Structure | M | Spectral data | Nav 1.7 activity (nM) |
|---|---|---|---|---|
| 280 | 5-(3-{4-amino-6-[methyl(phenyl)amino]-1,3,5-triazin-2-yl}-1,2,4-oxadiazol-5-yl)-N-(2,2,2-trifluoroethyl)pyridine-2-carboxamide | | Method A HPLC-MS: MH+ requires m/z = 472; Found: m/z = 472.5, Rt = 4.04 min (99%). 1H NMR (500 MHz, CDCl$_3$) δ ppm 9.44 (1H, s), 8.71 (1H, d), 8.41 (1H, d), 8.36 (1H, t), 7.44 (2H, t), 7.32 (3H, dd), 5.43 (2H, br. s). 4.15 (2H, m) and 3.63 (3H, s). | 513[c] |
| 281 | 6-[5-(3,5-difluoropyridin-2-yl)-1,2,4-oxadiazol-3-yl]-2-N-methyl-2-N-phenyl-1,3,5-triazine-2,4-diamine | 1 | Method B HPLC-MS: MH+ requires m/z = 383; Found: m/z = 383, Rt = 1.78 min (96%). 1H NMR (500 MHz, DMSO-d6) δ ppm 8.82 (1H, d), 8.33 (1H, ddd), 7.49 (1H, s), 7.41 (4H, dt), 7.27 (2H, dd) and 3.48 (3H, s) | 1805[c] |
| 282 | 6-[5-(3,5-dimethoxypyridin-2-yl)-1,2,4-oxadiazol-3-yl]-2-N-methyl-2-N-phenyl-1,3,5-triazine-2,4-diamine | | Method A HPLC-MS: MH+ requires m/z = 407; Found: m/z = 407, Rt = 1.74 min (100%). 1H NMR (500 MHz, DMSO-d6) δ ppm 8.12 (1H, d), 7.40 (5H, dt), 7.32 (1H, d), 7.25 (1H, dd), 7.22 (1H, s), 3.98 (6H, s) and 3.47 (3H, s). | 308[b] |

| Example | Name Structure | M | Spectral data | Nav 1.7 activity (nM) |
|---|---|---|---|---|
| 283 | 2-N-methyl-6-[5-(6-methylpyridin-3-yl)-1,2,4-oxadiazol-3-yl]-2-N-phenyl-1,3,5-triazine-2,4-diamine 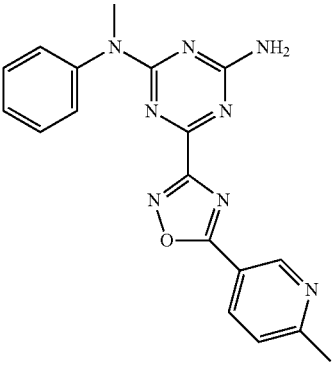 [SMILES: Cc1ccc(-c2nc(-c3nc(N)nc(N(C)c4ccccc4)n3)no2)cn1] | 1 | Method A HPLC-MS: MH+ requires m/z = 361; Found: m/z = 361, Rt = 1.83 min (98%). 1H NMR (500 MHz, DMSO-d6) δ ppm 9.16 (1H, d), 8.38 (1H, dd), 7.55 (1H, d), 7.42 (5H, dt), 7.27 (2H, t), 3.48 (3H, s) and 2.61 (3H, s). | 1377[c] |
| 284 | 5-(3-{4-amino-6-[methyl(phenyl)amino]-1,3,5-triazin-2-yl}-1,2,4-oxadiazol-5-yl)pyridine-2-carboxamide 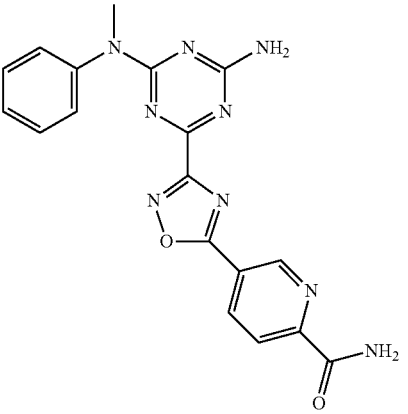 [SMILES: CN(c1ccccc1)c1nc(N)nc(-c2noc(-c3ccc(C(N)=O)nc3)n2)n1] |  | Method C HPLC-MS: MH+ requires m/z = 390; Found: m/z = 389.9, Rt = 1.23 min (92%). 1H NMR (500 MHz, DMSO-d6) δ ppm 9.30 (1H, d), 8.67 (1H, dd), 8.33 (1H, s), 8.27 (1H, d), 7.89 (1H, s), 7.48 (1H, d), 7.41 (4H, dt), 7.27 (2H, t) and 3.49 (3H, s). | 711[c] |
| 285 | methyl 6-(3-{4-amino-6-[methyl(phenyl)amino]-1,3,5-triazin-2-yl}-1,2,4-oxadiazol-5-yl)pyridine-3-carboxylate 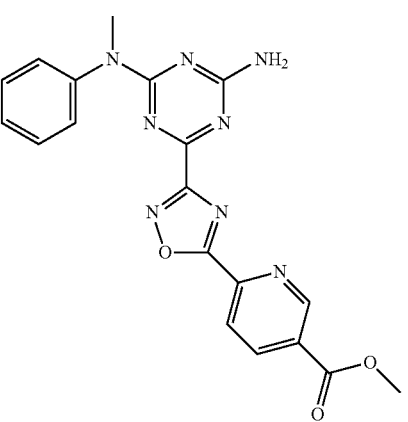 [SMILES: COC(=O)c1ccc(-c2nc(-c3nc(N)nc(N(C)c4ccccc4)n3)no2)nc1] | 1 | Method C HPLC-MS: MH+ requires m/z = 405.5; Found: m/z = 405.5, Rt = 1.36 min (94%). 1H NMR (500 MHz, DMSO-d6) δ ppm 9.29 (1H, s), 8.58 (1H, d), 8.40 (1H, d), 7.42 (5H, dt), 7.28 (2H, d), 3.95 (3H, s) and 3.49 (3H, s). | 308[c] |

| Example | Name Structure | M | Spectral data | Nav 1.7 activity (nM) |
|---|---|---|---|---|
| 286 | 5-(3-{4-amino-6-[methyl(phenyl)amino]-1,3,5-triazin-2-yl}-1,2,4-oxadiazol-5-yl)-N-cyclobutylpyridine-2-carboxamide | 15 | Method B HPLC-MS: MH+ requires m/z = 444; Found: m/z = 444.5, Rt = 2.04 min (96%). 1H NMR (500 MHz, DMSO-d6) δ ppm 9.30 (1H, d), 9.18 (1H, d), 8.68 (1H, dd), 8.25 (1H, d), 7.49 (1H, s), 7.42 (4H, dt), 7.27 (2H, m), 4.49 (1H, dd), 3.49 (3H, s), 2.21 (4H, m) and 1.69 (2H, m). | 1070[c] |
| 287 | 5-(3-{4-amino-6-[methyl(phenyl)amino]-1,3,5-triazin-2-yl}-1,2,4-oxadiazol-5-yl)-N-cyclopropylpyridine-2-carboxamide | 15 | Method B HPLC-MS: MH+ requires m/z = 430; Found: m/z = 430, Rt = 1.90 min (96%). 1H NMR (500 MHz, DMSO-d6) δ ppm 9.26 (1H, d), 8.99 (1H, d), 8.67 (1H, dd), 8.25 (1H, d), 7.48 (1H, s), 7.41 (4H, m), 7.27 (2H, t), 3.48 (3H, s), 2.95 (1H, m) and 0.72 (4H, d). | 1894[c] |

| Example | Name Structure | M | Spectral data | Nav 1.7 activity (nM) |
|---|---|---|---|---|
| 288 | 5-(3-{4-amino-6-[methyl(phenyl)amino]-1,3,5-triazin-2-yl}-1,2,4-oxadiazol-5-yl)-N-(cyclopropylmethyl)pyridine-2-carboxamide | 15 | Method A HPLC-MS: MH+ requires m/z = 444.5; Found: m/z = 444.5, Rt = 4.20 min (97%). 1H NMR (500 MHz, DMSO-d6) δ ppm 9.31 (1H, s), 9.07 (1H, t), 8.68 (1H, d), 8.27 (1H, d), 7.49 (1H, s), 7.41 (4H, dt), 7.27 (2H, t), 3.48 (3H, s), 3.20 (2H, t), 1.09 (1H, m), 0.43 (2H, d) and 0.27 (2H, d). | 1143[c] |
| 289 | propan-2-yl 5-(3-{4-amino-6-[methyl(phenyl)amino]-1,3,5-triazin-2-yl}-1,2,4-oxadiazol-5-yl)pyridine-2-carboxylate | 15 | Method A HPLC-MS: MH+ requires m/z = 433; Found: m/z = 433, Rt = 4.19 min (94%). 1H NMR (500 MHz, CDCl$_3$) δ ppm 9.50 (1H, s), 8.57 (1H, d), 8.21 (1H, d), 7.38 (2H, m), 7.24 (3H, m), 5.46 (2H, br. s), 5.30 (1H, m), 3.54 (3H, s) and 1.36 (6H, d). | 390[c] |

| Example | Name Structure | M | Spectral data | Nav 1.7 activity (nM) |
|---|---|---|---|---|
| 290 | cyclopentyl 5-(3-{4-amino-6-[methyl(phenyl)amino]-1,3,5-triazin-2-yl}-1,2,4-oxadiazol-5-yl)pyridine-2-carboxylate | 15 | Method A HPLC-MS: MH+ requires m/z = 459.5; Found: m/z = 459.5, Rt = 4.49 min (92%). 1H NMR (500 MHz, CDCl$_3$) δ ppm 9.58 (1H, s), 8.65 (1H, d), 8.25 (1H, d), 7.44 (2H, t), 7.32 (3H, dd), 5.51 (3H, m), 3.63 (3H, s), 2.05 (2H, m), 1.89 (4H, m) and 1.69 (2H, m). | 59[c] |
| 291 | 2-N-methyl-2-N-phenyl-6-(5-{6-[(2,2,2-trifluoroethoxy)methyl]pyridin-3-yl}-1,2,4-oxadiazol-3-yl)-1,3,5-triazine-2,4-diamine | | Method B HPLC-MS: MH+ requires m/z = 459.5; Found: m/z = 459.5, Rt = 2.07 min (91%). 1H NMR (500 MHz, CDCl$_3$) δ ppm 9.41 (1H, s), 8.56 (1H, d), 7.68 (1H, d), 7.44 (2H, t), 7.32 (3H, m), 5.40 (2H, br. s), 4.90 (2H, s), 4.03 (2H, q) and 3.63 (3H, s). | 73 |

| Example | Name Structure | M | Spectral data | Nav 1.7 activity (nM) |
|---|---|---|---|---|
| 292 | 6-(3-{4-amino-6-[methyl(phenyl)amino]-1,3,5-triazin-2-yl}-1,2,4-oxadiazol-5-yl)-N-(2,2,2-trifluoroethyl)pyridine-3-carboxamide | 15 | Method C HPLC-MS: MH+ requires m/z = 472; Found: m/z = 472, Rt = 1.33 min (97%). 1H NMR (500 MHz, DMSO-d6) δ ppm 9.57 (1H, t), 9.24 (1H, d), 8.52 (1H, dd), 8.40 (1H, d), 7.43 (5H, m), 7.27 (2H, t), 4.18 (2H, dd) and 3.49 (3H, s). | 2714[c] |
| 293 | 2-N-methyl-2-N-phenyl-6-{5-[6-(pyrrolidin-1-ylmethyl)pyridin-3-yl]-1,2,4-oxadiazol-3-yl}-1,3,5-triazine-2,4-diamine | 16 | Method A HPLC-MS: MH+ requires m/z = 430; Found: m/z = 430, Rt = 3.03 min (98%). 1H NMR (500 MHz, MeOD) δ ppm 9.32 (1H, s), 8.57 (1H, d), 7.75 (1H, d), 7.43 (2H, q), 7.35 (2H, d), 7.30 (1H, t), 3.96 (2H, s), 3.56 (3H, s), 2.71 (4H, s) and 1.87 (4H, s). | 1354[c] |
| 294 | 2-N-methyl-2-N-phenyl-6-(5-{5-[1-(pyrrolidin-1-yl)ethyl]pyridin-2-yl}-1,2,4-oxadiazol-3-yl)-1,3,5-triazine-2,4-diamine | | Method B HPLC-MS: MH+ requires m/z = 444; Found: m/z = 444, Rt = 1.46 min (98%). 1H NMR (500 MHz, CDCl₃) δ ppm 8.76 (1H, s), 8.35 (1H, d), 7.94 (1H, s), 7.43 (2H, t), 7.34 (2H, d), 7.29 (1H, t), 5.41 (2H, br. s), 3.63 (3H, s), 3.51-3.27 (1H, m), 2.58 (2H, s), 2.41 (2H, s), 1.80 (4H, s) and 0.84 (3H, d). | 3975[c] |

| Example | Name Structure | M | Spectral data | Nav 1.7 activity (nM) |
|---|---|---|---|---|
| 295 | [5-(3-{4-amino-6-[methyl(phenyl)amino]-1,3,5-triazin-2-yl}-1,2,4-oxadiazol-5-yl)pyridin-2-yl]methanol | | Method A HPLC-MS: MH+ requires m/z = 377; Found: m/z = 377, Rt = 3.72 min (98%). 1H NMR (500 MHz, CDCl$_3$) δ ppm 9.43 (1H, s), 8.53 (1H, d), 7.50 (1H, d), 7.45 (2H, t), 7.32 (3H, dd), 5.42 (2H, br. s), 4.89 (2H, s), 3.64 (3H, s) and 3.49 (1H, br. s). | 5190[c] |
| 296 | 1-[6-(3-{4-amino-6-[methyl(phenyl)amino]-1,3,5-triazin-2-yl}-1,2,4-oxadiazol-5-yl)pyridin-3-yl]ethan-1-one | 1 | Method A HPLC-MS: MH+ requires m/z = 389; Found: m/z = 389, Rt = 3.74 min (100%). 1H NMR (500 MHz, DMSO) δ ppm 9.33 (1H, d), 8.57 (1H, dd), 8.40 (1H, d), 7.47 (5H, m), 7.27 (2H, t), 3.49 (3H, s) and 2.72 (3H, s). | 274[c] |
| 297 | methyl 5-{3-[4-amino-6-(phenylamino)-1,3,5-triazin-2-yl]-1,2,4-oxadiazol-5-yl}pyridine-2-carboxylate | 1 | Method C HPLC-MS: MH+ requires m/z = 391; Found: m/z = 391, Rt = 1.19 min (100%). 1H NMR (500 MHz, DMSO) δ ppm 10.03 (1H, s), 9.42 (1H, d), 8.71 (1H, dd), 8.31 (1H, m), 7.87 (2H, d), 7.71 (1H, s), 7.50 (1H, s), 7.31 (2H, t), 7.03 (1H, t) and 3.95 (3H, s). | 210[c] |

-continued

| Example | Name Structure | M | Spectral data | Nav 1.7 activity (nM) |
|---|---|---|---|---|
| 299 | 2-N-methyl-6-{5-[6-(morpholin-4-ylmethyl)pyridin-3-yl]-1,2,4-oxadiazol-3-yl}-2-N-phenyl-1,3,5-triazine-2,4-diamine | 16 | Method A HPLC-MS: MH+ requires m/z = 446; Found: m/z = 446, Rt = 2.79 min (100%). 1H NMR (500 MHz. CDCl$_3$) δ ppm 9.41 (1H, s), 8.49 (1H, d), 7.67 (1H, d), 7.44 (2H, dd), 7.34 (3H, m), 5.38 (2H, br. s), 3.76 (6H, t), 3.62 (3H, s) and 2.53 (m, 4H). | 1111[c] |
| 300 | 6-(5-{6-[(cyclobutylamino)methyl]pyridin-3-yl}-1,2,4-oxadiazol-3-yl)-2-N-methyl-2-N-phenyl-1,3,5-triazine-2,4-diamine | 16 | Method A HPLC-MS: MH+ requires m/z = 430; Found: m/z = 430, Rt = 2.89 min (99%). 1H NMR (500 MHz, CDCl$_3$) δ ppm 9.40 (1H, s), 8.46 (1H, d), 7.54 (1H, d), 7.44 (2H, t), 7.32 (3H, m), 5.34 (2H, br. s), 3.94 (2H, s), 3.63 (3H, s), 3.32 (1H, m), 2.22 (2H, m), 1.74 (3H, m) and 1.64 (2H, m). | 619[c] |
| 301 | 2-N-methyl-2-N-phenyl-6-(5-{2-[(2,2,2-trifluoroethoxy)methyl]pyridin-3-yl}-1,2,4-oxadiazol-3-yl)-1,3,5-triazine-2,4-diamine | 7 | Method A HPLC-MS: MH+ requires m/z = 459; Found: m/z = 459. Rt = 4.16 min (100%). 1H NMR (500 MHz, CDCl$_3$) δ ppm 8.81 (1H, d), 8.51 (1H, d), 7.48 (1H, dd), 7.44 (2H, t), 7.32 (3H, m), 5.48 (2H, br. s), 5.28 (2H, br. s), 4.02 (2H, br. s) and 3.60 (3H, s). | 338[c] |

-continued

| Example | Name Structure | M | Spectral data | Nav 1.7 activity (nM) |
|---|---|---|---|---|
| 302 | 2-N-methyl-2-N-phenyl-6-(5-{3-[(2,2,2-trifluoroethoxy)methyl]pyridin-2-yl}-1,2,4-oxadiazol-3-yl)-1,3,5-triazine-2,4-diamine | 7 | Method A HPLC-MS: MH+ requires m/z = 459; Found: m/z = 459, Rt = 4.26 min (93%). 1H NMR (500 MHz, CDCl$_3$) δ ppm 8.79 (1H, d), 8.12 (1H, d), 7.57 (1H, dd), 7.44 (2H, t), 7.35 (2H, d), 7.30 (1H, t), 5.56 (2H, br. s), 5.26 (2H br. s), 4.01 (2H, br.. s) and 3.60 (3H, s). | 406[c] |
| 303 | 2-N-phenyl-6-(5-{6-[(2,2,2-trifluoroethoxy)methyl]pyridin-3-yl}-1,2,4-oxadiazol-3-yl)-1,3,5-triazine-2,4-diamine | 16 | Method A HPLC-MS: MH+ requires m/z = 445; Found: m/z = 445, Rt = 4.18 min (98%). 1H NMR (500 MHz, CDCl$_3$) δ ppm 9.45 (1H, d), 8.59 (1H, dd), 7.70 (1H, d), 7.61 (2H, t), 7.48 (1H, d), 7.38 (2H, t), 7.15 (1H, t), 5.66 (2H, br. d), 4.91 (2H, s) and 4.04 (2H, q). | 24[b] |
| 304 | 1-[5-(3-{4-amino-6-[methyl(phenyl)amino]-1,3,5-triazin-2-yl}-1,2,4-oxadiazol-5-yl)pyridin-2-yl]ethan-1-one | | Method C HPLC-MS: MH+ requires m/z = 389; Found: m/z = 389, Rt = 1.31 min (97%). 1H NMR (500 MHz, CDCl$_3$) δ ppm 9.52 (1H, s), 8.66 (1H, d), 8.21 (1H, d), 7.45 (2H, t), 7.33 (3H, m), 5.41 (2H, br. s), 3.63 (3H, s) and 2.79 (3H, s). | 746[c] |

| Example | Name Structure | M | Spectral data | Nav 1.7 activity (nM) |
|---|---|---|---|---|
| 305 | 6-[5-(4-ethenylphenyl)-1,2,4-oxadiazol-3-yl]-2-N-methyl-2-N-phenyl-1,3,5-triazine-2,4-diamine | 1 | Method B HPLC-MS: MH+ requires m/z = 372; Found: m/z = 372, Rt = 2.16 min (98%). 1H NMR (500 MHz, CDCl$_3$) δ ppm 8.22 (2H, d), 7.56 (2H, d), 7.44 (2H, t), 7.34 (2H, d), 7.30 (1H, t), 6.77 (1H, dd), 5.91 (1H, d), 5.43 (1H, d), 5.44 (2H, br. s) and 3.63 (s, 3H). | 804[c] |
| 306 | 6-(5-(1,3-dihydro-2-benzofuran-5-yl)-1,2,4-oxadiazol-3-yl]-2-N-methyl-2-N-phenyl-1,3,5-triazine-2,4-diamine | 1 | Method A HPLC-MS: MH+ requires m/z = 388; Found: m/z = 388, Rt = 4.03 min (98%). 1H NMR (500 MHz, CDCl$_3$) δ ppm 8.19 (1H, d), 8.14 (1H, s), 7.43 (3H, dd), 7.32 (3H, m), 5.38 (2H, br. s), 5.18 (4H, s) and 3.63 (3H, s). | 2666[c] |
| 307 | 2-N-methyl-2-N-phenyl-6-{5-[1-(propane-1-sulfonyl)azetidin-3-yl]-1,2,4-oxadiazol-3-yl}-1,3,5-triazine-2,4-diamine | 9 | Method A HPLC-MS: MH+ requires m/z = 431; Found: m/z = 431, Rt = 3.82 min (99%). 1H NMR (500 MHz, CDCl$_3$) δ ppm 7.43 (2H, t), 7.30 (3H, dd), 5.43 (2H, br d), 4.41 (2H, t), 4.32 (2H, t), 4.14 (1H, m), 3.59 (3H, s), 2.96 (2H, m), 1.85 (2H, m) and 1.06 (3H, t). | 8047[c] |

| Example | Name Structure | M | Spectral data | Nav 1.7 activity (nM) |
|---|---|---|---|---|
| 308 | 2-N-methyl-2-N-phenyl-6-{5-[1-(propane-2-sulfonyl)azetidin-3-yl]-1,2,4-oxadiazol-3-yl}-1,3,5-triazine-2,4-diamine | 9 | Method A HPLC-MS: MH+ requires m/z = 431; Found: m/z = 431, Rt = 3.82 min (95%). 1H NMR (500 MHz, CDCl$_3$) δ ppm 7.43 (2H, t), 7.30 (3H, dd), 5.30 (2H, br. s), 4.42 (2H, t), 4.36 (2H, d), 4.17 (1H, m), 3.59 (3H, s), 3.14 (1H, dt) and 1.35 (6H, t). | 8774[c] |
| 309 | 6-{5-[1-(ethanesulfonyl)azetidin-3-yl]-1,2,4-oxadiazol-3-yl}-2-N-methyl-2-N-phenyl-1,3,5-triazine-2,4-diamine | 9 | Method A HPLC-MS: MH+ requires m/z = 417; Found: m/z = 417, Rt = 3.70 min (99%). 1H NMR (500 MHz, CDCl$_3$) δ 7.43 (2H, t), 7.30 (3H, dd), 5.41 (2H, br. s), 4.42 (2H, t), 4.34 (2H, t), 4.17 (1H, m), 3.59 (3H, s), 3.01 (2H, q) and 1.37 (3H, t). | 1727[c] |

| Example | Name Structure | M | Spectral data | Nav 1.7 activity (nM) |
|---|---|---|---|---|
| 310 | 2-N-methyl-2-N-phenyl-6-(5-{1-[(2,2,2-trifluoroethane)sulfonyl]azetidin-3-yl}-1,2,4-oxadiazol-3-yl)-1,3,5-triazine-2,4-diamine | 9 | Method A HPLC-MS: MH+ requires m/z = 471; Found: m/z = 471. Rt = 4.02 min (100%). 1H NMR (250 MHz, CDCl$_3$) δ ppm 7.46 (2H, m), 7.32 (3H, m), 5.20 (2H, br. s), 4.50 (4H, m), 4.20 (1H, m), 3.85 (2H, q) and 3.61 (3H, s). | 968[c] |
| 311 | methyl 5-(3-{4-amino-6-[(2-methoxyethyl)(phenyl)amino]-1,3,5-triazin-2-yl}-1,2,4-oxadiazol-5-yl)pyridine-2-carboxylate | 1 | Method B HPLC-MS: MH+ requires m/z = 449; Found: m/z = 449, Rt = 1.79 min (100%). 1H NMR (500 MHz, DMSO) δ ppm 9.38 (1H, s), 8.67 (1H, d), 8.28 (1H, d), 7.36 (7H, m), 4.13 (2H, t), 3.94 (3H, s), 3.52 (2H, t) and 3.24 (3H, s). | 451[c] |

| Example | Name Structure | M | Spectral data | Nav 1.7 activity (nM) |
|---|---|---|---|---|
| 312 | 2-N-(2-methoxyethyl)-2-N-phenyl-6-(5-{6-[(2,2,2-trifluoroethoxy)methyl]pyridin-3-yl}-1,2,4-oxadiazol-3-yl)-1,3,5-triazine-2,4-diamine 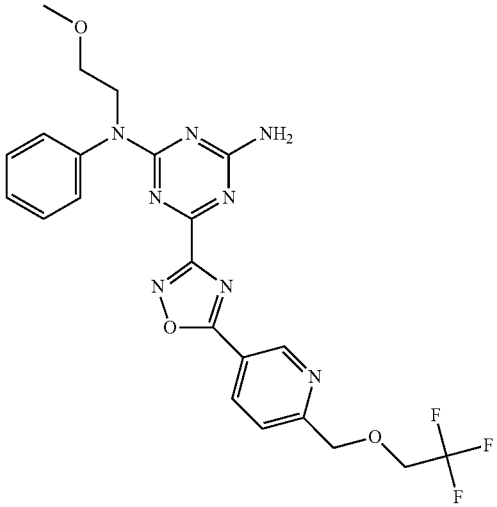 [SMILES: COCCN(c1ccccc1)c1nc(N)nc(-c2noc(-c3ccc(COCC(F)(F)F)nc3)n2)n1] | 17 | Method A HPLC-MS: MH+ requires m/z = 503; Found: m/z = 503, Rt = 4.25 min (98%). 1H NMR (500 MHz, CDCl$_3$) δ ppm 9.39 (1H, s), 8.54 (1H, s), 7.67 (1H, d), 7.43 (2H, t), 7.32 (3H, m), 5.49 (2H, br. s), 4.89 (2H, br. s), 4.25 (2H, s), 4.02 (2H, q), 3.63 (2H, t) and 3.34 (3H, s). | 139[c] |
| 313 | 6-{5-[1-(benzenesulfonyl)azetidin-3-yl]-1,2,4-oxadiazol-3-yl}-2-N-methyl-2-N-phenyl-1,3,5-triazine-2,4-diamine 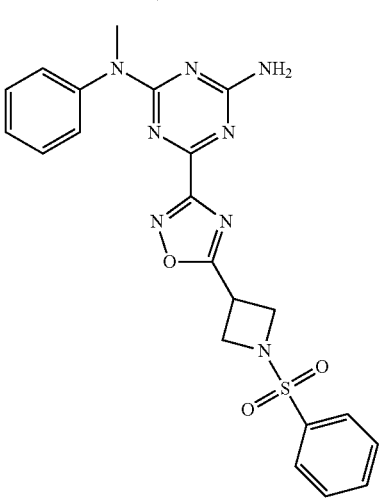 [SMILES: CN(c1ccccc1)c1nc(N)nc(-c2noc(C3CN(S(=O)(=O)c4ccccc4)C3)n2)n1] | 9 | Method A HPLC-MS: MH+ requires m/z = 465; Found: m/z = 465t Rt = 4.01 min (100%). 1H NMR (500 MHz, CDCl$_3$) δ ppm 7.87 (2H, d), 7.67 (1H, t), 7.60 (2H, t), 7.42 (2H, m), 7.30 (3H, d), 5.30 (2H, br. s), 4.28 (2H, t), 4.15 (2H, t), 4.05 (1H, dd) and 3.57 (3H, s). | 4864[c] |

| Example | Name Structure | M | Spectral data | Nav 1.7 activity (nM) |
|---|---|---|---|---|
| 314 | 2-N-methyl-2-N-phenyl-6-{5-[1-(2,2,2-trifluoroethyl)azetidin-3-yl]-1,2,4-oxadiazol-3-yl}-1,3,5-triazine-2,4-diamine | | Method B HPLC-MS: MH+ requires m/z = 407; Found: m/z = 407, Rt = 1.86 min (99%). 1H NMR (500 MHz, CDCl$_3$) δ ppm 7.43 (2H, t), 7.30 (3H, m), 5.34 (2H, br. s), 4.17 (1H, m), 3.98 (2H, t), 3.72 (2H, m), 3.60 (3H, s) and 3 09 (2H, q). | 3066$^c$ |
| 315 | 2-N-methyl-2-N-phenyl-6-{5-[6-(3,3,3-trifluoropropyl)pyridin-3-yl]-1,2,4-oxadiazol-3-yl}-1,3,5-triazine-2,4-diamine | 1 | Method A HPLC-MS: MH+ requires m/z = 443; Found: m/z = 443, Rt = 4.56 min (100%). 1H NMR (250 MHz, CDCl$_3$) δ ppm 9.39 (1H, s), 8.45 (1H, d), 7.40 (6H, m), 5.40 (2H, br s), 3.63 (3H, s), 3.15 (2H, m) and 2.70 (2H, m). | 170$^c$ |

-continued

| Example | Name Structure | M | Spectral data | Nav 1.7 activity (nM) |
|---|---|---|---|---|
| 316 | 2-N-methyl-2-N-phenyl-6-[5-(6-{[(2,2,2-trifluoroethyl)sulfanyl]methyl}pyridin-3-yl)-1,2,4-oxadiazol-3-yl]-1,3,5-triazine-2,4-diamine | 17 | Method B HPLC-MS: MH+ requires m/z = 475; Found: m/z = 475, Rt = 2.21 min (89%). 1H NMR (500 MHz, CDCl$_3$) δ ppm 9.41 (1H, s), 8.51 (1H, d), 7.54 (1H, d), 7.44 (2H, t), 7.34 (3H, m), 5.41 (2H, br. s), 4.03 (2H, s), 3.62 (3H, s) and 3.16 (2H, q). | 13$^c$ |
| 317 | 2-N-methyl-2-N-phenyl-6-[5-(6-{[(2,2,2-trifluoroethane)sulfinyl]methyl}pyridin-3-yl)-1,2,4-oxadiazol-3-yl]-1,3,5-triazine-2,4-diamine | 18 | Method A HPLC-MS: MH+ requires m/z = 491; Found: m/z = 491, Rt = 3.69 min (100%). 1H NMR (500 MHz, CDCl$_3$) δ ppm 9.49 (1H, s), 8.57 (1H, d), 7.58 (1H, d), 7.44 (2H, t), 7.32 (3H, m), 5.42 (2H, br. s), 4.50 (1H, d), 4.25 (1H, d), 3.94 (1H, dq), 3.62 (3H, s) and 3.29 (1H, dq). | 2767$^c$ |

| Example | Name Structure | M | Spectral data | Nav 1.7 activity (nM) |
|---|---|---|---|---|
| 318 | 2-N-methyl-2-N-phenyl-6-(5-{6-[(2,2,2-trifluoroethyl)sulfanyl]pyridin-3-yl}-1,2,4-oxadiazol-3-yl)-1,3,5-triazine-2,4-diamine | 2 | Method A HPLC-MS: MH+ requires m/z = 461; Found: m/z = 461, Rt = 4.61 min (100%). 1H NMR (500 MHz, CDCl$_3$) δ ppm 9.28 (1H, s), 8.34 (1H, d), 7.43 (3H, m), 7.32 (3H, m), 5.37 (2H, br. s), 4.12 (2H, q) and 3.60 (3H, s). | 1886$^c$ |
| 319 | 2-N-phenyl-6-{5-[6-(3,3,3-trifluoropropyl)pyridin-3-yl]-1,2,4-oxadiazol-3-yl}-1,3,5-triazine-2,4-diamine | 2 | Method A HPLC-MS: MH+ requires m/z = 429; Found: m/z = 429, Rt = 4.16 mm (99%). 1H NMR (500 MHz, DMSO) δ ppm 10.02 (1H, br. s), 9.25 (1H, d), 8.47 (1H, dd), 7.87 (2H, d), 7.69 (2H, d), 7.48 (1H, s), 7.31 (2H, t), 7.03 (1H, t), 3.16 (2H, m) and 2.81 (2H, m). | 150$^c$ |

-continued

| Example | Name Structure | M | Spectral data | Nav 1.7 activity (nM) |
|---|---|---|---|---|
| 320 | 2-N-methyl-2-N-phenyl-6-(5-{6-[(2,2,2-trifluoroethane)sulfinyl]pyridin-3-yl}-1,2,4-oxadiazol-3-yl)-1,3,5-triazine-2,4-diamine | 18 | Method A HPLC-MS: MH+ requires m/z = 477; Found: m/z = 477, Rt = 4.09 min (100%). 1H NMR (500 MHz, CDCl$_3$) δ ppm 9.49 (1H, s), 8.81 (1H, d), 8.29 (1H, d), 7.44 (2H, t), 7.32 (3H, dd), 5.51 (2H, br. s), 4.04 (1H, dq) and 3.61 (4H, m). | 276[b] |
| 321 | 2-N-methyl-2-N-phenyl-6-[5-(6-{[(2,2,2-trifluoroethane)sulfonyl]methyl}pyridin-3-yl)-1,2,4-oxadiazol-3-yl]-1,3,5-triazine-2,4-diamine | 10 | Method A HPLC-MS: MH+ requires m/z = 507; Found: m/z = 507, Rt = 3.95 min (98%). 1H NMR (500 MHz, CDCl$_3$) δ ppm 9.49 (1H, s), 8.62 (1H, d), 7.66 (1H, d), 7.45 (2H, t), 7.32 (3H, dd), 5.35 (2H, br. s), 4.65 (2H, s), 4.09 (2H, q) and 3.63 (3H, s). | 149[c] |
| 322 | 2-N-methyl-2-N-phenyl-6-(5-{[4-(3,3,3-trifluoropropylidene)piperidin-1-yl]carbonyl}-1,2,4-oxadiazol-3-yl)-1,3,5-triazine-2,4-diamine | 4 | Method A HPLC-MS: MH+ requires m/z = 475; Found: m/z = 475, Rt = 4.35 min (98%). 1H NMR (500 MHz, CDCl$_3$) δ ppm 7.43 (2H, t), 7.31 (3H, m), 5.36 (1H, m), 5.32 (2H, br. s), 3.80 (2H, dt), 3.66 (2H, br. s), 3.59 (3H, s), 2.86 (2H, ddd) and 2.37 (4H, d). | 3268[c] |

-continued

| Example | Name Structure | M | Spectral data | Nav 1.7 activity (nM) |
|---|---|---|---|---|
| 323 | 2-N-methyl-2-N-phenyl-6-(5-{5H,6H,7H-pyrrolo[3,4-d]pyrimidin-6-yl}-1,2,4-oxadiazol-3-yl)-1,3,5-triazine-2,4-diamine | | Method A HPLC-MS: MH+ requires m/z = 389; Found: m/z = 389, Rt = 3.21 min (100%). 1H NMR (500 MHz, CDCl₃) δ ppm 9.21 (1H, s), 8.78 (1H, s), 7.43 (2H, t), 7.30 (3H, dd), 5.30 (2H, br. s), 5.12 (2H, s), 5.05 (2H, s) and 3.60 (3H, s). | 6450ᶜ |
| 324 | 2-N-methyl-2-N-phenyl-6-{5-[4-(3,3,3-trifluoropropylidene)piperidin-1-yl]-1,2,4-oxadiazol-3-yl}-1,3,5-triazine-2,4-diamine | | Method A HPLC-MS: MH+ requires m/z = 447; Found: m/z = 447, Rt = 4.34 min (94%). 1H NMR (500 MHz. CDCl₃) δ ppm 7.44 (2H, t), 7.32 (3H, dd), 5.38 (1H, t), 5.34 (2H, br. s), 3.76 (4H, dd), 3.61 (3H, s), 2.99-2.79 (2H, m) and 2.40 (4H, t). | 2360ᶜ |
| 325 | 2-N-(5-chloro-2-fluorophenyl)-6-[5-(pyridin-2-yl)-1,2,4-oxadiazol-3-yl]-1,3,5-triazine-2,4-diamine | 14 | Method B HPLC-MS: MH+ requires m/z = 385 Found: m/z = 385, Rt = 1.75 min (95%). | 435ᶜ |

-continued

| Example | Name Structure | M | Spectral data | Nav 1.7 activity (nM) |
|---|---|---|---|---|
| 326 | 6-{5-[5-(cyclopropylmethoxy)pyridin-2-yl]-1,2,4-oxadiazol-3-yl}-2-N-methyl-2-N-phenyl-1,3,5-triazine-2,4-diamine | 2 | Method B HPLC-MS: MH+ requires m/z = 417; Found: m/z = 417, Rt = 1.99 min (87%). | 293[c] |
| 327 | 2-N-methyl-2-N-phenyl-6-(5-{6-[(2,2,2-trifluoroethyl)amino]pyridin-3-yl}-1,2,4-oxadiazol-3-yl)-1,3,5-triazine-2,4-diamine | 19 | Method B HPLC-MS: MH+ requires m/z = 444; Found: m/z = 444, Rt = 2.00 min (100%). 1H NMR (500 MHz, MeOD) δ ppm 8.90 (1H, d), 8.17 (1H, dd), 7.44 (2H, m), 7.35 (2H, m), 7.29 (1H, m), 6.77 (1H, d), 4.25 (2H, q) and 3.57 (3H, s). | 1855[c] |
| 328 | 2-N-methyl-6-(5-{6-[(oxolan-3-yl)amino]pyridin-3-yl}-1,2,4-oxadiazol-3-yl)-2-N-phenyl-1,3,5-triazine-2,4-diamine | 19 | Method B HPLC-MS: MH+ requires m/z = 432; Found: m/z = 432, Rt = 1.79 min (98%). | 7957[c] |

-continued

| Example | Name Structure | M | Spectral data | Nav 1.7 activity (nM) |
|---|---|---|---|---|
| 329 | 6-{5-[6-(2-methoxyethoxy)pyridin-3-yl]-1,2,4-oxadiazol-3-yl}-2-N-methyl-2-N-phenyl-1,3,5-triazine-2,4-diamine | 2 | Method A HPLC-MS: MH+ requires m/z = 421; Found: m/z = 421, Rt = 4.08 min (96%). | 894[c] |
| 330 | 2-{[5-(3-{4-amino-6-[methyl(phenyl)amino]-1,3,5-triazin-2-yl}-1,2,4-oxadiazol-5-yl)pyridin-2-yl]oxy}acetonitrile | | Method B HPLC-MS: MH+ requires m/z = 402; Found: m/z = 402, Rt = 1.66 min (100%). | 9214[c] |
| 331 | 6-[5-(6-cyclobutoxypyridin-3-yl)-1,2,4-oxadiazol-3-yl]-2-N-methyl-2-N-phenyl-1,3,5-triazine-2,4-diamine | 2 | Method A HPLC-MS: MH+ requires m/z = 417; Found: m/z = 417, Rt = 4.73 min (99%). | 140[c] |

-continued

| Example | Name Structure | M | Spectral data | Nav 1.7 activity (nM) |
|---|---|---|---|---|
| 332 | 2-N-methyl-2-N-phenyl-6-(5-{6-[(propan-2-yl)amino]pyridin-3-yl}-1,2,4-oxadiazol-3-yl)-1,3,5-triazine-2,4-diamine | 20 | Method B HPLC-MS: MH+ requires m/z = 404; Found: m/z = 404, Rt = 1.79 min (99%). | 1107[c] |
| 333 | 6-(5-{6-[(cyclopropylmethyl)amino]pyridin-3-yl}-1,2,4-oxadiazol-3-yl)-2-N-methyl-2-N-phenyl-1,3,5-triazine-2,4-diamine | 20 | Method A HPLC-MS: MH+ requires m/z = 416; Found: m/z = 416, Rt = 3.95 min (96%). | 126[c] |
| 334 | 5-(3-{4-amino-6-[methyl(phenyl)amino]-1,3,5-triazin-2-yl}-1,2,4-oxadiazol-5-yl)-1,2-dihydropyridin-2-one | 1 | Method B HPLC-MS: MH+ requires m/z = 363; Found: m/z = 363, Rt = 1.52 min (87%). | 8449[c] |

| Example | Name Structure | M | Spectral data | Nav 1.7 activity (nM) |
|---|---|---|---|---|
| 335 | 2-N-methyl-2-N-phenyl-6-{5-[4-(2,2,2-trifluoroethoxy)piperidin-1-yl]-1,2,4-oxadiazol-3-yl}-1,3,5-triazine-2,4-diamine | 4 | Method A HPLC-MS: MH+ requires m/z = 451; Found: m/z = 451, Rt = 4.10 min (96%). 1H NMR (500 MHz, DMSO-d6) δ ppm 7.31 (7H, m), 4.12 (2H, q), 3.76 (3H, m), 3.42 (5H, m), 1.95 (2H, ddd) and 1.60 (2H, dtd). | 701[b] |
| 336 | 2-N-methyl-6-[5-(4-phenoxypiperidin-1-yl)-1,2,4-oxadiazol-3-yl]-2-N-phenyl-1,3,5-triazine-2,4-diamine | 4 | Method A HPLC-MS: MH+ requires m/z = 445; Found: m/z = 445, Rt = 4.48 mm (99%). 1H NMR (500 MHz, DMSO-d6) δ ppm 7.19 (12H, m), 4.67 (1H, br. s.), 3.82 (2H, d), 3.55 (2H, br. s.), 3.43 (3H, br. s.), 2.04 (2H, br. s.), 1.74 (2H, br. s.). | 255[c] |
| 337 | 2-N-methyl-2-N-phenyl-6-(5-{[(1r,4r)-(2,2,2-trifluoroethoxy)cyclohexyl]amino}-1,2,4-oxadiazol-3-yl)-1,3,5-triazine-2,4-diamine | 4 | Method B HPLC-MS: MH+ requires m/z = 465; Found: m/z = 4655, Rt = 2.01 min (99%). 1H NMR (500 MHz, DMSO-d6) δ ppm 8.47 (1H, d), 7.31 (7H, m), 4.02 (2H, m), 3.64 (1H, br. s.), 3.55 (1H, m), 3.42 (3H, s), 1.82 (2H, m) and 1.63 (6H, m). | 7803[c] |

| Example | Name Structure | M | Spectral data | Nav 1.7 activity (nM) |
|---|---|---|---|---|
| 338 | 6-{5-[4-(benzyloxy)piperidin-1-yl]-1,2,4-oxadiazol-3-yl}-2-N-methyl-2-N-phenyl-1,3,5-triazine-2,4-diamine | 4 | Method B HPLC-MS: MH+ requires m/z = 459; Found: m/z = 459, Rt = 2.11 min (100%). 1H NMR (500 MHz, DMSO-d6) δ ppm 7.30 (12H, m), 4.55 (2H, s), 3.77 (2H, m), 3.67 (1H, br. s.), 3.44 (5H, m), 1.95 (2H, ddd) and 1.64 (2H, td). | 597[c] |
| 339 | 6-[5-(2,3-dihydro-1-benzofuran-5-yl)-1,2,4-oxadiazol-3-yl]-2-N-methyl-2-N-phenyl-1,3,5-triazine-2,4-diamine | 2 | Method B HPLC-MS: MH+ requires m/z = 388; Found: m/z = 388, Rt = 2.02 min (100%). 1H NMR (500 MHz, DMSO-d6) δ ppm 7.99 (1H, s), 7.93 (1H, m), 7.41 (5H, m), 7.26 (2H, t), 7.00 (1H, d), 4.68 (2H, t), 3.47 (3H, s) and 3.30 (4H, m). | 107[c] |
| 340 | 2-N-methyl-2-N-phenyl-6-{5-[5-(2,2,2-trifluoroethoxy)pyridin-2-yl]-1,2,4-oxadiazol-3-yl}-1,3,5-triazine-2,4-diamine | 2 | Method A HPLC-MS: MH+ requires m/z = 445 Found: m/z = 445, Rt = 4.28 min (98%). 1H NMR (500 MHZ, DMSO-d6) δ ppm 8.66 (1H, d), 8.29 (1H, d), 7.81 (1H, dd), 7.43 (5H, m), 7.27 (2H, t), 5.07 (2H, q) and 3.49 (3H, s). | 818[c] |

-continued

| Example | Name Structure | M | Spectral data | Nav 1.7 activity (nM) |
|---|---|---|---|---|
| 341 | 2-N-methyl-6-[5-(4-methyl-1,3-thiazol-2-yl)-1,2,4-oxadiazol-3-yl]-2-N-phenyl-1,3,5-triazine-2,4-diamine | 4 | Method A HPLC-MS: MH+ requires m/z = 367 Found: m/z = 367, Rt = 3.91 min (98%). 1H NMR (500 MHZ, DMSO-d6) δ ppm 7.95 (1H, s), 7.55 (1H, br s), 7.47 (4H, m), 7.33 (2H, t), 3.54 (3H, s) and 2.57 (3H, s). | 1492[b] |
| 342 | 2-N-methyl-6-[5-(5-methyl-1,3-thiazol-2-yl)-1,2,4-oxadiazol-3-yl]-2-N-phenyl-1,3,5-triazine-2,4-diamine | 1 | Method A HPLC-MS: MH+ requires m/z = 367 Found: m/z = 367, Rt = 3.94 min (100%). 1H NMR (500 MHZ, CDCl$_3$) δ ppm 7.83 (1H, s), 7.47 (2H, m), 7.33 (3H, m), 5.29 (2H, br s), 3.65 (3H, s) and 2.65 (3H, s). | 2025[c] |
| 343 | 2-N-(2,5-difluorophenyl)-6-{5-[6-(2,2,2-trifluoroethoxy)pyridin-3-yl]-1,2,4-oxadiazol-3-yl}-1,3,5-triazine-2,4-diamine | 1 | Method A HPLC-MS: MH+ requires m/z = 467 Found: m/z = 467, Rt = 4.50 min (100%). 1H NMR (500 MHZ, DMSO-d6) δ ppm 9.67 (1H, br s), 9.00 (1H, d), 8.48 (1H, dd), 7.82 (1H, m), 7.73 (1H, brs), 7.51 (1H, br s), 7.28 (2H, m), 7.02 (1H, m) and 5.16 (2H, q). | 195[c] |

| Example | Name Structure | M | Spectral data | Nav 1.7 activity (nM) |
|---|---|---|---|---|
| 344 | 2-N-methyl-6-{5-[(4-methylpiperazin-1-yl)carbonyl]-1,2,4-oxadiazol-3-yl}-2-N-phenyl-1,3,5-triazine-2,4-diamine | 4 | Method A HPLC-MS: MH+ requires m/z = 396 Found: m/z = 396, Rt = 2.82 min (97%). 1H NMR (500 MHZ, CDCl$_3$) δ ppm 7.24 (2H, t), 7.12 (3H, m), 5.11 (2H, br s), 3.51 (4H, br s), 3.15 (3H, s) and 2.27 (7H, br m). | 5760[c] |
| 345 | 2-N-methyl-2-N-phenyl-6-{5-[4-(trifluoromethyl)-1,3-thiazol-2-yl]-1,2,4-oxadiazol-3-yl}-1,3,5-triazine-2,4-diamine | 2 | Method A HPLC-MS: MH+ requires m/z = 421 Found: m/z = 421, Rt = 4.67 min (97%). 1H NMR (500 MHZ, DMSO-d6) δ ppm 9.03 (1H, s), 7.52 (1H, br s), 7.41 (4H, m), 7.29 (2H, m) and 3.49 (3H, s). | 1974[c] |
| 346 | 6-[5-(3-fluoropyridin-2-yl)-1,2,4-oxadiazol-3-yl]-2-N-phenyl-1,3,5-triazine-2,4-diamine | | Method A HPLC-MS: MH+ requires m/z = 351 Found: m/z = 351, Rt = 3.56 min (99%). 1H NMR (500 MHZ, DMSO-d6) δ ppm 10.04 (1H, br s), 8.73 (1H, d), 8.12 (1H, m), 7.88 (3H, m), 7.68 (1H, br s), 7.49 (1H, br s), 7.31 (2H, t) and 7.03 (1H, t). | 337[b] |

-continued

| Example | Name Structure | M | Spectral data | Nav 1.7 activity (nM) |
|---|---|---|---|---|
| 347 | 1-[4-(3-{4-amino-6-[methyl(phenyl)amino]-1,3,5-triazin-2-yl}-1,2,4-oxadiazol-5-yl)piperazin-1-yl]-2,2,2-trifluoroethan-1-one | 9 | Method A HPLC-MS: MH + requires m/z = 450 Found: m/z = 450, Rt = 3.98 min (97%). 1H NMR (500 MHZ, CDCl₃) δ ppm 7.44 (2H, m), 7.30 (3H, m), 5.05 (2H, br s), 3.83 (6H, br s), 3.75 (2H, br s) and 3.63 (3H, s). | 5811[c] |
| 348 | 2-N-methyl-2-N-phenyl-6-{5-[3-(trifluoromethyl)pyridin-2-yl]-1,2,4-oxadiazol-3-yl}-1,3,5-triazine-2,4-diamine | 2 | Method A HPLC-MS: MH+ requires m/z = 415 Found: m/z = 415, Rt = 4.30 min (100%). 1H NMR (500 MHZ, MeOH-d4) δ ppm 9.05 (1H, d), 8.48 (1H, d), 7.92 (1H, dd), 7.45 (2H, t), 7.38 (2H, m), 7.31 (1H, t) and 3.58 (3H, s). | 328[c] |
| 349 | 2-N-methyl-2-N-phenyl-6-(5-{5-[(2,2,2-trifluoroethoxy)methyl]pyridin-2-yl}-1,2,4-oxadiazol-3-yl)-1,3,5-triazine-2,4-diamine | 2 | Method A HPLC-MS: MH+ requires m/z = 459 Found: m/z = 459, Rt = 4.27 min (100%). 1H NMR (500 MHZ, CDCl₃) δ ppm 8.79 (1H, s), 8.43 (1H, d), 7.94 (1H, d), 7.45 (2H, m), 7.32 (3H, m), 5.30 (2H, br s), 4.83 (2H, s), 3.97 (2H, q) and 3.64 (3H, s). | 2.5[c] |

| Example | Name Structure | M | Spectral data | Nav 1.7 activity (nM) |
|---|---|---|---|---|
| 350 | 2-N-phenyl-6-(5-{5-[(2,2,2-trifluoroethoxy)methyl]pyridin-2-yl}-1,2,4-oxadiazol-3-yl)-1,3,5-triazine-2,4-diamine | 2 | Method A HPLC-MS: MH+ requires m/z = 445 Found: m/z = 445, Rt = 4.13 min (100%). 1H NMR (500 MHZ, DMSO-d6) δ ppm 10.06 (1H, br s), 8.83 (1H, s), 8.31 (1H, d), 8.08 (1H, d), 7.87 (2H, d), 7.70 (1H, s), 7.51 (1H, br s), 7.30 (2H, t), 7.03 (1H, t), 4.88 (2H, s) and 4.24 (2H, q). | 4[c] |
| 351 | 2-N-methyl-2-N-phenyl-6-(5-{4-[(2,2,2-trifluoroethoxy)methyl]phenyl}-1,2,4-oxadiazol-3-yl)-1,3,5-triazine-2,4-diamine | 2 | Method A HPLC-MS: MH+ requires m/z = 458 Found: m/z = 458, Rt = 4.60 min (90%). 1H NMR (500 MHZ, DMSO-d6) δ ppm 8.16 (2H, d), 7.61 (2H, d), 7.43 (5H, m), 7.27 (2H, t), 4.80 (2H, s), 4.19 (2H, q) and 3.49 (3H, s). | 11[c] |

| Example | Name Structure | M | Spectral data | Nav 1.7 activity (nM) |
|---|---|---|---|---|
| 352 | 2-N-methyl-2-N-phenyl-6-[5-(4-phenylpiperidin-1-yl)-1,2,4-oxadiazol-3-yl]-1,3,5-triazine-2,4-diamine 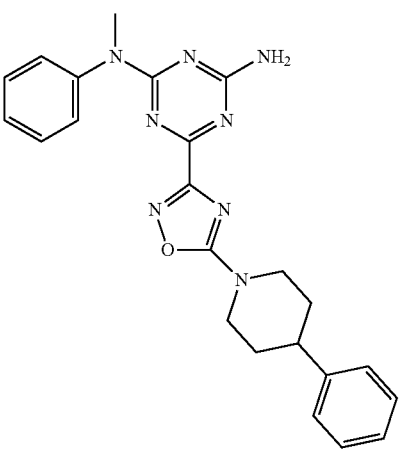 [SMILES: CN(c1ccccc1)c1nc(N)nc(-c2noc(N3CCC(c4ccccc4)CC3)n2)n1] | 4 | Method A HPLC-MS: MH+ requires m/z = 429 Found: m/z = 429, Rt = 4.45 min (97%). 1H NMR (500 MHZ, CDCl$_3$) δ ppm 7.42 (2H, t), 7.32 (5H, m), 7.22 (3H, m), 5.07 (2H, br s), 4.41 (2H, d), 3.60 (3H, s), 3.25 (2H, t), 2.77 (1H, t), 1.98 (2H, d) and 1.81 (2H, m). | 1278[c] |
| 353 | tert-butyl (2R)-2-(3-{4-amino-6-[methyl(phenyl)amino]-1,3,5-triazin-2-yl}-1,2,4-oxadiazol-5-yl)pyrrolidine-1-carboxylate 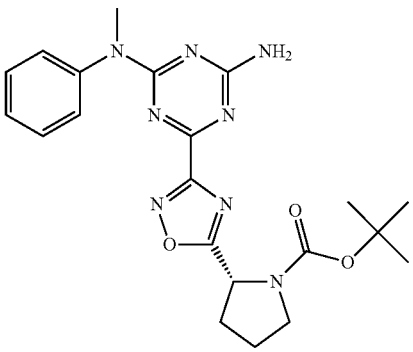 [SMILES: CN(c1ccccc1)c1nc(N)nc(-c2noc([C@H]3CCCN3C(=O)OC(C)(C)C)n2)n1] | 2 | Method A HPLC-MS: MH+ requires m/z = 439 Found: m/z = 439, Rt = 4.22 min (98%). 1H NMR (500 MHZ, CDCl$_3$) δ ppm 7.44 (2H, t), 7.35 (3H, m), 5.27 (2H, br s), 5.16 (1H, m), 2.43 (1H, m), 2.20 (1H, m), 2.10 (1H, m), 2.00 (1H, m), 1.47 (3H, s) and 1.33 (6H, s). | 893[c] |
| 354 | 2-N-methyl-2-N-phenyl-6-{5-[4-(pyridin-2-yloxy)piperidin-1-yl]-1,2,4-oxadiazol-3-yl}-1,3,5-triazine-2,4-diamine 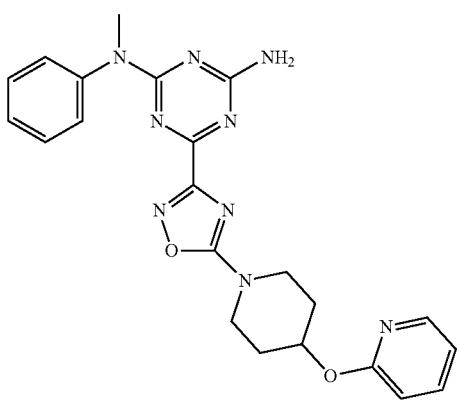 [SMILES: CN(c1ccccc1)c1nc(N)nc(-c2noc(N3CCC(Oc4ccccn4)CC3)n2)n1] | 4 | 1H NMR (500 MHZ, CDCl$_3$) δ ppm 8.12 (1H, d), 7.59 (1H, t), 7.41 (2H, t), 7.29 (3H, m), 6.88 (1H, t), 6.74 (1H, d), 5.35 (1H, m), 5.25 (2H, br s), 3.97 (2H, m), 3.74 (2H, m), 3.59 (3H, s), 2.09 (2H, m) and 1.94 (2H, m). | 1202[c] |

-continued

| Example | Name Structure | M | Spectral data | Nav 1.7 activity (nM) |
|---|---|---|---|---|
| 355 | 1-(3-{4-amino-6-[methyl(phenyl)amino]-1,3,5-triazin-2-yl}-1,2,4-oxadiazol-5-yl)-4-phenylpiperidin-4-ol | 4 | Method A HPLC-MS: MH+ requires m/z = 445 Found: m/z = 445, Rt = 3.94 min (95%). 1H NMR (500 MHZ, CDCl$_3$) δ ppm 7.41 (2H, m), 7.34 (4H, m), 7.24 (4H, m), 5.23 (2H, br s), 4.17 (2H, d), 3.61 (2H, td), 3.53 (3H, s), 2.09 (2H, td), 1.82 (2H, d) and 1.57 (1H, s). | 2621[c] |
| 356 | 6-{5-[6-(cyclohexyloxy)pyridin-3-yl]-1,2,4-oxadiazol-3-yl}-2-N-methyl-2-N-phenyl-1,3,5-triazine-2,4-diamine | 2 | Method A HPLC-MS: MH+ requires m/z = 445 Found: m/z = 445, Rt = 5.25 min (93%). 1H NMR (500 MHZ. CDCl$_3$) δ ppm 8.95 (1H, s), 8.26 (1H, d), 7.36 (2H, t), 7.25 (3H, m), 6.74 (1H, d), 5.42 (2H, br s), 5.10 (1H, m), 3.55 (3H, s), 1.96 (2H, m), 1.73 (2H, m), 1.50 (3H, m), 1.38 (2H, m) and 1.24 (1H, m). | 20[c] |
| 357 | 2-N-methyl-2-N-phenyl-6-(5-{6-[(1,1,1-trifluoropropan-2-yl)oxy]pyridin-3-yl}-1,2,4-oxadiazol-3-yl)-1,3,5-triazine-2,4-diamine | 2 | Method A HPLC-MS: MH+ requires m/z = 459 Found: m/z = 459, Rt = 4.86 min (96%). 1H NMR (500 MHZ, CDCl$_3$) δ ppm 9.03 (1H, s), 8.43 (1H, d), 7.43 (2H, m), 7.31 (3H, m), 6.97 (1H, d), 5.87 (1H, m), 5.46 (2H, br s), 3.62 (3H, s) and 1.54 (3H, d). | 55[c] |

| Example | Name Structure | M | Spectral data | Nav 1.7 activity (nM) |
|---|---|---|---|---|
| 358 | 2-N-methyl-2-N-phenyl-6-(5-{5-[1-(2,2,2-trifluoroethoxy)ethyl]pyridin-2-yl}-1,2,4-oxadiazol-3-yl)-1,3,5-triazine-2,4-diamine | | Method A HPLC-MS: MH+ requires m/z = 473 Found: m/z = 473, Rt = 4.45 min (89%). 1H NMR (500 MHZ, CDCl$_3$) δ ppm 8.76 (1H, s), 8.42 (1H, d), 7.93 (1H, d), 7.45 (2H, m), 7.33 (3H, m), 5.18 (2H, br s), 4.73 (1H, q), 3.78 (2H, q), 3.64 (3H, s) and 1.57 (3H, d). | 56$^c$ |
| 359 | 2-N-methyl-2-N-phenyl-6-{5-[6-(3,3,3-trifluoropropoxy)pyridin-3-yl]-1,2,4-oxadiazol-3-yl}-1,3,5-triazine-2,4-diamine | 2 | Method A HPLC-MS: MH+ requires m/z = 459 Found: m/z = 459, Rt = 4.65 min (97%). 1H NMR (500 MHZ, CDCl$_3$) δ ppm 9.06 (1H, s), 8.41 (1H, d), 7.47 (2H, m), 7.34 (3H, m), 6.91 (1H, d), 5.19 (2H, br s), 4.68 (2H, t), 3.65 (3H, s) and 2.68 (2H, m). | 24$^c$ |

| Example | Name Structure | M | Spectral data | Nav 1.7 activity (nM) |
|---|---|---|---|---|
| 360 | 6-[5-(4-methoxy-4-phenylpiperidin-1-yl)-1,2,4-oxadiazol-3-yl]-2-N-methyl-2-N-phenyl-1,3,5-triazine-2,4-diamine | 4 | Method A HPLC-MS: MH+ requires m/z = 459.5 Found: m/z = 459.5, Rt = 4.49 min (96%). 1H NMR (500 MHZ, CDCl$_3$) δ ppm 7.33 (7H, m), 7.23 (3H, m), 5.09 (2H, br s), 4.12 (2H, d), 3.53 (5H, m), 2.95 (3H, s), 2.09 (2H, d) and 1.93 (2H, td). | 2136[c] |
| 361 | 2-N-methyl-6-{5-[6-(oxan-4-yloxy)pyridin-3-yl]-1,2,4-oxadiazol-3-yl}-2-N-phenyl-1,3,5-triazine-2,4-diamine | 2 | Method A HPLC-MS: MH+ requires m/z = 447 Found: m/z = 447, Rt = 4.30 min (100%). 1H NMR (500 MHZ, CDCl$_3$) δ ppm 8.96 (1H, s), 8.28 (1H, d), 7.38 (2H, m), 7.25 (3H, m), 6.79 (1H, d), 5.31 (1H, m), 5.23 (2H, br s), 3.93 (2H, m), 3.58 (5H, m), 2.01 (2H, d) and 1.76 (2H, m). | 273[c] |

| Example | Name Structure | M | Spectral data | Nav 1.7 activity (nM) |
|---|---|---|---|---|
| 362 | 2-N-methyl-2-N-phenyl-6-(5-{4-[(2,2,2-trifluoroethyl)sulfanyl]piperidin-1yl}-1,2,4-oxadiazol-3-yl)-1,3,5-triazine-2,4-diamine | 4 | Method A HPLC-MS: MH+ requires m/z = 467 Found: m/z = 467, Rt = 4.36 min (99%). 1H NMR (500 MHZ, CDCl$_3$) δ ppm 7.44 (2H, t), 7.32 (3H, m), 5.26 (2H, br s), 4.21 (2H, d), 3.61 (3H, s), 3.38 (2H, t), 3.16 (2H, q), 3.10 (1H, m), 2.13 (2H, m) and 1.71 (2H, m). | 711[c] |
| 363 | 2-N-phenyl-6-{5-[6-(3,3,3-trifluoropropoxy)pyridin-3-yl]-1,2,4-oxadiazol-3-yl}-1,3,5-triazine-2,4-diamine | 2 | Method A HPLC-MS: MH+ requires m/z = 445 Found: m/z = 445, Rt = 4.43 min (90%). 1H NMR (500 MHZ, DMSO-d6) δ ppm 9.95 (1H, br s), 8.99 (1H, s), 8.42 (1H, d), 7.86 (2H, d), 7.73 (1H, s), 7.52 (1H, br s), 7.31 (2H, t), 7.12 (1H, d), 7.03 (1H, t), 4.63 (2H, t) and 2.87 (2H, m). | 7[c] |

| Example | Name Structure | M | Spectral data | Nav 1.7 activity (nM) |
|---|---|---|---|---|
| 364 | 2-N-methyl-6-(5-{6-[(1-methylpyrrolidin-3-yl)oxy]pyridin-3-yl}-1,2,4-oxadiazol-3-yl)-2-N-phenyl-1,3,5-triazine-2,4-diamine | 2 | Method A HPLC-MS: MH+ requires m/z = 446 Found: m/z = 446, Rt = 3.06 min (100%). 1H NMR (500 MHZ, CDCl$_3$) δ ppm 9.01 (1H, s), 8.34 (1H, d), 7.47 (2H, m), 7.34 (3H, m), 6.87 (1H, d), 5.57 (1H, m), 5.21 (2H, br s), 3.65 (3H, s), 2.93 (2H, m), 2.77 (1H, m), 2.40 (5H, m) and 2.02 (1H, m). | 1615[c] |
| 365 | 2-N-methyl-2-N-phenyl-6-(5-{4-[(2,2,2-trifluoroethane)sulfonyl]piperidin-1-yl}-1,2,4-oxadiazol-3-yl)-1,3,5-triazine-2,4-diamine | 10 | Method A HPLC-MS: MH+ requires m/z = 499 Found: m/z = 499, Rt = 3.74 min (99%). 1H NMR (500 MHZ, CDCl$_3$) δ ppm 7.44 (2H, t), 7.32 (3H, m), 5.28 (2H, br s), 4.52 (2H, d), 3.83 (2H, q), 3.61 (3H, s), 3.36 (1H, t), 3.27 (2H, t), 2.27 (2H, d) and 2.04 (3H, m). | >8461[c] |

| Example | Name Structure | M | Spectral data | Nav 1.7 activity (nM) |
|---|---|---|---|---|
| 366 | 2-N-methyl-2-N-phenyl-6-(5-{6-[2-(2,2,2-trifluoroethoxy)ethoxy]pyridin-3-yl}-1,2,4-oxadiazol-3-yl)-1,3,5-triazine-2,4-diamine | 2 | Method A HPLC-MS: MH+ requires m/z = 489 Found: m/z = 489, Rt = 4.58 min (100%). 1H NMR (500 MHZ, CDCl$_3$) δ ppm 9.06 (1H, s), 8.41 (1H, d), 7.47 (2H, m), 7.34 (3H, m), 6.96 (1H, d), 5.34 (2H, br s), 4.64 (2H, t), 4.04 (2H, t), 3.97 (2H, q) and 3.65 (3H, s). | 52.5$^e$ |
| 367 | 2-N-methyl-2-N-phenyl-6-{5-[4-(propan-2-ylsulfanyl)piperidin-1-yl]-1,2,4-oxadiazol-3-yl}-1,3,5-triazine-2,4-diamine | 4 | Method A HPLC-MS: MH+ requires m/z = 427 Found: m/z = 427, Rt = 4.47 min (100%). 1H NMR (500 MHZ, CDCl$_3$) δ ppm 7.44 (2H, t), 7.32 (3H, m), 5.32 (2H, br s), 4.13 (2H, d), 3.61 (3H, s), 3.42 (2H, t), 3.05 (1H, m), 2.99 (1H, m), 2.06 (2H, d), 1.70 (2H, m) and 1.30 (6H, d). | 2056.5$^e$ |

-continued

| Example | Name Structure | M | Spectral data | Nav 1.7 activity (nM) |
|---|---|---|---|---|
| 368 | 2-N-methyl-2-N-phenyl-6-{5-[4-(propane-2-sulfinyl)piperidin-1-yl]-1,2,4-oxadiazol-3-yl}-1,3,5-triazine-2,4-diamine | 4 | Method A HPLC-MS: MH+ requires m/z = 443 Found: m/z = 443, Rt = 3.28 min (88%). 1H NMR (500 MHZ, CDCl$_3$) δ ppm 7.44 (2H, t), 7.32 (3H, m), 5.28 (2H, br s), 4.39 (2H, dt), 3.61 (3H), 3.32 (2H, t), 2.85 (2H, m), 2.18 (1H, d), 1.94 (3H, m) and 1.36 (6H, d). | 6700$^c$ |
| 369 | 2-(3-{4-amino-6-[methyl(phenyl)amino]-1,3,5-triazin-2-yl}-1,2,4-oxadiazol-5-yl)-N-(cyclopropylmethyl)pyridine-3-carboxamide | 15 | Method A HPLC-MS: MH+ requires m/z = 444; Found: m/z = 444, Rt = 3.92 min (98%). 1H NMR (500 MHz, DMSO-d6) δ ppm 8.98 (1H, t), 8.91 (1H, dd), 8.32 (1H, dd), 7.81 (1H, dd), 7.40 (5H, m), 7.25 (2H, t), 3.47 (3H, s), 3.11 (2H, t), 1.01 (1H, m), 0.41 (2H, m) and 0.21 (2H, m). | 1323$^c$ |
| 370 | 3-(3-{4-amino-6-[methyl(phenyl)amino]-1,3,5-triazin-2-yl}-1,2,4-oxadiazol-5-yl)-N-(cyclopropylmethyl)pyridine-2-carboxamide | 15 | Method A HPLC-MS: MH+ requires m/z = 444; Found: m/z = 444, Rt = 3.68 min (99%). 1H NMR (500 MHz, DMSO-d$_6$) δ ppm 8.86 (1H, dd), 8.73 (1H, t), 8.11 (1H, dd), 7.78 (1H, dd), 7.40 (5H, m), 7.26 (2H, t), 3.47 (3H, s), 3.07 (2H, t), 0.97 (1H, m), 0.37 (2H, m) and 0.15 (2H, m). | 3511$^c$ |

| Example | Name Structure | M | Spectral data | Nav 1.7 activity (nM) |
|---|---|---|---|---|
| 371 | 2-(3-{4-amino-6-[methyl(phenyl)amino]-1,3,5-triazin-2-yl}-1,2,4-oxadiazol-5-yl)-N-cyclobutylpyridine-3-carboxamide | 15 | Method A HPLC-MS: MH+ requires m/z = 444; Found: m/z = 444, Rt = 3.70 min (95%). 1H NMR (500 MHz, DMSO-$d_6$) δ ppm 8.84 (2H, m), 8.12 (1H, d), 7.79 (1H, m), 7.41 (5H, m), 7.23 (2H, m), 4.29 (1H, m), 3.47 (3H, s), 2.17 (2H, m), 1.92 (2H, m) and 1.63 (2H, m). | 7302[c] |
| 372 | 6-{5-[6-(2,2-difluoroethoxy)pyridin-3-yl]-1,2,4-oxadiazol-3-yl}-2-N-methyl-2-N-phenyl-1,3,5-triazine-2,4-diamine | 1 | Method A HPLC-MS: MH+ requires m/z = 427; Found: m/z = 427, Rt = 4.29 min (100%). 1H NMR (500 MHz. CDCl3) δ ppm 9.06 (1H, s), 8.44 (1H, dd), 7.45 (2H, m), 7.32 (3H, m), 6.99 (1H, d), 6.16 (1H, m), 5.53 (2H, m), 4.65 (2H, td) and 3.63 (3H, s). | 155[c] |
| 373 | 3-(3-{4-amino-6-[methyl(phenyl)amino]-1,3,5-triazin-2-yl}-1,2,4-oxadiazol-5-yl)-N-cyclopropylpyridine-2-carboxamide | 15 | Method A HPLC-MS: MH+ requires m/z = 430; Found: m/z = 430, Rt = 3.71 min (100%). 1H NMR (500 MHz, DMSO-d6) δ ppm 8.09 (1H, d), 8.05 (1H, dd), 7.52 (1H, d), 6.97 (1H, dd), 6.59 (5H, m), 6.44 (2H, m), 2.66 (3H, s) and 1.98 (1H, m) and −0.18 (4H, m). | 4882[c] |

| Example | Name Structure | M | Spectral data | Nav 1.7 activity (nM) |
|---|---|---|---|---|
| 374 | 3-(3-{4-amino-6-[methyl(phenyl)amino]-1,3,5-triazin-2-yl}-1,2,4-oxadiazol-5-yl)-N-cyclobutylpyridine-2-carboxamide | 15 | Method A HPLC-MS: MH+ requires m/z = 444; Found: m/z = 444, Rt = 3.99 min (100%). 1H NMR (500 MHz, DMSO-d6) δ ppm 9.10 (1H, d), 8.90 (1H, dd), 8.32 (1H, dd), 7.80 (1H, dd), 7.40 (5H, m), 7.25 (2H, m), 4.32 (1H, sxt), 3.47 (3H, s), 2.14 (5H, m) and 1.65 (1H, m). | 2076[c] |
| 375 | 3-(3-{4-amino-6-[methyl(phenyl)amino]-1,3,5-triazin-2-yl}-1,2,4-oxadiazol-5-yl)-N-(2,2,2-trifluoroethyl)pyridine-2-carboxamide | 15 | Method A HPLC-MS: MH+ requires m/z = 472; Found: m/z = 472. Rt = 3.99 min (100%). 1H NMR (500 MHz, DMSO-d6) δ ppm 9.54 (1H, t), 8.95 (1H, dd), 8.38 (1H, dd), 7.87 (1H, dd), 7.40 (5H, m), 7.24 (2H, m), 4.04 (2H, m) and 3.47 (3H, s). | 1511[c] |
| 376 | 2-(3-{4-amino-6-[methyl(phenyl)amino]-1,3,5-triazin-2-yl}-1,2,4-oxadiazol-5-yl)-N-cyclopropylpyridine-3-carboxamide | 15 | Method A HPLC-MS: MH+ requires m/z = 430; Found: m/z = 430, Rt = 3.44 min (95%). 1H NMR (500 MHz, DMSO-d6) δ ppm 8.03 (1H, br s), 7.84 (1H, br s), 7.27 (1H, m), 6.94 (1H, m), 6.47 (7H, m), 2.66 (3H, br s), 1.84 (1H, m) and −0.24 (4H, m). | 9502[c] |

| Example | Name Structure | M | Spectral data | Nav 1.7 activity (nM) |
|---|---|---|---|---|
| 377 | cyclopropylmethyl 2-(3-{4-amino-6-[methyl(phenyl)amino]-1,3,5-triazin-2-yl}-1,2,4-oxadiazol-5-yl)pyridine-3-carboxylate | 15 | Method A HPLC-MS: MH+ requires m/z = 445; Found: m/z = 445, Rt = 4.29 min (100%). 1H NMR (500 MHz, CDCl$_3$) δ ppm 8.83 (1H, dd), 8.26 (1H, d), 7.55 (1H, dd), 7.36 (2H, m), 7.23 (3H, m), 5.49 (2H, m), 3.97 (2H, d), 3.53 (3H, s), 0.96 (1H, br s), 0.44 (2H, d) and 0.14 (2H, d). | 232$^c$ |
| 378 | cyclopropylmethyl 3-(3-{4-amino-6-[methyl(phenyl)amino]-1,3,5-triazin-2-yl}-1,2,4-oxadiazol-5-yl)pyridine-2-carboxylate | 15 | Method A HPLC-MS: MH+ requires m/z = 445; Found: m/z = 445, Rt = 4.14 min (99%). 1H NMR (500 MHz, MeOH-d4) δ ppm 8.90 (1H, dd), 8.51 (1H, dd), 7.83 (1H, dd), 7.44 (2H, m), 7.35 (2H, d), 7.30 (1H, m), 3.32 (2H, m),, 4.13 (2H, d), 3.57 (3H, s), 1.12 (1H, m), 0.53 (2H, m) and 0.27 (2H, m). | 399$^c$ |
| 379 | cyclopentyl 2-(3-{4-amino-6-[methyl(phenyl)amino]-1,3,5-triazin-2-yl}-1,2,4-oxadiazol-5-yl)pyridine-3-carboxylate | 15 | Method A HPLC-MS: MH+ requires m/z = 459; Found: m/z = 459, Rt = 4.41 min (99%). 1H NMR (500 MHz, MeOH-d4) δ ppm 8.92 (1H, dd), 8.45 (1H, dd), 7.82 (1H, dd), 7.43 (2H, m), 7.36 (2H, d), 7.29 (1H, m), 5.31 (1H, m), 3.56 (3H, s), 3.31 (2H, m), 1.85 (2H, m), 1.67 (2H, m) and 1.55 (4H, m). | 386$^c$ |

| Example | Name Structure | M | Spectral data | Nav 1.7 activity (nM) |
|---|---|---|---|---|
| 380 | cyclopentyl 3-(3-{4-amino-6-[methyl(phenyl)amino]-1,3,5-triazin-2-yl}-1,2,4-oxadiazol-5-yl)pyridine-2-carboxylate 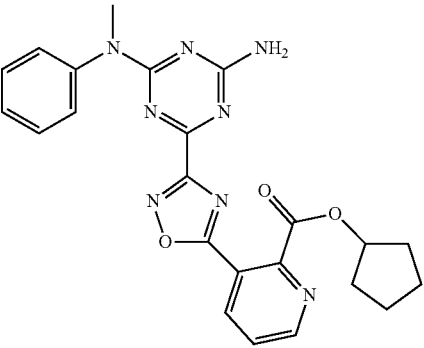 [SMILES: CN(c1ccccc1)c1nc(N)nc(-c2noc(-c3cccnc3C(=O)OC3CCCC3)n2)n1] | 15 | Method A HPLC-MS: MH+ requires m/z = 459; Found: m/z = 459, Rt = 4.31 min (100%). 1H NMR (500 MHz, MeOH-d4) δ ppm 8.89 (1H, dd), 8.48 (1H, dd), 7.81 (1H, dd), 7.44 (2H, m), 7.36 (2H, s), 7.29 (1H, m), 5.38 (1H, m), 3.57 (3H, s), 3.31 (2H, m), 1.89 (2H, m), 1.78 (2H, m) and 1.58 (4H, m). | 83[c] |
| 381 | 2-(3-{4-amino-6-[methyl(phenyl)amino]-1,3,5-triazin-2-yl}-1,2,4-oxadiazol-5-yl)-N-(2,2,2-trifluoroethyl)pyridine-3-carboxamide 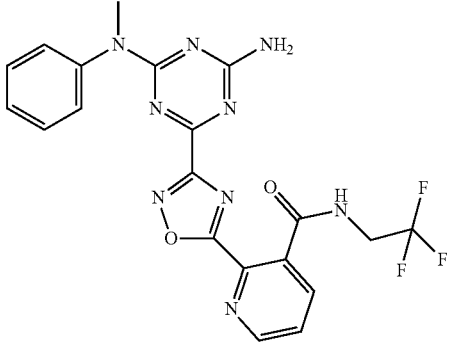 [SMILES: CN(c1ccccc1)c1nc(N)nc(-c2noc(-c3ncccc3C(=O)NCC(F)(F)F)n2)n1] | 15 | Method A HPLC-MS: MH+ requires m/z = 472; Found: m/z = 472, Rt = 3.77 min (100%). 1H NMR (500 MHz, MeOH-d4) δ ppm 8.88 (1H, d), 8.11 (1H, d), 7.78 (1H, m), 7.44 (2H, m), 7.35 (2H, d), 7.29 (1H, m), 4.00 (2H, m), 3.56 (3H, d), 3.31 (2H, m) and 2.03 (1H, d). | 4927[c] |
| 382 | tert-butyl 3-(3-{4-amino-6-[methyl(phenyl)amino]-1,3,5-triazin-2-yl}-1,2,4-oxadiazol-5-yl)azetidine-1-carboxylate 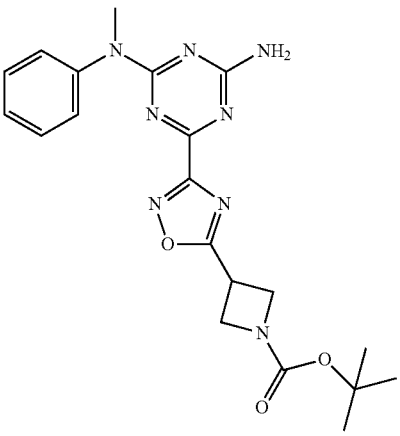 [SMILES: CN(c1ccccc1)c1nc(N)nc(-c2noc(C3CN(C(=O)OC(C)(C)C)C3)n2)n1] | 2 | Method A HPLC-MS: MH+ requires m/z = 425 Found: m/z = 425, Rt = 4.24 min (99%). 1H NMR (500 MHz, CDCl3) δ ppm 7.44 (2H, m), 7.31 (3H, m), 5.34 (2H, m), 4.36 (4H, d), 4.14 (1H, m), 3.61 (3H, s) and 1.46 (9H, s). | 4807[c] |

| Example | Name Structure | M | Spectral data | Nav 1.7 activity (nM) |
|---|---|---|---|---|
| 383 | 6-[5-(1-benzylazetidin-3-yl)-1,2,4-oxadiazol-3-yl]-2-N-methyl-2-N-phenyl-1,3,5-triazine-2,4-diamine | 2 | Method A HPLC-MS: MH+ requires m/z = 415 Found: m/z = 415. Rt = 2.98 min (100%). 1H NMR (500 MHz, CDCl₃) δ ppm 7.27 (10H, m), 6.06 (2H, m), 3.98 (1H, t), 3.69 (2H, t), 3.61 (2H, s) and 3.52 (5H, m). | 1543[c] |
| 384 | 1-[3-(3-{4-amino-6-[methyl(phenyl)amino]-1,3,5-triazin-2-yl}-1,2,4-oxadiazol-5-yl)azetidin-1-yl]ethan-1-one | | Method A HPLC-MS: MH+ requires m/z = 367 Found: m/z = 367, Rt = 3.30 min (99%). 1H NMR (500 MHz, CDCl₃) δ ppm 7.38 (2H, m), 7.25 (3H, m), 5.49 (2H, m), 4.51 (2H, m), 4.41 (1H, m), 4.31 (1H, m), 4.13 (1H, m), 3.54 (3H, s) and 1.86 (3H, s). | >8589[c] |
| 385 | 2-N-methyl-2-N-phenyl-6-{5-[1-(3,3,3-trifluoropropyl)azetidin-3-yl]-1,2,4-oxadiazol-3-yl}-1,3,5-triazine-2,4-diamine | 8 | Method A HPLC-MS: MH+ requires m/z = 421 Found: m/z = 421. Rt = 2.92 min (100%). 1H NMR (500 MHz, MeOH-d4) δ ppm 7.43 (2H, m), 7.34 (2H, m), 7.29 (1H, m), 4.90 (2H, s), 4.08 (1H, quin), 3.82 (2H, t), 3.59 (2H, t), 3.55 (3H, s), 2.78 (2H, m) and 2.28 (2H, m). | 2215[c] |

| Example | Name Structure | M | Spectral data | Nav 1.7 activity (nM) |
|---|---|---|---|---|
| 386 | 6-(3-{4-amino-6-[methyl(phenyl)amino]-1,3,5-triazin-2-yl}-1,2,4-oxadiazol-5-yl)-3-benzyl-3-azabicyclo[3.1.0]hexane-2,4-dione | | Method A HPLC-MS: MH+ requires m/z = 469 Found: m/z = 469, Rt = 4.34 min (99%). | >9976[c] |
| 387 | 2-N-methyl-2-N-phenyl-6-{5-[6-[(2,2,2-trifluoroethoxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 463 Found: m/z = 463, Rt = 4.22 min (100%). 1H NMR (500 MHz, CDCl$_3$) δ ppm 7.42 (2H, m), 7.30 (3H, m), 5.20 (2H, br. s.), 3.95 (2H, d), 3.83 (2H, q), 3.73 (2H, d), 3.58 (5H, m), 1.71 (2H, br. s.) and 1.02 (1H, m). | 1419[c] |

| Example | Name Structure | M | Spectral data | Nav 1.7 activity (nM) |
|---|---|---|---|---|
| 388 | 4-(3-{4-amino-6-[methyl(phenyl)amino]-1,3,5-triazin-2-yl}-1,2,4-oxadiazol-5-yl)-N,N-dimethylpiperazine-1-sulfonamide | 9 | Method A HPLC-MS: MH+ requires m/z = 461 Found: m/z = 461, Rt = 3.77 min (100%). 1H NMR (500 MHz, CDCl$_3$) δ ppm 7.42 (2H, m), 7.30 (3H, m), 5.27 (2H, br. s.), 3.81 (4H, m), 3.59 (3H, s), 3.38 (4H, m) and 2.86 (6H, s). | 2814$^c$ |
| 389 | 2-N-methyl-2-N-phenyl-6-(5-{4-[(2,2,2-trifluoroethane)sulfonyl]piperazin-1-yl}-1,2,4-oxadiazol-3-yl)-1,3,5-triazine-2,4-diamine | 9 | Method A HPLC-MS: MH+ requires m/z = 500 Found: m/z = 500, Rt = 3.73 min (100%). 1H NMR (500 MHz, CDCl$_3$) δ ppm 7.43 (2H, m), 7.31 (3H, m), 5.44 (2H, br s), 3.85 (4H, br s), 3.78 (2H, q), 3.60 (3H, s) and 3.52 (4H, br s). | 5986$^c$ |

-continued

| Example | Name Structure | M | Spectral data | Nav 1.7 activity (nM) |
|---|---|---|---|---|
| 390 | 2-N-phenyl-6-{5-[6-[(2,2,2-trifluoroethoxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 449 Found: m/z = 449, Rt = 4.07 min (99%). 1H NMR (500 MHz, CDCl$_3$) δ ppm 7.58 (2H, d), 7.44 (1H, br s), 7.35 (2H, t), 7.12 (1H, t), 5.76 (2H, m), 3.96 (2H, d), 3.83 (2H, q), 3.74 (2H, d), 3.58 (2H, d), 1.72 (2H, br s) and 1.03 (1H, m). | 702[c] |
| 391 | 2-N-methyl-6-{5-[6-(phenoxymethyl)-3-azabicyclo[3.1.0]hexan-3-yl]-1,2,4-oxadiazol-3-yl}-2-N-phenyl-1,3,5-triazine-2,4-diamine | 4 | Method A HPLC-MS: MH+ requires m/z = 457 Found: m/z = 457, Rt = 4.49 min (100%). 1H NMR (500 MHz, CDCl$_3$) δ ppm 7.46 (2H, m), 7.32 (5H, m), 6.96 (1H, t), 6.88 (2H, d), 4.90 (2H, br s), 3.96 (4H, m), 3.77 (2H, d), 3.64 (3H, br s), 1.81 (2H, br s) and 1.19 (1H, br s). | 539[c] |

| Example | Name Structure | M | Spectral data | Nav 1.7 activity (nM) |
|---|---|---|---|---|
| 392 | 6-{5-[6-(phenoxymethyl)-3-azabicyclo[3.1.0]hexan-3-yl]-1,2,4-oxadiazol-3-yl}-2-N-phenyl-1,3,5-triazine-2,4-diamine | 4 | Method A HPLC-MS: MH+ requires m/z = 443 Found: m/z = 443, Rt = 4.30 min (100%). 1H NMR (500 MHz, CDCl$_3$) δ ppm 7.58 (2H, d), 7.49 (1H, br. s.), 7.35 (2H, t), 7.29 (2H, m), 7.11 (1H, m), 6.96 (1H, t), 6.88 (2H, d), 5.86 (2H, m), 4.00 (2H, d), 3.93 (2H, d), 3.77 (2H, d), 1.79 (2H, br s) and 1.19 (1H, tt). | 433[c] |
| 393 | 6-{5-[6-[(cyclopropylmethoxy)methyl]-3-azabicyclo[3.1.0]hexan-3-yl]-1,2,4-oxadiazol-3-yl}-2-N-phenyl-1,3,5-triazine-2,4-diamine | 4 | Method A HPLC-MS: MH+ requires m/z = 421 Found: m/z = 421, Rt = 4.00 min (99%). 1H NMR (500 MHz, CDCl$_3$) δ ppm 7.59 (2H, d), 7.38 (3H, m), 7.12 (1H, m), 5.51 (2H, m), 3.97 (2H, d), 3.75 (2H, d), 3.40 (2H, d), 3.27 (2H, d), 1.68 (2H, br s), 1.04 (2H, m), 0.55 (2H, m) and 0.21 (2H, q). | 884[c] |

-continued

| Example | Name Structure | M | Spectral data | Nav 1.7 activity (nM) |
|---|---|---|---|---|
| 394 | 2-N-phenyl-6-{5-[6-[(3,3,3-trifluoropropoxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 463 Found: m/z = 463, Rt = 4.11 min (100%). 1H NMR (500 MHz, CDCl$_3$) δ ppm 7.58 (2H, d), 7.45(1H, br. s.), 7.35 (2H, t), 7.12 (1H, m), 5.79 (2H, m), 3.95 (2H, d), 3.74 (2H, d), 3.65 (2H, t), 3.42 (2H, d), 2.40 (2H, m), 1.68 (2H, br s) and 0.98 (1H, m). | 664$^c$ |
| 395 | 6-{5-[6-[(cyclopropylmethoxy)methyl]-3-azabicyclo[3.1.0]hexan-3-yl]-1,2,4-oxadiazol-3-yl}-2-N-methyl-2-N-phenyl-1,3,5-triazine-2,4-diamine | 4 | Method A HPLC-MS: MH+ requires m/z = 435 Found: m/z = 435, Rt = 4.03 min (100%). 1H NMR (500 MHz, CDCl$_3$) δ ppm 7.41 (2H, m), 7.28 (3H, m), 5.47 (2H, br. s), 3.92 (2H, d), 3.71 (2H, m), 3.57 (3H, s), 3.38 (2H, d), 3.26 (2H, d), 1.65(2H, br s), 1.03 (2H, m), 0.54 (2H, m) and 0.20 (2H, m). | 2658.5$^c$ |

-continued

| Example | Name Structure | M | Spectral data | Nav 1.7 activity (nM) |
|---|---|---|---|---|
| 396 | 2-N-methyl-2-N-phenyl-6-{5-[6-[(3,3,3-trifluoropropoxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 477 Found: m/z = 477, Rt = 4.13 min (99%). 1H NMR (500 MHz, CDCl$_3$) δ ppm 7.42 (2H, m), 7.28 (3H, m), 5.40 (2H, m), 3.93 (2H, d), 3.72 (2H, d), 3.64 (2H, t), 3.58 (3H, s), 3.41 (2H, d), 2.40 (2H, m), 1.66 (2H, br s) and 0.97 (1H, m). | 1130[c] |
| 397 | 2-N-methyl-2-N-phenyl-6-{5-[6-[(propan-2-yloxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 423 Found: m/z = 423, Rt = 4.06 min (100%). 1H NMR (500 MHz, CDCl$_3$) δ ppm 7.42 (2H, m), 7.30 (3H, m), 5.20 (2H, br s), 3.94 (2H, d), 3.71 (2H, d), 3.59 (3H, s), 3.57 (1H, m), 3.37 (2H, d), 1.64 (2H, br s), 1.15 (6H, d) and 0.97 (1 H, m). | 3936[c] |

-continued

| Example | Name Structure | M | Spectral data | Nav 1.7 activity (nM) |
|---|---|---|---|---|
| 398 | 2-N-phenyl-6-{5-[(1R,5S,6S)-6-[(propan-2-yloxy)methyl]-3-azabicyclo[3.1.0]hexan-3-yl]-1,2,4-oxadiazol-3-yl}-1,3,5-triazine-2,4-diamine | 4 | Method A HPLC-MS: MH+ requires m/z = 409 Found: m/z = 409, Rt = 3.97 min (100%). 1H NMR (500 MHz, CDCl$_3$) δ ppm 7.59 (2H, d), 7.36 (3H, t), 7.12 (1H, m), 5.50 (2H, m), 3.96 (2H, d), 3.74 (2H, d), 3.58 (1H, m), 3.38 (2H, d), 1.66 (2H, br s), 1.16 (6H, d) and 0.98 (1H, m). | 691$^e$ |
| 399 | 6-{5-[6-[(cyclopentyloxy)methyl]-3-azabicyclo[3.1.0]hexan-3-yl]-1,2,4-oxadiazol-3-yl}-2-N-methyl-2-N-phenyl-1,3,5-triazine-2,4-diamine | 4 | Method A HPLC-MS: MH+ requires m/z = 450 Found: m/z = 450, Rt = 4.40 min (100%). 1H NMR (500 MHz, CDCl$_3$) δ ppm 7.42 (2H, m), 7.30 (3H, m), 5.19 (2H, br s), 3.94 (2H, d), 3.88 (1H, m), 3.71 (2H, d), 3.59 (3H, s), 3.33 (2H, d), 1.72 (4H, m), 1.62 (4H, m), 1.51 (2H, m) and 0.95 (1H, m). | 620$^e$ |

-continued

| Example | Name Structure | M | Spectral data | Nav 1.7 activity (nM) |
|---|---|---|---|---|
| 400 | 6-{5-[6-[(cyclopentyloxy)methyl]-3-azabicyclo[3.1.0]hexan-3-yl]-1,2,4-oxadiazol-3-yl}-2-N-phenyl-1,3,5-triazine-2,4-diamine | 4 | Method A HPLC-MS: MH+ requires m/z = 435 Found: m/z = 435, Rt = 4.28 min (99%). 1H NMR (500 MHz, CDCl$_3$) δ ppm 7.59 (2H, d), 7.37 (3H, d), 7.12 (1H, m), 5.48 (2H, m), 3.96 (2H, d), 3.89 (1H, m), 3.74 (2H, d), 3.35 (2H, d), 1.73 (4H, m), 1.65 (4H, br. s.), 1.51 (2H, m) and 0.97 (1H, m). | 292.5$^c$ |
| 401 | 2-N-methyl-2-N-phenyl-6-{5-[(4-{[(2,2,2-trifluoroethyl)sulfanyl]methyl}piperidin-1-yl)carbonyl]-1,2,4-oxadiazol-3-yl}-1,3,5-triazine-2,4-diamine | 21 | Method A HPLC-MS: MH+ requires m/z = 509 Found: m/z = 509, Rt = 4.56 min (100%). 1H NMR (500 MHz, CDCl$_3$): δ ppm 7.43 (2H, m), 7.30 (3H, m), 5.60 (2H, m), 4.73 (1H, d), 4.05 (1H, d), 3.59 (3H, s), 3.18 (1H, t), 3.08 (2H, q), 2.85 (1H, td), 2.65 (2H, dd), 1.93 (1H, d), 1.82 (2H, m) and 1.33 (2H, m). | 1044$^c$ |
| 402 | 2-N-methyl-2-N-phenyl-6-(5-{[6-[(2,2,2-trifluoroethoxy)methyl]-3-azabicyclo[3.1.0]hexan-3-yl]carbonyl}-1,2,4-oxadiazol-3-yl)-1,3,5-triazine-2,4-diamine | 21 | Method A HPLC-MS: MH+ requires m/z = 491 Found: m/z = 491, Rt = 4.28 min (100%).1H NMR (500 MHz, CDCl$_3$): δ ppm 7.44 (2H, m), 7.32 (3H, m), 5.35 (2H, m), 4.25 (1H, d), 4.12 (1H, d), 3.98 (1H, m), 3.83 (2H, q), 3.66 (2H, m), 3.61 (3H, s), 3.50 (1H, dd), 1.72 (1H, m), 1.68 (1H, m) and 1.03 (1H, m). | 3965$^c$ |

| Example | Name Structure | M | Spectral data | Nav 1.7 activity (nM) |
|---|---|---|---|---|
| 403 | 2-N-methyl-2-N-phenyl-6-(5-{[-6-[(3,3,3-trifluoropropoxy)methyl]-3-azabicyclo[3.1.0]hexan-3-yl]carbonyl}-1,2,4-oxadiazol-3-yl)-1,3,5-triazine-2,4-diamine | 21 | Method A HPLC-MS: MH+ requires m/z = 505 Found: m/z = 505, Rt = 4.32 min (100%). 1H NMR (500 MHz, CDCl$_3$) δ ppm 7.44 (2H, m), 7.32 (3H, m), 5.40 (2H, m), 4.22 (1H, d), 4.11 (1H, d), 3.96 (1H, d), 3.68 (1H, m), 3.64 (2H, t), 3.60 (3H, s), 3.46 (1H, dd), 3.35 (1H, dd), 2.40 (2H, m), 1.67 (2H, m) and 0.98 (1H, br s). | 1288[c] |
| 404 | 6-(5-{[-6-[(cyclopropylmethoxy)methyl]-3-azabicyclo[3.1.0]hexan-3-yl]carbonyl}-1,2,4-oxadiazol-3-yl)-2-N-methyl-2-N-phenyl-1,3,5-triazine-2,4-diamine | 21 | Method A HPLC-MS: MH+ requires m/z = 463 Found: m/z = 463, Rt = 4.24 min (100%). 1H NMR (500 MHz, CDCl$_3$) δ ppm 7.44 (2H, m), 7.33 (3H, m), 5.32 (2H, m), 4.22 (1H, d), 4.11 (1H, d), 3.96 (1H, d), 3.67 (1H, dd), 3.61 (3H, s), 3.44 (1H, dd), 3.34 (1H, dd), 3.27 (2H, d), 1.65 (2H, m), 1.03 (2H, m), 0.55 (2H, m) and 0.21 (2H, m). | 3459[c] |
| 405 | 6-(5-{[-6-[(cyclopentyloxy)methyl]-3-azabicyclo[3.1.0]hexan-3-yl]carbonyl}-1,2,4-oxadiazol-3-yl)-2-N-methyl-2-N-phenyl-1,3,5-triazine-2,4-diamine | 21 | Method A HPLC-MS: MH+ requires m/z = 477 Found: m/z = 477, Rt = 4.52 min (100%). 1H NMR (500 MHz, CDCl$_3$) δ ppm 7.44 (2H, m), 7.33 (3H, m), 5.30 (2H, m), 4.21 (1H, d), 4.11 (1H, d), 3.96 (1H, m), 3.88 (1H, m), 3.66 (1H, dd), 3.61 (3H, s), 3.39 (1H, dd), 3.26 (1H, dd), 1.70 (4H, m), 1.63 (4H, m), 1.52 (2H, m) and 0.97 (1H, m). | 1278[c] |

| Example | Name Structure | M | Spectral data | Nav 1.7 activity (nM) |
|---|---|---|---|---|
| 406 | 2-N-methyl-6-(5-{[-6-(phenoxymethyl)-3-azabicyclo[3.1.0]hexan-3-yl]carbonyl}-1,2,4-oxadiazol-3-yl)-2-N-phenyl-1,3,5-triazine-2,4-diamine | 21 | Method A HPLC-MS: MH+ requires m/z = 485 Found: m/z = 485, Rt = 4.56 min (100%). 1H NMR (500 MHz, CDCl$_3$) δ ppm 7.44 (2H, m), 7.32 (5H, m), 6.96 (1H, m), 6.89 (2H, m), 5.38 (2H, m), 4.30 (1H, d), 4.16 (1H, d), 3.99 (2H, dd), 3.85 (1H, dd), 3.72 (1H, dd), 3.61 (3H, s), 1.79 (2H, m) and 1.19 (1H, d). | 623.5[c] |
| 407 | 2-N-(3-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine | 1 | Method A HPLC-MS: MH+ requires m/z = 463 Found: m/z = 463, Rt = 4.55 min (91%). 1H NMR (500 MHz, CDCl$_3$) δ ppm 9.07 (1H, s), 8.48 (1H, d), 7.40 (1H, m), 7.14 (2H, m), 7.02 (2H, m), 5.35 (2H, br s), 4.87 (2H, q) and 3.63 (3H, s). | 201[c] |
| 408 | 2-N-(2-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 463 Found: m/z = 463, Rt = 4.47 min (99%). 1H NMR (500 MHz, DMSO-d6) δ ppm 8.98 (1H, br s), 8.45 (1H, br s), 7.39 (7H, m), 5.14 (2H, q) and 3.43 (3H, br s). | 139[c] |

| Example | Name Structure | M | Spectral data | Nav 1.7 activity (nM) |
|---|---|---|---|---|
| 409 | 2-N-(3-chlorophenyl)-2-N-methyl-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 480 Found: m/z = 480, Rt = 4.74 min (95%). 1H NMR (500 MHz, DMSO-d6) δ ppm 8.97 (1H, m), 8.46 (1H, m), 7.55 (2H, br s), 7.36 (5H, m), 5.13 (2H, q) and 3.48 (3H, s). | 261[c] |
| 410 | 2-N-(4-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 463 Found: m/z = 463, Rt = 4.50 min (94%). 1H NMR (500 MHz, DMSO-d6) δ ppm 9.01 (1H, m), 8.45 (1H, m), 7.46 (3H, m), 7.25 (4H, m), 5.13 (2H, q) and 3.46 (3H, s). | 1146[c] |

| Example | Name Structure | M | Spectral data | Nav 1.7 activity (nM) |
|---|---|---|---|---|
| 411 | 2-N-(2,3-difluorophenyl)-2-N-methyl-6-{5-[6-(2,2,2-trifluoroethoxy)pyridin-3-yl]-1,2,4-oxadiazol-3-yl}-1,3,5-triazine-2,4-diamine | 1 | Method A HPLC-MS: MH+ requires m/z = 481 Found: m/z = 481, Rt = 4.66 min (89%). 1H NMR (500 MHz, CDCl$_3$) δ ppm 9.05 (1H, m), 8.42 (1H, m), 7.16 (3H, m), 7.05 (1H, m), 5.38 (2H, br s), 4.87 (2H, q) and 3.58 (3H, s). | 17[b] |
| 412 | 2-N-methyl-2-N-(3-methylphenyl)-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 459 Found: m/z = 459, Rt = 4.72 min (99%). 1H NMR (500 MHz, CDCl$_3$) δ ppm 9.07 (1H, s), 8.48 (1H, d), 7.33 (1H, t), 7.14 (3H, m), 7.05 (1H, d), 5.29 (2H, br s), 4.87 (2H, q), 3.62 (3H, s) and 2.41 (3H, s). | 82[c] |

-continued

| Example | Name Structure | M | Spectral data | Nav 1.7 activity (nM) |
|---|---|---|---|---|
| 413 | 2-N-(3-chloro-4-fluorophenyl)-6-{5-[6-(2,2,2-trifluoroethoxy)pyridin-3-yl]-1,2,4-oxadiazol-3-yl}-1,3,5-triazine-2,4-diamine | 1 | Method A HPLC-MS: MH+ requires m/z = 482 Found: m/z = 482, Rt = 4.73 min (95%). 1H NMR (500 MHz, CDCl$_3$)) δ ppm 9.11 (1H, d), 8.50 (1H, d), 7.88 (1H, m), 7.37 (2H, m), 7.15 (1H, t), 7.07 (1H, t), 5.73 (1H, br s), 5.50 (1H, br s) and 4.89 (2H, q). | 9019[e] |
| 414 | 2-N-(3-chloro-4-fluorophenyl)-2-N-methyl-6-{5-[6-(2,2,2-trifluoroethoxy)pyridin-3-yl]-1,2,4-oxadiazol-3-yl}-1,3,5-triazine-2,4-diamine | | Method A HPLC-MS: MH + requires m/z = 497 Found: m/z = 497, Rt = 4.86 min (98%). 1H NMR (500 MHz, CDCl$_3$) δ ppm 9.07 (1H, s), 8.47 (1H, d), 7.42 (1H, d), 7.21 (2H, m), 7.05 (1H, d), 5.36 (2H, br s), 4.87 (2H, q) and 3.62 (3H, s). | 410[e] |
| 415 | 6-[5-(6-methoxypyridin-2-yl)-1,2,4-oxadiazol-3-yl]-2-N-methyl-2-N-phenyl-1,3,5-triazine-2,4-diamine | 2 | Method A HPLC-MS: MH+ requires m/z = 377 Found: m/z = 377, Rt = 4.23 min (99%). 1H NMR (500 MHz, CDCl$_3$) δ ppm 7.98 (1H, d), 7.76 (1H, t), 7.45 (2H, m), 7.34 (3H, m), 6.98 (1H, d), 5.55 (2H, br s), 4.06 (3H, s) and 3.64 (3H, s). | 567[e] |

| Example | Name Structure | M | Spectral data | Nav 1.7 activity (nM) |
|---|---|---|---|---|
| 416 | 2-N-(3,4-difluorophenyl)-6-{5-[6-(2,2,2-trifluoroethoxy)pyridin-3-yl]-1,2,4-oxadiazol-3-yl}-1,3,5-triazine-2,4-diamine | 1 | Method A HPLC-MS: MH+ requires m/z = 467 Found: m/z = 467, Rt = 4.59 min (92%). 1H NMR (500 MHz, CDCl$_3$) δ ppm 9.10 1H, s), 8.50 (1H, d), 7.82 (1H, m), 7.47 (1H, m), 7.10 (3H, m), 5.75 (1H, br s), 5.50 (1H, br s) and 4.88 (2H, q). | 1501[c] |
| 417 | 2-N-(2,4-difluorophenyl)-2-N-methyl-6-{5-[6-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 481 Found: m/z = 481, Rt = 4.64 min (95%). 1H NMR (250 MHz, DMSO-d6) δ ppm 8.92 (1H, br s), 8.44 (1H, br s), 7.40 (6H, m), 5.16 (2H, q) and 3.40 (3H, s). | 28[c] |
| 418 | 6-[5-(6-chloropyridin-3-yl)-1,2,4-oxadiazol-3-yl]-2-N-methyl-2-N-phenyl-1,3,5-triazine-2,4-diamine | 2 | Method A HPLC-MS: MH+ requires m/z = 381 Found: m/z = 381, Rt = 4.08 min (97%). 1H NMR (500 MHz, CDCl$_3$) δ ppm 9.30 (1H, s), 8.47 (1H, d), 7.56 (1H, d), 7.45 (2H, t), 7.35 (3H, m), 5.30 (2H, br s) and 3.64 (3H, s). | 1638[c] |

| Example | Name Structure | M | Spectral data | Nav 1.7 activity (nM) |
|---|---|---|---|---|
| 419 | 6-[5-(2-ethoxypyridin-3-yl)-1,2,4-oxadiazol-3-yl]-2-N-methyl-2-N-phenyl-1,3,5-triazine-2,4-diamine | 2 | Method A HPLC-MS: MH+ requires m/z = 391 Found: m/z = 391, Rt = 4.32 min (100%). 1H NMR (500 MHz, CDCl$_3$) δ ppm 8.53 (1H, d), 8.38 (1H, d), 7.45 (2H, t), 7.33 (3H, m), 7.04 (1H, t), 5.55 (2H, br s), 4.57 (2H, q), 3.64 (3H, s) and 1.47 (3H, t). | 1453[c] |
| 420 | 2-N-methyl-2-N-phenyl-6-{5-[5-(trifluoromethyl)pyridin-2-yl]-1,2,4-oxadiazol-3-yl}-1,3,5-triazine-2,4-diamine | 2 | Method A HPLC-MS: MH+ requires m/z = 415 Found: m/z = 415, Rt = 3.86 min (97%). 1H NMR (500 MHz, DMSO-d6) δ ppm 9.23 (1H, s), 8.49 (2H, m), 7.38 (7H, m) and 3.49 (3H, s). | 2297[c] |
| 421 | 6-[5-(4-methanesulfonylphenyl)-1,2,4-oxadiazol-3-yl]-2-N-methyl-2-N-phenyl-1,3,5-triazine-2,4-diamine | 2 | Method A HPLC-MS: MH+ requires m/z = 424 Found: m/z = 424, Rt = 3.86 min (94%). 1H NMR (500 MHz, DMSO-d6) δ ppm 8.40 (2H, d), 8.14 (2H, d), 7.49 (1H, m), 7.40 (4H, m), 7.25 (2H, m), 3.49 (3H, s) and 3.31 (3H, s). | 1426[c] |

| Example | Name Structure | M | Spectral data | Nav 1.7 activity (nM) |
|---|---|---|---|---|
| 422 | 6-[5-(4-aminocyclohexyl)-1,2,4-oxadiazol-3-yl]-2-N-methyl-2-N-phenyl-1,3,5-triazine-2,4-diamine | 23 | Method A HPLC-MS: MH+ requires m/z = 367 Found: m/z = 367, Rt = 2.88 min (100%). 1H NMR (500 MHz, DMSO-d6) δ ppm 7.39 (5H, m), 7.24 (2H, m), 3.45 (3H, s), 3.09 (2H, m), 2.17 (2H, m), 1.82 (4H, m) and 1.45 (2H, m). | 9426[c] |
| 423 | tert-butyl N-[4-(3-{4-amino-6-[methyl(phenyl)amino]-1,3,5-triazin-2-yl}-1,2,4-oxadiazol-5-yl)cyclohexyl]carbamate | 2 | Method A HPLC-MS: MH+ requires m/z = 467 Found: m/z = 467, Rt = 4.40 min (98%). 1H NMR (500 MHz, CDCl3) δ ppm 7.44 (2H, m), 7.32 (3H, m), 5.34 (2H, br s), 4.67 (1H, br s), 3.76 (1H, br s), 3.61 (3H, s), 3.23 (1H, m), 2.10 (2H, m), 1.97 (2H, m), 1.78 (4H, m) and 1.46 (9H, s). | 684[c] |
| 424 | 4-(3-{4-amino-6-[methyl(phenyl)amino]-1,3,5-triazin-2-yl}-1,2,4-oxadiazol-5-yl)cyclohexan-1-ol | 2 | Method A HPLC-MS: MH+ requires m/z = 368 Found: m/z = 368, Rt = 3.72 min (100%). 1H NMR (500 MHz, CDCl3) δ ppm 7.45 (2H, m), 7.33 (3H, m), 5.31 (2H, br s), 3.72 (1H, m), 3.62 (3H, s), 3.04 (1H, m), 2.25 (2H, d), 2.14 (2H, d), 1.81 (2H, q) and 1.45 (2H, q). | 2811[c] |

| Example | Name Structure | M | Spectral data | Nav 1.7 activity (nM) |
|---|---|---|---|---|
| 425 | N-[4-(3-{4-amino-6-[methyl(phenyl)amino]-1,3,5-triazin-2-yl}-1,2,4-oxadiazol-5-yl)cyclohexyl]-2-methylpropanamide 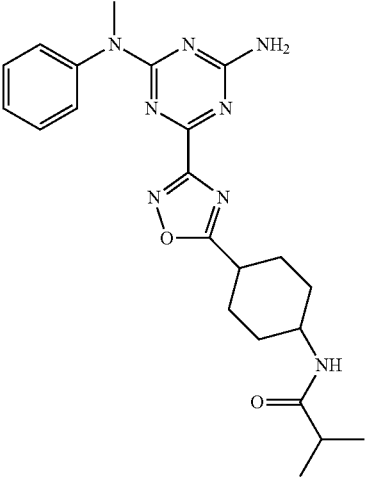 [SMILES: CC(C)C(=O)NC1CCC(c2nc(-c3nc(N)nc(N(C)c4ccccc4)n3)no2)CC1] | 22 | Method A HPLC-MS: MH+ requires m/z = 437 Found: m/z = 437, Rt = 3.95 min (94%). 1H NMR (500 MHz, CDCl$_3$) δ ppm 7.45 (2H, m), 7.32 (3H, m), 5.37 (1H, br s), 5.23 (2H, br s), 4.05 (1H, m), 3.62 (3H, s), 3.28 (1H, m), 2.33 (1H, m), 2.15 (2H, m), 2.00 (2H, m), 1.83 (2H, m), 1.70 (2H, m) and 1.07 (6H, d). | 2447[c] |
| 426 | N-[4-(3-{4-amino-6-[methyl(phenyl)amino]-1,3,5-triazin-2-yl}-1,2,4-oxadiazol-5-yl)cyclohexyl]-2-cyclopropylacetamide 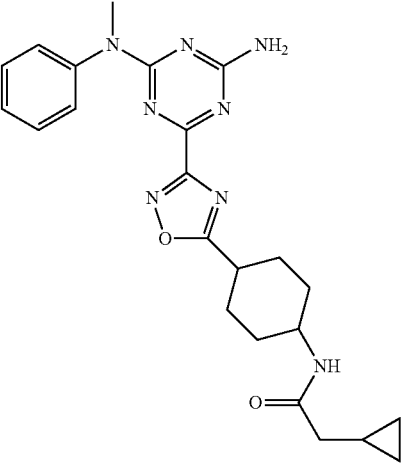 [SMILES: CN(c1ccccc1)c1nc(N)nc(-c2noc(C3CCC(NC(=O)CC4CC4)CC3)n2)n1] | 22 | Method A HPLC-MS: MH+ requires m/z = 449 Found: m/z = 449, Rt = 3.98 min (98%). 1H NMR (500 MHz, CDCl$_3$) δ ppm 7.46 (2H, m), 7.32 (3H, m), 5.96 (1H, br s), 5.31 (2H, br s), 4.08 (1H, m), 3.61 (3H, s), 3.29 (1H, m), 2.17 (4H, m), 2.02 (2H, m), 1.85 (2H, m), 1.69 (2H, br s), 0.95 (1H, m), 0.60 (2H, m) and 0.20 (2H, m). | 6682[c] |

| Example | Name Structure | M | Spectral data | Nav 1.7 activity (nM) |
|---|---|---|---|---|
| 427 | N-[4-(3-{4-amino-6-[methyl(phenyl)amino]-1,3,5-triazin-2-yl}-1,2,4-oxadiazol-5-yl)cyclohexyl]-3,3,3-trifluoropropanamide 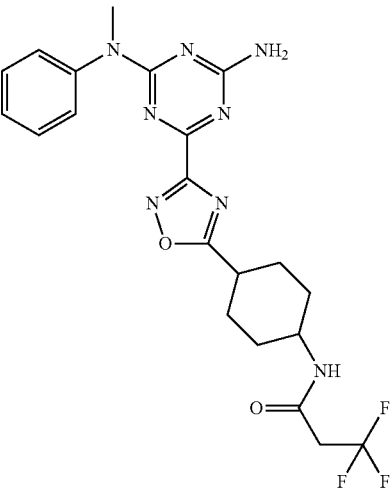 [SMILES: CN(c1ccccc1)c1nc(N)nc(-c2noc(C3CCC(NC(=O)CC(F)(F)F)CC3)n2)n1] | 9 | Method A HPLC-MS: MH+ requires m/z = 477 Found: m/z = 477, Rt = 3.95 min (96%). 1H NMR (500 MHZ, CDCl$_3$) δ ppm 7.38 (2H, m), 7.25 (3H, m), 5.90 (1H, br s), 5.13 (2H, br s), 4.00 (1H, m), 3.54 (3H, s), 3.24 (1H, m), 2.99 (2H, q), 2.05 (2H, m), 1.91 (2H, m), 1.77 (2H, m) and 1.69 (2H, m). | 4915[c] |
| 428 | N-[4-(3-{4-amino-6-[methyl(phenyl)amino]-1,3,5-triazin-2-yl}-1,2,4-oxadiazol-5-yl)cyclohexyl]-2,2,2-trifluoroacetamide 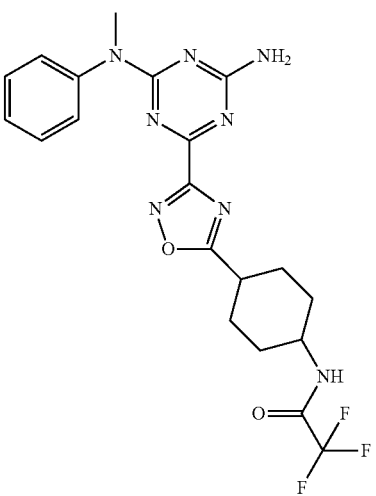 [SMILES: CN(c1ccccc1)c1nc(N)nc(-c2noc(C3CCC(NC(=O)C(F)(F)F)CC3)n2)n1] | 9 | Method A HPLC-MS: MH+ requires m/z = 463 Found: m/z = 463, Rt = 4.22 min (88%). 1H NMR (500 MHz, CDCl$_3$) δ ppm 7.43 (2H, m), 7.32 (3H, m), 6.34 (1H, br s), 5.42 (2H, br s), 4.08 (1H, m), 3.60 (3H, s), 3.31 (1H, m), 2.23 (2H, m), 2.03 (2H, m), 1.91 (2H, m) and 1.72 (2H, m). | 5948[c] |

-continued

| Example | Name Structure | M | Spectral data | Nav 1.7 activity (nM) |
|---|---|---|---|---|
| 429 | 2-N-methyl-6-[5-(4-phenoxycyclohexyl)-1,2,4-oxadiazol-3-yl]-2-N-phenyl-1,3,5-triazine-2,4-diamine | | Method A HPLC-MS: MH+ requires m/z = 444 Found: m/z = 444, Rt = 4.95 min (97%). 1H NMR (500 MHz, CDCl$_3$) δ ppm 7.44 (2H, m), 7.32 (5H, m), 6.94 (3H, m), 5.38 (2H, br s), 4.60 (1H, m), 3.65 (3H, s), 3.17 (1H, m), 2.26 (2H, m), 2.16 (2H, m), 2.00 (2H, m) and 1.73 (2H, m). | 289[c] |
| 430 | 2-N-phenyl-6-{5-[3-(trifluoromethyl)pyridin-2-yl]-1,2,4-oxadiazol-3-yl}-1,3,5-triazine-2,4-diamine | 2 | Method A HPLC-MS: MH+ requires m/z = 401 Found: m/z = 401, Rt = 3.94 min (99%). 1H NMR (500 MHz, CDCl$_3$) δ ppm 9.02 (1H, d), 8.25 (1H, d), 7.73 (1H, m), 7.64 (2H, m), 7.39 (3H, t), 7.15 (1H, t) and 5.58 (2H, br s). | 146[c] |
| 431 | 6-[5-(3-chloropyridin-2-yl)-1,2,4-oxadiazol-3-yl]-2-N-phenyl-1,3,5-triazine-2,4-diamine | 2 | Method A HPLC-MS: MH+ requires m/z = 366 Found: m/z = 366, Rt = 3.75 min (97%). 1H NMR (500 MHz, CDCl$_3$) δ ppm 8.77 (1H, d), 7.98 (1H, d), 7.64 (2H, m), 7.53 (1H, dd), 7.46 (1H, br s), 7.38 (2H, t), 7.15 (1H, t) and 5.72 (2H, br s). | 142[c] |

| Example | Name Structure | M | Spectral data | Nav 1.7 activity (nM) |
|---|---|---|---|---|
| 432 | 2-N-(6-fluoropyridin-3-yl)-2-N-methyl-6-{5-[6-(2,2,2-trifluoroethoxy)pyridin-3-yl]-1,2,4-oxadiazol-3-yl}-1,3,5-triazine-2,4-diamine 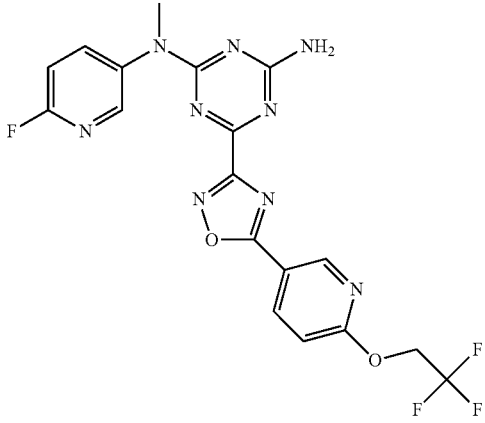 [SMILES: CN(c1ccc(F)nc1)c1nc(N)nc(-c2noc(-c3ccc(OCC(F)(F)F)nc3)n2)n1] | | Method A HPLC-MS: MH+ requires m/z = 464 Found: m/z = 464, Rt = 4.39 min (97%). 1H NMR (500 MHz, CDCl$_3$) δ ppm 9.07 (1H, s), 8.47 (1H, m), 8.25 (1H, d), 7.82 (1H, m), 7.03 (2H, m), 5.34 (2H, br s), 4.88 (2H, q) and 3.64 (3H, s). | 6294$^c$ |
| 433 | 2-N-methyl-6-{5-[(3S)-3-phenoxypyrrolidin-1-yl]-1,2,4-oxadiazol-3-yl}-2-N-phenyl-1,3,5-triazine-2,4-diamine 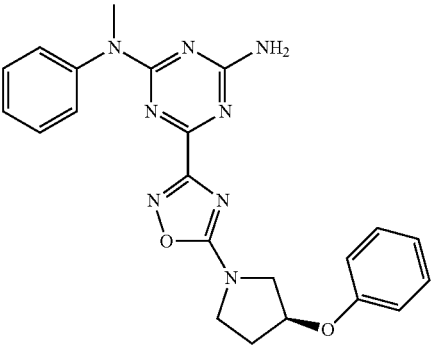 [SMILES: CN(c1ccccc1)c1nc(N)nc(-c2noc(N3CC[C@H](Oc4ccccc4)C3)n2)n1] | 4 | Method A HPLC-MS: MH+ requires m/z = 431 Found: m/z = 431, Rt = 4.35 min (91%). 1H NMR (500 MHz, CDCl$_3$) δ ppm 7.42 (2H, m), 7.31 (5H, m), 7.00 (1H, t), 6.89 (2H, m), 5.28 (2H, br s), 5.04 (1H, m), 4.19 (1H, m), 3.92 (3H, m), 3.60 (3H, s), 2.41 (1H, m) and 2.24 (1H, m). | 161$^c$ |
| 434 | 2-N-methyl-6-{5-[(3R)-3-phenoxypyrrolidin-1-yl]-1,2,4-oxadiazol-3-yl}-2-N-phenyl-1,3,5-triazine-2,4-diamine 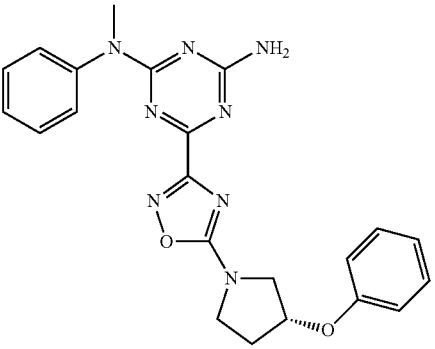 [SMILES: CN(c1ccccc1)c1nc(N)nc(-c2noc(N3CC[C@@H](Oc4ccccc4)C3)n2)n1] | 4 | Method A HPLC-MS: MH+ requires m/z = 431 Found: m/z = 431, Rt = 4.21 min (92%). 1H NMR (500 MHz, CDCl$_3$) δ ppm 7.43 (2H, m), 7.32 (5H, m), 7.00 (1H, t), 6.88 (2H, m), 5.21 (2H, br s), 5.07 (1H, m), 3.85 (4H, m), 3.60 (3H, s), 2.40 (1H, m) and 2.27 (1H, m). | 140$^c$ |

| Example | Name Structure | M | Spectral data | Nav 1.7 activity (nM) |
|---|---|---|---|---|
| 436 | 2-N-(2-methoxyethyl)-6-[5-(3-phenoxyazetidin-1-yl)-1,2,4-oxadiazol-3-yl]-2-N-phenyl-1,3,5-triazine-2,4-diamine | | Method A HPLC-MS: MH+ requires m/z = 461 Found: m/z = 461, Rt = 4.33 min (97%). 1H NMR (500 MHz, CDCl₃) δ ppm 7.42 (2H, m), 7.32 (5H, m), 7.0 (1H, t), 6.77 (2H, d), 5.23 (2H, br s), 5.15 (1H, m), 4.70 (2H, m), 4.42 (2H, m), 4.22 (2H, m), 3.63 (2H, t) and 3.33 (3H). | 171ᶜ |
| 437 | 6-[5-(2-fluoro-6-methoxyphenyl)-1,2,4-oxadiazol-3-yl]-2-N-(2-methoxyethyl)-2-N-phenyl-1,3,5-triazine-2,4-diamine | 2 | Method A HPLC-MS: MH+ requires m/z = 438 Found: m/z = 438, Rt = 4.28 min (88%). 1H NMR (500 MHz, CDCl₃) δ ppm 7.52 (1H, m), 7.43 (2H, m), 7.34 (3H, m), 6.84 (2H, m), 6.17 (1H, br d), 5.52 (1H, br s), 4.25 (2H, m), 3.80 (3H, s), 3.66 (2H, t) and 3.35 (3H, s). | 167ᶜ |

| Example | Name Structure | M | Spectral data | Nav 1.7 activity (nM) |
|---|---|---|---|---|
| 438 | 2-N-methyl-2-N-phenyl-6-{5-[(2S)-pyrrolidin-2-yl]-1,2,4-oxadiazol-3-yl}-1,3,5-triazine-2,4-diamine hydrochloride | 23 | Method A HPLC-MS: MH+ requires m/z = 339 Found: m/z = 339, Rt = 2.68 min (98%). 1H NMR (500 MHz, MeOH-d4) δ ppm 7.49 (2H, m), 7.39 (3H, m), 5.26 (1H, m), 3.65 (3H, s), 3.55 (2H, m), 2.69 (1H, m), 2.44 (1H, m) and 2.27 (2H, m). | 2088[c] |
| 439 | 2-N-methyl-2-N-phenyl-6-{5-[(2R)-pyrrolidin-2-yl]-1,2,4-oxadiazol-3-yl}-1,3,5-triazine-2,4-diamine hydrochloride | 23 | Method A HPLC-MS: MH+ requires m/z = 339 Found: m/z = 339, Rt = 2.66 min (99%). 1H NMR (500 MHz, MeOH-d4) δ ppm 7.50 (2H, m), 7.38 (3H, m), 5.25 (1H, m), 3.64 (3H, s), 3.55 (2H, m), 2.68 (1H, m), 2.42 (1H, m) and 2.27 (2H, m). | 4059[c] |
| 440 | tert-butyl (2S)-2-(3-{4-amino-6-[methyl(phenyl)amino]-1,3,5-triazin-2-yl}-1,2,4-oxadiazol-5-yl)pyrrolidine-1-carboxylate | 2 | Method A HPLC-MS: MH+ requires m/z = 439 Found: m/z = 439, Rt = 4.28 min (97%). 1H NMR (500 MHz, CDCl3) δ ppm 7.43 (m, 2 H), 7.32 (3H, m), 5.33 (2H, br s), 5.13 (1H, m), 3.70 (1H, m), 3.60 (3H, s), 3.49 (1H, m), 2.40 (1H, m), 2.18 (1H, m), 2.10 (1H, m), 1.99 (1H, m), 1.45 (3H, s) and 1.32 (6H, s). | 1297[c] |

| Example | Name Structure | M | Spectral data | Nav 1.7 activity (nM) |
|---|---|---|---|---|
| 441 | 2-N-methyl-2-N-phenyl-6-{5-[(2S)-1-(3,3,3-trifluoropropyl)pyrrolidin-2-yl]-1,2,4-oxadiazol-3-yl}-1,3,5-triazine-2,4-diamine | 24 | Method A HPLC-MS: MH+ requires m/z = 435 Found: m/z = 435, Rt = 4.19 min (95%). 1H NMR (500 MHz, CDCl$_3$) δ ppm 7.44 (2H, m), 7.32 (3H, m), 5.28 (2H, br s), 4.14 (1H, m), 3.61 (3H, s), 3.22 (1H, m), 2.90 (1H, m), 2.72 (1H, m), 2.59 (1H, q), 2.31 (3H, m), 2.15 (2H, m) and 1.99 (1H, m). | 1449[c] |
| 442 | 2-N-methyl-2-N-phenyl-6-{5-[(2R)-1-(3,3,3-trifluoropropyl)pyrrolidin-2-yl]-1,2,4-oxadiazol-3-yl}-1,3,5-triazine-2,4-diamine | 24 | Method A HPLC-MS: MH+ requires m/z = 435 Found: m/z = 435, Rt = 4.20 min (97%). 1H NMR (500 MHz, CDCl$_3$) δ ppm 7.43 (2H, m), 7.32 (3H, m), 5.28 (2H, br s), 4.14 (1H, m), 3.61 (3H, s), 3.22 (1H, m), 2.90 (1H, m), 2.72 (1H, m), 2.60 (1H, q), 2.31 (3H, m), 2.15 (2H, m) and 1.97 (1H, m). | 7178[c] |
| 443 | 2-N-methyl-2-N-phenyl-6-{5-[(3R)-3-(2,2,2-trifluoroethoxy)pyrrolidin-1-yl]-1,2,4-oxadiazol-3-yl}-1,3,5-triazine-2,4-diamine | 4 | Method A HPLC-MS: MH+ requires m/z = 437 Found: m/z = 437, Rt = 4.07 min (99%). 1H NMR (500 MHz, CDCl$_3$) δ ppm 7.43 (2H, m), 7.31 (3H, m), 5.35 (2H, br s), 4.38 (1H, m), 3.82 (6H, m), 3.59 (3H, s), 2.27 (1H, m) and 2.13 (1H, m). | 7290[c] |

| Example | Name Structure | M | Spectral data | Nav 1.7 activity (nM) |
|---|---|---|---|---|
| 444 | 6-{5-[(2R)-2-(methoxymethyl)pyrrolidin-1-yl]-1,2,4-oxadiazol-3-yl}-2-N-methyl-2-N-phenyl-1,3,5-triazine-2,4-diamine | 4 | Method A HPLC-MS: MH+ requires m/z = 383 Found: m/z = 383, Rt = 4.08 min (99%). 1H NMR (500 MHz, CDCl$_3$) δ ppm 7.42 (2H, m), 7.31 (3H, m), 5.32 (2H, br s), 4.23 (1H, m), 3.70 (2H, m), 3.61 (3H, s), 3.57 (2H, m), 3.35 (3H, s), 2.10 (3H, m) and 1.98 (1H, m). | 7999[c] |
| 445 | 2-N-methyl-2-N-phenyl-6-{5-[(3S)-3-(2,2,2-trifluoroethoxy)pyrrolidin-1-yl]-1,2,4-oxadiazol-3-yl}1,3,5-triazine-2,4-diamine | | Method A HPLC-MS: MH+ requires m/z = 437 Found: m/z = 437, Rt = 4.08 min (98%). 1H NMR (500 MHz, CDCl$_3$) δ ppm 7.44 (2H, m), 7.32 (3H, m), 5.48 (2H, br s), 4.38 (1H, m), 3.83 (6H, m), 3.59 (3H, s), 2.27 (1H, m) and 2.14 (1H, m). | 3301[c] |
| 446 | 6-{5-[(2S)-2-(methoxymethyl)pyrrolidin-1-yl]-1,2,4-oxadiazol-3-yl}-2-N-methyl-2-N-phenyl-1,3,5-triazine-2,4-diamine | 4 | Method A HPLC-MS: MH+ requires m/z = 383 Found: m/z = 383, Rt = 3.92 min (95%). 1H NMR (500 MHz, CDCl$_3$) δ ppm 7.43 (2H, m), 7.31 (3H, m), 5.43 (2H, br s), 4.23 (1H, m), 3.70 (2H, m), 3.60 (3H, s), 3.57 (2H, m), 3.35 (3H, s), 2.10 (3H, m) and 1.97 (1H, m). | 3616[c] |

| Example | Name Structure | M | Spectral data | Nav 1.7 activity (nM) |
|---|---|---|---|---|
| 447 | 2-N-methyl-6-{5-[(2R)-1-[(2-methylpropane)sulfonyl]pyrrolidin-2-yl]-1,2,4-oxadiazol-3-yl}-2-N-phenyl-1,3,5-triazine-2,4-diamine | 9 | Method A HPLC-MS: MH+ requires m/z = 459 Found: m/z = 459, Rt = 4.11 min (98%). 1H NMR (500 MHz, CDCl₃) δ ppm 7.44 (2H, m), 7.32 (3H, m), 5.50 (2H, br s), 5.33 (1H, m), 3.71 (1H, q), 3.59 (3H, s), 3.54 (1H, m), 2.99 (2H, m), 2.46 (1H, m), 2.29 (2H, m), 2.15 (2H, m) and 1.10 (6H, m). | 1089$^c$ |
| 448 | 2-N-methyl-2-N-phenyl-6-{5-[(2R)-1-[(2,2,2-trifluoroethane)sulfonyl]pyrrolidin-2-yl]-1,2,4-oxadiazol-3-yl}-1,3,5-triazine-2,4-diamine | 9 | Method A HPLC-MS: MH+ requires m/z = 485 Found: m/z = 485, Rt = 4.04 min (100%). 1H NMR (500 MHz, CDCl₃) δ ppm 7.43 (2H, m), 7.31 (3H, m), 5.42 (1H, m), 5.31 (2H, br s), 4.27 (1H, brs), 4.05 (1H, br s), 3.75 (1H, m), 3.63 (1H, br s), 3.57 (3H, s), 2.54 (1H, m), 2.37 (1H, m) and 2.14 (2H, m). | 287$^c$ |
| 449 | 1-[(2R)-2-(3-{4-amino-6-[methyl(phenyl)amino]-1,3,5-triazin-2-yl}-1,2,4-oxadiazol-5-yl)pyrrolidin-1-yl]-2-cyclopropylethan-1-one | 22 | Method A HPLC-MS: MH+ requires m/z = 421 Found: m/z = 421, Rt = 3.73 min (100%). 1H NMR (500 MHz, CDCl₃) δ ppm 7.42 (2H, m), 7.32 (3H, m), 5.43 (1H, m), 5.30 (2H, br s), 3.78 (1H, m), 3.57 (3H, s), 3.53 (1H, m), 2.25 (6H, m), 1.07 (1H, m), 0.55 (2H, d) and 0.17 (2H, d). | 2574$^c$ |

| Example | Name Structure | M | Spectral data | Nav 1.7 activity (nM) |
|---|---|---|---|---|
| 450 | 1-[(2S)-2-(3-{4-amino-6-[methyl(phenyl)amino]-1,3,5-triazin-2-yl}-1,2,4-oxadiazol-5-yl)pyrrolidin-1-yl]-2-cyclopropylethan-1-one | 22 | Method A HPLC-MS: MH+ requires m/z = 421 Found: m/z = 421, Rt = 3.88 min (95%). 1H NMR (500 MHz, CDCl$_3$) δ ppm 7.43 (2H, m), 7.32 (3H, m), 5.45 (1H, m), 5.35 (2H, br s), 3.78 (1H, m), 3.58 (3H, s), 3.54 (1H, m), 2.28 (6H, m), 1.07 (1H, m), 0.55 (2H, m) and 0.14 (2H, m). | 9529[c] |
| 451 | 1-[(2S)-2-(3-{4-amino-6-[methyl(phenyl)amino]-1,3,5-triazin-2-yl}-1,2,4-oxadiazol-5-yl)pyrrolidin-1-yl]-3,3,3-trifluoropropan-1-one | 22 | Method A HPLC-MS: MH+ requires m/z = 449 Found: m/z = 449, Rt = 3.81 min (96%). 1H NMR (500 MHz, CDCl$_3$) δ ppm 7.43 (2H, m), 7.31 (3H, m), 5.55 (2H, br s), 5.48 (1H, m), 3.86 (1H, m), 3.65 (1H, m), 3.48 (3H, s), 3.25 (2H, q), 2.42 (1H, m) and 2.19 (3H, m). | 7952[c] |
| 452 | 6-(5-{6-[(cyclopropylmethyl)sulfanyl]pyridin-3-yl}-1,2,4-oxadiazol-3-yl)-2-N-methyl-2-N-phenyl-1,3,5-triazine-2,4-diamine | 2 | Method A HPLC-MS: MH+ requires m/z = 432 Found: m/z = 432, Rt = 4.90 min (100%). 1H NMR (500 MHz, CDCl$_3$) δ ppm 9.23 (1H, d), 8.25 (1H, dd), 7.44 (2H, t), 7.35 (4H, m), 5.33 (2H, br s), 3.64 (3H, s), 3.22 (2H, d), 1.18 (1H, m), 0.64 (2H, m) and 0.36 (2H, m). | 61[c] |

| Example | Name Structure | M | Spectral data | Nav 1.7 activity (nM) |
|---|---|---|---|---|
| 453 | 2-N-methyl-2-N-phenyl-6-{5-{6-[(3,3,3-trifluoropropyl)sulfanyl]pyridin-3-yl}-1,2,4-oxadiazol-3-yl)-1,3,5-triazine-2,4-diamine | 2 | Method A HPLC-MS: MH+ requires m/z = 474 Found: m/z = 474, Rt = 4.88 min (100%). 1H NMR (500 MHz, CDCl$_3$) δ ppm 9.29 (1H, d), 8.30 (1H, d), 7.45 (2H, t), 7.35 (4H, m), 5.31 (2H, br s), 3.64 (3H, s), 3.43 (2H, m) and 2.61 (2H, m). | 121[c] |
| 454 | 2-N-methyl-2-N-phenyl-6-(5-{6-[(3,3,3-trifluoropropane)sulfonyl]pyridin-3-yl}-1,2,4-oxadiazol-3-yl)-1,3,5-triazine-2,4-diamine | 18 | Method A HPLC-MS. MH+ requires m/z = 507 Found: m/z = 507, Rt = 4.17 min (99%). 1H NMR (500 MHz, CDCl$_3$) δ ppm 9.59 (1H, s), 8.85 (1H, d), 8.31 (1H, d), 7.46 (2H, m), 7.33 (3H, m), 5.31 (2H, br s), 3.74 (2H, m), 3.64 (3H, m) and 2.76 (2H, m). | 290[c] |

| Example | Name Structure | M | Spectral data | Nav 1.7 activity (nM) |
|---|---|---|---|---|
| 455 | 2-N-methyl-2-N-phenyl-6-(5-{6-[(3,3,3-trifluoropropane)sulfinyl]pyridin-3-yl}-1,2,4-oxadiazol-3-yl)-1,3,5-triazine-2,4-diamine | 18 | Method A HPLC-MS: MH+ requires m/z = 491 Found: m/z = 491, Rt = 4.01 min (100%). 1H NMR (500 MHz, CDCl$_3$) δ ppm 9.50 (1H, s), 8.78 (1H, d), 8.22 (1H, d), 7.45 (2H, t), 7.36 (3H, m), 5.28 (2H, br s), 3.64 (3H, s), 3.47 (1H, m), 3.25 (1H, m), 2.75 (1H, m), 2.18 (1H, m). | 57[c] |
| 456 | 6-{5-[6-(cyclopropylmethane)sulfinylpyridin-3-yl]-1,2,4-oxadiazol-3-yl}-2-N-methyl-2-N-phenyl-1,3,5-triazine-2,4-diamine | 18 | Method A HPLC-MS: MH+ requires m/z = 449 Found: m/z = 449, Rt = 3.82 min (100%). 1H NMR (500 MHz, CDCl$_3$) δ ppm 9.45 (1H, s), 8.77 (1H, d), 8.26 (1H, d), 7.48 (2H, t), 7.34 (3H, m), 5.31 (2H, br s), 3.64 (3H, s), 3.04 (2H, m), 1.26 (1H, m), 0.72 (1H, m), 0.59 (1H, m), 0.41 (1H, m) and 0.16 (1H, m). | 310[c] |
| 457 | 2-N-phenyl-6-(5-{[4-(2,2,2-trifluoroethoxy)piperidin-1-yl]carbonyl}-1,2,4-oxadiazol-3-yl)-1,3,5-triazine-2,4-diamine | 6 | Method A HPLC-MS. MH+ requires m/z = 465 Found: m/z = 465, Rt = 4.03 min (100%). 1H NMR (500 MHz, CDCl$_3$) δ ppm 7.59 (2H, d), 7.39 (3H, m), 7.13 (1H, t), 5.84 (1H, s), 5.47 (1H, s), 3.85 (6H, m), 3.58 (1H, t), 1.87 (4H, m). | 1299[c] |

-continued

| Example | Name Structure | M | Spectral data | Nav 1.7 activity (nM) |
|---|---|---|---|---|
| 458 | 6-{5-[(4-ethoxypiperidin-1-yl)carbonyl]-1,2,4-oxadiazol-3-yl}-2-N-methyl-2-N-phenyl-1,3,5-triazine-2,4-diamine | 21 | Method A HPLC-MS: MH+ requires m/z = 465 Found: m/z = 465, Rt = 4.03 min (100%). 1H NMR (500 MHz, CDCl$_3$) δ ppm 9.78 (2H, t), 9.69 (2H), 9.64 (1H, t), 6.33 (2H, m), 5.98 (8H, m), 4.32 (2H, td), 4.04 (2H, m) and 3.58 (4H, dt) | 4717[c] |
| 459 | 6-[5-({4-[(cyclopropylmethoxy)methyl]piperidin-1-yl}carbonyl)-1,2,4-oxadiazol-3-yl]-2-N-methyl-2-N-phenyl-1,3,5-triazine-2,4-diamine | 21 | Method A HPLC-MS: MH+ requires m/z = 465 Found: m/z = 465, Rt = 4.44 min (100%). 1H NMR (500 MHz, CDCl$_3$) δ ppm 7.44 (2H, dd), 7.30 (3H, dd), 5.30 (2H, s), 4.71 (1H, d), 3.96 (1H, d), 3.59 (3H, s), 3.30 (4H, m), 3.19 (1H, t), 2.85 (1H, t), 1.88 (3H, dd), 1.29 (2H, dd), 1.05 (1H, m), 0.53 (2H, m) and 0.20 (2H, m). | 3250[c] |
| 460 | 2-N-methyl-2-N-phenyl-6-[5-({4-[(2,2,2-trifluoroethoxy)methyl]piperidin-1-yl]carbonyl)-1,2,4-oxadiazol-3-yl]-1,3,5-triazine-2,4-diamine | 21 | Method A HPLC-MS: MH+ requires m/z = 494 Found: m/z = 494, Rt = 4.42 min (100%). 1H NMR (500 MHz, CDCl$_3$) δ ppm 7.43 (2H, t), 7.30 (3H, dd), 5.30 (2H, s), 4.73 (1H, d), 4.02 (1H, d), 3.82 (2H, m), 3.59 (3H, s), 3.49 (2H, m), 3.19 (1H, t), 2.85 (1H, dd), 1.90 (3H, m) and 1.34 (2H, dt). | 3027[c] |

| Example | Name Structure | M | Spectral data | Nav 1.7 activity (nM) |
|---|---|---|---|---|
| 461 | 2-N-phenyl-6-[5-({4-[(2,2,2-trifluoroethoxy)methyl]piperidin-1-yl}carbonyl)-1,2,4-oxadiazol-3-yl]-1,3,5-triazine-2,4-diamine | 21 | Method A HPLC-MS: MH+ requires m/z = 480 Found: m/z = 480, Rt = 4.15 min (100%). 1H NMR (500 MHz. CDCl₃) δ ppm 7.61 (2H, d), 7.40 (3H, dd), 7.14 (1H, t), 5.73 (1H, s), 5.45 (1H, s), 4.74 (1H, d), 3.98 (1H, s), 3.82 (2H), 3.50 (2H, m), 3.23 (1H, m), 2.87 (1H, td), 1.92 (3H, m) and 1.37 (2H, m). | 1644ᶜ |
| 462 | 6-(5-{[4-(cyclopropylmethoxy)piperidin-1-yl]carbonyl}-1,2,4-oxadiazol-3-yl)-2-N-phenyl-1,3,5-triazine-2,4-diamine | 21 | Method A HPLC-MS: MH+ requires m/z = 437 Found: m/z = 437, Rt = 4.17 min (98%). 1H NMR (500 MHz, MeOD) δ ppm 7.53 (2H, d), 7.09 (2H, t), 6.84 (1H), 3.79 (2H, m), 3.51 (1H, m), 3.42 (2H, ddd), 3.15 (2H, dt), 1.76 (2H, m), 1.50 (2H, m), 0.84 (1H, m), 0.31 (2H, m) and 0.01 (2H, q). | 3610ᶜ |
| 463 | 6-[5-({4-[(cyclopropylmethoxy)methyl]piperidin-1-yl}carbonyl)-1,2,4-oxadiazol-3-yl]-2-N-phenyl-1,3,5-triazine-2,4-diamine | 21 | Method A HPLC-MS: MH+ requires m/z = 451 Found: m/z = 451, Rt = 4.28 min (100%). 1H NMR (500 MHz, CDCl₃) δ ppm 7.61 (2H, d), 7.38 (3H, dd), 7.14 (1H), 5.92 (1H, s), 5.48 (1H, s), 4.72 (1H, d), 3.92 (1H, d), 3.28 (5H, m), 2.87 (1H, td), 1.92 (3H, m), 1.32 (2H, m), 1.04 (1H, m), 0.53 (2H, m) and 0.19 (2H, q). | 1822ᶜ |

-continued

| Example | Name Structure | M | Spectral data | Nav 1.7 activity (nM) |
|---|---|---|---|---|
| 464 | 2-N-methyl-2-N-phenyl-6-[5-({4-[(3,3,3-trifluoropropoxy)methyl]piperidin-1-yl}carbonyl)-1,2,4-oxadiazol-3-yl]-1,3,5-triazine-2,4-diamine | | Method A HPLC-MS: MH+ requires m/z = 507 Found: m/z = 507, Rt = 4.52 min (99%). 1H NMR (500 MHz, CDCl$_3$) δ ppm 7.43 (2H, t), 7.30 (3H, dd), 5.38 (2H, s), 4.71 (1H, d), 3.98 (1H, d), 3.63 (2H, t), 3.59 (3H, s), 3.32 (2H, m), 3.18 (1H, t), 2.85 (1H, dd), 2.38 (2H, m), 1.86 (3H, m) and 1.33 (2H, m). | 719[c] |
| 465 | 2-N-methyl-2-N-phenyl-6-[5-({4-[(2,2,2-trifluoroethyl)sulfanyl]piperidin-1-yl}carbonyl)-1,2,4-oxadiazol-3-yl]-1,3,5-triazine-2,4-diamine | 21 | Method A HPLC-MS: MH+ requires m/z = 450 Found: m/z = 450, Rt = 4.50 min (99%). 1H NMR (500 MHz, CDCl$_3$) δ ppm 7.43 (2H, t), 7.31 (3H, dd), 5.37 (2H, s), 4.42 (1H), 4.05 (1H, dt), 3.59 (3H, s), 3.38 (1H, t), 3.25 (1H, dd), 3.13 (3H, m), 2.13 (2H, ddd) and 1.67 (3H, m). | 1037.5[c] |
| 466 | 2-N-phenyl-6-[5-({4-[(2,2,2-trifluoroethyl)sulfanyl]piperidin-1-yl}carbonyl)-1,2,4-oxadiazol-3-yl]-1,3,5-triazine-2,4-diamine | 21 | Method A HPLC-MS: MH+ requires m/z = 481 Found: m/z = 481, Rt = 4.34 min (97%). 1H NMR (500 MHz, CDCl$_3$) δ ppm 7.59 (2H, t), 7.40 (3H, m), 7.15 (1H, t), 5.94 (1H, s), 5.50 (1H, s), 4.43 (1H, dt), 4.01 (1H, d), 3.40 (1H, ddd), 3.28 (1H, ddd), 3.13 (4H, m), 2.13 (2H, m) and 1.69 (3H, m). | 740.5[c] |

| Example | Name Structure | M | Spectral data | Nav 1.7 activity (nM) |
|---|---|---|---|---|
| 467 | 2-N-methyl-6-[5-(2-methylpyrimidin-5-yl)-1,2,4-oxadiazol-3-yl]-2-N-phenyl-1,3,5-triazine-2,4-diamine | 1 | Method B HPLC-MS: MH+ requires m/z = 362; Found: m/z = 362, Rt = 1.75 min (99%). 1H NMR (250 MHz, CDCl$_3$) δ ppm 9.44 (2H, s), 7.44 (2H, m), 7.32 (3H, m), 5.64 (2H, m), 3.62 (3H, s) and 2.87 (3H, s). | 9933$^c$ |
| 468 | 2-N-methyl-2-N-phenyl-6-[5-(pyrazin-2-yl)-1,2,4-oxadiazol-3-yl]-1,3,5-triazine-2,4-diamine | 1 | Method A HPLC-MS: MH+ requires m/z = 348; Found: m/z = 348, Rt = 3.60 min (99%). 1H NMR (250 MHz, CDCl$_3$) δ ppm 9.61 (1H, s), 8.83 (2H, m), 7.45 (2H, m), 7.32 (4H, m), 5.61 (2H, m) and 3.63 (3H, s). | 8911$^c$ |
| 469 | 2-N-methyl-2-N-phenyl-6-[5-(pyridazin-4-yl)-1,2,4-oxadiazol-3-yl]-1,3,5-triazine-2,4-diamine | 1 | Method A HPLC-MS: MH+ requires m/z = 348; Found: m/z = 348, Rt = 3.45 min (97%). 1H NMR (250 MHz, CDCl$_3$) δ ppm 9.90 (1H, s), 9.45 (1H, s), 7.39 (2H, m), 7.28 (3H, m), 5.40 (2H, br s) and 3.58 (3H, s). | 2925$^c$ |

| Example | Name Structure | M | Spectral data | Nav 1.7 activity (nM) |
|---|---|---|---|---|
| 470 | 6-[5-(2-methoxypyridin-4-yl)-1,2,4-oxadiazol-3-yl]-2-N-methyl-2-N-phenyl-1,3,5-triazine-2,4-diamine | 1 | Method A HPLC-MS: MH+ requires m/z = 377; Found: m/z = 377, Rt = 4.16 min (100%). 1H NMR (500 MHz, CDCl$_3$) δ ppm 8.39 (1H, d), 7.66 (1H, d), 7.57 (1H, s), 7.45 (2H, m), 7.33 (3H, m), 5.46 (2H, m), 4.02 (3H, s) and 3.63 (3H, s). | — |
| 471 | 2-N-methyl-2-N-phenyl-6-(5-{5-[(2,2,2-trifluoroethyl)amino]pyridin-2-yl}-1,2,4-oxadiazol-3-yl)-1,3,5-triazine-2,4-diamine | 2 | Method A HPLC-MS: MH+ requires m/z = 444; Found: m/z = 444, Rt = 4.15 min (98%). 1H NMR (500 MHz, CDCl$_3$) δ ppm 8.92 (1H, s), 8.15 (1H, d), 7.26 (6H, m) 6.53 (1H, d), 5.62 (2H, m), 5.29 (1H, t), 4.14 (2H, m) and 3.54 (3H, s). | 731[c] |
| 472 | 2-N-methyl-2-N-phenyl-6-{5-[2-(2,2,2-trifluoroethoxy)pyridin-4-yl]-1,2,4-oxadiazol-3-yl}-1,3,5-triazine-2,4-diamine | 1 | Method A HPLC-MS: MH+ requires m/z = 445; Found: m/z = 445, Rt = 4.57 min (94%). 1H NMR (500 MHz, CDCl$_3$) δ ppm 8.38 (1H, d), 7.78 (1H, d), 7.69 (1H, s), 7.45 (2H, m), 7.33 (3H, m), 5.58 (2H, m), 4.84 (2H, q) and 3.63 (3H, s). | 900[b] |

| Example | Name Structure | M | Spectral data | Nav 1.7 activity (nM) |
|---|---|---|---|---|
| 473 | 2-N-methyl-2-N-phenyl-6-{5-[6-(piperidin-1-yl)pyridin-3-yl]-1,2,4-oxadiazol-3-yl}-1,3,5-triazine-2,4-diamine | 1 | Method A HPLC-MS: MH+ requires m/z = 430; Found: m/z = 430, Rt = 4.22 min (99%). 1H NMR (500 MHz, CDCl$_3$) δ ppm 9.00 (1H, d), 8.20 (1H, dd), 7.36 (5H, m), 6.69 (1H, d), 5.42 (2H, m), 3.73 (4H m), 3.64 (3H, s) and 1.71 (6H, m). | 310[c] |
| 474 | 2-N-(4-fluorophenyl)-6-[5-(3-fluoropyridin-2-yl)-1,2,4-oxadiazol-3-yl]-2-N-methyl-1,3,5-triazine-2,4-diamine | 2 | Method A HPLC-MS: MH+ requires m/z = 383; Found: m/z = 383, Rt = 3.83 min (95%). 1H NMR (500 MHz, Acetone-d$_6$) δ ppm 8.70 (1H, m), 8.09 (1H, m), 7.86 (1H, m), 7.59 (2H, m), 7.27 (6H, m) and 3.44 (3H, s). | 289[c] |
| 475 | 2-N-(2-fluorophenyl)-6-[5-(3-fluoropyridin-2-yl)-1,2,4-oxadiazol-3-yl]-2-N-methyl-1,3,5-triazine-2,4-diamine | 2 | Method B HPLC-MS: MH+ requires m/z = 383; Found: m/z = 383, Rt = 1.83 min (96%). 1H NMR (500 MHz, DMSO-d$_6$) δ ppm 8.70 (1H, m), 8.09 (1H, m), 7.86 (1H, m), 7.59 (2H, m), 7.27 (4H, m) and 3.44 (3H, s). | 69[c] |

| Example | Name Structure | M | Spectral data | Nav 1.7 activity (nM) |
|---|---|---|---|---|
| 476 | 2-N-(3-fluorophenyl)-6-[5-(3-fluoropyridin-2-yl)-1,2,4-oxadiazol-3-yl]-2-N-methyl-1,3,5-triazine-2,4-diamine | 2 | Method A HPLC-MS: MH+ requires m/z = 383; Found: m/z = 383, Rt = 3.91 min (100%). 1H NMR (500 MHz, CDCl$_3$) δ ppm 8.70 (1H, d), 7.71 (1H, s), 7.63 (1H, d), 7.39 (1H, d), 7.15 (2H, dd), 7.01 (1H, s), 5.31 (2H, br d) and 3.64 (3H, s). | 366[c] |
| 477 | 2-N-methyl-2-N-phenyl-6-{5-[2-(2,2,2-trifluoroethoxy)pyridin-3-yl]-1,2,4-oxadiazol-3-yl}-1,3,5-triazine-2,4-diamine | 1 | Method C HPLC-MS: MH+ requires m/z = 445; Found: m/z = 445, Rt = 1.43 min (97%). 1H NMR (500 MHz, DMSO-d$_6$) δ ppm 8.55 (2H, m), 7.41 (6H, m), 7.26 (2H, m), 5.20 (2H, m) and 3.48 (3H, s). | 172[b] |
| 478 | 5-(3-{4-amino-6-[methyl(phenyl)amino]-1,3,5-triazin-2-yl}-1,2,4-oxadiazol-5-yl)-N,N-dimethylpyridine-2-carboxamide | | Method A HPLC-MS: MH+ requires m/z = 418; Found: m/z = 418, Rt = 3.47 min (86%). 1H NMR (500 MHz, CDCl$_3$) δ ppm 9.45 (1H, br. s.), 8.63 (1H, d), 7.85 (1H, d), 7.45 (2H, m), 7.33 (3H, m), 5.40 (2H, m), 3.64 (3H, s) and 3.16 (6H, m). | 8809[c] |

-continued

| Example | Name Structure | M | Spectral data | Nav 1.7 activity (nM) |
|---|---|---|---|---|
| 479 | 2-N-methyl-2-N-phenyl-6-[5-(pyridazin-3-yl)-1,2,4-oxadiazol-3-yl]-1,3,5-triazine-2,4-diamine | 2 | Method A HPLC-MS: MH+ requires m/z = 348; Found: m/z = 348, Rt = 3.41 min (100%). 1H NMR (500 MHz, DMSO-d$_6$) δ ppm 9.51 (1H, d), 8.45 (1H, m), 8.02 (1H, m), 7.41 (5H, m), 7.27 (2H, s) and 3.49 (3H, s). | 1144$^c$ |
| 480 | 6-[5-(3-ethoxypyridin-2-yl)-1,2,4-oxadiazol-3-yl]-2-N-methyl-2-N-phenyl-1,3,5-triazine-2,4-diamine | 2 | Method A HPLC-MS: MH+ requires m/z = 391; Found: m/z = 391, Rt = 3.96 min (100%). 1H NMR (500 MHz, CDCl$_3$) δ ppm 8.42 (1H, d), 7.44 (4H, m), 7.35 (2H, d), 7.30 (1H, t), 5.75 (2H, br d.), 4.23 (2H, q), 3.64 (3H, s) and 1.49 (3H, t). | 313$^c$ |
| 481 | 6-{5-[3-(cyclopropylamino)pyridin-2-yl]-1,2,4-oxadiazol-3-yl}-2-N-methyl-2-N-phenyl-1,3,5-triazine-2,4-diamine | | Method A HPLC-MS: MH+ requires m/z = 402; Found: m/z = 402, Rt = 4.31 min (99%). 1H NMR (500 MHz. CDCl$_3$) δ ppm 8.16 (1H, d), 7.91 (1H, m), 7.60 (1H, d), 7.45 (2H, m), 7.33 (4H, m), 5.93 (2H, m), 3.61 (3H, br. s), 2.54 (1H, m), 0.86 (2H, d) and 0.57 (2H, m). | 1902$^c$ |

| Example | Name Structure | M | Spectral data | Nav 1.7 activity (nM) |
|---|---|---|---|---|
| 482 | 6-[5-(3-fluoropyridin-2-yl)-1,2,4-oxadiazol-3-yl]-2-N-methyl-2-N-phenyl-1,3,5-triazine-2,4-diamine | 26 | Method A HPLC-MS: MH+ requires m/z = 365; Found: m/z = 365, Rt = 3.73 min (98%). 1H NMR (500 MHz, CDCl$_3$) δ ppm 8.70 (1H, d), 7.72 (1H, m), 7.63 (1H, dt), 7.46 (2H, m), 7.33 (3H, m), 5.82 (2H, s) and 3.65 (3H, s). | 647[c] |
| 483 | 6-{5-[3-(2-methoxyethoxy)pyridin-2-yl]-1,2,4-oxadiazol-3-yl}-2-N-methyl-2-N-phenyl-1,3,5-triazine-2,4-diamine | 2 | Method A HPLC-MS: MH+ requires m/z = 421; Found: m/z = 421, Rt = 3.72 min (99%). 1H NMR (500 MHz, CDCl$_3$) δ ppm 8.41 (1H, d), 7.48 (4H, m), 7.31 (4H, m), 5.78 (1H, m), 4.31 (2H, m), 3.78 (2H, m), 3.64 (3H, s) and 3.41 (3H, s). | 2399[c] |
| 484 | 2-N-methyl-2-N-phenyl-6-{5-[3-(propan-2-yloxy)pyridin-2-yl]-1,2,4-oxadiazol-3-yl}-1,3,5-triazine-2,4-diamine | 2 | Method A HPLC-MS: MH+ requires m/z = 405; Found: m/z = 405, Rt = 4.06 min (99%). 1H NMR (500 MHz, CDCl$_3$) δ ppm 8.26 (1H, dd), 7.36 (4H, m), 7.29 (2H, m), 7.20 (1H, m), 5.93 (2H, br s), 4.60 (1H, m), 3.55 (3H, s) and 1.34 (6H, d). | 695[c] |

| Example | Name Structure | M | Spectral data | Nav 1.7 activity (nM) |
|---|---|---|---|---|
| 486 | 2-N-methyl-2-N-phenyl-6-{5-[3-(2,2,2-trifluoroethoxy)pyridin-2-yl]-1,2,4-oxadiazol-3-yl}-1,3,5-triazine-2,4-diamine | 2 | Method A HPLC-MS: MH+ requires m/z = 445; Found: m/z = 445, R = 4.06 min (100%). 1H NMR (500 MHz, CDCl$_3$) δ ppm 8.48 (1H, dd), 7.47 (2H, m), 7.36 (2H, m), 7.27 (2H, d), 7.22 (1H, m), 6.74 (1H, br s), 5.64 (1H, br s), 4.48 (2H, d) and 3.54 (3H, s). | 1223[c] |
| 487 | 6-(5-{3-[(cyclopropylmethyl)amino]pyridin-2-yl}-1,2,4-oxadiazol-3-yl)-2-N-methyl-2-N-phenyl-1,3,5-triazine-2,4-diamine | 25 | Method A HPLC-MS: MH+ requires m/z = 416; Found: m/z = 416, Rt = 4.59 min (94%). 1H NMR (500 MHz, CDCl$_3$) δ ppm 8.12 (1H, d), 7.90 (1H, br. s), 7.44 (2H, m), 7.32 (4H, m), 7.17 (1H, d), 5.80 (2H, m), 3.63 (3H, s), 3.17 (2H, br s), 1.16 (1H, br s), 0.58 (2H, br s) and 0.33 (2H, br s). | >6592[c] |
| 488 | 6-{5-[3-(cyclobutylamino)pyridin-2-yl]-1,2,4-oxadiazol-3-yl}-2-N-methyl-2-N-phenyl-1,3,5-triazine-2,4-diamine | 25 | Method A HPLC-MS: MH+ requires m/z = 416; Found: m/z = 416, Rt = 4.55 min (97%). 1H NMR (500 MHz, CDCl$_3$) δ ppm 8.04 (1H, d), 7.93 (1H, br s), 7.37 (2H, m), 7.23 (4H, m), 6.95 (1H, d), 5.23 (2H, s), 3.94 (1H, m), 3.55 (3H, br s), 2.40 (2H, br s) and 1.81 (4H, m). | 838[c] |

-continued

| Example | Name Structure | M | Spectral data | Nav 1.7 activity (nM) |
|---|---|---|---|---|
| 489 | 2-N-methyl-6-[5-(3-phenoxyazetidin-1-yl)-1,2,4-oxadiazol-3-yl]-2-N-phenyl-1,3,5-triazine-2,4-diamine | 4 | Method A HPLC-MS: MH+ requires m/z = 417; Found: m/z = 417, Rt = 4.21 min (99%). 1H NMR (500 MHz, CDCl$_3$) δ ppm 7.43 (2H, m), 7.32 (5H, m), 7.04 (1H, t), 6.78 (2H, m), 5.44 (2H, m), 5.14 (1H, ddd), 4.71 (2H, dd), 4.43 (2H, dd) and 3.59 (3H, s) | 127[b] |
| 490 | 2-N-methyl-6-{5-[3-(morpholin-4-yl)pyridin-2-yl]-1,2,4-oxadiazol-3-yl}-2-N-phenyl-1,3,5-triazine-2,4-diamine | 25 | Method C HPLC-MS: MH+ requires m/z = 432; Found: m/z = 432, Rt = 1.29 min (97%). 1H NMR (500 MHz, CDCl$_3$) δ ppm 8.46 (1H, m), 7.52 (1H, m), 7.46 (3H, m), 7.33 (3H, m), 6.5 (1H, br s), 5.6 (1H, br s), 3.86 (4H, br s), 3.62 (3H, s) and 3.05 (4H, br s). | 464[c] |
| 491 | 6-[5-(3-cyclobutoxypyridin-2-yl)-1,2,4-oxadiazol-3-yl]-2-N-methyl-2-N-phenyl-1,3,5-triazine-2,4-diamine | 26 | Method A HPLC-MS: MH+ requires m/z = 417; Found: m/z = 417, Rt = 4.31 min (97%). 1H NMR (500 MHz, CDCl$_3$) δ ppm 8.30 (1H, dd), 7.36 (3H, m), 7.28 (2H, m), 7.20 (2H, m), 7.04 (1H, brs), 5.71 (1H, br s), 4.67 (1H, t), 3.56 (3H, s), 2.40 (2H, m), 2.23 (2H, m), 1.82 (1H, d) and 1.64 (1H, m). | 1040[c] |

-continued

| Example | Name Structure | M | Spectral data | Nav 1.7 activity (nM) |
|---|---|---|---|---|
| 492 | 2-N-methyl-2-N-phenyl-6-{5-[3-(propan-2-yloxy)azetidin-1-yl]-1,2,4-oxadiazol-3-yl}-1,3,5-triazine-2,4-diamine | 27 | Method A HPLC-MS: MH+ requires m/z = 383; Found: m/z = 383, Rt = 4.00 min (99%). 1H NMR (250 MHz, CDCl$_3$) δ ppm 7.41 (2H, m), 7.29 (3H, m), 5.30 (2H, br s), 4.49 (3H, m), 4.21 (2H, m), 3.64 (1H, m), 3.58 (3H, s) and 1.17 (6H, d). | >8076[c] |
| 493 | 6-[5-(3-methoxyazetidin-1-yl)-1,2,4-oxadiazol-3-yl]-2-N-methyl-2-N-phenyl-1,3,5-triazine-2,4-diamine | 27 | Method A HPLC-MS: MH+ requires m/z = 432; Found: m/z = 432, Rt = 3.56 min (100%). 1H NMR (500 MHz, CDCl$_3$) δ ppm 7.44 (2H, m), 7.31 (3H, m), 5.28 (2H, m), 4.49 (2H, m), 4.40 (1H, m), 4.24 (2H, dd), 3.60 (3H, s) and 3.35 (3H, s). | >9349[c] |
| 494 | 2-N-methyl-2-N-phenyl-6-{5-[3-(2,2,2-trifluoroethoxy)azetidin-1-yl]-1,2,4-oxadiazol-3-yl}-1,3,5-triazine-2,4-diamine | 27 | Method A HPLC-MS: MH+ requires m/z = 423; Found: m/z = 423, Rt = 3.96 min (100%). 1H NMR (500 MHz, CDCl$_3$) δ ppm 7.42 (2H, m), 7.29 (3H, m), 5.32 (2H, m), 4.61 (1H, d), 4.54 (2H, dd), 4.31 (2H, dd), 3.87 (2H, q) and 3.59 (3H, s). | 1976[c] |

| Example | Name Structure | M | Spectral data | Nav 1.7 activity (nM) |
|---|---|---|---|---|
| 495 | 2-N-methyl-6-{5-[3-(phenoxymethyl)azetidin-1-yl]-1,2,4-oxadiazol-3-yl}-2-N-phenyl-1,3,5-triazine-2,4-diamine 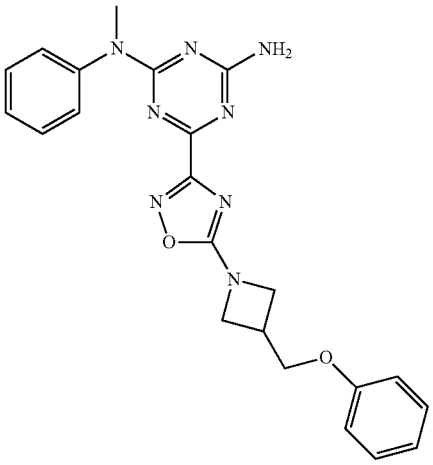 [SMILES: CN(c1ccccc1)c1nc(N)nc(-c2noc(N3CC(COc4ccccc4)C3)n2)n1] | 28 | Method B HPLC-MS: MH+ requires m/z = 431; Found: m/z = 431, Rt = 2.07 min (94%). 1H NMR (500 MHz, CDCl$_3$) δ ppm 7.42 (2H, m), 7.31 (5H, m), 7.00 (1H, d), 6.92 (2H, t), 5.34 (2H, br s), 4.73 (1H, br d), 4.48 (2H, m), 4.27 (1H, m,), 4.16 (2H, m,), 3.60 (3H, s) and 3.26 (1H, m). | 1911$^c$ |
| 496 | 2-N-methyl-2-N-phenyl-6-(5-{3-[(3,3,3-trifluoropropoxy)methyl]azetidin-1-yl}-1,2,4-oxadiazol-3-yl)-1,3,5-triazine-2,4-diamine 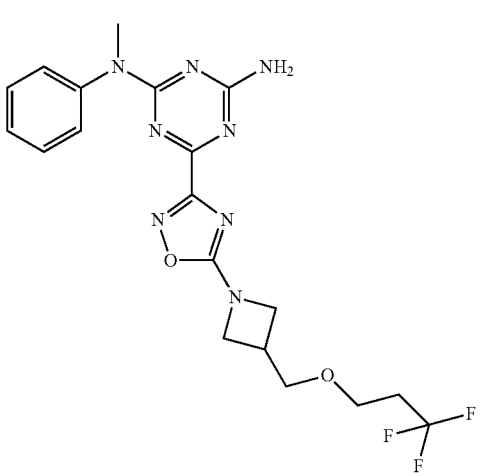 [SMILES: CN(c1ccccc1)c1nc(N)nc(-c2noc(N3CC(COCCC(F)(F)F)C3)n2)n1] | 28 | Method B HPLC-MS: MH+ requires m/z = 451; Found: m/z = 451, Rt = 1.97 min (100%). 1H NMR (250 MHz, CDCl$_3$) δ ppm 7.42 (2H, m), 7.30 (3H, m), 5.30 (2H, br s), 4.37 (2H, m), 4.12 (2H, m), 3.69 (4H, m), 3.59 (3H, s), 3.04 (1H, m) and 2.41 (2H, m). | 1222$^c$ |

| Example | Name Structure | M | Spectral data | Nav 1.7 activity (nM) |
|---|---|---|---|---|
| 497 | 2-N-methyl-2-N-phenyl-6-(5-{5-[(2,2,2-trifluoroethoxy)methyl]furan-2-yl}-1,2,4-oxadiazol-3-yl)-1,3,5-triazine-2,4-diamine | 2 | Method B HPLC-MS: MH+ requires m/z = 448; Found: m/z = 448, Rt = 2.08 min (100%). 1H NMR (500 MHz, CDCl₃) δ ppm 7.44 (3H, m), 7.31 (3H, m), 6.64 (1H, d), 5.72 (2H, br d), 4.73 (2H, s), 3.93 (2H, q) and 3.62 (3H, s). | 473ᶜ |
| 498 | 6-{5-[3-(cyclopropylmethoxy)azetidin-1-yl]-1,2,4-oxadiazol-3-yl}-2-N-methyl-2-N-phenyl-1,3,5-triazine-2,4-diamine | 27 | Method B HPLC-MS: MH+ requires m/z = 395; Found: m/z = 395, Rt = 1.88 min (83%). 1H NMR (250 MHz, CDCl₃) δ ppm 7.41 (2H, d), 7.30 (3H, m), 5.22 (2H, br s), 4.49 (3H, m), 4.27 (2H, m), 3.59 (3H, s), 3.30 (2H, d), 0.96 (1H, m), 0.59 (2H, m) and 0.23 (2H, m). | 902ᶜ |

-continued

| Example | Name Structure | M | Spectral data | Nav 1.7 activity (nM) |
|---|---|---|---|---|
| 499 | 2-N-methyl-2-N-phenyl-6-{5-[3-(pyridin-2-yloxy)azetidin-1-yl]-1,2,4-oxadiazol-3-yl}-1,3,5-triazine-2,4-diamine | 27 | Method A HPLC-MS: MH+ requires m/z = 418; Found: m/z = 418, Rt = 4.07 min (95%). 1H NMR (250 MHz, CDCl$_3$) δ ppm 8.03 (1H, m), 7.55 (1H, m), 7.33 (2H, m), 7.20 (3H, m), 6.85 (1H, ddd), 6.73 (1H, d), 5.43 (3H, m), 4.64 (2H, dd), 4.30 (2H, dd) and 3.50 (3H, s). | 4590[c] |
| 500 | 2-N-methyl-6-(5-{8-oxa-3-azabicyclo[3.2.1]octan-3-yl}-1,2,4-oxadiazol-3-yl)-2-N-phenyl-1,3,5-triazine-2,4-diamine | 4 | Method B HPLC-MS: MH+ requires m/z = 381; Found: m/z = 381, Rt = 1.71 min (100%). 1H NMR (500 MHz, CDCl$_3$) δ ppm 7.42 (2H, d), 7.31 (3H, m), 5.26 (2H, br s), 4.46 (2H, d), 3.82 (2H, s), 3.59 (3H, s), 3.51 (2H, m), 2.02 (2H, m.) and 1.89 (2H, d). | >9120[c] |
| 501 | 2-N-methyl-2-N-phenyl-6-(5-{4-[(3,3,3-trifluoropropoxy)methyl]piperidin-1-yl}-1,2,4-oxadiazol-3-yl)-1,3,5-triazine-2,4-diamine | 23, 4 | Method A HPLC-MS: MH+ requires m/z = 479; Found: m/z = 479, Rt = 4.41 min (100%). 1H NMR (250 MHz, CDCl$_3$) δ ppm 7.42 (2H, m,), 7.30 (3H, m), 5.20 (2H, br s), 4.31 (2H, d), 3.65 (2H, t), 3.60 (3H, s), 3.33 (2H, d), 3.13 (2H, s), 2.40 (2H, m), 1.85 (3H, m) and 1.34 (2H, d). | 344[c] |

| Example | Name Structure | M | Spectral data | Nav 1.7 activity (nM) |
|---|---|---|---|---|
| 502 | 2-N-phenyl-6-{5-[2-(2,2,2-trifluoroethoxy)pyridin-3-yl]-1,2,4-oxadiazol-3-yl}-1,3,5-triazine-2,4-diamine | 2 | Method A HPLC-MS: MH+ requires m/z = 431; Found: m/z = 431, Rt = 4.32 min (99%). 1H NMR (500 MHz, CDCl$_3$) δ ppm 8.65 (1H, dd), 8.41 (1H, dd), 7.63 (2H, d), 7.46 (1H, br s), 7.39 (2H, t), 7.21 (1H, dd), 7.15 (1H, t), 5.71 (2H, br d) and 4.99 (2H, q). | >8945[c] |
| 503 | 6-[5-(3-phenoxyazetidin-1-yl)-1,2,4-oxadiazol-3-yl]-2-N-phenyl-1,3,5-triazine-2,4-diamine | 4 | Method A HPLC-MS: MH+ requires m/z = 403; Found: m/z = 403, Rt = 4.17 min (100%). 1H NMR (500 MHz, CDCl$_3$) δ ppm 7.60 (2H, d), 7.43 (1H, m), 7.34 (4H, m), 7.12 (1H, t), 7.03 (1H, t), 6.77 (2H, m), 5.58 (2H, m), 5.15 (1H, m), 4.74 (2H, dd) and 4.45 (2H, dd). | 461.5[c] |
| 504 | 2-N-methyl-2-N-phenyl-6-{5-[4-(propane-2-sulfonyl)piperazin-1-yl]-1,2,4-oxadiazol-3-yl}-1,3,5-triazine-2,4-diamine | 9 | Method B, to afford title compound as a white solid (1 mg, 3%). Method B HPLC-MS: MH+ requires m/z = 460; Found: m/z = 460, Rt = 1.82 min (99%). 1H NMR (500 MHz, CDCl$_3$) δ ppm 7.42 (2H, m), 7.32 (3H, m), 5.70 (2H, br s) 3.81 (4H, m), 3.59 (3H, s), 3.50 (4H, m), 3.22 (1H, m) and 1.37 (6H, d). | >5370[c] |

| Example | Name Structure | M | Spectral data | Nav 1.7 activity (nM) |
|---|---|---|---|---|
| 505 | tert-butyl 4-(3-{4-amino-6-[methyl(phenyl)amino]-1,3,5-triazin-2-yl}-1,2,4-oxadiazol-5-yl)piperidine-1-carboxylate | 2 | Method B HPLC-MS: MH+ requires m/z = 453; Found: m/z = 453, Rt = 2.11 min (90%). 1H NMR (250 MHz, CDCl$_3$) δ ppm 7.43 (2H, m), 7.33 (3H, m), 5.27 (2H, br s), 4.16 (2H, m), 3.60 (3H, s), 3.22 (1H, m), 2.93 (2H, m), 2.13 (2H, m), 1.92 (2H, m) and 1.47 (9H, s). | 982[c] |
| 506 | 6-{5-[1-(cyclopropanesulfonyl)piperidin-4-yl]-1,2,4-oxadiazol-3-yl}-2-N-methyl-2-N-phenyl-1,3,5-triazine-2,4-diamine | 23, 9 | Method B HPLC-MS: MH+ requires m/z = 457; Found: m/z = 457, Rt = 1.88 min (100%). 1H NMR (250 MHz, CDCl$_3$) δ ppm 7.43 (2H, m), 7.32 (3H, d), 5.46 (2H, br s), 3.81 (2H, m), 3.60 (3H, s), 3.23 (1H, m), 3.08 (2H, m), 2.23 (5H, m), 1.19 (2H, m) and 1.01 (2H, m). | 7101[c] |

| Example | Name Structure | M | Spectral data | Nav 1.7 activity (nM) |
|---|---|---|---|---|
| 507 | 2-N-methyl-6-(5-{1-[(2-methylpropane)sulfonyl]piperidin-4-yl}-1,2,4-oxadiazol-3-yl)-2-N-phenyl-1,3,5-triazine-2,4-diamine | 23, 9 | Method A HPLC-MS: MH+ requires m/z = 474; Found: m/z = 474, Rt = 4.23 min (100%). 1H NMR (500 MHz, CDCl$_3$) δ ppm 7.44 (2H, m), 7.31 (3H, m), 5.39 (2H, br s), 3.79 (2H, m), 3.60 (3H, s), 3.22 (1H, m), 3.02 (2H, t), 2.77 (2H, d), 2.28 (3H, m), 2.12 (2H, m) and 1.12 (6H, d). | 1234c |
| 508 | 6-{5-[1-(butane-2-sulfonyl)piperidin-4-yl]-1,2,4-oxadiazol-3-yl}-2-N-methyl-2-N-phenyl-1,3,5-triazine-2,4-diamine | 23, 9 | Method A HPLC-MS: MH+ requires m/z = 473; Found: m/z = 473, Rt = 4.03 min (100%). 1H NMR (500 MHz, CDCl$_3$) δ ppm 7.44 (2H, m), 7.31 (3H, m), 5.37 (2H, br s), 3.84 (2H, d), 3.60 (3H, s), 3.24 (1H, m), 3.12 (2H, td), 2.94 (1H, m), 2.22 (2H, d), 2.05 (3H, m), 1.54 (1H, m), 1.33 (3H, d) and 1.03 (3H, t). | 2434c |

| Example | Name Structure | M | Spectral data | Nav 1.7 activity (nM) |
|---|---|---|---|---|
| 509 | 6-{5-[1-(cyclopentanesulfonyl)piperidin-4-yl]-1,2,4-oxadiazol-3-yl}-2-N-methyl-2-N-phenyl-1,3,5-triazine-2,4-diamine | 23, 9 | Method A HPLC-MS: MH+ requires m/z = 485; Found: m/z = 485, Rt = 4.23 min (100%). 1H NMR (500 MHz, CDCl$_3$) δ ppm 7.44 (2H, m), 7.32 (3H, m), 5.33 (2H, br s), 3.84 (2H, d), 3.60 (3H, s), 3.45 (1H, m), 3.23 (1H, m), 3.08 (2H, m), 2.23 (2H, m), 2.08 (2H, m), 2.00 (4H, m), 1.81 (2H, m) and 1.64 (2H, m). | 1106.5$^c$ |
| 510 | 2-N-methyl-6-{5-[1-(2-methylpropyl)piperidin-4-yl]-1,2,4-oxadiazol-3-yl}-2-N-phenyl-1,3,5-triazine-2,4-diamine | 29, 8 | Method A HPLC-MS: MH+ requires m/z = 409; Found: m/z = 409, Rt = 2.97 min (98%). 1H NMR (500 MHz, CDCl$_3$) δ ppm 7.44 (2H, m), 7.32 (3H, m), 5.31 (2H, br s), 3.60 (3H, s), 3.06 (1H, br s), 2.94 (2H, br s), 2.10 (6H, br s), 1.72 (3H, m) and 0.91 (6H, m). | 1262$^c$ |

-continued

| Example | Name Structure | M | Spectral data | Nav 1.7 activity (nM) |
|---|---|---|---|---|
| 512 | tert-butyl 4-{3-[4-amino-6-(phenylamino)-1,3,5-triazin-2-yl]-1,2,4-oxadiazol-5-yl}piperidine-1-carboxylate | 2 | Method C HPLC-MS: MH+ requires m/z = 439; Found: m/z = 439, Rt = 1.41 min (96%). 1H NMR (500 MHz, CDCl$_3$) δ ppm 7.61 (2H, d), 7.42 (1H, br s), 7.38 (2H, t), 7.14 (1H, t), 5.59 (2H, br d), 4.19 (2H, m), 3.26 (1H, m), 2.94 (2H, m), 2.13 (2H, m), 1.95 (2H, m) and 1.48 (9H, s). | 603$^c$ |
| 513 | 6-{5-[1-(cyclopropanesulfonyl)piperidin-4-yl]-1,2,4-oxadiazol-3-yl}-2-N-phenyl-1,3,5-triazine-2,4-diamine | 9 | Method A HPLC-MS: MH+ requires m/z = 443; Found: m/z = 443, Rt = 3.80 min (100%). 1H NMR (250 MHz, CDCl$_3$) δ ppm 7.61 (2H, d), 7.51 (1H, br. s), 7.37 (2H, t), 7.14 (1H, t), 5.85 (2H, br. d), 3.85 (2H, m), 3.24 (1H, m), 3.07 (2H, m), 2.29 (3H, m), 2.14 (2H, m) 1.19 (2H, m) and 1.00 (2H, m). | 631$^c$ |
| 514 | 6-{5-[1-(butane-2-sulfonyl)piperidin-4-yl]-1,2,4-oxadiazol-3-yl}-2-N-phenyl-1,3,5-triazine-2,4-diamine | 9 | Method A HPLC-MS: MH+ requires m/z = 459; Found: m/z = 459, Rt = 4.07 min (100%). 1H NMR (500 MHz, CDCl$_3$) δ ppm 7.60 (2H, d), 7.48 (1H, br s), 7.38 (2H, t), 7.15 (1H, t), 5.65 (2H, br d), 3.87 (2H, d), 3.26 (1H, m), 3.12 (2H, m), 2.95 (1H, m), 2.24 (2H, dd), 2.09 (2H, m), 1.56 (2H, m), 1.34 (3H, d) and 1.03 (3H, t). | 1728.5$^c$ |

| Example | Name Structure | M | Spectral data | Nav 1.7 activity (nM) |
|---|---|---|---|---|
| 515 | 2-N-phenyl-6-{5-[1-(propane-2-sulfonyl)piperidin-4-yl]-1,2,4-oxadiazol-3-yl}-1,3,5-triazine-2,4-diamine | 9 | Method B HPLC-MS: MH+ requires m/z = 445; Found: m/z = 445, Rt = 1.79 min (100%). 1H NMR (500 MHz, CDCl$_3$) δ ppm 7.60 (2H, d), 7.47 (1H, br s), 7.38 (2H, t), 7.15 (1H, t,), 5.66 (2H, br d), 3.88 (2H, m), 3.17 (4H, m), 2.25 (2H, dd), 2.11 (2H, m) and 1.36 (6H, d). | 797[c] |
| 516 | 6-{5-[1-(cyclopentanesulfonyl)piperidin-4-yl]-1,2,4-oxadiazol-3-yl}-2-N-phenyl-1,3,5-triazine2,4-diamine | 9 | Method A HPLC-MS: MH+ requires m/z = 471; Found: m/z = 471, Rt = 3.93 min (100%). 1H NMR (500 MHz, CDCl$_3$) δ ppm 7.60 (2H, d), 7.48 (1H, br s), 7.37 (2H, t), 7.14 (1H, t), 5.75 (2H, br d), 3.86 (2H, m), 3.46 (1H, m), 3.24 (1H, m), 3.08 (2H, m), 2.25 (2H, dd), 2.11 (2H, m), 2.01 (4H, m), 1.82 (2H, m) and 1.63 (2H, m). | >9561[c] |

| Example | Name Structure | M | Spectral data | Nav 1.7 activity (nM) |
|---|---|---|---|---|
| 517 | 4-{3-[4-amino-6-(phenylamino)-1,3,5-triazin-2-yl]-1,2,4-oxadiazol-5-yl}-N,N-dimethylpiperidine-1-sulfonamide | 9 | Method A HPLC-MS: MH+ requires m/z = 446; Found: m/z = 446, Rt = 3.85 min (100%). 1H NMR (500 MHz, CDCl$_3$) δ ppm 7.59 (2H, d), 7.50 (1H, br s), 7.37 (2H, t), 7.14 (1H, m), 5.84 (2H, br. s), 3.75 (2H, m), 3.21 (1H, m), 3.01 (2H, m), 2.84 (6H, s), 2.25 (2H, m) and 2.08 (2H, m). | 570$^c$ |

Example 269, Example 298, Example 435, Example 485 and Example 511 do not exist.

Intermediate 1: 4-Amino-N-hydroxy-6-(methyl-phenyl-amino)-[1,3,5]triazine-2-carboxamidine A solution of 4-amino-6-(methyl-phenyl-amino)-[1,3,5]triazine-2-carbonitrile (Intermediate 2, 138 mg, 0.6 mmol) in EtOH (4 mL) was added to a solution of hydroxylamine hydrochloride (51 mg, 0.7 mmol) and sodium hydrogencarbonate (61 mg, 0.73 mmol) in water (2 mL). The mixture was heated at 70 C for 2 h, allowed to cool to room temperature and the solvent evaporated. The crude solid residue was slurried with water (4 mL) before filtering under reduced pressure to afford Intermediate 1 (95 mg, 60%). Method C HPLC-MS: MH+ requires m/z=260. Found: m/z=260, Rt=0.88 min (98%).

The following N-hydroxy-carboxamidime intermediates were prepared in an analogous manner to Intermediate 1.

| | | |
|---|---|---|
| 4 | 4-Amino-N-hydroxy-6-phenylamino-[1,3,5]triazine-2-carboxamidine | Method C HPLC-MS: MH+ requires m/z = 246; Found: m/z = 246, Rt = 0.82 min (98%) |
| 6 | 4-amino-N-hydroxy-6-(methyl-3-methylphenyl-amino)-[1,3,5]triazine-2-carboxamidine | Method B HPLC-MS: MH+ requires m/z = 274; Found: m/z = 274, Rt = 1.31 min (96%) |
| 8 | 4-Amino-N-hydroxy-6-(methyl-4-methylphenyl-amino)-[1,3,5]triazine-2-carboxamidine | Method B HPLC-MS: MH+ requires m/z = 274; Found: m/z = 274, Rt = 1.33 min (96%) |
| 10 | 4-Amino-N-hydroxy-6-(methyl-3-methoxyphenyl-amino)-[1,3,5]triazine-2-carboxamidine | Method B HPLC-MS: MH+ requires m/z = 290; Found: m/z = 290, Rt = 1.25 min (88%) |
| 12 | 4-Amino-N-hydroxy-6-(methyl-4-methoxyphenyl-amino)-[1,3,5]triazine-2-carboxamidine | Method B HPLC-MS: MH+ requires m/z = 290; Found: m/z = 290, Rt = 1.23 min (97%) |
| 14 | 4-Amino-N-hydroxy-6-(methyl-3-chlorophenyl-amino)-[1,3,5]triazine-2-carboxamidine | Method B HPLC-MS: MH+ requires m/z = 294/296; Found: m/z = 294/296, Rt = 1.40 min (60%) |
| 16 | 4-Amino-N-hydroxy-6-(methyl-4-chlorophenyl-amino)-[1,3,5]triazine-2-carboxamidine | Method B HPLC-MS: MH+ requires m/z = 294/296; Found: m/z = 294/296, Rt = 1.40 min (87%) |
| 22 | 4-Amino-6-[(2-fluoro-phenyl)-methyl-amino]-N-hydroxy-[1,3,5]triazine-2-carboxamidine | Method B HPLC-MS: MH+ requires m/z = 278; Found: m/z = 278, Rt = 1.23 min (98%) |
| 24 | 4-Amino-6-[(3-fluoro-phenyl)-methyl-amino]-N-hydroxy-[1,3,5]triazine-2-carboxamidine | Method B HPLC-MS: MH+ requires m/z = 278; Found: m/z = 278, Rt = 1.26 min (95%) |
| 26 | 4-Amino-6-[(4-fluoro-phenyl)-methyl-amino]-N-hydroxy-[1,3,5]triazine-2-carboxamidine | Method B HPLC-MS: MH+ requires m/z = 278; Found: m/z = 278, Rt = 1.23 min (98%) |
| 28 | 4-Amino-6-[(2-chloro-phenyl)-methyl-amino]-N-hydroxy-[1,3,5]triazine-2-carboxamidine | Method C HPLC-MS: MH+ requires m/z = 294; Found: m/z = 294, Rt = 0.95 min (98%) |

| | | |
|---|---|---|
| 30 | 4-Amino-N-hydroxy-6-(methyl-o-tolyl-amino)-[1,3,5]triazine-2-carboxamidine | Dried further by toluene azeotrope Method B HPLC-MS: MH+ requires m/z = 274; Found: m/z = 274, Rt = 1.74 min (100%) |
| 32 | 4-Amino-6-(benzyl-methyl-amino)-N-hydroxy-[1,3,5]triazine-2-carboxamidine | Method C HPLC-MS: MH+ requires m/z = 274; Found: m/z = 274, Rt = 0.94 min (77%) |
| 35 | 4-Amino-6-(ethyl-phenyl-amino)-N-hydroxy-[1,3,5]triazine-2-carboxamidine | Method C HPLC-MS: MH+ requires m/z = 274; Found: m/z = 274, Rt = 0.94 min (86%) |
| 38 | 4-Amino-6-(2,3-dihydro-indol-1-yl)-[1,3,5]triazine-2-carboxamidine | Dried further by toluene azeotrope Method B HPLC-MS: MH+ requires m/z = 272; Found: m/z = 272, Rt = 1.48 min (75%) |
| 43 | 4-Amino-N-hydroxy-6-(isopropyl-phenyl-amino)-[1,3,5]triazine-2-carboxamidine | Method C HPLC-MS: MH+ requires m/z = 288; Found: m/z = 288, Rt = 1.10 min (75%) |
| 46 | 4-Amino-6-(3-chloro-phenylamino)-N-hydroxy-[1,3,5]triazine-2-carboxamidine | Method C HPLC-MS: MH+ requires m/z = 280/282; Found: m/z = 280/282, Rt = 0.97 min (80%) |
| 49 | 4-Amino-N-hydroxy-6-[methyl-(3-trifluoromethyl-phenyl)-amino]-[1,3,5]triazine-2-carboxamidine | Method C HPLC-MS: MH+ requires m/z = 328; Found: m/z = 328, Rt = 1.06 min (60%) |
| 52 | 4-Amino-N-hydroxy-6-(methyl-2,3-difluorophenyl-amino)-[1,3,5]triazine-2-carboxamidine | Method B HPLC-MS: MH+ requires m/z = 296; Found: m/z = 296, Rt = 1.29 min (93%) |
| 64 | 4-Amino-6-(5-chloro-2-fluoro-phenyl-amino)-N-hydroxy-[1,3,5]triazine-2-carboxamidine | Method B HPLC-MS: MH+ requires m/z = 298; Found: m/z = 298, Rt = 1.18 min (58%) |
| 67 | 4-Amino-6-(2,5-difluoro-phenyl-amino)-N-hydroxy-[1,3,5]triazine-2-carboxamidine | Method B HPLC-MS: MH+ requires m/z = 282; Found: m/z = 282, Rt = 1.72 min (77%) |
| 70 | 4-Amino-6-(2-fluoro-5-methyl-phenyl-amino)-N-hydroxy-[1,3,5]triazine-2-carboxamidine | Method B HPLC-MS: MH+ requires m/z = 278; Found: m/z = 278, Rt = 1.75 min (94%) |
| 73 | 4-Amino-6-(3-chloro-2-fluoro-phenyl-amino)-N-hydroxy-[1,3,5]triazine-2-carboxamidine | Method B HPLC-MS: MH+ requires m/z = 298; Found: m/z = 298, Rt = 1.18 min (62%) |
| 76 | 4-Amino-6-(2-fluoro-3-methyl-phenyl-amino)-N-hydroxy-[1,3,5]triazine-2-carboxamidine | Method B HPLC-MS: MH+ requires m/z = 278; Found: m/z = 278, Rt = 1.78 min (88%) |
| 79 | 4-Amino-6-(2,3-difluoro-phenyl-amino)-N-hydroxy-[1,3,5]triazine-2-carboxamidine | Method B HPLC-MS: MH+ requires m/z = 282; Found: m/z = 282, Rt = 1.51 min (87%) |
| 82 | 4-Amino-N-hydroxy-6-(3,4-dihydroquinolin-1-yl)-[1,3,5]triazine-2-carboxamidine | Method C HPLC-MS: MH+ requires m/z = 286; Found: m/z = 286, Rt = 0.87 min (76%) |
| 85 | 4-Amino-6-(3-fluoro-phenylamino)-N-hydroxy-[1,3,5]triazine-2-carboxamidine | Method C HPLC-MS: MH+ requires m/z = 264; Found: m/z = 264, Rt = 0.90 min (53%) |
| 89 | 4-Amino-N-hydroxy-6-[(2-methoxy-ethyl)-phenyl-amino]-[1,3,5]triazine-2-carboxamidine | Method C HPLC-MS: MH+ requires m/z = 304; Found: m/z = 304, Rt = 0.94 min (34%) |
| 91 | 4-Amino-6-(cyclopropylmethyl-phenyl-amino)-N-hydroxy-[1,3,5]triazine-2-carboxamidine | Method C HPLC-MS: MH+ requires m/z = 300; Found: m/z = 300, Rt = 1.05 min (33%) |
| 97 | 4-Amino-6-(2-fluoro-phenyl-amino)-N-hydroxy-[1,3,5]triazine-2-carboxamidine | Method B HPLC-MS: MH+ requires m/z = 264; Found: m/z = 264, Rt = 1.16 min (96%) |
| 107 | Methyl 3-({4-amino-6-[(Z)-N'-hydroxycarbamimidoyl]-1,3,5-triazin-2-yl}amino)benzoate | Method B HPLC-MS: MH+ requires m/z = 304 Found: m/z = 304, Rt = 1.35 min (91%) |
| 110 | (Z)-4-Amino-N'-hydroxy-6-[(3-methanesulfonylphenyl)amino]-1,3,5-triazine-2-carboximidamide | Batch 1 (precipitate): Method B HPLC-MS: MH+ requires m/z = 324 Found: m/z = 324, Rt = 1.15 min (48%). Batch 2: (conc. filtrate) Found: m/z = 324, Rt = 1.15 min (81%) |
| 117 | 4-Amino-6-[(3-chloro-4-fluorophenyl)amino]-N'-hydroxy-1,3,5-triazine-2-carboximidamide | Method D HPLC-MS: MH+ requires m/z = 312 Found: m/z = 312, Rt = 2.03 min (92%) |
| 153 | 4-Amino-6-[(2,4-difluorophenyl)(methyl)amino]-N'-hydroxy-1,3,5-triazine-2-carboximidamide | Method B HPLC-MS: MH+ requires m/z = 296 Found: m/z = 296, Rt = 1.37 min (98%) |
| 156 | 4-Amino-6-[(6-fluoropyridin-3-yl)(methyl)amino]-N'-hydroxy-1,3,5-triazine-2-carboximidamide | Method B HPLC-MS: MH+ requires m/z = 279 Found: m/z = 279, Rt = 1.12 min (83%) |
| 160 | 4-Amino-N'-hydroxy-6-[(2-methoxyethyl)(phenyl)amino]-1,3,5-triazine-2-carboximidamide | Method B HPLC-MS: MH+ requires m/z = 304 Found: m/z = 304, Rt = 1.27 min (95%) |
| 164 | 4-Amino-6-[(3,4-difluorophenyl)amino]-N'-hydroxy-1,3,5-triazine-2-carboximidamide | Method B HPLC-MS: MH+ requires m/z = 282 Found: m/z = 282, Rt = 1.37 min (91%) |

Intermediate 2: 4-Amino-6-(methyl-phenyl-amino)-[1,3,5]triazine-2-carbonitrile

To 2-amino-4-chloro-6-cyano-[1,3,5]triazine (Intermediate 3, 243 mg, 1.6 mmol) was added anhydrous DMF (5 mL), diisopropylethylamine (0.54 mL, 3.1 mmol) and N-methyl-aniline (184 mg, 1.7 mmol). The mixture was heated at 90 C in a pressure tube for 18 h before allowing to cool to room temperature. The reaction mixture was diluted with EtOAc (20 mL), washed with water (2×10 mL) and the organic layer was dried over anhydrous sodium sulfate and concentrated under reduced pressure to furnish the desired product which was used directly without further purification (138 mg, 39%). Method C HPLC-MS: MH+ requires m/z=227. Found: m/z=227, Rt=1.20 min (93%).

The following carbonitriles were prepared according to a similar procedure to Intermediate 2.

| 5 | 4-Amino-6-phenylamino-[1,3,5]triazine-2-carbonitrile | Method C HPLC-MS: MH+ requires m/z = 213; Found: m/z = 213, Rt = 1.14 min (79%) |
| 23 | 4-Amino-6-[(2-fluoro-phenyl)-methyl-amino]-[1,3,5]triazine-2-carbonitrile | Method C HPLC-MS: MH+ requires m/z = 245; Found: m/z = 245, Rt = 1.41 min (73%) |
| 25 | 4-Amino-6-[(3-fluoro-phenyl)-methyl-amino]-[1,3,5]triazine-2-carbonitrile | Method C HPLC-MS: MH+ requires m/z = 245; Found: m/z = 245, Rt = 1.41 min (82%) |
| 27 | 4-Amino-6-[(4-fluoro-phenyl)-methyl-amino]-[1,3,5]triazine-2-carbonitrile | Method C HPLC-MS: MH+ requires m/z = 245; Found: m/z = 245, Rt = 1.40 min (82%) |
| 29 | 4-Amino-6-[(2-chloro-phenyl)-methyl-amino]-[1,3,5]triazine-2-carbonitrile | Method C HPLC-MS: MH+ requires m/z = 260; Found: m/z = 261, Rt = 1.31 min (60%) |
| 31 | Amino-6-(methyl-o-tolyl-amino)-[1,3,5]triazine-2-carbonitrile | Method C HPLC-MS: MH+ requires m/z = 241; Found: m/z = 241, Rt = 1.24 min (94%) |

Alternatively, 4-amino-6-(methyl-phenyl-amino)-[1,3,5]triazine-2-carbonitrile was prepared according to the following method:

To a stirring solution of 6-chloro-N-methyl-N-phenyl-[1,3,5]triazine-2,4-diamine (Intermediate 41, 360 mg, 2.67 mmol) in DMF (25 ml) was added potassium cyanide (435 mg, 6.68 mmol). The reaction was stirred at 120 C under nitrogen for 2 h. The reaction mixture was diluted with EtOAc (80 ml); the solution was then extracted with 5% aq. sodium hydrogencarbonate solution (2×20 mL), and saturated brine (2×5 mL). After evaporation of the solvent, the crude residue was purified by FCC over silica gel eluting with heptane:EtOAc 1:0 to 8:2 to 6:4 to furnish the desired product (380 mg, 63%). Method C HPLC-MS: MH+ requires m/z=227. Found: m/z=227, Rt=1.24 min (95%).

The following carbonitriles were prepared according to a similar procedure to Intermediate 2.

| 160 | 4-Amino-N'-hydroxy-6-[(2-methoxyethyl)(phenyl)amino]-1,3,5-triazine-2-carboximidamide | Method B HPLC-MS: MH+ requires m/z = 304 Found: m/z = 304, Rt = 1.27 min (95%) |

Intermediate 3: 2-Amino-4-chloro-6-cyano-[1,3,5]triazine

To 2-amino-4-cyano-6-oxo-1,3,5-triazine (J. Am. Chem. Soc., 1961, 83, 1261-2, 2.30 g, 16.8 mmol) was added phosphoryl trichloride (50 mL, 547 mmol) and the mixture heated at 90 C for 2 h. The reaction mixture was cooled to room temperature before pouring onto ice-water (250 mL) and basifying to pH 8 with solid sodium carbonate. The mixture was then extracted into DCM (3×250 mL) and the combined organics were dried over anhydrous sodium sulfate and concentrated under reduced pressure to afford the desired compound, which was used crude without further purification (343 mg, 13%). Method C HPLC-MS: 2 MH+ requires m/z=311. Found: m/z=311, Rt=0.74 min (100%).

Intermediate 7: 4-Cyano-N-methyl-N-3-methylphenyl-[1,3,5]triazine-2,6-diamine

To 2-amino-4-chloro-6-cyano-[1,3,5]triazine (Prepared in an analogous way to Intermediate 3, 46 mg, 296 μmol) was added 1 mL anhydrous DMSO, diisopropylethylamine (77 μL, 444 μmol) and N-methyl-m-toluidine (40 mg, 326 μmol). The mixture was heated at 90 C for 2 h, allowed to cool and diluted with 10 mL ethyl acetate. The mixture was then extracted with water (10 mL), 0.5 M HCl (3×10 mL), water (10 mL) and saturated brine (10 mL). The organic layer was dried further over anhydrous sodium sulfate and evaporated to give the desired product which was used directly without further purification or characterization (42 mg, 59%).

The following carbonitriles were prepared according to a similar procedure to Intermediate 7.

| 9 | 4-Cyano-N-methyl-N-4-methylphenyl-[1,3,5]triazine-2,6-diamine | Used directly without further purification or characterization (42 mg, 59%) |
| 11 | 4-Cyano-N-methyl-N-3-methoxyphenyl-[1,3,5]triazine-2,6-diamine | Used directly without further purification or characterization (69 mg, 91%) |
| 13 | 4-Cyano-N-methyl-N-4-methoxyphenyl-[1,3,5]triazine-2,6-diamine | Used directly without further purification or characterization (56 mg, 73%) |
| 15 | 4-Cyano-N-methyl-N-3-chlorophenyl-[1,3,5]triazine-2,6-diamine | Used directly without further purification or characterization (60 mg, 78%) |
| 17 | 4-Cyano-N-methyl-N-4-chlorophenyl-[1,3,5]triazine-2,6-diamine | Used directly without further purification or characterization (72 mg, 94%) |

Intermediate 18: Pyridine-2-carbonyl chloride

Commercially available.

Intermediate 19: 5-Chloro-thiophene-2-carbonyl chloride

Commercially available.

Intermediate 20: 6-Cyclopentoxynicotinoyl chloride

To 6-cyclopentoxynicotinic acid (Intermediate 21, 74 mg, 358 µmol) was added 2 mL DCE and oxalyl chloride (63 µL, 716 µmol) under an atmosphere of nitrogen. The mixture was heated at 80 C for 1 h and after cooling to room temperature, evaporated to give a clear oil (81 mg, 100%). Method B HPLC-MS (in MeOH, identifying the methyl ester): MH+ requires m/z=222. Found: m/z=222, Rt=2.19 min (94%).

The following acid chlorides were prepared in an analogous manner to Intermediate 20.

| 56 | 1H-Pyrazole-3-carbonyl chloride | Method C HPLC-MS (in MeOH, identifying the methyl ester): MH+ requires m/z = 127; Found: m/z = 127, Rt = 0.65 min (96%) |
| --- | --- | --- |
| 59 | 3-Bromo-pyridine-2-carbonyl chloride | Method C HPLC-MS (in MeOH, identifying the methyl ester): MH+ requires m/z = 217; Found: m/z = 218, Rt = 1.08 min (100%) |
| 88 | 5-Methoxy-pyridine-2-carbonyl chloride | Method C HPLC-MS (in MeOH, identifying the methyl ester): MH+ requires m/z = 168; Found: m/z = 168, Rt = 0.95 min (100%) |
| 170 | 6-Cyclopropylmethoxy-nicotinoyl chloride | Method B HPLC-MS: MH+ requires m/z = 208 (methyl ester); Found: m/z = 208, Rt = 2.06 min (97%) |
| 172 | 6-(Tetrahydro-furan-3-yloxy)-nicotinoyl chloride | Method B HPLC-MS: Methyl ester MH+ requires m/z = 224; Found: m/z = 224, Rt = 1.69 min (97%) |

Intermediate 21: 6-Cyclopentoxynicotinic acid

Commercially available.

Intermediate 33: 4-Amino-6-(benzyl-methyl-amino)-[1,3,5]triazine-2-carbonitrile To N-Benzyl-6-chloro-N-methyl-[1,3,5]triazine-2,4-diamine (Intermediate 34, 350 mg, 1.40 mmol) was added tetra n-butylammonium cyanide (1.15 g, 4.28 mmol) and anhydrous acetonitrile (15 mL). The reaction mixture was stirred at 50 C for 1 h, diluted with EtOAc (20 mL), extracted with water (2×10 mL), dried over anhydrous sodium sulfate and concentrated under reduced pressure to furnish the desired product, which was used directly without further purification (327 mg, 97%). Method C HPLC-MS: MH+ requires m/z=241. Found: m/z=241, Rt=1.29 min (86%).

The following carbonitriles were prepared in an analogous manner to Intermediate 33.

| 118 | 4-Amino-6-[(3-chloro-4-fluorophenyl)amino]-1,3,5-triazine-2-carbonitrile | Method D HPLC-MS: MH+ requires m/z = 265 Found: m/z = 265, Rt = 2.75 min (90%) |
| --- | --- | --- |

Intermediate 34: N-Benzyl-6-chloro-N-methyl-[1,3,5]triazine-2,4-diamine

To cyanuric chloride (250 mg, 1.4 mmol) were added anhydrous THF (10 mL), diisopropylethylamine (0.36 mL, 2.0 mmol) and N-methylbenzylamine (164 mg, 1.4 mmol). The mixture was stirred at 0 C for 0.5 h and then allowed to stir and warm to room temperature for an additional 1.5 h. The reaction mixture was treated with concentrated ammonia (d=0.88, 0.4 mL, 6.2 mmol) and allowed to stir at room temperature for 18 h. The solvent was evaporated and reaction mixture was diluted with EtOAc (10 mL) and washed with 1M aq. HCl (5 mL) and saturated sodium chloride (5 mL). The organic layer was dried over anhydrous sodium sulfate and concentrated under reduced pressure to furnish the desired product which was used directly without further purification (350 mg, 103%). Method C HPLC-MS: MH+ requires m/z=250. Found: m/z=250, Rt=1.25 min (95%).

The following triazine-diamines were prepared in an analogous manner to Intermediate 34.

| 37 | 6-Chloro-N-ethyl-N-phenyl-[1,3,5]triazine-2,4-diamine | Method C HPLC-MS: MH+ requires m/z = 250; Found: m/z = 250, Rt = 1.24 min (99%) |
| --- | --- | --- |
| 40 | 4-Chloro-6-(2,3-dihydro-indol-1-yl)-[1,3,5]triazin-2-ylamine | Method B HPLC-MS: MH+ requires m/z = 248; Found: m/z = 248, Rt = 2.01 min (100%) |
| 45 | 6-Chloro-N-isopropyl-N-phenyl-[1,3,5]triazine-2,4-diamine | Method C HPLC-MS: MH+ requires m/z = 264; Found: m/z = 264, Rt = 1.29 min (98%) |
| 48 | 6-Chloro-N-(3-chloro-phenyl)-[1,3,5]triazine-2,4-diamine | Method C HPLC-MS: MH+ requires m/z = 256/258; Found: m/z = 256/258, Rt = 1.25 min (85%) |
| 51 | 6-Chloro-N-methyl-N-(3-trifluoromethyl-phenyl)-[1,3,5]triazine-2,4-diamine | Method C HPLC-MS: MH+ requires m/z = 304; Found: m/z = 304, Rt = 1.34 min (97%) |
| 55 | 2-Amino-4-chloro-6-(2,3-difluorophenylamino)-[1,3,5]triazine | Method B HPLC-MS: MH+ requires m/z = 258; Found: m/z = 258, Rt = 1.61 min (65%) |
| 66 | 6-Chloro-N-(5-chloro-2-fluoro-phenyl)-[1,3,5]triazine-2,4-diamine | Method B HPLC-MS: MH+ requires m/z = 274; Found: m/z = 274, Rt = 1.86 min (51%) |
| 69 | 6-Chloro-N-(2,5-difluoro-phenyl)-[1,3,5]triazine-2,4-diamine | Method B HPLC-MS: MH+ requires m/z = 258; Found: m/z = 258, Rt = 1.75 min (70%) |
| 72 | 6-Chloro-N-(2-fluoro-5-methyl-phenyl)-[1,3,5]triazine-2,4-diamine | Method B HPLC-MS: MH+ requires m/z = 254; Found: m/z = 254, Rt = 1.77 min (97%) |

| 75 | 6-Chloro-N-(3-chloro-2-fluoro-phenyl)-[1,3,5]triazine-2,4-diamine | Method B HPLC-MS: MH+ requires m/z = 274; Found: m/z = 274, Rt = 1.72 min (55%) |
| 78 | 6-Chloro-N-(2-fluoro-3-methyl-phenyl)-[1,3,5]triazine-2,4-diamine | Method B HPLC-MS: MH+ requires m/z = 254; Found: m/z = 254, Rt = 1.67 min (97%) |
| 81 | 6-Chloro-N-(2,3-difluoro-phenyl)-[1,3,5]triazine-2,4-diamine | Method B HPLC-MS: MH+ requires m/z = 258; Found: m/z = 258, Rt = 1.61 min (65%) |
| 84 | 6-Chloro-4-(3,4-dihydroquinolin-1-yl)-[1,3,5]triazine-2-amine | Method C HPLC-MS: MH+ requires m/z = 262; Found: m/z = 262, Rt = 1.29 min (100%) |
| 87 | 6-Chloro-N-(3-fluoro-phenyl)-[1,3,5]triazine-2,4-diamine | Method C HPLC-MS: MH+ requires m/z = 240; Found: m/z = 240, Rt = 1.18 min (60%) |
| 99 | 6-Chloro-N-(2-fluoro-phenyl)-[1,3,5]triazine-2,4-diamine | Method B HPLC-MS: MH+ requires m/z = 240; Found: m/z = 240, Rt = 1.61 min (97%) |
| 112 | 6-Chloro-2-N-(3-methanesulfonylphenyl)-1,3,5-triazine-2,4-diamine | Method B HPLC-MS: MH+ requires m/z = 300/302 Found: m/z = 300/302, Rt = 1.45 min (90%) |
| 119 | 6-Chloro-2-N-(3-chloro-4-fluorophenyl)-1,3,5-triazine-2,4-diamine | Method D HPLC-MS: MH+ requires m/z = 289 Found: m/z = 289, Rt = 1.79 min (97%) |
| 155 | 6-Chloro-2-N-(2,4-difluorophenyl)-2-N-methyl-1,3,5-triazine-2,4-diamine | Method B HPLC-MS: MH+ requires m/z = 272 Found: m/z = 272, Rt = 1.84 min (99%) |
| 159 | 6-Chloro-2-N-(6-fluoropyridin-3-yl)-1,3,5-triazine-2,4-diamine | Method B HPLC-MS: MH+ requires m/z = 241 Found: m/z = 241, Rt = 1.40 min (100%) |
| 162 | 6-Chloro-2-N-(2-methoxyethyl)-2-N-phenyl-1,3,5-triazine-2,4-diamine | Method B HPLC-MS: MH+ requires m/z = 280 Found: m/z = 280, Rt = 1.76 min (99%) |

Intermediate 36: 4-Amino-6-(ethyl-phenyl-amino)-[1,3,5]triazine-2-carbonitrile 6-Chloro-N-ethyl-N-phenyl-[1,3,5]triazine-2,4-diamine (Intermediate 37, 400 mg, 1.60 mmol) was dissolved in anhydrous DMSO (5 mL) before the addition of potassium cyanide (200 mg, 3.07 mmol). The reaction mixture was stirred at 120 C in a pressure tube for 2 h before allowing to cool to room temperature. The product mixture was diluted with EtOAc (20 mL), extracted with water (2×10 mL), saturated sodium chloride (5 mL), dried over anhydrous sodium sulfate and concentrated under reduced pressure. The desired product was obtained and used directly without further purification (300 mg, 78%). Method C HPLC-MS: MH+ requires m/z=241. Found: m/z=241, Rt=1.27 min (89%).

The following nitriles were prepared in an analogous manner to Intermediate 36.

Intermediate 39: 4-Amino-6-(2,3-dihydro-indol-1-yl)-[1,3,5]triazine-2-carbonitrile 4-Chloro-6-(2,3-dihydro-indol-1-yl)-[1,3,5]triazin-2-ylamine (Intermediate 40, 680 mg, 2.48 mmol), potassium cyanide (323 mg, 4.96 mmol) and 18-crown-6 (328 mg, 1.24 mmol) were charged to a round-bottomed flask then taken up in DMF (12 mL). The resulting mixture was lowered into a heating block preheated to 110 C and stirred under nitrogen for 2 h and then at room temperature for 56 h. The reaction was then diluted with EtOAc (60 ml) and extracted with 5% aq. sodium carbonate solution (2×10 ml), brine (10 ml) and dried further over anhydrous magnesium sulfate. After evaporation of the solvent the crude residue was purified by FCC over silica gel eluting with heptane:EtOAc 1:0 to 8:2 to 1:1 to 0:1 and the column flushed with THF to give the title compound (155 mg, 26%). Method B HPLC-MS: MH+ requires m/z=239. Found: m/z=239, Rt=1.36 min (75%).

| 44 | 4-Amino-6-(isopropyl-phenyl-amino)-[1,3,5]triazine-2-carbonitrile | Method C HPLC-MS: MH+ requires m/z = 255; Found: m/z = 255, Rt = 1.33 min (93%) |
| 47 | 4-Amino-6-(3-chloro-phenylamino)-[1,3,5]triazine-2-carbonitrile | Method C HPLC-MS: MH+ requires m/z = 247/249; Found: m/z = 247/249, Rt = 1.38 min (68%) |
| 50 | 4-Amino-6-[methyl-(3-trifluoromethyl-phenyl)-amino]-[1,3,5]triazine-2-carbonitrile | Method C HPLC-MS: MH+ requires m/z = 295; Found: m/z = 295, Rt = 1.43 min (55%) |
| 86 | 4-Amino-6-(3-fluoro-phenylamino)-[1,3,5]triazine-2-carbonitrile | Used immediately without further characterization or purification |
| 108 | Methyl 3-[(4-amino-6-cyano-1,3,5-triazin-2-yl)amino]benzoate | Method B HPLC-MS: MH+ requires m/z = 271 Found: m/z = 271, Rt = 1.74 min (97%) |
| 111 | 4-Amino-6-[(3-methanesulfonylphenyl)amino]-1,3,5-triazine-2-carbonitrile | Method B HPLC-MS: MH+ requires m/z = 291 Found: m/z = 291, Rt = 1.55 min (81%) |
| 154 | 4-Amino-6-[(2,4-difluorophenyl)(methyl)amino]-1,3,5-triazine-2-carbonitrile | Method B HPLC-MS: MH+ requires m/z = 262 Found: m/z = 262, Rt = 1.84 min (92%) |
| 157 | 4-Amino-6-[(6-fluoropyridin-3-yl)(methyl)amino]-1,3,5-triazine-2-carbonitrile | Method B HPLC-MS: MH+ requires m/z = 246 Found: m/z = 246, Rt = 1.58 min (74%) |
| 161 | 4-Amino-6-[(2-methoxyethyl)(phenyl)amino]-1,3,5-triazine-2-carbonitrile | Method B HPLC-MS: MH+ requires m/z = 271 Found: m/z = 271, Rt = 1.81 min (97%) |

Intermediate 41: 6-Chloro-N-methyl-N-phenyl-[1,3,5]triazine-2,4-diamine

To a stirred solution of (4,6-dichloro-[1,3,5]triazin-2-yl)-methyl-phenyl-amine (Intermediate 42, 2.7 g, 10.58 mmol) in THF (45 ml) was added a solution of conc. aqueous ammonia (3 ml, 52.91 mmol). The reaction was allowed to stir at room temperature for 1 h, the reaction was then diluted with THF (50 ml), treated with conc. aqueous ammonia (1 ml, 17.64 mmol) and stirred for 18 h. The reaction was concentrated under vacuum and taken up in DCM (150 ml); the solution was then extracted with 2M aq. HCl (2×50 mL), and saturated brine (20 mL) and dried further over anhydrous sodium sulfate. The organic phase was evaporated to dryness to furnish the product as an off white solid (2.743 g, 110%). Method B HPLC-MS: MH+ requires m/z=236. Found: m/z=236, Rt=1.76 min (88%). 1H NMR (500 MHz, CDCl$_3$) δ ppm 7.09-7.44 (5H, m), 5.21-5.65 (2H, m), 3.40 (3H, s).

Intermediate 42: (4,6-Dichloro-[1,3,5]triazin-2-yl)-methyl-phenyl-amine

To a stirred solution of cyanuric chloride (2 g, 10.84 mmol) in DCM (40 ml) at 0-5° C. was added dropwise a solution of N-methyl aniline (1.16 ml, 10.84 mmol) and DIPEA (2.08 ml, 12.26 mmol) in DCM (30 ml). The resulting mixture was allowed to warm to room temperature and stirred for 48 h. The reaction mixture was diluted with DCM (40 ml) the solution was then extracted with 2M aq. HCl (2×40 mL) and saturated brine (30 mL) and dried further over anhydrous sodium sulfate. The organic phase was evaporated to dryness to furnish the title compound as an off white solid (2.726 g, 99%). Method C HPLC-MS: MH+ requires m/z=255. Found: m/z=255, Rt=1.48 min (100%). 1H NMR (500 MHz, CDCl3) δ ppm 7.35-7.42 (2H, m), 7.29 (1H, d), 7.15-7.21 (3H, m), 3.48 (3H, s).

Intermediate 53: 2-Amino-4-cyano-6-(2,3-difluorophenyl-N-methylamino)-[1,3,5]triazine To 2-amino-4 cyano-6-(2,3-difluorophenylamino)-[1,3,5]triazine (Intermediate 54, 332 mg, 1.34 mmol) were added potassium carbonate (203 mg, 1.46 mmol), methyl iodide (83 µL, 1.34 mmol) and anhydrous DMF (3 mL). The mixture was stirred at room temperature for 1 h and then diluted with 1M aq. citric acid (10 mL). The resulting mixture was extracted with ethyl acetate (2×10 mL) and the combined extracts washed with water (4×10 mL), saturated brine (10 mL) and dried further over anhydrous sodium sulfate. Evaporation of the solvent gave a gum which was loaded onto a silica column and eluted with heptane-30% ethyl acetate to give the desired compound (320 mg, 91%). Method B HPLC-MS: MH+ requires m/z=262. Found: m/z=262, Rt=1.76 min (98%).

Intermediate 54: 2-Amino-4 cyano-6-(2,3-difluorophenylamino)-[1,3,5]triazine To 2-amino-4-chloro-6-(2,3-difluorophenylamino)-[1,3,5]triazine (Intermediate 55, 1.0 g, 3.89 mmol) was added DABCO (540 mg, 4.67 mmol), tetra n-butylammonium cyanide (1.15 g, 4.28 mmol) and anhydrous acetonitrile (15 mL). The reaction mixture was stirred at 50 C for 1 h, diluted with 50 mL ethyl acetate, extracted with 1M aq. citric acid (2×50 mL), water (2×50 mL), saturated brine (50 mL) and dried further over anhydrous sodium sulfate. Evaporation of the solvent gave a red gum which was purified by column chromatography on silica eluting with DCM-2% ethyl acetate to give the desired compound (429 mg, 69%). Method B HPLC-MS: MH+ requires m/z=249. Found: m/z=249, Rt=1.64 min (91%).

The following nitriles were prepared in an analogous manner to Intermediate 54.

| | | |
|---|---|---|
| 65 | 4-Amino-6-(5-chloro-2-fluoro-phenyl-amino-[1,3,5]triazine-2-carbonitrile | Method B HPLC-MS: MH+ requires m/z = 265; Found: m/z = 265, Rt = 1.84 min (55%) |
| 68 | 4-Amino-6-(2,5-difluoro-phenyl-amino)-[1,3,5]triazine-2-carbonitrile | Method B HPLC-MS: MH+ requires m/z = 249; Found: m/z = 249, Rt = 2.04 min (67%) |
| 71 | 4-Amino-6-(2-fluoro-5-methyl-phenyl-amino)-[1,3,5]triazine-2-carbonitrile | Method B HPLC-MS: MH+ requires m/z = 249; Found: m/z = 249, Rt = 2.08 min (97%) |
| 74 | 4-Amino-6-(3-chloro-2-fluoro-phenyl-amino)-[1,3,5]triazine-2-carbonitrile | Method B HPLC-MS: MH+ requires m/z = 265; Found: m/z = 265, Rt = 1.82 min (56%) |
| 77 | 4-Amino-6-(2-fluoro-3-methyl-phenyl-amino)-[1,3,5]triazine-2-carbonitrile | Method B HPLC-MS: MH+ requires m/z = 245; Found: m/z = 245, Rt = 2.03 min (84%) |
| 80 | 4-Amino-6-(2,3-difluoro-phenyl-amino)-[1,3,5]triazine-2-carbonitrile | Purified using DCM-1% MeOH on silica (778 mg, 53%). Method B HPLC-MS: MH+ requires m/z = 249; Found: m/z = 249, Rt = 1.63 min (96%) |
| 83 | 4-Amino-N-hydroxy-6-(3,4-dihydroquinolin-1-yl)-[1,3,5]triazine-2-carbonitrile | Method C HPLC-MS: MH+ requires m/z = 253; Found: m/z = 253, Rt = 1.58 min (100%) |
| 98 | 4-Amino-6-(2-fluoro-phenyl-amino-[1,3,5]triazine-2-carbonitrile | Method B HPLC-MS: MH+ requires m/z = 231; Found: m/z = 231, Rt = 1.66 min (97%) |

The following oxadiazoles were prepared according to Method 2.

| | | |
|---|---|---|
| 58 | N-Methyl-N-phenyl-6-[5-(3-hydroxypyridin-2-yl)-[1,2,4]oxadiazol-3-yl]-[1,3,5]triazine-2,4-diamine | Method A HPLC-MS: MH+ requires m/z = 363; Found: m/z = 363, Rt = 3.75 min (100%) |
| 63 | 3-{3-[4-Amino-6-(methyl-phenyl-amino)-[1,3,5]triazin-2-yl]-[1,2,4]oxadiazol-5-yl}-pyridin-2-ol | Method B HPLC-MS: MH+ requires m/z = 363; Found: m/z = 363, Rt = 1.51 min (64%) |
| 102 | 3-{3-[4-Amino-6-(methyl-phenyl-amino)-[1,3,5]triazin-2yl]-[1,2,4]oxadiazol-5-yl}-8-aza-bicyclo[3.2.1]octane-8-carboxylic acid tert-butyl ester | Method B HPLC-MS: MH+ requires m/z = 479; Found: m/z = 479, Rt = 2.11 min (91%) |

| | | |
|---|---|---|
| 106 | tert-Butyl-4-(3-{4-amino-6-[methyl(phenyl)amino]-1,3,5-triazin-2-yl}-1,2,4-oxadiazol-5-yl)piperidine-1-carboxylate | Method B HPLC-MS: MH+ requires m/z = 452 Found: m/z = 453, Rt = 2.04 min (100%) |
| 114 | tert-Butyl 3-(3-{4-amino-6-[methyl(phenyl)amino]-1,3,5-triazin-2-yl}-1,2,4-oxadiazol-5-yl)pyrrolidine-1-carboxylate | Method B HPLC-MS: MH+ requires m/z = 439 Found: m/z = 439, Rt = 2.02 min (95%) |
| 141 | 1-[6-(3-{4-Amino-6-[methyl(phenyl)amino]-1,3,5-triazin-2-yl}-1,2,4-oxadiazol-5-yl)pyridin-3-yl]ethan-1-one | Method C HPLC-MS: MH+ requires m/z = 389 Found: m/z = 389, Rt = 1.26 min (78%) |
| 147 | Mixture of methyl 2-(3-{4-amino-6-[methyl(phenyl)amino]-1,3,5-triazin-2-yl}-1,2,4-oxadiazol-5-yl)pyridine-3-carboxylate and methyl 3-(3-{4-amino-6-[methyl(phenyl)amino]-1,3,5-triazin-2-yl}-1,2,4-oxadiazol-5-yl)pyridine-2-carboxylate | Used without further purification |
| 150 | tert-Butyl 3-(3-{4-amino-6-[methyl(phenyl)amino]-1,3,5-triazin-2-yl}-1,2,4-oxadiazol-5-yl)azetidine-1-carboxylate | Method A HPLC-MS: MH+ requires m/z = 425; Found: m/z = 425, Rt = 4.24 (99%) |

Intermediate 57:
6-(2,2,2-Trifluoro-ethoxy)-nicotinoyl chloride

To 6-(2,2,2-trifluoro-ethoxy)-nicotinic acid (100 mg, 0.45 mmol) was added DCE (5 mL) and oxalyl chloride (60 ul, 0.68 mmol) under an atmosphere of nitrogen. The mixture was stirred at rt for 1.5 h then heated at 80 C for 2 h and after cooling to room temperature, evaporated to give the title compound as a pale yellow oil (110 mg, 100%). Method C HPLC-MS (in MeOH, identifying the methyl ester): MH+ requires m/z=236. Found: m/z=236, Rt=1.41 min (95%).

Intermediate 60: N-Methyl-N-phenyl-6-(5-trichloromethyl-[1,2,4]oxadiazol-3-yl)-[1,3,5]triazine-2,4-diamine To 4-amino-N-hydroxy-6-(methyl-3-methylphenyl-amino)-[1,3,5]triazine-2-carboxamidine (prepared according to an analogous method to Intermediate 1, 1 g, 3.86 mmol) in anhydrous toluene (2.5 mL) under nitrogen was added trichloroacetic anhydride (845 µL, 4.63 mmol). The mixture was stirred at room temp for 1 h at which point anhydrous pyridine (2.5 mL) was added and the mixture stirred for 45 min. Anhydrous pyridine (10 mL), and trichloroacetic anhydride (300 µL, 1.64 mmol) were then added and the mixture stirred at room temp for 30 min then heated to 85 C for 35 min. The reaction mixture was diluted with EtOAc (100 mL), and the solution was extracted with sat.aq. sodium hydrogencarbonate solution (3×50 ml), brine (50 mL) and dried over anhydrous sodium sulfate. The title compound was obtained as a brown solid (1.22 g, 82%). Method B HPLC-MS: MH+ requires m/z=386. Found: m/z=386, Rt=2.20 min (77%).

Intermediate 61: 6-Methoxy-nicotinic acid

Potassium tert-butoxide (323 mg, 2.88 mmol) and methanol (64 µL, 1.58 mmol) were taken up in anhydrous THF (6 mL) in a RBF under nitrogen, the mixture was stirred for 10 min at which time a solution of 6-chloropyridine-3-carbonitrile (200 mg, 1.44 mmol) in anhydrous THF (2 mL) was added slowly. The mixture was stirred at room temperature for 18 h. The reaction was treated with methanol (6 µL, 0.148 mmol), stirred for 2 h, then treated with methanol (20 µL, 0.494 mmol), stirred for 2 h, then treated with potassium tert-butoxide (50 mg, 0.446 mmol) and stirred for 18 h. The mixture was then concentrated in vacuo, suspended in sat. aq. sodium hydrogencarbonate solution and extracted with EtOAc (5×10 mL). The combined extracts were washed with brine (10 mL) and concentrated in vacuo to give the title compound was obtained (80 mg, 36%). 1H NMR (500 MHz, CDCl$_3$) δ ppm 8.94 (1H, s), 8.22 (1H, dd, J=8.4, 1.8 Hz), 6.82 (1H, d, J=8.7 Hz), 4.03 (3H, s).

Intermediate 62: 5-{3-[4-Amino-6-(methyl-phenyl-amino)-[1,3,5]triazin-2-yl][1,2,4]oxadiazol-5-yl}-thiophene-2-carboxylic acid To a stirred solution of 5-{3-[4-amino-6-(methyl-phenyl-amino)-[1,3,5]triazin-2-yl]-[1,2,4]oxadiazol-5-yl}-thiophene-2-carboxylic acid methyl ester (Example 82, 1.02 g, 2.45 mmol) in methanol (5 mL) was added aqueous sodium hydroxide solution (2M, 5 mL). The mixture was stirred for 18 h then acidified with hydrochloric acid (1M, 10 mL). The precipitate formed was filtered off and dried in vacuo at 50 C for 2 h to give the title compound (450 mg, 46%). Method B HPLC-MS: MH+ requires m/z=396. Found: m/z=396, Rt=1.84 min (68%).

Intermediate 90: 4-Amino-6-[(2-methoxy-ethyl)-phenyl-amino]-[1,3,5]triazine-2-carbonitrile A mixture of 4-amino-6-phenylamino-[1,3,5]triazine-2-carbonitrile (prepared in an analogous manner to Intermediate 5, 100 mg, 470 µmol), 1-bromo-2-methoxyethane (50 µl, 0.52 mmol) and potassium carbonate 130 mg, 0.94 mmol) in DMF (5 ml) was heated to 100 C and stirred 3 h. The mixture was cooled to room temperature, diluted with ethyl acetate, washed with water, dried over sodium sulfate and concentrated under vacuum to give the crude product which was used without further purification (400 mg, >100%, contains DMF). Method C HPLC-MS: MH+ requires m/z=271. Found: m/z=271, Rt=1.23 min (52%).

Intermediate 92: 4-Amino-6-(cyclopropylmethyl-phenyl-amino)-[1,3,5]triazine-2-carbonitrile To a solution of 4-amino-6-phenylamino-[1,3,5]triazine-2-carbonitrile (prepared in an analogous manner to Intermediate 5, 160 mg, 0.75 mmol) in DMF (6 mL) was added potassium carbonate (207 mg, 150 μmol) followed by bromomethyl-cyclopropane (111 mg, 830 μmol). The mixture was heated at 120 C for 3 h, allowed to cool to room temperature before extracting into ethyl acetate (10 mL) and washing with water (3×10 mL). The organic layer was dried over anhydrous sodium sulfate, filtered and concentrated under reduced pressure to afford the title compound, which was used without further purification (300 mg, >100%). Method C HPLC-MS: MH+ requires m/z=267. Found: m/z=267, Rt=1.38 min (43%).

Intermediate 93: 3-Methoxypyridine-2-carbonyl chloride

To a stirred suspension of sodium 3-methoxypyridine-2-carboxylate (Intermediate 94, ~3.3 mmol) in dichloromethane (10 ml) and pyridine (5 ml) at 0 C (ice-bath) was added dropwise oxalyl chloride (0.58 ml, 6.6 mmol). The mixture was stirred 10 minutes, then DMF (1 drop) was added. The mixture was warmed to room temperature and stirred 2 h then concentrated under vacuum. The residue was dissolved in dichloromethane (10 ml) and filtered through a plug of cotton wool. The filtrate was concentrated under vacuum to give the title compound as a brown oil (0.16 g) which was used without further purification or characterisation.

Intermediate 94: Sodium 3-methoxypyridine-2-carboxylate

To a stirred solution of methyl 3-methoxypyridine-2-carboxylate (Intermediate 95, 0.55 g, 3.3 mmol) in methanol (10 ml) was added dropwise aqueous sodium hydroxide solution (1M, 4 ml, 4 mmol). The mixture was left to stand overnight. The mixture was concentrated under vacuum to give a white solid, which was used without further purification or characterisation.

Intermediate 95: Methyl 3-methoxypyridine-2-carboxylate

A mixture of methyl 3-hydroxypyridine-2-carboxylate (Intermediate 96, 1.2 g, 7.8 mmol), potassium carbonate (1.2 g, 8.7 mmol), iodomethane (0.63 ml, 1.0 mmol) and DMF (10 ml) was stirred overnight. The mixture was diluted with water (20 ml) and extracted with ethyl acetate (2×20 ml). The combined organic extracts were washed with water and concentrated under vacuum. The residue (0.82 g) was purified by flash column chromatography (5 g silica; heptane-ethyl acetate, 1:0-5:1-2:1) to give the title compound as a clear oil (0.58 g, 45%). Method C HPLC-MS: MH+ requires m/z=168. Found: m/z=168, Rt=0.76 min (100%).

Intermediate 96: Methyl 3-hydroxypyridine-2-carboxylate

A mixture of 3-hydroxypyridine-2-carboxylic acid (2.0 g, 14.4 mmol), conc sulfuric acid (0.5 ml) and methanol (100 ml) was heated to reflux and stirred for 48 hours. The mixture was cooled to room temperature and stirred for 60 hours then concentrated under vacuum. The residue was dissolved in water (20 ml), basified to pH 8 using solid sodium carbonate (care: gas evolution!) and extracted with ethyl acetate (3×20 ml). The combined organic extracts were washed with water and concentrated under vacuum to give the title compound as a white solid (1.22 g, 55%). Method C HPLC-MS: MH+ requires m/z=154. Found: m/z=154, Rt=0.78 min (100%).

Intermediate 100: 6-[5-(6-N-toluene sulfonyl-hydrazonomethyl-pyridin-3-yl)-[1,2,4]oxadiazol-3-yl]-N-methyl-N-phenyl-[1,3,5]triazine-2,4-diamine To (5-{3-[4-Amino-6-(methyl-phenyl-amino)-[1,3,5]triazin-2-yl]-[1,2,4]oxadiazol-5-yl}-pyridin-2-yl)-methanol (prepared in an analogous manner to Example 297, 150 mg, 0.40 mmol) in DCM (5 mL) was added Dess-Martin periodinane (185 mg, 0.44 mmol) and the mixture stirred at room temperature for 1 h. The reaction mixture was evaporated and to the crude residue added p-toluenesulfonylhydrazide (74 mg, 0.40 mmol) and glacial acetic acid (4 mL). The mixture was heated at 50 C for 2 h and then evaporated. The residue was taken up in DCM (5 mL), extracted with a 1M aq. solution of sodium bicarbonate solution (5 mL) and dried over anhydrous sodium sulfate to give 268 mg crude solid. The solid was then triturated with EtOH (4×3 mL) to give the title compound (104 mg, 535) Method B HPLC-MS: MH+ requires m/z=543. Found: m/z=543, Rt=1.99 min (64%).

Intermediate 101: Racemic 6-[(1R,3R,5S)-5-(8-Aza-bicyclo[3.2.1]oct-3-yl)-[1,2,4]oxadiazol-3-yl]-N-methyl-N-phenyl-[1,3,5]triazine-2,4-diamine To 3-{3-[4-amino-6-(methyl-phenyl-amino)-[1,3,5]triazin-2-yl]-[1,2,4]oxadiazol-5-yl}-8-aza-bicyclo[3.2.1]octane-8-carboxylic acid tert-butyl ester (Intermediate 102, 125 mg, 0.37 mmol) was added DCM (3 mL) and trifluoroacetic acid (3 mL). The mixture was stirred at room temperature for 1 h and then evaporated. The residue was taken up in DCM (5 mL) and washed with 1M sodium bicarbonate solution (5 mL), saturated brine (5 mL) and dried over sodium sulfate, Evaporation afforded the title compound which was used directly for the next stage (74 mg, 53%). Method B HPLC-MS: MH+ requires m/z=379. Found: m/z=379, Rt=1.37 min (95%).

Intermediate 103: 8-Aza-bicyclo[3.2.1]octane-3,8-dicarboxylic acid 8-tert-butyl ester To 3-cyano-8-aza-bicyclo[3.2.1]octane-8-carboxylic acid tert-butyl ester (Intermediate 104, 190 mg, 0.81 mmol) was added potassium hydroxide (270 mg, 4.83 mmol), EtOH (3 mL) and water (1 mL). The mixture was heated at 95 C for 4 h, allowed to cool and acidified to pH=2 with a 1 M aq. solution of citric acid. The mixture was then extracted with EtOAc (2×5 mL) and the combined extracts washed with saturated brine (10 mL), and dried over anhydrous sodium sulfate. Evaporation gave the crude title compound which was used directly without further purification (190 mg, 94%). Method B HPLC-MS: MH+ requires m/z=255. Found: m/z=200 (MH-$^t$Bu), Rt=1.68 min (76%).

Intermediate 104: 3-Cyano-8-aza-bicyclo[3.2.1]octane-8-carboxylic acid tert-butyl ester To 3-oxo-8-aza-bicyclo[3.2.1]octane-8-carboxylic acid tert-butyl ester (300 mg, 1.33 mmol) was added DME (9 mL) and EtOH (0.2 mL). The mixture was cooled to 0 C when TOSMIC (530 mg, 2.65 mmol) and potassium tert-butoxide (609 mg, 5.2 mmol) were added. The mixture was stirred to room temperature and then heated at 50 C for 18 h. After this time the reaction was evaporated and loaded onto a silica column and eluted with heptane-10% to 30% ethyl actetate to give the title compound (216 mg, 69%). Method B HPLC-MS: MH+ requires m/z=237. Found: m/z=237, Rt=1.35 min (86%).

Intermediate 105: 2-N-Methyl-2-N-phenyl-6-[5-(piperidin-4-yl)-1,2,4-oxadiazol-3-yl]-1,3,5-triazine-2,4-diamine hydrochloride tert-Butyl-4-(3-{4-amino-6-[methyl(phenyl)amino]-1,3,5-triazin-2-yl}-1,2,4-oxadiazol-5-yl)piperidine-1-carboxylate (Intermediate 106, 934 mg, 2.06 mmol) and 4M hydrogen chloride in 1,4-dioxane (5 mL) was combined in DCM (5 mL) at 0 C. The reaction was warmed to RT and left to stir for 18 h. The mixture was concentrated under reduced pressure to give title compound as a yellow solid (832 mg). Method B HPLC-MS: MH+ requires m/z=352 Found: m/z=353, Rt=1.23 min (100%).

Intermediate 109: Methyl 3-[(4-amino-6-chloro-1,3,5-triazin-2-yl)amino]benzoate

Methyl 3-aminobenzoate (0.69 g, 4.55 mmol) and a 1N NaOH aqueous solution (0.91 mL, 0.91 mmol) were added to a solution of 4,6-dichloro-1,3,5-triazin-2-amine (0.75 g, 4.55 mmol) in a 1:1 MeCN/water mixture (40 mL) at 0 C. The mixture was stirred at 0 C for 1 h and room temperature for 3 days. The acetonitrile was removed under vacuum and the resulting white solid in water was filtered and dried under vacuum to provide the title compound (1.1 g, 87%). Method B HPLC-MS: MH+ requires m/z=280/282 Found: m/z=280/282, Rt=1.69 min (95%).

Intermediate 113: 2-N-Methyl-2-N-phenyl-6-[5-(pyrrolidin-3-yl)-1,2,4-oxadiazol-3-yl]-1,3,5-triazine-2,4-diamine hydrochloride salt A 4N solution of HCl in dioxane (7 mL, 28.2 mmol) was added slowly to a solution of tert-butyl 3-(3-{4-amino-6-[methyl(phenyl)amino]-1,3,5-triazin-2-yl}-1,2,4-oxadiazol-5-yl)pyrrolidine-1-carboxylate (Intermediate 114, 1.24 g, 2.82 mmol) in dioxane (15 mL) at room temperature. The reaction mixture was stirred at room temperature for 18 h. The reaction mixture was concentrated under vacuum to afford the title compound as a yellow solid (1.05 g, 100%). Method B HPLC-MS: MH+ (free-based) requires m/z=339 Found: m/z=339, Rt=1.20 min (96%).

Intermediate 115: Ethyl 3-{4-amino-6-[(3-fluorophenyl)amino]-1,3,5-triazin-2-yl}-1,2,4-oxadiazole-5-carboxylate Ethyl chlorooxoacetate (0.12 g, 0.84 mmol) was added to a mixture of (4-amino-6-[(3-fluorophenyl)amino]-N-hydroxy-1,3,5-triazine-2-carboximidamide (prepared in an analogous manner to Intermediate 97, 0.20 g, 0.76 mmol) in pyridine (0.12 mL) and toluene (4 mL) at room temperature. The reaction mixture was stirred at room temperature for 1 h and at 110 C for 3 h. The mixture was then cooled at room temperature; DCM (20 mL) and 1M aq. HCl (50 mL) were added. The phases were separated and the aqueous phase was extracted with DCM (2×20 mL). The organic extracts were combined, dried over sodium sulfate, and concentrated. The crude residue was washed with diethyl ether. The organic filtrate was concentrated and purified by flash chromatography to afford the title compound as a yellow solid (45 mg, 17%). Method D HPLC-MS: MH+ requires m/z=346 Found: m/z=346, Rt=2.70 min (40%).

Intermediate 116: 2-N-(3-Fluorophenyl)-6-[5-(trichloromethyl)-1,2,4-oxadiazol-3-yl]-1,3,5-triazine-2,4-diamine Trichloroacetic anhydride (2.61 mL, 14.3 mmol) was added to a solution of 4-amino-6-[(3-fluorophenyl)amino]-N-hydroxy-1,3,5-triazine-2-carboximidamide (prepared in an analogous manner to Intermediate 97, 3.13 g, 11.9 mmol) in dioxane (60 mL) containing molecular sieves (3 spoons) at 0 C. The reaction mixture was stirred at room temperature for 3.5 h, at 100 C for 30 min and at 110 C for 30 min. The reaction mixture was concentrated; the resulting residue was dissolved in EtOAc (100 mL) and washed successively with 1M aq. HCl and saturated aq. sodium bicarbonate. The organic phase was concentrated to afford the title compound (4.2 g, 91%) which was used in the subsequent step without further purification.

The following amino-oxadiazoles were prepared according to Method 4.

| 121 | tert-Butyl N-[1-(3-{4-amino-6-[methyl(phenyl)amino]-1,3,5-triazin-2-yl}-1,2,4-oxadiazol-5-yl)piperidin-4-yl]carbamate | Method C HPLC-MS: MH+ requires m/z = 468 Found: m/z = 468, Rt = 1.33 min (98%) |
|---|---|---|
| 132 | 1-(3-{4-Amino-6-[methyl(phenyl)amino]-1,3,5-triazin-2-yl}-1,2,4-oxadiazol-5-yl)piperidin-4-ol | Method C HPLC-MS: MH+ requires m/z = 369; Found: m/z = 369, Rt = 1.14 min (69%) |
| 138 | tert-Butyl 4-(3-{4-amino-6-[methyl(phenyl)amino]-1,3,5-triazin-2-yl}-1,2,4-oxadiazol-5-yl)piperazine-1-carboxylate | 1H NMR (500 MHZ, CDCl$_3$) δ ppm 7.45 (2H, t), 7.32 (3H, m), 5.13 (2H, br s), 3.72 (4H, br s), 3.61 (3H, s), 3.57 (4H, m) and 1.50 (9H, s) |
| 152 | tert-Butyl 4-(3-{4-amino-6-[methyl(phenyl)amino]-1,3,5-triazin-2-yl}-1,2,4-oxadiazol-5-yl)piperazine-1-carboxylate | Method B HPLC-MS: MH+ requires m/z = 454; Found: m/z = 454, Rt = 2.00 min (96%) |
| 166 | 1-{3-[4-Amino-6-(methyl-phenyl-amino)-[1,3,5]triazin-2-yl]-[1,2,4]oxadiazol-5-yl}-azetidin-3-ol | Method C HPLC-MS: MH+ requires m/z = 341; Found: m/z = 341, Rt = 1.10 min (92%) |

Intermediate 122: 3-(4-Fluorophenoxy)azetidine hydrochloride

To a stirred solution of 1-(diphenylmethyl)-3-(4-fluorophenoxy)azetidine (Intermediate 123, 3.2 g, 9.6 mmol) in DCE (20 ml) was added dropwise 1-chloroethylchloroformate (1.6 ml, 1.5 eq). The mixture was stirred 10 min then heated to reflux for 6 h. More 1-chloroethylchloroformate was added (1.6 ml) and heating was continued for 3 h. The mixture was cooled to room temperature and concentrated under vacuum. The residue was dissolved in MeOH (20 mL) and left to stand overnight. The mixture was heated under reflux and stirred for 1 h, then cooled to room temperature and concentrated under vacuum. The residue was crystallised under diethyl ether; the solid was broken up with a spatula, filtered off—washing with diethyl ether—and dried under vacuum to give the title compound as a cream solid (1.78 g, 91%). Method B HPLC-MS: MH+ requires m/z=168 Found: m/z=168, Rt=0.69 min (92%). 1H NMR (250 MHZ, DMSO-d6) δ ppm 9.50 (2H, br s), 7.15 (2H, t), 6.89 (2H, dd), 5.03 (1H, m), 4.39 (2H, m), and 3.93 (2H, m).

Intermediate 123: 1-(Diphenylmethyl)-3-(4-fluorophenoxy)azetidine

To a stirred suspension of sodium hydride (60% dispersion in mineral oil, 0.80 g, 20 mmol) in anhydrous DMF (10 ml) under nitrogen was added dropwise a solution of 1-benzhydryl-azetidin-3-ol (3.5 g, 15 mmol) in DMF (10 ml)—Care: hydrogen gas evolution! The mixture was stirred 30 min after gas evolution had ceased then 1,4-difluorobenzene (1.8 mL, 18 mmol) was added dropwise. The mixture was heated to 100 C and stirred for 12 h, then cooled to room temperature and poured into aq sodium hydrogencarbonate solution (50 ml) and extracted twice with EtOAc (2×50 ml). The combined organic layers were washed with water, concentrated under vacuum and purified by flash column chromatography (25 g silica gel; heptane-EtOAc: 1:0-9:1). The product-containing fractions were combined, concentrated under vacuum, washed with heptane and dried under vacuum to give the title compound (3.256 g, 67%). Method B HPLC-MS: MH+ requires m/z=334 Found: m/z=334, Rt=1.69 min (89%). 1H NMR (250 MHz, CDCl$_3$) δ ppm 7.48-7.39 (4H, m), 7.39-7.12 (6H, m), 6.94 (2H, t), 6.71 (2H, dd), 4.75 (1H, m), 4.46 (1H, s), 3.78-3.65 (2H, m), and 3.20-3.07 (2H, m).

Intermediate 124; 5-(3-{4-Amino-6-[methyl(phenyl)amino]-1,3,5-triazin-2-yl}-1,2,4-oxadiazol-5-yl)pyridine-2-carboxylic acid To a solution of (methyl 5-(3-{4-amino-6-[methyl(phenyl)amino]-1,3,5-triazin-2-yl}-1,2,4-oxadiazol-5-yl)pyridine-2-carboxylate) (prepared in an analogous manner to Example 279, 500 mg, 1.23 mmol) in MeOH (20 mL) was added a 1M sodium hydroxide aq. solution (1.85 mL, 1.85 mmol). The solution was stirred at room temperature overnight and evaporated to dryness. The resulting solid was dissolved in water (20 mL) and the solution acidified to pH 3 with a 1M HCl aq. solution. The resulting solid was filtered and dried to afford the desired product as a beige solid (418 mg, 87%). Method C HPLC-MS: MH+ requires m/z=391. Found: m/z=390.9, Rt=1.16 min (95%).

Intermediate 126: [2-(3-{4-amino-6-[methyl(phenyl)amino]-1,3,5-triazin-2-yl}-1,2,4-oxadiazol-5-yl)pyridin-3-yl]methyl methanesulfonate[3-(3-{4-amino-6-[methyl(phenyl)amino]-1,3,5-triazin-2-yl}-1,2,4-oxadiazol-5-yl)pyridin-2-yl]methyl methanesulfonate and [2-(3-{4-amino-6-[methyl(phenyl)amino]-1,3,5-triazin-2-yl}-1,2,4-oxadiazol-5-yl)pyridin-3-yl]methyl methanesulfonate[3-(3-{4-amino-6-[methyl(phenyl)amino]-1,3,5-triazin-2-yl}-1,2,4-oxadiazol-5-yl)pyridin-2-yl]methyl methanesulfonate (mixture of regioisomers)

To a solution of [2-(3-{4-amino-6-[methyl(phenyl)amino]-1,3,5-triazin-2-yl}-1,2,4-oxadiazol-5-yl)pyridin-3-yl]methanol and [3-(3-{4-amino-6-[methyl(phenyl)amino]-1,3,5-triazin-2-yl}-1,2,4-oxadiazol-5-yl)pyridin-2-yl]methanol; (Intermediate 127-mixture of regioisomers, 300 mg, 0.797 mmol) in DCM (25 mL) under nitrogen was added methanesulfonyl chloride (93 µL, 1.19 mmol) and triethylamine (177 µL, 1.27 mmol). The reaction mixture was stirred at room temperature for 4 h and then washed with water (3×25 ml). The organic phase was dried over magnesium sulfate and evaporated to dryness to afford the title compound which was used without further purification (312 mg, 86%). Method C HPLC-MS: MH+ requires m/z=455. Found: m/z=455, Rt=1.25 min (70%).

The following mesylates were prepared according to the procedure described for Intermediate 126.

| | | |
|---|---|---|
| 128 | Methanesulfonic acid 5-{3-[4-amino-6-(methyl-phenyl-amino)-[1,3,5]triazin-2-yl]-[1,2,4]oxadiazol-5-yl}-pyridin-2-ylmethyl ester | Used immediately in the next step |
| 181 | tert-Butyl 4-[(methanesulfonyloxy)methyl]piperidine-1-carboxylate | Method C HPLC-MS: MH+ requires m/z = 294 Found: m/z = 237 (MH+ − tBu), Rt = 1.38 min (100%) |
| 189 | Methyl 6-[(methanesulfonyloxy) methyl] pyridine-3-carboxylate | Method B HPLC-MS: MH+ requires m/z = 246 Found: m/z = 246, Rt = 1.39 min (78%) |
| 193 | Methyl 6-[1-(methanesulfonyloxy) ethyl]pyridine-3-carboxylate | Method B HPLC-MS: MH+ requires m/z = 260 Found: m/z = 260, Rt = 1.67 min (85%) |
| 239 | tert-Butyl 4-(methanesulfonyloxy)piperidine-1-carboxylate | 1H NMR (500 MHZ, CDCl$_3$) δ ppm 4.02 (2H, br s), 3.14 (2H, q), 2.98 (3H, m), 1.97 (2H, d), 1.52 (2H, m) and 1.48 (9H, s) |
| 258 | [(1R,5S,6S)-3-Benzyl-3-azabicyclo[3.1.0]hexan-6-yl]methyl methanesulfonate | Method B HPLC-MS: MH+ requires m/z = 282; Found: m/z = 282, Rt = 1.01 min (65%) |
| 288 | 3-Methanesulfonyloxymethyl-azetidine-1-carboxylic acid tert-butyl ester | Method C HPLC-MS: MNa+ requires m/z = 288; Found: m/z = 288, Rt = 1.25 min (100%) |

Intermediate 127: [2-(3-{4-amino-6-[methyl(phenyl) amino]-1,3,5-triazin-2-yl}-1,2,4-oxadiazol-5-yl)pyridin-3-yl]methanol and [3-(3-{4-amino-6-[methyl (phenyl)amino]-1,3,5-triazin-2-yl}-1,2,4-oxadiazol-5-yl)pyridin-2-yl]methanol (mixture of regioisomers)

To a solution of 3-{3-[4-amino-6-(methyl-phenyl-amino)-[1,3,5]triazin-2-yl]-[1,2,4]oxadiazol-5-yl}-pyridine-2-carboxylic acid methyl ester and 2-{3-[4-amino-6-(methyl-phenyl-amino)-[1,3,5]triazin-2-yl]-[1,2,4]oxadiazol-5-yl}-nicotinic acid methyl ester (Intermediate 147-mixture of regioisomers, 800 mg, 1.98 mmol) in anhydrous THF (75 mL) was added sodium borohydride (187 mg, 4.95 mmol) portion-wise under nitrogen at 0 C. The solution was allowed to warm to room temperature and stirred for a further 16 h. The reaction mixture was quenched with water (10 mL) and extracted into EtOAc (3×50 mL). Combined organics were washed with brine, dried over magnesium sulfate, evaporated to dryness and triturated with diethyl ether. The isolated light yellow solid was dried under vacuum to afford the title compound (540 mg, 73%). Method A HPLC-MS: MH+ requires m/z=377. Found: m/z=377, Rt=3.40 min (64%).

Intermediate 130: [5-(3-{4-Amino-6-[(2-methoxyethyl)(phenyl)amino]-1,3,5-triazin-2-yl}-1,2,4-oxadiazol-5-yl)pyridin-2-yl]methanol To a solution of methyl 5-(3-{4-amino-6-[(2-methoxyethyl)(phenyl)amino]-1,3,5-triazin-2-yl}-1,2,4-oxadiazol-5-yl)pyridine-2-carboxylate (Example 311, 212 mg, 0.472 mmol) in anhydrous THF (50 mL) at 0 C, under nitrogen, was added sodium borohydride (45 mg, 1.18 mmol) portion-wise. The resulting reaction mixture was stirred at room temperature for 16 h and then quenched with a saturated ammonium chloride aq. solution (10 mL). The solution was extracted into EtOAc (3×25 mL) and combined organics washed with brine, dried over magnesium sulfate and evaporated to dryness to afford the title compound as a yellow solid (186 mg, 94%). Method C HPLC-MS: MH+ requires m/z=421. Found: m/z=421, Rt=1.19 min (73%).

Intermediate 131: 1-(3-{4-amino-6-[methyl(phenyl) amino]-1,3,5-triazin-2-yl}-1,2,4-oxadiazol-5-yl)piperidin-4-one To a solution of 1-(3-{4-amino-6-[methyl(phenyl)amino]-1,3,5-triazin-2-yl}-1,2,4-oxadiazol-5-yl)piperidin-4-ol (Intermediate 132, 120 mg, 0.325 mmol) in DCM (20 mL) at 0 C was added Dess-Martin Periodinane (138 mg, 0.325 mmol). The resulting reaction mixture was stirred at room temperature for 2 h and then further Dess-Martin Periodinane (138 mg, 0.325 mmol) was added. The reaction mixture was stirred for a further 16 h at room temperature and then quenched with a saturated sodium bicarbonate aq. solution (10 mL). The resulting bi-layer was separated and the organics washed further with a 1M aq. HCl solution (10 mL). Organics were dried over magnesium sulfate, evaporated to dryness and purified by silica chromatography (0 to 3% MeOH in DCM) to afford the title compound as an off-white solid (Dess-Martin Periodinane impurities (17%) also present) (179 mg, 150%). Method C HPLC-MS: MH+ requires m/z=367. Found: m/z=367, Rt=1.14 min (74%).

Intermediate 133: Ethyl 3-[4-amino-6-(phenylamino)-1,3,5-triazin-2-yl]-1,2,4-oxadiazole-5-carboxylate Ethyl oxalyl chloride (0.396 mL, 3.55 mmol) was added to a solution of (Z)-4-amino-N'-hydroxy-6-(phenylamino)-1,3, 5-triazine-2-carboximidamide (prepared in an analogous manner to Intermediate 4, 0.792 g, 3.23 mmol) in a 1:1 mixture of toluene and pyridine (40 mL) at 0 C. The mixture was warmed to room temperature and heated at 50 C for 2 h. The mixture was cooled to room temperature, and concentrated under vacuum. The residue was diluted with water and the resulting solid was collected by filtration and dried under vacuum to afford the title compound as a yellow solid (0.923 g) without further purification. Method B HPLC-MS: MH+ requires m/z=328. Found: m/z=328, Rt=1.77 min (42%).

Intermediate 134: 2-N-Phenyl-6-[5-(trichloromethyl)-1,2,4-oxadiazol-3-yl]-1,3,5-triazine-2,4-diamine Trichloroacetyl 2,2,2-trichloroacetate (0.875 mL, 4.90 mmol) was added slowly to a suspension of (Z)-4-amino-N'-hydroxy-6-(phenylamino)-1,3,5-triazine-2-carboximidamide (prepared in an analogous manner to Intermediate 4, 1.00 g, 4.08 mmol) in toluene (20 mL) at 0 C. Pyridine (0.62 mL) was added at 0 C and the mixture was stirred at room temperature for 45 min before being heated at 65 C for 45 min. The mixture was then cooled to room temperature, and a further 0.6 equivalent of trichloroacetyl 2,2,2-trichloroacetate was added. The reaction mixture was stirred at room temperature for 10 min and 65 C for 40 min. The mixture was concentrated under vacuum. The resulting residue was dissolved in EtOAc (60 mL), washed with a saturated aqueous solution of sodium bicarbonate (3×20 mL), dried over sodium sulfate, filtered and concentrated under vacuum to afford the title compound as a light brown solid (1.445 g, 95%). Method B HPLC-MS: MH+ requires m/z=372/374. Found: m/z=372/374, Rt=1.41 min (72%).

Intermediate 135: 6-[5-(6-Chloropyridin-3-yl)-1,2,4-oxadiazol-3-yl]-2-N-methyl-2-N-phenyl-1,3,5-triazine-2,4-diamine 6-Chloropyridine-3-carboxylic acid (Ig, 6.35 mmol) and thionyl chloride (10 mL, 138 mmol) were heated to reflux for 2 hours. The mixture was concentrated under vacuum and the residue was azeotroped with diethyl ether and evaporated. A portion of this acid chloride (0.75 g, 4.26 mmol) was then added to a solution of 4-amino-N-hydroxy-6-[methyl(phenyl)amino]-1,3,5-triazine-2-carboximidamide (prepared in an analogous manner to Intermediate 1, 0.920 g, 3.55 mmol) in pyridine (12 mL) and the mixture was stirred at room temperature overnight before being heated to 70 C for 3 h. The mixture was cooled to room temperature and concentrated under vacuum. Water was added and the mixture was stirred for 30 min. The solids were filtered and washed with further water. The solid was then azeotroped with toluene and dried under vacuum to afford the title compound, which was used without purification in the next step. Method B HPLC-MS: MH+ requires m/z=381 Found: m/z=381, Rt=1.99 min (35%).

Intermediate 136: 5-(3-{4-Amino-6-[methyl(phenyl) amino]-1,3,5-triazin-2-yl}-1,2,4-oxadiazol-5-yl)pyridin-2-ol Prepared according to the method described for Intermediate 135 above from 6-Hydroxypyridine-3-carboxylic acid (0.556 g, 4 mmol, thionyl chloride (1.2 mL, 16 mmol) and 4-amino-N-hydroxy-6-[methyl(phenyl)amino]-1,3,5-triazine-2-carboximidamide (prepared in an analogous manner to Intermediate 1, 0.52 g, 2 mmol). Method B HPLC-MS: MH+ requires m/z=363 Found: m/z=363, Rt=1.52 min (87%).

Intermediate 139: 1-[6-(3-{4-Amino-6-[methyl(phenyl)amino]-1,3,5-triazin-2-yl}-1,2,4-oxadiazol-5-yl)pyridin-3-yl]ethyl 2,2,2-trichloroethanecarboximidate 1-[6-(3-{4-Amino-6-[methyl(phenyl)amino]-1,3,5-triazin-2-yl}-1,2,4-oxadiazol-5-yl)pyridin-3-yl]ethan-1-ol (Intermediate 140, 0.400 g, 1.02 mmol) was suspended in DCM. Trichloroacetonitrile (0.123 mL, 1.22 mmol) and 1,8-diazabicycloundec-7-ene (few drops) were added and the mixture was stirred at room temperature for 19 h. DCM (30 mL) and water (30 mL) were added, the organic layer was separated and washed with brine (30 mL), before being dried over sodium sulfate and concentrated under vacuum to afford the title compound as a golden-brown solid (0.497 g, 91%), which was used in the next step without further purification. Method C HPLC-MS: MH+ requires m/z=534 Found: m/z=534, Rt=1.55 min (57%).

Intermediate 140: 1-[6-(3-{4-Amino-6-[methyl(phenyl)amino]-1,3,5-triazin-2-yl}-1,2,4-oxadiazol-5-yl)pyridin-3-yl]ethan-1-ol

1-[6-(3-{4-Amino-6-[methyl(phenyl)amino]-1,3,5-triazin-2-yl}-1,2,4-oxadiazol-5-yl)pyridin-3-yl]ethan-1-ol 1-[6-(3-{4-Amino-6-[methyl(phenyl)amino]-1,3,5-triazin-2-yl}-1,2,4-oxadiazol-5-yl)pyridin-3-yl]ethan-1-one (Intermediate 141, 0.934 g, 2.40 mmol) was suspended in THF (60 mL), sodium borohydride (0.227 g, 6.01 mmol) was added and the mixture stirred at room temperature for 2 h. EtOAc (50 mL) and water (100 mL) were added and the organic layer separated. The aqueous layer was neutralised using 1M aq. hydrochloric acid and extracted with EtOAc (3×30 mL). The combined organic layers were dried over sodium sulfate and concentrated under vacuum to afford the title compound as a pale yellow solid (1.0 g), which was used in the next step without further purification. Method C HPLC-MS: MH+ requires m/z=391 Found: m/z=391, Rt=1.18 min (84%).

Intermediate 142: 1:1 mixture of 2-(3-{4-Amino-6-[methyl(phenyl)amino]-1,3,5-triazin-2-yl}-1,2,4-oxadiazol-5-yl)pyridine-3-carboxylic acid and 3-(3-{4-Amino-6-[methyl(phenyl)amino]-1,3,5-triazin-2-yl}-1,2,4-oxadiazol-5-yl)pyridine-2-carboxylic acid 4-Amino-N'-hydroxy-6-[methyl(phenyl)amino]-1,3,5-triazine-2-carboximidamide (prepared in an analogous manner to Intermediate 1, 500 mg, 1.93 mmol) and 2,3-pyridinedicarboxylic anhydride (290 mg, 1.92 mmol) in pyridine (10 mL) were stirred at 80 C for 18 h and then an additional 1 equivalent of 2,3-pyridinedicarboxylic anhydride was added and the mixture was further heated at 80 C for 12 h. The reaction mixture was cooled to room temperature, concentrated under reduced pressure and purified by preparative HPLC, Method C to provide a 1:1 mixture of the title compounds (135 mg, 18%). Method B HPLC-MS: MH+ requires m/z=392. Found: m/z=392, Rt=1.52 and 1.58 min (45 and 53%).

Intermediate 143: 2-(3-{4-Amino-6-[methyl(phenyl)amino]-1,3,5-triazin-2-yl}-1,2,4-oxadiazol-5-yl)pyridine-3-carboxylic acid The aqueous layer from the preparation of Intermediate 147 was acidified with 1N aq. HCl and extracted with EtOAc (3×100 mL). The combined organic layers were washed with brine (50 mL), dried over magnesium sulfate and concentrated under reduced pressure to provide a crude mixture of acid isomers which was purified by preparative HPLC, Method C, to provide the title compound (120 mg, 3%). Method B HPLC-MS: MH+ requires m/z=391. Found: m/z=391, Rt=1.62 (100%).

Intermediate 144: 3-(3-{4-Amino-6-[methyl(phenyl)amino]-1,3,5-triazin-2-yl}-1,2,4-oxadiazol-5-yl)pyridine-2-carboxylic acid 3-(3-{4-Amino-6-[methyl(phenyl)amino]-1,3,5-triazin-2-yl}-1,2,4-oxadiazol-5-yl)pyridine-2-carboxylic acid was prepared from the same mixture as described in Intermediate 143 and purified by preparative HPLC, Method C, to provide the title compound (160 mg, 4%). Method B HPLC-MS: MH+ requires m/z=391. Found: m/z=391 1.55 (100%).

Intermediate 145: (3:1) Mixture of 3-(Methoxycarbonyl)pyridine-2-carboxylic acid and 2-(Methoxycarbonyl)pyridine-3-carboxylic acid 2,3-Pyridinedicarboxylic anhydride (5 g, 33.11 mmol) was dissolved in MeOH (25 mL) and the mixture was heated at 80 C for 4 h. The reaction mixture was cooled to room temperature, concentrated under reduced pressure to provide the title mixture as a white solid (6 g, quant.). Method B HPLC-MS: MH+ requires m/z=182. Found: m/z=182, Rt=0.75 min (94%).

Intermediate 146: (1:1.25) Mixture of 2-(3-{4-Amino-6-[methyl(phenyl)amino]-1,3,5-triazin-2-yl}-1,2,4-oxadiazol-5-yl)pyridine-3-carboxylic acid and 3-(3-{4-Amino-6-[methyl(phenyl)amino]-1,3,5-triazin-2-yl}-1,2,4-oxadiazol-5-yl)pyridine-2-carboxylic acid A 3:1 mixture of methyl 2-(3-{4-amino-6-[methyl(phenyl)amino]-1,3,5-triazin-2-yl}-1,2,4-oxadiazol-5-yl)pyridine-3-carboxylate and methyl 3-(3-{4-amino-6-[methyl(phenyl)amino]-1,3,5-triazin-2-yl}-1,2,4-oxadiazol-5-yl)pyridine-2-carboxylate (Intermediate 147, 1.4 g, 3.46 mmol) was dissolved in a 1:1 mixture of MeOH: THF (40 mL) and then 2M aq. sodium hydroxide (14 mL) was added and mixture was stirred for 14 h. The reaction mixture was concentrated under reduced pressure and acidified with 1N aq. HCl (pH 1-2) and extracted with EtOAc (4×50 mL). The combined organic layers were washed with water (50 mL) then brine (50 mL) and concentrated under reduced pressure. The residue was purified by preparative HPLC, Method C, to provide the title mixture (135 mg). Method B HPLC-MS: MH+ requires m/z=391. Found: m/z=391, Rt=1.51 and 1.56 min (59 and 41%).

Intermediate 158: 6-Chloro-2-N-(6-fluoropyridin-3-yl)-2-N-methyl-1,3,5-triazine-2,4-diamine To a solution of 6-chloro-2-N-(6-fluoropyridin-3-yl)-1,3,5-triazine-2,4-diamine (Intermediate 159, 0.52 g, 2.17 mmol) in DMF (1 mL) at 0 C under nitrogen was added portionwise sodium hydride (60% dispersion in mineral oil, 0.0869 g, 2.17 mmol). The mixture was stirred for 5 min, then iodomethane (0.3 g, 2.17 mmol) was added and the mixture was heated to 50 C for 16 h. EtOAc was added and the organic layer was washed with saturated aq. sodium bicarbonate, dried over sodium sulfate and concentrated. The residue was purified by FCC, eluting with 10-50% EtOAc in heptane to afford the title compound (0.089 g, 16% yield). Method B HPLC-MS: MH+ requires m/z=255 Found: m/z=255, Rt=1.52 min (74%).

Intermediate 163: N-(2-Methoxyethyl)aniline

To phenylboronic acid (5 g, 41.0 mmol) in DCM (50 mL) was added copper (II) acetate (0.78 g, 4.1 mmol) and the mixture was stirred for 5 min at room temperature. 2-Methoxyethanamine (3.08 g, 41.0 mmol) was added and the mixture was stirred at 40 C for 19 h. The mixture was then passed through a silica plug and then purified by FCC, eluting with 10% EtOAc in heptane to afford the title compound (1.065 g, 17% yield). Method B HPLC-MS: MH+ requires m/z=152 Found: m/z=152, Rt=1.08 min (87%).

Intermediate 168: Methyl 5-aminopyridine-2-carboxylate

5-Aminopyridine-2-carboxylic acid (1.60 g, 11.6 mmol) was dissolved in MeOH (100 mL) and concentrated sulfuric acid (1.7 mL, 12.8 mmol) was added and the mixture was heated to 80 C for 5 hours. The reaction mixture was concentrated under vacuum, neutralised by adding 1M aq. sodium bicarbonate and extracted with EtOAc. The organic layer was dried over sodium sulfate and concentrated under vacuum to afford the title compound as a pale yellow solid (1.813 g, quant.). Method B HPLC-MS: MH+ requires m/z=153 Found: m/z=153, Rt=0.35 min (by MS).

Intermediate 169: 5-(Trifluoromethoxy)pyridine-2-carbonyl chloride

A mixture of methyl 5-(trifluoromethoxy)pyridine-2-carboxylate (0.313 g, 1.41 mmol), potassium hydroxide (0.076 g, 1.35 mmol) in a 5:1 MeOH:water mixture (3 mL) was stirred at room temperature for 1 h. Additional potassium hydroxide (0.015 g, 0.267 mmol) in water (0.2 mL) was added and the mixture was stirred at room temperature for 1 h. The reaction mixture was evaporated to dryness and azeotroped twice with toluene to give the potassium 5-(trifluoromethoxy)pyridine-2-carboxylate intermediate (404 mg 100%). A fraction of this intermediate (0.173 g, 0.706 mmol) was dissolved in oxalyl chloride (4 mL) and the mixture was stirred at room temperature for 2 h before being evaporated to dryness and used without further purification in the next step.

Intermediate 171: 6-(Tetrahydro-furan-3-yloxy)-nicotinic acid

To 6-chloro-nicotinic acid (415 mg, 2.59 mmol), was added 3-hydroxytetrahydrofuran (468 mg, 5.16 mmol), potassium hydroxide (579 mg, 10.3 mmol) and DMSO (5 mL). The mixture was heated at 120 C for 24 h. Further potassium hydroxide (579 mg) and 3-hydroxytetrahydrofuran (468 mg) was added and the mixture heated at 120 C for 24 h. The reaction was allowed to cool to room temperature, acidified to pH=1-2 with a 2M aq. solution of HCl (13 mL) and extracted into EtOAc (3×5 mL). The combined extracts were washed with water (5×20 mL), saturated brine (2×20 mL) and dried over anhydrous sodium sulfate. Evaporation of the solvent afforded the title compound as an orange solid which was dried under high vacuum to remove traces of solvent (209 mg, 39%). Method B HPLC-MS: MH+ requires m/z=210. Found: m/z=210, Rt=1.32 min (100%).

Intermediate 173: 6-(Cyclopropylmethoxy)pyridine-3-carboxylic acid

6-Chloropyridine-3-carboxylic acid (1.00 g, 6.347 mmol), cyclopropylmethanol (0.759 mL, 9.520 mmol) and potassium hydroxide (1.424 g, 25.39 mmol) were dissolved in DMSO (25 mL) and heated at 100 C for 18 h. The reaction mixture was cooled to room temperature; water was added and acidified to pH 4-5 with 1M hydrochloric acid. The resultant precipitate was filtered off under vacuum to afford the title compound (1.079 g, 88%). Method B HPLC-MS: MH+ requires m/z=193 Found: m/z=194, Rt=1.95 min (96%).

Intermediate 174: 6-(2,2,2-Trifluoroethoxy)pyridine-2-carboxylic acid

6-Chloropyridine-2-carboxylic acid (1.00 g, 6.347 mmol), 2,2,2-trifluoroethan-1-ol (0.683 mL, 9.520 mmol) and potassium hydroxide (1.424 g, 25.387 mmol) were dissolved in DMSO (25 mL) and heated at 100 C for 18 h. The reaction mixture was re-treated with potassium hydroxide (0.356 g, 6.347 mmol) and heated at 100 C for 18 h. The reaction mixture was then re-treated with 2,2,2-trifluoroethan-1-ol (1.367 mL, 19.040 mmol) and potassium hydroxide (0.356 g, 6.347 mmol) and heated at 110 C for 18 h. The reaction mixture was then further re-treated with potassium hydroxide (0.356 g, 6.347 mmol) and 2,2,2-trifluoroethan-1-ol (0.683 mL, 9.520 mmol) and the mixture was stirred at room temperature for 72 h. Water (10 mL) was added and acidified to pH 1 with 1M hydrochloric acid. The aqueous was extracted with EtOAc (3×15 mL) and the organic layer was washed with brine (15 mL). This was dried over anhydrous sodium sulfate, filtered and concentrated under reduced pressure to give a brown gum. The crude material was purified by FCC (DCM: MeOH, 90:10) to afford the title compound as a yellow solid (1.26 g, 90%). Method B HPLC-MS: MH+ requires m/z=222 Found: m/z=222, Rt=1.71 min (79%).

Intermediate 175: 4-(Methoxymethyl)piperidine hydrochloride

A solution of 4M hydrogen chloride in 1,4-dioxane (807 µL, 3.23 mmol) was added to tert-butyl 4-(methoxymethyl) piperidine-1-carboxylate (Intermediate 176, 74 mg, 0.323 mmol) and the mixture was stirred at room temperature for 18 h before being evaporated to dryness to provide the title compound (47.7 mg, 89%). Method B HPLC-MS: MH+ requires m/z=130 Found: m/z=130, Rt=0.24 min.

The following Intermediates were prepared according to the method described for Intermediate 175.

| 120 | 6-[5-(4-Aminopiperidin-1-yl)-1,2,4-oxadiazol-3-yl]-2-N-methyl-2-N-phenyl-1,3,5-triazine-2,4-diamine hydrochloride | Method C HPLC-MS: MH+ requires m/z = 368 Found: m/z = 368, Rt = 0.99 min (98%) |
|---|---|---|

| | | |
|---|---|---|
| 129 | 6-[5-(Azetidin-3-yl)-1,2,4-oxadiazol-3-yl]-2-N-methyl-2-N-phenyl-1,3,5-triazine-2,4-diamine hydrochloride | Method C HPLC-MS: MH+ requires m/z = 325; Found: m/z = 325, Rt = 0.94 min (66%) |
| 137 | 2-N-Methyl-2-N-phenyl-6-[5-(piperazin-1-yl)-1,2,4-oxadiazol-3-yl]-1,3,5-triazine-2,4-diamine hydrochloride | Method A HPLC-MS: MH+ requires m/z = 354 Found: m/z = 354, Rt = 2.61 min (99%) |
| 149 | 6-[5-(Azetidin-3-yl)-1,2,4-oxadiazol-3-yl]-2-N-methyl-2-N-phenyl-1,3,5-triazine-2,4-diamine (DCM/bicarb partition) | Method B HPLC-MS: MH+ requires m/z = 325; Found: m/z = 325, Rt = 1.04 min (93%) |
| 151 | 2-N-Methyl-2-N-phenyl-6-[5-(piperazin-1-yl)-1,2,4-oxadiazol-3-yl]-1,3,5-triazine-2,4-diamine hydrochloride | Method B HPLC-MS: MH+ requires m/z = 354; Found: m/z = 354, Rt = 1.24 min (98%) |
| 167 | N-Phenyl-6-(5-piperidin-4-yl-[1,2,4]oxadiazol-3-yl)-[1,3,5]triazine-2,4-diamine hydrochloride | Method C HPLC-MS: MH+ requires m/z = 339; Found: m/z = 339, Rt = 0.96 min (96%) |
| 177 | 4-(Phenoxymethyl)piperidine hydrochloride | Method B HPLC-MS: MH+ requires m/z = 192 Found: m/z = 192, Rt = 1.24 min |
| 182 | 4-{[(2,2,2-Trifluoroethyl)sulfanyl] methyl} piperidine hydrochloride | Method B HPLC-MS: MH+ requires m/z = 213 Found: m/z = 213, Rt = 1.13 min |
| 184 | 4-[(Phenylsulfanyl)methyl] piperidinehydrochloride | Method B HPLC-MS: MH+ requires m/z = 207 Found: m/z = 207, Rt = 1.32 min |
| 186 | 4-[(Propan-2-ylsulfanyl)methyl] piperidine hydrochloride | Method B HPLC-MS: MH+ requires m/z = 174 Found: m/z = 174, Rt = 1.11 min |
| 200 | 4-(Cyclobutoxymethyl)piperidine hydrochloride | Method B HPLC-MS: MH+ (free-based) requires m/z = 170 Found: m/z = 170, Rt = 0.96 min |
| 211 | 4-(3,3,3-Trifluoropropylidene) piperidine (DCM/bicarb partition) | 1H NMR (500 MHz, CDCl$_3$) δ ppm 5.09 (1H, t), 2.81 (4H, m), 2.73 (2H, m), 2.30 (1H, br. s) and 2.14 (4H, dd) |
| 220 | 1R,4R)-4-(2,2,2-trifluoroethoxy)cyclohexan-1-amine hydrochloride | used in the subsequent step without further purification |
| 232 | 4-Methoxy-4-phenylpiperidine hydrochloride | 1H NMR (500 MHZ, DMSO-d6) δ ppm 8.97 (2H, br s), 7.40 (5H, m), 3.18 (2H, m), 3.06 (2H, m), 2.89 (3H, s) and 2.14 (4H, m) |
| 237 | 4-[(2,2,2-Trifluoroethyl)sulfanyl]piperidine hydrochloride | 1H NMR (500 MHZ, MeOH-d4) δ ppm 3.42 (4H, q), 3.19 (1H, m), 3.10 (2H, t), 2.28 (2H, dd) and 1.76 (2H, m) |
| 244 | 4-(Propan-2-ylsulfanyl)piperidine hydrochloride | 1H NMR (500 MHZ, MeOH-d4) δ ppm 3.40 (2H, m), 3.09 (4H, m), 2.21 (2H, m), 1.74 (2H, m) and 1.29 (6H) |
| 246 | 4-(Propane-2-sulfinyl)piperidine hydrochloride | 1H NMR (500 MHZ, MeOH-d4) δ ppm 3.33 (2H, m), 2.98 (4H, m), 2.11 (2H, m), 1.86 (1H, m), 1.63 (1H, m) and 1.21 (6H, m) |
| 267 | 4-{[(2,2,2-trifluoroethyl)sulfanyl] methyl}piperidine hydrochloride | Method B HPLC-MS: MH+ requires m/z = 214 Found: m/z = 214, Rt = 1.09 min (100%) |
| 269 | (3S)-3-Phenoxypyrrolidine hydrochloride | Method B HPLC-MS: MH+ requires m/z = 164 Found: m/z = 164, Rt = 0.82 min (95%) |
| 271 | (3R)-3-Phenoxypyrrolidine hydrochloride | Method B HPLC-MS: MH+ requires m/z = 164 Found: m/z = 164, Rt = 0.72 min (100%) |
| 273 | (3R)-3-(2,2,2-trifluoroethoxy)pyrrolidine hydrochloride | Used without further purification or characterisation |
| 277 | 4-(Cyclopropylmethoxy)piperidine hydrochloride | 1H NMR (500 MHz, MeOD) δ ppm 3.69 (1H, m), 3.34 (2H, t), 3.10 (2H, m), 2.00 (2H, ddd), 1.84 (2H, ddd), 1.05 (1H, m), 0.53 (2H, m) and 0.22 (2H, m) |

Intermediate 176: tert-Butyl 4-(methoxymethyl)piperidine-1-carboxylate

A solution of tert-butyl 4-(hydroxymethyl)piperidine-1-carboxylate (0.300 g, 1.395 mmol) in DMF (2.5 mL) was added dropwise to a suspension of sodium hydride (60% dispersion in mineral oil, 0.067 g, 1.674 mmol) in anhydrous DMF (2.5 mL) at 0 C. The reaction mixture was stirred at 0 C for 10 min followed by dropwise addition of iodomethane (86 µL, 1.395 mmol). The mixture was warmed to room temperature and stirred for 18 h. The reaction mixture was re-treated with sodium hydride (60% dispersion in mineral oil, 0.067 g, 1.674 mmol) and iodomethane (86 µL, 1.395 mmol) and was stirred at room temperature for 18 h. The reaction mixture was evaporated under reduced pressure, dissolved in DCM and washed with a saturated aqueous solution of sodium bicarbonate. The organic extracts were combined, dried over anhydrous sodium sulfate, filtered and concentrated under reduced pressure. The crude material was purified by FCC (EtOAc: heptane, 1:1) to afford the title compound (0.074 g, 23%). Method B HPLC-MS: MH+ requires m/z=229 Found: m/z=174 (MH+-tBu) Rt=1.98 min (99%).

The following ethers were prepared in an analogous manner to Intermediate 176.

| | | |
|---|---|---|
| 199 | tert-Butyl 4-[(cyclopropylmethoxy) methyl]piperidine-1-carboxylate (Heated to 80 C.) | Method B HPLC-MS: MH+ requires m/z = 270 Found: m/z = 214 (MH+ − tBu), Rt = 2.33 min (83%) |

| | | |
|---|---|---|
| 233 | tert-Butyl 4-methoxy-4-phenylpiperidine-1-carboxylate (Heated to 80 C.) | 1H NMR (500 MHZ, CDCl$_3$) δ ppm 7.39 (4H, m), 7.31 (1H, m), 4.04 (2H, br d), 3.17 (2H, br s), 3.00 (3H, s), 2.02 (2H, br s), 1.87 (2H, br s) and 1.49 (9H, s) |
| 278 | tert-butyl 4-(cyclopropylmethoxy)piperidine-1-carboxylate (Heated to 80 C.) | 1H NMR (500 MHz, CDCl$_3$) δ ppm 3.81 (2H, s), 3.44 (1H, m), 3.29 (2H, d), 3.01 (2H, m), 1.83 (2H, d), 1.50 (11H, m), 1.04 (1H, m), 0.53 (2H, m) and 0.19 (2H, m) |

Intermediate 178: tert-Butyl 4-(phenoxymethyl)piperidine-1-carboxylate tert-Butyl 4-(hydroxymethyl)piperidine-1-carboxylate (0.300 g, 1.393 mmol), phenol (0.122 mL, 1.393 mmol), triphenylphosphine (0.440 g, 1.672 mmol) and N-{[(tert-butoxy)carbonyl]imino}(tert-butoxy)formamide (0.390 g, 1.672 mmol) were combined in THF (4 mL) and stirred at room temperature for 18 h. The reaction mixture was concentrated under reduced pressure and purified by FCC (EtOAc: heptane, 1:1) to afford a white solid. This was further purified by trituration with diethyl ether to afford the title compound (0.289 g, 71%). Method B HPLC-MS: MH+ requires m/z=292 Found: m/z=235 (MH+-tBu), Rt=2.44 min (71%).

Intermediate 179: 4-[(2,2,2-Trifluoroethoxy)methyl]piperidine hydrochloride

A solution of 4M hydrogen chloride in 1,4-dioxane (2.48 mL, 9.93 mmol) was added to tert-butyl 4-[(2,2,2-trifluoroethoxy)methyl]piperidine-1-carboxylate (Intermediate 180, 0.289 g, 0.993 mmol) and the mixture was stirred at room temperature for 18 h before being evaporated to dryness to provide the title compound (0.136 g, 59%). Method B HPLC-MS: MH+ (HCl salt) requires m/z=198 Found: m/z=198, Rt=0.72 min.

Intermediate 180: tert-Butyl 4-[(2,2,2-trifluoroethoxy)methyl]piperidine-1-carboxylate tert-Butyl 4-(hydroxymethyl)piperidine-1-carboxylate (0.300 g, 1.393 mmol), 2,2,2-trifluoroethan-1-ol (1.00 mL, 13.935 mmol), triphenylphosphine (0.440 g, 1.672 mmol) and N-{[(tert-butoxy)carbonyl]imino}(tert-butoxy)formamide (0.390 g, 1.672 mmol) were combined in THF (10 mL) and stirred at room temperature for 36 h before being heated to 75 C for 18 h. The reaction mixture was concentrated under reduced pressure and purified by FCC (EtOAc: heptane, 1:1) to afford the title compound (0.192 g, 50%). Method B HPLC-MS: MH+ requires m/z=297 Found: m/z=242 (MH+-tBu), Rt=2.25 min (100%).

The following trifluoroethoxy ethers were prepared in an analogous manner to Intermediate 180.

Intermediate 183: tert-Butyl 4-{[(2,2,2-trifluoroethyl)sulfanyl]methyl}piperidine-1-carboxylate 2,2,2-Trifluoroethane-1-thiol (0.151 mL, 1.636 mmol) was added dropwise to a suspension of sodium hydride (60% dispersion in mineral oil, 0.065 g, 1.636 mmol) in anhydrous DMF (3 mL) at 0 C. A solution of tert-butyl 4-[(methanesulfonyloxy)methyl]piperidine-1-carboxylate (Intermediate 181, 0.320 g, 1.091 mmol) in DMF (4 mL) was then added dropwise and the reaction mixture was stirred at room temperature for 4 h. The mixture was diluted with EtOAc (30 mL) and washed with a saturated aqueous solution of sodium bicarbonate (10 mL) followed by brine (10 mL). The organic layer was dried over anhydrous sodium sulfate, filtered and evaporated under reduced pressure. The crude material was purified by FCC (EtOAc: heptane, 20:80) to provide the title compound as a colourless oil (0.288 g, 82%). Method B HPLC-MS: MH+ requires m/z=313 Found: m/z=257 (M minus tert-butyl), Rt=2.28 min (97%).

Intermediate 185: tert-Butyl 4-[(phenylsulfanyl)methyl]piperidine-1-carboxylate tert-Butyl 4-[(phenylsulfanyl)methyl]piperidine-1-carboxylate was prepared from tert-butyl 4-(hydroxymethyl)piperidine-1-carboxylate (Intermediate 181, 0.320 g, 1.091 mmol) and thiophenol (0.117 mL, 1.145 mmol) according to the method described for Intermediate 183 to afford the title compound (0.483 g). 1H NMR (250 MHz, CDCl$_3$) δ ppm 7.22 (5H, m), 4.10 (2H, m), 2.83 (2H d), 2.64 (2H, t), 1.84 (2H, d), 1.63 (1H, m), 1.44 (9H, s) and 1.17 (2H, m).

Intermediate 187: tert-Butyl 4-[(propan-2-ylsulfanyl) methyl]piperidine-1-carboxylate tert-Butyl 4-[(propan-2-ylsulfanyl)methyl]piperidine-1-carboxylate was prepared from tert-butyl 4-(hydroxymethyl) piperidine-1-carboxylate (Intermediate 181, 0.320 g, 1.091 mmol) and sodium propanethiolate (0.161 g, 1.636 mmol) according to the method described for Intermediate 183 to afford the title compound (0.180 g, 60%). Method B HPLC-MS: MH+ requires m/z=274 Found: m/z=218 (M-tert-Bu), Rt=2.51 min.

| | | |
|---|---|---|
| 203 | tert-Butyl 4-(2,2,2-trifluoroethoxy)piperidine-1-carboxylate | 1H NMR (300 MHz, CDCl$_3$) δ ppm 3.81 (2H, q), 3.61-3.75 (3H, m), 3.15 (2H, m), 1.81 (2H, m), 1.58 (2H, m) and 1.45 (9H, s) |
| 221 | tert-Butyl N-[(1R,4R)-4-(2,2,2-trifluoroethoxy)cyclohexyl]carbamate | Method B HPLC-MS: MH+ requires m/z = 297; Found: m/z = 242 (MH+ − 56), Rt = 2.09 min (100%) |

Intermediate 188: 6-{[(1,1,1-Trifluoropropan-2-yl)oxy]methyl}pyridine-3-carboxylic acid 1,1,1-Trifluoropropan-2-ol (0.406 mL, 4.483 mmol) was added drop wise to a suspension of sodium hydride (60% in mineral oil) (0.239 g, 5.977 mmol) in dry THF (20 mL) at 0 C. The mixture was stirred at 0 C for 15 minutes. A solution of methyl 6-(methanesulfonyloxy)methyl]pyridine-3-carboxylate (Intermediate 189, 0.733 g, 2.989 mmol) in THF (10 mL) was added drop wise. The reaction mixture was stirred at 0 C for 30 minutes and room temperature for 3 days. The reaction mixture was quenched with water (10 mL) and diluted with EtOAc (30 mL). The phases were separated, and the organic phase was extracted with a saturated aqueous solution of sodium bicarbonate (3×15 mL). The aqueous extracts were combined, washed with EtOAc (1×10 mL). The organic phase was discarded and the aqueous phase was acidified to pH 4 using 2N HCl and extracted with EtOAc (3×30 mL). The organic extracts were combined, dried over sodium sulfate, filtered and evaporated to provide a brown crude residue. The crude material was purified by flash chromatography (DCM: MeOH 98:2) to afford the title compound as a beige solid (0.345 g, 46%). Method B HPLC-MS: MH+ requires m/z=250 Found: m/z=250, Rt=1.61 min (89%).

The following ethers were prepared in an analogous manner to Intermediate 188, with heating up to 80 C as appropriate.

Intermediate 190: Methyl 6-(hydroxymethyl)pyridine-3-carboxylate

Calcium chloride (22.7 g, 204.9 mmol) was added to a suspension of dimethylpyridine-2,5-dicarboxylate (10.0 g, 51.2 mmol) in a mixture 1:2 THF: MeOH (300 mL). The mixture was cooled at 0 C, sodium borohydride (4.85 g, 128.1 mmol) was added portion wise. The reaction mixture warmed slowly to room temperature and stirred for 18 h. An additional 2.5 equivalent of sodium borohydride was added and the reaction mixture was stirred at room temperature for 2 days. Additional THF (100 mL) and MeOH (100 mL) was added and the mixture was stirred for ~15 h. An additional 2.5 equivalent of sodium borohydride (newer batch) was added and the reaction mixture was stirred at room temperature for 15 h. The mixture was slowly poured onto ice-water and diluted with EtOAc (~200 mL). The white solid was filtered and discarded. Phases from the filtrate were separated, the organic phase was washed with water (3×100 mL). The aqueous washes were combined and re-extracted with EtOAc (2×100 mL). The organic extracts were combined, dried over sodium sulfate, filtered and concentrated under vacuum to afford the title compound as an off white solid (5.8 g, 73%). Method B HPLC-MS: MH+ requires m/z=168 Found: m/z=168, Rt=0.91 min (100%).

Intermediate 194: Methyl 6-(1-hydroxyethyl)pyridine-3-carboxylate

A solution of methyl magnesium bromide (1M in THF) (3.03 mL, 3.03 mmol) was added drop wise to a solution of

| | | |
|---|---|---|
| 191 | 6-[(Cyclopropylmethoxy)methyl]pyridine-3-carboxylic acid (ester hydrolysed in reaction) | Method B HPLC-MS: MH+ requires m/z = 208 Found: m/z = 208, Rt = 1.33 min (85%) |
| 192 | 6-[1-(2,2,2-Trifluoroethoxy)ethyl]pyridine-3-carboxylic acid (ester hydrolysed in reaction) | Method B HPLC-MS: MH+ requires m/z = 250 Found: m/z = 250, Rt = 1.77 min (65%) |
| 196 | 6-[(2,2,2-Trifluoroethoxy)methyl]pyridine-3-carboxylic acid (ester hydrolysed in reaction) | Method B HPLC-MS: MH+ requires m/z = 236 Found: m/z = 236, Rt = 1.44 min (65%) |
| 197 | 6-(Cyclobutoxymethyl)pyridine-3-carboxylic acid | Method B HPLC-MS: MH+ requires m/z = 208 Found: m/z = 208, Rt = 1.38 min (68%) |
| 201 | tert-Butyl 4-(cyclobutoxymethyl)piperidine-1-carboxylate | Method B HPLC-MS: MH+ requires m/z = 270 Found: m/z = 214 (MH+ − tBu), Rt = 2.28 min (35%) |
| 257 | (1R,5S,6S)-3-Benzyl-6-(phenoxymethyl)-3-azabicyclo[3.1.0]hexane | Method B HPLC-MS: MH+ requires m/z = 280; Found: m/z = 280, Rt = 1.49 min (100%) |
| 260 | (1R,5S,6S)-3-Benzyl-6-[(cyclopropylmethoxy)methyl]-3-azabicyclo[3.1.0]hexane | Method B HPLC-MS: MH+ requires m/z = 258; Found: m/z = 258, Rt = 1.29 min (94%) |
| 262 | (1R,5S,6S)-3-Benzyl-6-[(3,3,3-trifluoropropoxy)methyl]-3-azabicyclo[3.1.0]hexane | Method B HPLC-MS: MH+ requires m/z = 300; Found: m/z = 300, Rt = 1.12 min (92%) |
| 264 | (1R,5S,6S)-3-Benzyl-6-[(propan-2-yloxy)methyl]-3-azabicyclo[3.1.0]hexane | Method B HPLC-MS: MH+ requires m/z = 246; Found: m/z = 246, Rt = 1.27 min (81%) |
| 266 | (1R,5S,6S)-3-Benzyl-6-[(cyclopentyloxy)methyl]-3-azabicyclo[3.1.0]hexane | Method B HPLC-MS: MH+ requires m/z = 272; Found: m/z = 272, Rt = 1.40 min (17%) |
| 287 | 3-Phenoxymethylazetidine-1-carboxylic acid tert-butyl ester | Method C HPLC-MS: ((MH+)-tert -butyl) requires m/z = 208; Found: m/z = 208, Rt = 1.51 min (100%) |
| 289 | 3-(3,3,3-Trifluoro-propoxymethyl)-azetidine-1-carboxylic acid tert-butyl ester | Method C HPLC-MS: ((MH+)-tert butyl) requires m/z = 208; Found: m/z = 208, Rt = 1.51 min (100%) |
| 291 | 4-(3,3,3-Trifluoropropoxymethyl)-piperidine-1-carboxylic acid tert-butyl ester | Method C HPLC-MS: ((MH+)-tert butyl) requires m/z = 256; Found: m/z = 256, Rt = 1.57 min (100%) | methyl 6-formylpyridine-3-carboxylate (Intermediate 195, 0.50 g, 3.03 mmol) in THF (20 mL) at −78 C. The reaction mixture was stirred at −78 C for 1 h and water (20 mL) was added. The mixture was warmed to room temperature and extracted with EtOAc (3×20 mL). The organic extracts were combined, dried over sodium sulfate, filtered and concentrated under vacuum to provide the title compound as an off-white solid (0.407 g, 74%). Method B HPLC-MS: MH+ requires m/z=182 Found: m/z=182, Rt=1.11 min (98%).

Intermediate 195: Methyl 6-formylpyridine-3-carboxylate

Dess-Martin periodinane (2.54 g, 5.98 mmol) was added to a solution of methyl 6-(hydroxymethyl)pyridine-3-carboxylate (Intermediate 190, 1.00 g, 5.98 mmol) in DCM (75 mL) at room temperature. The reaction mixture was stirred at room temperature for 24 hrs before being diluted with DCM (50 mL), washed with a 1:1 mixture of saturated aqueous solution of sodium bicarbonate and sodium thiosulfate (3×75 mL). The organic phase was dried over sodium sulfate, filtered and evaporated under vacuum to provide the title compound (1.02 g, 105%). Method B HPLC-MS: MH+ requires m/z=166 Found: m/z=166, Rt=1.44 min (62%).

Intermediate 198: 4-[(Cyclopropylmethoxy)methyl]piperidine hydrochloride salt

A solution of 4N HCl in dioxane (5 mL, 20.0 mmol) was added to a solution of tert-butyl 4-[(cyclopropylmethoxy)methyl]piperidine-1-carboxylate (Intermediate 199, 0.75 g, 2.77 mmol) in dioxane (3 mL) at room temperature. The reaction mixture was stirred at room temperature for 3 h before being evaporated to dryness to provide the title compound as a pale pink sticky solid (0.7 g, 125%). Method B HPLC-MS: MH+ (free-based) requires m/z=170 Found: m/z=170, Rt=0.87 min.

Intermediate 199: tert-Butyl 4-[(cyclopropylmethoxy)methyl]piperidine-1-carboxylate A solution of N-boc-4-piperidinemethanol (0.500 g, 2.322 mmol) in DMF (10 mL) was added drop wise to a suspension of sodium hydride (60% in mineral oil) (0.186 g, 4.645 mmol) in dry DMF (15 mL) at 0 C. The mixture was stirred at 0 C for 15 minutes and room temperature for 10 minutes before being cooled down again and (bromomethyl)cyclopropane (0.227 mL, 2.322 mmol) was added drop wise. The reaction mixture was stirred at 0 C for 10 minutes, room temperature for 1 h and 80 C for 4 h. The reaction mixture was diluted with EtOAc (60 mL) and washed with water (3×20 mL). The aqueous washes were combined and re-extracted with EtOAc (3×20 mL). The organic extracts were combined, dried over sodium sulfate, filtered and evaporated to provide the title compound as a colorless oil (0.614 g, 98%). Method B HPLC-MS: MH+ requires m/z=270 Found: m/z=214 (MH+-tBu), Rt=2.33 min (83%).

Intermediate 202: 4-(2,2,2-Trifluoroethoxy)piperidine

Trifluoroacetic acid (1.15 mL) was added dropwise to a solution of tert-butyl 4-(2,2,2-trifluoroethoxy)piperidine-1-carboxylate (prepared in an analogous manner to Intermediate 203, 1.14 g, 4.0 mmol) in DCM (10 mL) at room temperature. The reaction mixture was stirred at room temperature for 16 h. The mixture was then concentrated under vacuum, the crude residue was dissolved in water and product was extracted with diethylether (2 times). The aqueous phase was basicified to pH 10 using solid potassium carbonate and extracted with DCM (4 times). The organic extracts were combined, dried over sodium sulfate and concentrated under vacuum to afford the title compound (610 mg, 83%). 1H NMR (300 MHz, CDCl$_3$) δ ppm 3.84 (2H, q), 3.53 (1H, m), 3.10 (2H, m), 2.61 (2H, m), 1.76 (2H, m) and 1.54 (2H, s).

Intermediate 204: Methyl 1-(2,2,2-trifluoroethyl)-1H-pyrazole-3-carboxylate

Methyl 1H-pyrazole-3-carboxylate (1.0 g, 7.94 mmol) was dissolved in DMF (25 mL) and cesium carbonate (12.9 g, 39.7 mmol) was added. The mixture was cooled to 0 C and 2,2,2-trifluoroethyl methanesulfonate (2.4 mL, 19.8 mmol) was gradually added. The mixture was warmed to room temperature and stirred for 16 h. Water was added and the mixture was extracted with EtOAc (3×25 mL). The combined organic extracts were washed with brine (3×10 mL) and concentrated under vacuum. The residue was purified by FCC, eluting with hexane followed by 0.5% MeOH in DCM to afford the title compound as a yellow oil (0.312 g, 19%). Method D HPLC-MS: MH+ requires m/z=209 Found: m/z=209, Rt=2.08 min (98%).

Intermediate 205: Methyl 1-(2,2,2-trifluoroethyl)-1H-pyrazole-5-carboxylate

Methyl 1-(2,2,2-trifluoroethyl)-1H-pyrazole-5-carboxylate was prepared from the same mixture as described for Intermediate 204 to afford the title compound as a yellow oil (0.063 g, 4%). Method D HPLC-MS: MH+ requires m/z=209 Found: m/z=209, Rt=1.26 min (96%).

Intermediate 206: 6-(2,2,2-Trifluoroethoxy)pyridine-3-carboxylic acid

A mixture of 6-chloropyridine-3-carboxylic acid (6.0 g, 38.1 mmol), 2,2,2-trifluoroethanol (8.2 mL, 114.2 mmol) and potassium hydroxide (10.7 g, 190.4 mmol) in DMSO (50 mL) was stirred at 120 C for 18 h and left standing at room temperature for 2 days. A further 2 equivalents of potassium hydroxide and 1.5 equivalent of 2,2,2-trifluoroethanol were added and the reaction mixture was stirred at 120 C for 18 h. The mixture was acidified with a concentrated aqueous solution of HCl until a cream precipitate appeared. The precipitate was collected by filtration, washed with a 1N aqueous solution of HCl before being dissolved in EtOAc, washed 3 times with a 1N aqueous solution of HCl and 3 times with brine. The organic phase was dried over sodium sulfate, filtered and concentrated under vacuum to afford the title compound as a cream solid (6.9 g, 82%). Method C HPLC-MS: MH+ requires m/z=222 Found: m/z=222, Rt=1.24 min (98%).

Intermediate 207: 6-(3,3,3-trifluoropropyl)pyridine-3-carboxylic acid

To a solution of 6-(3,3,3-trifluoropropyl)pyridine-3-carbonitrile (Intermediate 208, 189 mg, 0.945 mmol) in EtOH (20 mL) was added potassium hydroxide (265 mg, 4.72 mmol). The solution was heated at 100 C for 6 h and then additional potassium hydroxide (53 mg, 0.94 mmol) added. After stirring for a further 3 h at 105 C, the reaction mixture was cooled to room temperature, evaporated to dryness and re-dissolved in water (20 mL). The solution was acidified to pH 3 with a 1M aq. HCl solution and extracted with EtOAc (3×25 mL). Combined organics were dried over magnesium sulfate and evaporated to dryness to afford the title compound as a light brown solid (183 mg, 89%). Method C HPLC-MS: MH+ requires m/z=220. Found: m/z=220, Rt=1.12 min (91%).

Intermediate 208:
6-(3,3,3-Trifluoropropyl)pyridine-3-carbonitrile

To a solution of 6-methyl-nicotinonitrile (118 mg, 1.0 mmol) in anhydrous THF (20 mL) at −78 C under nitrogen was added lithium diisopropylamine (2M solution in THF/heptane/ethylbenzene, 550 µL, 1.1 mmol) drop-wise. The resulting solution was allowed to warm to room temperature for 5 min and then cooled back to −78 C. 1,1,1-Trifluoro-2-iodo-ethane (524 mg, 2.5 mmol) was then added to the solution drop-wise and the reaction mixture was allowed to warm to room temperature and stirred at this temperature for 2 h. The reaction mixture was cooled at 0 C and quenched with water; the resulting solution was extracted with EtOAc (3×25 mL). Combined organics were washed with brine (25 mL), dried over magnesium sulfate and purified by silica chromatography (25% EtOAc in heptane) to afford the title compound as a pale yellow oil (191 mg, 95%). Method C HPLC-MS: MH+ requires m/z=201. Found: m/z=201, Rt=1.22 min (86%).

Intermediate 209: 6-[(2,2,2-Trifluoroethyl)sulfanyl]pyridine-3-carboxylic acid

To a solution of methyl 6-[(2,2,2-trifluoroethyl)sulfanyl]pyridine-3-carboxylate (Intermediate 210, 345 mg, 1.37 mmol) in MeOH (10 mL) was added a 2M sodium hydroxide aq. solution (1.37 mL, 2.74 mmol). The resulting reaction mixture was stirred at room temperature for 4 h and then evaporated to dryness. The remaining residue was dissolved in water (20 mL), acidified to pH 4.5 with a 1M aq. HCl solution and extracted with DCM (3×25 mL). Combined organics were dried over magnesium sulfate and evaporated to dryness to afford the title compound as a white solid (300 mg, 93%). Method C HPLC-MS: MH+ requires m/z=238. Found: m/z=238, Rt=1.35 min (98%).

Intermediate 210: Methyl 6-[(2,2,2-trifluoroethyl)sulfanyl]pyridine-3-carboxylate To a solution of sodium hydride (60% dispersion in mineral oil, 90 mg, 2.25 mmol) in anhydrous THF (40 mL) at 0 C was added 2,2,2-trifluoro-ethanethiol (200 µL, 2.25 mmol) drop-wise under nitrogen. The resulting solution was stirred for 15 min and added to a solution of 6-chloro-nicotinic acid methyl ester (257 mg, 1.5 mmol) in anhydrous THF (40 mL) at 0 C drop-wise. The reaction mixture was allowed to warm to room temperature and stirring was continued for a further 3 h. The solution was quenched with water at 0 C and extracted into EtOAc (3×50 mL). Combined organics were washed with brine (20 mL), dried over magnesium sulfate, evaporated to dryness and purified by silica chromatography (25% EtOAc in heptane) to afford the title compound as a colourless oil (370 mg, 98%). Method C HPLC-MS: MH+ requires m/z=252. Found: m/z=252, Rt=1.41 min (94%).

Intermediate 212: tert-butyl 4-(3,3,3-trifluoropropylidene)piperidine-1-carboxylate To a solution of triphenyl(3,3,3-trifluoropropyl)phosphanium bromide (Intermediate 213, 972 mg, 2 mmol) in THF (20 mL) at 0 C under nitrogen was added potassium tert-butoxide (235 mg, 2.1 mmol). The resulting reaction mixture was stirred at 0 C for 15 min and then a solution of 4-oxo-piperidine-1-carboxylic acid tert-butyl ester (398 mg, 2 mmol) in THF (5 mL) was added. The solution was stirred for a further 1 h at 0 C and then evaporated to dryness. The resulting residue was dissolved in EtOAc (25 mL) and washed with water (2×25 mL). Combined organics were washed with brine, dried over magnesium sulfate and evaporated to dryness. The crude solid was dissolved in diethyl ether (50 mL) and then filtered to remove insoluble impurities. The filtrate was evaporated to dryness to afford tert-butyl 4-(3,3,3-trifluoropropylidene)piperidine-1-carboxylate (Intermediate 212, 0.99 g, triphenylphosphine detected as impurity) which was used without further purification.

Intermediate 213:
Triphenyl(3,3,3-trifluoropropyl)phosphanium bromide

To a solution of 1,1,1-trifluoro-3-iodo-propane (3 g, 0.0133 mol) in toluene (20 mL) was added triphenylphosphine (3.51 g, 0.0133 mol). The resulting suspension was heated at 90 C for 28 h and then cooled to rt. The reaction mixture was evaporated to dryness and sonicated in diethyl ether (100 mL) for 5 min. The resulting white precipitate was filtered, washed with further diethyl ether and dried under vacuum to afford the title compound as a white crystalline solid (3.89 g, 60%). Method C HPLC-MS: MH+ requires m/z=359 (free salt). Found: m/z=359, Rt=1.06 min (100%).

Intermediate 214:
5-(Cyclopropylmethoxy)pyridine-2-carboxylic acid 5-(Cyclopropylmethoxy)pyridine-2-carbonitrile (Intermediate 215, 0.12 g, 0.622 mmol) was dissolved in EtOH (2 mL) and an aqueous solution of sodium hydroxide (35% w/w) (2 mL) was added. The mixture was stirred at 90 C for 3 h and left standing at room temperature for 2 days. The EtOH was removed under vacuum. The resulting white precipitate was collected by filtration, dried under vacuum and azeotroped with toluene and dried under high vacuum for 6 h to afford the title compound (120 mg, 90%). Method B HPLC-MS: MH+ requires m/z=193. Found: m/z=193, Rt=1.21 min (98%).

Intermediate 215:
5-(Cyclopropylmethoxy)pyridine-2-carbonitrile

Cyclopropylmethanol (0.120 mL, 1.504 mmol) was added to a suspension of sodium hydride (60% in mineral oil) (0.072 g, 1.805 mmol) in DMF (4 mL) at room temperature. The mixture was stirred at room temperature for 30 min, 4-chlorobenzonitrile (0.139 g, 1.002 mmol) was added. The reaction mixture was stirred at room temperature for 18 h. The mixture was diluted with water and extracted with EtOAc (3 times). The organic extracts were combined, washed with water (2 times), brine (2 times), dried and evaporated under vacuum. The crude residue was purified by flash chromatography (hexane:EtOAc 9:1 to 85:15) to afford the title compound (0.120 g, 69%). Method B HPLC-MS: MH+ requires m/z=175. Found: m/z=175, Rt=1.73 min (100%).

Intermediate 216: 6-Ethoxypyridine-3-carboxylic acid

Potassium hydroxide powder (0.373 g, 12.005 mmol) and EtOH (0.3 mL, 6.002 mmol) were added to a solution of 6-chloropyridine-3-carboxylic acid (0.473 g, 3.001 mmol) in DMSO (12 mL) at room temperature. The reaction mixture was heated at 100 C for 21 h, and cooled to room temperature. A 1M aqueous solution of HCl was added. The resulting precipitate was collected by filtration, washed with water and dried under vacuum to afford the title compound (356 mg, 71%). Method B HPLC-MS: MH+ requires m/z=168. Found: m/z=168, Rt=1.50 min (95%).

The following alkoxypyridines were prepared in an analogous manner to Intermediate 216.

| 217 | 6-(Propan-2-yloxy)pyridine-3-carboxylic acid | Method B HPLC-MS: MH+ requires m/z = 182; Found: m/z = 182, Rt = 1.57 min (100%) |
| 218 | 6-(2-Methoxyethoxy)pyridine-3-carboxylic acid (extracted into EtOAc after acidification) | Method B HPLC-MS: MH+ requires m/z = 198; Found: m/z = 198, Rt = 1.28 min (100%) |
| 219 | 6-Cyclobutoxypyridine-3-carboxylic acid | Method B HPLC-MS: MH+ requires m/z = 194; Found: m/z = 194, Rt = 1.76 min (96%) |

Intermediate 222: 5-(2,2,2-Trifluoroethoxy)pyridine-2-carboxylic acid

Methyl 5-(2,2,2-trifluoroethoxy)pyridine-2-carboxylate (Intermediate 223, 0.650 g, 2.77 mmol) was dissolved in MeOH (10 mL), 2M aq. sodium hydroxide (3.46 mL, 6.93 mmol) was added and the mixture stirred at room temperature for 2 h. MeOH was removed under vacuum and the aqueous suspension neutralised by adding 2M aq. hydrochloric acid (3.5 mL). The resultant precipitate was filtered, washed with diethyl ether and dried under vacuum to afford the title compound as a white solid (0.179 mg, 29%). 1H NMR (500 MHZ, MeOH-d4) δ ppm 8.41 (1H, d), 8.15 (1H, d), 7.59 (1H, dd) and 4.77 (2H, q).

Intermediate 223: Methyl 5-(2,2,2-trifluoroethoxy)pyridine-2-carboxylate

Methyl 5-hydroxypyridine-2-carboxylate (Intermediate 224, 0.610 g, 3.59 mmol) was dissolved in DMF (5 mL), cesium carbonate (1.40 g, 4.31 mmol) and 2,2,2-trifluoroethyl trifluoromethanesulfonate (1.0 g, 4.31 mmol) were added and the mixture stirred at room temperature for 18 h. The mixture was partitioned between EtOAc (50 mL) and water (15 mL) and the aqueous layer extracted with further EtOAc (2×20 mL). The combined organic layers were dried over sodium sulfate and concentrated under vacuum. The crude material was purified by FCC, eluting with a gradient of 0-50% EtOAc in heptane to afford the title compound as a white solid (0.652 g, 77%). 1H NMR (500 MHZ, CDCl$_3$) δ ppm 8.40 (1H, d), 8.09 (1H, d), 7.27 (1H, dd), 4.41 (2H, q) and 3.93 (3H, s).

Intermediate 224: Methyl 5-hydroxypyridine-2-carboxylate

6-Hydroxypicolinic acid (0.500 g, 3.59 mmol) was dissolved in MeOH (20 mL) and cooled to 0 C under nitrogen. Thionyl chloride (0.651 mL, 8.98 mmol) was added dropwise, the mixture was warmed to room temperature and stirred for 2 h. TLC indicated no reaction, so further thionyl chloride (0.781 mL, 10.77 mmol) was added and the mixture heated to 75 C for 8 h. The mixture was concentrated under vacuum to afford the title compound as a white solid (0.685 g), which was used in the next step without further purification. NMR shows approximately 25% unreacted 5-hydroxypicolinic acid. 1H NMR (500 MHZ, MeOH-d4) δ ppm 8.44 (1H, d), 8.39 (1H, d), 8.02 (1H, dd) and 4.09 (3H, s).

Intermediate 225: 5-[(2,2,2-Trifluoroethoxy)methyl]pyridine-2-carboxylic acid Powdered potassium hydroxide (0.331 g, 5.90 mmol) was dissolved in EtOH (2 mL) and added to 5-[(2,2,2-trifluoroethoxy)methyl]pyridine-2-carbonitrile (Intermediate 226, 0.255 g, 1.18 mmol). The mixture was heated to 110 C for 16 h. After cooling the residue was dissolved in water (3 mL), acidified to pH 1 by adding 10% aq. hydrochloric acid and extracted with EtOAc (3×20 mL). The combined organic layers were dried over sodium sulfate and concentrated to afford the title compound as a brown gum (0.252 g, 91%), which was used in the next step without further purification. Method C HPLC-MS: MH+ requires m/z=236 Found: m/z=236, Rt=0.83 min (82%).

Intermediate 226: 5-[(2,2,2-Trifluoroethoxy)methyl]pyridine-2-carbonitrile

2-Chloro-5-[(2,2,2-trifluoroethoxy)methyl]pyridine (Intermediate 227, 0.537 g, 2.38 mmol) was dissolved in DMF (6 mL) and zinc cyanide (0.279 g, 2.38 mmol) was added. The mixture was degassed by stirring under a flow of nitrogen for 10 min. Tetrakis(triphenylphosphine)palladium(0) (0.275 g, 0.24 mmol) and further DMF (2 mL) were added and the mixture heated to 100 C in a sealed tube for 6 h. The mixture was partitioned between EtOAc (50 mL) and water (50 mL) and the organic layer washed with further water (2×50 mL). The organic layer was dried over sodium sulfate and concentrated to yield an orange oil. This was purified by FCC, eluting with a gradient of 0-30% EtOAc in heptane to afford the title compound as a colourless oil (0.255 g, 50%). 1H NMR (500 MHZ, CDCl$_3$) δ ppm 8.62 (1H, d), 7.79 (1H, dd), 7.66 (1H, d), 4.72 (2H, s) and 3.89 (2H, q).

Intermediate 227: 2-Chloro-5-[(2,2,2-trifluoroethoxy)methyl]pyridine (6-Chloropyridin-3-yl)methanol (1.0 g, 6.97 mmol) was dissolved in THF (20 mL), potassium tert-butoxide (0.860 g, 7.66 mmol) was added and the mixture stirred at room temperature. 2,2,2-Trifluoroethyl trifluoromethanesulfonate (1.78 g, 7.66 mmol) was added dropwise with ice cooling and then the mixture stirred at room temperature for 2 h. EtOAc (50 mL) and water (50 mL) were added, the organic layer was separated and the aqueous layer neutralised to pH 6. The aqueous layer was then further extracted with EtOAc (3×20 mL), combined organic layers were dried over sodium sulfate and concentrated to yield a yellow solid. This was purified by FCC, eluting with a gradient of 0-50% EtOAc in heptane to afford the title compound as a colourless oil (0.537 g, 34%). 1H NMR (500 MHZ, CDCl$_3$) δ ppm 8.30 (1H, d), 7.61 (1H, dd), 7.30 (1H, d), 4.61 (2H, s) and 3.82 (2H, q).

Intermediate 228: 6-(Cyclohexyloxy)pyridine-3-carboxylic acid

6-Chloronicotinic acid (0.500 g, 3.17 mmol), powdered potassium hydroxide (0.712 g, 12.69 mmol) and cyclohexanol (0.636 g, 6.35 mmol) were combined in DMSO (12 mL) and heated in a sealed tube to 100 C for 18 h and then to 120 C for 21 h. The mixture was acidified to pH 1 by adding 2M hydrochloric acid. The mixture was then left to stand at room temperature overnight and the resultant precipitate filtered off, washed with water and dried under vacuum to afford the title compound as a cream solid (0.389 g, 55%). 1H NMR (500 MHZ, MeOH-d4) δ ppm 8.76 (1H, d), 8.19 (1H, dd), 6.79 (1H, d), 5.11 (1H, m), 2.03 (2H, m), 1.83 (2H, m), 1.64 (1H, m), 1.56 (2H, m), 1.47 (2H, m) and 1.38 (1H, m).

Intermediate 229: 6-[(1,1,1-Trifluoropropan-2-yl)oxy]pyridine-3-carboxylic acid 6-Chloronicotinic acid (0.500 g, 3.17 mmol), powdered potassium hydroxide (0.712 g, 12.69 mmol) and 1,1,1-trifluoropropan-2-ol (0.724 g, 6.35 mmol) were combined in DMSO (12 mL) and heated in a sealed tube to 100 C for 18 h. The mixture was acidified to pH 1 by adding 2M hydrochloric acid. The mixture was then left to stand at room temperature overnight and the resultant precipitate filtered off, washed with water and dried under vacuum to afford the title compound as a cream solid (0.527 g, 71%). 1H NMR (500 MHZ, MeOH-d4) δ ppm 8.82 (1H, d), 8.29 (1H, dd), 6.94 (1H, d), 5.96 (1H, m) and 1.52 (3H, d).

Intermediate 230: 6-(3,3,3-Trifluoropropoxy)pyridine-3-carboxylic acid

Methyl 6-(3,3,3-trifluoropropoxy)pyridine-3-carboxylate (Intermediate 231, 0.240 g, 0.91 mmol) was dissolved in EtOH (7.5 mL) and 2M aq. sodium hydroxide (1.37 mL, 2.74 mmol) was added. The mixture was stirred at room temperature for 3 h. The mixture was then concentrated to a minimum volume and acidified by adding 2M hydrochloric acid.

The mixture was extracted with DCM, the organic layer separated and concentrated under vacuum to afford the title compound as a white solid (0.102 g, 48%). 1H NMR (250 MHZ, MeOH-d4) δ ppm 8.76 (1H, d), 8.20 (1H, dd), 6.80 (1H, d), 4.61 (2H, t) and 2.71 (2H, m).

Intermediate 231: Ethyl 6-(3,3,3-trifluoropropoxy)pyridine-3-carboxylate 3,3,3-Trifluoropropanol (0.338 g, 2.96 mmol) was dissolved in THF (5 mL) and cooled to 0 C under nitrogen. Potassium tert-butoxide (0.332 g, 2.96 mmol) was added and the mixture stirred for 5 min. Ethyl 6-chloronicotinate (0.500 g, 2.69 mmol) was added, the mixture was warmed to room temperature and stirred for 3 h. Brine (10 mL) was added and the mixture extracted with EtOAc (3×10 mL). The combined organic layers were dried over sodium sulfate and concentrated to yield a yellow oil. This was purified by FCC, eluting with a gradient of 0-10% EtOAc in heptane to afford the title compound as a colourless oil (0.240 g, 34%), which was used in the next step without further purification. NMR shows approximately 15% unreacted ethyl 6-chloronicotinate. 1H NMR (500 MHZ, MeOH-d4) δ ppm 8.75 (1H, d), 8.11 (1H, dd), 6.71 (1H, d), 4.55 (2H, t), 4.31 (2H, q), 2.57 (2H, m) and 1.33 (3H, t).

Intermediate 234: tert-Butyl 4-hydroxy-4-phenylpiperidine-1-carboxylate

4-Hydroxy-4-phenylpiperidine (1.0 g, 5.64 mmol) and di-tert-butyl dicarbonate (1.35 g, 6.21 mmol) were combined in DCM (30 mL) and stirred at room temperature for 3 h. The mixture was diluted with DCM (100 mL) and washed with saturated aq. sodium bicarbonate (3×30 mL). The organic layer was dried over sodium sulphate and concentrated to afford the title compound as a pale yellow oil (1.759 g), which was used in the next step without further purification. 1H NMR (500 MHZ, CDCl$_3$): 7.50 (2H, d), 7.40 (2H, t), 7.31 (1H, t), 4.06 (2H, br s), 3.27 (2H, br s), 2.03 (2H, br s), 1.73 (2H, d) and 1.51 (9H, s).

Intermediate 235: 6-(Oxan-4-yloxy)pyridine-3-carboxylic acid

Ethyl 6-(oxan-4-yloxy)pyridine-3-carboxylate (Intermediate 236, 0.239 g, 0.95 mmol) was dissolved in EtOH (5 mL), 2M aq. sodium hydroxide (1.43 mL, 2.85 mmol) was added and the mixture was stirred at room temperature for 4 h. The mixture was concentrated under vacuum and the residue acidified to pH 6 by adding 2M aq. hydrochloric acid. The mixture was then extracted with DCM, followed by chloroform/isopropanol. The organic layer was separated using a hydrophobic frit and concentrated under vacuum to afford the title compound as a white solid (0.162 g, 47%), which was used directly in the next step without further purification. Method C HPLC-MS: MH+ requires m/z=224 Found: m/z=224, Rt=1.06 min (91%).

Intermediate 236: Ethyl 6-(oxan-4-yloxy)pyridine-3-carboxylate

Oxan-4-ol (0.302 g, 2.96 mmol) was dissolved in THF (5 mL) and cooled to 0 C under nitrogen. Potassium tert-butoxide (0.332 g, 2.96 mmol) was added and the mixture stirred for 5 min. Ethyl 6-chloronicotinate (0.500 g, 2.69 mmol) was added, the mixture was warmed to room temperature and stirred for 3 h. Water (5 mL) was added and the mixture extracted with EtOAc (2×10 mL). The organic layers were dried over sodium sulfate and concentrated under vacuum. The residue was purified by FCC, eluting with a gradient of 5-20% EtOAc in heptane to afford the title compound as a colourless oil (0.239 g, 35%). 1H NMR (250 MHZ, CDCl$_3$) δ ppm 8.80 (1H, dd), 8.14 (1H, m), 6.73 (1H, dd), 5.25 (1H, m), 4.39 (2H, dq), 3.96 (2H, m), 3.60 (2H, m), 2.05 (2H, m), 1.81 (2H, m) and 1.40 (3H, dt).

Intermediate 238: tert-Butyl 4-[(2,2,2-trifluoroethyl)sulfanyl]piperidine-1-carboxylate 2,2,2-Trifluoroethanol (0.133 mL, 1.49 mmol) was dissolved in DMF and cooled to 0 C under nitrogen. Sodium hydride (60% dispersion in mineral oil, 0.060 g, 1.49 mmol) was added and the mixture stirred for 10 min. tert-Butyl 4-(methanesulfonyloxy)piperidine-1-carboxylate (Intermediate 239, 0.320 g, 1.15 mmol) was added and the mixture was stirred at room temperature for 18 h. The mixture was then diluted with EtOAc (30 mL) and washed with water (10 mL), followed by saturated aq. sodium bicarbonate (10 mL) and brine (10 mL). The organic layer was dried over sodium sulfate and concentrated under vacuum to yield a pale yellow oil. This was purified by FCC, eluting with a gradient of 0-20% EtOAc in heptane to afford the title compound as a colourless oil (0.197 g, 57%). 1H NMR (500 MHZ, CDCl$_3$) δ ppm 4.02 (2H, br s), 3.14 (2H, q), 2.98 (3H, m), 1.97 (2H, d), 1.52 (2H, m) and 1.48 (9H, s).

Intermediate 240: 6-[(1-Methylpyrrolidin-3-yl)oxy]pyridine-3-carboxylic acid Ethyl 6-[(1-methylpyrrolidin-3-yl)oxy]pyridine-3-carboxylate (Intermediate 241, 0.089 g, 0.36 mmol) was dissolved in EtOH (2 mL), 2M aq. sodium hydroxide (0.53 mL, 1.07 mmol) was added and the mixture was stirred at room temperature for 4 h. The mixture was concentrated under vacuum and the residue acidified to pH 6 by adding 2M hydrochloric acid. The mixture was then concentrated and dried under vacuum to afford the title compound as a cream solid (0.136 g), which was used directly in the next step without further purification. Method C HPLC-MS: MH+ requires m/z=223 Found: m/z=223, Rt=0.38 min (17% by ELS).

Intermediate 241: Ethyl 6-[(1-methylpyrrolidin-3-yl)oxy]pyridine-3-carboxylate Ethyl 6-[(1-methylpyrrolidin-3-yl)oxy]pyridine-3-carboxylate was prepared from 1-methylpyrrolidin-3-ol (0.161 g, 1.59 mmol) and ethyl 6-chloronicotinate (0.269 g, 1.45 mmol) according to the method described for Intermediate 236. The crude material was purified by FCC, eluting with a gradient of 0-20% MeOH in EtOAc to afford the title compound as a colourless oil (0.089 g, 25%). 1H NMR (250 MHZ, CDCl$_3$) δ ppm 8.82 (1H, m), 8.13 (1H, dt), 6.74 (1H, m), 5.43 (1H, m), 4.39 (2H, dq), 2.82 (3H, m), 2.40 (3H, s), 2.39 (2H, m), 2.04 (1H, m) and 1.40 (3H, dt).

Intermediate 242: 6-[2-(2,2,2-Trifluoroethoxy)ethoxy]pyridine-3-carboxylic acid Methyl 6-[2-(2,2,2-trifluoroethoxy)ethoxy]pyridine-3-carboxylate (Intermediate 243, 0.453 g, 1.62 mmol) was dissolved in MeOH (5 mL), 2M aq. sodium hydroxide (1.62 mL, 3.24 mmol) was added and the mixture was stirred at room temperature for 1 h. The mixture was then concentrated under vacuum and acidified with 2M hydrochloric acid. The resultant precipitate was filtered off and dried under vacuum to afford the title compound as a white solid (0.245 g, 57%). 1H NMR (500 MHZ, MeOH-d4) δ ppm 8.79 (1H, d), 8.23 (1H, dd), 6.90 (1H, d), 4.55 (2H, dd), 4.03 (2H, q) and 4.01 (2H, dd).

Intermediate 243: Methyl 6-[2-(2,2,2-trifluoroethoxy)ethoxy]pyridine-3-carboxylate 2-(2,2,2-Trifluoroethoxy)ethanol (0.462 g, 3.21 mmol) was dissolved in THF (5 mL) and cooled to 0 C. Potassium tert-butoxide (0.360 g, 3.21 mmol) was added, the mixture was stirred for 5 min and methyl 6-chloronicotinate (0.500 g, 2.91 mmol) was added. The mixture was warmed to room temperature and stirred for 3 h. Brine (10 mL) was added and the mixture was extracted with EtOAc (3×20 mL). The combined organic layers were dried over sodium sulfate and concentrated to yield a yellow oil, which was purified by FCC to afford the title compound as a colourless oil (0.453 g, 56%). 1H NMR (500 MHZ, CDCl$_3$) δ ppm 8.73 (1H, d), 8.10 (1H, dd), 6.74 (1H, d), 4.50 (2H, t), 3.93 (2H, t), 3.87 (2H, q) and 3.84 (3H, s).

Intermediate 245: tert-Butyl 4-(propan-2-ylsulfanyl)piperidine-1-carboxylate tert-Butyl 4-(methanesulfonyloxy)piperidine-1-carboxylate (Intermediate 239, 0.320 g, 1.15 mmol) and sodium 2-propanethiolate (0.147 g, 1.50 mmol) were combined in DMF (3 mL) and stirred at room temperature for 18 h. The mixture was then diluted with EtOAc (30 mL) and washed with water (3×10 mL). The organic layer was dried over sodium sulfate and concentrated to yield a yellow oil. This was purified by FCC, eluting with a gradient of 0-20% EtOAc in heptane to afford the title compound as a colourless oil (0.179 g, 60%). 1H NMR (500 MHZ, CDCl$_3$) δ ppm 3.88 (2H, br s), 2.94 (1H, m), 2.86 (2H, m), 2.77 (1H, m), 1.83 (2H, d), 1.42 (2H, m), 1.38 (9H, s) and 1.20 (6H, d).

Intermediate 247: tert-Butyl 4-(propane-2-sulfinyl)piperidine-1-carboxylate tert-Butyl 4-(propan-2-ylsulfanyl)piperidine-1-carboxylate (prepared in an analogous manner to Intermediate 245, 0.160 g, 0.62 mmol) was dissolved in DCM (3 mL) and cooled to 0 C. m-Chloroperbenzoic acid (0.138 g, 0.62 mmol) was added, the mixture was warmed to room temperature and stirred for 17 h. Further m-chloroperbenzoic acid (0.040 g, 0.18 mmol) was added and the mixture was stirred at room temperature for 3 h. The mixture was then diluted with DCM (10 mL) and washed with saturated aq. sodium thiosulfate (10 mL). The organic layer was separated and purified by FCC, eluting with 50-100% EtOAc in heptane followed by 10% MeOH in EtOAc to afford the title compound as a colourless oil (0.124 g, 73%). Method C HPLC-MS: MH+ requires m/z=276 Found: m/z=298 (M+Na), Rt=1.14 min (100%).

Intermediate 248: 4-[(2,2,2-Trifluoroethoxy)methyl]benzoic acid

Methyl 4-[(2,2,2-trifluoroethoxy)methyl]benzoate (Intermediate 249, 1.05 g, 4.23 mmol) was dissolved in MeOH (10 mL), 2M aq. sodium hydroxide (6.4 mL, 12.69 mmol) was added and the mixture was stirred at room temperature for 3 h. THF (2 mL) was then added and the mixture stirred at room temperature over the weekend. The mixture was then concentrated under vacuum and the residue acidified by adding 2M hydrochloric acid. The mixture was diluted with a little water and extracted with DCM (3×20 mL). The combined organic layers were dried over sodium sulfate and concentrated under vacuum to afford the title compound as a white solid (0.974 g, 98%). 1H NMR (500 MHZ, CDCl$_3$) δ ppm 8.14 (2H, d), 7.49 (2H, d), 4.79 (2H, s) and 3.91 (2H, q).

Intermediate 249: Methyl 4-[(2,2,2-trifluoroethoxy)methyl]benzoate 2,2,2-Trifluoroethanol (0.35 mL, 4.80 mmol) was dissolved in THF (2 mL) and cooled to 0 C under nitrogen. Sodium hydride (60% dispersion in mineral oil, 0.192 g, 4.80 mmol) was added portionwise and the mixture stirred for 10 min. A solution of methyl 4-(bromomethyl)benzoate in THF (3 mL) was added, the mixture was warmed to room temperature and then heated to 50 C for 3 h. The mixture was then diluted with water (15 mL) and EtOAc (20 mL). The organic layer was separated and the aqueous neutralised with 1M hydrochloric acid. The aqueous layer was further extracted with EtOAc (2×20 mL). The combined organic layers were dried over sodium sulfate and concentrated under vacuum to afford the title compound as a colourless oily residue (1.05 g, 97%). 1H NMR (500 MHZ, CDCl$_3$) δ ppm 7.95 (2H, d), 7.33 (2H, d), 4.64 (2H, s), 3.83 (3H, s) and 3.77 (2H, q).

Intermediate 250: 6-(2,2-Difluoroethoxy)pyridine-3-carboxylic acid

Powdered potassium hydroxide (712 mg, 12.7 mmol) was added to a mixture of 6-chloronicotinic acid (500 mg, 3.17 mmol) and 2,2-difluoroethanol (520 mg, 6.35 mmol) in DMSO (15 mL) and the mixture was stirred at 120 C for 14 h. An additional two equivalents of 2,2-difluoroethanol and potassium hydroxide were added and the mixture was heated for 24 h. The mixture was cooled to room temperature, diluted with water (5 mL), acidified with 1N aq. HCl (to pH 1) and extracted with EtOAc (3×50 mL). The combined organic layers were washed with water (2×25 mL) then brine (50 mL) and concentrated under reduced pressure to provide title compound as a beige solid (620 mg, 96%). Method B HPLC-MS: MH+ requires m/z=204. Found: m/z=204, Rt=1.54 min (90%).

Intermediate 251: (1R,5S,6S)-6-[(2,2,2-Trifluoroethoxy)methyl]-3-azabicyclo[3.1.0]hexane (1R,5S,6S)-3-Benzyl-6-[(2,2,2-trifluoroethoxy)methyl]-3-azabicyclo[3.1.0]hexane (Intermediate 252, 360 mg, 1.26 mmol) and palladium hydroxide on carbon (20 wt. %, 108 mg, 0.15 mmol) were combined in EtOH (95 mL) and the mixture was heated to 50 C under a 4 bar atmosphere of hydrogen for 18 h. The mixture was filtered through celite, fresh catalyst was added to the filtrate and the mixture was heated to 60 C under a 4 bar atmosphere of hydrogen for 14 h. The mixture was filtered through celite and concentrated under reduced pressure to afford the title compound as an oil (203 mg, 82%). Method B HPLC-MS: MH+ requires m/z=196. Found: m/z=196, Rt=0.23 min (by MS).

The following intermediates were prepared in an analogous manner to Intermediate 251.

| 256 | (1R,5S,6S)-6-(Phenoxymethyl)-3-azabicyclo[3.1.0]hexane | Method B HPLC-MS: MH+ requires m/z = 190; Found: m/z = 190, Rt = 1.09 min (92%) |
| --- | --- | --- |
| 259 | (1R,5S,6S)-6-[(Cyclopropylmethoxy)methyl]-3-azabicyclo[3.1.0]hexane | Method B HPLC-MS: MH+ requires m/z = 168; Found: m/z = 168, Rt = 0.87 min (by MS) |
| 261 | (1R,5S,6S)-6-[(3,3,3-Trifluoropropoxy)methyl]-3-azabicyclo[3.1.0]hexane | Method B HPLC-MS: MH+ requires m/z = 210; Found: m/z = 210, Rt = 0.87 min (by MS) |
| 263 | (1R,5S,6S)-6-[(Propan-2-yloxy)methyl]-3-azabicyclo[3.1.0]hexane | Method B HPLC-MS: MH+ requires m/z = 156; Found: m/z = 156, Rt = 0.65 min (by MS) |
| 265 | (1R,5S,6S)-6-[(Cyclopentyloxy)methyl]-3-azabicyclo[3.1.0]hexane | Method B HPLC-MS: MH+ requires m/z = 182; Found: m/z = 182, Rt = 1.08 min (by MS) |

Intermediate 252: (1R,5S,6S)-3-Benzyl-6-[(2,2,2-trifluoroethoxy)methyl]-3-azabicyclo[3.1.0]hexane Methanesulfonyl chloride (320 μL, 4.13 mmol) was added to a solution of [(1R,5S,6S)-3-benzyl-3-azabicyclo[3.1.0]hexan-6-yl]methanol (Intermediate 253, 600 mg, 2.95 mmol) and triethylamine (620 μL, 4.43 mmol) in DCM (20 mL) at room temperature. The mixture was stirred for 3 h and then saturated aq. ammonium chloride (20 mL) was added. The mixture was extracted with DCM (3×20 mL). The combined organic layers were washed with water (20 mL) then brine (20 mL) and concentrated under reduced pressure to provide the desired mesylate intermediate. A mixture of 2,2,2-trifluoroethanol (255 μL, 3.54 mmol) and sodium hydride (60% dispersion in mineral oil, 141 mg, 3.54 mmol) in DMF (3 mL) was stirred at 0 C for 30 minutes and was then added to a solution of the mesylate intermediate in DMF (5 mL) at 0 C. The resulting mixture was stirred at room temperature for 14 h. Saturated aq. ammonium chloride (20 mL) was added and the mixture was extracted with EtOAc (4×50 mL). The combined organic layers were washed with water (3×20 mL) then brine (20 mL), concentrated under reduced pressure and purified by flash chromatography (40% EtOAc: heptane) to provide the title compound as a light yellow solid (360 mg, 42%). Method B HPLC-MS: MH+ requires m/z=286. Found: m/z=286, Rt=1.24 min (73%).

Intermediate 253: [(1R,5S,6S)-3-Benzyl-3-azabicyclo[3.1.0]hexan-6-yl]methanol

A solution of lithium aluminium hydride (5.6 g, 147.5 mmol) in dry THF (50 mL) was added dropwise to a solution of ethyl (1R,5S,6S)-3-benzyl-2,4-dioxo-3-azabicyclo[3.1.0]hexane-6-carboxylate (Intermediate 254, 10 g, 36.6 mmol) at 0 C, the mixture was warmed to room temperature and heated at 70 C for 18 h. The mixture was cooled to room temperature and quenched with saturated aq. ammonium chloride (5 mL) followed by water (1 mL) and stirred for 1 h. The residue was filtered off and washed with EtOAc. The filtrate was dried over magnesium sulfate and concentrated under reduced pressure to afford title compound as yellow oil (7.7 g, quant.). Method B HPLC-MS: MH+ requires m/z=204. Found: m/z=204, Rt=0.67 min (60%).

Intermediate 254: Ethyl (1R,5S,6S)-3-benzyl-2,4-dioxo-3-azabicyclo[3.1.0]hexane-6-carboxylate Ethyl 5-benzyl-4,6-dioxo-1H,3aH,4H,5H,6H,6aH-pyrrolo[3,4-c]pyrazole-3-carboxylate (Intermediate 255, 40 g, 132.9 mmol) was heated in 500 mL flask at 190 C. After evolution of nitrogen additional ethyl 5-benzyl-4,6-dioxo-1H,3aH,4H,5H,6H,6aH-pyrrolo[3,4-c]pyrazole-3-carboxylate (3×10 g) was added portionwise and the mixture was heated for 30 min until gas evolution stopped. The mixture was cooled to room temperature and diluted with diethyl ether and stirred at room temperature for 1 h. The mixture was cooled to −30 C and stirred for 30 min. The mixture was filtered and washed with cold diethyl ether to provide the title compound as an off white solid (26.1 g, 40%). Method B HPLC-MS: MH+ requires m/z=274. Found: m/z=274, Rt=1.96 min (82%).

Intermediate 255: Ethyl 5-benzyl-4,6-dioxo-1H,3aH,4H,5H,6H,6aH-pyrrolo[3,4-c]pyrazole-3-carboxylate Ethyl diazoacetate (30.3 mL, 288.5 mmol) was added dropwise over a period of 30 min to a solution of N-benzylmaleimide (49.5 g, 264.7 mmol) in diethyl ether (300 mL) and the mixture was stirred for 4 days at room temperature. The resulting precipitate was filtered off, washed with diethyl ether (100 mL) and dried under vacuum to provide title compound as a white solid (72 g, 90%). Method B HPLC-MS: MH+ requires m/z=302. Found: m/z=302, Rt=1.74 min (83%).

Intermediate 268: tert-Butyl 4-{[(2,2,2-trifluoroethyl)sulfanyl]methyl}piperidine-1-carboxylate 2,2,2-Trifluoroethane-1-thiol (471 µL, 3.41 mmol) was added dropwise to a suspension of sodium hydride (60% dispersion in mineral oil, 0.065 g, 1.636 mmol) in dry DMF (10 mL) at 0 C and the mixture was stirred for 15 min. A solution of tert-butyl 4-[(methanesulfonyloxy)methyl]piperidine-1-carboxylate (prepared in an analogous manner to Intermediate 181, 1 g, 3.41 mmol) in DMF (5 mL) was added dropwise and the mixture was stirred at room temperature for 5 h. The reaction mixture was diluted with water (50 mL) and extracted with EtOAc (3×50 mL). The combined organic layers were washed with saturated aq. sodium bicarbonate (25 mL) then brine (25 mL), dried over magnesium sulfate and concentrated under reduced pressure to provide the title compound as a light yellow oil (1.13 g, quant.). Method B HPLC-MS: MH+ requires m/z=314 Found: m/z=258 (MH+-tBu), Rt=2.39 min (98%).

Intermediate 270: tert-Butyl (3S)-3-phenoxypyrrolidine-1-carboxylate

Diisopropyl azodicarboxylate (1.19 g, 5.87 mmol) was added to an ice cooled mixture of tert-butyl (3R)-3-hydroxypyrrolidine-1-carboxylate (1 g, 5.34 mmol), phenol (0.5 g, 5.34 mmol) and triphenylphosphine (1.5 g, 5.8 mmol) in THF (14 mL). The mixture was stirred at room temperature for 20 h. The mixture was then concentrated under vacuum and the residue was twice triturated with diethyl ether. The resultant solid was filtered off and discarded. The filtrate was washed with 1M aq. sodium hydroxide, dried over sodium sulfate and concentrated. The residue was purified by FCC, eluting with 10% EtOAc in heptane to afford the title compound (0.893 g, 63%). Method B HPLC-MS: MH+ requires m/z=208 Found: m/z=208, Rt=2.20 min (91%).

Intermediate 272: tert-Butyl (3R)-3-phenoxypyrrolidine-1-carboxylate tert-Butyl (3R)-3-phenoxypyrrolidine-1-carboxylate was prepared from tert-butyl (3S)-3-hydroxypyrrolidine-1-carboxylate (0.43 g, 2.286 mmol) according to the method described for Intermediate 270 to afford the title compound (0.312 g, 51% yield). Method B HPLC-MS: MH+ requires m/z=208 Found: m/z=208, Rt=2.20 min (100%).

Intermediate 274: tert-Butyl (3R)-3-(2,2,2-trifluoroethoxy)pyrrolidine-1-carboxylate Di-tert-butyl azodicarboxylate (2.96 g, 12.83 mmol) was added to an ice cooled mixture of tert-butyl (3S)-3-hydroxypyrrolidine-1-carboxylate (2 g, 10.70 mmol), 2,2,2-trifluoroethanol (10.70 g, 106.95 mmol) and triphenylphosphine (3.37 g, 12.83 mmol) in THF (24 mL). The mixture was stirred at 70 C for 16 h. The mixture was concentrated under vacuum and the residue was purified by FCC, eluting with a gradient of EtOAc in heptane. The white solid collected was washed with heptane and the filtrate was concentrated to afford the title compound (1.263 g, 44%), which was used without further purification. Method B HPLC-MS: MH+ requires m/z=270 Found: m/z=214 (M minus tert-butyl), Rt=2.02 min (82%).

Intermediate 275: 6-[(Cyclopropylmethyl)sulfanyl]pyridine-3-carboxylic acid

6-[(Cyclopropylmethyl)sulfanyl]pyridine-3-carboxylic acid was prepared from 6-sulfanylpyridine-3-carboxylic acid (0.5 g, 3.22 mmol) and (bromomethyl)cyclopropane (0.44 g, 3.22 mmol) according to the method described for Intermediate 276 to afford the title compound (0.521 g, 61%). Method B HPLC-MS: MH+ requires m/z=210 Found: m/z=210, Rt=1.77 min (79%).

Intermediate 276: 6-[(3,3,3-Trifluoropropyl)sulfanyl]pyridine-3-carboxylic acid To a stirred solution of 6-sulfanylpyridine-3-carboxylic acid (0.5 g, 3.22 mmol) in EtOH (50 mL) at 0 C was added sodium acetate (0.26 g, 3.22 mmol) and 1,1,1-trifluoro-3-iodopropane (0.72 g, 3.22 mmol) and the mixture was heated at 80 C for 24 h. The mixture was concentrated under vacuum, water was added and the mixture was acidified to pH 4 using acetic acid. The resultant yellow precipitate was collected by filtration and purified by FCC, eluting with 2% MeOH in DCM to afford the title compound (0.459 g, 57%). Method B HPLC-MS: MH+ requires m/z=252 Found: m/z=252, Rt=1.84 min (91%).

Intermediate 279: 5-(2,2,2-Trifluoroethylamino)-pyridine-2-carboxylic acid 5-(2,2,2-Trifluoroethylamino)-pyridine-2-carboxylic acid methyl ester (Intermediate 280, 75 mg, 0.320 mmol) was dissolved in a mixture of THF (0.75 mL) and water (0.25 mL) and lithium hydroxide monohydrate (27 mg, 0.640 mmol) was added. The mixture was stirred at room temperature for 18 h. The mixture was diluted with water (5 mL), brought to approximately pH 4 by the addition of 1M HCl, then extracted with DCM (4×9 mL). The combined organic extracts were washed with brine (5 mL), dried over sodium sulfate and evaporated under vacuum to afford the title compound as a white solid (51 mg, 72%). Method B HPLC-MS: MH+ requires m/z=221. Found: m/z=221, Rt=1.30 min (100%).

Intermediate 280: 5-(2,2,2-Trifluoro-ethylamino)-pyridine-2-carboxylic acid methyl ester Methyl 5-aminopyridine-2-carboxylate (Intermediate 168, 200 mg, 1.31 mmol) and cesium carbonate (642 mg, 1.97 mmol) were dissolved in anhydrous DMF (2 mL) and stirred under nitrogen for 10 min. 2,2,2-Trifluoroethyl trifluoromethanesulfonate (246 µL, 1.70 mmol) was added and the mixture was stirred at room temperature for 18 h. Further cesium carbonate (642 mg, 1.97 mmol) and 2,2,2-trifluoroethyl trifluoromethanesulfonate (246 µL, 1.70 mmol) were added and the mixture was stirred at 85 C for 6 h. The mixture was diluted with EtOAc (50 mL) and washed with water (3×20 mL), then brine (20 mL) and then dried over sodium sulfate and evaporated under vacuum. The crude residue was purified by flash chromatography (0-10% EtOAc in heptane) to afford the title compound as a white solid (75 mg, 24%). Method B HPLC-MS: MH+ requires m/z=235. Found: m/z=235, Rt=1.76 min (84%).

Intermediate 281: 2-(2,2,2-Trifluoroethoxy)pyridine-4-carboxylic acid

2-Chloropyridine-4-carboxylic acid (200 mg, 1.27 mmol), potassium tert-butoxide (381 mg, 3.81 mmol) and 2,2,2-trifluoroethanol (2.6 mL) were charged to a sealed tube under nitrogen and stirred at 170 C for 3 h. 2,2,2-Trifluoroethanol (1 mL) was added and the reaction stirred at 170 C for 17 h. The mixture was evaporated under vacuum and the residue was dissolved in water (5 mL). 2M HCl was added to bring the solution to pH 5 and the mixture was extracted with DCM (3×10 mL). 2M HCl was then added to the aqueous layer to bring the solution to pH 3 and the mixture was extracted with DCM (4×6 mL). The combined organic extractions were washed with brine (5 mL), dried over sodium sulfate and evaporated under vacuum to afford the title compound as a white solid (210 mg, 75%). Method C HPLC-MS: MH+ requires m/z=222. Found: m/z=222, Rt=1.26 min (95%).

Intermediate 282: 2-(2,2,2-Trifluoroethoxy)nicotinic acid

2-Fluoropyridine-3-carboxylic acid (200 mg, 1.42 mmol) was dissolved in 2,2,2-trifluoroethanol (2 mL) and potassium tert-butoxide (477 mg, 4.25 mmol) was added. The mixture was then heated to 90 C for 4 h. The mixture was diluted with water (4 mL), 2M HCl was added to bring the solution to pH 4 and the mixture was extracted with DCM (3×4 mL). 2M HCl was added to the aqueous layer to bring the solution to pH 3 and the mixture was extracted with DCM (4×5 mL). The combined organic extractions were dried over sodium sulfate and evaporated under vacuum to afford the title compound (100 mg, 32%). Method C HPLC-MS: MH+ requires m/z=222. Found: m/z=222, Rt=1.17 min (100%).

Intermediate 283: 3-(2-Methoxyethoxy)-pyridine-2-carboxylic acid

3-Fluoropyridine-2-carboxylic acid (150 mg, 1.06 mol), 2-methoxyethanol (1.5 mL) and potassium tert-butoxide (356 mg, 3.18 mmol) were charged to a sealed tube under nitrogen then stirred at 100 C for 18 h. The mixture was then diluted with water (3 mL), 1M HCl was added to bring the solution to pH 5 and the mixture was extracted with DCM (2×5 mL). 1M HCl was added to the aqueous layer to bring the solution to pH 3 and the mixture was extracted with DCM (2×5 mL). The combined organic extractions were dried over sodium sulfate and evaporated under vacuum to afford the title compound as a brown gum (54 mg, 26%). Method C HPLC-MS: MH+ requires m/z=198. Found: m/z=198, Rt=0.29 min.

Intermediate 285: 3-(2,2,2-Trifluoroethoxy)-pyridine-2-carboxylic acid

Potassium tert-butoxide (954 mg, 8.51 mmol) was charged to a sealed tube with 2,2,2-trifluoroethanol (4 mL) and 3-fluoropyridine-2-carboxylic acid (400 mg, 2.84 mmol) and the mixture was heated to 130 C for 26 h, then to 150 C for 4 h, and then to 120 C for approximately 18 h. The mixture was diluted with water (6 mL) and washed with DCM (2×4 mL), which was then discarded. 1M HCl was added to bring the solution to pH 7 and the aqueous was extracted with DCM (2×4 mL). The extraction process was repeated as above at pH 5, 4 and 3. The combined organic extractions were dried over sodium sulfate and evaporated under vacuum to afford the title compound as a white solid (305 mg, 49%). Method B HPLC-MS: MH+ requires m/z=222. Found: m/z=222, Rt=0.73 min (100%).

Intermediate 286: 3-Cyclobutoxy-pyridine-2-carboxylic acid

Potassium tert-butoxide (358 mg, 3.19 mmol) was suspended in cyclobutanol (0.5 mL), 3-fluoropyridine-2-carboxylic acid (150 mg, 1.06 mmol) was added and the reaction was stirred at 100 C for 18 h. The mixture was evaporated under vacuum to afford the title compound (100% conversion assumed), which was used in the next step without further purification. Method C HPLC-MS: MH+ requires m/z=194. Found: m/z=194, Rt=0.83 min (100%).

Intermediate 290: 5-(2,2,2-Trifluoroethoxymethyl)-furan-2-carboxylic acid

Sodium hydride (60% dispersion in mineral oil, 60 mg, 1.50 mmol) was added to 2,2,2-trifluoroethanol (99 µL, 1.38 mmol) in anhydrous DMF (1 mL) and the mixture was stirred under nitrogen for 20 min. 5-Chloromethylfuran-2-carboxylic acid methyl ester (200 mg, 1.15 mmol) was then added and the mixture was stirred at room temperature for 18 h, then at 60 C for 3 h, then at 100 C for 3 h. Sodium hydride (60% dispersion in mineral oil, 30 mg, 0.75 mmol) was added under nitrogen and the reaction mixture was stirred at room temperature for 18 h. Sodium hydride (60% dispersion in mineral oil, 30 mg, 0.75 mmol) was added and the mixture was stirred at room temperature for 3 h. The reaction mixture was diluted with EtOAc (30 mL) then washed with saturated aq. sodium bicarbonate (4×6 mL), saturated aq. ammonium chloride (2×6 mL) and then brine (6 mL). The aqueous extractions were combined and brought to pH 1 by the addition of 2M HCl and then extracted with DCM (5 mL). The combined organic extractions were washed with water (3×6 mL), then brine (6 mL) and then dried over sodium sulfate and evaporated under vacuum to afford the title compound (123 mg, 48%), which was used without further purification. Method C HPLC-MS: (MH+) requires m/z=225. Found: m/z=252, Rt=1.15 min (97%).

Intermediate 125, Intermediate 148, Intermediate 165 and Intermediate 284 do not exist.

Biological Data

Whole-Cell Voltage Clamp Electrophysiology Assay

Patch-clamp electrophysiology is considered the gold standard technique for investigation of ion channel function and pharmacology. Using this method, sodium channel currents can be measured in cells, which stably (or transiently) express the sodium channel subtype of interest. Application of compounds during such experiments provides a functional measure of the activity and potency of compounds affecting the ion channel of interest.

Electrophysiological studies can be performed using automated or manual patch-clamp techniques. Automated patch-clamp instruments suitable for this work include the Ion Works HT (MDS), Ion Works Quattro (MDS), PatchLiner (Nanion technologies), Port-A-Patch (Nanion technologies), QPatch (Sophion) or any other suitable platform.

For recording in automated patch-clamp instruments, cells expressing the voltage-gated sodium channel subtype of interest are dispensed in appropriate chips (plates with more than one recording chambers each containing one or more apertures to generate whole-cell patches), as provided by the manufacturer. Typically, the whole-cell perforated patch configuration is used for probing the pharmacology of compounds in automated patch-clamp electrophysiology on sodium channels. Extracellular and intracellular buffers for such experiments are composed according to the literature, or according to the instructions provided by the manufacturer of the instruments. Test solutions, which contain the compounds to be tested, are applied to the cells expressing the sodium channel of interest by a pipetting system, typically integrated into the robots.

Electrophysiological studies can also be performed using the whole cell configuration of the standard manual patch clamp technique as described in the literature (e.g. Pflugers Arch., 1981, 391(2), 85-100). In this assay, cells that express the voltage-gated sodium channel protein of interest are exposed to the drugs by conventional microperfusion systems, or by a home-built perfusion system. A suitable voltage stimulus protocol is used to activate the voltage-gated sodium channels.

A suitable voltage stimulus protocol is used to activate voltage-gated sodium channel proteins of interest. A typical stimulus protocol may consist of sweeps of sequential voltage pulses starting from a holding potential (i.e. −65 mV), to a more positive and depolarising test pulse potential (i.e. −10 mV) and finally to a more negative and hyperpolarising potential (i.e. −100 mV). According to the biophysics of the voltage-gated ion channel of interest and interest in channel configuration the voltages and durations of the pulses as well as the overall frequency of sweeps applied might vary. Accordingly, a stimulus protocol was designed to assess compounds due to their potential to block NaV1.7 channels primarily in inactivated state. Selectivity over other voltage-gated sodium channel members was assessed by protocols that reflect the native function of the channels (i.e. heart rate or firing of neurons).

Electrophysiological studies can also be performed using the whole cell configuration of the standard manual patch clamp technique as described in the literature (e.g. Pflugers Arch., 1981, 391(2), 85-100). In this assay, cells that express the human voltage-gated sodium channel protein of interest are exposed to the drugs by conventional microperfusion systems, or by a home-built perfusion system. A suitable voltage stimulus protocol is used to activate the voltage-gated sodium channels. A suitable voltage stimulus protocol may consist of sequential voltage pulses from a holding potential, each first hyperpolarizing the cell, then depolarizing the channels for a brief period. A particularly suitable holding potential may be a voltage allowing a fraction of channels to remain in an inactivated state, like −60 mV. A suitable hyperpolarizing voltage and duration may be −120 mV for 100 ms, and depolarization voltage and duration may be −20 mV for 25 ms, and a suitable frequency of pulses may be 0.1 Hz, but may also have other parameters. Accordingly, a stimulus protocol was designed to assess compounds due to their potential to block NaV1.7 channels primarily in inactivated state. Selectivity over other voltage-gated sodium channel members was assessed by protocols that reflect the native function of the channels (i.e. heart rate or firing of neurons).

Inhibition of Nav1.5 by Compounds of formula (I) as measured using QPatch

| Example | IC50/nM |
|---------|---------|
| 39 | 891 |
| 41 | 334 |
| 43 | 1031 |
| 50 | 5889 |
| 67 | 7060 |
| 71 | 3020 |
| 72 | 5964 |
| 130 | 1672 |

Inhibition of Nav1.5 by Compounds of formula (I) as measured using manual patch clamp

| Example | IC50/nM |
|---------|---------|
| 1 | 2426 |
| 7 | 847 |
| 16 | 1050 |

| Example | IC50/nM |
|---------|---------|
| 21 | 2055 |
| 68 | >10000 |
| 86 | 300 |
| 95 | 3695 |
| 100 | 126 |
| 103 | 215 |
| 118 | 3340 |
| 125 | 917 |
| 132 | 2602 |

Pharmacological Model

Compounds of formula (I) may show analgesic activity in the FCA (Freund's Complete Adjuvant) test in the rat, a model of inflammatory pain which is induced by intraplantar injection of Complete Freund's Adjuvant (Stein et al. Pharmac. Biochem. Behav., 1988, 31, 445-451). The analgesic effects in the model may be obtained at doses that do not produce tissue concentrations leading to conduction block in nerve fibres. Thus, the local anesthetic effect may not mask the analgesic properties of the compounds (Scott et al., British Journal of Anaesthesia, 1988, 61, 165-8). Examples 125 and 130 were shown to be efficacious at a dose of 1 mg/kg (p.o.) and Example 67 was shown to be efficacious at a dose of 3 mg/kg (p.o.). All compounds were tested 72 h post FCA injection.

EMBODIMENTS

Embodiment 1

A compound of formula (I) or a pharmaceutically acceptable salts thereof,

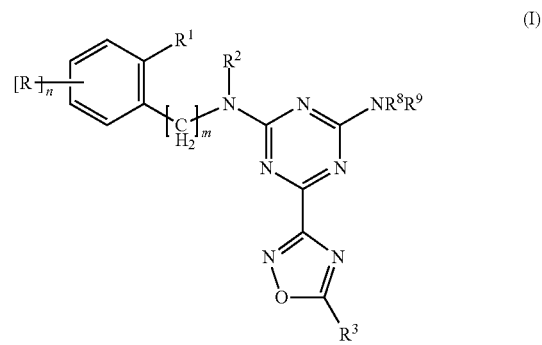

wherein
$R^1$ is selected from
  hydrogen-
  halogen-
  $C_1$-$C_7$-alkyl-
  halo-$C_1$-$C_7$-alkyl-;
$R^2$ is selected from
  hydrogen-
  $C_1$-$C_7$-alkyl-
  halo-$C_2$-$C_7$-alkyl-
  amino-$C_2$-$C_7$-alkyl-
  N—$C_1$-$C_7$-alkyl-amino-$C_2$-$C_7$-alkyl-
  N,N-di-$C_1$-$C_7$-alkyl-amino-$C_2$-$C_7$-alkyl-
  hydroxy-$C_2$-$C_7$-alkyl-
  $C_1$-$C_7$-alkoxy-$C_2$-$C_7$-alkyl-
  $C_3$-$C_{10}$-cycloalkyl-$C_1$-$C_7$-alkyl-
  cyano-$C_2$-$C_7$-alkyl-;

or $R^1$ and $R^2$, together with the atoms to which they are attached, form a 4-7 membered, saturated or partially saturated heterocyclic ring, which is unsubstituted or substituted by 1-3 substituents selected from
  $C_1$-$C_7$-alkyl-
  halo-$C_1$-$C_7$-alkyl-
  amino-$C_1$-$C_7$-alkyl-
  N—$C_1$-$C_7$-alkyl-amino-$C_1$-$C_7$-alkyl-
  N,N-di-$C_1$-$C_7$-alkyl-amino-$C_1$-$C_7$-alkyl-
  hydroxy-$C_1$-$C_7$-alkyl-
  $C_1$-$C_7$-alkoxy-$C_1$-$C_7$-alkyl-
  $C_3$-$C_{10}$-cycloalkyl-$C_1$-$C_7$-alkyl-
  cyano-$C_1$-$C_7$-alkyl-;

R is selected from
  halogen-
  $C_1$-$C_7$-alkyl-
  halo-$C_1$-$C_7$-alkyl-
  $C_1$-$C_7$-alkoxy-
  cyano-
  halo-$C_1$-$C_7$-alkoxy-
  nitro;
  —C(O)—O—R', wherein R' is selected from hydrogen, $C_1$-$C_7$-alkyl; $C_3$-$C_{10}$-cycloalkyl; $C_1$-$C_7$-alkoxy; halo-$C_1$-$C_7$-alkyl aryl; aryl-$C_1$-$C_7$-alkyl-; heteroaryl and heteroaryl $C_1$-$C_7$-alkyl-; heterocyclyl;
  —S(=O)$_2$—$C_1$-$C_7$-alkyl; —S(=O)$_2$—$C_3$-$C_{10}$-cycloalkyl; —S(=O)$_2$—$C_1$-$C_7$-alkoxy;

$R^3$ is selected from
(a) -L-Y, wherein
  -L- is selected from a direct bond; —(CH$_2$)$_p$—, —C(O)—, —NR$^7$—, —NR$^7$—C(O)— or —C(O)—NR$^7$—, wherein p is selected from 1, 2 or 3
  $R^7$ is selected from hydrogen and $C_1$-$C_7$-alkyl
  Y is selected from cycloalkyl, aryl, heteroraryl, heterocyclyl, spirocyclyl, which are unsubstituted or substituted by 1-3 substituents selected from
    halogen-;
    $C_1$-$C_7$-alkyl-;
    halo-$C_1$-$C_7$-alkyl-;
    halo-$C_1$-$C_7$-alkyl-oxy-$C_1$-$C_7$-alkyl; halo-$C_1$-$C_7$-alkyl-oxy-$C_1$-$C_7$-alkyl-oxy;
    $C_1$-$C_7$-alkoxy-; $C_1$-$C_7$-alkoxy-$C_1$-$C_7$-alkoxy-; NC—$C_1$-$C_7$-alkoxy-;
    $C_1$-$C_7$-alkoxy-$C_1$-$C_7$-alkyl-;
    $C_3$-$C_{10}$-cycloalkyl-oxy-$C_1$-$C_7$-alkyl-;
    $C_3$-$C_{10}$-cycloalkyl-$C_1$-$C_7$-alkyl-oxy-;
    $C_3$-$C_{10}$-cycloalkyl-oxy-;
    $C_3$-$C_{10}$-cycloalkyl-NR$^{7'}$—$C_1$-$C_7$-alkyl-, wherein R$^{7'}$ is selected from hydrogen and $C_1$-$C_7$-alkyl;
    $C_3$-$C_{10}$-cycloalkyl-$C_1$-$C_7$-alkoxy-$C_1$-$C_7$-alkyl-;
    $C_2$-$C_7$-alkenyl; halo-$C_2$-$C_7$-alkenyl;
    hydroxy-;
    hydroxy-$C_1$-$C_7$-alkyl-;
    halo-$C_1$-$C_7$-alkyl-oxy-;
    amino-;
    N—$C_1$-$C_7$-alkyl-amino-;
    N-halo-$C_1$-$C_7$-alkyl-amino-;
    N-heterocyclyl-amino-, N—$C_3$-$C_{10}$-cycloalkyl-amino-, wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;
    N—$C_3$-$C_{10}$-cycloalkyl-$C_1$-$C_7$-alkyl-amino-;
    N,N-di-$C_1$-$C_7$-alkyl-amino-; N,N-di-halo-$C_1$-$C_7$-alkyl-amino-;
    N,N-di-heterocyclyl-amino-, N,N-di-$C_3$-$C_{10}$-cycloalkyl-amino- wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;
    cyano-; oxo;
    $C_1$-$C_7$-alkoxy-carbonyl-;
    $C_1$-$C_7$-alkoxy-$C_1$-$C_7$-alkoxy-$C_1$-$C_7$-alkyl-;
    aryl; aryl-$C_1$-$C_7$-alkyl-; aryl-oxy;
    heterocyclyl;
    heterocyclyl-$C_1$-$C_7$-alkyl-; heterocyclyl-oxy-;
    heterocyclyl-oxy-$C_1$-$C_7$-alkyl-; aryl-oxy-$C_1$-$C_7$-alkyl-; heteroaryl-oxy-$C_1$-$C_7$-alkyl-;
    hydroxy-carbonyl-;
    —S— halo-$C_1$-$C_7$-alkyl; —S—$C_1$-$C_7$-alkyl; —S—aryl;
    halo-$C_1$-$C_7$-alkyl-S—$C_1$-$C_7$-alkyl; $C_1$-$C_7$-alkyl-S—$C_1$-$C_7$-alkyl;
    —S(=O)$_2$—$C_1$-$C_7$-alkyl; —S(=O)$_2$— halo-$C_1$-$C_7$-alkyl; —S(=O)$_2$-aryl; —S(=O)$_2$-heteroaryl; —S(=O)$_2$—NR$^{4'}$R$^4$; —S(=O)$_2$-heterocyclyl;
    halo-$C_1$-$C_7$-alkyl-S(=O)$_2$—$C_1$-$C_7$-alkyl; $C_1$-$C_7$-alkyl-S(=O)$_2$—$C_1$-$C_7$-alkyl;
    —S(=O)—$C_1$-$C_7$-alkyl; —S(=O)-halo-$C_1$-$C_7$-alkyl; —S(=O)—$C_1$-$C_7$-alkoxy; —S(=O)—$C_3$-$C_{10}$-cycloalkyl;
    —C(O)—$C_1$-$C_7$-alkyl; —C(O)— halo-$C_1$-$C_7$-alkyl; —C(O)—$C_1$-$C_7$-alkoxy; —C(O)—$C_3$-$C_{10}$ cycloalkyl;
    —C(O)O—$C_1$-$C_7$-alkyl; —C(O)O—$C_3$-$C_{10}$-cycloalkyl; —C(O)O-halo-$C_1$-$C_7$-alkyl; —C(O)O—$C_1$-$C_7$-alkoxy;
    —C(O)—NR$^{4'}$R$^4$ or —NHC(O)—R$^4$, wherein
    $R^4$ is selected from hydrogen, $C_1$-$C_7$-alkyl, halo-$C_1$-$C_7$-alky, $C_3$-$C_{10}$-cycloalkyl, $C_3$-$C_{10}$-cycloalkyl-$C_1$-$C_7$-alkyl and $C_1$-$C_7$-alkoxy;
    $R^{4'}$ is selected from hydrogen;
    or $R^4$ and $R^{4'}$ together with the nitrogen atom to which they are attached, form a 4-7 membered, saturated or partially saturated monocyclic heterocyclic ring, optionally containing a further heteroatom selected from N, O or S, and wherein said heterocyclic ring is optionally substituted with aryl, aryl-oxy-, $C_1$-$C_7$-alkyl, halo-$C_1$-$C_7$-alkyl or $C_1$-$C_7$-alkoxy, and said aryl is optionally substituted with halogen, $C_1$-$C_7$-alkyl, halo-$C_1$-$C_7$-alkyl or $C_1$-$C_7$-alkoxy.

or
(b) —C(O)—NR$^{5'}$R$^5$ or —C(O)—O—R$^5$, wherein
  $R^5$ and $R^{5'}$ are selected from hydrogen, $C_1$-$C_7$-alkyl; $C_3$-$C_{10}$-cycloalkyl; $C_1$-$C_7$-alkoxy; halo-$C_1$-$C_7$-alkyl aryl; aryl-$C_1$-$C_7$-alkyl-; aryl; heteroaryl; heteroaryl $C_1$-$C_7$-alkyl-; heterocyclyl; indane; or $R^5$ and $R^{5'}$ together with the nitrogen atom to which they are attached, form a 4-9 membered, saturated or partially saturated monocyclic or bicyclic heterocyclic ring, optionally containing a further heteroatom selected from N, O or S;
  wherein said $C_3$-$C_{10}$-cycloalkyl; aryl, heteroaryl, heterocyclyl and indane are optionally substituted with 1 to 3 substituents selected from $C_1$-$C_7$-alkyl, halo-$C_1$-$C_7$-alkyl, $C_1$-$C_7$-alkoxy, halo-$C_1$-$C_7$-alkyl-oxy-, halo-$C_1$-$C_7$-alkyl-oxy-$C_1$-$C_7$-alkyl, $C_1$-$C_7$-alkyl-oxy-$C_1$-$C_7$-alkyl and hydroxy-$C_1$-$C_7$-alkyl;

or
(c) —NR$^{6'}$R$^6$, wherein
  $R^6$ is selected from hydrogen, $C_1$-$C_7$-alkyl,
  $R^{6'}$ is selected from hydrogen, $C_1$-$C_7$-alkyl, $C_1$-$C_7$-alkyl carbonyl-; $C_3$-$C_{10}$-cycloalkyl;

or R⁶ and R⁶' together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which monocyclic and bicyclic heterocyclic ring is unsubstituted or substituted by 1-3 substituents selected from $C_1$-$C_7$-alkyl-, halo-$C_1$-$C_7$-alkyl-, $C_1$-$C_7$-alkoxy-, halo-$C_1$-$C_7$-alkoxy-, halo-$C_1$-$C_7$-alkoxy-$C_1$-$C_7$-alkyl-, hydroxy- and $C_1$-$C_7$-alkoxy-carbonyl-;

(d) —NR⁵'—C(O)—R⁵, wherein
R⁵ is selected from hydrogen, $C_1$-$C_7$-alkyl; $C_3$-$C_{10}$-cycloalkyl; $C_1$-$C_7$-alkoxy; halo-$C_1$-$C_7$-alkyl; aryl; aryl-$C_1$-$C_7$-alkyl-; heteroaryl; heteroaryl-$C_1$-$C_7$-alkyl-; heterocyclyl; R⁵' is selected from hydrogen, $C_1$-$C_7$-alkyl;
m is 0-1; and
n is 0-2;
R⁸ is hydrogen and R⁹ is selected from hydrogen, $C_1$-$C_7$-alkoxy-$C_1$-$C_7$-alkyl-, $C_1$-$C_7$-alkyl, $C_1$-$C_7$-alkoxy and halo-$C_1$-$C_7$-alkyl;
wherein $C_1$-$C_7$-alkyl, $C_1$-$C_7$-alkoxy, heterocyclyl, aryl, heteroaryl are optionally substituted by aryl, heteroaryl, heterocyclyl, $C_1$-$C_7$-alkyl, $C_1$-$C_7$-alkoxy, halo-$C_1$-$C_7$-alkyl; OH;
with the proviso that 6-[5-(2-furanyl)-1,2,4-oxadiazol-3-yl]-N2-methyl-N2-phenyl-1,3,5-triazine-2,4-diamine and 6-[5-(2-furanyl)-1,2,4-oxadiazol-3-yl]-N,N,N'-methyl-N'-phenyl-1,3,5-triazine-2,4-diamine are excluded.

Embodiment 2

A compound according to embodiment 1, wherein

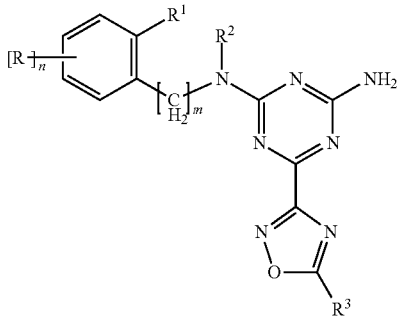
(I)

wherein
R¹ is selected from
hydrogen-
halogen-
$C_1$-$C_7$-alkyl-
halo-$C_1$-$C_7$-alkyl-;
R² is selected from
hydrogen-
$C_1$-$C_7$-alkyl-
halo-$C_2$-$C_7$-alkyl-
amino-$C_2$-$C_7$-alkyl-
N—$C_1$-$C_7$-alkyl-amino-$C_2$-$C_7$-alkyl-
N,N-di-$C_1$-$C_7$-alkyl-amino-$C_2$-$C_7$-alkyl-
hydroxy-$C_2$-$C_7$-alkyl-
$C_1$-$C_7$-alkoxy-$C_2$-$C_7$-alkyl-
$C_3$-$C_{10}$-cycloalkyl-$C_1$-$C_7$-alkyl-
cyano-$C_2$-$C_7$-alkyl-;
or
R¹ and R², together with the atoms to which they are attached, form a 4-7 membered, saturated or partially saturated heterocyclic ring, which is unsubstituted or substituted by 1-3 substituents selected from
$C_1$-$C_7$-alkyl-
halo-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
hydroxy-$C_1$-$C_7$-alkyl-
$C_1$-$C_7$-alkoxy-$C_1$-$C_7$-alkyl-
$C_3$-$C_{10}$-cycloalkyl-$C_1$-$C_7$-alkyl-
cyano-$C_1$-$C_7$-alkyl-;
R is selected from
halogen-
$C_1$-$C_7$-alkyl-
halo-$C_1$-$C_7$-alkyl-
$C_1$-$C_7$-alkoxy-
cyano-
halo-$C_1$-$C_7$-alkoxy-
nitro;
R³ is selected from
(a) -L-Y, wherein
-L- is selected from a direct bond; —(CH₂)$_p$—, —C(O)—, —NR⁷—, —NR⁷—C(O)— or —C(O)—NR⁷—, wherein p is selected from 1, 2 or 3
R⁷ is selected from hydrogen, $C_1$-$C_7$-alkyl
Y is selected from cycloalkyl, aryl, heteroaryl, heterocyclyl, which are unsubstituted or substituted by 1-3 substituents selected from
halogen-
$C_1$-$C_7$-alkyl-
halo-$C_1$-$C_7$-alkyl-
$C_1$-$C_7$-alkoxy-
$C_3$-$C_{10}$-cycloalkyl-oxy-
hydroxy-
halo-$C_1$-$C_7$-alkyl-oxy-
amino-
N—$C_1$-$C_7$-alkyl-amino-
N,N-di-$C_1$-$C_7$-alkyl-amino-
cyano-
$C_1$-$C_7$-alkoxy-carbonyl-
hydroxy-carbonyl-
—C(O)—NR⁴'R⁴, wherein
R⁴ is selected from hydrogen, $C_1$-$C_7$-alkyl;
R⁴' is selected from hydrogen,
or R⁴ and R⁴' together with the nitrogen atom to which they are attached, form a 4-7 membered, saturated or partially saturated monocyclic heterocyclic ring, optionally containing a further heteroatom selected from N, O or S;
or
(b) —C(O)—NR⁵'R⁵ or —C(O)—O—R⁵, wherein
R⁵ and R⁵' are selected from hydrogen, $C_1$-$C_7$-alkyl;
or
(c) —NR⁶'R⁶, wherein
R⁶ is selected from hydrogen, $C_1$-$C_7$-alkyl,
R⁶' is selected from hydrogen, $C_1$-$C_7$-alkyl, $C_1$-$C_7$-alkyl carbonyl-,
m is 0-1; and
n is 0-2;
with the proviso that 6-[5-(2-furanyl)-1,2,4-oxadiazol-3-yl]-N2-methyl-N2-phenyl-1,3,5-triazine-2,4-diamine is excluded.

Embodiment 3

A compound according to embodiment 1 or 2, wherein

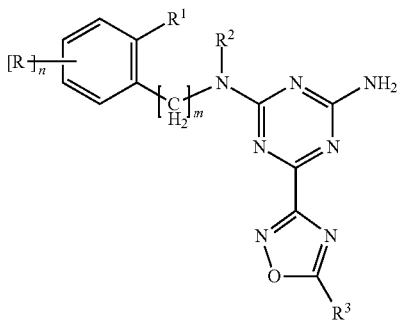

(I)

wherein
$R^1$ is selected from
  hydrogen-
  halogen-
  $C_1$-$C_7$-alkyl-
  halo-$C_1$-$C_7$-alkyl-;
$R^2$ is selected from
  hydrogen-
  $C_1$-$C_7$-alkyl-
  halo-$C_2$-$C_7$-alkyl-
  amino-$C_2$-$C_7$-alkyl-
  N—$C_1$-$C_7$-alkyl-amino-$C_2$-$C_7$-alkyl-
  N,N-di-$C_1$-$C_7$-alkyl-amino-$C_2$-$C_7$-alkyl-
  hydroxy-$C_2$-$C_7$-alkyl-
  $C_1$-$C_7$-alkoxy-$C_2$-$C_7$-alkyl-
  $C_3$-$C_{10}$-cycloalkyl-$C_1$-$C_7$-alkyl-
  cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
  $C_1$-$C_7$-alkyl-
  halo-$C_1$-$C_7$-alkyl-
  amino-$C_1$-$C_7$-alkyl-
  N—$C_1$-$C_7$-alkyl-amino-C1-$C_7$-alkyl-
  N,N-di-$C_1$-$C_7$-alkyl-amino-$C_1$-$C_7$-alkyl-
  hydroxy-$C_1$-$C_7$-alkyl-
  $C_1$-$C_7$-alkoxy-$C_1$-$C_7$-alkyl-
  $C_3$-$C_{10}$-cycloalkyl-$C_1$-$C_7$-alkyl-
  cyano-$C_1$-$C_7$-alkyl-;
R is selected from
  halogen-
  $C_1$-$C_7$-alkyl-
  halo-$C_1$-$C_7$-alkyl-
  $C_1$-$C_7$-alkoxy-
  cyano-
  halo-$C_1$-$C_7$-alkoxy-
  nitro;
$R^3$ is selected from
(a) —$(CH_2)_p$—Y, wherein
  p is selected from 0, 1, 2 or 3, and
  Y is selected from aryl, heteroaryl, heterocyclyl, which are unsubstituted or substituted by 1-3 substituents selected from
    halogen-
    $C_1$-$C_7$-alkyl-
    halo-$C_1$-$C_7$-alkyl-
    $C_1$-$C_7$-alkoxy-
    $C_3$-$C_{10}$-cycloalkyl-oxy-
    hydroxy-
    halo-$C_1$-$C_7$-alkyl-oxy-
    amino-
    N—$C_1$-$C_7$-alkyl-amino-
    N,N-di-$C_1$-$C_7$-alkyl-amino-
    cyano-
    $C_1$-$C_7$-alkoxy-carbonyl-
    hydroxy-carbonyl-
    —C(O)—$NR^{4'}R^4$, wherein
      $R^4$ is selected from hydrogen, $C_1$-$C_7$-alkyl;
      $R^{4'}$ is selected from hydrogen,
      or $R^4$ and $R^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—$NR^{5'}R^5$ or —C(O)—O—$R^5$, wherein
  $R^5$ is selected from hydrogen, benzyl, indanyl, tetrahydrofuranyl, tetrahydropyranyl, oxiranyl, $C_3$-$C_{10}$-cycloalkyl, $C_1$-$C_7$-alkyl;
  $R^{5'}$ is selected from hydrogen, $C_1$-$C_7$-alkyl,
  or $R^5$ and $R^{5'}$ together with the nitrogen atom to which they are attached, form a 4-7 membered, saturated or partially saturated monocyclic or bicyclic heterocyclic ring, optionally containing a further heteroatom selected from N, O or S;
or
(c) —$NR^{6'}R^6$, wherein
  $R^6$ is selected from hydrogen, benzyl, $C_3$-$C_{10}$-cycloalkyl, $C_1$-$C_7$-alkyl,
  $R^{6'}$ is selected from hydrogen, $C_1$-$C_7$-alkyl, $C_1$-$C_7$-alkyl carbonyl-,
  or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S;
  which are unsubstituted or substituted by 1-3 substituents selected from $C_1$-$C_7$-alkyl-
    hydroxy-
    $C_1$-$C_7$-alkoxy-carbonyl-
or
(d) —$NR^{5'}$—C(O)—$R^5$, wherein
  $R^5$ is selected from $C_3$-$C_{10}$-cycloalkyl;
  $R^{5'}$ is selected from hydrogen, $C_1$-$C_7$-alkyl;
m is 0-1; and
n is 0-1;
with the proviso that 6-[5-(2-furanyl)-1,2,4-oxadiazol-3-yl]-N2-methyl-N2-phenyl-1,3,5-triazine-2,4-diamine is excluded.

Embodiment 4

A compound according to any one of embodiments 1 to 3, wherein

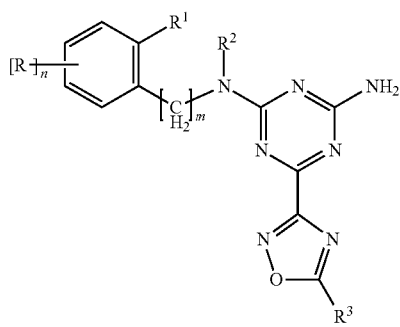

$R^1$ is selected from
hydrogen-
halogen-
$C_1$-$C_7$-alkyl-
halo-$C_1$-$C_7$-alkyl-;
$R^2$ is selected from
hydrogen-
$C_1$-$C_7$-alkyl-
halo-$C_2$-$C_7$-alkyl-
amino-$C_2$-$C_7$-alkyl-
N—$C_1$-$C_7$-alkyl-amino-$C_2$-$C_7$-alkyl-
N,N-di-$C_1$-$C_7$-alkyl-amino-$C_2$-$C_7$-alkyl-
hydroxy-$C_2$-$C_7$-alkyl-
$C_1$-$C_7$-alkoxy-$C_2$-$C_7$-alkyl-
$C_3$-$C_{10}$-cycloalkyl-$C_1$-$C_7$-alkyl-
cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
$C_1$-$C_7$-alkyl-
halo-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
hydroxy-$C_1$-$C_7$-alkyl-
$C_1$-$C_7$-alkoxy-$C_1$-$C_7$-alkyl-
$C_3$-$C_{10}$-cycloalkyl-$C_1$-$C_7$-alkyl-
cyano-$C_1$-$C_7$-alkyl-;
R is selected from
halogen-
$C_1$-$C_7$-alkyl-
halo-$C_1$-$C_7$-alkyl-
$C_1$-$C_7$-alkoxy-
cyano-
halo-$C_1$-$C_7$-alkoxy-
nitro;
$R^3$ is selected from
(a) —(CH$_2$)$_p$—Y, wherein
p is selected from 0, 1, 2 or 3, and
Y is selected from aryl, heteroaryl, heterocyclyl, which are unsubstituted or substituted by 1-3 substituents selected from
halogen-
$C_1$-$C_7$-alkyl-
halo-$C_1$-$C_7$-alkyl-
$C_1$-$C_7$-alkoxy-
$C_3$-$C_{10}$-cycloalkyl-oxy-
hydroxy-
halo-$C_1$-$C_7$-alkyl-oxy-
amino-
N—$C_1$-$C_7$-alkyl-amino-
N,N-di-$C_1$-$C_7$-alkyl-amino-
cyano-
$C_1$-$C_7$-alkoxy-carbonyl-
hydroxy-carbonyl-
—C(O)—NR$^{4'}$R$^4$, wherein
$R^4$ is selected from hydrogen, $C_1$-$C_7$-alkyl;
$R^{4'}$ is selected from hydrogen,
or $R^4$ and $R^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—NR$^{5'}$R$^5$ or —C(O)—O—R$^5$, wherein
$R^5$ is selected from hydrogen, benzyl, indanyl, tetrahydrofuranyl, tetrahydropyranyl, oxiranyl, $C_3$-$C_{10}$-cycloalkyl, $C_1$-$C_7$-alkyl;
$R^{5'}$ is selected from hydrogen, $C_1$-$C_7$-alkyl,
or $R^5$ and $R^{5'}$ together with the nitrogen atom to which they are attached, form a 4-7 membered, saturated or partially saturated monocyclic or bicyclic heterocyclic ring, optionally containing a further heteroatom selected from N, O or S;
or
(c) —NR$^{6'}$R$^6$, wherein
$R^6$ is selected from hydrogen, benzyl, $C_3$-$C_{10}$-cycloalkyl, $C_1$-$C_7$-alkyl,
$R^{6'}$ is selected from hydrogen, $C_1$-$C_7$-alkyl, $C_1$-$C_7$-alkyl carbonyl-,
or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from $C_1$-$C_7$-alkyl-
hydroxy-
$C_1$-$C_7$-alkoxy-carbonyl-
or
(d) —NR$^{5'}$—C(O)—R$^5$, wherein
$R^5$ is selected from $C_3$-$C_{10}$-cycloalkyl;
$R^{5'}$ is selected from hydrogen, $C_1$-$C_7$-alkyl;
m is 0-1; and
n is 0-1;
with the proviso that 6-[5-(2-furanyl)-1,2,4-oxadiazol-3-yl]-N2-methyl-N2-phenyl-1,3,5-triazine-2,4-diamine is excluded.

Embodiment 5

A compound according to any one of embodiments 1-3, wherein
$R^1$ is selected from
hydrogen-
halogen-
$C_1$-$C_4$-alkyl-
halo-$C_1$-$C_4$-alkyl-.

Embodiment 6

A compound according to any one of embodiments 1-5, wherein $R^1$ is selected from hydrogen-, chloro-, fluoro- and methyl-.

Embodiment 7

A compound according to any one of embodiments 1-6, wherein $R^1$ is selected from hydrogen- and fluoro-.

Embodiment 8

A compound according to any one of embodiments 1-7, wherein
$R^2$ is selected from
   hydrogen-
   $C_1$-$C_4$-alkyl-
   halo-$C_2$-$C_4$-alkyl-
   N,N-di-$C_1$-$C_2$-alkyl-amino-$C_2$-$C_4$-alkyl-
   hydroxy-$C_2$-$C_4$-alkyl-
   $C_1$-$C_2$-alkoxy-$C_2$-$C_4$-alkyl-
   $C_3$-$C_6$-cycloalkyl-$C_1$-$C_7$-alkyl-.

Embodiment 9

A compound according to any one of embodiments 1-8, wherein
$R^2$ is selected from
   hydrogen-
   methyl-
   ethyl-
   isopropyl-
   2,2,2-trifluoro-ethyl-
   N,N-di-methyl-amino-ethyl-
   hydroxy-ethyl-
   methoxy-ethyl-
   cyclopropyl-methyl-.

Embodiment 10

A compound according to any one of embodiments 1-9, wherein
$R^2$ is selected from
   hydrogen-
   methyl-
   ethyl-
   2,2,2-trifluoro-ethyl-.

Embodiment 11

A compound according to any one of embodiments 1-4, wherein
$R^1$ and $R^2$, together are selected from
—$CH_2$—$CH_2$—, —$CH_2$—$CH_2$—$CH_2$—, —CH=CH—, —CH=CH—$CH_2$— or —$CH_2$—CH=CH—.

Embodiment 12

A compound according to any one of embodiments 11, wherein $R^1$ and $R^2$, together are selected from —$CH_2$—$CH_2$— or —$CH_2$—$CH_2$—$CH_2$—.

Embodiment 13

A compound according to any one of embodiments 1-4, wherein $R^1$ is selected from
   hydrogen-
   chloro-
   fluoro-
   methyl-;
$R^2$ is selected from
   hydrogen-
   $C_1$-$C_4$-alkyl-
   halo-$C_2$-$C_4$-alkyl-
   N,N-di-$C_1$-$C_2$-alkyl-amino-$C_2$-$C_4$-alkyl-
   hydroxy-$C_2$-$C_4$-alkyl-
   $C_1$-$C_2$-alkoxy-$C_2$-$C_4$-alkyl-
   $C_3$-$C_6$-cycloalkyl-$C_1$-$C_7$-alkyl-.

Embodiment 14

A compound according to any one of embodiments 1-13, wherein
R is selected from
   halogen-
   $C_1$-$C_4$-alkyl-
   halo-$C_1$-$C_4$-alkyl-
   $C_1$-$C_4$-alkoxy-
   cyano-.

Embodiment 15

A compound according to any one of embodiments 1-14, wherein
R is selected from
   chloro-
   fluoro-
   methyl-
   trifluoromethyl-
   methoxy-
   cyano-.

Embodiment 16

A compound according to any one of embodiments 1-15, wherein
$R^3$ is selected from
   —$(CH_2)_p$—Y, wherein
   p is selected from 0, 1, 2 or 3, and
   Y is selected from aryl, heteroaryl, heterocyclyl, which are unsubstituted or substituted
   by 1-3 substituents selected from
      halogen-
      $C_1$-$C_7$-alkyl-
      halo-$C_1$-$C_7$-alkyl-
      $C_1$-$C_7$-alkoxy-
      $C_3$-$C_{10}$-cycloalkyl-oxy-
      hydroxy-
      halo-$C_1$-$C_7$-alkyl-oxy-
      amino-
      N—$C_1$-$C_7$-alkyl-amino-
      N,N-di-$C_1$-$C_7$-alkyl-amino-
      —S(=O)$_2$—$C_1$-$C_7$-alkyl; —S(=O)$_2$— halo-$C_1$-$C_7$-alkyl;
      —S(=O)—$C_1$-$C_7$-alkyl;   —S(=O)-halo-$C_1$-$C_7$-alkyl;

$C_3$-$C_{10}$-cycloalkyl-$C_1$-$C_7$-alkoxy-$C_1$-$C_7$-alkyl-;
cyano-
$C_1$-$C_7$-alkoxy-carbonyl-
hydroxy-carbonyl-
—C(O)—$NR^{4'}R^4$, wherein
   $R^4$ is selected from hydrogen, $C_1$-$C_7$-alkyl;
   $R^{4'}$ is selected from hydrogen,
   or $R^4$ and $R^{4'}$ together with the nitrogen atom to which they are attached, form a 4-7 membered, saturated or partially saturated monocyclic heterocyclic ring, optionally containing a further heteroatom selected from N, O or S.

Embodiment 17

A compound according to any one of embodiments 1-16, wherein
$R^3$ is selected from
—Y, wherein
   Y is selected from aryl, heteroaryl, heterocyclyl, which are unsubstituted or substituted by 1-2 substituents selected from
   halogen-
   $C_1$-$C_4$-alkyl-
   halo-$C_1$-$C_4$-alkyl-
   $C_1$-$C_4$-alkoxy-
   $C_3$-$C_7$-cycloalkyl-oxy-
   hydroxy-
   halo-$C_1$-$C_4$-alkyl-oxy-
   amino-
   cyano-
   $C_1$-$C_4$-alkoxy-carbonyl-
   hydroxy-carbonyl-
   —S(=O)$_2$—$C_1$-$C_7$-alkyl; —S(=O)$_2$— halo-$C_1$-$C_7$-alkyl;
   —S(=O)—$C_1$-$C_7$-alkyl; —S(=O)-halo-$C_1$-$C_7$-alkyl
   $C_3$-$C_{10}$-cycloalkyl-$C_1$-$C_7$-alkoxy-$C_1$-$C_7$-alkyl-;
   —C(O)—$NR^{4'}R^4$, wherein
      $R^4$ is selected from hydrogen, $C_1$-$C_4$-alkyl;
      $R^{4'}$ is selected from hydrogen,
      or $R^4$ and $R^{4'}$ together with the nitrogen atom to which they are attached, form a 4-7 membered, saturated or partially saturated monocyclic heterocyclic ring, optionally containing a further heteroatom selected from N, O or S.

Embodiment 18

A compound according to any one of embodiments 1-17, wherein
$R^3$ is selected from
—Y, wherein
   Y is selected from aryl, heteroaryl, heterocyclyl, which are unsubstituted or substituted by 1-2 substituents selected from
   halogen-
   $C_1$-$C_4$-alkyl-
   halo-$C_1$-$C_4$-alkyl-
   $C_1$-$C_4$-alkoxy-
   $C_3$-$C_7$-cycloalkyl-oxy-
   hydroxy-
   halo-$C_1$-$C_4$-alkyl-oxy-
   amino-
   cyano-
   $C_1$-$C_4$-alkoxy-carbonyl-
   hydroxy-carbonyl-
   —C(O)—$NR^{4'}R^4$, wherein
      $R^4$ is selected from hydrogen, $C_1$-$C_4$-alkyl;
      $R^{4'}$ is selected from hydrogen,
      or $R^4$ and $R^{4'}$ together with the nitrogen atom to which they are attached, form a 4-7 membered, saturated or partially saturated monocyclic heterocyclic ring, optionally containing a further heteroatom selected from N, O or S.

Embodiment 19

A compound according to any one of embodiments 1-17, wherein
$R^3$ is selected from
   phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
   halogen-
   $C_1$-$C_4$-alkyl-
   halo-$C_1$-$C_4$-alkyl-
   $C_1$-$C_4$-alkoxy-
   $C_3$-$C_7$-cycloalkyl-oxy-
   hydroxy-
   halo-$C_1$-$C_4$-alkyl-oxy-
   amino-
   cyano-
   $C_1$-$C_4$-alkoxy-carbonyl-
   —S(=O)$_2$—$C_1$-$C_7$-alkyl; —S(=O)$_2$— halo-$C_1$-$C_7$-alkyl;
   —S(=O)—$C_1$-$C_7$-alkyl; —S(=O)-halo-$C_1$-$C_7$-alkyl
   $C_3$-$C_{10}$-cycloalkyl-$C_1$-$C_7$-alkoxy-$C_1$-$C_7$-alkyl-;
   —C(O)—$NR^{4'}R^4$, wherein
      $R^4$ is selected from hydrogen, $C_1$-$C_4$-alkyl;
      $R^{4'}$ is selected from hydrogen,
      or $R^4$ and $R^{4'}$ together with the nitrogen atom to which they are attached, form morpholinyl, piperidinyl, pyrrolidinyl.

Embodiment 20

A compound according to any one of embodiments 1-18, wherein
$R^3$ is selected from
   phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
   chloro-
   bromo-
   fluoro-
   methyl-
   trifluoromethyl-
   2,2,2-trifluoro-ethyl-
   2,2,2-trifluoro-ethyl-oxy-methyl-
   cyclopropyl-methoxy-methyl-1
   —S(=O)$_2$-2,2,2-trifluoro-ethyl-;
   —S(=O)$_2$-propyl;
   —S(=O)-3,3,3-trifluoro-propyl;
   3,3,3-trifluoro-propyl-oxy-methyl-;
   methoxy-
   cyclopentyl-oxytrifluoromethyl-oxy-
2,2,2-trifluoro-ethyl-oxy-
amino-
cyano-
methoxy-carbonyl-
—C(O)—NR$^{4'}$R$^4$, wherein
R$^4$ is selected from hydrogen, methyl;
R$^{4'}$ is selected from hydrogen,
or R$^4$ and R$^{4'}$ together with the nitrogen atom to which they are attached, form morpholinyl, piperidinyl, pyrrolidinyl.

Embodiment 21

A compound according to any one of embodiments 1-18, wherein
R$^3$ is selected from
phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
chloro-
bromo-
fluoro-
methyl-
trifluoromethyl-
2,2,2-trifluoro-ethyl-
cyclopropyl-methoxy-methyl-
methoxy-
cyclopentyl-oxy-
trifluoromethyl-oxy-
2,2,2-trifluoro-ethyl-oxy-
amino-
cyano-
methoxy-carbonyl-
—C(O)—NR$^{4'}$R$^4$, wherein
R$^4$ is selected from hydrogen, methyl;
R$^{4'}$ is selected from hydrogen,
or R$^4$ and R$^{4'}$ together with the nitrogen atom to which they are attached, form morpholinyl, piperidinyl, pyrrolidinyl.

Embodiment 22

A compound according to any one of embodiments 1-21, wherein
R$^3$ is selected from
—C(O)—NR$^{5'}$R$^5$ or —C(O)—O—R$^5$, wherein
R$^5$ is selected from hydrogen, benzyl, indanyl, tetrahydrofuranyl, tetrahydropyranyl, oxiranyl, C$_3$-C$_{10}$-cycloalkyl, C$_1$-C$_7$-alkyl;
R$^{5'}$ is selected from hydrogen, C$_1$-C$_7$-alkyl,
or R$^5$ and R$^{5'}$ together with the nitrogen atom to which they are attached, form a 4-7 membered, saturated or partially saturated monocyclic or bicyclic heterocyclic ring, optionally containing a further heteroatom selected from N, O or S.

Embodiment 23

A compound according to any one of embodiments 1-22, wherein
R$^3$ is selected from
—NR$^{6'}$R$^6$, wherein
R$^6$ is selected from hydrogen, benzyl, C$_3$-C$_{10}$-cycloalkyl, C$_1$-C$_7$-alkyl,
R$^{6'}$ is selected from hydrogen, C$_1$-C$_7$-alkyl, C$_1$-C$_7$-alkyl carbonyl-,
or R$^6$ and R$^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from C$_1$-C$_7$-alkyl-
hydroxy-
C$_1$-C$_7$-alkoxy-carbonyl-.

Embodiment 24

A compound according to any one of embodiments 1-23, wherein
R$^3$ is selected from
—NR$^{5'}$—C(O)—R$^5$, wherein
R$^5$ is selected from C$_3$-C$_{10}$-cycloalkyl;
R$^{5'}$ is selected from hydrogen, C$_1$-C$_7$-alkyl.

Embodiment 25

A compound according to any one of embodiments 1-24, wherein
m is 0.

Embodiment 26

A compound according to any one of embodiments 1-25, wherein
n is 0 or 1, particularly 0.

Embodiment 27

A compound according to embodiment 1, wherein
R$^1$ is selected from
hydrogen-
fluoro-;
R$^2$ is selected from
hydrogen-
C$_1$-C$_4$-alkyl-
halo-C$_2$-C$_4$-alkyl-
N,N-di-C$_1$-C$_2$-alkyl-amino-C$_2$-C$_4$-alkyl-
hydroxy-C$_2$-C$_4$-alkyl-
C$_1$-C$_2$-alkoxy-C$_2$-C$_4$-alkyl-
C$_3$-C$_6$-cycloalkyl-C$_1$-C$_7$-alkyl-;
or
R$^1$ and R$^2$, together are selected from
—CH$_2$—CH$_2$— or —CH$_2$—CH$_2$—CH$_2$—;
R is selected from
halogen-
C$_1$-C$_4$-alkyl-
halo-C$_1$-C$_4$-alkyl-
C$_1$-C$_4$-alkoxy-
cyano-; and
R$^3$ is selected from
—(CH$_2$)$_p$—Y, wherein
p is selected from 0, 1, 2 or 3, and
Y is selected from aryl, heteroaryl, heterocyclyl, which are unsubstituted or substituted by 1-3 substituents selected from
halogen-
C$_1$-C$_7$-alkyl-
halo-C$_1$-C$_7$-alkyl-
C$_1$-C$_7$-alkoxy-
C$_3$-C$_{10}$-cycloalkyl-oxy-
hydroxy-
halo-C$_1$-C$_7$-alkyl-oxyamino-
N—$C_1$-$C_7$-alkyl-amino-
N,N-di-$C_1$-$C_7$-alkyl-amino-
cyano-
$C_1$-$C_7$-alkoxy-carbonyl-
—S(═O)$_2$—$C_1$-$C_7$-alkyl; —S(═O)$_2$— halo-$C_1$-$C_7$-alkyl;
—S(═O)—$C_1$-$C_7$-alkyl; —S(═O)-halo-$C_1$-$C_7$-alkyl
$C_3$-$C_{10}$-cycloalkyl-$C_1$-$C_7$-alkoxy-$C_1$-$C_7$-alkyl-;
—C(O)—NR$^{4\prime}$R$^4$, wherein
R$^4$ is selected from hydrogen, $C_1$-$C_7$-alkyl;
R$^{4\prime}$ is selected from hydrogen,
or R$^4$ and R$^{4\prime}$ together with the nitrogen atom to which they are attached, form a 4-7 membered, saturated or partially saturated monocyclic heterocyclic ring, optionally containing a further heteroatom selected from N, O or S,
m is 0; and
n is 0-1.

Embodiment 28

A compound according to embodiment 1, wherein
R$^1$ is selected from
hydrogen-
fluoro-;
R$^2$ is selected from
hydrogen-
$C_1$-$C_4$-alkyl-
halo-$C_2$-$C_4$-alkyl-
N,N-di-$C_1$-$C_2$-alkyl-amino-$C_2$-$C_4$-alkyl-
hydroxy-$C_2$-$C_4$-alkyl-
$C_1$-$C_2$-alkoxy-$C_2$-$C_4$-alkyl-
$C_3$-$C_6$-cycloalkyl-$C_1$-$C_7$-alkyl-;
or
R$^1$ and R$^2$, together are selected from
—CH$_2$—CH$_2$— or —CH$_2$—CH$_2$—CH$_2$—;
R is selected from
halogen-
$C_1$-$C_4$-alkyl-
halo-$C_1$-$C_4$-alkyl-
$C_1$-$C_4$-alkoxy-
cyano-; and
R$^3$ is selected from
phenyl, furanyl, thiophenyl, pyridyl, thiazolyl, pyrazolyl, isoxazolyl, imidazolyl, pyrrolyl, benzofuranyl, pyrimidinyl, oxazolyl, morpholinyl, piperidinyl, tetrahydrofuranyl, tetrahydropyranyl, pyrrolidinyl, dihydrobenzofuranyl which are unsubstituted or substituted by 1-2 substituents selected from
halogen-
$C_1$-$C_4$-alkyl-
halo-$C_1$-$C_4$-alkyl-
$C_1$-$C_4$-alkoxy-
$C_3$-$C_7$-cycloalkyl-oxy-
hydroxy-
halo-$C_1$-$C_4$-alkyl-oxy-
amino-
cyano-
$C_1$-$C_4$-alkoxy-carbonyl-
—S(═O)$_2$—$C_1$-$C_7$-alkyl; —S(═O)$_2$— halo-$C_1$-$C_7$-alkyl;
—S(═O)—$C_1$-$C_7$-alkyl; —S(═O)-halo-$C_1$-$C_7$-alkyl
$C_3$-$C_{10}$-cycloalkyl-$C_1$-$C_7$-alkoxy-$C_1$-$C_7$-alkyl-;

—C(O)—NR$^{4\prime}$R$^4$, wherein
R$^4$ is selected from hydrogen, $C_1$-$C_4$-alkyl;
R$^{4\prime}$ is selected from hydrogen,
or R$^4$ and R$^{4\prime}$ together with the nitrogen atom to which they are attached, form morpholinyl, piperidinyl, pyrrolidinyl,
m is 0; and
n is 0-1.

Embodiment 29

A compound of formula (I) or a pharmaceutically acceptable salt thereof, for use in medicine,

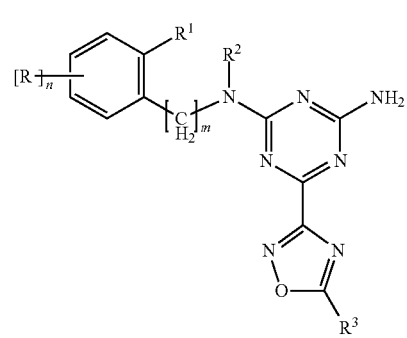

(I)

wherein
R$^1$ is selected from
hydrogen-
halogen-
$C_1$-$C_7$-alkyl-
halo-$C_1$-$C_7$-alkyl-;
R$^2$ is selected from
hydrogen-
$C_1$-$C_7$-alkyl-
halo-$C_2$-$C_7$-alkyl-
amino-$C_2$-$C_7$-alkyl-
N—$C_1$-$C_7$-alkyl-amino-$C_2$-$C_7$-alkyl-
N,N-di-$C_1$-$C_7$-alkyl-amino-$C_2$-$C_7$-alkyl-
hydroxy-$C_2$-$C_7$-alkyl-
$C_1$-$C_7$-alkoxy-$C_2$-$C_7$-alkyl-
$C_3$-$C_{10}$-cycloalkyl-$C_1$-$C_7$-alkyl-
cyano-$C_2$-$C_7$-alkyl-;
or
R$^1$ and R$^2$, together with the atoms to which they are attached, form a 4-7 membered, saturated or partially saturated heterocyclic ring, which is unsubstituted or substituted by 1-3 substituents selected from
$C_1$-$C_7$-alkyl-
halo-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
hydroxy-$C_1$-$C_7$-alkyl-
$C_1$-$C_7$-alkoxy-$C_1$-$C_7$-alkyl-
$C_3$-$C_{10}$-cycloalkyl-$C_1$-$C_7$-alkyl-
cyano-$C_1$-$C_7$-alkyl-;
R is selected from
halogen-
$C_1$-$C_7$-alkyl-
halo-$C_1$-$C_7$-alkyl-
$C_1$-$C_7$-alkoxy-
cyano-
halo-$C_1$-$C_7$-alkoxy-
nitro;

—C(O)—O—R', wherein R' is selected from hydrogen, $C_1$-$C_7$-alkyl; $C_3$-$C_{10}$-cycloalkyl; $C_1$-$C_7$-alkoxy; halo-$C_1$-$C_7$-alkyl aryl; aryl-$C_1$-$C_7$-alkyl-; heteroaryl; heteroaryl $C_1$-$C_7$-alkyl-; heterocyclyl; —S(=O)$_2$—$C_1$-$C_7$-alkyl; —S(=O)$_2$—$C_3$-$C_{10}$-cycloalkyl; —S(=O)$_2$—$C_1$-$C_7$-alkoxy;

$R^3$ is selected from (a) -L-Y, wherein

-L- is selected from a direct bond; —(CH$_2$)$_p$—, —C(O)—, —NR$^7$—, —NR$^7$—C(O)— or —C(O)—NR$^7$—, wherein p is selected from 1, 2 or 3

$R^7$ is selected from hydrogen and $C_1$-$C_7$-alkyl

Y is selected from cycloalkyl, aryl, heteroraryl, heterocyclyl, spirocyclyl, which are unsubstituted or substituted by 1-3 substituents selected from halogen-;

$C_1$-$C_7$-alkyl-;

halo-$C_1$-$C_7$-alkyl-;

halo-$C_1$-$C_7$-alkyl-oxy-$C_1$-$C_7$-alkyl; halo-$C_1$-$C_7$-alkyl-oxy-$C_1$-$C_7$-alkyl-oxy;

$C_1$-$C_7$-alkoxy-; $C_1$-$C_7$-alkoxy-$C_1$-$C_7$-alkoxy-; NC—$C_1$-$C_7$-alkoxy-;

$C_1$-$C_7$-alkoxy-$C_1$-$C_7$-alkyl-;

$C_3$-$C_{10}$-cycloalkyl-oxy-$C_1$-$C_7$-alkyl-;

$C_3$-$C_{10}$-cycloalkyl-$C_1$-$C_7$-alkyl-oxy-;

$C_3$-$C_{10}$-cycloalkyl-oxy-;

$C_3$-$C_{10}$-cycloalkyl-NR$^{7'}$—$C_1$-$C_7$-alkyl-, wherein R$^{7'}$ is selected from $R^7$ is selected from hydrogen and $C_1$-$C_7$-alkyl;

$C_3$-$C_{10}$-cycloalkyl-$C_1$-$C_7$-alkoxy-$C_1$-$C_7$-alkyl-;

$C_2$-$C_7$-alkenyl; halo-$C_2$-$C_7$-alkenyl;

hydroxy-;

hydroxy-$C_1$-$C_7$-alkyl-;

halo-$C_1$-$C_7$-alkyl-oxy-;

amino-;

N—$C_1$-$C_7$-alkyl-amino-;

N-halo-$C_1$-$C_7$-alkyl-amino-;

N-heterocyclyl-amino-, N—$C_3$-$C_{10}$-cycloalkyl-amino-, wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;

N—$C_3$-$C_{10}$-cycloalkyl-$C_1$-$C_7$-alkyl-amino-;

N,N-di-$C_1$-$C_7$-alkyl-amino-; N,N-di-halo-$C_1$-$C_7$-alkyl-amino-;

N,N-di-heterocyclyl-amino-, N,N-di-$C_3$-$C_{10}$-cycloalkyl-amino- wherein the heterocyclyl and cycloalkyl are optionally substituted by halo-$C_1$-$C_7$-alkyl-oxy, $C_1$-$C_7$-alkyl; $C_3$-$C_{10}$-cycloalkyl and $C_1$-$C_7$-alkoxy;

cyano-; oxo;

$C_1$-$C_7$-alkoxy-carbonyl-;

$C_1$-$C_7$-alkoxy-$C_1$-$C_7$-alkoxy-$C_1$-$C_7$-alkyl-;

aryl; aryl-$C_1$-$C_7$-alkyl-; aryl-oxy;

heterocyclyl;

heterocyclyl-$C_1$-$C_7$-alkyl-; heterocyclyl-oxy-;

heterocyclyl-oxy-$C_1$-$C_7$-alkyl-; aryl-oxy-$C_1$-$C_7$-alkyl-; heteroaryl-oxy-$C_1$-$C_7$-alkyl-;

hydroxy-carbonyl-;

—S— halo-$C_1$-$C_7$-alkyl; —S—$C_1$-$C_7$-alkyl; —S—aryl;

halo-$C_1$-$C_7$-alkyl-S—$C_1$-$C_7$-alkyl; $C_1$-$C_7$-alkyl-S—$C_1$-$C_7$-alkyl;

—S(=O)$_2$—$C_1$-$C_7$-alkyl; —S(=O)$_2$— halo-$C_1$-$C_7$-alkyl; —S(=O)$_2$-aryl; —S(=O)$_2$-heteroaryl; —S(=O)$_2$—NR$^{4'}$R$^4$; —S(=O)$_2$-heterocyclyl; halo-$C_1$-$C_7$-alkyl-S(=O)$_2$—$C_1$-$C_7$-alkyl; $C_1$-$C_7$-alkyl-S(=O)$_2$—$C_1$-$C_7$-alkyl;

—S(=O)—$C_1$-$C_7$-alkyl; —S(=O)-halo-$C_1$-$C_7$-alkyl; —S(=O)—$C_1$-$C_7$-alkoxy; —S(=O)—$C_3$-$C_{10}$-cycloalkyl;

—C(O)—$C_1$-$C_7$-alkyl; —C(O)— halo-$C_1$-$C_7$-alkyl; —C(O)—$C_1$-$C_7$-alkoxy; —C(O)—$C_3$-$C_{10}$ cycloalkyl;

—C(O)O—$C_1$-$C_7$-alkyl; —C(O)O—$C_3$-$C_{10}$-cycloalkyl; —C(O)O-halo-$C_1$-$C_7$-alkyl; —C(O)O—$C_1$-$C_7$-alkoxy;

—C(O)—NR$^{4'}$R$^4$ or —NHC(O)—R$^4$, wherein $R^4$ is selected from hydrogen, $C_1$-$C_7$-alkyl, halo-$C_1$-$C_7$-alky, $C_3$-$C_{10}$-cycloalkyl, $C_3$-$C_{10}$-cycloalkyl-$C_1$-$C_7$-alkyl and $C_1$-$C_7$-alkoxy;

$R^{4'}$ is selected from hydrogen;

or $R^4$ and $R^{4'}$ together with the nitrogen atom to which they are attached, form a 4-7 membered, saturated or partially saturated monocyclic heterocyclic ring, optionally containing a further heteroatom selected from N, O or S, and wherein said heterocyclic ring is optionally substituted with aryl, aryl-oxy-, $C_1$-$C_7$-alkyl, halo-$C_1$-$C_7$-alkyl or $C_1$-$C_7$-alkoxy, and said aryl is optionally substituted with halogen, $C_1$-$C_7$-alkyl, halo-$C_1$-$C_7$-alkyl or $C_1$-$C_7$-alkoxy.

or (b) —C(O)—NR$^{5'}$R$^5$ or —C(O)—O—R$^5$, wherein $R^5$ and $R^{5'}$ are selected from hydrogen, $C_1$-$C_7$-alkyl; $C_3$-$C_{10}$-cycloalkyl; $C_1$-$C_7$-alkoxy; halo-$C_1$-$C_7$-alkyl aryl; aryl-$C_1$-$C_7$-alkyl-; aryl; heteroaryl; heteroaryl $C_1$-$C_7$-alkyl-; heterocyclyl; indane; or $R^5$ and $R^{5'}$ together with the nitrogen atom to which they are attached, form a 4-9 membered, saturated or partially saturated monocyclic or bicyclic heterocyclic ring, optionally containing a further heteroatom selected from N, O or S;

wherein said $C_3$-$C_{10}$-cycloalkyl; aryl, heteroaryl, heterocyclyl and indane are optionally substituted with 1 to 3 substituents selected from $C_1$-$C_7$-alkyl, halo-$C_1$-$C_7$-alkyl, $C_1$-$C_7$-alkoxy, halo-$C_1$-$C_7$-alkyl-oxy- and hydroxy-$C_1$-$C_7$-alkyl;

or (c) —NR$^{6'}$R$^6$, wherein $R^6$ is selected from hydrogen, $C_1$-$C_7$-alkyl, $R^{6'}$ is selected from hydrogen, $C_1$-$C_7$-alkyl, $C_1$-$C_7$-alkyl carbonyl-; $C_3$-$C_{10}$-cycloalkyl;

or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which monocyclic and bicyclic heterocyclic ring is unsubstituted or substituted by 1-3 substituents selected from $C_1$-$C_7$-alkyl-, halo-$C_1$-$C_7$-alkyl-, $C_1$-$C_7$-alkoxy-, hydroxy- and $C_1$-$C_7$-alkoxy-carbonyl-;

(d) —NR$^{5'}$—C(O)—R$^5$, wherein $R^5$ is selected from hydrogen, $C_1$-$C_7$-alkyl; $C_3$-$C_{10}$-cycloalkyl; $C_1$-$C_7$-alkoxy; halo-$C_1$-$C_7$-alkyl; aryl; aryl-$C_1$-$C_7$-alkyl-; heteroaryl; heteroaryl-$C_1$-$C_7$-alkyl-; heterocyclyl;

$R^{5'}$ is selected from hydrogen, $C_1$-$C_7$-alkyl;

m is 0-1; and n is 0-2;

$R^8$ is hydrogen and $R^9$ is selected from hydrogen, halo-$C_1$-$C_7$-alkyl-, $C_1$-$C_7$-alkoxy-$C_1$-$C_7$-alkyl-, $C_1$-$C_7$-alkyl, $C_1$-$C_7$-alkoxy and halo-$C_1$-$C_7$-alkyl;

wherein $C_1$-$C_7$-alkyl, $C_1$-$C_7$-alkoxy, heterocyclyl, aryl, heteroaryl are optionally substituted by aryl, heteroaryl, heterocyclyl, $C_1$-$C_7$-alkyl, $C_1$-$C_7$-alkoxy, halo-$C_1$-$C_7$-alkyl; OH.

Embodiment 30

A compound according to embodiment 29, wherein

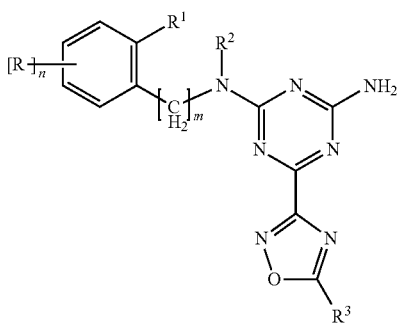
(I)

wherein
$R^1$ is selected from
  hydrogen-
  halogen-
  $C_1$-$C_7$-alkyl-
  halo-$C_1$-$C_7$-alkyl-;
$R^2$ is selected from
  hydrogen-
  $C_1$-$C_7$-alkyl-
  halo-$C_2$-$C_7$-alkyl-
  amino-$C_2$-$C_7$-alkyl-
  N—$C_1$-$C_7$-alkyl-amino-$C_2$-$C_7$-alkyl-
  N,N-di-$C_1$-$C_7$-alkyl-amino-$C_2$-$C_7$-alkyl-
  hydroxy-$C_2$-$C_7$-alkyl-
  $C_1$-$C_7$-alkoxy-$C_2$-$C_7$-alkyl-
  $C_3$-$C_{10}$-cycloalkyl-$C_1$-$C_7$-alkyl-
  cyano-$C_2$-$C_7$-alkyl-;
or
$R^1$ and $R^2$, together with the atoms to which they are attached, form a 4-7 membered, saturated or partially saturated heterocyclic ring, which is unsubstituted or substituted by 1-3 substituents selected from
  $C_1$-$C_7$-alkyl-
  halo-$C_1$-$C_7$-alkyl-
  amino-$C_1$-$C_7$-alkyl-
  N—$C_1$-$C_7$-alkyl-amino-$C_1$-$C_7$-alkyl-
  N,N-di-$C_1$-$C_7$-alkyl-amino-$C_1$-$C_7$-alkyl-
  hydroxy-$C_1$-$C_7$-alkyl-
  $C_1$-$C_7$-alkoxy-$C_1$-$C_7$-alkyl-
  $C_3$-$C_{10}$-cycloalkyl-$C_1$-$C_7$-alkyl-
  cyano-$C_1$-$C_7$-alkyl-;
R is selected from
  halogen-
  $C_1$-$C_7$-alkyl-
  halo-$C_1$-$C_7$-alkyl-
  $C_1$-$C_7$-alkoxy-
  cyano-
  halo-$C_1$-$C_7$-alkoxy-
  nitro;
$R^3$ is selected from
(a) -L-Y, wherein
  -L- is selected from a direct bond; —$(CH_2)_p$—, —C(O)—, —$NR^7$—, —$NR^7$—C(O)— or —C(O)—$NR^7$—, wherein p is selected from 1, 2 or 3
  $R^7$ is selected from hydrogen, $C_1$-$C_7$-alkyl
  Y is selected from cycloalkyl, aryl, heteroaryl, heterocyclyl, which are unsubstituted or substituted by 1-3 substituents selected from
    halogen-
    $C_1$-$C_7$-alkyl-
    halo-$C_1$-$C_7$-alkyl-
    $C_1$-$C_7$-alkoxy-
    $C_3$-$C_{10}$-cycloalkyl-oxy-
    hydroxy-
    halo-$C_1$-$C_7$-alkyl-oxy-
    amino-
    N—$C_1$-$C_7$-alkyl-amino-
    N,N-di-$C_1$-$C_7$-alkyl-amino-
    cyano-
    $C_1$-$C_7$-alkoxy-carbonyl-
    hydroxy-carbonyl-1
    —C(O)—$NR^{4'}R^4$, wherein
      $R^4$ is selected from hydrogen, $C_1$-$C_7$-alkyl;
      $R^{4'}$ is selected from hydrogen,
      or $R^4$ and $R^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—$NR^{5'}R^5$ or —C(O)—O—$R^5$, wherein
  $R^5$ and $R^{5'}$ are selected from hydrogen, $C_1$-$C_7$-alkyl;
or
(c) —$NR^{6'}R^6$, wherein
  $R^6$ is selected from hydrogen, $C_1$-$C_7$-alkyl,
  $R^{6'}$ is selected from hydrogen, $C_1$-$C_7$-alkyl, $C_1$-$C_7$-alkyl carbonyl-,
m is 0-1; and
n is 0-2.

Embodiment 31

A compound according to embodiment 29 or 30, wherein

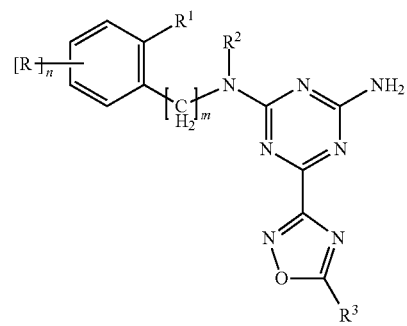
(I)

wherein
$R^1$ is selected from
  hydrogen-
  halogen-
  $C_1$-$C_7$-alkyl-
  halo-$C_1$-$C_7$-alkyl-;
$R^2$ is selected from
  hydrogen-
  $C_1$-$C_7$-alkyl-
  halo-$C_2$-$C_7$-alkyl-
  amino-$C_2$-$C_7$-alkyl-
  N—$C_1$-$C_7$-alkyl-amino-$C_2$-$C_7$-alkyl-
  N,N-di-$C_1$-$C_7$-alkyl-amino-$C_2$-$C_7$-alkyl-
  hydroxy-$C_2$-$C_7$-alkyl-
  $C_1$-$C_7$-alkoxy-$C_2$-$C_7$-alkyl-
  $C_3$-$C_{10}$-cycloalkyl-$C_1$-$C_7$-alkyl-
  cyano-$C_2$-$C_7$-alkyl-;

or
R$^1$ and R$^2$, together with the atoms to which they are attached, form a 4-7 membered, saturated or partially saturated heterocyclic ring, which is unsubstituted or substituted by 1-3 substituents selected from
  C$_1$-C$_7$-alkyl-
  halo-C$_1$-C$_7$-alkyl-
  amino-C$_1$-C$_7$-alkyl-
  N—C$_1$-C$_7$-alkyl-amino-C$_1$-C$_7$-alkyl-
  N,N-di-C$_1$-C$_7$-alkyl-amino-C$_1$-C$_7$-alkyl-
  hydroxy-C$_1$-C$_7$-alkyl-
  C$_1$-C$_7$-alkoxy-C$_1$-C$_7$-alkyl-
  C$_3$-C$_{10}$-cycloalkyl-C$_1$-C$_7$-alkyl-
  cyano-C$_1$-C$_7$-alkyl-;
R is selected from
  halogen-
  C$_1$-C$_7$-alkyl-
  halo-C$_1$-C$_7$-alkyl-
  C$_1$-C$_7$-alkoxy-
  cyano-
  halo-C$_1$-C$_7$-alkoxy-
  nitro;
R$^3$ is selected from
(a) —(CH$_2$)$_p$—Y, wherein
  p is selected from 0, 1, 2 or 3, and
  Y is selected from aryl, heteroaryl, heterocyclyl, which are unsubstituted or substituted by 1-3 substituents selected from
    halogen-
    C$_1$-C$_7$-alkyl-
    halo-C$_1$-C$_7$-alkyl-
    C$_1$-C$_7$-alkoxy-
    C$_3$-C$_{10}$-cycloalkyl-oxy-
    hydroxy-
    halo-C$_1$-C$_7$-alkyl-oxy-
    amino-
    N—C$_1$-C$_7$-alkyl-amino-
    N,N-di-C$_1$-C$_7$-alkyl-amino-
    cyano-
    C$_1$-C$_7$-alkoxy-carbonyl-
    hydroxy-carbonyl-
    —C(O)—NR$^4$'R$^4$, wherein
      R$^4$ is selected from hydrogen, C$_1$-C$_7$-alkyl;
      R$^{4'}$ is selected from hydrogen,
      or R$^4$ and R$^{4'}$ together with the nitrogen atom to which they are attached, form a 4-7 membered, saturated or partially saturated monocyclic heterocyclic ring, optionally containing a further heteroatom selected from N, O or S;
or
(b) —C(O)—NR$^{5'}$R$^5$ or —C(O)—O—R$^5$, wherein
  R$^5$ is selected from hydrogen, benzyl, indanyl, tetrahydrofuranyl, tetrahydropyranyl, oxiranyl, C$_3$-C$_{10}$-cycloalkyl, C$_1$-C$_7$-alkyl;
  R$^{5'}$ is selected from hydrogen, C$_1$-C$_7$-alkyl,
  or R$^5$ and R$^{5'}$ together with the nitrogen atom to which they are attached, form a 4-7 membered, saturated or partially saturated monocyclic or bicyclic heterocyclic ring, optionally containing a further heteroatom selected from N, O or S;
or
(c) —NR$^{6'}$R$^6$, wherein
  R$^6$ is selected from hydrogen, benzyl, C$_3$-C$_{10}$-cycloalkyl, C$_1$-C$_7$-alkyl,
  R$^{6'}$ is selected from hydrogen, C$_1$-C$_7$-alkyl, C$_1$-C$_7$-alkyl carbonyl-, or R$^6$ and R$^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from
    C$_1$-C$_7$-alkyl-
    hydroxy-
    C$_1$-C$_7$-alkoxy-carbonyl-
or
(d) —NR$^{5'}$-C(O)—R$^5$, wherein
  R$^5$ is selected from C$_3$-C$_{10}$-cycloalkyl;
  R$^{5'}$ is selected from hydrogen, C$_1$-C$_7$-alkyl;
m is 0-1; and
n is 0-1.

Embodiment 32

A compound according to any one of embodiments 29 to 31, wherein

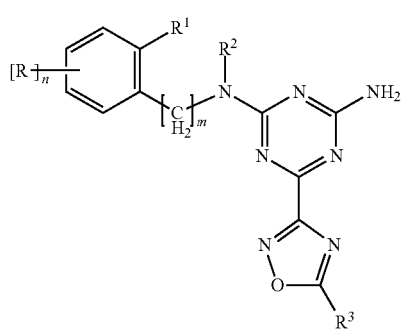

(I)

R$^1$ is selected from
  hydrogen-
  halogen-
  C$_1$-C$_7$-alkyl-
  halo-C$_1$-C$_7$-alkyl-;
R$^2$ is selected from
  hydrogen-
  C$_1$-C$_7$-alkyl-
  halo-C$_2$-C$_7$-alkyl-
  amino-C$_2$-C$_7$-alkyl-
  N—C$_1$-C$_7$-alkyl-amino-C$_2$-C$_7$-alkyl-
  N,N-di-C$_1$-C$_7$-alkyl-amino-C$_2$-C$_7$-alkyl-
  hydroxy-C$_2$-C$_7$-alkyl-
  C$_1$-C$_7$-alkoxy-C$_2$-C$_7$-alkyl-
  C$_3$-C$_{10}$-cycloalkyl-C$_1$-C$_7$-alkyl-
  cyano-C$_2$-C$_7$-alkyl-;
or
R$^1$ and R$^2$, together with the atoms to which they are attached, form a 4-7 membered, saturated or partially saturated heterocyclic ring, which is unsubstituted or substituted by 1-3 substituents selected from
  C$_1$-C$_7$-alkyl-
  halo-C$_1$-C$_7$-alkyl-
  amino-C$_1$-C$_7$-alkyl-
  N—C$_1$-C$_7$-alkyl-amino-C$_1$-C$_7$-alkyl-
  N,N-di-C$_1$-C$_7$-alkyl-amino-C$_1$-C$_7$-alkyl-
  hydroxy-C$_1$-C$_7$-alkyl-
  C$_1$-C$_7$-alkoxy-C$_1$-C$_7$-alkyl-
  C$_3$-C$_{10}$-cycloalkyl-C$_1$-C$_7$-alkyl-
  cyano-C$_1$-C$_7$-alkyl-;

R is selected from
- halogen-
- $C_1$-$C_7$-alkyl-
- halo-$C_1$-$C_7$-alkyl-
- $C_1$-$C_7$-alkoxy-
- cyano-
- halo-$C_1$-$C_7$-alkoxy-
- nitro;

$R^3$ is selected from
(a) —$(CH_2)_p$—Y, wherein
  p is selected from 0, 1, 2 or 3, and
  Y is selected from aryl, heteroaryl, heterocyclyl, which are unsubstituted or substituted by 1-3 substituents selected from
  - halogen-
  - $C_1$-$C_7$-alkyl-
  - halo-$C_1$-$C_7$-alkyl-
  - $C_1$-$C_7$-alkoxy-
  - $C_3$-$C_{10}$-cycloalkyl-oxy-
  - hydroxy-
  - halo-$C_1$-$C_7$-alkyl-oxy-
  - amino-
  - N—$C_1$-$C_7$-alkyl-amino-
  - N,N-di-$C_1$-$C_7$-alkyl-amino-
  - cyano-
  - $C_1$-$C_7$-alkoxy-carbonyl-
  - hydroxy-carbonyl-
  - —C(O)—$NR^{4'}R^4$, wherein
    - $R^4$ is selected from hydrogen, $C_1$-$C_7$-alkyl;
    - $R^{4'}$ is selected from hydrogen,
    - or $R^4$ and $R^{4'}$ together with the nitrogen atom to which they are attached, form a 4-7 membered, saturated or partially saturated monocyclic heterocyclic ring, optionally containing a further heteroatom selected from N, O or S;

or (b) —C(O)—$NR^{5'}R^5$ or —C(O)—O—$R^5$, wherein
  $R^5$ is selected from hydrogen, benzyl, indanyl, tetrahydrofuranyl, tetrahydropyranyl, oxiranyl, $C_3$-$C_{10}$-cycloalkyl, $C_1$-$C_7$-alkyl;
  $R^{5'}$ is selected from hydrogen, $C_1$-$C_7$-alkyl,
  or $R^5$ and $R^{5'}$ together with the nitrogen atom to which they are attached, form a 4-7 membered, saturated or partially saturated monocyclic or bicyclic heterocyclic ring, optionally containing a further heteroatom selected from N, O or S;

or (c) —$NR^{6'}R^6$, wherein
  $R^6$ is selected from hydrogen, benzyl, $C_3$-$C_{10}$-cycloalkyl, $C_1$-$C_7$-alkyl,
  $R^{6'}$ is selected from hydrogen, $C_1$-$C_7$-alkyl, $C_1$-$C_7$-alkyl carbonyl-,
  or $R^6$ and $R^{6'}$ together with the nitrogen atom to which they are attached, form a 4-7 membered, saturated or partially saturated monocyclic, or 7-12 membered, saturated or partially saturated bicyclic heterocyclic ring, optionally containing a further heteroatom selected from N, O or S; which are unsubstituted or substituted by 1-3 substituents selected from
  - $C_1$-$C_7$-alkyl-
  - hydroxy-
  - $C_1$-$C_7$-alkoxy-carbonylor (d) —$NR^{5'}$—C(O)—$R^5$, wherein
  $R^5$ is selected from $C_3$-$C_{10}$-cycloalkyl;
  $R^{5'}$ is selected from hydrogen, $C_1$-$C_7$-alkyl;
m is 0-1; and
n is 0-1.

Embodiment 33

A pharmaceutical composition comprising a therapeutically effective amount of a compound of formula (I) according to any one of embodiments 1 to 28 and one or more pharmaceutically acceptable carriers/excipients.

Embodiment 34

A combination in particular a pharmaceutical combination, comprising a therapeutically effective amount of a compound of formula (I) according to any one of embodiments 1 to 28, and one or more therapeutically active agents, particularly pain-relieving agents.

Embodiment 35

Use of a compound of formula (I) according to any one of embodiments 1 to 28 for the manufacture of a medicament for the treatment of chronic pain.

Embodiment 36

Use of a compound of formula (I) according to any one of embodiments 1 to 28 for the manufacture of a medicament for the treatment of one or more Nav 1.7 mediated disorders or disease.

Embodiment 37

Use of a compound of formula (I) according to any one of embodiments 1 to 28 for the treatment of one or more Nav 1.7 mediated disorders or diseases.

Embodiment 38

Use of a compound of formula (I) according to any one of embodiments 1 to 28 for the treatment of chronic pain.

Embodiment 39

Use according to embodiment 37 for the treatment of a disorder or disease selected from chronic pain, such as positive symptoms of chronic pain e.g. parethesias, dyesthesias, hyperalgesia, allodynia and spontaneous pain as well as negative symptoms e.g. loss of sensation.

Embodiment 40

A method for the treatment of chronic pain, comprising the step of administering to a subject a therapeutically effective amount of a compound of formula (I) according to any one of embodiments 1 to 28.

Embodiment 41

A method according to embodiment 40 where the disorder or disease is selected from chronic pain, such as positive symptoms of chronic pain e.g. parethesias, dyesthesias, hyperalgesia, allodynia and spontaneous pain as well as negative symptoms e.g. loss of sensation.

Embodiment 42

A method of modulating Nav 1.7 activity in a subject, comprising the step of administering to a subject a therapeutically effective amount of a compound of formula (I) according to any one of embodiments 1 to 28.

Embodiment 43

A compound according to embodiment 1, selected from Examples 1 to 517, or a pharmaceutically acceptable salt thereof.

Embodiment 44

A compound according to embodiment 43, wherein the compound is selected from
2-N-methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine;
6-(5-{4-[(cyclopropylmethoxy)methyl]piperidin-1-yl}-1,2,4-oxadiazol-3-yl)-2-N-methyl-2-N-phenyl-1,3,5-triazine-2,4-diamine;
2-N-(3-fluorophenyl)-6-[5-(3-fluoropyridin-2-yl)-1,2,4-oxadiazol-3-yl]-1,3,5-triazine-2,4-diamine;
2-N-methyl-2-N-phenyl-6-(5-{6-[2-(2,2,2-trifluoroethoxy)ethoxy]pyridin-3-yl}-1,2,4-oxadiazol-3-yl)-1,3,5-triazine-2,4-diamine;
2-N-methyl-2-N-phenyl-6-{5-[(2R)-1-[(2,2,2-trifluoroethane)sulfonyl]pyrrolidin-2-yl]-1,2,4-oxadiazol-3-yl}-1,3,5-triazine-2,4-diamine;
2-N-methyl-2-N-phenyl-6-(5-{6-[(3,3,3-trifluoropropane)sulfinyl]pyridin-3-yl}-1,2,4-oxadiazol-3-yl)-1,3,5-triazine-2,4-diamine;
2-N-methyl-2-N-phenyl-6-(5-{4-[(3,3,3-trifluoropropoxy)methyl]piperidin-1-yl}-1,2,4-oxadiazol-3-yl)-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine; and
N-Methyl-N-phenyl-6-{5-[6-(2,2,2-trifluoroethoxy)-pyridin-3-yl]-[1,2,4]oxadiazol-3-yl}-[1,3,5]triazine-2,4-diamine;
or a pharmaceutically acceptable salt thereof.

The invention claimed is:
1. A compound which is selected from
2-N-methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine;
6-(5-{4-[(cyclopropylmethoxy)methyl]piperidin-1-yl}-1,2,4-oxadiazol-3-yl)-2-N-methyl-2-N-phenyl-1,3,5-triazine-2,4-diamine;
2-N-(3-fluorophenyl)-6-[5-(3-fluoropyridin-2-yl)-1,2,4-oxadiazol-3-yl]-1,3,5-triazine-2,4-diamine;
2-N-methyl-2-N-phenyl-6-(5-{6-[2-(2,2,2-trifluoroethoxy)ethoxy]pyridin-3-yl}-1,2,4-oxadiazol-3-yl)-1,3,5-triazine-2,4-diamine;
2-N-methyl-2-N-phenyl-6-{5-[(2R)-1-[(2,2,2-trifluoroethane)sulfonyl]pyrrolidin-2-yl]-1,2,4-oxadiazol-3-yl}-1,3,5-triazine-2,4-diamine;
2-N-methyl-2-N-phenyl-6-(5-{6-[(3,3,3-trifluoropropane)sulfinyl]pyridin-3-yl}-1,2,4-oxadiazol-3-yl)-1,3,5-triazine-2,4-diamine;
2-N-methyl-2-N-phenyl-6-(5-{4-[(3,3,3-trifluoropropoxy)methyl]piperidin-1-yl}-1,2,4-oxadiazol-3-yl)-1,3,5-triazine-2,4-diamine;
2-N-methyl-2-N-phenyl-6-{5-[1-(propane-2-sulfonyl)piperidin-4-yl]-1,2,4-oxadiazol-3-yl}-1,3,5-triazine-2,4-diamine; and
N-Methyl-N-phenyl-6-{5-[6-(2,2,2-trifluoroethoxy)-pyridin-3-yl]-[1,2,4]oxadiazol-3-yl}-[1,3,5]triazine-2,4-diamine;
or a pharmaceutically acceptable salt thereof.

2. A pharmaceutical composition comprising a therapeutically effective amount of a compound according to claim 1 and one or more pharmaceutically acceptable carriers/excipients.

3. A method for the treatment of chronic pain, comprising the step of administering to a subject, who is in need of such treatment, a therapeutically effective amount of a compound according to claim 1.

4. A method according to claim 3 where the chronic pain is a positive symptoms of chronic pain selected from parethesias, dyesthesias, hyperalgesia, allodynia and spontaneous pain.

5. The compound according to claim 1, which is
2-N-methyl-2-N-phenyl-6-(5-{4-[(2,2,2-trifluoroethoxy)methyl]piperidin-1-yl}-1,2,4-oxadiazol-3-yl)-1,3,5-triazine-2,4-diamine;
or a pharmaceutically acceptable salt thereof.

6. The compound according to claim 1, which is
2-N-methyl-2-N-phenyl-6-{5-[1-(propane-2-sulfonyl)piperidin-4-yl]-1,2,4-oxadiazol-3-yl}-1,3,5-triazine-2,4-diamine;
or a pharmaceutically acceptable salt thereof.

7. The compound according to claim 1, which is
6-(5-{4-[(cyclopropylmethoxy)methyl]piperidin-1-yl}-1,2,4-oxadiazol-3-yl)-2-N-methyl-2-N-phenyl-1,3,5-triazine-2,4-diamine;
or a pharmaceutically acceptable salt thereof.

8. The compound according to claim 1, which is
2-N-(3-fluorophenyl)-6-[4-(3-fluoropyridin-2-yl)-1,2,4-oxadiazol-3-yl]-1,3,5-triazine-2,4-diamine;
or a pharmaceutically acceptable salt thereof.

9. The compound according to claim 1, which is
2-N-methyl-2-N-phenyl-6-(5-{6-[2-(2,2,2-trifluoroethoxy)ethoxy]pyridin-3-yl}-1,2,4-oxadiazol-3-yl)-1,3,5-triazine-2,4-diamine;
or a pharmaceutically acceptable salt thereof.

10. The compound according to claim 1, which is
2-N-methyl-2-N-phenyl-6-[5-[(2R)-1-[(2,2,2-trifluoroethane)sulfonyl]pyrrolidin-2-yl]-1,2,4-oxadiazol-3-yl]-1,3,5-triazine-2,4-diamine;
or a pharmaceutically acceptable salt thereof.

11. The compound according to claim 1, which is
2-N-methyl-2-N-phenyl-6-(5-{6-[(3,3,3-trifluoropropane)sulfinyl]pyridin-3-yl}-1,2,4-oxadiazol-3-yl)-1,3,5-triazine-2,4-diamine;
or a pharmaceutically acceptable salt thereof.

12. The compound according to claim 1, which is
2-N-methyl-2-N-phenyl-6-(5-[4-[(3,3,3-trifluoropropoxy)methyl]piperidin-1-yl]-1,2,4-oxadiazol-3-yl)-1,3,5-triazine-2,4-diamine;
or a pharmaceutically acceptable salt thereof.

13. The compound according to claim 1, which is
2-N-methyl-2-N-phenyl-6-{5-[1-(propane-2-sulfonyl)piperidin-4-yl]-1,2,4-oxadiazol-3-yl}-1,3,5-triazine-2,4-diamine;
or a pharmaceutically acceptable salt thereof.

14. The compound according to claim 1, which is
N-Methyl-N-phenyl-6-{5-[6-(2,2,2-trifluoroethoxy)-pyridin-3-yl]-[1,2,4]oxadiazol-3-yl}-[1,3,5]triazine-2,4-diamine;
or a pharmaceutically acceptable salt thereof.

* * * * *